(12) United States Patent
Katz et al.

(10) Patent No.: US 8,933,209 B2
(45) Date of Patent: Jan. 13, 2015

US008933209B2

(54) DEP2 AND ITS USES IN MAJOR DEPRESSIVE DISORDER AND OTHER RELATED DISORDERS

(75) Inventors: David A. Katz, Chicago, IL (US);
Jeremy C. Packer, Wadsworth, IL (US);
Anahita Bhathena, Evanston, IL (US);
Christopher Neff, Salt Lake City, UT (US); Victor Abkevich, Salt Lake City, UT (US); Donna Shattuck, Salt Lake City, UT (US); Srikanth Jammulapati, Salt Lake City, UT (US)

(73) Assignees: AbbVie Inc., North Chicago, IL (US);
Myriad Genetics, Inc., Salt Lake City, UT (US)

(*) Notice: Subject to any disclaimer, the term of this patent is extended or adjusted under 35 U.S.C. 154(b) by 1146 days.

(21) Appl. No.: 11/509,296

(22) Filed: Aug. 24, 2006

(65) Prior Publication Data

US 2007/0256149 A1 Nov. 1, 2007

Related U.S. Application Data

(63) Continuation-in-part of application No. 11/412,184, filed on Apr. 26, 2006, now abandoned.

(51) Int. Cl.
*C12N 15/11* (2006.01)
*C12N 15/63* (2006.01)
*C12Q 1/68* (2006.01)
*C07K 14/47* (2006.01)

(52) U.S. Cl.
CPC .......... *C07K 14/47* (2013.01); *C12Q 2600/106* (2013.01); *C12Q 1/6883* (2013.01); *C12Q 2600/158* (2013.01); *C12Q 2600/172* (2013.01); *C12Q 2600/156* (2013.01); *C12Q 2600/136* (2013.01)
USPC ...................................... 536/23.1; 435/320.1

(58) Field of Classification Search
USPC ...................................... 536/23.1; 435/320.1
See application file for complete search history.

(56) References Cited

U.S. PATENT DOCUMENTS

| | | | |
|---|---|---|---|
| 4,582,788 A | 4/1986 | Erlich | |
| 4,683,194 A | 7/1987 | Saiki et al. | |
| 4,683,202 A | 7/1987 | Mullis | |
| 4,736,866 A | 4/1988 | Leder et al. | |
| 5,107,065 A | 4/1992 | Shewmaker et al. | |
| 5,231,020 A | 7/1993 | Jorgensen et al. | |
| 5,254,678 A | 10/1993 | Haseloff et al. | |
| 5,888,780 A | 3/1999 | Dahlberg et al. | |
| 5,888,819 A | 3/1999 | Goelet et al. | |
| 5,891,643 A | 4/1999 | Fesik et al. | |
| 5,912,120 A | 6/1999 | Goldstein et al. | |
| 5,952,174 A | 9/1999 | Nikiforov et al. | |
| 5,989,827 A | 11/1999 | Fesik et al. | |
| 6,001,567 A | 12/1999 | Brow et al. | |
| 6,004,744 A | 12/1999 | Goelet et al. | |
| 6,043,024 A | 3/2000 | Fesik et al. | |
| 6,043,031 A | 3/2000 | Koster et al. | |
| 6,045,996 A | 4/2000 | Cronin et al. | |
| 6,068,818 A | 5/2000 | Ackley et al. | |
| 6,132,964 A | 10/2000 | Bandman et al. | |
| 6,569,662 B1 | 5/2003 | Tang et al. | |
| 6,897,337 B2 | 5/2005 | Fesik et al. | |

FOREIGN PATENT DOCUMENTS

| | | |
|---|---|---|
| EP | 0 050 424 | 9/1985 |
| EP | 0 084 796 | 5/1990 |
| EP | 0 237 362 | 3/1992 |
| EP | 0 201 184 | 12/1992 |
| EP | 0 258 017 | 6/1997 |
| WO | 99/67641 | 12/1999 |
| WO | 00/39587 | 7/2000 |
| WO | 01/53312 A1 | 7/2001 |

OTHER PUBLICATIONS

Ota et al, (Nature Genetics, 36(1): 40-45, 2004.*
Bork (2000, Genome Research 10:398-400).*
Kimchi-Sarfaty et al., 2007, Science, pp. 525-528.*
Abkevich, V., et al., "Predisposition Locus for Major Depression at Chromosome 12q22-12q23.2", *Am. J. Hum. Genet.*, 73:1271-1281 (2003).
Altschul, S.F., et al., "Gapped BLAST and PSI-BLAST: a new generation of protein database search programs", *Nucleic Acids Res.*, 25(17):3389-3402 (1997).
Arias, B., et al., "Analysis of structural polymorphisms and C-1018G promoter variant of the 5-HT receptor gene as putative risk factors in major depression", *Molec. Psych.*, 7(9):930-932 (2002).
Arias, B., et al., "Evidence for a combined genetic effect of the $5-HT_{1A}$ receptor and serotonin transporter genes in the clinical outcome of major depressive patients treated with citalopram", *J. Psychopharmacol.*, 19(2):166-172 (2005).
Barnes, N. M. & Sharp T., "A review of central 5-HT receptors and their function", *Neuropharm.*, 38:1083-1152 (1999).
Bodnoff, S.R., et al., "A comparison of the effects of diazepam versus several typical and atypical anti-depressant drugs in an animal model of anxiety", *Psychopharm.*, 97:277-279 (1989).
Borsini, F. & Meli, A., "Is the forced swimming test a suitable model for revealing antidepressant activity?", *Psychopharm.*, 94:147-160 (1988).
Burns, D.J., "Receptor Reporter Systems", *Curr. Protocols in Pharm.*, Units 6.2.1-6.2.11; 6.4.1-6.4.11 (1998); 9.4.9-9.4.10; 9.4.12-9.4.13 (2003).
Carola, V., et al., "Evaluation of the elevated plus-maze and open-field tests for the assessment of anxiety-related behaviour in inbred mice", *Beh. Brain Res.*, 134:49-57 (2002).

(Continued)

*Primary Examiner* — Marcia S Noble
*Assistant Examiner* — Magdalene Sgagias
(74) *Attorney, Agent, or Firm* — Lisa V. Mueller; Michael Best & Friedrich LLP

(57) ABSTRACT

The present invention relates to DEP2, as well as other proteins, and their uses in connection with the treatment of major depression or related disorders.

1 Claim, 107 Drawing Sheets

(56) References Cited

OTHER PUBLICATIONS

Crawley, J.N., "Neuropharmacologic Specificity of a Simple Animal Model for the Behavioral Actions of Benzodiazepines", *Pharm. Biochem. & Behav.*, 15:695-699 (1981).

Crawley, J.N., "Behavioral phenotyping of transgenic and knockout mice: experimental design and evaluation of general health, sensory functions, motor abilities, and specific behavioral tests", *Brain Res.*, 835:18-26 (1999).

DeAlmeida, E.R.P., et al., "Transgenic expression of two marker genes under the control of an *Arabidopsis rbcS* promoter: Sequences encoding the Rubisco transit peptide increase expression levels", *Mol. Gen. Genet.*, 218:78-86 (1989).

DeFeyter, R. & Gaudron, J., "Expressing Ribozymes in Plants", *Meth. In Molec. Biol.*, 74(C43):403-415, 2008.

Doudna, J.A. & Cech, T.R., "The chemical repertoire of natural ribozymes", *Nature*, 418:222-228 (2002).

Ducottet, C., et al., "Effects of the selective nonpeptide corticotropin-releasing factor receptor 1 antagonist antalarmin in the chronic mild stress model of depression in mice", *Prog. In Neuro-Psychopharm. & Biol. Psychiatry*, 27:625-631 (2003).

Felix, R. & Fleisch, H., "Properties of Inorganic Pyrophosphatase of Pig Scapula Cartilage", *J. Biochem.*, 147:111-118 (1975).

First, M.B., et al., "User's Guide for the Structured Clinical Interview for DSM-IV Axis I Disorders", *Amer. Psychiatric Press*, Table of Contents (1997).

US 5,804,398, 09/08/1993, Fesik, et al. (withdrawn).

Gelmini, S., et al., "Quantitative polymerase chain reaction-based homogeneous assay with fluorogenic probes to measure c-*erb*B-3 oncogene amplification", *Clin. Chem.*, 43(5):752-758 (1997).

Gold, L.H., "Hierarchical strategy for phenotypic analysis in mice", *Psychopharm.*, 147:2-4 (1999).

Hachimori, A., et al., "Purification and Properties of Inoganic Pyrophosphatase from Porcine Brain", *J. Biochem.*, 93:257-264 (1983).

Hamilton, M., "A Rating Scale for Depression", *J Neurol. Neurosurg. Psychiat.*, 23:56-62 (1960).

Hegde, P., et al., "A Concise Guide to cDNA Microarray Analysis", *Biotechniques*, 29(3):548-562 (2000).

Hélène, C., "The anti-gene strategy: control of gene expression by triplex-forming-oligonucleotides", *Anti-Cancer Drug Des.*, 6:569-584 (1991).

Higgins, D.G. & Sharp, P.M., "Fast and sensitive multiple sequence alignments on a microcomputer", *CABIOS Comm.*, 5(2):151-153 (1989).

Hiraishi, H., et al., "Purification and Characterization of Hepatic Inorganic Pyrophosphatase Hydrolyzing Imidodiphosphate", *Arch. Of Biochem. & Biophysics*, 341(1), 153-159 (1997).

Hogan, B., et al., "Manipulating the Mouse Embryo—A Laboratory Manual", $2^{nd}$ Ed.:Table of Contents, Cold Spring Harbor Lab. Press (1994).

Holden, C., "Global Survey Examines Impact of Depression", *Science*, 288(5463):39-40 (2000).

Holland, P.M., et al., "Detection of specific polymerase chain reaction product by utilizing the 5'→ 3' exonuclease activity of *Thermus aquaticus* DNA polymerase", *Proc. Natl. Acad. Sci. USA*, 88:7276-7280 (1991).

Huang, Y.-y., "Human 5-HT1A receptor C(-1019)G polymorphism and psychopathology", *Intn'l J. of Neurophychopharm.*, 7:441-451 (2004).

Jaenisch, R., "Germ Line integration and Mendelian transmission of the exogenous Moloney leukemia virus", *Proc. Natl. Acad. Sci. USA*, 73(4):1260-1264 (1976).

Jones, J.D.G., et al., "High level expression of introduced chimaeric genes in regenerated transformed plants", *The EMBO J.*, 4(10):2411-2418 (1985).

Kopp, C., et al., "The effects of melatonin on the behavioural disturbances induced by chronic mild stress in $C_3H$/He mice", *Behav. Pharm.*, 10:73-83 (1999).

Kroenke, K., et al., "Similar Effectiveness of Paroxetine Fluoxetine, and Sertraline in Primary Care", *JAMA*, 286(23):2947-2955 (2001).

Lemonde, S., et al., "Impaired Repression at a 5-Hydroxytryptamine 1A Receptor Gene Polymorphism Associated with Major Depression and Suicide", *J. of Neurosci.*, 23(25):8788-8799 (2003).

Lemonde, S., et al., "Association of the C(-1019)G 5-HT1A functional promoter polymorphism with antidepressant response", *Intn'l . J. of Neuropsychopharm.*, 7:501-506 (2004).

Lister, R.G., "The use of a plus-maze to measure anxiety in the mouse", *Psychopharm.*, 92:180-185 (1987).

Lois, C., et al., "Germline Transmission and Tissue-Specific Expression of Transgenes Delivered by Lentiviral Vectors", *Science*, 295:868-872 (2002).

Maher, L.J., et al., "Oligonucleoticde-Directed DNA triple-Helix Formation: An Approach to Artificial Repressors?", *Antisense Res. & Dev.*, 1:277-281 (1991).

Mann, J.J., "The Medical Management of Depression", *New Engl. J. of Medicine*, 353(17):1819-1834 (2005).

Mann, J.J., et al., "ACNP Task Force Report on SSRIs and Suicidal Behavior in Youth", *Neuropsychopharm.*, 31:473-492 (2006).

Montgomery, S.A. & Asberg, M., "A New Depression Scale Designed to be Sensitive to Change",*Brit. J. Psychiat.*, 134:382-389 (1979).

Mueller, T.I., et al., "Recurrence After Recovery From Major Depressive Disorder During 15 Years of Observational Follow-up", *The Amer. J. of Psychiat.*, 156(7):1000-1006 (1999).

Mullis, K., et al., "Specific Enzymatic Amplification of DNA in Vitro: The Polymerase Chain Reaction", *Cold Spring Harbor Symp. Quant. Biol.*, L1:263-273 (1986).

Needleman, S.B. & Wunsch, C.D., "A General Method Applicable to the Search for Similarities in the Amino Acid Sequence of Two Proteins", *J. Mol. Biol.*, 49:443-453 (1970).

Pearson, W.R. & Lipman, D.J., "Improved tools for biological sequence comparison", *Proc. Natl. Acad. Sci, USA*, 85:2444-2448 (1988).

Perriman, R., et al., "Effective ribozyme delivery in plant cells", *Proc. Natl. Acad. Sci. USA*, 92:6175-6179 (1995).

Porsolt, R.D., et al., "Behavioural Despair in Mice: A Primary Screening Test for Antidepressants", *Arch. Int. Pharmacodyn*, 229:327-336 (1977).

Rothe, C., et al., "Associatoin of a functional—1019C<G 5-HT1A receptor gene polymorphism with panic disorder with agoraphobia", *Intn'l J. of Neuropsychopharm.*, 7:189-192 (2004).

Sambrook, J., et al., "Molecular Cloning; A Laboratory Manual", *Cold Spring Harbor Laboratory Press*, $2^{nd}$ Ed.:Table of Contents (1989).

Seal, U.S. & Binkley, F., "An Inorganic Pyrophosphatase of Swing Brain",*J of Biol. Chem.*, 228:193-199 (1957).

Seligman, M.E.P. & Maier, S.F., "Failure to Escape Traumatic Shock", *J. of Exp. Psychology*, 74(1):1-9 (1967).

Serretti, Al., et al., "The C(-10919)G polymorphism of the 5-HT1A gene promoter and antidepressant response in mood disorders: preliminary findings", *Intn'l of Neuropsychopharm.*, 7:453-460 (2004).

Shuker, S.B., et al., "Discovering High-Affinity Ligands for Proteins: SAR by NMR", *Science*, 274:1531-1534 (1996).

Smirnova, I.N. & Baykov, A.A., "Reversible Inactivation of Rat Liver Inorganic Pyrophosphatase by Substrate and Its Analogs", *Arch. of Biochem. & Biophysics*, 287(1):135-140 (1991).

Smith, T.F., "Comparison of Biosequences", *Adv. In Appl. Math.*, 2:482-489 (1981).

Stahl, S.M., "Placebo-Controlled Comparison of the Selective Serotonin Reuptake Inhibitors Citalopram and Sertraline", *Biol. Psychiatry*, 48:894-901 (2000).

Steru, L., et al., "The tail suspension test: A new method for screening antidepressants in mice", *Psychopharm.*, 85:367-370 (1985).

Strobel, A., et al., "Allelic variation in 5-$HT_{1A}$ receptor expression is associated with anxiety- and depression-related personality traits", *J. Neural. Transm.*, 110:1445-1453 (2003).

Tateiwa, H., et al., "Molecular cloning and characterization of human PTB-like protein: a possible retinal autoantigen of cancer-associated retinopathy", *J. of Neuroimmunology*, 120:161-169 (2001).

Tyagi, S. & Kramer, F.R., "Molecular Beacons: Probes that Fluoresce upon Hybridization", *Nat. Biotechnol.*, 14:303-308 (1996).

Tyagi, S., et al., "Multicolor molecular beacons for allele discrimination", *Nat. Biotechnol.*, 16:49-53 (1998).

(56) References Cited

OTHER PUBLICATIONS

Wall, R.J., et al., "Making Transgenic Livestock: Genetic Engineering on a Large Scale", *J. of Cell. Biochem.*, 49:113-120(1992).

Wu, S. & Comings, D.E., "A common C-1018G polymorphism in the human 5-HT$_{1A}$ receptor gene", *Psychiatric Genetics*, 9:105-106 (1999).

Yokoi, F., et al., "Molecular Cloning of a cDNA for the Human Phospholysine Phosphohistidine Inorganic Pyrophosphate Phosphatase", *J. Biochem.*, 133:607-614 (2003).

Yoshida, C., et al., "Purification anf Properties of Inorganic Pyrophosphatase of Rat Liver and Hepatoma 3924A", *Cancer Res.*, 42:3526-3531 (1982).

EBI Accession No. BP307619, "*Homo sapiens* cDNA clone: NRB01993, Sugano cDNA library, expressed in brain, 5'-EST," EMBL Database, Published on Sep. 10, 2004.

Neff, et al., Molecular Psychiatry, vol. 14, No. 6, Jun. 2009, pp. 621-630, XP002556935, Abstract.

Database Accession No. BP307619, dated Feb. 11, 2011.
GenBank Accession No. H51378, dated Sep. 18, 1995.
GenBank Accesstion No. H51555, dated Sep. 18, 1995.
GenBank Accession No. R11923, dated Apr. 11, 1995.
GenBank Accession No. R15274, dated Apr. 13, 1995.
GenBank Accession No. Z44231, dated Jan. 25, 2011.
GenBank Accession No. AK127935, dated Jul. 3, 2008.
GenBank Accession No. AW867792, dated May 9, 2010.
GenBank Accession No. BG397886, dated Mar. 12, 2001.
GenBank Accession No. BI489679, dated Jan. 11, 2011.
GenBank Accession No. BI669229, dated Sep. 12, 2001.
GenBank Accession No. BI754006, dated Sep. 25, 2001.
GenBank Accession No. BI756098, dated Jan. 10, 2011.
GenBank Accession No. BX952014, dated Dec. 25, 2010.
Extended European Search Report for Application No. EP12173174, mailed on Nov. 29, 2012, 9 pages.
Supplementary European Search Report for Application No. EP07782635, mailed on Feb. 9, 2010, 2 pages.

\* cited by examiner

```
aagaactttaaaaatcactagtgtgggccggcacgtgctaacgcctgtaatcccagcactttgagatgctgaggcaggtgg
atcacgaggtcaggagatcgagaccatcctgatcaacacggagaaaaccccg
[SEQUENCE GAP]
gtagatttgctataacaggctgaaagctcagtcagtggtgtatgcttcctgcacactatgtgttcatgtgccacctgctagct
ctggcccaaagatgcaaatgagagtccattggatcaggttctgggaaagcttttgctttctgggtataaagggtcagactcagc
tgtcacatgccctttttctttttctttcccctccttcctgcctgaaatgcagtcatgatgcctcggtggagcaggaatcttgcta
gcgtgaggagcaggccacatgctgagagagtggtggagcagaaagcaggaggcagcctgatgtcctggagctgttgtccatcc
aggattcctccctcttggcttctttgatatatgaggaaaagtaaatctgatttggttgggcaactatgctgggtttctgttaca
tgtagcaaatgcaacctaacatagacaatgcctacactcattgcatcccaagaaaagctgaattttcagatcaagtttag
cctatcagtggccacactttagagacttgcttaaaacaacagattattatttcaggtgagggacctggatcctgtatttgttctttgtcactactgca
agaaattaccatatactagtggcttaaaacaacagattattatagttctggagtaagagtcctaaacttgaagtaccag
cagggctgcattcctttgtattcaaggccagtagcacgtatcttcacactctcttgcctgacctctgcttctgtcacacctcttc
tcatggcccctttgtattcaaggccagtagcacgtatcttcacactctcttgcctgacctctgcttctgtcacacctcttc
tctgactctgactctctctgcttccctctttccttatgaggactcatgtcattcagtcagtaatatattgaggttgtgggattgggag
tctccctacaggagcataggctctgcaagatctaagtctgtctactgtagtcgtagaagaacaccccttttctctctaggcctgaagcctaaagcccagcat
gtggacatctcaaggggcactatctgtctactgtagtcgtagaagaacaccccttttctctctaggcctgaagctaaagcccagcat
gaaaagaacaactatggtaggctcacacactttgtgccactaggtcttccattgttctctgccagtcttgatcctgaagg
tctccaagtccatttcaggtgcacacactttgtgccactaggtcttccattgttctctgccagtcttgatcctgaagg
gtgtcactcattgccacttgagaactttttgtgccaacactaaaactgcatttccagactccttttgcagcgtgggctaggttccaccaagc
caaggatcacacccctagaactttttgtgccaacactaaaactgcatttccagactccttttgcagcgtgggctaggttccaccaagc
tctccaaactgactcactcagccctgagaacactaaaactgcatttccagactccttttgcagcgtgggctaggttccaccaagc
cagacacagtgaaagtgatgggtggccacagtggagggccacagtggtatgtttctcgtggctgcatgctcctgctgtgtagg
ggctgcactaagtgatggggcagtggtcccaatggagtagtaaaattaagtgtttctcgtggctgcatgctcctgctgtgtagg
acttagacccgtcatctgtaagctcatcatgtaaacaaaacccctcacctcagctgagtggtgtctattgtctgcgactaaga
```

FIG. 1-1 accccttatataaggtatactactcccaccccattagtggaaatcccaaagggtaggaactgtattttatttcacttgtaaacag
ctccctagtaagcatgtcaacaaatatacacaattcattgaacccataacattcaacgaattcctcatccttctgtgaatc
aagagcctgaaaagaaatggtgaaataatatgatcctctctttgaaagctcaaagctatgttggaccagaagtaaagtgttct
cgtttctatttaataacttgaaagttccgagggccattggagaaactcctccctttaatatcaatgtgtatttattgcaaaaa
taatgtagcatcgagtggtatttttatagcttatccaaaacctctggtttaacgcattgtgatagtccgttttcttctcagcc
caggtcctatgcatcctcatctatgcagggctgttatctgcaacctccgcctcactgacacctccgcaacctagtgattttttgt
cggctggagtggcagtggtgtcaatctggctcactgacatccgcaacctagtgattttttgtattttttagtagagacagggttt
agctgggactacaggcatgcgccaccacacctagtgattttttgtattttttagtagagacagggtttcaccatgttgaccaggct
ggtctcgaactcctgatctcaagcgatcacccgcctcagcctcccaaagtgctggattacaggcataagccactacccgcc
tcaattttgtattgtacttttcttttctttgcctccaaagtgctgggattgcaggcgtgaaccaccgcccctgctacagtgcctcttgtct
acaagctgtccgcccgttctgcctccaaagtgctgggattgcaggcgtgaaccaccgcccctgctacagtgcctcttgtct
caatttgccttgtgcgggactacagttccgaggcgctcaggtctcaggtctcaccgccgttgcccgtctttgccctgcc
aaggacaccgtttcagggg*ctaagctcagcccgct*cctgcgcgccgcgcggcgccgcgagcgcgaggcgg[a]gctga
ggagcaggccgggcgccATGGCACCGTGGGGCAAGCGGCTGGCTGGCGTGCGCGGGTGCTGCTTGACATCTCGGGCGTGCTGTA
CGACAGCGGCGGCGGCGGCACGGCCATCGCCGGCTCGGTGGAGGCGGTGGCCCAGtgagtgggcccCAGCGCCGCTGGGGC
*cgccgagcctaagctcagcccgct*cctgcgcgccgcgcggcgccgcgagcgcgaggcgg[a]gctga
*ggttaggg*gctgcgcggtcagacagggcggcgcacctgtacgtgcgctgcgtgcgcagtctgaattgagatgt
gctaagctaaaatgcataccgattaacagacttagccggccgcgtgctcgcatctgtgattctagcacttgcagagcag
aggggagaggaggatcgcttgaggctaggggttgagcccaccttgggagctgaggcagaggagatcgcttgaggcaggagtcaagc
tagccgggtgtgtggtgcacgcctgtagccccactgactctagcctgactgcagacgagacggtctcataaacaaacccaaaaacaccag
tacagtgagctgtgataaaatgtaaaataaaacatgaaaatgggttatgttgtttgcttgttgaaatgatatactttttgtgtttgt
acttcgtgagtaaaatgtaaaataaaacatgaaaatgggttatgttgtttgcttgttgaaatgatatactttttgtgtttgt
ttgttctttttcagatggagtcttgctctgtcgcccaggctggagtcaatggcacgatctcggctcactgcaacctccgcctcc
gggtgcaagtgattctcccccttcaggctccgagtagctggattacaggcgcccgccatcatgccagttacttttttatttg

FIG.1-2

```
ttttgttgagacggagttttgctcttgttgcccaggctggagtgcaatggcgtgatcctcgctgactgcaacctccgcctcccag
gttcaagcgattctcctgcctcagcctgcccgagtagctgggattacaggcatgtgccaccacaccggctaatttttgtatttt
agtagagacggggtttcaccatgttggccaggctggtctcaactcctgacctcaggtgatccactgcctcggcctcccaaagtg
ctggattataggcgtgagccacatgcccagtgatatatttttaatatactgttttaggttaaaatattgaaattaagtatac
cttttttttaactttttgttaatgtgcttattagaaaacttaaattaccttgtgcctcattataattcttggactgcat
tggtttaggtgagaggaggaagaggaacatgtgccagcaagactgaccatgaggacacttttttttttttggagacagtttt
gctccttgttgcccaggctggagtgcagtggcgcgatctgggctcactgcaacctctgcctcccaggttcaagtgattcctgcct
cagcctcccaagtatctgggattacaggcaccgccacccgcccagctaatttttgtattttgtagacatgggtttcaccat
actggctggtctcgaactcctgacctcaactgatccactgcctcggcctttaaagtgctgggattacaggcgtgagcca
ccgcacctggctgacactttcttgtataattttttgagacaaggtctcattgttgccagggtggtcttgaactcctt
ggctcaggcagtcctcctgcctttgtctccaaagtgctaggattacaggcatgagccaccacaccctggctaattttttttctt
ttttttttttttttgagacaaggtcttactttgccaccccaggctggagtgcagtggttcaatctcactgcaacctctaccta
agggctcaagatcctcccacctcagctcccaagtagctgaactacaggcacgtgccaccatgcccagctaatttttttgtgt
tttttgtagagatgggtttttgccatgttgcccaggctgacctcttgaactcctgggctgaagtgatctgcctgcctcagcta
gttctgggattagaggtgtgagccactgcctggcatccaggttggcatcagcagccgcaggactaactgttggcaccactgag
taaggcctcctgttgcatccaggtcagcagctgccatgtgtgatgtcactggactcaataccctatctgtaggtggcaattaactgagt
ggagtcactagctgaggcaccctgctggtagccggttactggagctccctatctgtaggtggcaattaactgagt
ctcttgtccttcttagagaccccattctaccaatctgatgtctgggagctgctgagataataggaccaaacggtc
ccgcatagtgaagccggagggtgtttgggaggctggagctttcaggttgtgctcggagaacaggagactgttcaggagcacaagggcagcc
cagacctaggacactccgctgggtcctggttctgctccagttgtgctcgagttcaggttaagtgcattcctgaccttattctc
cattactccaaagctttagactagctcagtcacagatgagccaggagccattctgtgatggcactgttgagagctggagcgggctctgg
gcagtgttttgggtgaagtggcctcactctctctgggcgagcaggagcccagagctcagtctgaaactcaagactgggctcatgg
gagccctgccactcattgttgcgaagatacatttgacattatctaccagtgttccacttctgagattgcgcttgtctcat
gcgtgagaaatgacatgagtacaaggtcattcctgcagtacctttaaatagcaaaagactgaaacagctcagatacccatcag
tagggagtattagtgcctatgcttcaaagccaaatgagccaaagctgtttgaagaagacagctcagttgggca
cacgggtaaagcgcatcatcacaggtaggctaaggcgaggagctaagggcctaaggggtgtgaagacgggagggtactgagagtgtgagtgtgagtgtgattgatgacgaggggtgtttgtgccctgt
```

FIG. 1-3 gctagagaggggtcgggacagctctgaggagaaggcactgacagacccgggaggataagagggaactgtctgcaggaagaggcg
gaggaagcgcattccaggcagaaggaatggtagctgcaaagactcaggaagagagcacttggcgagttcgaggcgtggggtggg
ggagtgggtacaccagcaggcaggaactgagggcacggagagagttcccgactttatcctgagtggcaggaagtcagtgaagactct
agataggcatatcatgtggctgatttatatgttttaaagaaatacaaatgagacatacaagtcaaatgaaagcaag
ggagatttccttttgaaacctttgagagaaggccttttacatccaggccttgaaatctagaaagtcaaaacaacgaacaagcagccca
atagcaatatgagcaaaagtgcaaacagttcatggaagaggaagtgagagaggctccgccttactcaataagaggtgtgatc
tcggctcactgcagcctctgcctcctggttcaagccactcttgtgcctcagctcctgagcagctgggactacaggcatatgcca
ccgtgccagctaattttttgtattttttagtagagggcaggattttaccatgatgccagctggtccccgaacctgcttcaagt
cgtgcccagctaattttgcctcccaagtgctgggatcacagcgtgagccactgccaaaatgcaaattaaaactata
tcaagctgccctgtttcatcaatttgacaagatacattttgacattatctaccagtggttgccttgcgtttgtctatctcgtgt
agaccctgccacacattgcttgcagaagatacaaggtcattcctgacaagtacaaagactgaagcagctcagatatccatcagtagg
gagaaggacacaagtacaaggtcattcctgacaagtacaaagactgaagcagctcagatatccatcagtagg
ggagtttaggtctgtctgtttatacagcagaataacatgcagtgtaagaaggaatgagtaactgtctatagacatattactag
tggagacagcaagcacacagcaggacgcaggctgcttcagagtctgggaagagctggaggataagagaaaatgcaagaatgtatttctcctgct
gtgtttgcataaagacactggaaggacgcaggctgcttcagagtctgtataacttgtataccaacgtttttgtttttgaaacagagtgttg
ggttggagacagggtaggagaaagactcttcactgtaaaacttggcttactgtaacctctgcctctgggttcaagtgattatcctgcctca
ctctgtcaccagattgggggcagtggtgcaattggcaccacctgatctcgcccaaccctggactcctcaatttttgtattttttagtagagatgggggttttgccacat
gcctcccgagtagctgagattacaggcaccgacctgatctcgcccaaccctgggactctgggattacaggtgtgagccacc
tggccaggctggtttcgaactcctgacctcatgtgatttttaaactatgtgaatgtgtttttcattcaaaatcaaaattcaaatattaaatt
gcgccagctgcatatcatttaagatttttaaactatgtggcacagtggctcatacctgtaatcccagcacttgggaggctgaggtagaagga
gaatatataaaattcaaaatattaacgtctggcacagtggctcatacctgtaatcccagcacttgggaggctgaggtagaagga
ttgagaccagctgggcaacacagcgagacccccatctctacaaaatacaaaattagccgggcatggtggtgcacgcctgtag
tcccaactacttgggaggctgaggcaggagaactgcttgagcccaggagtttgaggcgtgagctgtgctatgacgcac
tccagcctgggtgacagatgagactctaaaaaaaaaaaaccattgttttttaaataaatatttcaaggagatctctctggctgca
gtgtggagaacaggctgcagagtaggcagaggtggggggcttggactggtagaaggcaatggagatgggggaggaagccatgaa
ttaaagaggtgttttgaagcaggaccatggagacctgaacctgagcctgcgcgacatacgggtattgtggggttcagggagggtcagggaggaacttgaataaagg

FIG.1-4

```
tggtttccggtgtctgactggaacagctggcagggtggagaggggcagggaggggtcatggggcggaaccatgatggctcatg
atgtatgtcaagttcctggcctggtgtttggcacacagtagaccacacagtgtaacattaaagaccacttcttttcttttct
ttttttttttttgagacaggatcttgatctgtctcccaggctgagtgcagtgacacaatcacggctcactgcagccttgacc
tcctcctaggctcaaaaaatcttttctaccaagttcccagatagctggactggagctgggacagtatacctccacatgcaggttttctttt
tgtgtgtgtgtgtttttgttgttgttgttgttgttcttgggtttcaaggattctcctgcctcagagtagctgggattacaggtgcctgccacca
gatccggctcagcctcgcctccgcctccctgggttcaaggattctcctgcctcagagtagctgggattacaggtgcctgccacca
tgcctggttaatcatttgtatttttagtagagacgggttttcaccatgttgacaggctgtctcaaactcctgacctcaagtgat
ccactgcctgggcctccaaagtgctggattacaggcatgagccatgcccagccccaagggacagtttgagcctggtct
gccaaccagaccctacttggaatccttcaggagagaagggtgttggaaatgtcacaggcttctctaacagcttattttgag
cagatgaccccacgtgatatagaactgtccaacaaacgtgcagattccaggttgtgacattggaaagggttctgttaacttctct
gggttctggggttggtgtctctgactgattgatctgccaggagggttttgtttgattttgctttgctctcctgcagattatctagct
ggggtgtctctggtagcagctatactgtatacatcaacagcaatgtataacatcccgaaatacaccagctgttatgtag
ctgggagagctaaaatctccctccaaaagcatatggattatttttggtgagggacatcacaccgtgatatgggaggtttt
gttattgtgctgtctgtgggcctgcagaaccgatgcctggtctctcaacccatggcttccatgccataggaccaagtccca
tgtcctgccttgtccacgaggaccttctcaactgacctttgtgcctcttccactgcctggccccagttacacagacttcttggtggg
ttttcactgaaggggccgctgagctgtcagcaccacaaacctgtttccgcccacacagcgtgccttcggctctcgcagacc
ttggcagggccccctcagccttctgttgcttttaagggcaaggccccctccactctggccagtgcctctggggccagatcatc
accctcagggccgggaagctccgtacacccctccctgcctgcatgctgtggggctcgtgggctgcagagtggctgcgaaggtgg
tgcaggaaacgccccctccaggaaagtgtgcctgttttggaattttccctgggatttccagagatgcaggacacctgttttcc
tcgcctggttgattgagccggaagccttcatggagcagccctactgccagtgaagtctgtttgaagtcctgcaggagctcaaaggaagttcctgg
agtgcctgcctttgagccgcgccagagagggaaagtgtgattggagtggggtggggggtcttaggttgcaggggaacacatgcctcgt
ggtgagaccaggccgccgccaccatggcctccctggcagcatgtcgttcgttctgagcctgcgaggggcgacacactgtcaccattcttcttc
ggcagctcccggcaccatggcctccctggcagcatgtcgttcgttctgagcctgcgaggggcgacacactgtcaccattcttcttc
ttggattttctgtgatgatggtctccgatttattgaggcctgtcgtgcgccaggcaggtgcttaacaccccaccttccttcacac
atccacacaacagtcaccccgcatgaggggcctgtcgtgcgccaggcaggtgcttaacaccccaccttccttcacacc
agccctgagtgtgggggcttcctcttttcaaagtgaggaccaaaaatcggagagattcaggaactggcagaagtagaaaatgt
```

FIG.1-5 tgccgagccctcattaaagatgcatgcacacacacattcgttcatttattccttttttttattttttttcattcattcattcctt
tactcatacactcaacaagcaaacattgagtgctctgctgctgtactaaagacaccatcctaggcctgggatgtgcagcagtgaac
agtggagccgatgctgcagtcgtgggagaccagcagcgacagcgtgacacgcagtgag
gtgggagccctggctgggacctggcctgcagatcccatggcgagggagctggattggaggatgctgagcgagccagcagg
caggcatctggctaagagagcatccagatgaaggaggaggaggcccaaacctctgaggccacactgtgctgctgctgcaggcagg
cccactgctgctctaggactttgtgggtgggcgtggtcacaggccggaggacatctgtaaccggccgtgtccccccaacaggccct
ttattgaagccctttcatgggcgattgggttcccgagggagcattcagaggcagggccagcacagcgaggggtgcagaggc
cggcctcgggccctatgctggaggcatctgcatgtgaaaggggtgggcattactgctcatcctgtcttggccacta
aagcacatctgctgggccagccagccgccccgatcgatcggctcggcttgtggagccaggccacagccccttcgtccagtagcacct
taaagcaattccccaccagaccgccgcccgatcgatcggctcggcttgtggagccaggccacagccccttcgtccagtagcacct
ctcaatccctgtgtctctggtgcttcggatctgataaaacgtaggtgcctcctagtaggtctgaacagcgaaggccagg
ccagggattctttgaagtccagctgctgtcctggcacccagtatccctcctcatgccccggctccctggtaccatccagcctag
ggacacagtcccttgggagtagcagcaatagtaacaacaacaacaacaaccccacacgcgtgtggcacctgccggagggtctgc<u>aggacatt</u>
<u>gtaggagaggg</u>cggctgggctggaacttcatctctattgctgttttgtttgcattgttttgtgtccattgtgttccattgttagtttgt
cgagaacgtgctgtcgtcactgtgctgtcccattttgctgtgcaggagtgaagcacttttgtcttcagagatgggagccggtgctcttt
cacccgggttctgtgatttcagctgtcgtcatttcaacatttaagttccataagaatagggtggcctcttatgtaaacattctcac
cagcctgaatacagagtgaaagtccaagttccatccctgaccaagtccccagggtgacttccccagggtgacacaatacatc
cttttcctcgtattcctcaaaagcacacagaggattttgagatgcagcctcgtttgttagtcacagttcacagttgcacca
atcactcttgaatgccaccgccaccattgcccaaggcatgtgttttggttagtcacagttactggaggctgagacccccttgca
ggtcccggccaggagtttttgaattctttgtagcctcagagcacttatccaaccaaatgaaatttgagtagaacttccaaaatta
tatatatatatatatatattttatatatttttatatatttttatatatatttatatattttatatatttatatattttatata
tatatttatatattttttatatatttttatatatttatatatacatatttttatatttttatatatttatatatttatatgt
atttataaattttttatatgtatattttatatttgtatatatatattttatatttgtatatatttatatttatgtatatat
atttgtatatatttgtatatatatttatattatatatataatatttatgaaacagtgtttgaatagtatagtatttaataggg

FIG.1-6 atggatcttaatatattgccaggctggtctcaaactcctgcctcaaggagtcctctgcctcagcctaccagtagctggat
tataggtgtgtgccaccgtgtctagctcagaatggaatatgttttctgttcaaatttataatgtttgttctgagtcaactgat
gagaatgatggaagtgtttttatgaataacatgttgggctggtgcagtgcctgcagcctgtaatccctgcactttgggaggcca
aagcgggcagatcacataaggtcaggagttgagaccagctggccacatagtgaaaccccgtctttactaatatacaaaaat
cagctgggtgtgtgttgtgcgcctgtaatcctagctactgggagctgaggcagaattgcttgaacccagagggcagaggc
tggggtgagccaagattgtgctactgcacccagcctggagacaacagcagaactctgtctcaaaaaaatgttgaggtctgcagc
agtgaaccacacacagtttatatgcttagaagtttatgtgagtgctggaagcgagcttattaggagggatgagtgaatgtttt
ctggtttatccagacttcagactgttagacagctatgaaagaatgacttcgctctgttgtgctgacattagttatatgatatg
agtgctgtatataccaagtgaaaagctgtagaataatgtgtataaacttacttttttttttttgagacgcagtctcgctct
gtcacccaggctgagtgcagtggcgcctgcacacggctgcaactcctgctaacttttgtattttagtagagacggagtttcactatgttgacc
ctgagtagctggactacaggcgcctgccacaccgtcccgccgcctcagtgatccgcccgcctcagcttcccaaagtgctggattacaggcgtgagcactgcgcc
aggctggttttgaacttcattttttgttaagagaagactgaggaaaatctgatgctgttcacctgcctgaaagctttcccgtgctgctgctggcaggagtaaggtc
aaacttgaactgtatgaaagagactgaggaaaatctgatgctgttcacctgcctgaaagctttcccgtgctgctgctggcaggagtaaggtc
tgcttctcagtttctgatctcagccttggtgggcgggggtcacctgttggaagccctggcaattacaagggagtggtgcacaagttacaaagctcatg
tattggtttacctgcccctacccagtgcccacaaggcccaacaggcacgttgctgtcagcttgctgtcagcttctgcagggcaggcaggagcaggcaccacctgccactgtggtg
aatggagtcctgcccttggagggggactgaggcctctagtgtgagagcgtggttccaatccagcctctgcccatagtgccatgtggc
tcctgtcacagaaagtgccaggtcagttccgtgtcagctgcccattagctgcagctcaaggccccagttcctatgtaattcctgtaccag
ctcaaggaagtccctagcgttccgtcacccattagctgcagctcaaggccccagttttcctatgtaattcctgtaccag
gctgcaagaattaagtgaaatattttctcttaaccatgttgggtgggcgaggcgactcatgctgtaatcccagcactttgg
gaggccgaggcaagtggatcacctgaggtcaggagttcaagaccagcctggccaacatgtgaaaccccgtcctactaaaaatata
aaaaattagctgggtgcagtggtttgcacctgtaatccctagctctaataccagctggcaataccagcgagactcggtctcaaaaagcaaaacaaacaaa
ttgcagtgagctgagattgcaccactgcactcctgcctgggcaatgccagcgagactcggtctcaaaaagcaaaacaaacaaa
gccaacgttttcctttttttgtttttttcctttttcacttttaaactatcaggagataaaagccaacgttttactt

FIG.1-7

```
attccatatctcgaggagctaaaggagcatttttgttgttgaaggtcaaataattttgaagagtgggttgcttttgccctttttttttt
tttttttttttttttgagacagggtctcacttttgtccactttgtcacctaggctggagtgcagtggcacatcttggctcactgcagcctgacc
tcctgggctcaagcgatcctttcacctcagccccaaagtagctgagactacaagtgcacaccaggcacaccactggccaattttgta
tttagtacagacaaggttttgccacgttgccacggttgccaggctggtcttgaactcagagctcttgtagttgttgaactgctaaccaaa
aagtgtttggattacaagtatgaaccaccgtgccggccatatgaagtcttgtagttgttgaactcggtgtacatgctaaacaaa
gcacacagttctgctcaaggagctgtatttccacatctgtttgtattttcatgaagcaacataaaaggattctcatcccagttc
tgtccctagacaagtcactgaacccctcaaacaccaggtccatctccaaacagcaggtccatctctaaaccacaggtccatc
tccaaaccacaggtccatctgtaaatgaaacatgaaccacctctcagactgtcaagaggattcgatgtgaacatgccgttggg
gctcggtggaggaggagccagtcaccgggcgtgctgtagccactctgggctctgctgtgaacactcaccctgcagttcacctgtgtgtaaac
tttcccctctttctaaaggtgccctggcgatacactctggctctcctgctgcctctccccaggcacctggcttcctctc
agaatgtacctgcccaacagtgggttgtcagagacgtggttgtcattgtcaccacacagcaattactgccatttatttagtat
ttgaaatgccaggtgcttctcatgtcttttttttgaaatgagtctcgctctgtcgccaggctgagtgcagtggtgcat
ctcagcgactgcaacctctgccaccagttctagtgattctcctgcctcagcctcctgaatagctgggattacaggtgtgacc
accaccccagctaacttttgtattttaaatagagatgggttttcactgttgttgccatgttggccaggctggtctcaaactc
ctgacctcaagtgaccaccgcttggcctcccaaagtgctggggattacaggcatgagccgtggtcagggattcgagaccagc
ctggccaacatgtgaaaccccatctctactaaaaatacaaaaaattagctgggcatagtggcgggtgcctgtaatcccagctact
tgggaggctgaggcaggagatcacttgaacctgggaggcagaggttgcagtgagccaagatcatgccactgcactccagcctggg
tgactgagtgagactccgtctcaaaaataaaatccaaaaataaaatgatcttcatgacacccagtcatacaggagggaggtgtgtct
gttggtgcctcatttacaggtgaggaaactgaggttgcagagggttaggtgacaagccacgtcatacaggagggaggtgtgtct
gcttcccgagctgagctcctcaccttacagggctgagagggcctgccttgtccctgcccgcagccaccatgccctcagggacgtcgggctg
ctgctgaggctcctagctgaggagtggaagaaggagccaggatcccacactcggctgtgtgttccaaagtctctgctgccgattccatgtac
cctctgggcttagtatcccctctgtgaaatgagacactcggctgtgtgttctccaaagtctctgctgccgattccatgtac
ttcattctaaattgcgtttatgatcctggacatcgatgctgtgggatcaacatgtccctgtgattggtctcgtggcacag
gcacttcagagaacactctagatggagttctgccgacttgcctccgccagctcattgcctccgcctaaggtgactgccagacaggaggccagc
gccctagctgggggccgggcccagctcgatttcaattttgactctgatgactcaaggtctgtgcaggtgctcaa
taggtcccagctcctgctgcttctgtctttctttctttctttcttcattcaacttggactctgatgactcaaggtctgtgcaggtgctcaa
```

FIG. 1-8 cagcgtctcagtggacctgttgcctgccggtcagctggccgtgaaggaggagcaagtcaggaggctcagctggagccagtgtgaggccg
tgccctgccaggggccgtggcatctctgctgtgccagcttcttgctggttccaagactccacagcctggtgcgcgccaagtggtgttcatggtgc
tgggcaccaccatcactgtttatgctcggttctgttgctgctccttacctgcaggtggtccccagccaagctggtgtgtctcatggtgc
cccacgccaggggacagatgcgatctgttgctgctccttacctgcaggtggtccccagccaagctggtgtgtctcatggtgc
aggcacgggtgggctcatgcgcacatcagtgtgggcgtcccggacatatgtgaataactgtatttttctattgaaaaacaa
ctctgctctgcttacgggctcctgcttgctccttgttttggaaaattggattttggaggaaatcagcacctttgggtttcaa
ttctccaaacatgcgtgttcaatctccattgctttccaaaagggagcgactgaagatcgaaaattagacagtggctagcactgc
ccagagccccgttattaaaacatttcaaggccggtgccggtcgttaccctgtaatccagcactttgggagctgagactg
gcggatcacgaggtcaggagttcaagaccagctagcaacatagcgaaaaccgtctactaaaaatacaaaaattagctgtgcatg
gtggcacgcgcctagtccaactactcgggaggttgaggcaggagaatcgcttgaacctgggaggcagaggttgtggtaagttg
agattgtgccactgcactccagcctgggcaacgagtgagactctgtctcaaaacaaaaacatttcatgccagtggcattgctgag
ggcctgggctggtgctgcacctgtatttctctgcactggttcccatttcagtagtaataggaccctcagcaccagtgatgtctg
aaactgaggcattgagcttgtatttctctgcactggttcccatttcagtagtaataggaccctcagcaccagtgatgtctg
caatgtggcccagaggcaggagcaggctggagttaggagctgaagctgatgtggggagcgctgcccccaaccactccc
tgggaaccaacctccacccttgcctgcctgctcctccacaccctttctctgcgtgaatttctcattaccaagtgggccg
tcagatctgaacttggtagttagtgctcttcccagtaaagcacctactgtgctgggtactgtgctgtgccggtagattt
tgggcaggattctagagagcatctgcaaagttgctgcaggaaaggccagtcactgcctgccagttcgccccctgtgaatgcac
gagttgacattttctcaaattccagcctccactttgtgggcaggcagccttctgacctatgagctgcaaactgagccttttgatg
acactgcccccgagattccctgcagccatcctacaaggagatgctgggtgactcctctgttgtaaccaaggctctggttgctgaggatggggct
gctcactgccctcatcctacacaggagatgctgggtgactcctctgttgttgggcaccaggcatgcagaggtgcagcagacaa
ggtcctgccgcagggtgccccagttgccccagttgctgatcttggctccactgtggtttgggcaccaggcatgcagaggtgcagcagacaa
acctgccctcccagccgggcttgcagagagcaggaggaggaggtgtgatgtcaggagcagagcagcaccaagggtgt
gtgggcagctcggagatgggatctggctgcatggctgtgggcctgtggggcctcaggaagaggtgtatgaaccctgctttgta
ggatgatcaggtcaggccccaggggagcatgaaagacaaagactcaggtgtcatatgaggcctcggcacacgaaggtgaccag
taccgggggctcagaggtcagggccccagctggggggcccatctgcctttcctgaggccctgctgcctgcccagtctccc
ctccgagggatccaattcccctccagccctccacgcccagaccctcagaacctcagagggctagctattgagctgtccaaggtcactca

FIG.1-9 ggatgtccaataattgtcctaacagtttacctgctgtgtggaacagtatgagagggttttcattatttgcgggtgagcgctcctggc
agatgccaacagccagcagatgtggagagtccgagtgattgtaagggccgttcatctgatgcacgttaattgcccgggcgat
gttgtcactcagaggctcgtcctgcctgctgagatgaggtaaagtcagttcaaagatccagtttggccagcgcgtggctca
ggccgggtgccatgcgtcacgctggctcacgcctgtaattccagcactttgggaggccgaggcaggtggatcactgagattgggagttcaagacc
agcctgggcaacatgtgagacccgtctctactaaaaatatagaaaattagccgggcatggtggtgggcatgcctgtaatcccagcta
ctcgggagactgaggcaggagaattgcttgaaccaggaggcgagggttgcagtgagccgagattgcgccattgcactccagcctg
gctgacagagtgagagactctgtctcaaaaaaaaaaaaaagatccagtttggctacaggaagtgggagcaaatcccactccat
gggactcctgggaggaggcagcgtgctgagtgggtgggggaacagccatccgcacctgactaggctttcctgatatttgcttcctgtctagtcggctgggc
cctttcccaagttcttggtgtggggtggggtggtggagccgcacctgactaggctttcctgatatttgcttcctgtctagtcggctgggc
gctctctgcaagcctgtgacatctgatgacagttcaacagacagagacgttatttttcacagttctgaaggctgaaggctgatatcagg
caaggcttagtctctgtgacatctgatgacagttcaacagacagagacgttatttttcacagttctgaaggctgaaggctgatatcagg
tgccataacaagtgccattgactgggacttcaacagcccctttctggctgaggcccttttctggagctgtgaagcagcagtgccggctgcatgtgctgtgtcccaccttatgcttcatt
ggtcggcatgccagtttctggtgaggcccttttctggagctgtgaagcagcagtgccggctgcatgtgctgtgtcccaccttatgcttcatt
gtgcattcatgagggtgctctctggtgtctcctggtgtctcctagacactgatcctgtcatgtgggactcccatctggctcacaggccttgc
tcacctgaattactactccacaaaggcctgtctcctggtgtctcctagacactgatcctgtcatgtgggactcccatctggctcacaggccttgc
tgcttacaagctgtgtgacttacccagtgggtacgacttactgagggccacctgacagcaggcaccgacctgggccttggggatgtccattagg
cctcataggctcgtttacccagtgggtacgacttactgagggccacctgacagcaggcaccgacctgggccttggggatgtccattagg
gacagcaaatacctggggcgaggacaaaatcagatcatgatcctgagtgacaaatcagcactgttcttatttcagtaattaaaataaggaagagcaacct
ataatgttgtattaatattttactctttaaacaatagtgctacttctttatttcagtaattaaaataaggaagagcaacct
gggctggtccctggtggtcagaatgggtctctgtgacggctcaaagggggtgtgtccgggcgcagaaggacagaaccaat
gggagcggacttacccagtcgtcacatcgattttcaggatagattttcgtctctaaactagcactttgatattataagagca
tataggctgaatgaacttatattgctattcagaggaggccagtggcttaagagtccaaagtgagttctgtgacttactcatgtt
tcatccacatctgaagttgtgtttggaataacagatgtgaggcactgtcatctcactgtcacatcgattgctcactgttctgagaa
gtcacatcattcattagcaatatagtcccaggggaccccctgcactcttcactcactgctctattcattaacttggtgcaa
atcacacgttccagtgccaatcaatgagatctatccataatgtacaaggtgacgctattagttacaatatattaactgcctaat
ttaaaataaactatctttatgaagggcaattaaccactaagtgtaattgataattcataaacctctgattaggaaagacaaata

FIG.1-10 ataagaaaggaatgaatcacccatcctattgaagaagacgttgccagcctctgtctgcattcactatgtggtcagcagatctaca
gatttcttcctaaattgcacctgtcagctcagggctgggggtctggaggctcattcagtgcagaaacatgtgttttcaccactg
aagcctgtctgttttctgttggggttataaggaggtgcaggctgcagcaccctcaggaagtagtgggtgaggtcatttagact
tctcagtcagtcagtcattcagcaaatgttaatggggattgtggagtgccagcctgtgggaagcctgggatgccgtgaga
cccgaatagattcatcctgaactcctgagctcgtaggcgtcagtgagaagacaattgcgtaaatcagatgattggagacactggt
tagtgttacaaacaaaaactgacagagacagggcgggaggcaatggcacactggatggtgggaggaaaggagacattggctgagtcct
gccaccttttgtagtagctgtcactacctcatggctgctgtatttgggccctctctcactgtgggaatcgtgctggcttatc
tgcccccttttttttttttttgcgacagagtctcactgtgaccaggctgagtgcagttgaccctgaggcagtggcttgatcttgctcac
tgtgacctccacctctgggttcaagagattcttctacctcagcctcccgagtagctaggactacaggtgccgccaccacctg
gctaattttttttgtattttagtacagacaggatttctccatgttgaccaggctgatctcaaactcctgccctcagtgatcca
cccacctcgacctccaaagtgctgggttacagaactgagccaccatgctctgcctctcgagttcttttctatccgagagggttgggccagtgcacactgc
agcctcattttctggctccaccttccacataccccaccctgccctgccttgtcctcctagttttctgccatctcctgtcctgtcagtctccagttggg
ctgtgcgcaagtgggtggcccttccaccactggctgtgtcttccactatgtgggagagctccaggagtgctgatttcctg
cctgaatcccagtcttttaagacccccacactggctcatctccaaagtcagctccaggctgcagcgaacagaaagccctgacattctgg
ttcctgactccactgtgtgtagatatcagctccatctccaaagtcagctgcagccggttcagtttgagttgagttttagttggtctcacttgct
gattcagtcctccaccataacatgataattacattcacactggggttgaatcgtgtattcattcattggccacatctgtaaacag
cagatggaagttgatttcaagccgtagttctagtaactgggttcagtttctataaattttaaattattcattaacactattgcttagttataaaaat
aacttgagcacatgcctcctctctatgtgtgttttctataaattttctataaattttgagatcagtgaatgtgtgtttcggacctgtctgag
acacaacttgaaagaataggtgaagagccaagatgtctgcatctttggagatcagtgaatgtgtgtttcggacctgtctgag
aacagtgccagatgcaattagcatgcttgcttgattaatttctactagggttcttaaaagtgcctcccgccttgggcttgcagcttga
tgtcttttccacgagtccacactgcagctccatgcagatgtcaaatatgaccgctgccttgtgggccggttgtccaggaagg
atcttgatcttggcgaggagccaggtcctgcctgctcaccctcccccagtctgagtgaccaccccagctgcctctgtaggt
tcctctagcacgctcgggtcccttccttgcgtgggcgcagttcctccctcctgccagcctgccagcctgccttctcacccctgccct
ctctctgcttcccagggaggctctccctgaccctcctaccccaccttgtctcctgtctgctcaccctgtttatattctgca
tagcgtctctcttctcagtcacaaattgccttccttgcagggttctcttgttcctattccaacctcctcctattccaactgg
atggtggcctgaagatcagggagaacttttccatgctcacgactacagctctgtgaccagcctacagcttgtgaccaggcacgtagtaggcgct

FIG.1-11 cagtgacagtttgcagaaggtggatgttacttcattggtgcgttctgagaacttgccagtgcagcctgattcgcgggtctc
ctatgaagtcaggaggaagaagctcggtgccgccggaatgttggtgtccctgatgacttrtgcaaaccttttctcattgacagtgatgagaag
aggtccacgtcctgtctcatccggaatgttggtgtccctgatgacttrtgcaaaccttttctcattgacagtgatgagaag
acaaacctgtctcgggccatctgccttttrtacttttrtgggaagtatrgatccagagttartaaggcgtrgacgtrtrgcagctcact
tgcaagtggaaatgccaaatgtgtrggaaagggacagagaaatagctrgtrgacattcagaggtrggccctagcrcaggctgagcagg
attgtrggagaggaggtattrgcatrgatctcaggggctrgggtragaaggtrggccaggcaggtgggccaggcacggtrgcrcacacctgt
aatcccagcactttrggacacctrgaggtrcagagttcgagaccagcctgctraacatagtgaaaccccatctgtactaaaataca
aaaattagccaggtatgatggcaggcgcctgtaatrcccagctgctctrggaggctrgaggcaggaggaatcgcttrgaatctrgggaggc
ggaggttgcagtrgagctrgagatcatgccactcagctrgacacagagcgagactccatctcaaaaataagaaataaa
aaaataaagaagtgcacagtrgagaggcggrgggacagagttgcattrcagggaagggaggcaatrgaaaaggggtrcag
gtrgggaacctcggggagctcagtrgtratrgaagtccagtrgagatrgaaaaagagttrgtcgggcgtrggtratrgggtrcctctrgag
aaggatctgcttcagctrgggagctrgagccagctgaacacatcctrgatcagccaggacccctcagggctcgcagtrgcctagtc
tgctctgggcttgctggatgcccttcgagaatcaccgcgcaacctcctcagaggccaacactccacgtgctgcttccccggc
ctgtrgtctccccrgctgccgcagACTGAAGGCGTTCCGGCTGAAGGTGAGGTTCTGCACCAACGAGTGCAGAAGTCCGGGCAGAGCT
GGTGGGGCAGCTTCAGAGGCTTGGGATTTGACATCTCTGAGCAGGAGGTGACCGCCCGGCACCAGCTGCCTGCCAGATCCTGAAGG
AGCGAGGCCTGCGACCATACCTGCTTCATCCATGACGgtaggcctgtcggacaccaggacctcacggggtgaaagctccccttcc
caggtrgggggctgtrgcagagagctctrttrcactgggccaaaccactgactgagctaggccaccaacactcatggttrggggtaa
aacctcatgggacttcctgctrggggagcaggttraggacccagctctgtccattccttrgcctcacaccagagggtcctt
agagcaggttctggatggctcctrgggaggaaaatcctaggctctcttrtcctgatctaggatrgaccaagcggccagggaattgtca
agtgcgagttctagctcctgttgagaagagacagagagagagagagagaccttcaactatgtgaaaacagccctgctcttt
tataatgaagagctacattrgaggtccatagctrctrgaccatagcctrctrgacctrcaactatgtgaaaacagccctgctcttt
ggaacagttrgcaaatrgcgtaggaacaaggttrgcatcctgatttrtagtctgaagaacagcagccccttrtgaccctcag
tgggagttttrctttrggaatgaagcagaagaacaatattrtactrggtrgcctcctgaatatttrtaaaagaagacattrgcaattcc
agacacttrctcattrgtccactrggtccctcaggcaaggtrgggctccaagaagtrgggtrgctcctggaaagcctagtrgtrgactrcatag
catrgtttrttrccttrccaggcaaggtrgggctccaagaagtrgggtrgctcctggaaagcctagtrgtrgactrcatag
cctggtrgccagttraaggtrgacaggcctrggcctrtraaaaatcatgtttrctcaaaattccttctctrgtaattrctagatccctgctag

FIG.1-12

```
tgcctttagaacatggtctttcaaagaagaagagattaagaaaatatctgcccacccctccagaaagggttgctggacccggga
gtggagctggaagaagccagcaggagagaggaagtgggcatccgcttggagggtggccttggccagtgaataacagcagacggc
aaagctgggaggctgaaggaggaggaatgccctcctcagctgtaatccgtgttttcataactagacccttgttttc
agacttggaatttttttttcagtcattggtggattttctgtctaacatttatgaaaattcaagcatccaacaaagttcaat
aatttttacttggaatagtttggttttttttttggagacagagtcttgctcgtgtcaccagctgagtacaacagtggtgtgat
cttggcttcctgtgactccgctttccgttcaagcagttcttctgcctcagccaagtagctggggttacaggtgtgcc
accacgcccgcctaattttttgtattttttagtagagatggggtttcaccatgttggccaggctgtcttaaactcctgacctcaggt
gatccaccacctggcctcccaaagtgctggattacaggcgtgagccaccgctccgtcttacttggcatagtttatacct
tcacctagattgtcaatgacattttttgatatttttcttcacttatatcatccatcctcgtctgtctatcatgttattattt
agatgcatttccgagtaaaatgcagacacggtatactccctatacactttcagcatcattggagtttgtatttgttttacggt
ttttcctgtttgatgtaaaatttacatacaatgaaatgtacaacgtcaagtgtacttttgctgagttttgacatatgcatgcacc
catggaaccaaccctgaagagctagaccatcaccactgtttggattttttccgttataaataagttttcctattctagaattttatgtaaataga
acccctgtcccctagaggcaaccactgtgctgggcctccagtgctacccccaggctgataatgattcattagcaggactcacagaactagaaaa
atcatacagtataattgtgctgggaccttattactgtgaaagaataaagattaaattcagcgaagagagagacacatggggcaaagtcta
ggtattacactcccagttagacttccagttgtccttcgaaatggagtcctactggcacacttgattctcccagcgatgatgtgtgac
ggagaagacaggcatgaactttcagttgtcccttcgaaatggagtcctactggcacacttgattctcccagcgatgatgtgtgac
aacacatgggaagcattggccaccaggaagctcactggagcctcagtgtccaggttttttgtgtagacattagcacctgtgtgac
tgactttagcgactcagtctccagcccacagagtccaaactgatacagctgggccagggccagggatacagaaacaggtgttc
actgtaagccaagctgttagcgtaaatgatctggtcagactgagagagcagggcccgaggcctgagcatacaaaaccccttatca
ggtagaacattgcagtgcagagagttatctcccaggagccagtcctgaagacaggccttttttggaatgtacagggtttgagca
acctagtcctgctgagttaacccttcccgtcacagtgttcttcttttactccccaacgtaatgttttttgagactca
tccatattattgcatgtatccagcagtgttgttcattttattggcagaatagtattccattgagtgaacagaccacagtttatccat
tcacatgttgttgataccttggattgtgaccagttcagtctcattatgagcaaatctgctatgaacattcttacacagttcttttgg
gtaaatacctagcagcagcgaaattactggtcataggtacatgtatgttcaccttgtaaaattctgccagaccttttttttcagagg
gattgcaatatattttacacgtcctccttcatctgctgcagctgtcagtatcctcaccagacttggtgttatcagtcttttttaattctc
accattctggtgggtatgaaatcgtatctcattgtgatttcagttctgtattttttttttttttgagacagagtct
```

```
cccaaagtgctgggattacaggcatgagccaccgccccccaacctcttgtaatttttttttttttttctgcttataagttt
attcaatgcaaaataacctcaccagtttactgaggtggctgaccatgtccacgaccaaatacgcctgtaaactgaaattcggtt
gctgaccattcccagctccagcttctctctgctggtggtgtcttcgccatctgtgggtgtctctttctgtctctatggctgt
ctgtctgtgggtgtctctctgtctgtggtgtctttggtgatcctctctgtgggtgtctctgtctgtggtgtctctctgtgag
tgggtgtccatctctgtctttggtgtctctttggagtgctctcctgtctgtggtatctccctgtctgtgggtgtctgttggcttccc
tgtccctgtgagtgtctctgtgtgtgggtgtctctctgtctcagacctttaggccgcagctcccagacctccagacctgcagtcc
cacttgtggtcttgcagtggtcgtcacgctcagacttcgcagagattcgatcccagtgggtgagtaccagtagaaatgtctccagc
gacacgctctccagggcagatggtggtaatcgagagactgctgcctggcctcatgactgaaggttggcacattctcatctgccagctccg
aaactccttcctgcaacctcagagagactgctgcctggctaccgtgactcctcctaaaaaggagttcataaatagcaatctggttcttcttag
ggtcttaggcaggtggacattctcttctggctaccgtgactcctcctaaaaaggagttcataaatagcaatctggttcttcttag
gcatcaacatctctgcagctgtaggtccagtccgggctgatgagcatcttgtgcattcgatgactctccagatacgttacagaac
gattgttcctggtttttcaccataccagggctgtgatgagcatcttgtgcattcgatgactctccagatacagttacagaac
gagtattttgaggttcttgaggcatgttgccaagttgttccagaaagctgcacagcttattctgcacagctagagattctaga
atcacagggttctgcacaacctagagttctgcacacagctagaggttctgcacagctagaattctagaatccacagggttctgcacagct
agaattctagaatcacagggttctgcacacagctagagttctgcacacagctagaggttctgcacagctagggttctgaatcacagg
ttctgcacagctagaattcagaatcacagggttctgcacacagctagagttctgcacacagctagagttctacacag
ggaatcacagggttctgcacacagctagaattctagaatcacagggttctgcacacagcttctaccagagttctgcacag
ctagaattctagaatcacagggttctgcacacagcttctaccagagttctgcacacagctagagttctgcacacagctggggtacgggg
aggcggtggcgggaggaagtgtttttccatctttcggtgtcttcttctggtgacagcgctcactgcctctgctgctgctacgggg
accagctgatgaaccgacaggaggaggactttttatctgccattggccactgccacacactttgtgtacccgttttgtgtaatt
ctgactacaacccttgtgggatctaggcagttcattgctgtttttgcaagtgggtttgttgaagccacaggagatgaaataagctgct
gtcccccagccattgagtgctgataggatcaggagtgccagttggtggctgacccagaccctgcgtgcgttaccctctaagcta
cattctagagcagacttttgccacacagccttaaatgtggctgggacagtggctcacgccggtaatccagcactttggga
ggacaaggtgggcagatcacctgaggcagggttcaagaccagcctgccaacatgtgaaaccctgtctctactaaaatacaa
aaattagccaggtgtggtgcgtgcctatagtcccagctactcgggaggctgacgcatgagcatgagaattgcttgaacctgggagcag
aggttgcagtaagtcaagactgccattgcactctagcctgggcgacagagcaagactccatctgaaaaacaacaaaaacctt
``` aaatgtattttgaggctgtgtttaaaaatgggatatattttacacaaatatccagatttctggattcttttgaagaatcagaaga
tctgacaatacggagcctcacattcctgcacacacagcagccat[g]ctggagccactgctgcctccattagtttgaatttactgcagac
cccactcctccctgtcctgtccctgtctctccagaccacagagttagttgtcattgatcgtgccatttgttgttttttcaaagtaga
gaagtacttcttcacgctgtgtctctcatcaaaatgacaagtgaaagatgtttcaagaaatgaaaagattttttagtgacaaa
aatttctagtatgttttctcatataaatgtgtccgagtccaaatctgcaggcagggctggcaggactagggactcaggaatgcgcagca
atatgtagagagattgtggaggctggcgagtccaaatctgcaggcagggctggcaggactagggactcaggaatgcgcagca
gagtcgtaaggctgtgtggtgtggatctgtgcctgggaaggtcagtcttttgttctttgtaagcctgcaactgttgatgtgg
tccacccacattgcgaaggaatgactactctcctccttagttcaccgttcaccgttcaccgttcaaaatgttaatctcatccaaaacaccttcacagaa
catccagaataatgtttgaccacatatctggcaccgtgccaagtggccaagtggccaagtggccaagtgtgacatattaattaacctttgtagtcccttta
aacttacaccattgcaattgcagtcgctgctatgaagcaagcacagaaccatatatctattaactatttaccggctgaccat
taggcctttgagtcaccaacacctcactagagaacaagcataatgaagaagctctgctgtaattcgttatgttaacacttttttc
tttaaagatgtctcatgctgagcttcgtgtgcagcagcttgtcgcagcagcttgtctagctttgggagctgagatgaggatggcttgagct
cagaggttcgagaccagctggcagcatagtaagattccgtctctccacaaaagaaagaaaaaagttgtctataattattaa
aaaccactattccagatcatgataataataagtcagaacaggtatattgttgaaaagaaaaaaccggaagcagtcgctt
cagctttgtaataccagccagcaaatgtcatagtagacaaggtttttttaaagtaggagattagtggctctctgctgatgggggtt
ctgggtgtttaaaaccagagaaggaaccggcggttttaggactagtccagcttccaggacagctccagcttcgactgcgcttcgactgcgcgagaccccgaga
gctgccatcaccatgcgctcctggctgtgggtcactgctgtgaggtccatcctgcactgcgggacacaggctgagc
ggtgcccaaggagcaggaggcacaggtggaggcggtgaggcgcgggacagactgctcctcctctgaaatggagtgattacatttggc
atctgtttggacccagagtggaattggctttgtaattttctttgtcatgccgctctcatgtgcagggaggctgtgctgaataatctgaaacggcagaagaa
_c_tatggaaggttaacggctctttcggaaaggtcaagtgtcattgcagggaggctgtgctgaataatctgaaacggcagaagaa
taaagcataaaatcgcatctgactcctcctccccggttcttccccctttcttttccagcatccacg[g]gttcctcttgtgctagaaca
ttcacgtcctaagtggggctgccgttggctggtttaaccagtaaccagtagagaaatacgtccatctctagtgtgtgag
attaccggcctttttttgttttttatattaaaaaaatttaagtgcttatattgctgtctgtcttaaaaatctggcactataaaatcaagccagattcagttttta
caagatgccttttttgtttttttctgaatgaataagaataaagaaaaattctggcactataaaatcaagcccagattcagtttttta
aaaataaacgttaagtttctcattttgattctgaagttctgtgttcccttgactctaaagattagcatgcaaagacaggt
tttgattgtgtatttttcagttgcacgttcagtttttttaaaatcccatccagactaaatttaaacataagaaaatccaggtttct

FIG.1-16

```
ttcgttttcgaagaggctgcaggaacttgaggccagaggaagtggcgccgcgtgggtccccttaggaggttttgccagatgatgg
gaggtgcttgctccgtccccaacctctagctcctcagcccaaggtagctgagggacagggtctgggccagaagcc
cccagaatcctcagctcagctccaaacagagctgtacctgtcgcaatgagtagtttgttgattcagtttctttgtgctgggtaa
gcatttcctgtgtgggtatattctttcctcctgcttacttccacacatcacttcattaggaggccctcctaccacct
cgatgccctcctctcctgcacagtgggcaggaggggacgaggtcatggcctttgaggcctgcagagggccttgcctgtggt
gggtggccacccctgttcctcagcagggtgctcagtggattccaaggtgctccctgaccccgaccctccccttcacttccttttag
ctcaggtctcagcttcatgcctctgctcctgcctcctgaaccagcctgtccccgccctgttcaagcagactgccctccctg
gtcctgccctttaaagtttgtctgtgggcttctttgctcccccaccagactgtgagtcctgtggagcaggcaggctgggagta
tccctgagtcctgcaaaggtcctggagcatctggatcgttaatgccaaggggaccaaggtaacctggccatttgcagcacca
gccagtgcaggcccagaccccgtgtctccctcactgtttctgagaactctgaccccactaaggaaaccatcagacaaagtag
ctgattgtccaactgggaaaaaagacagtacttttttaggccatgtaaatgcaaaatacatttgaagtctgcgtttaaga
catgaacttagagatttctaagcctgttttggggtcactctaaaaggaggcattttcagttccccctctgtgagcattcac
agcatcccagccagcctgtatccctgtgccgtgaccccagagacagagcctggaacagcctgtgggttcacgtgg
agagtcccagccacgtcatgacaggagatgcccacacttcaacacagactccaagctccaaagctgcctaacagagtggc
aggggaccagccccaggtttggctgaagcccagttcatctccagtggctgctcacgttgtaagttttagcgggaagcatcgag
gcagcagtggaggacgcacagggtgccaggagtggccgagctggaagggcacagccacagggctgtgttcatttttcttcccccagctcatcttat
gcagaaagggacaggcaggtgccaggaacacatttcagccccaaattgaacagggctgttcattttttcttccccagctcatcttat
cacacccagtggtcacagaacacatttcagccccaaattgaacagggctgttcattttttcttccccagctcatcttat
tgcttgtgctggtgaaagttattatataatattctcctgtcctcatctgggcagcttctgcatgaaggtaccgagtt
aataactttgcatgcgttatttgttcaagcttcacgcaatccgtgagtagtattgttgttgtcgttttgccattttaca
gattaggaaactgaggccacaggctaagcaaccaaagtcacaccgttagaaggcagtgagatctgaatgctcaagtcagcatg
cgctcttcttccctctcgtttctgcatacgtgcttttccacgtcttccacgtctcatatcgtaagggcatggcaggagaggaactg
atgtgatggtgatggcaaaacattttagtggttgttccaagaatcaagccccctttgtatttctttggctttcaatgaactgctcttc
agagcagcgcaggttaaaccacttctgcctcattgtagtcaattggcttagttcagccagacccaggtctgccccatgtgt
ctggactgtgagtgcctgaggctcagtgacgcgatcgtaggtgagcctggccgggctgcagccagccagccagccgcaccaagccagcctg
ggctcaaagagcagtgaggcattttgagagagaatgctccccctgcagagcctgtctccacctccatgagacgggaaggaaca
```

FIG. 1-17

```
gttgtctttctcataaaagcatctggcgccatgaaacctggcacctgcttgacctccggctaacggatgcggcagggtgctgtg
gaactaatggagttctcttcttcagccagcaattagggtttaattattagcaattagggttcgccacataccccgtggacctgct
gttccttcccaggacacaggtcacttgtcattctctgtgttagcaactgaaaccgtctgcctctggtccctgttaatcattgc
agcagggtcccacgagtctgacagcagggttgcgttctgtgcgactgtgcgtcatccctggagctgctggctgctgcctgcccc
actgggtgtggcctgcctgcgccgccgggcctctgtggtgctggtccctgcggtcattctcagcgtagcgcctggactgccctcagcc
gcgcttggctctgcgcagccagccagggagcagaccccggctgctcagctccgatacttagcatctcgcggtcagcatcctccccgtgctcagca
tccgtgctccgttctgctctctcctagGCGTTACTACAAGGAGACCTCTGGCCTGATGCTGGACGTTGGTCCCTACATGAAGGCG
CTTGAGgtaccagccctggttctgtcccaaactctcttcagacctcagggcacctgggacttttgggtctttgttgagaagaggc
tgtgcttaattaacgtacaaatggccttttgggctccacaaaggctgccttcctattctgggctccccctggccgggccctcgggc
cctcagcctcagctgtcctcctccccatctctccccattcctcccatcctccccatcctccccatcctccccatcctcctgccacact
tcccatctctcccatctcccagtgggcgcagcccctgccagcccctgccgctctctgacctgaccctggaatcgcagcacctcaagcttgacgg
ctctcggcttgtggctttctgtatcagtgctgacacggcatctgtgccaggccatctctgccatcctcacagctgcagccagctgtccctgggtcca
gtcctcactggctcctcttcctgactctcccctcagttcccctcagtcagcctcacatccgtccatcctcacagctgcagccagctgtccctgcc
ctcggccagtcccattagctgccccaggtcccagtgcagatggagcctgtgatgagctgcgagtggcagggaggagaggggaggatg
gtcaggtgggagggaggcagacgagcagagcagagcacctgctctgctggccctgtagtttgccagctctggatgccctt
agaggacggaattgcaggGAGGcggatgatgagtgcaggcaggccccctgtagtttgaccccggagcccttctggagttgtg
ctgctgtggtaggccttgatgatgagttctcaggccacagcatccgctcttcttcaaggccctgacttgactctggggacag
aggctcctgctgtgagatgagttctcaggccacagcatccgctcttcttcaaggccctgacttgactctggggacag
tgtttccgtgctggcatacacctgttccttgatccaaacttatgccatgtccctGCAAGCGATAGGAGTGGAAGCCACCAGtaggttg
AAAGCCGAGGTGGTGGGGAAGCCTTCTCCTGAGTTTTCAAGTCTGCCCTGCAAGCGATAGGAGTGGAAGCCACCAGtaggttg
gcgccttgtgaagtgggtcagggaggcagcccgtcagggagccctggagcttggaatggattacaggactcaggcagcctgtg
gggttggccaggccagccaagctggctccctgtgaaagctgacctggctgggaaggaggagggaagacagcagcaaacgaaatccactg
aatagtttcaacctgaagttactttcagtatgaaagcaagaagaaatgctgccggttttcctgagttttttgctgctttctct
gaaaggataagaattgacaagtcctatcagtgtgttaatatatctcactggcaagacagtgtaacagcaagattacaacaatatgg
aggaaataataaagtcactcatttgacctttatcatttgactatttgggatagattgccttcaaacttcaaattttagaa
aggaaaagaatcggttatgatttttattgtctacacctaaccccaactaagtgagtctggcttcgtcctccagtgggttttcttt
```

FIG.1-18

```
tctttttcttttttttttttttttttttgagccaatgtctccatttgtcacctggctagagtgcagtgtagtggcacagtcat
ggctcactgcagcctgacctccaggctcaagctgatcctgccatctcagtgccccttaaccccttactaaccaggcccccc
ccgccaacccaactgagtagctggactacaggtatatgccaccacgcctggcaaacttttttttttttttgagacagagtc
tcactctgtcaccaggctggagtgcagtggcgctgtctgcggctcactgcaacctccacctcctggttcaagcaattcttctgcc
tcagcctcctgatgagctgggactacaggtgtgcaccaccaccagccagctaattttttatttttagtagagacagggtttcaccatg
ttgccaggctggtctcaaattcctgacctcaggtgtatctgccgcgtccgccttggcctctcaaagtgctgggattacaggtgtgagccac
catgccaccagcccgctaacttttgtattttccatagagatggggtttttgccatgttgccaggctggttaaactcctagctca
agccgtcctcctgcctcggcctcccaaagtgctgggattacaggcatgagccaccacacagccccctcagcaggtttttctga
aagattgtaaggaatagtgggcagccggcagcctgaggctgacgctgtagtcccaacacttgggaggctgaggcagtggatcact
tgaggtcaggagttttgagaccagctggccaatgtgatgaaaccccatctctactaaatacagaaaatacaaaaaaattagctg
ggcgaggtggtgcatgcctgtaatcccagctactttgggaggctgaggatgagaattgcttgaacctgggaggcagaagttgcag
cgagccgagatcatgccactgcactccacctgggtgatagagtgagagccagcagaagcatggttgggggtccctcaggtgtcaagcctggtgca
agctgcccaggctgtcctgtcctgctccagaacactggtgctcatggtgcttgagaaagatggccaaagctgccaaatctagac
tgtttccctgtgtgcatttcggtccagatccatagagatcagaagatgtcagcgtgtctggagtccccagaaacacctgggaaatgtc
actgcacctgccctgagatccctgagatggttgtgttttaatgagtgagaactgcagcaataaataacctgcttttactacctttgct
acattagtctgttgagaaggaaagtttgtgttttattagagatttgccacattcctttcttctcttttttccttttaaaaaattactggctgggtgt
tcatagggcagaattctttttttttattagagatttgccacattcctttcttctcttttttccttttaaaaaattactggctgggtgt
catccagcttcagtggttaagatttgccagcacttgggaggctgaggcaggtggatcacctgaggtcaggagttcaagaccagcctggcca
ggtggccacgcctgtaatcccagcacttggcaggaggctgaggcaggtggatcacctgaggtcaggagttcaagaccagcctggcca
acatggtgaaaccccgtctctactaaaaatataaaaaattagccgggtggtggcgggtggtgtgcctgtaatcccagctactcaggaggct
gaggcaggagaattgcttgaacccaggaggtggaggttgcagtgagccgaaattgcgccactgcactccagcctgggcgacagagt
gagactctatttccaagtaatagtaatagtaatgataataataattactatttttgctcatatttttaaagcaaatcttcaa
ttgtatccttttcatgttgtagcatgacatttaaaaatcacgattttttgatgtaatacaatacattaaaatcctaacatggcca
acaggcataacaaaagatactcaatcaatatcatcattcatcagaatgcaaaactccagtgagatcaaacctccacctcacctaagat
gactgtatagttaaaaaaaaaaataagaaatgaaatgttgacaagtgttggcaagatgtagagaaattggaaccccttctctattgctgctggg
aaggtgaaatgacaatgctgccacgaaagccacttggtggttcctcaaagttaaacatagaattgccgtatgactcagcaaccc
```

FIG.1-19

```
atttccagtcctataccagaagaactgaaacacgtgttcaaacaaaaacttgtacacagatattcatagcagctccatacacaat
agccaaaagtaaaaaaagccaagatacctgccatcaactgatgaaggataaccaaatggtatgtccatacagtgaatatt
attcagccataagagaggaatgaagttctgacacatgtctgatagtcacagtgtagatgaacttggtagcattatgctaagtgaaggagccaa
acacaaaaggacacatattgtattctccatgtatgatagcaatgtctagaatggcaatccatagagatggaaggagattagtgg
ttggcaggggtcgggtgcaggggaatggggagtgcagcttcaggtgcggttccttttggatgatacaaatattctgaact
gggccgggcacagcagctcacacctgtaaccacgcacttgggaggctgaggagggtgaatcacttgaggtcaggagttcgagat
cagcctggccaacatggtgaaacccgtctccactaaaaatacaaacattagcacgagcagctgggtgtggcactataatcctagcc
actcgggaggctgaggtgggagaattgcttgaaccaggaggtggagattgcagtgagccgagatcgtgaactgtgctccagcct
gggcgacagagccagactctgtctttaaaaaaaaaaatactctggtcacggtcataaatttatgtaatgtgtatttaccacaataaac
cgttctctgaatgtgctcagtgcgcagtgaattgaatactgatttttgttagtattattaatagcaaccatattaaatttcctgactgttca
attttaaaaccactcaaaaattaacagtgattttttgtctgttggaatccaatctgaagaagctccgtgactgttgtcgttttctgacctc
gaaatgctctttttaccgttgatctgtttgatcatatagaacattgaaatttaaattgttttcaactttcatttgaagtaactgacactcacaaaagttgc
tctttttagcctccatcataactaataaccacttaaaatgtttttcaacttttcatttgaagtaactgacactcacaaaagttgc
tgcttttaataattatcaactaataaccacttaaaatgtttttcaacttttcatttgaagtaactgacactcacaaaagttgc
aaacatagtacaaaatgttcacgttcacgttaccgttcagcagcttcccatcatcatcgagcagtgataaaccggaaatcaacactgg
cacaaggcggttagctaacctagagagcttattcagacaccacaccagtcatccactcatgctttctgggacacgttgcatgtag
cagtcatgacccctagtgtccttatctgtgaactctgatcactctgttgagacgagtctcgctgtgtcacccaagtgcagtgcgcttcagc
ttgtccctttcagtaattatctttttttttttttgagacagatccattctcctgcctcagctcccagtagctgggactgcaggcgccgccaccatg
tcactgcaagctccgctcctgggttcacgcattctcctgcctcagctcccagtagctgggactgcaggcgccgccaccatg
cctgagtaattttgtttttgtattttagtagagatggggtcttcaccatgttagccaggatggtctgatctcctgacctgtga
tctgcccgttcggctcccaaagtgccgggattacagacgtgagccaccacgccagcctttttttttttttttttgag
caggaatctcatcctgtcaccaggctggagtagctggattacaggtacaatagcatgatctcagctcactgcaacctcctccacctctggttcaagtg
atttctcctgcctcagcctcccgagtagctgggattacaggcacctgccaccagccggctaattttgtatttttagtagagaca
gggtttctcatgttggccaggctggtcttgaactcctgacctcaggtgatctgcctgcctcggcctcccaaagtgctgggattac
aagcgtgagcactgcatccaacctaataagtatcttgtgggaaagttctttgacactatgtaaatattctctttctgatcatta
gttctaatttttggcatctcttgataattctttattttttattttttgagacagagtttcactcctgttgcccaggctggagtgc
```

FIG. 1-20 agtggtgcctgggctcaccacaaccccctcctcctggttcaagcaattctcctgcctcagcctcttgagtagctgggattacagg
catgtgccaccacgccatccatctaatttgtgtttttagtagagacgggtttctccatgttggtcaggctggtctcaaactctcaat
ctcaggtgatccgcccgcctcggcctcccaaagtgctggattacaggcatgagccaccacatccggcttcattggtgtatttta
tgtgtggcccaagacatttcttcttccagtatggtggtgcagggaagccaaaagatcggacaccccctgctctcagaggtttatgaccaa
atactgtatttaaagctgctgggaataattcttttttgtgggtggtattccccaagtggacgctcttttgaattcattttcatttt
gatgtttaggaattggcttaacatttacatttgttttgtagttatgtaaaacatttatatgttctaaaatcaaatccacaaagc
aagacatattcaaagagtccaactctcttttctctattttgttttttacctgtctctgtggtagccatgtttataaatattaa
agctataaatatttttataaatattatagctttttttattttaaaaataagcaactatgtatatatttgtattccctcataggatg
aattaagagacaaattctcaaaataatgtgttttatatagagagaaaggctaatgcttaagtttaaaaatcagtatttaaaa
gtttataagtaggctgggcatggtggctcacacctgtaatctcagcactttaggagtccaaggagggcggatcacttgaggtcaga
agttccagaccagcctgccaacatggccaaacatgcaaaatcccatctctactacaaaaatagccgggcgtggtggcgcaggtgcctgt
aatcccagctactcaggaggctgaggtgagactgaatcacttgaacccaggaggcggaggttacagtgagccgagatcctgccactgc
actccagcctgggtgacagagtgagactctgtctcaaaaataaaacaaaccctgccactgcctgaaaataagacctgccaggtgccatggctca
gcccccttcccccgaccccaaacaaacccaaacaaaaccctgccactgcctgaaaataagacctgccaggtgccatggctca
cgcctgaaatcccagcacttttgggaggccgagtggccaggtcattagagccaaaagtttgagaccagcctgggcaacacggaaa
aaccccgtctctacagaaaaatgcaaaaaaaggcagatgtggttgcatgtgcctatgttcagctacttggggggct
gaggtggcagattgcttgggcccaggaggttgagtttgcagcaagctgagattgcaccactgcactccagcctgggcaactgagc
gagacccctgtctcaaaaaaaaaaataggaagcaagaaggaaggaaggaaggaaggaaggaaggaaggaaggaaggaagag
agggaggagacagactggctgtccagatggccattgctggtgatatttggatgtgatagatacagcccaactcaccgccgaaagaagaccc
ttgtggcatttcagttattttcacagtcagcttcttcacatttcgaatgatgagatacagcccaactcaccgccgaaagaagaccc
tcatggggtctggtgaatctggtttgctgttttgcctcctgccctgccatccacctgacatctgtggcctgagagcgggctgtggattcctggt
gggtcaccgtggctgcctgtttgagcttgtgtctccgacatatggcaaagctgtcttattcacctccacctgccatccctcataatgttt
tcctctggtggctccgacatatggcagtgcagtgcatgtccgaacgtccgaacgccattcaaatgactgtcttatgcacaggta
tctgcctgtcccttgacagtgagtgacatgacagtgcagtgcatgtccgaacgtccgaacgccattcaaatgactgtcttatgcacaggta
atttgactctcaggatgtgtagacatttttaagcatgtatttcaagataagccatttcaaatgactgtcttatgcacaggta
ataattctgttcctggcttttttattttaatgaaaatgcctcaaggacctctcttgctgctgaatgccaggctgtggcaa

FIG.1-21 ccttaaattttccagctgcttaatcaataagttatcaccagtcattccctgatcactgctgcttccgagacctgacctg
cttcttgctgctgagttttcagtctgcactgagaatagatataactccaaatccaatttcattttaaccttcctcagtgcc
tagaaatcacagattgctggtattatgctaatagattggaaattcaaacctcttagaggcaacctggcccttctaggattcagta
ataaggcaaagaataacatacctaaagttacttctagaaatatctaattctcacgtttaagcttctgaatcagtggatggttt
tatagcttcatatgaccaccaagtgatgtgaaggttttggcagttctccatcatcataagaagttctgtgggatgcaaatcctgc
agtttagtggagattgagactgttcaaaccagagcacttagttatatgtgacagccaagaaccctgcctgggggcccgtttc
acaggtgaggagcctgaagcttagagatgaaacacccttgtcatagccgtttgcattccaccatgaggttaagacaggattctc
aggctgggcgcagttgctcacacctgtaatcccagcactttgggaggccgaggtgggatcacgagccaggagttcgagacca
gcctggtaacatggtgaaaccctgtctctacaaaaaatacaaaaattaactgggcatggtggctggcacatgcctgtgtccca
gctgctcaggaagctgacgcagagattcgcttgaatctggaggcagggtttgcagtgagccaagatgtaccactgtactctag
gctggacaagagagtaagaccttgtctcaaaaaaaacaacaaaccccccacccgcgtttctcaacctgacactggtgt
ttttgactggtcattttgtggtgagggatgtcctatgcattgtaggtgctaaacagcatcccactgtccgcccactacatgg
gaccacccctccaagctgtgaaacaaattgtctgtagacccaagattacttttgccctgggagaaccgcagcattaagcggt
attaagagaacggttacggagaactctagtactgaaccagatctagtactgccaatgaggagtgaagccaggcaccaaaccatcgt
cttccagcccgtccagtgctctttgccatagcccaactctcaggagaccagcggtcagcgggtaggagaagatttcaagtggaggtgggga
gggtagggaggagaaaatttcaagtgggggtaggaagatttcaagtggggggtagggaggattcaagtggggtaagaggat
ttcaggtgggggtagggaggattccaagtagggggtaggaagatttcaggtgggggtaggaggattcaggtggggtagggaggatttt
gggattgggggtagggaggattccaggtagggggtagggagatttcaggtgggggtagacaggatttcaggtgggggtaggagggggt
caggttgggggtagacaggatttcaggtgggggtagggagatttcaggtgggcgggtagacaggatttcaggtgggtgggggt
agggaggattttcaggtcgggggtagacaggatttcaggtgggggtagacaggatttcaggtgtagaggattcaggtgggagaggttca
ggtgggggtagggaggatttcaggtgcagggtagacaggatttcaggtcggggggatagagaggatttcaggtgtgaggtgcaggatttcag
gcaggatttcaggggtagacaggatttcaggtgggggatagaaggatttcaggtgtgaggtagcaggattttcag
gtcggggtgggatagacaggatttcaggtgggggtagacaggatttcaggtgtgaggtagacaggatattttcaggtggggggtag
ggaggatttcaggtgtggacaggatttcaggtgggggtagacaggatttcaggtgtggaggtagggaggatttcag
gtgtggaggtagacaggatttcaggtggggggatagagaggatttcaggtgtggaggtagggat

```
gtgtggagggtagacaggatttcaggtgtggagggtagacaggatttcaggtggggggatagggagtatttcaggtggggagggta
gacaggatttcaggtgtggagggtagacaggatttcaggtggggggtagggaggatttcaggtgtggagggtagacaggatttca
ggtggggggataggagtatttcaggtggggggtagggaggatttcaggtgtggagggtagacaggatttcaggtggggggta
ggaggatttcaggtgtggagggtaggcaggatttcaggtggggggtagacaggatttcaggtggggggaggtaggcatggggct
gcagtgatcttcatggctccgcaccctcagaactgcctgtgaaaatggggtgaggtttgcaggcttatccagaggcctgccata
taaactcaaaggtgccctaccatttcgttcctgattctcagggcatcagttcgactataggggtctgggacagtctgtacccc
tagggggaggctggtgagtggggagtacatgtctgtccacatggggccactccggccagtcctccccagccgtgggcatttcttgtgcctccc
ccatggtgtttccactgaggcctccccacgaactctgttgctgagccgtgctgcccacttccagcactgcctgaaagaatgggcc
gtgtgggatgaccctgctcaactcctgactgggagcaggctggccctgggccgtgccactcagcactggcacctgcctgca
caggacgggtcagcgccctcctgcagccctggtttgaattggaaactctgtcacgatgctggcttttgtctttgtgatgtgtcctagtcataaggtgctctg
gctgtgggtctgaaactgacggagttgcaggagctccggcctggcttgtctttgtgatgtgtcctagtcataaggtgctctg
agacctcatgcttagttttcttcagagttttttctccttggaggctttttttttaagtagattttattttctctcaa
aacaagtatttaaaatatctgattatgaagcaactcatgctcattaaaggagctaagaaaaattcaggaaagtacaagaagaaa
agaaaccactcatttcaccagccagataacacaaatcatgcttgatctgccattttttgtctatatacatttttaaca
caaattgggataatctttgtatctgctgttgaaatctgagttttcccctaatatctattgggacaattttttgttaacttat
attttaggttcagggatacgtgtgcaggtttgtgatacaggtacattgtgtctgggggtttgtgtgcagattattttgtcct
ccagtcataagcctagtacctgttgggtagtttcaatcctccacttataagtgcaaacacacagtatttgttttctgttcctgca
tgttgtgccctgtgtccatgtgtattcagtattttagcccctgagctcatcctctgagtgcaaaacgactgacctgttctttttttaggggacagctgtct
ttagtttgcttaggataatgcctccagttcctccagttcacagtgcatactttgtgcttccctgatgaacacatcttgtatgtacatcctcttgta
ttcctattgatgagagctgcttccagttcgcctcttgtgctgggaggctgtgatgcatgttgcttatttctgtttcagaaggtgtgt
catttctaattattctccaaatctagtgtgtgctatacagatgctgtttcccacatcctaccaacaccatgatttctgacttttttttt
ccgttcaccttcctgacctgctgctatgttgtctgtcttatgaaggtgtcgaccacagtgcaattactcagcattgcactgtctc
aaagtgtcttagttttgcttgtctgtgtttggggcctggttcctttgggccctgattcaggctcaggcttcaggtcaggagtagagtgctcatctcaggcatctcctg
ggggatatgtgcacccagagctgcagttacagacactgagctcactccaccttcaccaccccagccctgctgcttccgccctaat
```

FIG. 1-23

```
cctcctggcagagccctggataaggaaaatatttgtgaaccacggaagctctttggtgctggaatttgcactccaaagcatcgc
cgcctgttagatgatgtttccctcagcacctagacactgaagagagacaggcaggcaggcagatgcgtaagagggaggatt
gactgctgtagcaccgaccagacacctgcctctggactgtggcgcctccatccggtctctggatcctggttctgggggt
ccgacctttcattttttctccgcctcacaccccacctgtgtctgcagtggttctttaaatcctaaatgattggcaatatgtc
tttatttcccctgacagcgcacctcctgactctatcttcttgccagtgattttttaaatcctaaatgatttggcaataattgctc
ctccttgcctgattattgcccttcaccgatagtaaatctggaatctgggtcctgagcgcactttggtgatgcggagccaca
agctgcctggacaggcatcactgctccaggcagctgtgcaccagctgtgcccggctccgccccagcctccgcctcctcg
ccgacagcttcccggggctctgcctggaggcagctccgtgggcacctcatccccagaacctccacgctgttcctgatgaaactcttcct
ccaagagaccacgttcctctgtcctgttttgtatgtgggaggagcatgcacacagtttcatttccccgaagcatggaggtgtagga
gagggaaacctgtgtgctgtctggttttgtatgtgggaggagcatgcacacagtttcatttccccgaagcatggaggtgtagga
tgacatgtaatatttggaagaccattgtcatttccaaggaaccttctagcaggatgccctggagtctctggcagcagtgacatg
gtccttgaattggagtgctgtgaatgttcactgctgccagatgccagcagccgtggggctgcccgccagccctgcttttccaaccctcagagt
cggggctctggccggccgccctgctgccagatgccagcagccgtggggctgcccgccagccctgcttttccaaccctcagagt
gccccttgtgcatgcagcagacactgttgctggtcccattccgggagcagcacgcggtgccactgtcttctgaaaaacactttgaatttt
ttggtttgatagactcgaaaacctcatttggcaggatttttcctaacatcagtcattacttcacgttttcttaaaattgattcatttatt
taccatatctggtatttttaccatatctggtacttgccactagctctataaatgaaaaccagaatctctcacttactacatatagattaat
actaaataaatgtatttaaaaggaacttttgatgactactaaaatgtatgtcctgtcctgctggtcaaatagtatgtcaccgtgtgcatgaca
cactctgggaagcacaggggtgggtgggaggaaagatcagagaaaatcgtggaaagtatgaagtagagagcaccacaccaggaaga
cgtggtttatttcagtacctcatgtctcgcggtggctgccgctaccagtaactggcagaattctcaacattgtgccctgcagcc
acctcctccgagctctctcagcaccatccgtttcagctgaaactacctccctggcttctctgagggagccctctgcttgactatgataca
tgtcgagtccatgccgagtggcagaaaagctccgttttcagctgaaactacctccctggcttctctgagggagccctctgcttgactatgataca
ttgtactttcaatgctcctgattcctggttatctgaagcctgtttggggagacggttccaggagacagttgcttcaggct
tatatgtgtgctgtccacctggaattcacagcatgcgtgccctggtgagtggtgggagatgggtagtgaacagtgtggtagcccc
tgctggcgtgtccacctggaattcacagcatgcgtgccctggtgagtggtgggagatgggtagtgaacagtgtggtagcccc
ctctgggaggcctttcctgaccaccacaagcccacagtaggtcaggaggtcaggcctcacagcctccacgcctgtgttattccaggccct
```

FIG.1-24

```
gatgatgagactgtgtgaattacctgattaatgtctgtctttagcacttgtcgtgagctcgtaagtgctgggactgcatgtgtctg
attcacactgtgtgccactgctgctggcctggcactgcctggcgaaggctaggcaaagtatcaagtaaccaggcaagggtgcc
tgttgcagtgcgggggcctctctgatgtggtgagataggaatttcctcaacgaaacatttcctcatgttttctgtttcctttgtaa
catgtttaggccgcggtggctcacacctgtaattccagcacttggaggctgaggcaggtggatgactggtcaggagatc
aagaccatcttgttaacacggtgaaaccccgtctctactaaaatacaaacaaacagcggggcatggtggcagccgcctgtaat
cccagctactcaggaggctgaggcaggagaatggcgtgaacctgggagccgagcttgcagtgagccgagatcgcactgcact
ccagcctgggtgacagagcgggactccgtctcaaaaaaaaaaaaaaaaagtttagtaatgtattatgtcctgccctgt
gctgggtgcttcactaagatgattccttaaacgccacacctgttataccattttacagatggaggtggaggctggccaaggt
cacacagccagcaaacaggagagctggaatctccacccactgctctcagctgcgtgagacaggagtgagtctgtgcatctgctg
gccacatcgggccgccccctctttctggtccccttcccccagatggagagcaaattccacctgaccgtcctgcaggcaga
gtccaaatctatgggacacacactcagtaagactcccctggcttgggcatgctcatagtcatcgttttcatttttgtcttgattttg
gtttgtgtatttatcggttagccctcttagcatctgaattcagtgagaagacatgtagttttgtttgtttgttttgttgttgtt
tgttttaagacagagtttgctcttctcgcccaggctgcttggctcattctcctgcctcagcctcca
agtagctggattacaggcatccgccaccatgctgcccaggtttcaccatgttgcccaggc
tggtctggaactcctgggctcaagtgatctgctccctgggcctccccacagtgctgaattacaggcatgagtcactgcgccagc
tttaatcagatttggagtagggagtgagaggagctggtggttggtggttttttttcttaaaattattattactttttttttt
ctttaaaattattattacttttttttttttttttgagaccagtctcactcactccatgccagtctcggagttcagtggcacaat
ctcagctcactgcaacctccacctccagggttcaagcaattcgtgtgcctcagcctcccgagtatccgatccgatcgcatgc
gggctaatttgtatatttttagtgaagactggtttcactatgttgccaggctgggtctcgaactcctgacctcaagtgatccacc
gcctcagcctcccaaagtgctggattataggtgtgctaccactcccagcttgtttttcttttttcttaattacatatatttattata
ttaaaaaaaaaaaaagagcattaagcaatacacatgttaatgtggcaaaaggagaccacaaatgactgacgtttc
agccacactgccgaggactgtatgactccctccactctatgtaggtgaccaatggaagtcttgttgcctcataagtgtgtcc
agacacagcagccgtgccgctaatgccgctcagcagacactcagctgctcaagacacattgctgagcgtcaaccaagtgccagttgtcaacc
cagattcccttgtcctccagagtgtcttttggagagccacacaccagctgggatgagagtgcattatgctgcactatgacacgggtggcac
cagggtgtgatcccagagtgcttttggagagccacacaaccagctgggggcagaggagaaggtggtcaccagactgagtcc
tgaaggcctgggggaattagcagcagagagggaggaggtgagcaggcacgtgccacaagtcagcacgtgcaggtaatttctggtgt
```

FIG. 1-25

```
tgatgtgtatttccagctattgtcattgtcattttcccttgcccaaggactcttctacattctttgtaggtagatctcttggtgatga
attattccgcttcggatgtctgattgtctgaaatatcttattcatcttcatttgaaagatatttttgctggtacagatttctagatgg
gcagttttttctttttactgcttaaaagacggcactccacagtcttctcacttgcattgtttccaacagaaatctaacgtcttaat
cttcgttttctctgtacataacatgtctcttttgtgttcttttgtgttttctttgtgttgttcattggaattttctcactgcttgagcaatttgatt
atgatgtgccttaataacagtttttctttgttttcttgtgtgttttcattgggatcttggatctgtggatttattattttttatc
aagtttgaaaagtttcagtcactatttcttcaaatatatattatgtctctcatctcactttttttttttaatcaattag
agacagggtcttgctctgtcgctcaggctggagtgcagtggcacaaacagctcactgcagtcttcaaactcccgggctcaagtga
tcctcccacctcagtcctccaagtagctagctgggactaggagcgtgccgccaccacatctgctaattttttaaattttttatagagacag
ggtcttgcgtgttgcctaggctggcctgactctcacttttgaggaactctaattgctgtacatcaggccgcttgaagttgtgccatagct
ggtgagcactgtgccagctcatctcactttgaggaactctaattgctgtacatcaggccgcttgaagttgtgccatagct
cactgatgctctgttcattttgaaaataattttctgcctctgttcattttggcagtttcattgcatgtctccagttcat
tcatctttttcctgcggtatcttcttgcattaatcccaccagtgtattttgatcctgacattgtagtttcatctctagaa
gcttggtttgatttttttatcttctcattttctgtcagttcggataaactcatcttctctcttctgcatgatactttccttc
cgtctgctcattctgatcattttattgggtgcagacgtgcagttaaattacttgaaaacagtttgatcctccagatcttgctgtgataccatt
tttgcacgtctgatcattttattgggtgcagacgtgcagttaaattacttgaaaacagtttgatcctccagatcttgctgttaagatttggg
aaagaatttgaacttgttgtgggatgccctggctgggtgaatcattcctcatagtgaagccagcagggacacaggcaccgtttcctagtattgg
gcagcaccagacagagggttgccctggctgggtgaatcattcctcatagtgaagccagcagggacacaggcaccgtttcctagtattgg
tcgtgagtgagctttcccagctcagggagttcctcccacgtgctgctggcagtggctgcgtgactctgctcctgggctcccagatcctagc
tgtgattctttcccagctcagggagttcctcccacgtgctgctggcagtggctgcgtgactctgctcctgggctcccagatcctagc
ctccacagctctttctccatgcagccttctccatgcagccttctccatggctctactggttttccctggtattagtcagccagtcctgtcatacaaacacca
tttgtctcccagttcaggatccatggctctactggttttccctggtattagtcagccagtcctgtcatacaaacacca
cagactgtgattcaacagacagaactttttttccactgttctgcagtgccgcctttcttgcagtgtcctccatggcctcctcgtcttgcatgga
tttctggtgagggctctctcttcccagcttgtagatgccgcctttcttgcagtgtcctccatggcctcctcgtcttgcatgga
gagggcactccagtgcctcttcctgtaaggacagcagtcccatcagatcaggccccctcttgacctcattgcccttaaagaa
ttacctccttacaggccctgtctccaaatacagtcacgtgcgggctagtgaatttgtggggacacacttgagttcacgacacc
ctcctgtgtccacagtctgaagcatcgaaggcagtgggcagtaggcagtggggcagtcacaggagcacctcattgtttcctgcgtctcaga
```

FIG.1-26 agtcattgtccttcgttgcttgatgtccggtgtcctgaaagctgttggttcataatttggttttttcaggtgagagag
tttatcccagaggctagttttgaaatgatacccaggctgtgagcattcctctgtgtgtgtgtgaatttggtttgtatatta
ttttgttttaaggcaatacctcaccattgaaagcaaaactatataaagcaaaacttacaaagatttgccagagatttgcttca
ctttcatggaatcaagggcaaataaccaggttacagagtcttttaggtcaggtcagtctgtgttcaggaggtgttgccttgc
agcgttcagcatcccgcacgtccttgggcgccaaatcactttgacgtctgcttgatttgattcaaattgcacagatatatactgt
tcaaagctgtgtggcctacgggggcagtgtgagatattcaaggtgggttgactttaatcaatacgatgacaatattatcttgttt
aatttgtatgatggtggttgtaaacatcaaatcaagccattttattattgtcaaaaaagatgaaggagcccggaataaactctcc
tgacatcacttctgagcgtatttcactgccgtgacagGCCGTCATGATTGGGGACGATATCGTGGGCGACGTCGGCGGTGCCCAGC
GGTGTGGAATGAGAGCCTGCAGGTGCCGCACCGGGAAGTTCAGtcagtgccagctggagtcatttattcaccttcctt*cagggg*
*atgaccacatt*ctcattctgttttgttcttcaaatataaaggggatat*tctttccaaatcaaagagcagtatgtgggcatt*cactat
cttgtatgtaatgaccttctaagaacagggctgagtggtcttttatagcagacagtgataaagtagagtg*gcttttgatacagggt*
*ctggg*ttttgaatggcgt*gcagtgcagagagaaataag*caaaggcactatccatcctgccggcgccaccaggagttggg*cg*
*aatttgtgctgtcc*ctttggcatttgatcagaccct*gcactacggcagttacagct*gtgggcactcagccccttgacagcc
tccctctccttttgttcacttctccactctgtaagacacagagagcctggagacgacagaggttgctcaggcatgccctggagc
agaacctccatctcaagaagaagttgtgtttttattgctgtgtaccaagctccagctcgcctgctctgcgagcagctgtcagggttgggagct
ccaggcatgtgaggggccctgtggtgacctcagctccagctccagcctggtctccagagagtctgaggagagtgtgcttgcc
cttatgctagatggtttcgattgtgtggggcagttacatttgtcctgagagatctgcttaggcaggaagactgttgaaacatggttacc
tggaggtacttggattttggggtgggggcagtgtggctgtgagtgctggtgagtgagccaggaagaagacagatcagaggg
cccgaccgtcgtctgaagtctctcctgcggtgggagtccctccagctttccccagctttccccaggctgtatgacatatggcctttctttc
ccagggtcaggaagttggtccctccttgtgtctccccttggtaggcctggcctaagggagtgagggagaccccactcacagccacaggaacg
ttcttgaagttgggttttggtttgtgtcccccttgttaggcctgccaatctgccttcctgccaaagtcgcagagcctgtcttgctgctgc
ttttttccaagagaccaggggctctccgtgacagcggcaccacctgggcctatagttgatgcggtgctgcctgcgtcaggagc
tcccaggcgagggctccccatgcgtctcagggcacactgaccacctccctgcttgggagcacagcggtgtg
ccagcccggccgcgcccatgcgtctcagggagaacctactgtgttgtactgggcttcttccagttcttggagagaaacatgtctgtcct
gctcggcaggaggtggaaaggggagaaccgtactgtgttgtactgggcttcttccagttcttggagagaaacatgtctgtcct
gaatgccaccctcagttggggtcttctgccagcccaggccagccaggtcgccctataaactgagaatggcctcgaagaggcccc

FIG.1-27

```
acagcccacgaatgcagtgggcacgaggaggctgtgcccacctacgcagcagcaaggttggtgctttcagattccggttacct
gcatgctatttaaagaagatacgaggtgggcatcccccatgacactgtctccggagagagaaactctgttttttgttttttg
tttttgtttttttgagacagagtctccctgtcgcccaggctggagtacagaggtgcgatcgctcagctcactgcaacctcg
cctccaggctcaagtgattctcctgcctcagctcccgagtagctggactaggtgtgcaccacgcctggctagtttttg
tattttagtggagacggggttttcaccatgttggccaggctggtctgaactcctgacctcaggcgaaccaccgcctcttctcc
ggaagtgctgggattatacgcgtgagccaccgcgcccgcccagagagagaaactccatcaacagtttgccgaatccttccacac
tgccttctctgcatagataaacagactggtaatattttgttttttttcttttataaaatgggatgatattgtttgcagcctcct
ttttcctgaacactgtttatggcctcttttcacaagtgtcttagtggtcttagtggtgatttctgagattttgtgcaccatcacccgagcagtat
tggagaacagtggtgtttggttacatgcataagttctttagtggtgatttctgagattttggtgcaccatcacccgagcagtat
acactgtaccagtgtgtagtctttatttctcacctacctccgcaagcccaaagtccattgtattattttta
tgcctttgcgtcctataacttagctccatctcagttgctgtcgttaatgccattatttcgttccttttatgctaagtagtattccatgtgtatat
ttgagtctccaactcatctagtttgcttgtgttatttttcttttttttctttgagatagagtcttgctctgtcaccaggctgagtgcagtggcg
gtaccacattttttttcttgttcttttctttttgttttttttcttttctttgagatagagtcttgctctgtcaccaggctgagtgcagtggcgc
cagtctcggctcactgcaagctccgcctcccggttcacgccattctcctgcctcagcctcccagtagctgggactacaggcgcc
caccacgcccggctaatttttgtatttttagtagagacggcgtttcaccatgttagccaggatggtctctgatctcctgacc
ccgtgatctgccacctggctccacctaaaagtgctaggattacataggtgaacatgtcatggggttattgtacagattatttcatcactca
tttaagttcaggtgtacatgtcaggttcattacataggtgaacatgtcatggggttattgtacagattatttcatcactca
gatattaaactagtaccattagttatttttcctgatgtcgtaggaaaggaatcagtgtagtgccggcacacagcaagccctcagcaaatggca
ttatcctgtatccatgttcagatgctgtaggaaaggaatcagtgtagtgccggcacacagcaagccctcagcaaatggca
gggtgggagcacgtgcgccactactgtccatatccatcgtagctagtgccatgccatatccacccagactccagacatgga
gtcacctgcctccattgaagaggatggcctagccatttgttcctaacgagattaaaatgtcagaccttttgatttgttgta
aggatgcaaatctgcctttgttaacatgcagacaaaggggagaagagtgttagcttgctaaggtagggaccagtgcgtgggga
ggccacatgggcatcaaaggaggtgggctcgtgtgtagtgtgccgagttaaaggatggggtctccagccattggtg
actctctggactgcactgtgcagacacagtagccgagccgcaggggtgactgtgagctcgcccacagtgagacgtgcaggaag
tgtaaaatacacactgactttcagagatgtggtgggagaaagattgtgaaagagctcatgatatttttatatcgctgcat
gttgaaatgctgatatttcgttgttaattttccaccatttaatttgtttaacgtggctactagaaaaggttcgctggcttct
```

FIG.1-28 gcaggagtgttggtggcccaggtggcagctgccctctcctgcactgtccccttctccctgcactgtccttggtacacaga
tacactgaaatgctggagggcgtgggtcctggatgagtggctgatgggctggggacctctgagggctgttttggactgaat
tgcctgcgtggtgctccctatgatgtgtggccagcctggggccagcagcacacagcctctggagtcagccggggcacctgccgctgggc
cggcatccctccttcctgcagaatacccccagctcagctctatggagcagcagcctgcccttccaggccacccccagcctctgg
cacctcagcacggcccattctgcacagcggtgagccccagggcgtgtctcctctgcagctggtcagctgatgtgtcgc
aacctgtgctgagcctctctctcctgcaagtggccaaagaggcctcaacagggcagcagctgaccactgatgggtcagctgggc
atcagaaggcctccaggctctgtcctctgttggttgcttggcggaatgggagaatgaaggggaggaggggtggcttgtcct
gggccaggtggcagagagccctgcagtgagtaactgctcctgcgtcacacttggttgaggccagggcagcatgggaggccgtccaggc
tgggcagctggcggtgggggagcagcggtggacgtgcctcagccaagtcttctagtagcacgcacgtgcacttacacgtacac
ctccactggtcctgctgtggactgtgcctcagccaagtcttctagtagcacgcacgtgcacacgtgcacttacacgtacac
acacacacacacaattgttctgaggcagctgtcaggagtctgagaggtgctgagagtggattcggccgctga
ctggcagtgagatccttgtcacttagatgtatccattctccttgttttcattataaaatgccaaagagagtgaagcctcgg
ggttggagagattgcaggtggcttagctctggaggaaagttttgcagggcctgctctcccaggaaagcatcatccccggcaggg
gtgtctggagcttgccacacaggctgccaacaggctgccaacagggctgccacagggaagcacaaagctttcttttcatacctgctcctgtgga
aatcctgccagccagggcgccctcaccttgctgcaggtaaagccttctggtgttcctgcctgctgctgctgctgctggaact
cctgccgcattgacatgctgggggttctgtgtgcatgggacatgccaaatcctcatgatgccatgagtcctgcagccccagagggtgctgc
agtgtctcctccgtgagaggcttttttcagatgggacagctaggacctggccaaggccactggccaaggttttacagaagctggactggaac
cctgccgtgagaggcttttttcagatgggacagctaggacctggccaaggccactggccaaggttttacagaagctggactggaac
ctgccgccccagtccctggcctggcggtgttgctttcctgcactttccctgggccacatttgcagc
agtcacaggcctggctcactccaggctccaggtccatgtttgatgcgaggccagtgcccagtgggtaagtgcactgctgccacgcccccccc
aagcactgtctgctcctccctgcttgctgtcaaggcagctcatctttccttggagatggggctgggctgggagctgcg
ccctccattctgacaaatgagtagaggaaggaaggacgttttgccagttccaaggtgccctctgtcctcagtgagaaggaaga
gccgctggcacatctgagccacagaccctctgcctcttatcccaccaacctgtgttcctgtgacatgccagaaaccaggc
cgtgtggcctctcaccaccatcactctgttcgtgttgtgtaaataaagccgatgcggagctgcctctggtctttctcttattgtttacc
gggaagcccctgcctagtcctgctgtgtgctgtgtgtaataaagccgatgcggagctgcctctggtctttctcttattgtttacc
caaggctggcagatgttttataagcccgaacgttcttgacaaacagtttgccctttgccagaggggaaagtttcctggaccgtgatt

FIG. 1-29

```
cccgacatcctgcaaggtcccttcctagctgtggcctggtgtgctgggggtttccccccagtggggtggcagccgatctaggatt
ccagccgccttgcacaaagctgacaaagctggaagacgaggggtgcaggtgcaggtcatggctggctgtcggagctgcttcctgcaggagagagtgcccc
acgcctggccttgaccttgaaggggcgctgccgtcaaagacaggcagcttgcctggtcttccagacttcgcagtgacggatttca
gagtgtttcctgttacgagaaggctgtggattcgcttggaacatgacagatttttttctgtcacgtggagtgtgaggaagg
aagtgaaactggtgttaattttcagcagtcacatgtcaaagtgagtgctgcagcagcagcagggggtcagggtgtggtggccctgg
tcagccttccaggagtcaggaccctcctgctgcctctgtgtaaacagacagcaggcaatccgagccagcccggtggagag
aaagggccagtgctgggcttgggagctcaccccagttcctcggtactcatcctggcagtgcagggaagggcaccgggaacaggc
ctgtggaaaaatccactgtgcaatgagtcgtgaatccagacatcctcagcagcctcgtcctgccgggatagaggctgt
ggcttctgtgtgtagtgggcacttctgggctctgtctttttgtcagcttcagagtgggtcattagctcactgagtcaccgagttcacagaggccaccccaattt
aagcctgtacacttttttcttttgtctcttttgtaacagcttttatgaaatcactcccacgctgtataactcagtggttttca
tacattcacagagctgtgcagtgtcgtcaccacattccaccagccacacagcccagacaatcactacttatgtcatactttcttttttgttttcattttt
tagcaaagaccccccacatttccaccagccacactgagccccagacaatcactacttatgtcataactttcttttttgttttcatttt
tttttttttttgagacagagtctcactctgacagccaggctgagtgcagtgcatgctgcagccacctccgcct
cccagttcaagcgattctcctgcctcagcctcccaagtagctgggattatagcacgcaccacatgcccagccaactaattatgtat
ttttagtagagatggggtttcaccacgtttcaccacgttggccaaactggtctcaaactcctgaccttcaatgatccccgccttgacctcccaa
agtgctgggattacaggcatgagccaccgtgcccagccaacatagcgagaccggcttattgtcatcaaaaattagaaaaatttaaattgccca
ggagtttgagaccagctcgggaggctgaggcaacatagcgagaccttgtcatcatttcattcaaaaattagcacggtgtgtgacaccacctgt
ggtcccagctactcgggaggctgaggacaggaacttgtctcaaaagaaatttttaaccaggagtccacgagctgcagtgagctgatcataccac
tgcacttcagcctggtgacagagacaagaccttgtctcaaaagaaattttttaaattggtaaaatatataacataaaata
tgccattaaacaattgtgatgtgaagtgaataaatttgaatacacagcatatgataacaagcaaacactctaaggtcaagaa
ttaggagctatcagctcccagaagactagtccctgattgacatgccagtcctgcagaggcgccccgccttgccgtgggcac
agtggccgcggtgactgggcctgcttcttcttcccaacatggcgctgcttcctcttcttctctgacctt
tatccaagtgaatgcacactgtaccgttgagctgtgcttgttcatcgtgctcctgtgtctccaaccccctctcgccgtc
cctcagagggaacatctgggtggtccagtttggcccttctgcactggctgccaggaatgttctgtttttttgtctcctggacaca
tgggcgtgagtccttctggggcgatctgctgatagatgctgctggttcatggagcagcatatgttcaacttggccagatgag
gccagacgggtttatgcccaccacggggaccctgttgctccccgccccgaccatcacgagctgtttctggagggaggcccat
```

FIG. 1-30

```
gttcttcccagtttacggtcctggaggtttctggacattgtcagcatgtggcagtccggacgctggcctcctgagagagtggg
gaggagaccggaggcggaggcgagtgtgtgaaggaggctgtgggtccacatggctgcagtgaacatgggtttccagggg
cagacaccccatcgtggccccatgcttggttgggcagcatcagcttcctctgctgtttcctgcttctgttgctgc
tgggcaggggagacaggattgggaacagtgttaaaacctgaacccctgcttggtgccgctgtggaaaaccgtggctga
catgtccagggcaagagggggaaagatgttaaaacctgaaccccctgcttggtgccgctgtggaaaaccgtggctga
gggctgggggctctgagctgagaccccctgtaggcagcctcccaacccaggaatttgctcttggaacgtgcagtccctgagggtcctgg
aaggcgctggagtggtgggacagggattgagggagctcagcagggccctctcttctccctagagccgctcaacacgtgttgcaag
gcacgtgctctgacctggtgctcad[a]cgtgctctctcccaagacactccctgaagcgcgttcccaggagctggaagggggata
acgcaggtatgctcatggcggggccagtgctgctcatgttacacacactcagctcagctcgtctacaccctgcaacagcccagaga
agcaccccgcttcttaccctaccattagatttgcaaatgaagctcagagaggtgaagtaacttgccaaggccacaggcct
accagtgtcagaatcgggattcgaaccacctctgcctgactccaaggcctgtgccctgaacattctcaagcaccccaatta
gccaagtgttgctggagctctgagcagggccgggctccacacacacgacctgctgagctggactaagcagaccctgctctggggcttct
ccgccctcccccgctttggccctgaagttggtcattagacccaccaccctgagagctggcggagatgtgacaggtgacagcccag
gactaggcagcccctgaagttggtcattagacccaccaccctgagagctggcggagatgtgacaggtgacagcccag
aagtccatcgttgctgccttttgtgctggttaaagtccgctgaaccaagcgctctcttcccctccagtgtgtggtggaggtgggga
gggaccaggcagatctgggaagccgtggccaggccgtggccacctgccacagacgccccaaatgttctcaacctggccactggccttgggctctgctgga
gtggccaccgtgctctgccacctgccagagcccctgaagtcaacgcaggccctgccctgaccctggtggtgcctgccacagccatgaaccgtgggcaagc
tgccccaggggctgccaggacctgccccgccacagatgtcctgcgctggggacacgcaggctggtggcgcttacagcccaggggcaggggaggca
catccccacagcattcaccattgctgctgtgtttgaccctgagctcattttgaccctttgattgctacatctttttc
cagcctgaaaagtgaagaaggaaaaggggggctcagtgttttattgtgcacagtggttcctgtgtcatggtggtccccagatgggtccaggatgtgaaccggtgtgc
ttttcaaccatcttgcacagtggtttattgtgcacagtggttcctgtgtcatggtggtccccagatgggtccaggatgtgaaccggtgtgc
tcctctagctccactgtcctcaggttggggacagcaggacaaggccccctactccagcttccaaacgtagttccaggtgggtg
cccttgccaggccagcccaccctccagagggggtagccccgggttagcccggtgctcctcctgactttcatgaggccgggggctgaaaccagagcagcagcagggag
acagaaagccagccgccctccagagggagtcagctgccggagaccccaagagcactgccagaatctgggtatgagacc
```

FIG. 1-31 cagtccctgccgcgtgctaaccatgtaaccttggacgtgatctctttgtgtctttttttgttttttctttttgagatgcg
gtcttgttctgtttcctagtgggagtgcagtggcaccatcatgccactgcaacctcctgaacctcgggcacaagtgattctccc
gcctcagcctcccaaatagctggaaacaggtttatgccaccgccccaactaattttttaaattttttataaagatggagtctccc
tgtgttgcccagctcctggctctgtcaagtgatctccccgcttggcctcccaaagtgctgggattactgccggcttgagcatgatcttt
ttgccttgcttggctctgggttttcctcatgtgtcaagtggggctggctatggcatatttcctaacggttccatttggtctgtcctgctagacc
gccctagagtgagggcccgccatgtggtggctcctgggttctgtcgtccgtatgccacccgtgggtgtggtcaccacatggtcatggtgcttcctaggta
aggctggtgggacgtacactgctctgggttctgtcatttatttattatttttgaaacggagtcttgctctgttcagccttccaagtagctgg
gacttgaccttcccactgcttcattattatttattatttttattttttcagggttcaagagagacgggtttcgccatgttgccagcctggtcttga
agtgcaattgtgcgatcttggctcattgcaacctccgcctcccgggttcaagagagacgggtttcgccatgttgccaggctggtcttga
aatacagatgtctgccaccaaccccggctaattttttgtatttccactagagaacggggtttcgccatgttgccaggctggtcttga
actcctgacctcaggtgatctgccacctcagcctcccacgggaggagcccaaccctgtcctctgttagtccctgtcccgtagatatt
tgccttaaaatctctatgtcccactgccacctcagcctcccacgggaggagcccaaccctgtcctctgttagtccctgtcccgtagatatt
taccagcacctactatggccagccgctgttgaggatgtggggatcgagtgaatgtgcagtgccagcgtggcagtgtcccctctagggctgt
tcttccttctaggaggaggttcaagccctctctgatgccagctgcctcccagctgcagcctccagcgtcgcagatctctgtcttgttgtccc
ctgagtggccctgggccaccacataacactttttgtaagaataagagttatttttatgcacaatgcccctgcccctgggtttg
tgaatttggggattctttttttttttttgagacagagtcttgctctgtcgccagctgggagtgcagtggtgtga
tctcggctcactgtaagctccgcctcccggttcatgccattctcctgcctcagcctcccgaataggtagcaggatgatgtctcaatctcctgacc
cactaccatgccacctcggcctccacctcggcctaattttttgtatttttgtagagacggggtttcactgttttagccaggatggtctccaaactcctgacc
tcgtgatctgccactcggccttccacctcggcctaagtgctgggattacaggtgtggggattcttaaggaaaaccacctgaaagtgcgggg
ttattaaaacagaaccaaccatgccaccacactcacgagcagcccacagctccacctgtcccacctggtcagtgcactgaggctgctctccgac
gggtgagtgaaagttgctgaaaattagccctcctggtgaaatagcccctcctggtgaggaacctccagcagccctgtcagtgcactgaggctgctctccgac
tgtggcatccccatgtctgtcctcattactgacaaaaattgtgcagagaggtgctctacacatttcaaggtttaatccagga
gctgagggcagggccaggggctccatgactgtagactcaacatcctgggcacagccatccgtgaggggaggacgaggggccacgccctg
cactctgtcccagcatccccctctccctggagccatgcagcagatgcctcatttcatccccactcacatgcgggtcctagacacca
gctcatgcacatacacacactgccccacacacacacacagccacacacatgccacatgccaccgccactctctttgcctgtggg
aggcaggatccccagctgcccagtcccagcggggaaggggtgtggaaggtttgtgggaatcagccctgcagatgcggtgtgaggggcagacatggcatgct

FIG. 1-32

```
ggtctttggcagtgtggtcccaagtgggggcggctggagaggtgccttgccacagggccaggccaccgcatgcatcccatgagg
cgtccaagcccgtctgccctgcatcagagaggacacccaatgcggggaggagaacctggtgaagcaggagcggtgggcagg
ggcagcaaggatcccccaggatcccagcccctcctgctgcgtcctgcagccttctgccgtctctgatgcgacgcacctgctcgg
ctcccgcccaccccctcctgctgcgtcgcaggatgggacaggccgggctgctggagccaggccgctgcacgcacagctacatacactca
ccacagagggcgcctgctgcgaggggccccatcccacagatcccgcatccacatgtgcacgcaggccaggcccacaggttctc
cggggcccacgtgtgctcacagggccccactctcatgctggcctcatagtgcatgcacacacacactcatctccaggtcctttcaca
aggccaggccacacatccacagtgcccctcctgctggcctcatgtgggctgctcacacccactcattcctccagatgccgaccac
cactcacgccccagacccccccacgcccaggcacacatgtgggcctgtcaagaaccacgggcttgcttttagccaggcttccaca
cccatgccctgtgcctctgcctctgggggcccctctcctctgccacccttcacgggtgcagacgatgagcaggagaacacagcgca
agctgccccattcctcaggacactgagtctcctgcagcctgattcctggcctgaagcaggcaggcggccaaggtagcctcatca
cagggccgagggccaccatcagagtctttgtctccctggcaccttgtcagagagaggctaagaacacgctctggcattggggcctccag
gcctcaccagccctgcctcctttctttgagaggccaggtcctgagtcctggatgagacacgcccaagctctccctcctgccagtcccactgga
tgttccctgcgagtttggagaggcaggcctccctgcagtcctgcgccttcaactgtgctctggatcctgcctgctgcctgcctgcctgcctgcctgaa
cctggtgatgaatctcagagtcctccaattgcaagggctgagggatccgctgcctgcctccaaccccacacccgtctcaaggtc
atgtgctaatcccgtgcaagctggggtgtgggctggctggctgccatgtcaagctcgtttctgttgtaccaaaacacagtctcacctcc
agaagaattacctgcactccctggagttcccgcagccttcatttgccaatcattcatgaactcctctagagaggaagaccagtccg
catacacccttctcccagacagacccccattcaagctttgccattcatgatacaaccaagttacgcgtttgggctagcattgctttagaagt
tgaagattacgagacagtcattttgtgtgtgttttctcatggtttgccaaatattgctgatgttaaccttgacctttgtttaatgcaac
ggtgctgtgcttgttctcataggcatgtaatgttggtttgccccaaatattgctgatgttaaccttgacctttgtccactttcatctgcc
cacataatgtgtttttcccctttgtgattgatacgtatttgtggggagatgcttgaggtgatgcgatgtccacttttcttcttgtattt
agtttagtgccccttagtattttcttgtttgaatgaatgattttctatgatggtgccaaataactccatcattcttccttgtgttctctatgta
actcctgtgtttgttttactttaaggaaagatgttctctttccactgattcagatgtatgcagtgtggctgtgtggcttccagggctgg
attcagtgggtatcgtcgttaaccgtcatcactggatattcagatattcagatgctggcctttgagccctcaggctctcaggttcagtgcgaggctccttcaggctgg
cctgtgacctttcgcacatcctcaccgttcttttgagcccttccttgagttcattttgttc
```

FIG. 1-33 agtctttgcttcagccctggaatcggccattttctccaaggagcccagttccttccagtggagggcactgtttagaatctcagccc
agggcccagtgtgtgcttgttgtctctggcattgctgctgctcaggcctgctgctcaccacctggacctgcccaaaagcccagctcacagcagtgcctccgatt
gcaggtgtgacacacacagcctccatgctcatgcttcctccacctgatcttacacgttcatgcctccttccacagcaggagaagcctggcttcc
ccagtccagcagcacagggttccttctccactctgcttatcctctatccatgagagccaagtccctgaccttgcctgtggtggacactctgcgtttgtta
tcattctctccatctgcttatcctctatccatgagagccaagtccctgaccttgcctgtggtggacactctgcgtttgtta
aactgaataacaacaatcctccctattgggagaaaacctttcagcttctgcagccattctgcattttgtgttctcttccagcct
cttgggtaggcatagaaagtctttctgttttccaggaagctgcagactcaccagcatcaccagctgtaaggtgtagcagg
acagtgccagcatgtctgtccaactgtctgactggctgggactttgaaatgagaagaagccaggtcaaatgtccgagaaggggc
attctggatgtgttcaggtgctcaggtgctgagcctcagtttctcatctgtaaaatggacttatttggacttacttccagtatcctcagca
cttgctgcaggaagaccactgagcctcagtttctcatctgtaaaatggacttatttggacttacttccagtatcctcagca
cctttattacaggagctcattaatacatgctcaggaggtagtcaggaagcaatggagtggagtcagcataggaatgctggtgcatcacggc
ctgggttgtcagcctggcctctgcaggcattcgagatattcctgagggcagattcagccaggccaacacttctggatagaacac
agggccataaactgagagaccattgaggagaccttggcttgaaaactgcgccaggaccatgtgctctgatttgcaaaatgcac
ccccagagcggcttcctgccttcacttttgtgcagattgggggcgtgggggtgggttggatggaccatgtcacccaaaa
gtttgtcctcgatgggaagggagagcgtcgccaagcacagctgaggcttccctacttccgatgacccttgtggcagtc
agtgtcaccggacagagtgtggcacgcctgggacccagcagccccccagaaggataggcgcttgattggaaacgttgacttttca
tttaaataagtcaaggctcctgcatgcgggagagagagatggctcttccctgcctctgtcttcctccttacccccgtgag
tggacaaaccccccgtctccaccagtgcgttctgccaccgacctatatcaagacacagccagctttgcaggcacttg
ccgtgctccgcagtgtgcaggtgcagggtgatgaatgaacaagaccatggcctgaaggttcccacgctgcagagggcccagccag
ggccagaccccaagtgtgctgcaggttgctgaggtgactcaggggtgcgcagaggactcagtggatatggaatgcagggctgaggcata
gggagtgacacagggctcaggggcctttccatggagtcgaggctcattggttggcaggaccacatctgcctggtcgatgcctg
cccatgcaggctctaacggcagagtttgggattgggggatgcaggggcctgggtggggagcttgggggcagtgggcca
gcaaagcagagcccctttgctgtgttggaaaccctcagaggcctaggcgtgataagtgagtgtgaccagcaggagagtctctgc
atgggccaccacaattgcagagaagacgccctgcatgtcataggcttgcgccatgcccggaatttgacgccgtctttcc
tccggtgctgaggagctcagcagtcggaggcagtgcgattgtcttttctcaccgcagcaggcaggtagctgtctttttagtt
tgttttgttagtctcctgtatctgactctgcagagactgcaggaagagaggcagcaccggcaggaagaggcgcaccggcaccggcgaggacg

FIG. 1-34

```
gcttagacgggaggtccggagctctcagctgacctgaccagcctggctaggcgggaaaggctgggctttggggtcaagggcag
gggatgagatctcagaccacgacctaacattgacctgctgggccacttcaccctgctgcttcttcctgctgtctgtaaaagc
ggatcacgtgagggcctgcaggaagctctgaggcttcgggctggggtgaggcgagcaggcgagacctgctgagccgtcctt
ccgcccgtgcctgcaggttcctatgcctctcggggtgcaggtctgggctgtgacctgactgtataagtagcagtgaggcttaca
gcgctgtcgtggtggctggtgtgcaggcgagtgagagaggatcttgttgacctgaccttgtatttctcagttgtcctgactcctctgaaaga
agtagttctaggctggaaaaggaaaagagacaatgaatctgtattgtgttacagcacgcaggcaccgggctgtgcctaggggtgaa
tttcgccatggaaacattcctcctggtcctcggcgcctattgtacgcacgcaggcaccgggctgtgcctaggggtgaa
cctctctcgattgtgtggccataggtggttacttaactctctgtgcctcagcgttgccactgtgtgtggcgatagcaacatgtct
tcttcctaaggttgtgggaaacactgatcgcaacagtgacagatgcaggaccactccaccagaaattgttcatgagcttgtt
taccaccagacgcctgtatgagagagaactgacatcgtctctcacttgcagagaggttaagtaacttgcctaagtcacacagcc
tttgaacctggagtcgaactccgtcatctatgctctgaaccactctgccacatgtggtgttactgtcagttccattgtttcc
acacagcttaagttagtcctgtgtttgctttattttatttttaagacatgtcttgctctgtcaccaggctggagtgcagtg
gtgcaatcatagctcactgcagcctcgactcctgatgagattctgcatctcagcctcccaagtagccggactataggcacatgc
cacaatgctggctaattaaaaaaaacatttttttttttgtagagacaaagctgttgctatgttgcccaagctggtctttaaact
cctgcctcaagtgattctcccacatcgggatccaaagtgctgaattagcttggcgtgagccgccatgcctggcctagtctggt
gggtgtttaaacctttgctggcttagggtgcatgctgtgtgaagacctgtgggccagagccagggtatcaggagagagacactcagg
cctgttgaatcagctcagtgccacaggctgccacaggcgtgcaagagcagctgcttcaggctctccagccgtgggccctgagcaccagttctgc
tctgctccctcagggaactggggagatcaaggtggggacccctggacctccctaattcagccagagaagctctcatcttccgg
ggtcccagcaggattccctggctggggtgggagggttctgctgcttgtaagtgggggctgggccggcactggtcccggcttttccacc
gccctgttacagacgttacagacgtgctgtgcgactggcctgcggtcggcctgcatggcctggcctgcttgtcccgagtatttgccagag
cctgccgcgtgtgctgctgcaggatctgtctggggctgaagtcagtccttgttttgtcctgcagtgtcagcagggagaaggg
ccttgtgctttcaggatgtcttctggggctgaagtcagtccttgttcccgcatgcagtccaaatagactcctgctcctgctccaggcca
gttaacctgtctgaacctggaacaggaaggaagcgtagtgttcccgcatgcagtccaaatagactcctgctcctgctccaggcca
cccagcaggcaggcgatgacatggacaggccaaggctttgggctccagggaggccaaggtgctgggccagagaccctgctgtatcca
ggtcagggcaggacaggacaggccaaggctttgggctccagggaggccaaggtgctgggccagagacaggcagggctgcaaggtta
gagccaggaagaaccctccctgagggctctgtgagccaggagggctgtggggatgtcaagagacaggcagggctgcaaggtta
```

FIG.1-35

```
gagtgaggggaggggtacctggtgctgccatttggaaggaccctgaaggcaggaagcaggacagacccccgccattggcagaaga
cctctgaatcctgagatacttaaattccctgcgcagctcgagttccctctgctgctgagatgaaggaacagatcgggaggattggctagaacag
tgcatcctggtgggtcgtgttggaagctctctggagtccctctgctgctgagagatgaaggaatggagccctggctctgctgtggg
atgccaggctgccaggctccccgacctctccagcaacaaaatcataaacacagcatatgtaatatataataataaaagtaaca
gccatcttttcagaataatctagcacttagaatgtgctaggaacatacaagacattttctccttattacagtaagccttaaggt
aaatttcatcatctccagatttaagtaaagaatttagaatcagaagacattcacgcaacctggtgcacccgagcctggctgac
cccagcaccgctgctgcggcccactcactgctgccagtctccctgcttcccagtcccagccaccgtcgccgtgagatcctcttgttgccaga
gagcatgtgattgtggggtgcatggggtgcagctgtgtgggtgccctgagctgttgggggtgtcaggttctgccgtgagatcctcttgttgccaga
catgaggacctggactggcagctgtgtgggtgccctgagctgttgggggtgtcaggttctgccgtgagatcctcttgttgccaga
agctgccattggcgatgcgggaggctggcctccaaacttcccaagccctccacagtccacaagatggtgtctgcgaccgtgctcgtgaga
gcctgcagcagacaccatgagccccaaacttcccaagccctccacagtccacaagatggtgtctgcgaccgtgctcgtgaga
gatggcagcaggcagtcccacaggcaccattttcagctgccccatttttcagctgcccagagcaggaaactgaggcagaagccaggt
ggccaggagctggcttccccatttcctgctcctgtgggcccactgcagtgcccatggcccagtgtgctgatattaccgagacttcg
gagctctcacgggtgcagtaattaggctgcatgacacaagctgctggcttgagtcgcccgttatgaatgtgtgtgggtctgt
gccccttttcatgtgctgccacaggcccacgagtgtgctgaaaggggaagacacggccaaggggccatggtgacaggagaccttc
ttggggttcggttcgtggtggtgtccttgacccactctgactgactgagcacctgcccaaggcactgcattccaggccctgccatgtccctgagcctc
ccaccccaggccaccacctgctggtctctcccacacgcgagtctcagaccctccaccatgcaggggtcaccagtctgagtctcaccatgcaggt
caccacgagtctcaccatgcaggggtctccacatgccagtctcaccacaccaccaccacgtctcaccatgcaggtcaccatgggtcaccat
gcgggcctcaccatgtgggcttcaggagcttgctgctgcctttgctgctgtccacttcctgcagacccctccctgggtgcctcctcctggggtctgtaagcctccct
gggcctgagcagctcccagcctgctgctgcccagcccttgatgctgtgcagctttgatgctgtgcagctcctcagcctcagcctctctcagccctttggga
tgtttttttgtgaggaaggaggctttgatgctgtgccagagggggatatagtggacaggcctccatctgtagtgccactccagtgcctgccactccagtgcttcacagagcagcaggctgttt
gttctgagctgttccacctttgtgctgctgccagagggggatatagtggacaggcctccatctgtagtgccactccagtgcctgccactccagtgcttcacagagcagcaggctgttt
ccgctgtggcccataccggggcacacactgcctggccgtgctagctgctatgaagagtgtgctgtgagacccgtgaa
gagacgggaggatgaaattgtgttgccagatagtccatttgttgtttctgagactgccatgcctgggagaatcctggaattaactag
ctccttctct[c]catcccattttacagaaagtgagaccaaggtggtttctgacttgccagagagtcataactgcttggacagtc
atggtcctcagagcccacgtttgctgaccagtgcaggctctcacagccactcagctctgcagcctgctcctgcagccgtggcgtggcagaggaggaa
```

FIG. 1-36 gcacttcctggatttatgtgctccctgacatttcaaggccctcatttctctaaatattggaggagttgaattattttagtt
gagcctcaaggatcagagaataagcttgcagcaacgttggcagatgggcttcttctagcagagagtggttattcgggcctcta
ttgagagaatcgggtgatttgaggaaatctgggtgtcctgaggcataccagaggaccccagttttctgtggctcgtctgcc
atcaggaaaccaaaatgactccctcgtcctgagctctccaggtgtgacctggaatgcttaaggggaggcaatgcatatcttt
aagatgagcacagctccgagcactcgagtggccctgcttaatcccagcacttgggaggccaaggctggcagattgcttgagccag
aatggacagagttggccggttggccgctggagtggccctgcttaatcccagcactctactacaagtacaaaaattggccggcaggatttctgagcccag
gagtttgaagccagcctgggcaacatggcgaaacccatctctactacaagtacaaaaattggccggcatggtggctcatgctt
gtaatcccagcactttgggaggccaagagagcggatcactgaggccagaagctcgagacctactacaagtacaaaaatattgaacctggaagtagaggtt
agccaggcgtggtggctcacgcctgtaatctcagctactcgggtgctgaggcaggagaatcacttgaacctgggaagtagaggtt
gcagtgagctgagatgtgccactgagctctagcctgggcgacagagcaaacctgtctcaaaaaaaaaaaaaaattagtcag
gcatggtggcacacacctgtagtccagctactcaggaggctgaggtgggaggattgttgagccagaaggttgaggctgcattg
agctgagattgcaccactgcactccagcctgggcgacagagcgagacccgtgtctcaaaaaataaaatagacataataagagtacc
taccacctacggctgggagacagaatgagatatctgcaaaagcactcaccgcactcttcctgcacacagcaaggttcagcag
ttaccccgttctgctcattttctggtgttctcatcagtagtatcagcgccgttcatgcagcgcgtgctgtttctgtgtcgtgctttcgtggagatgctgtg
agggtttacctgcagtgcctgcccagcgttcatgcagcgcgtgctgtttctgtgtctgtgcttcgtggagatgctgtg
ggtgggtgggcaggtgtgcttgtgctgtgcctcccgagacaagaggctcccacctaagcaggtcctgcagccaggcacat
agccctgcctgcctgcaggttggcccctcacacggctaggggcaggggcggcagggacttgcgcgggaccagcctggt
ttctccggttttgcttgcttgcttgcttgcaggtccgcaggtgggccagggggctgcgcaggatgggcctttcaccactgcctgagcgctgcc
caccaacccactgacggctctcagttctccttttcccgagcgctcagtttgcaggtacagcacagcctgtgctcctggccc
actgcctgctcctttaagctgagttttgccttttgcagttttgcagttttgatgactattttctgggatcgggctgctgggtggcctc
gcacaccccctgcactttggctgcctgaacgtgacttgggttcacgtgctccatggttttgactcacagaccgggatcggctgctgggttccagcagc
aggggcagagaagagagccatctttccagccgccctacagaggccccggacccccaaaggctgactgaggttgccaccaaacag
ggggcagagtcctctaagttctgcctagatctagcctcaaggaaatgtttctccagatctccgggagttgatcagagaggaggccaacctggctcactct
ttagcaggttctgacacacacagatgccttttagggctcaagaaatgttttattattttaaaattagaaggaaaatatctctgaa
catttagggcaagaaatgttttaatgtttttctcatttgaaataataattcaaaatcattaattatttaacagctt
tttaatggaggaagggccccccaaatcacaaagtgccctggccctgatggccggaggagagctgccataccacgcagtg

FIG.1-37

```
tgcctgagtcctggagtgcgatgtattctgagccaccagaatgtgagtcaccaagagagcagcttggagtgggcctgccct
gcacactgtgctggggacacagccgacacagcctgcagtaccaggatagacaatttggctggagccaaacttgatcaga
gggaggctgactttatcgagggctgcttgtggcggggcgttcattgtggaaagagccaggaaggagctctgccttgcaagaac
attgcctgtgctcaaatggccacatgggatgcagttcctgagtggcagaagagccagcctctgctagcccagacctaacga
gttgcggctcatgccacctgaggaattccacctgggcgtttgtgtgtcctagcatatctgaatgcagctgagctcgaaag
tctcatgcctgtctgcagaccccgcgtgagctggaccaccgtgggacacagtgtgtgtctaggcaaatgcttggcactcg
aggggcactgaggcctgtgtgggtggagtccatgacgtcatcctcagtacaagctacgagggcttcttaga
acacgctggacactgggagggtcttaatgtatttgcacaaatttggagaccagagtggagtgggctgggcgggcca
ggcccggctgggatgggtgacctttcctcaccctactccgtcaagggtgctgcctcccagctcctcctacctgggaga
tgctgacatctggtcattcgcagagtgccctgtgccacatgtccctgtccagacatgaaacgacagcagaggggctttg
agggtctctcctgagacacctctccagctgagcctgcctggagttggaagccctgcagactcgtgctgcctcaccaaaggctc
catctgcattttgccccatgaccttccactgtgcctggaccgcagtagagctgaccagcacctggggcagtctgggtctggg
gctggcgttcggcagccagcagatgaccacagatgcctttcagtggctctgtgggcacggcttgcacagatcgactgtgaccccag
gctgtgggactcagccaccaagcgcttcacttattactgacctgaagttatccagcacttatgtgttacagatacctgcaca
acagccagagaggtacgaatacatttccactacagtgaggcacagagaggttaggacccacctgaggggatgcagcagagg
tggactgggcctggcagtctgtgtttccagctgtgtcagcctgtgtgtccagttcagctcctggactggagagggcgctgggaaatg
gagccgcctcctgagcctctgcatcagagcttctcctgctcagtcagaagaccttggtcccatccagcctgtgccaccggggaccagagggc
aggctggtaccagctgggaggggggagtaccagaaccctggcctccttgcctcctccccagccctgtgcacctgggccagcagg
ctgaggcccattttccagagagcccacctctgctcctcttcccccacgtttcatgggttttgtgacgcgctgcctttcatcagtggt
ttgcctactctccctgccctggctgaccgaggctgaggtcctgcacatctaggcccgtcacgtcgttcctccccgtcctgctgccatg
gtccagccgtctccctgaccgaggctgaggtctgcacatctaggcccgtcacgtcgttcctccccgtcctgctgccatg
gctcttgccacagtgggatgcagcagctctgggttgagtgtctgtcactgcgtgtcctgtgcccctgagctgtccctgtgagtggggctg
ctgtgccacactcactgccaccatgccaccatcccaggtgtgggccagcggtctcaggctgtacctgtcaggggctgata
cctggacagggcctgtccgaggttgactgggagagaaaatgccccccgttccagctcgggcagtacagcctcatcctcccaga
ctccaccctcctgctccttcctgtatgccccacaagggttgcaggggcactcccagagggcactcccagagggacaggagttgtgcca
acctgagggtagacactgctgctcctgtcctccagaccctagacaccccgtcggccagtgcgggtctgccagatcccacagcca
```

FIG.1-38 tctttccagcgaggacagtgcaggcgcaggtggctgctgtaccgtggctggtgatgtgctgactgggaacggcagagtgccctggg
aaggcggaggtctgggagcccacaagggctgagcctggggcctgagggagttctctggctcaggcctttctggag
atgggacttctagttgccaggggccactagccgtgaggagttcagctgcccatggtggcggctggctgtatcttgcacttct
cagctgtgtggagggggtccgtgggcctgtctgggccagcagcagacacatttttatatattttggattctatt
aatcctctagttttgtacatttttatgcaccttcaatttctttaaaattaatatattttttttctgataataataaga
aatgcatgcctttctttggaaaatacagaaaatcacaaagaaaataatcacacttccaaaagaaccacagttagcatt
ttgttcagcctgttttttaaaaacaaacaaaaaatgcatactaaaagcaacgatttataaactgtggttgtagagttaagc
tcataccagagttgccggcatctcaccagttcctctgcgaggcccttcccagagctgccttccagagctgcctgcctgc
agccaagctggtgacagcagtgggtgacctgcgaggcctgtgatgctgagagccagcagagctggaggggta
gggcagctccccagagctgatctgacagacgggtatgtgcctcaccggcatcaccaccgggaggcctcgtccgcccccat
gcagtcatgctggtccccccatctcgtctctgggaatggagcggaagacctccctctcgaacaggggtgggaggac
tgtgctcccagaatgaatattccttggctgtgggtgagcctgcagccgagccccagggtcaggagcagactggcagggc
catgcaacgactgggaacctgggagcagtgctcaaggccaggtgtccaacaagtatgggcattgagatcc
tgggtgatcagggagcaggctgctcaagctgacacagccaagtgtctttattcaccatgaggttgtgtggctgagagcgtgc
gccaacagtctcacctgcagggagccgttgcctctgtggccgctctgagtggccggctcgtgttctgtctctgaagtgggagaaggctgc
agagctctgggcacaagctctggctctgtggccggctcgagatgagatgcagaatcagtgtttctgtcctctgaagtgggagaaggctgc
cccgtcacgggaccctcacagtgttagatgagatcgaaggcgatcacatcgagtgttctggccactgtgggcgagtgcatatgtgccaggct
cctcctggtgcagacaccatcacgtggaaggcgatcacatcgagtgttctggccactgtgggcgagtgcatatgtgccaggct
gtgcatggcggcctgggtgggtgcttgagctgagtgaggaacttctctgagagcttggtgcctgccacctcctggtgccc
cactctgagatgtgggctgttgagctgagtgaggaacttctctgagagcttggtgcctgccacctcctggtgccc
gccccagacagagactgtcttacagggctccacagcccttgctgccccgaagccccttgcagtgaaggggctctgtgtgcg
gctccctccagatgacaaaaccaggtttgatgccggggcctgagtcccggcctgagtcctcgctgcttctctaagcattcctttcctgtct
ggaaagtggggtgtagtattgcgaaactcccaggccatcccaggatgaactgaactgagatcatgccataacatagacttccgcctg
gtccctgctcagagctcccgatgtcattgcgaacctgtcacactctaaacaaatttttcttcagctggggtgctgcggccccctgcagcg
gtgccacgcaggcagccccatgcacccaggcaggaagctgctttgtgcaggggtctttgtgcaggggcagtgtgggcagctggca
gcctcctgagcgcggcaggactatgcaggcgcttattgagctgtcagcgctgctgctcccaggtgctcccagtagcaggaagaagggccga

FIG.1-39

```
gctccacgtgggcatgaaaggccagcgggtgtgtcaggggcgggtgggtgggtgaagtgttagtgcgaatgtgagtgtgtgca
cgcttgcaggataaagatgagttttaaaatgtgtcctgtggttttgattttttaatcttttccaaaatcaatacaaacaa
ccacaggcataattggtctgtaaaggccgacgctgtcattctgctgcagagggaggggaagttcagttggggggaaatgcagc
gcttttgctgtcattaagtccaatggtgctggctgcgcctgcgacagtcagtggctgcctgcgctcgctggatgctgtccaag
accaggcgtgtgtgtttccggtgtgatgtgagaacccagggctcgctggctgtctcctccctcctcctcctccctcctgccaag
ctggtgggaaggccctgccaaagcgcacaagacccccttcacacagcagggcacaagctcttcgaggcagagtgcctgcaggtg
gggtggaagggtgcgcccagacccaagaatgcccgcctctccaagacatccctggctgtgtggtgacagggtaggagggttg
ttggcacctgctgtggccgggccctggcggccctggggcctggggttgttccttccttcctgtacacattgtgctctttgctgggtgcagccaccacgtatttctcaagggc
ctgtgctaggccctgcggcggcctgtttttttgttgtttgtttttgttttttgagacggagtctcactctgtcgcccaggctgagtgcagtggcgcgat
ctcggctcactgcaagctctgcctcctgggttcacacacacttcctgcctcacccctcccgagtagctggactacaggtgcctgcc
accacgcccggctaatttttttgtatttttagtagagatgctgaattacaggcgtgagccaccgcccggctcaccatgcttcgttgtatcttg
acctcatgatccgcccgctcagcctccccaaagtgctgaattacaggcgtgagccaccgcccacctcaccatgcatgcttcggttgctgtt
gtgggtaaggcaggtctttctatgaccacctgccagctccatcatccgtgctcccccacctaacagtagaagtacggtgtatttctacattttcagg
tgtccacaggctacttactttgttttatatcagtttttagatacaaaaatagtacaggtagaatacggtagatacggcacctcccgctcttcacctctccgctctccccacca
gaatatcacatcacacacacgctgctcttttcactgttttttcatgtttttctgcacacacacgcgcacacacagcgcacacacaaaaagggttgtcctgtttg
gatttagctctgttaaccttcaggcttctttttgtccttgttcctcttcctgttcctctgttcctcctgttcctgtgcaggtgctccagataccacttttctaagtca
gttttagaaatggaattgtcctgtctctctgtgttcctcttgttcctctgatcgctgagctgtcgtgagcggcgcacacttgctcatttctgtgtgtggagttccagttcatt
ccggcagaagcaggacctttgtgcttccagagattgttagactgttttcccttttcattacaaacaaaaaaaaattgctttcttaaact
cctgcagtccccctgttaacagatgttttcactgtgttagactgtttcccttttcattacaaacaaaaaaaattgctttcttaaact
tattttcatgttttttaaacttctagtttctcataaatattcactttagattctgttgtagttctgttagtgtcaggctttgc
agaggaaaggaaagttctagaagagttgcagctcgactgctcgtgttcccccccccaaccctgggcctcccctgggcctgtggggagtgagcatgca
aataggtgagcttctgtctccgctcctggccctggccatgctgagctgtagctgtagcttgcctgaaagcggaggaattctggctgctgctggggagtcgggc
ctccctgaaggccaccgccaggagaagcagtcgaggagggctgctcaggctgaccagcccctgaccagcgggccatcgggcgtcct
tgccctgcaccgaccaggatgtcgttccagtgatacacagcactttcgttcttctaaactgctgagtggtcagtgttatcagctgtcca
gggcccctgcaggcagccaggatgtcgttccagtgatacacagcactttcgttcttctaaactgctgagtggtcagtgttatcagtgtcca
```

FIG.1-40 catatattgcataatctcagatgctggcttgtaacagtgagtggaggtggccacactgtcccttttagaataatccacatggc
cctgtccaggcaggcagcctctggcctcccgccaccgcctgatgcctgtgcctgctggtgagcctggcctggcggtgtgtttgctg
tggatgggtgtgttccgagttctccggtcagcaagctccctttgtctctagggagttcctggagttaaagggagccttttcaa
gccacaagatcaccccagaaaaactacgtaagcactaaagttcagaaaaatcagcagccttgagctggggagactgcttcccttt
gggcccggccactccagagccattccgtgatggtaaaatgagtggggccccatgtcctctctctctcctgttgctcctgtgaacgccatcct
ctggttcttcaccttcaggctccccgatgagctgggtggttggttgttaactcctctctctcttccaagttcccaattttgctctactgattt
cagagctccagggagctccaccatagccagtagagaggaggcctctgtttactcctgttgtcgagtggtgggtctcagaacggcaggctgtccc
ttgtctgcggtgcataatcaatcagcctggacctgcacctgctgactgagcaggcctgagacatgtttctggggttcctgcttggcctgcacggctgggtggg
cctcctacctcggggccccactgtgctgctcactgagcaggcctgctgtttgaccacctcgggatcaagatgtcctgttagatgccagta
agagggcatgggaggtgatgctgcggcaggtggatcttcgagaatggagctccgaggacaggttggctgatctcagtgaacctgaggcttc
gagaccctgctggcgggcaggtggatcttcgagaatggagctccgaggacaggttggctgatctcagtgaacctgaggcttc
cccaaggccatacagcttgtctggcagagcctcagcagcccggctcccgacccggtccccgacaccgagctgctctttctgtgctt
ctcacagaccaaggtggatcgcagcttggtagccttgaagtctccctaacctggcaagacagtggagaaggggacagcagcg
ggacattccactgtagaataaatacatgcagcctcaaaacacttgacatctattaacttctaagtgcaagagtgattcttgtggtt
agacctgaatgggaacttgtaagtctaaagtgcacacagtgctcacatctgtattccacaaaacattttccgcaacgcattgtggaca
taaaggtttgatgaatgtatagccaggacccggcaacatagtgagacctctgtctgtctctatgtgatgacttgagctcaggaggttgaccatgatttcctttctaatctggggttgctt
gagcacaggatttgagacttgagctctggcaaacatagtgagactggctctgtctctatgaaaaaataattagcagggcatgacggtgtaaca
cctgagcccagctactcgggaggctgagcagaggcagagatcacttgagctcaaaaaaaaaagatttgccaatgaattttatcagta
gtagccatgcactcagcctgacaacagcagaccctgtctcaaaaaaaaaagatttgccaatgaattttatcagta
aactggatatttaagagaaaggaagaactccttatctttgagcctgttctgaaaagcttcttcttttttctcactttta
gtcttgttagcaaacttaacagttcatagaagaatcattttttccttacttttttcccttaatctgacacaacatctgggggttgc
catggtggtccattggtgttgttcaggacgggaccttacatctgggaagggctgccaggctggcctgcctctgcctgt
gggcatggcccggggtgggcatgcccggaaagcatggccttgccttgcttttctcatctgtaaatggggggtgcaatgccctagtagttgaatgtt
ggcactttgggacaaatgaccaccttctggagcctggcatggtaacgtggccgtgaggatgacgctgcctgccagggactgggtgg
aaataaaatgaagtcgtctgtgaagcacctggcatggtaacgtggccgtgaggatgacgctgcctgccagggactgggtgg
cacaggtgtcctgaccttggcatgcagggtgatgggccagcttccagccagtgctgatctcagaggccagggttagagaac

FIG. 1-41 taaggcctccagccaggctcctgttgcaaatgacttctctccttgtgtgctgtgaactgggcgtgaacacctcctgtgatg
gggagctcactccttgccagggagcctggtaaggctgccgcacagtcatcctcctctctgacctgtgtcttatggcc
tctgccccagcagctgcgggcagggggctgggtgaccccgtctgttggttgagccctttcactagctggagggtgactgt
cccccttctccccgacacaaggcacagccttttcttggctgtcaggagagagggcctgtctccttttgcgccacgctgccc
tgccttgtggcactgcattcaaagtgagtgcgctgcttctttcttcctctagaacttctgaaaacgtgggtggggagggt
gtgagggttcgtgcaccggtgtgtggctgcagtggcgtgaggcgccccagagggcagaggcgcagtgtgttatgtgca
cagggccgttccttcctctcatgtgaacaccagtgtacaaatgtgcacacaggcgtgtccccgcgcttttccctacc
ttggctgatcgtggggaagatagactcacttccctctccaggcgcgattcggaaaggaggctctggaatgcagctggggca
gggaagcagggcagccaggagggaccttagcaggcccacagagtctgggacagctgagcctctgccacgccctgccatcc
tgtgtgtcccaaggtaacgtccaagctctgcagcaggaccagcgccctggtcccacagaggagctggtcagtggtgactag
agctccgcttgtgccagtcagtgcagaggcccgccagccttcctaaccttgcgtctgggcctgtgccagctgttcggtctgcg
tgcctgttttctacacaacccatctgtaaatggggctgggtttcctgggagatggctccccccagccctgctcctcctgcacctcca
ccagcattagcaccagtgtctcatgaagtgggctgggctgatgagcaactcgctggggccccagagaggcccatccgctgggcacgccca
tgcgcagaaggagggcagctgggctgggacccccaggctctgactctccacccctcctgtggtgacaccatcagcaag
ggtccaagcctgtctgggcaccccaggctgacccccagcactgaccccagcccctccctcctggtgtgactcttgctcacgctgcctctgcagg
tttggcaccccccgccctcacactgacctgccagcctgccagcccctccacacttcctcaccagatcacagaccctgggtggaggctggtgcgtg
gtggggcgggggggcagagcctggtggtggaggccatcctcagcagggtcccagagtgggacagagcttaggaccccaccatgcgg
gggagtaaggtcaggtggtggatggggagaggctggaggtgagcaggagtgagcagaagtgcagccgcggcttggccgg
agggccagggtccctgggaagagaccacagctggagggcagttcatgcagggaggcaccctccctgccggcttggggagcaggc
cccccgggaagagaccacagctggagggcagttcatgcagggaggcaccctccctgccggcttggggagcaggc
aaggtccctgggagcaggctgcccacctgcagtgcttccaccagacgtgctgagggccagtgtcccatcaagcc
cccgggtggcagcttcctacagtgcttttcccaccaggaccgtgctcacctgtcttcctgtgggacctccagtg
tcccactgagcacagcacgtccatccctttccacctgtcacctggcactccaggcctgccctccctcctgcctcttgccc
cccatccctgcttgtcagaaggggctgggagaatgcaggcctggactccaggcgtgcactccaggcatggcagcctaagcacttt
tccagccttttcccaccctggaagtgagttcatgttaatgcagcagcatgtgcaccaggcactctgctaagcacttt
atgtacattcttaaattaccggatcccattacgaaacggagttcttaggttgaaaaactacttgaccaaggtcatcccagctgta agtgcagagcaggcccctgaatcaggcaaccaggctgatcaccacctgccaccaccacccctctctcacatacaggctctag
gcctcctgtctatactggatccccacagcagatccacatggagctgtctaaagaagcacctgccctccccagacaaggcaag
aaagccatctctacctggaggagagcagtgagggcatcattaatgggctgttggtgtcctgattctttgagagaagacgagc
tgagcaggcacagctcttaatcctccagccactgccccccaggctgggcctgcagcccaaattgaaccccctacctcaaatcg
ggtctagatgactggacggtggctgccagagaccatttcaatagctatcctggacaatcaggacgatcccttactaatttatatgc
cagcccagcatgaggccctgaaagtggcaacatttcaatagctatcctggacaatcaggacgatcccttactaatttatatgc
tatacgtttgggtttaattggagctgtaattgtaatccatatgctgttaaggtaattacacttataaacctaatatataatccataga
tcaatggttttggagctaattaaggacgccgctcagcgtcctcgcgcctccagcgtcttattctgcacaaggggccttctggggacctcg
tccgagctgataatgagcgcgctcagcgtgctgcttttagcaccccaggactctgatcaggaccccagctgatgagtgcagcaccatgggaag
atgttggagggcagtcagtgctgcttttagcaccccagagactctgatcaggaccccagctgatgagtgcagcaccatgggaag
ccagtccctgtgacttggccatcccagaacacggctgatttctgctcaatagactcagctgacaaagggaacttggagaa
agagaacaagaaatccatatgctgagctgggacagaaccaagtgggttctcatgtgggagcatatgggctttcctcctgcc
acccctgcacctgcagcaggatgcacctgagctcgacctgaaacccaggaaaatccaacagcgcaccataggcca
ggattacagccattctttttttttttttttgagacggagtctcgctctgtcgcccaggctggagtgcagtggca
caatctcagctcactgcaagctccgcctcccggttcacgccattctcctgcctcagcctcccgagtagctgggactacaggtgcc
cgccaccacgcccggctaatttttgtattttttagtagagacagggtttcaccgtgttagccaggatggtctcgatcctctgacc
ttgtgatccgcccgcctcggcctcccaaagtgccggattacaggcgtgagccacgccgcccggcccctcctcgttcagatgtt
gtatgactcccggtgatattgtcacctggagctgcacagagaccccccgggcaggccctctgttcttcctgctccagagaggagt
aaggggccaccacatctgtcttaccacaggctaagctgttggcatctgttcttcctgctccaggagggacagagcccccctgt
tgtccttgcgcaccatgctctggcacctgggaactgggcctcctgtggaactcatgtagtcttcttcgagagactccactgcgata
gaagaggcctgcagcctgtagttgcggggcgtggtcagcctggtcagctgccttacagcttccagctgctcgacatttacagctggg
acgacctgggccaggtagaggttttcaacctaagactcagttttatgtattcagttcatttattatttattcattttattgac
aggtcttgcttgtctgtcacctaggctggagtggtgcagtggtgcatctggtcactgggactcactcctctgactcaagtgatcct
cccacctccgcctcccctgggtaggatgcatgctgagtgggactcagtggctcaagttgtgatcctcctgccttggcctttaaaattcttg
cagagacaggtctccctgtgtgccaggctgtcctgaactgggctcttgaactgggctgatcctcctgccttcccaaaatactggg
attacaggcatgagccactacacccggcctgactcagtcagttcctcatatgggatatggcagttcagtttaataatgtgcatgcagttag

FIG. 1-43

```
cctagtgccggtgcagagccactgcttcattaatgctgctgctgtcttgtcatctctatcattgacagcctagacgagct
gaagggtgggccagtggaggggccagtggggcggccagtggctgtgtctgcacctcgttttccatctctgggcttactcctggtgggctgttag
cttgcgggtccagggctcactttgccccatcatcattctgtacactttttccatctctgggccttagggcctttccaaagac
tttgcaactctggcagatatttctagacagaattagttcttaacgaaggaatgaggcaaatgtggacagagattgttcataat
tgcggctgtcattattgagcacctgctgtgtctcttagcctctgggctaaacactgcacagacataattcactgattgccaaca
gcagcttatgcggctggcatttagttcacttagggtgaggaaactgaggctcagagaggctgaatcactgttgagtacgt
ccagcgagggcagctgggccaggatttgaagccagcattctcaacaccactgtctctgcctccgagtggaggcctgac
cccttgctctcttcctggtgggccagtgggatgggtgagggtgagtgtgtcaatgtttcctcagccagtagtgagaaca
ggcagggtgggcgaactcctgctgaccacagcacagtccctgcaggagcaccctgccaggcgagtgagcactgtagtctgg
gagacctagagtgagatggggctctacaaggcacagctctcctcctggagggaggaagggaggtttcctgcctacgggc
ctggccctcccccacttgtccaaagcccggctgggtctgtgtcagcgcttgcagtacacctgtgctgctaccaccaacctgt
gtccccgtctgatctccctgacctggccttattggagtcctcctttgctttaagtacttgtctatctgactgttaggctcttgctctgcag
agggcacctgtagggctggccttattggagtcctcctttgctttaagtacttgtctatctgactgttaggctcttatttttcaaaaaa
attgtttcatatatttatctgattttctagttgcttaagtaaaacactgacattattgagctcttgttctgggctcagttctgcc
aattcaatataatagtttgcattttttcttattgataataaaacactgacattattgagctcttgttctgggctcagttctgcc
ccgagctgtttgtacatgttaccttgctgaacctgcacccaagtcctcaggccccatatcccctttacagatgaatgaagtcactgg
cccgaggtcacacagctgggacgtagtgcaacaggctggcaacaggctgcaaaggccacagttatgatggcagaggtaaaccaccgaccagccactattattggtgcttac
atgcactggctcatttgtctctacagccttgcaaaggccacagttatgatggcagaggtgtattcaaattcaggccctaaa
cttgtctgtgttccctcttgatgcgctgacctctgaaaacttcagtaaactgaaactttccacccttccacagttcaccttgacatctcatcttgcggatcgtattcaaattcaggccctaaa
agtgacggtgacctctgatgcgctgacctctgaaaacttcagtaaactgaaaagcacagttccaccttccacagttgcacaaaaatgtgtcctctgttcttctagtccacagtg
agtcaggagcacaggctgtttggacatctctccgtgtggacgcatcctaaacagtccttagtattatgattagatgctccatgtg
gccatcgttttaatgctgaccctgctccgtgtggacgcatcctaaacagtccttagtattatgattttgatttttgctttaag
tttccaattcttcattattgtaaaccaactgctgctcatcctgtagcatagcttgcactttgcactttgattttttgctttaag
ataacttctcacacatggaattgctggtcaaagggtatgcaaaattctaagtgtttggtacttctgcagaattctcccctccaga
catcaagttgctctccatctgcactgtgatatttctgcaactctgacaccctcaccaacaataacaccgaggactagcagtg
tcatttttaaaacgcgcctccatcaatgggaaagaatggatcttctttgattgataatgagactaaaggctttttctgtcttcc
```

FIG.1-44 tcagtcgctgatatttgttttcttctataaattgcatattcatatcctttctagtcttttttgtatgttttttaaacgaaggctct
tctttaatggaaatctgcatttcatcaaagatggagcgcagagtctgtggttcatttattctggagaagatgcttcttttttg
ttctctaaccaatcagagaccagctgaagatgctagcaaattaattcaggcgcagagacaggcgtcggtgctcatgaggatc
ctggctgaggaaatcacatttagtccaactcctgaagtgttgaggccgcctgagtccacggaccagggttcaaatccca
ctcggccacttcctagcagcatgactttggatgtccctcagccatcagagacttcacttttctggctgtaccatgaggtgt
gtgcagtttaaaggaagtttggacgcgtgtggtgtggatagttctgagtgctcagtaggcagaccctggttttgagctgatagaaa
ggcccacgcgacggcagagctgggcctgccaggctgcactcagtagtgctcaccaaatgcctgttgcacaaggatggtg
cccaggtaacctgggtgagctacaaaccagagccgctgacgagttccaaaggaactcggcgcactagccccttgttgtgt
ttggagtgggagtcaccgtatagcttatttgattactttttaccatatcctcaggaattcaaggacaaggatacat
aacaaaatgatttttgtctcagataaatcacagtccacttggaaaatctccatcctagaggaggtgaggtgcaggtcttgggg
tgaggctggggatgaagcctcccatgactttgtggttacccctgctggtgggctcactcctgcagggccattggtggagtcacatg
atgccaggcaaggctggccaagcaggtacagacacactggggaggatggctgccgaacacatgagccgtgacatctagtgagcttagggc
aggatcccactggggtcttggcgtgctgagcgtggtgagcgtgttgcctgggctcctttcatgtcagcgtcctgacaccgtgacactgcgca
atggcaggggtgggtgcgtgcttgccctgcagcctgggcgcgcctggctccatcttctgcttcatctgcctggctcttggaggtgtaccagc
tggtcacatggaggagaagcagccacgggctgcctccgtttcttgtgctgccagcagatctagggggagcagatcagttccacttcctagtggc
tgtgagggagaagcagccacgggctgcctccgtttcttgtgctgcagcagatctagggagcagctggaaaggctgcctgtggcctccc
ctttctgtgaggagtcatagtgatgagtctggaagctggaagctgagcctggcttgggagcagccaccacctagtggcactccagtgggcccacgagc
tgagtggacgtcctctagagttgttgttcagctccctgtcccagcagcaccacttcagatgagggcgacaggaggagcatcactcacttgccaag
cgcgtgttgctatgcacagcccttacgagaatccacttcagatgagcgtgctgtcccgcttgcgttggagcgtctcagctctcc
gtccacggcaaggggctctgagtctggacgtggccttcagaagcagaggcttccagggcagaccaggaagcctgagtgggcatcct
caagagtgtgcctttgtgtcgctgttcagaaggcaggggcactccaccatgctaccaaccccatgcaccccaatgtgaacgc
ggtcagcctgtggggtgggcgagtggcagggggcacttggagcttggtcccattcctgttttcttacgtccagtgtcaagc
acgggctcaggactcacttttattttgtagagcttggagctccagtgggatatttggaaaaatgtcaaggcattcatttttctcgacttttctgttg
ttagtaggacagatgtctcagcaaacaaactagagcgcatcgagcaggccctgcgccatatgcattccatgctagcga
aaccaggccctcttgccaagcacttctttgggaggatatttggaaaaaatgtcaaggcattcatttttctcgacttttctgttg
gaatcgtggggcttaacactgaagtaaaggagttataagacacagctggcttcctgcaccggacagcccagtggccaggc

FIG.1-45

```
ctggccctattctccatctggccctcggtggtttctgcagaggttaccatgcacaagggccaggccgcggcccccacctatgtgc
aaagaagttgcaatgatgtcaggtagcaggtgcagcgggcaagtttctgaccagtttctaaggacacaggagactcgag
gagggaggaccagcagaggacactctatgggtggcttctgtgaaacagtgctatctgaagatgagtttgaagttaggaatg
tttgctgagttggcctggatattggaagtgccctttctttgagccctttggctctcttgcgttgaccatctgctgtggaacat
ggtgggctcccagagcacctgccctgtggtgtataccagctggatctcagctacacctacgaccctgcactggtatagatttgg
gtcccagttcccaccaggggctggctggcttcccacaccctccagcgaagtcacatcacaagttgtggaaatg
gaggtcaccaccctggccacagagtgaggctgtgaggccagagtgtacctgttgggatgctgcaacacttgaaatccggct
gcccgaggctggaagccgtcttgctgctatgtcacgtaggataatgagtggactcttttctcagtcctggaggacttcctcggcc
agtctggagtaagccatggctgcacctttgacctggaagtgctggttttcctgcatctttgtccttgtggcacaggcct
tcccttgcaggccttgcacctgtctgggtgtgtgccatagccagtgtagctcgtgatcagtcggactagcgca
ttttcagccagcgctgccaagtgctccctgcaatgtgttgccacctgaggtgccacccaaagcagaaaacctggggctggcaa
gacagcagctttcaggagctgggaggaggcatcatttccactttccaggccctgcgatctggtttgtagcctgtaccaggcactg
gagtcctgccttggcacagctcatggtctagaggaataacctcaggtccaggtgagacactcagcctgtgatggcttcatatggtc
actacgttgtatatggagagaggactcttttctggttttaattttataaatgtaatatattcacatgaa
aatttgaaattataaacaatcaaaagaagcagctaaaaaagtcctttcataatccaccgcaacatcagttaacatgtggcat
attcttcccgtctcctccactcccattttttttgacttctttaaacataattgagattgtttatgtacaatttatagcat
gtacttgttagctttgaaacagacaccatctgcgtttgcaattggcctgcagggagcgccgtggctcttgttctctccctgtcagtaca
tgtgggaaggaaatctaaaaatacccctccagtggttccgtggtgtgagctgtgcctcagagaacatgcagagggcctggggtttggctctgccgagg
gcagaattagccatgactgactcagatgagtcccggggtcttctgcagagcgaggctgagcctgccaactacagagggcctggggtttggctctgccgagg
tgagcggggcactagcctcaggggctctccgggtcttctgcagagagaacactttgagggagcatctgtagagactcttccacttccagcagatgagcagaa
agcccctctagggctctccctggctgcaagaggagaaatcaaaaccgtgagaggagcatttagagactcttcactccagcagatgagcagaa
aaagcccaccctggctgcaagaggagaaaatcaaaaccgtgagagagcatttagagactcttcactccagcagatggagcagaa
gtgccttttccctattcctcctgccaagtgcaatgaaccctgaggatccagaggacagtgagagccgcagagaggagaaggaaggag
aggaaggcagactgaccaggagagccagcaagagcctgcctcagaaggttcctttgccttgcacat
ctcagacgtgagctgagctaagagcagcagaagcagagacctctgcctccctggcctgaaggaccaagcagcagggcacctggc
gagacagaaacatttaggcaataactgtggtactccagcaatgtggtactccagcaacaccacagaaaaccctgtggcccctcagccagtctactgtcagt
```

FIG.1-46 caagggctcagcaggatcctgaccaaaacactgaccaggctgaaatgagccctaccactggggtgtcagagaaggccaagga
gggagccaggacaggtgggaatgaggtcccccactgacgggcagcatcatactgaagagtcaggacttcatcgccactcagaggttacaa
tggtgacaagacatccctccctcccactgacgggcagcatcatactgaagagtcaggacttcatcgccactcagaggttacaa
ggctatccgccccccacaacagtgacaatggagcccgcatggacacagtaatgagggattcctgcacctcccaaccaggggaa
aacttcctccttgaagagcagtaatgagagcaccctcttccctgcctgagttgtgtccagagaaggccactgaaaggaaggtttaaataa
cacccaagacagaataaggcagcactaccctcttccctgcctgagttgtgtccagagaaggccactgaaaggaaggtttaaataa
gactcagagtctcacacacaccacccaaaatgtccagcttgtggtacaaaccacctgtcatgctaagaaccaaggaaacccaac
atgaataagaagaagaaccaacagaccaccagcactgagatgacacagatgtcagggcaaagactaaaacagctactgaaaatg
cttcaaccagcaattgcaaatatgctcaaaacaatgacaaagtagaaagtctcagcaagaaataagaatacagggccaggtac
ggtggctcatgcctgtgatcccagcactttgggaggctgaggtcggtggatcacttgagcccaggagtttgagaccagacctggc
aacacagggagaccttgtctctacaaaattaaaaaattagctgagcatggtggcacacacctgtagtctcagctacttaggaggc
tgaggtgggaggatcacttgagcctgaaagtcaaggttgtagtgagctgagatcacgcactgcctccagtctgggcaacaggg
tgagaccctgtctcaaacaaacaaacaaacaaataaataacaaatagaatacaatgaagagccaaatgaaaatttagaactgaaaa
atacagtagccaaaatagaaaactccatgatgggtttgacagcagaatcaagggacagaggaaagagtctgtgaacttgaaggc
aggaaaatagagatgaccaatcagaacagaaaaatagactgagtcactgaggaaaatgaatgaacagacatttcaccaagatgatatccaaat
agcaaataagcacataaaagatgtcatggctgtggtggctcacacagctgtaatcccagcattttgaaggctaaggtgggatcacttgaggcca
aatgctaaaataggccagcctggccaacatggcaaaaccctgtctctcttattaaaatattaaaaaaatatataaaaaattacctaggcatggtggtgctcgcct
ggagctcgagaacagctggccaacatggcaaaaccctgtctctcttattaaaatattaaaaaaatatataaaaaattacctaggcatggtggtgctcgcct
gtaattccagctacttgggaggttgaggtgggaagatcacttgaactgggaggcagaggttgtagtgagccgagatcatgccact
gcacctcagcctgggcgacaaaacaagaaagatcacatctaaaaaaaaaaaaaaagaatgactaaaataaaataaaaaaatgcc
gatgagaacagtagagatgaatcactcagacattgctggtgtgaggaagttaaaatgatacaaatgctctggaaaatagcttggcag
tgtcttaaaactctaaatgtaaaactgtcacatgactcagcatgcatggtactcctggcagttatcagagaaatgaaaatttatatt
tacacaaaaacctatacacaaatgttcgttgcagttttattgatatgcccaactagaagcaatccaggtgtccttcagtggg
tgacgagaggaactacatccatgtcatgcaatgtactcagcaataaaagaaacaatctctctcttttttttttttttt
ttttgcataaatccagatcctgcagaaaaagaaacaaatttgatactcacaatgactgatgactccagtgaaaaagcct
atcccaaaggttatgtgtactttctgattccatgtata*gaacatcctcaaaatgacaaa*attctatcatgcaaaacagatactgttg

FIG.1-47 gatggggtggggcggggcaggagggcagtgggcgtggctggctataaagagcagcctgagggtcctgagtgtgatggaaagcttctta
tttcactgtatcaatgtcagtttgactttgatattgttctatagtttgcaatatattactgttaagagaaactgagtcagtgg
cgttcttacaactgcatgtgaatctccaattagcccaaattaaaagttta*ctaaagcaacaattgaacaaga*
aaagaaaagcctttgtacctagcaaccagaatgcctatgataagtgcaggagctgatgacagcagtcttctggttcagaacaat
gacaactctggacaagcatgccgctgggagaaagagaccagagctgcacagcagatgctgtctgtcaccaggctgagt
gggagtttggaatggttcatcattacttttttatattaacacttttttttttaagagatgaatgctctgtcaccagctgagt
gcagtggtatgatcgtggctcactgcaacttcgaactcctgggctcaagcgatcctcccacctcctgagtggctgacct
acaggtgcacattgaagcacccagctgatttaaaaaaaatttttttttttgagacggagtctcgctctgtcacccaggct
ggagtgcagtggcgcgatcttggctcattgcaactccgcctcccaggttcaagtgattctcctgcttcagcctcccgagtagctg
ggactacaggcacgcagcaccacccagctaattttttgtattttttagtagagacagggtttcaccatgttaccaagatggtct
caatctcctgatctctgcccacctggcctccaaagtgctggattgcaggcgtgagccaccgcgcccgccaatttt
tttttatagagacgagtctactgtgcccacctgtggcctagctggtctgaactcctgacctcaggtgatctctgacgtcc
agtgctggattacaggtgtgcccaccgtgcccagctggccacctgttcatttagcgtctgtcattgcagcctgccagcctggggacagt
ttcctacagatatgaacagagccctgctagcatgatctggagcataagctcctggttcccagtgagcataagctcctggttcccagtgagacgatgtgtaa
ggaggcagtctcaggtaggatgtgagtcttgggacagtgcactgtgccgtggaattatgaccacatcagtctcctgacgtcc (approximate)
ctaagtccaatgtgtgatggcatggttatattactaagtgaagtaactcaggaatgaaaagttatacatatatttaaatgaattaacagcatttgca
atgatctgatgagtatgaagacgcaaaggcatgagaatgataagcatcttcatgcaagctccatgagctctgatgtttgcaaacacgaccgccggcaat
tgggagctaagctatgaagacgcaaaggcatgagaatgataagcatcttcatgcaagctccatgagctctgatgtttgcaaacacgaccgccggcaat
gtccttgtccagcaagcgtctgtgtgagctctgggagtactcaaggggcttcactgcgccgaagctcccacagcaacctgagcttctgcaaaagctgag
aagtgaggcccccctgagtctactcaagggcttcactgcgccgaagctcccacagcaacctgagcttctgcaaaagctgag
agcacgcatgagaaggccacctccctgcttggaaataattttttggttgcagtagggggtttgttttgttgttgctgct
gctcgtagctgttcttctgcagaagagctgtctcttttgccatcctccttactgaggtgagaaatacagacaggtgttc
aggctccgtgcagccatagtcccagaattcactgtgagcctctgtggcagttatgttgaggattagttagtttggg
agaggagatccatggagctgggtttccagatttgatgtctaatttagaaaggacattgttcaggacgacttgttaaatcaatagctgtgcagcct
agcatactactctgaccctgtgccctaaggacgcactgggggaggacattgttcaggacgcactgttcaggaagaatgctac
cccacgccgtgcccaggcgcccactgtcgtccaagaatttccaggtctttttctggtatcacttcttggcacaggcggaagaag

FIG.1-48 ccatgttccatcgtcccaacatgcagctgggagacctgggagaccgctttggcctttctcaaggtcacaggaaggcagggggaaggc
tggcgagggccctgtgatccgccctgctccagccgtcggttacagcagtggggacaggagggggaagggtgtcactgca
ggagctaaggagaaatccaggttgacaccctcagaaactgaagaagaccaagaagcagagcgagagttgccccctgcagtccgc
agagggcctttgccaggtgggctggagcctggagcctgcgtcgccgtaccccctgggtggcccaaggccaaggccaggcttggctgctgccagccagcctgcc
gttgtgggcagttgccatgccactccggcggcagcaagagagcaggaggacagtggcagagccagtggcagagcccagtggttccagccagcctgcc
tccagcatcacctttctccagttacttgaagtgggcaggtcctggagacccaggtggttatgggctctccagattcttggcg
ccttcctgattgcaggtctggttggttggcatcatgtccctgggagcgctgggaggcctggagggacctgcaggtgccagctcacttctgccagctcct
acacactctgctacttgtccctgcactgtcaccaagccatggcctcaagcaacttgtgggtgcctgatttaggcctgtttggagcctgc
ctggtgtcctctgcactgtcaggagtcagttgtgatgtcttttgccagtctcttctgtagcttgaaattggcacggtggaagtattaca
ttggaccactggcaggagtcagttgtgatgtcttttgccagtctcttctgtagcttgaaattggcacggtggaagtattaca
ccatgaagttggcaaatgcacggaccagccagctcctacccatcccggagagcagtcagttaccggctgaggctgtgtgggaggccactg
ttttgtcggactgatgagtcgagagagctgagggcagcaggctgagggggcaggggcaggggcaggctgagggcaggcttggattctgttggattcctgcactttgt
agacagaggagaggctgagagtctgagggggcagcaggctgagggcaggggcaggccattggattcctgtgagcaggggtgcagaagag
ccagggggcagaagcctccctccagggtcaggcccagctcctccatccagctctcctccagatgacatctccaggcactggaccccacagaggcag
aaatggtccctcaggagccccacaccacccgctccgtggagagggggctccaggtggcctgagggagaggggtcaggcagctgaggg
gcctgctcagcctgcagagctccgagctgagaggggtcttgccctggcagcccatcctggatgccccagcctcatccagacctc
ggctcccagaactccacgagtccctgcagtggacctgggaagctccagtgggcagcctttgccgtggtcaggtcgccgtggtccacagg
tgctgtgattgtgtcaggacctgggagctggagacctgggaggaagctccagtgggcagcctttgccgtggtcacctgtgtccacagg
cctgggcagacaaactgatgagtgtctactaaatcagagagaagacacaccagggagcgagtgcacgcccgaccagggc
tgcgggcatatatccgctcagccgctcagcagtaagtgaggttcttgtcgcccgcctcatgcaatgttaatagatagtaactg
gtgggaataaataagagagtagaaaacgtaagtggctattggagttcttgagttcttaatatcccgataaccacaggcaacgctctggcttgacaag
gtgttatgactgaagactgtgtcttggtgcagagccacttgttccagctgtgcttgtgatctatggtgactgagc
gggcactgctgttcagcagccgcagccagccagcagcgccagcggcagcacactgttgttccagctgtgcttgtgatctatggtgactgagc
tgttactctctcgttagacacgcatatgcacacactgtaccacgtgcacacacgagtgcacgacacgagggctcactgtgatctgct
acatgacacatgcgcatgcacacactgtaccacgtgcacacacgagtgcacgacacgagggctcactgtgatctgct
ctaatgcatggtcttaatagctatatataatattccacgttctttttttctttttaagatggagtctcgctctgtgcc

FIG.1-49

```
aggctggagtgcagtggcgcgatctcggctcactgcaacctccgcctcccgggttcaagcgattctcctgcctcagcctccttagt
aggggggactacaggcgcgtgccaccacgcccggctaattttttgtattttcagtagagacggggttcaccgtgttggctagg
atggtctccatctctcgacctgtgatccgcccgcctcagcctccaaagtgctggataacagtgtgagccacatgcccggct
ggttcttattctttaatttattgaagaatacatacctacggagccgtgtgcatatcataaggtacaatttgatatactttca
tggagtgaaatacatccctgaaaccagctccgatcgagaagcaggacattcccacccctcttcttgccctttgctgcaacccc
atccccgggtgaccattccccgcccctctgccccggacagttttgttgctcttttatggaggtgaaacgcgcgatga
gccccttcgagtctggctgcttttgctttagcctgcgcttgtgagatccctgcgtgactcctccgcgtggcgagagtggccacttccc
gcttcgtgcaagtcgtgttctgccattctccgaataccgatgaggctctgtctgtctaatgctcttcatcctagacctgtgaattgtt
ctcatacagtcctggtgcaatgggcgtgtgctggcactggactttgagtgtgtcacctcgccttacacacgtcacttcattaatt
actgtttgtcccagggcagtgagagaggaggccagcttttctgctgtgctatagaagtgagagcaggtgcctgggacacttgaggccccct
tttaaacaacagtcctgctgccggtggcctttctggctggcgactggcatgttctgtcccccacgctccagcgtctccagcgccctccaca
agtttgtctgtaatgagcttgtgctggcgactggcattgcgaggctgagggtgagggtaagctttgttgttccaagg
gctttaggcaattaagacacgggcttgtcccctccacactgctgtgcctggttgggctcattcctgcgggtaaggcccggatcagg
cagctgtgccctggggctcttgtcccagaggagctgctctctcctcagtttttgagttgtgcaaacgtaggaatgaggccttca
aatggctgtctttcttcctgcccagaggagctgctctctcctcagtttttgagttgtgcaaacgtaggaatgaggcctttca
gctctagcaaagtggggattttttctctccagttggatcaggttttgagttgtgaagctacagagcagctcctcttccaggcattgctgca
cccgtcagttgtctgtcggctgtgtgcacagtggccctcggacagtggccctcgagttctgtcgcagaaagtctgagggcagagctgggaggcagcgtttcca
gggcctgctgtctctgctgctcctggccaggcagtggccctcgagttctgtcgcagaaagtctgagggcagagctgggaggcagcgtttcca
aagcaaatgaaaaggcaaacgggacgtggcggccctgtggccctgaaccaggctgggaaacacccttgtccatgcagctcattc
actcggccaggatttgccgagtggcttactgactctgtggccactctgtggcctgaaccaggctgggaaacacccttgtccatgcagctcattc
agatggtcacctgccacctccaccatcacagatgccatgaaggctgaaggaaacagacctgtaaggcagcggagcggagatgg
ggttgatgagtgtcaccagtcacaagtgtctgttctctcttctacatgttgatcgaggtataacaccaggaaaggaca
tcaagttgtacagtttgaattttgcacacagtacacacccgtaaccccacacagatcaagatgtagaacattccagcaccaga
agtttcccgtgcccttcccagtcagacccccgaccccagtcaccctgcctgacttgcagtgagctcaccggcact
tcctcttttgcccacagcaggtgaggaggcctttctactgggaaaaactgtgactattaattaggtttaaaatgtattggtaaca
ggcagatctggcagtcccagtccctccctgcttcaatctctccttggtagctctccaggattactcttaggagggactgaaggaaagcccct
```

FIG.1-50

```
ctctgtcccatgcaccacagtgacgtcacagcgtccctcctctggccctcactgccaccagtggactcactgtctccctctgcc
ctgtgcacagcttcttaatttggtccctctgttagctcagtgcagccagaattcaccagtgcctatgtgatcgggcactgg
gctggccaggggccttttgaatgagggacagtcgtgagctgagttgtcccaaatcagaggtgtgacctatgagcagcca
ggttttttaattttgtaattgagatattcacatgccatacataacaattcctcttaaaatacacaattcagtgtcttttaggttttaatat
attcacaatgctgtgcaactatcactcttaattcagaatattctgtcactccaagagaacctgtaccattagcagtgactt
cccactcccacacccagccctgcagcctccagcctcttttcaatcctctgtggattcgcccgctctggcatttcatgtaaat
ggaatcagacgatacatgtcttttgtgtctgagtaatattccactatgtggatagccacatttgttgatctgttatcagctgatgaca
cagagtttcacttcttttttggctgagtaatattccactatgtggatagccacatttgttgatctgttatcagctgatgaca
tttggattgcttcctgatatgttttgctgcatcccaaatcctgtctgaattccatgtgttgtgggagtaattgaatc
acggggcaggtctttccatgtcttgttcttctgttctgccgccatgtgagacatgcctttcaccttctgcgtgagcctcccagtcac
ccctgcacacgctctctcttctgtctgccgccatgtgagacatgcctttcaccttctgcgtgagcctcccagtcac
gtggaactgtaagtgcattaaacctcttttcttttgtaaactgccagtctctgtatgtctttttatcagcagtgtgaaaacggac
tgatacacttccacttttttgctattggaatagtggtgctgtgaacactaatgtataggttttgtgtggacacgttccagttg
tcttggatatataccagttgtggaattcctgctcatgtggtaattcatgtgttaacttttttgagtaacgagcggccattttttaaa
gactggataggaatatgtaaggaagaaagtaaattattcacttccgttcaggaaatttacctaccaaacaacatgctgaatggga
accttagggcttggctgaatgcccctgcacaagtgtccagatgcgaaaggttaagtaatgtgactctggtaatgcagttcagttcattatgaga
accagcaaagggcagagccccccgtgtttcagatggaaaggttaagtaatgtgactctggtaatgcagttcagttcattatgaga
tcatggacctcttatactacagactttttgtgtttttttgctgagtctttttgctccctaaccgttgtgcctcacatgctagcagaggagataga
cagcaccacgctggtcctcaggaagcatcatcagtcagagacacaggcctttgctgtggcctcacatgctagcagaggagataga
caacatgggcatgaccattgaagattgaaccagaccactgcagagcctgcagcctgagcctgcgaggggtaggggaagcattgg
tgaaccatgagatttgaaccagaccactgcagagcctgcagcctgagcctgcgaggggtaggggaagcattgg
ttccagtgaggaaacagcactgcagggcctgccaggcctctctctgccaggctggccatcacgggcttgcacagagaga
cagggagggcaggctggcaggcctgccaggcctctctctgccaggctggccatcacgggcttgcacagagaga
gcaatgacctgcttcagtttcaaaaggtccctgcccgctgtttgagaagtcacagtggatgaggcagagcaggggga
ctgctcaggaggcttttgcagtaaccgacgagtggtggcggtcactgccaggagtgtacatgctgcaaagaaaatactctg
ttcaggagaccaggtgcgtggctcacgcctgtaatcccagcacactttgggaggccgaggtgggtggaccacttgaggtcaggaatt
```

FIG.1-51 cgagaccagcctggccaatatgctgaaacctgtcaatactaaagatacaaacattagctgggcgtggtggtgggtgcctgtaatc
ccagctgctcgggaggctgaggcaggagaatcgcttgaacccaggaggtggaggttgcagtgaaccgagatcacgccattgcactc
cagcctgggcgacagagcgagactccatctcaaaaaagaaaagtaagaaagaaaggaaaggaaagaaaggaggagggtctgttcacataa
ggaggagaaggaaggaggaggaggaggaggagagggggaggaggtgcagaggtcatcgctgctcccatccagctcagt
taaagaaatccagaggtttgaccatggcgtcattctcatcactgcacttgctgggatcatagcagaatatcagctccaatcctggttcc
cctgtgtccctgtcgtgtgagaaacacatactctgtacgttgctgcatgagtgcctcgcgttcaactgctgtgtgggtaacgcagt
tcaatggcgacaccacgcactcaggcagtgtatcagtcatgtgtgccttctagttttttgctactaagcagtgtcacagtgaaca
tgtgccattgtgtctcacaattcccagactggtaaataatgttgcttctagttttttgctactaagcagtgtcacagtgaaca
ttcttttataaacgtgtttgtgttttaaaataagcttatttgaatatattcatatgtacagaaaagttatgagttaggatgt
tttcatccactcttcatccagtttcctctgtgaacacctcacacatctgtggtacattgttacaaccaagaaactgacattggta
cccacactattcatgagacaccagactcactatagtctccactcaagtgatcctccgctcagctccagtaggtgggagtacaggtgca
agtggcacagatcatagctcactataattttttttattttttgtagagacaggtctcactgttgcccaggctggtcttgaactcctgacctca
cgcccccacaccagctgccttggcctccaaagtgctgggattacaggcatgaaccactatatccagtcttttatttgattttactacaa
aaggatcctcctgccttggcctccaaagtgctggattgttaaggtacagtccctgaagtggattgccgtgcctgatcctgctgccaca
acatatgcttctgtatacttgtgactattgtttaaggtacagtccctgaagtggattgccgtgcctgatcctgctgccaca
tcatcatcccataggggacagggcccacctgctgtcccacagtgaaagtgaggctagctgcgagtttatgtctgagacctgccacacttgacaccca
ccagccagtctcttttgcagccaaggacctcagtgcccaaggaaagtgaggctagctgcgagtttatgtctgagacctgccacacttgacaccca
aacgctgattttgtttacatgagactcagtgcctgagtttatgtctgagacctgccacatgtgtcatctgcgtgcacatgtgaaa
acctgctccctgggcctgaggccaccgtgctgcccacagtgtcaccagtgctgcaggagcgcaggagcgcaggagcacctggcgtggtccagggacacg
aagcctggtgctggcctcctcccaacgccctgtgagttctgcctccatagaccacatgtgtcatctgcgtgcacatgtgaaa
cccgaaagacaagcagatgaccccgctgccaaatatttgctgccgcgcagaacagtaagtgttttgacatatgatctcag
cgcagcagccacacagcaaacagcgcgtggcgtgagggcacagttgctgggggcgtgagcgggagcatcgccagcagcagg
ctcgcccccctgcagggcgcgcacgattcgctcgccaccaagacagggcccaagagcagggcccctcgcttggtctcgggagtgttgtgtcag
cccagaacttcacaggcagagagcctggctgcgtcgaggatgggcgggacctggagcctgctcccagggccgatctgaacccggccaa
agctgtgggcaccggggctgcagagctttgcagagcttcagacctgagcctgctcccagggccgatctgaacccggcacctgtgctgaccca
gggtcaaccaaagtcctgagttgtgtggcgccgagagggagtggtcgcatcccaccggtgcctgaatggtgctggaggagg

```
cagcatctgatttgggccccgtagggccagaggggggatttgtagggacagagcaggaggggagtggagctgaggctggggaggc
atggtcggaggtccagaggtgggagaggggccgcatcctgaagcacaccctcctgtcttcctgaggcctccatccttcctga
tcttccagtcatgggctccaggcttgggccactgtcctctgccagcctcctgtccttctccactctcccaggaaccacctgggttgtggctta
aaccagccagatgatgcttctccagctctgccagctctcaaacttggcagcctcgaaacagagcccttgggagttaaggagaacagaatattttt
ctcccccttgccatcatgaagtatctcaaacttggcagcctcgaaacagagcccttgggagtttaagcagacagaatattttt
gcatagtcttaaagtaattccccccaccccaaatattgacaattacaaaggcaaaataggaagtttacggtggagaatcctgg
tggacacagccttggccagtgatcaagttcatgtcaccagtcatgaaggcggtgaccccctgtgtgctgagaagggcagctt
acctcctgcagtgccttgcccaacgcaccactcagctaaccatgggggacatcgacaaaacaagctgtccgcatctccaa
ggacaggcacactggggcttagggcttcagtgggggcggagttcactcctcctaatacgccattacttggagaagccctct
ccagctgctgaggcagaagcaccggttctctctctgccgttcctctgcagcctctcagtgctacaggtttcttgactcctacctcagcactttgg
catgacagtccctgtgccatgtcctgtaggcgtctgtaggactgcctgtgcctttgtgtgtctgtctttccctgtcctgccccttt
tccaagctctgagcagagacctctgtaggcgtctgcaggactgcctgtgcctttgtgtgtctgtctttccctgtcctgccccttt
gtccactcctgaccagcttccctgaccactgccaaggcattgtgatgtgatgagtgaaggaaaggctggcgtgttggtg
cttgcatcccgtccccacacccttgaccctgaccctgaccaaggcatttgtcatgtgatgagtgaaggaaaggctggcgtgttggtg
tgcgaggtcgcagggcatgaggtgctgacggcagagccaggtgagtgaggacctgggtgccaggtcaggtcgggggtctggca
gctggtggccctgaaaacgttcacatccttgggcctgctgtgtgatacatactaatcagtgcttcatgagaaaggtatgagcc
gaaagaaatggggttccactgattgtcgtgagggtgactcacatgagattataattgtactgcctaataagtgctcacactgttaaa
aacaccccgggcttgatcagctgctgagggtgacttcacatgagattataattgtactgcctaataagtgctcacactgttaaa
actacctggcaggcaggagtgagaatacagcttccagaacgtgttcaaagaaaacccattaccaaccggcagaacataaag
tactagtgtggggtatgagcagcatgtgggggcgctgggggtggcagcagggccagaccccactcaggggttgccccaggaccc
ccttgcgctaccgctatatccacccagactccttcactgagctgctccagaccccctcatatcatcctgcttccagaac
cctatatcttgctccccactccctacccattgtgttccagaccccctcctcatgcctgcccccagatcccttgctgcacc
cctatatcttacccagactccctcctcatcctctgccccatatctgccccagatcctccatgtctgcccccaggcctgctggtaatatgggata
cagaggtctcctactgcacacacaaactcttccctgagcaggagaccacattagtgtttgtgcaaagccctgtgcacctgt
gggttctttaggcaggagttacctgcctgtagacgggagacggggagaccacattagtgtttgtgcaaagccctgcgtgcacctgt
ccttccgtagccacgatacctcatccagccggcccgtgggtgggctgctgagcacccgacccagccagccacagcctccatgtgcca
```

FIG.1-53 ctgtcaagggacttggccgcatgatcctgagtgcacaggtacattgctccgccctctcaacagccacgaccagaaataaagt
aggcactgtaatttgcattttgaggataaggaaaccgaataatagagtctactgagcgcatactcagtcttttccagaccctagaaa
gtaggtaccattgtcatcctcattcagagctaggagagcagagccagacaggttccatagcctgctcaggtggtccgtgctgg
accaggagaagggcaggtaggctgatgggtcctgagcttgtgctccgaccgccaggctgtgtgtctgatggccgaggccaggt
ggctcagccagccagccaaccaagactagaccatcccagcgtccaccccagctctgggacagggtcacctccaccc
tggccaccatacagcctttttccatctaaccttttcttaaaggaaggcatcctttgaatgagtcaccctgagattttatgg
atccaaagaaaaaacttaattagctgcataaactgtcagttgagactctccagaggacacacctcggcttcaggttcccaggg
aatctgaggctctgagcaggtggacagcaggtccctcttaccacccagtaaccttagaggcctggcctgcctttcctca
ttttgaaatgtcacctgtgtcatctctctcctgatgtgaagcagtgaccagttctgcccatctcacacatgtgcacac
atacatgcacacatgtaaatacacatgcatgcacactgtgtgcacacatatgtgcactttggacttgaatcttgtgcccgtcacaactgtact
ccagggaaggccttccttgggcgtgccctccactctgcagcattggactctgagctctgagtgaggtgggcacactggtcccacctc
cagctactccagctcctgtgtgacctctggagtgcaccctggaggtccagggctgtctttccaaggctgaaggacctcttcctc
ggtgcagcacacacagcccatctgggagtgcaccagcgagaacctgcttcctaggccaagcccacacatgctgtcacctccaggaagcttcacagtt
tatgccagtgtgctagagtgggcccagccagcagaacctgactggaccaagccccagacagtggtcaggacagtggtcaggcacacctgagtcgc
tcttcctccatagacacacatttggagttcctactgcttcctccaggcgccccaccacatgctgtcacctccaggaagcttcacagtt
gctccctgctgatagcctgacctgctgcccactccagggcgctccagggcgctgcagtcctcaaggtcgtgcaggggctgtggct
ctggctcagcacacgcccgtgaccacctcaggggcgtctgcgagtcctcacgtgtcttctccgatctgctcactcattcatcattat
gctgggtcctctgcgagccgatgtgtcactggagcgtctgtgaagactggcgggacgcaaacggttacactggttgacgg
tcagcaggggttcttgagtgtctctgagtgggagcctcagaggtgctgtgaaggactggcggggacgcaaacggttacactggttgacgg
gctcgatcaggagcacagggtgttgggagctcagagtgtgaggtgacatctccacctgcttggccagtgtgggaggagagggttca
gggaggataactgtgtgtgcagtgctgtggtggcacagagctggggggacataggcacagttgctgatgcagggcttac
accgcgcacgcgtcagaagctagacagcaggggctgagcagctagcatctctgccctccccgttgcaccccaccatccagtgcagcccagc
acctaggggcatgggcccagtgcctgcctgctggcacattttgtcctgactgtggaaaaaaagctcttcacagccctgagtgctgctttagct
ttggctccaccatcttaggctgctcagaggctctgagggcctgcttgaagctgcttgcacactccctgaggctgttccaggcacgtcactgg
gggggggtccgctgtgtaagcctgggaaattctgctgcttggcacactccctgaggctgttccaggcacagtcactgg
gtctccccgtgaagtggctcaaggcaggtcttcccggttaccagcaggcaggaagcagacagatacatgttgtaacgggctgagagtgggtgt

FIG.1-54 atctcatatattcccagaggagcttacggacagcccctcttaaggaacatctcccgggccgagcgttctgagcgccctctgagcag
gcagcccaccacggggcgctggccagtctgagtcgccagtcagtcctgggaggcagtcaactctggggaaggcagaagaatcacagca
ctgagtgccgtccagtttcccctcaactatattcgcggacacggccgccaacagggaaaacttacatagcacctattcattctgag
gcctggccggcctctgaaatcagcatttcagtgttggccaggaaggaggccagaactgtgctgtagcattgtcaatgtatggctgt
cccacaatttatattccagtccccctgatgatggacatgtagggcggttccagttttttttcatgatcacagatcacacttctgtgaa
cagctctgatgtgtctccttgtgcaaatatgtgtcaggtctgctcctggtgggtctgatatttggagccaggaatcttttcttttcttta
ccttggggagtttgttaaatatacatatttccaggtctgcaagcttgcaaagctgcgaagactgcgctggagcaaacatgtatgttctg
acagatacttaagtgattcctgtgtccaggaagtttgcaagtggacgtgccatttctgtccctccagcagtaggaaagaatccatta
ttttactaattagatatacgctgttgatgactccaaagtggactccaaattttaaactctctctcttaagactatgatggtattttgttgtaatataa
tccacatcctgccagttcttggtgtgagcacttctcaaatgtttgatgaccttgagcattgaaacttccttttgtgaatt
tccacatttctatattattactgtcttgagcacttctcaaatgtttgatgaccttgagcattgaaacttccttttgtgaatt
acctattcatatctttgtagcttcactgtggaatgctgttactgatttgtagccatcttttatacattcactccactcgttt
gtcagttatatgtggtgcacacatcgctcccagtctgtgttgtcttccacttttgtctttcacttttgtgcctcttattggacacagttt
taaattaaaatataatcagatgtattaatcatgatgttgtagtttgtgcatttttctatcttgtctaagaaattcatcctcctcctt
gttatacttagaaagaaggatattctacattctccttcaggagttccttgcttgcacattgcttgcttgcacagttgctcattatcacttttttgagta
aatttgacttgtgtatatggtgaggtagggattgatttttatttctatgtggataacagttgttccattatcacttttgagta
gtccaccttttctctactgacttataatgccacctctgtcatgtcagcttcatatttatcagttcctgttaaatgtatcttta
aagctttattgagacataattcacatgatacaatttaccatcctaaagtgaataaagtttttattatattcatacaccatcg
ctatcagtcaattttagaacatttctttttttcttttttttgagatggagtcttgctgttgtcaccggctaga
gtgcaatggcacaatctggctcactgcaacctccgcctcccgggttcaagcgattctcctgcctcagcctcctgagtagctggga
ttacaggacccgccaccaccgcctggctaattttttgtattttagtagagacggggtttcgccatgttggccaggctggttttgaa
ctcctgatcttggtcttggatccaccccgcctggcctcccaaagtgctggattacagacgtaagcaccatgcccggctattt
tcattaccccaaataaccttgtaccctttagttaccctccatctgtaaccctaagcaaatactcatctgctttctgcttt
gtgggtttccctgtcttcctgtcttcaaatattttttatgaatggagtcatatagtatggcctttttctgtctttactctgcgtttt
aaggttcatccatgttgtagcatgtatcaggactcattctttttttatggctgaataatgtccactgtatggataaagaacagtt
atttattcattcctgtgtagtgtatttggttgttctgcctttggctattgcctattggttgatgcttatatgtgagtaatgctgtataaggattcatgggca

FIG. 1-55

```
agtttttgtgtggacataggtctcatttctcttgaatatatgcctaaggagtgaattgctggtcacgtggtatctatttttaa
tcacttgaggaattgccagactattcaaaagctgccaccatttatgccattttacattcccaccagtagtgtatgagggctga
tttatctatgtccttaccaacgcttcttatctgactgttaattctagccattcagtggctggtgaagtactatctcattcagat
tttgtttgcaattcctacaatgatgactagtgatgatgtcagcatcttttctgtacttattggccacctgtatgtcttcctgga
gaaatgtctattcaaattttttgcacaatttaatacacatacatatgtatatacacacacacacacatttttttcttttt
aaacagattctgcttttgtcggccagctggagtgcagtggcacacaggtgcccaccaccaccagtcattttttgtatttttagtagagatg
tctcctgcctcagcctcccaagtagctgggactacaggtgcccaccaccacctgtgatccaccaccacctgcctcccaaagtgctggattacag
gggtttcaccatgttagccaggatggtctcgatcctcctgacctgtctgtcacctaggctggagtgcagtggcacaa
gtgtgagccaccgcacctggcctattatatatatattttttaaagtcaggatctctgtcacctaggctaggactaggactaggtatgcac
tcacagctcactgcaacctgaactcctggctcaaaccatccttctgcctcagtctctcaagtagtcaagctggtctcaaactcttagcctc
caccattctggtgaattttatttttattttatagagatggggattataggtgtgagccaccacatctagcctcctttgcacattttaaaag
aagcaatcctcctggctaggcccctcaaagtgttgggattagagttgttgttatatattctggatataaggcctttatcaaatatatgattacag
tggattagttgcctttttatcattgagttgtaaagagttgtttatatattctgctgctgaaaatctgtatatacctttgactctccca
gtacagttgaccctttgaataacatggggttaaggtgtaaggtgctgctatgcagtgaaaatctgtatatacctttgactctccca
aaatttaactaacatacagataccctgctgttgactggaagactaactgagactaactaaacatgttaacacatatttttgtgtatgtatt
acacctatattcttacaataaggaagcagagaaaagaaaattaagaaaagcataaggggctggtgtgtgctcacacctg
taatccagcacttaggaggccgaggcaggcaggagattgcttgagctcaggagttcaagaccagcctgggcaacatggtgaaacctt
gtctctattcaaaaaaaaaaagaagaagaaaaaaaatataatatttactgttcatgaagcagaagtgaatcatcatgaaggtcttttatcttc
attgtcttcacattgagtagatgtgagtaggccatgaggcccatgcagttcaaaccagttgttaaggtcaactgtatttttctatatttgtgggtt
tagaagaaaactgcatataagtgggcccatgaggcccatgcagttcaaaccagttgttaaggtttaagtttgatgaagtccattgatctttttatttctctt
gtcttttcatttttctgatgttgtttttaaagcataaaagtttttgataatccttgatacattgtagattacccctgttttctcctaagaa
gttgcttatagttttggtggcatatccaagtggtttttgtatacagatagtttttgatacattgtaattcacttttgcatatgtgtgaggtaaggtacaacttct
ttatatattcttagctgtaacagataggttttttgtatacagatagtttttgatacattgtaattcacttttgcatatgtgtgaggtaaggtacaacttct
gttcttttcatggtgctatccagttgtcccagcagcatttgtgaggctattcttccctttgaatgtgtcatggcacttgt
caaaaatcagttgaccattgagttgtaggctgttcttgcactgtctgctataaagaaatacctgagcctgggtaatttataagaaagaaac
ttaaatggcttacagttctgtaggttgcacagaaagtaaagcagcatctgcttctgcagaaagcttcaggagctgaggaagcttcaggaagcttcaatcacagtg
```

FIG.1-56 gaaggcaaagcaggagtaggcattccacatggcgagaatgggagcaagagtggtaggggtgccgtatacttctaaatgaccagatc
tcatgagaacttactcactatcgcaaatatggcaccaagcctgagagatctgcccatgaccaaacacctcccaccatgccca
cctctagcatggagattacaattcaacgtgagatttggtgggacaaatattcaaactaaagcaaccatacacacaaagttta
tttccagatttacagttctattgcattgatcactgacatgattactgttcctttgtagtaagtttgaaattaggaagtatgaatc
ttcctactttgtacttcttttttctagatcattttgctattctggtccttttataattccatatgaatttttagattcagcttgtca
atttcaacaaataagtcagctgggattctgaaggggttctgaaggggttgtgtcacatccgtagccacatttgggagtgtcttagtccattttgtg
ctgctataacaaaatacctgaaagtgggtaatctataaagagaaatttagcttggcaacataaggagaccccatctctgaaa
aaaaaaaaattaggcatggtgccgtgcacctgtagtctcagctactcaggaggctgaggtgggagaatcacttgagcccaggagg
tcaaggcagcagtgaaccatgatcactattgcattccgcagagagactctgtctcaaaaaaaaaaaaaag
aaaagaacagcaatttatttcctcacgttctgggagctggaattccaatatcaaggcactgtaggttggtgtctggtgagtgc
tactctgtgctttcaagatgtgcctcttgttgtctcacgtggcaggagcagagccctcatgactgaatcacctcctaaaggcccacctcg
agcagctcttttatttataaattgctaatcctgttcatgagagcagagagccctcatgactgaatcacctcctaaaggcccacctcg
aatactatcacgttgctcgttagtttcaatacatgaattctggggggacattcagacctgagcaggagcgttgccatcttaac
aatattaagtatttgctccatgaacatggatgcttttctgttttattagatcttcttttaattcttttaacagtatcattaat
ccaaaatctgaaatctgtatgctccaaacctgaaactttcgacactaacatgacagcaacagtgaaaattccaccctgt
cctcacgcgatgggtgcagtcacatatgaaacaaatcaaaccttgtttcatgcacaaatatttaaattttgtataattaccctcag
gctatgtgtcaagcataatatataggagagaatttgaaacactttggtccatgcatttggatagatataaggatctttttacttgtattt
tccagaatcaaaaataatatataactataataataacaaacaatagctaaaatataaaattgcacttccgttgtcaaattacta
tgtagtgttcacaattattcttttttgagctaccataaatgggactgcattcctgttagatttttcttttttttaagaaatggag
ctggtattttattcttttttgagctgctcgtgcctataatcccagcagttgggaggcgggaggcgggcagtttgctgagttcaggagtttg
acttaggcaggagcggtgctgctcgtcgtcgtcgtgcctataatcccagcagttgggaggcgggaggcgggcagtttgctgagttcaggagtttg
agaccagcctgggcaacacagtgaaacccgactctctaaaatacaaaaattagccaggcatggtggctgcgcctagtccc
agctactcaggaggctgaggcaggagaattgcttgaaccaggatggtgcagttgagctgagtcgccatcacactcca
gtctgggcgacagaacagagactctatctctaaaaaaaaaaaagaaaagaaaagaaaaagaaaaagataaggagccttgctgttgct
caggctgacctcaaactcctgggctaagtaatccttctgcctagctccgagcagcaagcagcagggaccgagcagcagggaccat
aggagtatgtcactgtcctgtgcctggctagatgtgtgttttctttttttgagatagagtcttgctgctgctcagctcagctgagtgcagtg

FIG. 1-57

```
gcacaatctttggctcactgcaacctctgcgcctgggtttaagtgattctcctgcctcagcctccggagtagctggactatgct
gtgtgccaccaccagctaattttatattttagtagaggcggggttttccatgttggccaggctggtctcaaactcctgaac
tcaagtggtctgcctgacctcccaaagtgctgggattacaggcgtgagccacactacaccggcctagatatgtttctaaa
acaacattgtaggaaattttctttaggctggttcaggctaacatgctgaaggtccaggtagtgaacaggtgaacctgaag
gaccgtgcccctcccacaccactagcagctgttccacattgtagatggatcctcctacattgtcacctttctgtcta
aatgagaggtgggaggagggtgaagaccaatgagttagtcatccaagggtgggcgtgcagagaaagatggaact
gttccctagtcctcttcctttcctggagttgggagggaaatagccctgcccaacatgtgatcagcatgactatggtcagttac
aaatatgagtgagccaggccctgcctgaagacttgtttcatgaaggacagcagcagtgtctgtgcaggtccaggaggctccaca
tggggacacagtgctgtgccgagcttgaatttgttcatgaaggacagcagcagtgtctgtgcaggtccaggaggctccaca
ggggaagtgagatttgagctgagcttgaaagaaagtgaaccagagagagacgacttccagggcaggaagtggcctgcacagag
gccccgaggcgagaaggaccacaactctcctgtgacctcctcttgtacgatcagtttaattacgcaaaaaaattatgcagtta
aagctttgctcatttaaacagacttccctggattaagagtaattaggtttcattgtcttgaaaattgccttgccatga
cctgtgaacacagaattattataatatgtgtgcatagaaatcatctcatgattttttttaactgagatgaactggggattt
aaagtaacaaacaacccttctgctggtgtgtgggaagccaacggcacaatcttcactcattgtagtgctgctactttttttttttg
agacagtgtttttgctctgcctcagcctcccaggtagaagctgggattacaggcacctgccaccacaccgtctccgggttccag
cgattctccctgcagcctgttggccatgttggcaggctggtctcgaactctgttgtgtaaatattcctaccatgctgattctctggaagccat
agatggggtttggcaggtttggccaggctggtctcgaactctgttgtgtaaatattcctaccatgctgattctctggaagccat
attgcaagcataagccaccgccgcccggcctccacttctgtgttgtttatttcaaatgtgccaaatccacctgaggcaggcagtggctca
gtccctcacttctaccttcatgtgttctttgttttatttcaaatgtgccaaatccacctgaggcaggcagtggctca
cgtctgtaatcccagcactttgggaggccgagacgggcggatcacctgaggtcaggagtttgagccagcctgactaacacgggga
acccgtctctactaaaaatcacaaaattagcaggcatggtggcacactcctgtaatcccagcactggggaggctgaggcagga
gaatcgcttgaacctaggaggtggagatttgcagtgagccaagatcatgccactgccactgggagacacagccagactcca
tctaaaaaaaaaaaaaaaaaaaaccaaaaaaaccaccgagtttaaagaaaaggctaagaaatgcttgctggct
gtctcaggggtggcagtggagctccgtgcctcccacagatgaggacgtggagccctggccagtgctgaatgctgattcaggttggggga
cagggctgccggctctgtaaggatgggaccccagaccccaccggtgagctgggctgaaggcctgataaacacagcctacc
ctgcattgcccacctccactgcctcaccagctttgacggacgcagcccactgccactgcccctctccaggcaggccacattcacagg
```

FIG.1-58

```
tgttctgtacagagagcagaagtttgagaaacgtgaccactgaacagacacttgctgaggcccggggcttcatgtgtcaggcc
cagaggtggccacaggcacaacacgtcctcagccttgccacctgcccctcaagtgcctggtgcctcagctggccagaa
gcactgcttctggagcagcacttatgcttttactttttctcttttttttttaagactgagtcttgctctgttgcccagg
ctggagtgcagtggcacaatcttggctcactgcattctcagttcaagtgattctcctgcctcagcctcctgagtagctgagatta
caggcatctgccaccatgccccggctaattttgtatttttagtagagatgaatttgccatgttgaccagactagtcttgaactc
ctgaccagtgatccgcccgcccaaagtgctggattacaggcgtgagccacagtgcccgccagcttttcattttgaaatc
aatacaagtttttacagatgtctgcaaaaatatccatattgatgatcctggctcctcagaatctgaggttttacaaatgtctg
caaaaatatccatattgatgatcctggctcctcagaatctgaggtgacagcttgacagcagcttgcagaggacactgctccccaacactgc
cttccaagggagacatgccctacccaaggcctccttgtccctcctgggaatgaggaaggcaaaggttaggagaagacgtcagttc
actggccaccctccacacatgttgcacagtgccctgggcgtgccctgtcacctcaaggcttcccagcagcgcggctg
ttgaccagccagccggtgcagcgcggttattgtgcccgccggttatagccctggtgagcgccagagaaaatcaaggctttcccagcagcgcggctg
tgagggctccgagatgatctcatggtgccctccctgaaccatccagaaggaggcctgtcacttcaaggaccaatgcttc
tgccggactcaaggcagcagaacctgttcctgctgcaaggtttacaggcagcttgggacagtccgtgcagaaatgtcaggagcc
ttttcctgcataggcatctcagagcttatagcacctccttggcgtggcgctgcgcagcctgatacatggacctctgtctca
cttgcagtgtgcaccggtccagccggtcctaattcctatctgttccaaccacaaaagcttcactgctggatggagcctgttatcattca
ggcttctgagccactggaaggcaaaggcctctctgtgaaaatgaaaactggcttaaaagctggcatgggctcagcatggag
ttgcttagatgtagttcacaatctgcagaccacgaggagcaggattccaccaggagaagtcctggagtggccatgggctcagca
gaatgagccggggagagcaggactgttgacacgagcagggtcaggtcaggtgcacaggtccagtgtgcagaggactgcaccggc
cccagcttttcatcaccccatctgagatcggctccttcactcctgttctctgggggtgagtcggcttcgttcaggctgcagggtccctgg
ctttcttgtctatccccgacgaccgccttcccgatctctgggtgagtcggctcgttcagccttcagccttcgttcaggctgcagggtccctgg
tgccgcagccctcttggtggaagccctggcgcccctgcgtgcagcccgtcctccagcccgtcggagctgcagcctggccgtgcagcttgtttgactc
agcgccctggccgccaggctggcagttcttcgggctggcagttgctctgaagaagttctctgaagaatcagttgtttgacttc
atgtttcaaggccaaatcttccagaaagttctctccatccaccactccaccctccaccctccacctcccgcccctagaaaataaatgcgtgat
tgactggctttgcagttttttatccatcgttcttccacagccacatgaacagctcattgtgaacagtcattcgttcgtcctcc
ctctcccaatccctgtctctctctctctccttccacagccacatgaaattgaagtgggagaacatggtgtgagcattattgggggt
gggtgcggagcaggcactgctttgaggtctgcaaaggaaagcaccccactgcccaggctgctcaggagtggctcccaccc
```

FIG.1-59

```
tcgactgcggggaagtgctggaaccctccgcacgagggcaaccttttcttgggctctctgaaggcgcctctcatcctctgagccaagaa
gacttctgacccagaattctgagttgagttccgacgcaggcgtgggcgatggtgagcaactccaggctacccgagaaagccgctg
tgtgaccccattagggactttggctctctgccaagccccaccagcacctgtccttgtgtcatgactgactgttacttcta
gccagagctccagttgaagggactgtgttggtcctgtctgccagaggactctccaccgacactgtacctgtcccacagtg
gcaccaacaaggctcagctgagccttgccagagagacacgtgggaccagcagccccagcgctgccacctgcctcctctgcc
accgaggaagccatgtgcctcctgagcctgctcttctctgtccacaaacaaagactagataattagagtgcacacttgaggga
caggatggcttcgtatccatctggctgtgcctgtgcctgccctgtaactcaaggatggggactgtgtcattgtaaacactgcaacaggcctcctt
tccaggaaacaggatccctgtctcagacagaagcagtctcgccatcctgggctgagagcatcattccttttgtgagactcaaat
gtgagaattcctgttttcctcaagtctgtgtgggagtgcagagcagccctctgaggggtagcgtgtgcaggaaataagccgggg
ggaaggggcaccgcggtgggtggtgttaactgctgcttcgggtccagccggcatgcctgagctgccggtgagggagaggcctcaggggagaaaag
ctctctgtacctgatcagtgcatgtgtgctggctggctcacaagctgccctgccagtggggcagagtcgcagggctcttccacagtgcaggggctgtgaggaca
acaaagctgggtgccctgaaggtgggcagagctgggggcagagtcagggctcttccacagtgcaggcctgttgctgaggaca
cagtccatacacctccaaccaccacctccctgccagtgtgggggcaggctcctgagatgtgagagcagcctgaccct
accctggctgtccccgactctggttctctgaagccgtgggttccaggccatgcagcaggtagagaacaacaggtttaggaca
aagtcattgtgacactgaggccagaaaagggacttgccaaggccacacagcagttggccagcagcttcagtggagcttcagatcatttcagatctt
ttcctctctgcttgctttgggtttattttgtgctccttttcctacttcctttaagatgggagcttcagtgatcaatttcagatctt
tcctctcttctaacaagcatttggtactatatgaatttccctctgaatctgcttcagctgcatcccaacttctgatcactctgatacagtagga
gtaattgttctaagctccgcagctgactacagagagcggccacattgagaaacattcatctctgatcttggtctctgaca
atggagctagcaacacttcctggtttaaggctctgaggagcaaattagactgtctggtggtgaacaaccctagacaagtcagcactcaagtttat
ttaagatgccaacaggttcatctgctctcttcctcttcccacctttgtaacacaccctagacaaagagaaggcaagtcctatgggatggt
atggacaaataagcaagtaaaattagtttaggaaatcaaatatttggggttgggaacaataagagagaaggcaagcctatgggatggt
aaactgcagtataagccccattttgctggcacagtggtgtctgccccgtgtgactagggaggacagtgcgggtggcctgcctgca
tatgccagtttctgtgtatcacatctctcaccaggaagcaaaacctggcagatggcaccgggctggcctgatgctcctcaaccctct
cagcaccccaagaagaggaagtccccatccactcactcaccccagccctgtcagctctcgaactgcagcataccga
gctcttaaagcacactggacctaggggctcaggtttgagctttcatgatgagccctgaggtcactggcgggaaaatgagtcactg
gggcattcccgaacttgggaaaagccctgacccaggaatcctgagcctaaattgctgccaagttcccttccttccagtcct
```

FIG. 1-60 cagtttcccttctctccggcaccctcctgaggaccactgagcccaaccaccaccatggctggtgtgccagaggtggga
gctgtgagctgcctccaggccttcccgaggcctgctgtcttacttggtttgtggcttccagtaaacgtgggacaggac
cagggtctgaggaaaagcaaagcagtgttgacagagtgttcctggaggcagcttgtctcctggagatgaaactgaagaa
aacagattcgttctaggaatcgtccagggcgcggcagccgccggagagcccggcagcttgatgggtcctgtggcacaatc
ggccagtgtgggggcaccgccccaggcagccaggctcccgggggccagaatgaatgaccctcactgggcgctttgacagtt
tatgaggtgatgacgttgcagctatgattgatgaggtggcctggtccctcagtggcgtttcgggaacggtacaagttgctagggaaata
caggggagggtgctgccctcccactgcctccgtctggtcctgtgctatgcctcagtctccatctgtgtggagaactgat
gaagacagcacatgcccctgcctgtcctgattgcaagtccagacagaagagcgtcctggaagcagctgagagcacct
ctttctcttggtcctgcagccgtgggtgcaggcgtaacccatctgccagaaccaggctgcgctctcgggagggaaaca
gactcttatcctcttagtagctacagcctccctggcgcctcagttgggggatcactcttgtttcctgcagtgttttccagcattagagtca
ggagaggttgcatcctaaaggccctccatctctcagttgggggatcactcttgtttcctgcagtgttttccagcattagagtca
cactgggtccttgttctagcccccgtgtgttggctgcatgaccgaactttactccatgtctctcctcttgggggtgacatga
ggtcttcccaagtgcccgagtgaggcaccaccatgaccctgatggcagatccccaggcagatccctatccagagggtgtgga
cccaaacgcgacgtcccagtggcgtgcgtggctgagggagggttggggcgaggaccagctctgggcagtctccagtcatcatgccgt
ttgacgcaggaggttttgccggcccagggctccctggctttgaccgaggtgtccttactccataagtactgatatgtctgc
ggagcaggtggcatttgccatgcctggctgcgctgcagaggccagggctgtcctccccacagctattgaacacca
gtccttgctgctgcgtgctggctgcgcagaatacccttgacctttcagcatccttcatacctctgtggagtgctgcatgaccaa
ctagagactgttattattacgcacatttaagacagcatcggcgacggggcagcagcacttgaacctaggaggcagaggttgta
ggcgatcacttgaggtcaggagttcaacaccagctcagtggcgcagagtgagactccatctcaaaaaaaaaaaagacagc
tgggcatgatggtgcatgcctatataccactgcactcgctgggcgcagaggtgccaacatgggaaaccctgtctctactaaaatacaaaaactagc
gtagccaagatcatgcattgcactcgctgcagccgcagaggtgagactccatctcaaaaaaaaaaaaagacagc
atcactgtagccaaggaacttaaaagaaaaagtgcatgtttagacagttgttcatttcctccagttcctgccagccccttct
gtagctgtgggcacgtgcacatagtctcctttcctcaccctgtcattgttcatgtgcatatatatttacagagcagata
aactctgccggccttaactactccaggtcgaacgtctcctttctatcgtaaatatctctgcaattcctatagctttttcctt
caattcagtaaactttttttttttttttaattttgagtgagtctcactctgtcacccaggctggagctctggaatgcgtgatcagct
ctcactgcaacctctgcctcctgggtccaagcaattcctgcctcagcctcccgagtagctgagtagctggattaaacaggcatgccaccac

FIG. 1-61

```
acccggctaattttgtattttgtagagagaggtttcaccatgttggccaggctgtcttgaatgcctgatctcgagtgatcc
acctgcctcagcttcccaaagtgctgggattacaggcatgagccaccgcaccccttgctcttcctttgtcttctgcatg
attgtgaggcctcccccagccatggagttgtgagtccattaaactttcttcctttaaacattaccagttcaggtatgtcttca
ttagcagcatgaaaacagactaatacaccatgtcatttaatgaggctggcctgcctcttctgatggaatgaactctcccagt
gacagcatgtccccctcgtccctgtctgttctttcccaccctgcaacctggttgggacgcgaggagggcaccagcagctgccaggggaggag
atcagtcccagctctgttcttcccacccgtccccatggagcgaacctggttgggacgcgaggagggcaccagcagctgccaggggaggag
gagggactgcagtctggccagagccccgagaccccgttgtcccccatggaggccacacaggcacctcaggtttgcatcattggagtg
gccaggagtctgctgctggtgtgtgggaagaatggcttctgagcgccaaggtagccttggctgtggagctttgctgcatagaaggccattc
agtcccttgctgtcacacctggctgctgcctgggaaggctgtcactcctaaacagttatctgcttctgttgttaacctacaggattcc
ctctttgcttttggctgccagggaactcaaagctaagttttttgcctcccctttctctcttctctactgtgtttctgagccaccctgcaaacttcctctgca
ttactgtgtttctgagcctctggtgtagtatatctcccctttctctaggctatctggaccacctataaataaataaagacatctgtctgagc
tctgtcccagtacaaatatcactgtgtgccctttcaggctatctggtgtctgatgaatctgtacacaccgctctccctgcacagccaccaga
ttaacttgcatatagcaaagtgcatgaatccaagctgaagtgtggctgatgtgtgctcaaacactcttctcagaggaagctagcccgtgccttcacc
tgaagacaggagcacctccataccagctccatccaagctgaagttgagtgaatggctaaacttgagtgatgggtaaacttgagtgaatggctaaccacacccacc
ccgtcttctgctgacggtaaacttgagtgatgggtaaacttgagtgatgtgtttcatcacgaggctggaccacgatgtgttatatgtcactgttgctgt
cagccagactccatcctacggcatccgtgggtgatgtttcatcacgaggctggaccacgatgtgttcatgtcttggtgacatagcctca
cacatggctgtttctgcttgggcgtcaggagtgaggttgctgctccccgcagctcgctgagttccatagcaccatgtcttctgcagcacgatgtgcc
tttcatgtgtgactcaggagtgaggttgctgctccccgcagctcgctgagttccatagcaccatgtcttctgcagcacgatgtgcc
cagagtgtctgatgtactcaggtgaccggaggtgtcattctttcctctgagggcctgcatgaatccttttaggtgga
ggacctcccacgctggccattcaggtgaccggaggtgtcattctttcctctgagggcctgcatgaatccttttaggtgga
acacacagagtgggccgcgctcataagcgtccgtgtgaatcctgaagctgtgaggtagcacagctgcatctctaggt
tgggccactctttcttgaacaagagccctaaacgtggaccctaaacttaaggagacctgcttcctaagcaacaggccagacagaggctg
ggacaccatgaagctggtggacggtgggaggccgacttaaggagacctgcttcctaagcaacaggccagacagaggctg
caggtataagcccctgcccaccatgatggtgaatatgaggtgtcaacctgattgaaggatgtcaacctgattgaaggatgtgaagctgtaa
gttttgtttctgctgtggttaagtgtgtctgtgagggtgttgccagaggagactgacttttgagtcggtggaccgggtgacggagac
ccacctccgtgtgggtgggcaccattcatcggctgtccttgtgctgaacaaagacagatggaacagattgggaagactttgtt
```

```
tgctgggtcttctggctttcatccgtctccgtgctgatgcttcctgctctgggacatcagactccaggttctttgacctttgga
ctctggtttagctggagctctcggaggtgtcgttcccatctttgagattttgactggcttggccattacagcttctc
tcttcccagcttgctacggtctgtcgtgggacccgcctagtagtgatcgtgagccagttctcctaataactcctttcatgta
tagacatgatcctatgagtctttcctctggagcctgccttaacacagtggcatagagctccaggcagccctcacctgc
cttcagcttcagtttctttgcctactggctgaatattggtgtcaccaccagtcccatcagtgtcactgcacct
gtcgaagagatcccccagccgcaaggcacactcgggtctgtgagtggcagtggagatgacactggctctaagtagtgggctgctgact
ccagcgcccctaggacagcaaggcaccagacgtgggaggacactgtgccgcctccctgccccctgctttctcctgggcc
actgggctagacatgggctccctgagccggctgccagccagcgtgtgcctgtgcctgtgaaaagagaggaggtgggtggcactctgggatctgcc
gagtgagtgcgcactggaggacggagtcagctctttcaactaaacacaccaccaggtgcttaacgtgttttatcaaatatc
gttggagtgcgcactggaggacggagtcagctctgctccaagcctgcgtccctgccaaagcgagctttagtgagccct
aagcacagctgcaagaggctgtctgctccaagcctggggtcctgtgggccctgaccaggctgcaagcatatccaagtcatggcagtgagacgt
gccggccacctgctagccaggccccgctcctgtgggccctggactcctgagcctctgagcctcgttgggtcagtgtcagtggagctaagatggggcagtgcagtaatg
gcaagtgagcggaagcatggcagcccctgagggacaggctggacacagggcttccgttctcttgtctcaggggtcag
ggtgcccctgccatcagctgaggggacacaggctgggtcagcacagtggcctctgcctcgaaggtctggagtcgtgcagctgtctgttctgtcaggctgctt
ggcaccgcagggcaggtggcactgtgagcctgtgtgccgtgtggcctgccaccatctcctgagtggcgtgggcctgagggttgagttctattgataacccatgga
aaagccccctgagtgcttgggcatggcacgaggaattgctgggagcgtccatccaccagtcatccacccagtcagtcaccatcca
gttcccatgaggcaggccagcgcagcaggaattgctgggagcgtccatccaccagtcatccacccagtcagtcaccatcca
catccatatccacctgtccatcctgccattcatccaccctgctccaccgctgtaccgctgctccatcctgctgctcatccatcca
tctctgtccatcatctgtccatcccgtccatcctcatcctcatcctgtccttccatctcatctatcatctctgcca
catcaccctttctgtccatccatccatgtccatccatcctgtccatcatccatccatcatccatcctgatgcagtgc
tccatccatccatccacctgtccatccatccatcctgtcatccatccatcattccaccctgatgcagtgc
ctgccgtccaccttctgtccattccatccatcctcatccatgtccatccatcattgccatctgtccactccatcc
actcatccaccaccatcccatccatcccccaaccatcctgtgccatcgtcccatcaccatcctgtcatgcatcatcctctctccaa
```

FIG.1-63

```
ctgtctgtttgtccattccatcatctatccaccatccaccaggcgagcacctgccatgccacgacctgccaccattccggtg
aatctccatcgtagcccaggagggctcttttcagctgcacttcaggatgagagaaggaggctcttgagtgccattgccaa
ggtcacacagagctcagggccagcgcttccatgccaaagccagccctctgccagtccgctccgcctccggcttgcagtggag
cagccaggggttccgtactccctgccaggcagctgcactgctgcagccctcccctccagttcctcagcctggctatggaggccc
aagtcccacgtgtcactgaattcggaggagcctggctgctctcaaagctttctgtacaaacaaggagaaaaagaagccactttgc
tgtctggacatgctgtgggtgtcctggggaatgtgctggggcctgcttgggctgcttgagtgccaggagctgcgtctgca
ctgtggcttgaaccagtgtcgtgctctgtgacagagccatccactctgggggtgctcgtcctgcactgtcagccccattc
tggaagtccaactggtccccaggcctgtgtccagagaccttccagtcttcattcactgatcatgcatttatttttgggggt
aggataggtcctgaagacaccaggcaggatctctgagttgggtctttgcggaagtgaggagtgagagggtgttccaggcagag
gagtggcagagaaagccaccaagtgaggcaggggacatgagtgctcggagacaggtctggccttgttgtagcgcggccctcgcagtg
aagcagaggccagctccaaggccccctgtgggcacattaggagacaggtctggctttggcgcagccccgctcttgtgagcttttgttttctgttactgg
atggtccctgtcagacctccagatcctggttgctggttggcgcagccccgcctcttgcccaaagcacagagggctgcaggcctggggcag
acctgcagctcttcctaggcctctaggggccctgccctgagcttcactgccagaaacaggctgcgatctgggtgttgcctgggtggggtgcca
gtgggggctcgcctctagtctcagtctggatgtggggagaggttgttccatccagggcagttgtctccagaagcagttctctgtctgatctg
gcatgcgcaacctagttggcccggtctcacgtgccagtgagctgagctcaggagagtgagcttccagcctgaagtgcatgtgccctgcatg
ggtgctgcaacctagttggcccggtctcacgtgccagtgagctgagctcaggggagtcagcgtgagtgctgggccttgccaatgcaggcgaattca
agctgactctaggaggacaggagggtgagctcaggcagggcgcaagccctgagccgaggctcacaggaagccatgccagcgataa
attctccactcatgggagggactgcccccagccagtttctgtgtgctcattggagcaaggcatgaggccactaacgaatg
ccacagtcccagtgcagtgcagggatctcagtgtagtgaggtggcagcacacagttaaccaaacaattgtggaggaggcaaggttgcagatttatgggtcgctgatgggt
tcctgatctcaggatccggagtgcagagtgcagcacctaactgaggaggcaaggtttaggcagggaggactcaggaagacttcct
tccacacagttaccgtgcagccaggagcgcacccttaggcaggcagcagcagattcagagacaccccagggg
ggaggaggtgacttgttcttaggaatgaggccccaggagctaaagcttatggagggcagcagcagattcagagacaccccagggg
tagggggaagtgcactagagtgacgtgctgtgcctgccgtcacacgctgcagcgcagtgtgccatatttgtgggcc
gccttgccctttcaaggaagcagctgccgcgtcacacgctgcagcgcagtgtgccccatattgtgggatc
tttcagattttctcaagaagaagcctaggcgcctcacacgctgcgagcagtgtgccccatattgtggatc
aattggtgagggcctgagacaggcgggtgagcacttgcccacactccagccgacactttgaaaagtttgtgcagcggtttaccgcatttgccac
```

FIG.1-64

```
gtgagggagtctctggagaccaccaaccgctggtgggcggccaagcgtcaccaccagtcctctcagtgctgccacctctgttc
tcagccctgcgtgccgctgatcagtggggcagtgagaaccgcgcaggaaatagctggccgcatggtgtcggttctggttgacag
agtgccacctggctaaaccagccgactgctctctgcctggctgcacacgccttgcctcaggctgcctccggttctgttgacca
aaccctttcccgccagtccaaggaatgcaggcatctggtggcccacgtggagcacatgggaggcgctgggctaccaggcc
ccaggctgcagatcgcagcatgcaccactccttcctccagtccegttgacctccatgtgtgctgctgccccgtcctccgcactgcct
tgcgtgcactgctgcagcagccctccatccggggtgggtgggatggagacccctgcctacaggcctccgggtctagccagagtcaaccag
cttcgtagtgccccagctccatcceggggtatgcccacgtgccaggaggatctgctgacgtgagccagattcgattcttgtgcg
cccaccagagacaccagatgcaggctatgcccagctctgccacttctggctgtgacttgagcatggctgttcattcctgggtctctc
agggagacgaaccaggtttaaaccccagctctgcgcaccatggtgcgcactgtccaggagagcacatagagacgccaccagctgcttactg
ctcatctcagaggagcagatcatgtggtatcgctgatgtcctggagccacaagtctgctagctagaggagctcacctgcatcccgggc
cagaggtgtgggccattgtggagagctctggttgtgggcagcagcaggcctatttccagtgagtctgtgctcctggggtgtga
ctgccactgctggtggagagctctggttgtgggcagcagcaggcctatttccagtgagtctgtgctcctggggtgtgtga
gacctgggcagatccctcctgtgcctcggtttaccactaggctcagagccctgggggactgctcagtgagtgctccttct
gcgaggagactttttgtccttactagccagagacaggtcagccgggcaggctctgggcctgcaccaccactgaaggaa
agggggttcagttagcccagagcccctgcccccaatgaaagaaattggggttcagttagccagccctgccaccccagctcttca
cacatccagatccagatgggggccagaccaccacatgtgcacacaggaagactgtaaggatccaaggccgagggcaggagagcagtgcgccctctc
ctatttctggttgcaaccgccacaccctttgcaggccctgtcaggcctgtgacaggcccgaggagcaggagagcagtgcgccctctc
tagctctgagacacccttgtcaggcctgtcaggccaggccagggcaggaccaggtggggtgggtgcagtcgcagtcctgggag
gggtactgggcgtgggccaggccaggcaggacagagtttgggaatccagcccctcaccattgcctgcttttgtatgtagtg
ctgcctgcggcggcagctagctggactgggcagcccggtgcagtgctcatgccagccggtgcacagctttctcatccacacattccatgtgtagggg
aaggcgggcacggtggtttggctgggtgggcagccccaccccctcttgttacagaggcagatgccaaacgatgggagcaagcacctga
tcaggggaggggtcacctctcctcctcagctgggcagtgaggtccagccagcgatccagcagggactcttcagtcctggttttg
caggccactgctcctgctctcaggccccaggcagagaggtgagggaccaggatgagggaccccgagaaggtcctgtatgtgagcaggttggcaaggggaggcgg
cccatccctgctcctggtcccagccaggccaagtgactccaaagcgccgagaacttcaaagcgccgagaaggtcctgtatgtgagcaggttggcaagggggaggcgg
tttggatttttttttttctgccaagtgacttcaaagcgccgagaacttcaaagcgccgagaaggtcctgtatgtgagcaggttggcaaggggaggcgg
gtctccaagctgggagccctcctgcgcctcctgcgcctcctgcgccctgatgtgccctgatgtggccctgaccctccgtccctcaggcccaccctcgt
```

FIG.1-65 gccaggaccagctggcttcaatggcaggaggtgccctgggctgagggtccccacgctgggctcccaggttgactcag
cagtcccaggcctgtgggcagagctggcctgctgccccaggcacgggctgagcctgagcaatccctgatgagaacaggtagctgag
gctgagcctgtgtccccaggcagctgctgctaaggcccggctgggatgtgagtgctgggctcattgctcatgtgagctctttgca
ggcaggaccaggtcagagtccttgtgtgcctcttgaccccagtcctggagaagagggcttggaggcttggctgctggatgc
acaggctccatgggaaggagctcctgctcggtttctttgtaagcacgacacatggcaccttccagagtacatggtctggc
atgtcattcccgacctgcttcagaaccaggg*acgaggtcgagcag*cctgctgagatcttgtgccatctccactccgcca
cccagctacccgtaaggaggccaccgaccctcgggaccttgccagggaccccagctcaggccagtcacgggct*gatgtgggatg*
*ttctg*gccttttctgcccacctcactgtgtgtgtgatgtaccggtcagacatctgataagcagccttcagagaagctgcggtgtgcag
aacccatggg*c*acaggctagtgtgtgtgatgtaccggtcagacatctgataagcagccttcagagaagctgcggtgtgcag
gtggagcagacctcccagctccagtccatcctccagcacttgccaggtcaggctgcccttccactactcctcacctcatgaatcaccctct
ccccggggcttgggctctt*gggtttctgatg*gaagatgccctgcgtcacccttcgatgccagtgccagatccctgaattcactgggcag
gtccttgtcctgcaagtctgtgcgacacgccgagctggctgtcactgcttccaaagcaaat*gggacaggga*tacctgccccctccctggtaggcagctgtt
cgcccctgcacctggctgtgagagtctctgcccacacctggccccaggcagg*tcctgagagagg*cgggtgggcacgac
tgggagtcccgggcgtggctgcagtc*caggtccctc*agagccctcggggagagcgcaccccgtctccccttgtcagtgttcccagaggc
ggtgctggcctgctgccgtgacagagca*gactgtcctgtgaagctgtcctgtc*catgggctctctttgcttgggcctggccaccattttcc
ttcgattggtacaaagactgtccctgtgaactgtccctgtgaagctggcaggagga*gaatcactgatgacag*gcctgccagctgggggccttgttttattca
*ccctg*cattcggctgacagagcatgagggggaggag*gctgatgtgggga*caggcctgtggggggaccactgggggacagtgagtgggtcttgaaacgtg
tttggtgggcacttcctg*gtgctgctctgggtcagg*ctgtgggggagaggagcagcccc*agctttgatggcatgggt*ggtgggggcacattc
gaag*caagt*caacactgaactgccctgtggaaggag*catacag*tggaggagcatacagtgggacaggagtgagtgggtcttgaaacgtg
*tgcatgctcagaagagaga*gcaactcgccctgtggaaggagcattccaggcacacagtgggcaatggcacagcaggg*aagctgggatgtctgaaga*
aacaggagtttgcaggtggagcaggtttcaggacattccaggcacacagtgggcaatggcacagcaggg*aagctgggatgtctgaaga*
*gcagcagccagaca*ctgagtgctggcgaggagcgaggg*ccacagcagtttacacagg*ggaggaggagcagcacggccagctgagcatttagggaggccact
gggcaggctatgatgtgggcaataggg*ccacagcagtttacacagg*ggaggaggagcagcacggccagctgagcatttagggaggccact
ctggctgcaaaagagagaggagagcaggcagtggaggggagagcaggggaaggggaaggaacaggcttcagcag

FIG. 1-66 aagacctcctgcctcaaggggccggtcacctgtgggtcgtggttaaggccagcctcctgttcctgcagccacatgcctc
ccagctgtgtgctccgcttctacctcgaaaccgggcagcaggaccacctgcaggctcctgcgcaaggatggggaggtacc
tggagggccaccccacatcagagcagttcctcagcacagagacgccaaatgagcccgaggggaggctgccccaggagaggaga
ggagaaccgcagccgccccccagcgcagcaaggctgcctggggaaatcactcactgctcccacctccagcagcccagcagccaggcactct
ggcttagtgaagaagcaccccagcaaaggcctgtgtctccacaccattctggggggacagcagcaaggacgatggacggagca
gtgctcagcttaacgtccctgtttcggaagcgtcctgccctgtgacaactgtgatgtgtgaactgtgaacctgtgaaccctgtgaggcagatggtgga
ctccaggccctttttctttttccagcagcgccagcgccaggtgagctgcaggccccagaacgccaagccatgctaccttacagatgaggaaactgaggctcgtgtgcctttgcct
ggtggagggggccaggccagcgccaggtgagctgcaggccccagaacgccaagccatgctacctacagatgaggaaactgaggctcgtgggcagtctttgcct
cttttgtttcagatgcccatgactttttgggacagacaggtgctcagctgtctgggggcctgggctgggcaggggag
acggcctgggccatgactttttgggacagacaggtgctcagctgtctgggggcctgggctgggcaggggag
gagcagcgctgtgaccccacgtggggcagcccagcctctccctgcctctccctgttacaggccctgcccgtcttctgttcctgtcctgtgtcccatgcctgtccc
caggacacagaaccgtggggcagcccagcctctccctgcctctccctgttacaggccctgcccgtcttctgttcctgtcctgtgtcctgtgtcctgtctgt
ctccctccatgtgtctcctctgcctcctcctcgtgtgcgtgcttctcaccctctccgctcttctgttcaccactgccgaggacacacctt
tcatggttcctcctcctgcctcctcctcgtgtgcgtgcttctcaccctctccgctcttctgttcaccactgccgaggacacacctt
ccagtaggccactccggcaggatggtctgcggcccctcctgccgcctgcctgcctgctgcctctgaggtcacaggggcactggccagtgtggggcaggact
tgctgggttctttggttcagcttttgtaccgtgacatctctgaggtcacaggggcactggccagtgtggggcaggact
cctcctgccaggccattggacaaagcagagctgcttcagggggcttgggacatcacgtaattaagacataaaagtccacgatttccgctgcgtgggcaaacac
ccagctccctgggagacacagcccacagcagcgtcacgtaattaagacataaaagtccacgatttccgctgcgtgggcaaacac
cgccgggtgctaatgtacacgtgggggctgccccgattcttttagtgattcttgaattaaatgatatgtaatcacaaagcgtcatctttaaacataattagccacgacgcca
ttcggctaggtacacgtgggggctgccgatttcattacaaagcgtcatctcttatgggagaccttcatctgttcctct
cggggctggttgctttgctggacataagcctgccccaggcacctgggaaggtgtcaaggggaaggtgtcaaggagggggtcctgggcagt
cccccggggctcgatgatgaatcatgggcgtgttgctgaagaattttgttccgtgggaacaaggaaccaaactc
tcactgttgtggggagaaagttggaaatcagatggaactgctgcggtcacgtgcgtgccgctaccagagagacgtcagacccggcgcgcctcag
ccccgactcctttgtaagcgtggctgggtgggtcacacgtggctcgcgaggcgctggcgccgcacgagcagcagagagtagagacccagaggttgcagg
gagctgagggcagcctgcaggggctgatgcaggcagctgtgatgcaggcccatgcacacaggcagcagagagtaaggaagagacgccagaggttgcagg
ggcagaggggcaggaggggcagagctcggcgtaggagtgagcctcggcgtaggagtgagcctactggtcctcccgcaggcacccctagtgccaggtctg

FIG.1-67

```
ctggactccaggctgttggtatgcccctaggtctgctgcttgaccctcctgatccagtgctgctgccggcttc
ctcccactcacctgtcctcctgtgccccatgtgccatgctagccacacatcagtgtccgtccgtgctgctgcccccaccagcc
tgtgccaggggaaggctcaaggccggtcatgctctacctcctggccagcccagcccaccgtgcattcctggacag
gattgctgagtttccatttagcacacaacagcgccaacaacctgtcctgccacgaatattggctcctgcc
tcctcatgggagccatggtgcatgtctattatgacctcggtctagaggcaggcaggacacaaggcacaggggcttaggaagttgcct
gaggtcacgtggctggtagggggaggggagccagcttatcctcatggcacagatgaggaaactgaggcagagaggtgtttgccagg
gggctgattactgagcagccagccgccgttctgttttgtctctgctcgctcagaggaccccaccacctgcctaccca
gcttgccgtgtcctgccgcaggcagcagtctcaagaggtagagctgctgagagaagcctgtcatctgtcctccaagagggatctg
agtaagccgagagcatcagcagctcaagggacccttggaccctgcccaccttcattctgtaccagggcaggtgtgtctgca
cagcctgagccagtgtggctgcgcgcccagaagacaggccaacctgccagccagagcagccgcatctctgcagcagcg
gtgcacttgagtggaagcactggcttccaagagtaagagcttgagaagggcctgtccagagcctgccagcttccatttgtctcttttgcatat
agcccagggtccagccttctgtagggccgaatcgttaccactcaggctctgccagtcttccctctggccctacaatagcaactgt
tactctcttttttacaccccttttaaaatataaagacaggccgagtaggatttggccctctggaataacgcgcagcgtaggatcacctgtcaccaggttggaatgcagtggtgatcagctcaccac
gagcattatatgtgcttctcttttttgagactctcatctgtcaccaggttggaatgcagtggtgatcagctcaccac
agcctcaacctcccaggctcagtgatcctccacctcagcctcccaagtagctggactacagcgcctgccactacacctggct
gattttgtactttttgtagagatagggtttcaccatgttgccaggctggtctgaacctcctgggctcaagcaatcctcctgcc
ttagctcccaaagtgctctaaaagtgaagaataggatgttagccaccaggtcagatctgccagctctggagctctcgtaagtcagtctgctgt
cattagtacgtgccgtcccaccctgtcactagtctgttcactagtctcttcagtgctttgccagctcggagctctcgtaagtcagtctgctgt
ctttcgttaggaagctgccgtcccaccctgtcactagtctgttcactagtctgctctcagtctcttcagtgctttgccgcggcaggaactcacccagattgagc
gtgtattcctgagtctgactgctcttcagtctggttcctgtgtcttgttttccatctcccctgccggctggcggctcggtcagttgactt
cgttggagtattccagtgtgcaattctgcgtgtcagtgtgcctttgtgaacgtgcctttgtaacgtgcattttctgctgtgtac
tgctattgcaactaaagctgtgtggagcagtgcagtgcagtgaagtgcagtgcatgaagtgcagttttccaatgtgcgctgttaccgatgcatttctgctgtac
atacttaggagtggactgcaggtgtctgcaagtgcaagtgatatcaacaccaggtgcagtttccaatgcgaagttccatgcagtttccaatgcgtgggccgtaccatagaaaggcctcgtggtcgtggt
gatgccgagtccatattccagactgacgaggattgcgtggtgccaagtcctatttcagcactgacgcaggatcacgcatgtct
tcaatgccctctctagatcgtagaacacctgtgcatcaagaatgacacacaagaggcctcaagcctgaca
ctgacacgggttgttcttgctggggtgctaatggagcgggtgcgggtgcgggtgcgggtgcgggtgcgtgatggagcgggtgaggg
```

FIG. 1-68

*tgcgggtgagggtgctggtggagcgggtgagggtgcgggtgagggtgctggtggagcgggtgagggtgagggtgagggtgctgatg*
*cagcgggtgagggtgagggtgagggtgagggtgctgatggagcgggtgagggtgagggtgttgacggagcgggtgagggtgcgggt*
*gagggtgctgatggagcgggtgagggtgcgggtgagggtgctggtggagcgggtgcgggtgcgggtgcaggtgagggtgctgatgg*
*agcgggcgagggtgagggtgagggtgctgatggagcgggtgagggtgcgggtgagggtgctggtggagcgggtgcgggtgcgggtg*
*caggtgagggtgctgatggagcgggcgagggtgagggtgagggtgctgatggagcgggtgagggtgcgggtgagggtgctgatgga*
*gcgggtgagggtgcgggtgagggtgctgatggagcgggtgagggtgagggtgagggtgagggtgttgacggagcgggtgagggtga*
*gggtgagggtgctgatggagcgggtgagggtgagggtgagggtgctgatggagcgggcgagggtgagggtgagggtgctgatggag*
*cgggtgagggtgcgggtgagggtgctggtggagcgggtgagggtgttaatgaagcgggtgcgggtgagggtgctgatggagcgggt*
*gcgggtgaggggg*ccgcatactcatccccttgcctggtcccccaggctcctactttggtgtgtgctcattcaggagcagcagagtg
gccgtgcttgggacggccagccaagcgatccccactggtactggcatctgtaggtgcccctgcttggagcgggtgctggcaactgc
cctttgctggaaggggcagcaatgtccagcagtggtggaagctctcgaaagaacacagggctgggagtagaactcagtcagatccc
agctctgctctccctgctgtgtgacctatagcaagtctctgaacctttctgagctgtttcctcacctgttcaagatgggggtgacc
acttcttccttggaggatggaagggagagggatgtgaggctcgtgagtgctgtgctcggagactgtgcaggaggggaagcggccgt
agccccatacaagcaggtgggcaaggaagtgggggcgctggaggggcttaggggacaaggggttctgtccttgggacctggacaag
agccaaaaggtataccctcacagtcacaggggagcccacactgccctcccctcccagggactgcccctgtggcccccgtccaggtc
cacagcctcagcagtccctgagggccaggaggtagcctccaggccactgggctgagaacccttaaaagaaaaagccccccctgccca
tgacagtcattttagggtcaagaaagccctttgcagaaaccaaaccctttgaaagggccaacacggcttttagatgacgtgagaac
caacttcaagcacttcctctcagaccagggtggcagcttccaaagtgggggcgctgctgccgggagactgtggtttccctgcttct
cagggagcttgggccaggccgtggggagatccaagcaacatgtccctcggtagtggtaggtttgcagacgggccgctccccacttc
ctgccaagctccagcggcacctctgtgggtgcaaggctgtggggaggggccttctggctcacagccctccaggctgcccacagccc
ctaggatgaggtgccacttcctcaaatgactgtcaagactgggatgggggccgggcacggtggctcactcctgtaatcccagcact
ttgggaggctaaggcgggcaaatcacttgaggtcaggagtcggagaccggcctggccaacatggcgaaaccctatctctacactaa
aaaatacaaaaaaagccgggcgtggtggcgggtgcctgtagtcccagctactcaagagccgaggcaggagaatcgcttgaaactgg
gaggcagaggttgcagtgagccaagatcgcaccattgcactccagcctgggcaacagagtgacacttggtctcaaaaaaaataaaaa
ataaaaaaggctctggatgtctccacgaacccacctgaccccttcctgctcctggggctctcctctcccacccacgtgtctacccg
tagctcctgcctgccttcaggactcagcccacagccccttccacaaagtcccctggcagggcccggaggcctctgcactgtctcat

FIG.1-69

```
ggcttcattcctgtgtcctcagcatccagtgagacctcaggagatgcctggggaatgctgaggctttggagaggttgctgcccc
cagaatcccagcagagggcagtttatccaggagcccggtgcctcctctgttggtgggtggcctcagagggcaccaaccagaa
gacacatgctgtcactgacatgcgggccccagctaggccactgctcttaggcgcaggagcctccgagtctctaccccagctgtccccacagtgca
catggactaggctcctccaccaggcactaggccactgtgtctggctggagccagagggtgggtgagccctggggagcccagagcaggtacactca
tgtcccaccatccaaggtgagatgtcttgtctggagccagagggagctgggccgctgtcactccaccacaaggctgagcagg
ctccccagtgggagacaggtttgggaggtgtcaggttgagggcacagtcaggagggggcacagtgtgtgctgagtagggcagggg
aggaggggatggccagtggccacggccaggctgcctggcaggacctgcggaggtttcctcaagctaaggcaggccatgttagat
gctggagggtgggtggtgctgcagagggtcagcgtggggcactgactaacctccggccatcctctcagGCCAGTGACGAGC
ACCATCGGAAGTGAAGGCTGATGGGTACGTGGACAACCTCGCAGAGGCAGTGACCTGCTGCTGCAGCACGCGACAAGtgatgg
cctcctggagagcccgcgctcctccaccctgcctctccaccccctgcctctccctccacctgcccagtgcccagaccaacaaggcc
ggagagcccacctcctccaccctgcctctgccctgcatggccaggcattttgttcctacctgggtggcctgctccctgctgggccctga
tgacagccctgccttctgccctgcctctgcctgtagtgaagtccagagggtgggacaggcctgtcagcctgtcgggaatctccaaatcccagaactcaccactc
cttcagctccctgtagtgaagtccagagggtggacaggcctgtcagcctgtcgggaatctccaaatcccagaactcaccactc
accatggcctttaaatgcagtaaactccacctaaccagattcagggcactatgccactgcctcttcagactctttgcatt
tcagtgaagctggaagaaaccagggcctctatgcagcagccccgctctttttctatcctccagtcaccttgcagacaaagacc
agcacactgccaccaccccgaaacatgccagtccatgccacacagtgagaactgtagcctctgcgtcaaggcacacagggtactt
agggcagctccgagggcactgtgaaggctccacctaaccagatgccgtgtgtgcaggagaaactaacagttcagtaaactctgccttgac
tctgaccactgctgacagactgaaggtgtcatgccggtgtgtgcaggagaaactaacagttcagtaaactctgccttgac
cagcagccttgactcaggctttgactgctaggagaaccgtatggggaggaggccaccagcagggtctggccactgtctctagtcc
tgccttatgcttgagccactgaatatcagaggtgcgaggacaagggcccctgaaacacctcacctgctcagccccttcacttagc
agatggggaaactgaggccagagggccagtgagctgtgttggccctatctggaacgaggcagtccagggcaaactttggact
gccttcctaacggaacagctgtggcctggggtgtgagcttttgcttcccgaccaaggcgcggccttccacagggcc
ctggaacaaatcactcataactgaagtttcagaatcagtcagctgaacagataactgattgctccatttctcccaa
atcagttcagaagctactgataacccttgagaactgcttcttttatttattattatttattttgaaatggagttttgctt
tcgttgcccaggctggagtggcactggcgtgatctcagctcactgcaacctccgcctcccctgggttcaagctattctcccgcctcagc
```

```
ctcccgagtagctgggattatagtgcccgccaccacgcctggctaattttttgtatttttagtagagacagggtttcaccatgtt
ggtcaggctggtctcgaactcctgacctcaggtgatccgcccacctcggcctcccaaagtgctggtattacaggcatgagccactg
cgcccggcctgagagcgcttcttatgagagaagccatgggtctccggagcaggattccaccacatgaaggtgacgataagaaa
gtgtgggaccacgcggggagggcaagtacagccccccagtgctactgattgaggaggccatttgccctttagttgaaaatatgcag
ttcagcaagatgagagggccacagccgggcagtgctgatggca*gctccttaggagacaatacag*acgttcaggcggctgcagttcagtggc
atggctggctcctgatggagtccctgatgcgcggctgtgcgtgcgtgggtgatgcgcatgctgtgcgtgatgccgggtttgtg
agcctggaggggctgtgcgtgatgccgggctgcgggctgcgcgggttgtgggtgatgccgggttgtgggtgatgccgggctgt
ggtgatgccagtttgtgggtgatgcgggtgatgcgggtgatgcgggctgcgtgcgtgcgggtgcgggctgcgggtgatgccgggctgc
gcgtgatgccgggtctgtgtgtgctgtgcgtgggtgtgtgctgtgccggctgcgggctgcgtgcgggtgatgccgggtgccgggctg
gggtgatgcgggctgtgtgtgctgtgcgtgggtgtgtgctgtgcgggctgcgggctgcgtgcgggtgatgccgggtgccgggctg
tgcgtgatgccgggctgtgccgggctgccaggctgtgccggttgtttgttgtagttctttagttttttttctttttgtgtt
taatgggaagcttcccgcaagacagcagcaaccctctgggggaagagttcaagctgagacctctttttttttttttgagacgg
agtctcgctctgtcgcccaggctgggctgcagtgcaatctcggctcactgcaaactccgcctccgggttcacacattttcct
gcctcagcctcccgagtgctgggactacagaggtgcgccaccacgcccagtaatttttgtattttttagtagagacaggttt
caccgtgctagccaagatggtctcgatctcctgacctttgatctccgcctcggcctcccaaagtgctgagattacaggcgtga
gccactgcgcccagccagccgagccagccgagccagccagggagacagcagccccctggaggtgcagccc
cctgctttgttggggcgggagcatgccacccctctgagccgcgtgggctcagtgaagtgggtgttgtcatcctcctcccactgcacgg
gtctagagtctgggtgcgtgagctcgcgcgcgctgcgagggccaacagttagtgagggtgagggtgagctgcacttgcaggaaggtcc
agcccgcctcccaggccctttctagccctttctgttgccgtgctgcttcccacccttgcctgaatcctcctgtggggacgcat
gtggtggccctgtgctgacttccggctgagccagggcaccagtgtcctactctagagatgagctcttctgaggggtgagtc
cagccacacctgtgtggggtgtgtgtgagccgagcctgttaccccgtctataaacagaggattcacttcttttttacaggcacttc
ctggcctcggcggggtgcctgtctctgggtgagctggagagctgcagccgtggtgctgctgggggtcgtgtgtgttgcctagaagtg
aggaatgacctcttcaccctggctcttccggcagctggcactccagcatgtggaggggccgggcctggcagagacgg
tgtgaaccgccggccatgcgggctggagttcggggctgccaatgggctaaggccctgtt*tcaacacatgtcgcggaactgt
cgtgaaaaagactcaggacccacagttccgggtgctcccaggggtctttcccaccgaggctggagtggagctggagcagcctaggcc
cagccacacctcccaggctcccaggctgccaggccaggccaacccagggagctggcctgagggaggtgggggtggaggagcggaga
``` gcaggcctctcgggcctcaccacccttgcacctccagctctagggcccacacagtaccaagccctgggctcaatgtaccactta
tgaaactcaattcaaattggcttagtgcaacaaggtatttggtgtctcacatgactgacttgaacatccaggcctggctgtcacggga
accgcatctcttcccattgcagctacttgcaggtggcaggtatgtcccccagccaccgacgtcccctgctgctccgcaacccca
gggcctgcagaaaggcccacgagactcagagactggcagagactttaggcgaaccaggaacaggggcagtctccgtctgccaaa
ccctaaccagagaaacggcacgttgtgccagacggaggacggatgccagcgagggtccatgtcctcactgccgacaaggctgg
gaactgggccaagtgaagcagaggcctccacgtcagatgtgagcgccaccgggccagtgactgcagttcttccctccttccgttc
ggcttgagccctccagaggatcggaaaggctgagcctgacctggtgccgctgtcctgggtctgtcctgctggtcggttcct
gcccctcgggaggttgctgcagtggcaggtgaaagcctcctgttcctcaggcagaggtgggacaggggcggg
acgggcgagtgtggtgccctctggggtgtggtgctcttggtgccgatgtgcgtgtcaacagttccagctgcccc
tcagaactgtcctggttaggaggtgaacacacgggcagccacttctacgtggtttttaacattataaaagcagcatgtgt
tattacagaaatttaacagaagtatataaagaaaccagaagtca

FIG.1-72

FIGURE 2 attcggctgacagagcatgaggggaggaatcactgatgacaggcactggcctgcccagctgggggcctttgtttat
tcatttggtgggcacttcctgggtgcctgctctgggtcaggcctgtgggggggaccactgagggcaggaaacctggc
ctgtccctccaggaagcgaagtcaacactggcacctgcagatgaagtggcagagcagcccccagctttgatggcatg
gggtggttgggggcacattctgcatgctcagaagagagagcaactcgccctgtggaaggagcatacagtgggagat
ggggacaggcccagtgacgagcaccatccggaagtgaaggctgATGGGTACGTGGACAACCTCGCAGAGGCAGTGGA
CCTGCTGCTGCAGCACGCCGACAAGTGATGGCCTCCTGGGAGAGCCCCGCCTCCTCCACCCCTGCCTCTCCTCCACC
CCTGCCTCCCTCCACCCCTGCCTCTCCTCCACCCGCCAGGAGAGCCCCACCTCCTCACCCCTGCCTCTCCTCCA
CCCCTGCCTCCCCTCCACCTGCCCCAGTGCCCAGACCAACCAAGGCCCTGACAGCCCTGCCTTCTGCCCTCTGCCCT
GGATGGGCAGGCATTTGTTCCCTACCTGGGTGGCCTGCTCCCCTGCCTGGGCCCTGACTTCAGCTCCCTGTAGTGAA
GTCCAGGAGGGTGGGACAGGCCTGTCAGGCCTCTGGGAATCTCCCAAATCCCAGAACTCACCACTCACCATGGGCCT
TTAAatgcagtaaactccacctaaccagattcaggggcactATGCCCACTGCCTCCTCTTCAGACTCTTTGCATTTC
AGTGAAGAGCCTGGAAGAAACCCAGGGGCCTCCTATGCACAGATCTTGCAGCCCAGAACCAAGTCAGCCTCCCTGCG
ACTGCCCAGGCACACTGCCCACCACCCCACCCCCGAAACAATGCCAGCCCGCTGCTTTTTCTATCCTCCCAGTCACC
TTTGCAGACAAAGACCAGGGGCAGCTCCCGAGGGCACTGTGAAGGCTCCCATGCCACACAGTGAGAACTGTAGCCTC
TGCGTCCAAGGCACACAGGGTACTTTCTGGACCCACTGCTGGACAGACTTGAAGGTGTCATGCCCGGTGTGTGCAGG
AGGAAACTAAcagttcagtaaactctgccttgaccagca MGTWTTSQRWTCCCSTPTSDGLLGEPRLLHPCLSSTPASPPPLPLLHPPRRAPPPPPLPLLHPCLPSTCPSAQTNQ
GPDSPAFCPLPCMGRHLFPTWVACSPAWALTSAPCSEVQEGGTGLSGLWESPKSQNSPLTMGL

FIG. 3A

MPTASSSDSLHFSEEPGRNPGASYAQILQPRTKSASLRLPRHTAHHPTPETMPARCFFYPPSHLCRQRPGAAPEGTV
KAPMPHSENCSLCVQGTQGTFWTHCWTDLKVSCPVCAGGN

FIG. 3B tgagaacccagggctcgctgggatgctgtctcctccctccctcctctgcaagctgtgggaaggcccttgcca
aagcgcacaagacccctttcacacagcagggcacaagctcttcgaggcagagtcgcctgcaggtggggtggaagggg
tgcgccccagaccagaatcgcccgcctctccaagaccatccctgctgccagtgacgagcaccatccgga
agtgaaggctgATGGGTACGTGGACAACCTGCAGAGGCAGTGGACCTGCTGTGCAGCACGCCGACAAGTGATGGC
CTCCTGGGAGAGCCCCGCCTCCTCCACCCCTGCCTCTCCTCCAACCCTGCCTCCCCTGCCTGCCCCAGTGCCC
CCCGCCCAGGAGAGACCCCACCTCCTCCACCCCTGCCTTCTGCCCTGCCCTGCATGGCCAGGCATTGTTCCTACCTGGGTG
AGACCAACCAAGGCCCTGACAGCCCTGACTTCAGTCCCTGAAGTCCAGGAAGTCCAGGAGGGTGGACAGGCCTGTCAGGCCT
GCCTGCTCCCTGCCTGGCCCTGACTTCAGTCCCTGTAGTGAAGTCCCTGTAGTGAAGTCAAGAGGGTGGACAGGCCTGTCAGGCCT
CTGGGAATCTCCAAATCCCAGAACTCACCACTCCTTTAAatgcagtaaactccacctaaccagattc
agggcactaATGCCCACTGCCTCCTCTTGCATTTCAGTGAAGAGCCTGGAAGAAACCAGGGGCCT
CCTATGCACAGATCTTGCAGCCCAGAACAAGTCAGCTCCCTGCGACTGCCCAGGCACACTGCCCACCACCCACC
CCGAAACATGCCAGCCCCGTGCTTTTTCTATCCTCCCAGTCACCTTTGCGTCAGAACAAAGACCAGGGCAGCTCCGA
GGGCACTGTGAAGGCTCCCATGCCACACAGTGAGAACTGTAGCCTCTGCGTCCAAGGCACACAGGCACGGGTACTTTCTGGA
CCCACTGCTGGACAGACTTGAAGGTGTCATGCCCGGTGTGTGCAGGAGGAAACTAAcagttcagtaaacttctgcctt
gaccagcagcctt

FIG. 4 ctccgagtctctacccagtctgtcccacagtgcacatggactaggctctcccacggggcactaggccaggccagg
ggtgtgggtgagccctgggagcccagagcaggtacactcatgtcccacatccaaggccagtgacgagcac
catccggaagtgaaggctgATGGGTACGTGGACAACCTGCAGAGGCAGTGGACCTGCTGCTGCAGCACGCCGACAA
GTGATGGCCTCCTGGGAGAGCCCGGCCTCCTCCACCCCTGCCTCTCTCCACCCTGCCTCTCCACCCCTGCCT
CTCCTCCACCCGCCCAGGAGAGCCCCAACCTCCTCCAACCCTGACAGCCCTGCCCTGCCTTCTGCCCTGCATGGGCAGGCATTTGTTCCCTA
CAGTGCCCAGACCAACCAAGCCCTGACAGCCCTGCCTTCTGCCCTCCGTGCCCTGCATGGGCAGGCATTTGTTCCCTA
CCTGGGTGGCCTGCTCCCTGCCCTGGGCCTGCCCTGACTTCAGTCCCTGTAGTGAAGTCCAGGAGGGTGGGACAGGCCTG
TCAGGCCTCTGGGAATCCCAAATCCCACTGCCTCCTCTCCAGACTCTCTTGCATTTCAGTGAAGAGCCTGAAGAAACCA
ccagttcagggcactATGCCCACTGCCACTCTTCAGACTCTCTTGCATTTCAGTGAAGAGCCTGAAGAAACCA
GGGGCCTTCCTATGCACAGATCTTGCAGCCCAGAACCAAGTCAGCCTCCCCTGGCACTGCCCAGGCACACTGCCACCA
CCCACCCCGAAACAATGCCAGCCCGCTGCTTTTCTATCCTCCCAGTCACCTTTGCAGACAAAGACCAGGGGCAG
CTCCGAGGGCACTGTGAAGGCTCCCATGCCACAGAGTGAGAACTGTAGCCTCTGCGTCCAAGGCACACAGGGTACT
TTCTGGACCACTGCTGGACAGACTTGAAGGTGTCATGCCCGGTGTGTGCAGGAGGAAACTAAcagttcagtaaact
ctgccttgaccagcagccttt

FIG. 5 tgcattcggctgtgacagagcatgaggggaggaatcactgatgacaggcactggcctgcccagctggggcctttgtt
tattcatttggtgggcacttcctggtgcctgctcttggtcagcctgtggggggaccactgaggcaggaaacct
ggcctgtccctccaggaagcgaagtcaaactggcacctgcagatgaagtggcagagcagcccagctttgatggc
atgggtggttgggggcacattctgcatgctcagagagagagcaactcgccctgtggaaggagcatacagtggga
gatgggacaggccagtgacgagcaccatccggaagtgaaggctgatggtgacaacctcgcagaggcagt
ggacctgctgctgcacgcgcgacaagtgatggctcctgggagagccccgctcctccaccccctgcctccctcc
accctgcctctcctccaccgcccagagagcccaccctcctccacccctgcctcttcctccaccctgcctcccct
ccacctgcccagtgcccagaccaaccaaggccctgcctccctgcctgggccctgacttcagctcctgtagtcaggcat
ttgttcctacctggttggcctgctccctgctgggccctgacttcagctcctgtagtcctgtaagtcaggaggtgg
gacaggcctgtcaggcctctgggaatcccaaatcccagaactcaccactgggccttttaaatgcagtaaa
ctccacctaaccagattcaggggcactATGCCACACTCTTTGCATTTCAGTGAAGAGCCTGG
AAGAAACCAGGGCCTCCTATGCACAGATCTTGCAGCCCAGAACCAAGTCAGCCTCCCTGCGACTGCCAGGCACA
CTGCCCACCACCCCCGAAACAATGCCAGCCCGCTGCTTTTTCTATCCTCCCAGTACCTCACCTTTGCAGACAAAGA
CCAGGGCAGCTCCCGAGGGCACTGTGAAGGCTCCCATGCCACACAGTGAGAACTGTAGCCTCTGCGTCAAGGCAC
ACAGGGTACTTTCTGGACCACTGCTGGACAGACTTGAAGGTGTCATGCCCGGTGTGTGCAGGAGGAAACTAACagt
tcagtaaactctgcctttgaccagcagccttt

FIG.6 ctccgagtctctacccagctgtcccacagtgcacatggactaggctcctcccacggggcactaggccaggccagg
ggtgtgggtgagccctgggagcccagagagcaggtacactcatgtcccaccatccaaggcccagtgacgagcac
catccggaagtgaaggctgatgggctgtgggtacgtggacaaacctgcagaggcagtgacctgctgcagcacgccgacaa
gtgatggcctcctgggagagcccgcctctgcctctccaccctgcctccctccaccctgcctctcctccaccgccag
gagagccccacctcctccaccctgcctctccacccctgcatgggcaggcatttgttccctacctgggtgcctgctcc
aaggccctgacagcctgcttctgcctctcctgtagtgaagtccaggagggtgggacaggcctgtcaggcctctgggaatc
cctgcctgggcctgacttcagctcccgtagtcccatgggcctttaaatgcagtaaactcagtcgcggccctgtcaggcccgt
tccaaatcccagaactcaccactcaccatgggcctttaaatgcagtaaactcagttaccagattcaggggcact
ATGCCCACTGCCTCTCCTCTTTGCATTTCAGTGAAGAGCCTGGAAGAAACCAGGGGCCTCCTATGCACA
GATCTTGCAGCCCAGAACAAGTCAGCCTCCCTGGACTGCCCAGGCACACTGCCCACCACCCCACCCCGAAACAA
TGCCAGCCGCTGCTTTTCTATCCTCCCAGTCACCTTTCATGCCCTGCCCTGCGTCCAAGGACAAAGACCAGGGGCAGCTCCCGAGGGCACTGTG
AAGGCTCCCATGCCACACAGTGAGAACTGTAGCCTCTGCGTCCAAGGCACACAGGGTACTTTCTGGACCACTGCTG
GACAGACTTGAAGGTGTCATGCCCGGTGTGTGCAGGAGGAAACTAAcagttcagtaaactctgccttgaccagcagc
cttt aagaactttaaaaatcacctagtgtgtgggccgggcacggtggctcaagcctgtaatcccagcactttgagatgctga
ggcaggtggatcacgaggtcaggagatcgagaccatcctgataacacggagaaacccgcgagctgaggagcag
ggccgggcgccATGGCCACGTGGGGCGGCGGGCGGCCAAGGCTGGCTGGCGTGCGTGCCTGCTTGACATCTCGGGCGTGCTG
TACGACAGCGGCGCGGGGCGGCGGGGCCATCGCCGCGGCTCGGTGGAGGCGGTGGCCAGACTGAAGGTTCCCGGCT
GAAGGTGAGGTTCTGCACCAACGAGTCGCAGAAGTCCCGGCACCAGTGCCTGCAGATCCTGAAGGAGGAGGCCTGGATTTG
ACATCTCTGAGCAGGAGGTGACCGCCCCGGCGCTCAGAATTTGATCAGATGACACATCCAACCAAACTGTGTGGTAATTGCAGA
CTGCTCATCCATGACGGAGTCGCTCAAAAACATGAATAACGCCTTCCAGGTGCTCATGGACGTTGGTCCCTACATGAAGGCGTT
TATCACTGGGAAAAGGGCGTTACTACAAGCCGAGTGGTGGGGAAGCCTTCTCCTGAGTTTTCAAGTCTGCCTGCAAGCGAT
GAGTATGCCTGTGGCATCAAAGCCGGTCATGATTGGGGACGATATCGTGGGCGACGTCGGCGGTGCCAGCGGTGTGGAA
AGGAGTGGAAGCCACCAGCCCGTCATGATTGGGGACGATATCGTGGGCGACGTCGGCGGTGCCAGCGGTGTGGAA
TGAGAGCGGCTGCAGGTGCGCACCGGAGAAGTTCAGGCCTGCTGCTGCAGCACGCGACAAGtgatggctcctgggagagcccgcc
GTGGACAACCTCGACAGAGGCAGTGGACCTGCTGCTGCAGCACGCGACAAGtgatggctcctgggagagcccgcc
tcctcctccaccctgcctctcctcctgcctccctgctccctccacctgccagatgcccagaccaaggccctga
cctcctccaccctgcctctcctccaccctgcctccctgctccctccacctgccagatgcccagaccaaggccctga
cagccctgccttctgcctctgcctctgcatggcaggcagcatttgttccctacctggttgcctgctctcccctgcctggg
ccctgacttcagctcctgtagtgaagtccaggagggtgggacaggcctgtcaggcctcctgggaatctcccaatcc
cagaactcaccactccaccatgggctttaaatgcagtaaactccacctaaccagattcagggggcactatgccactg
cctcctcttcagactcttttgcatttcagtgaagagcctggaagaaaccaggggcctctatgcacagatctttgcag
cccagaaccaagtcagcctcccctgcgactgccccaggcacactgccccacccccgaaacaatgccagccg
ctgcttttttctatcctcccagtccatcacctttgcagacaaggcacacaggtactttctgacccactgctgaaggctcca
tgccacacagtgagaactgtagcctcgtcgaggaaactcagttcagtaactctgccttgaccagcagcttt
aaggtgtcatgccccgtgtgtgcaggaggaggaaactcagttcagtaactctgccttgaccagcagcttt

FIG. 8

MAPWGKRLAGVRGVLLDISGVLYDSGAGGGTAIAGSVEAVARLKRSRLKVRFCTNESQKSRAELVGQLQRLGFDISE
QEVTAPAPAACQILKERGLRPYLLIHDGVRSEFDQIDTSNPNCVVIADAGESFSYQMNNAFQVLMELEKPVLISLG
RGRYYKETSGLMLDVGPYMKALEYACGIKAEVVGKPSPEFFKSALQAIGVEAHQAVMIGDDIVGDVGGAQRCGMRAL
QVRTGKFRPSDEHHPEVKADGYVDNLAEAVDLLLQHADK

FIG. 9 aagaactttaaaaatcacctaggtgtgggccggcacggtggctaacgcctgtaatcccagcactttgagatgctga
ggcagtggatcacgaggtcaggagatcagagaccatcctgatdacacggagaaacccggcgagctgaggagcag
ggcgggcgccatggcCACGTGGGGCGGGGCGGCACGGCCATGCGCGGCTGGCTGGCGCGGGGTGCTGCTTGACATCTCGGGCGTGCTG
TACGACAGCAGCGGCGGCGGGGCGGCACGGCCATCGCCGGCTCGGTGGAGGCGGTGGCCAGAGCTGAAGCGGTTCCCGGCT
GAAGGTGAGGTTCTGCACCAACGAGAGTGCAGAAGTCCCGGCAGAGCTGGTGGGGCAGCTTCAGAGGCTGGGATTTG
ACATCTCTGAGCAGGAGGTGACCGCCCGGACCAGCTGCTGCCAGATCCTGAAGGAGCGAGGCCTGCCACCATAC
CTGCTCATCATCGACGGAGTCCGTCAGAATTTGATCAGATGACACATCCAACCAAACTGTGTGGTAATTGCAGA
CGCAGGAGAAAGCTTTTCTTATCAAAACATGAATAACGCCTTCCAGGTGCTCATGGAGCTGGAAAAACCTGTCTCA
TATCACTGGGAAAAGGGCGTTACTACAAGCCGAGGTGGGGAAGCCTTCTCCTGAGTTTTTCAAGTCTCTGCCCTGCAAGGCTT
GAGTATGCCTGTGGCATCAAAGCCGAGGTGGTGGGGAAGCCGTCATGATTGGGACGATATCGTGGGCGACGTGGCGGTGCCAGCGGTGTGGAA
AGGAGTGGAAGCCTGCAGGTGCGCAGAGCAGTGGACCTGCTGCTGCACACGCGACAAGTGAtggcctctggagagcccgcc
tcctccaccctgcctctgcctcccctcacctgcccagtgccagaccccaaccaaggccctgacagccctgcctctgccct
ctgccctgcatgggcaggcagttgttccctacctggtgcctccctgctggccctgctcccctgcctgacttcagctcccctg
tagtgaagtccaggagggtgggacaggcctgtcaggcctccacctagattcaggggcactatgcacagatcttcagactcttt
tgggccttaaatgcagtaaactccacctaaccagggcctccctatgcacagatcttcagccagaaccaagtcagcct
gcatttcagtgaagagcctggaagaaaccaggggcctccctatgcacagatcttcagccagaaccaagtcagcct
ccctgcgactgccaggcacactgccccaccccgaaacaatgccagccccgtgctttttctatcctccc
agtcacctttgcagacaaagaccaggggcagctcccgagggcactgtgaaggctccatgccacacagtgagaactg
tagcctctgcgtccaaggcacacaggtacttctgacccactgctgacacagactttgaagttgaagttgtcatgccggtgt
gtgcaggaggaaaactaacagttcagtaaactctgcctgaccagccttt

FIG. 10 aagaactttaaaaatcacctagtgtgtgggccgggcacgtgtggcacgcctgtaatcccagcactttgagatgctga
ggcagtggatcacgagtcaggagatcgaggagaccatcctgataacacgagaaaccccggcgggctgaggagcag
ggccgggcgccATGGCCACCGTGGAGGCGGCGGCAAGCGGCTGGCTGGCAGCGTGCCGGGAGTGCTGCTTGACATCTCGGCGTGCTG
TACGACAGCGGCGGCGGCGGCGGCACGGCCATCGCGCGGCTCGGTGGAGGCGGTGGCCAGAGACTGAAGGCGTTCCGGCT
GAAGGTGAGGTTCTGCACCAACGAGTGCGAGAAGTCCGGGCAGAGCGTGGGGCAGCTTCAGAGGCTGGGATTTG
ACATCTCTGAGCAGGAGGTGACCGCCCGGCACCGCCCAGCTGCCTGCCAGATCCTGAAGGAGGAGCCTGCGACCATAC
CTGCTCATCCATGACGGAGTCCGCTCAGAATTTGATCAGATCGACACATCCAACCCAAACTGTGTGGTAATTGCAGA
CGCAGGAGAAAAGCTTTTCTTATCAAAACATGAATAACGCCCTTCCAGGTGCTCATGAGCTGGAAAAACCTGTCTCA
TATCACTGGGAAAAGGGCGTTACTACAAGCGGTGGTGGGGAAGCCCTTCTCCTGAGTTTTCAAGTCTGCCCTGCAAGGCTT
GAGTATGCCCTGTGTGGCATCAAAGCCGACCAGCCCACCAGTGAcgagcaccaccaccaagtgatgatgtacgtgatggtgaaggctgccatccggaaccctcgca
gaggcagtggactgctgctgcagcacgccgacaagtgatgatggctcctcctggagagccccgcctccctcctccaccctgcc
tctcctccacccgctccccctgccctctcccctcaccctgccctgcccagtgcccagaccaacccaaggcccctgacagccctgcctctg
ccctcctccacccgctgcatgggcaggcattgttccctacctggtgcctctgggtggcctgcctcccctgcctgggcccctgacttcagctc
ccctgcctcgatgggcaggaggagtggacaggcctgcaggcctgtcaggccctaccctgggaatctcccaatcccagaactaccactc
cctgtagtgaaggccaggagggtgggaccagtaaactccacctaaccagattcagggggcctctgtgcacagatcttgcagccccagaaccaagtca
accatgggccttaaatgcagtaaactccacctaaccagattcagggggcactgtcccgagggcactgttgaaggctccatgccagccccgctgcttttcttatcc
ctttgcattcagtgaagagcctggaaggacactgcccaggcacactgcccaccccgaaacaatgccagcccgctgttttcttatcc
gcctcccctgcgactgccccaggcacactgcccaccccgaggggcactgcccaggcccggcactgttgaaggctccatgccacacagtgaga
tccagtcaccttgcagacaaagacaggcactgcccagggcagtgccccgaggggcactgtgaaggctccatgccacacagtgaga
actgtagcctctgcctccaaggcacacaggtacttcttcttggaccactgctggacagactgctggacacagactgctggatgtcatgccccg
gtgtgtgcaggaggaaactaacagttcagtaaactctgccttgaccagcagccttt MAPWGKRLAGVRGVLLDISGVLYDSGAGGGTAIAGSVEAVARLKRSRLKVRFCTNESQKSRAELVGQLQRLGFDISE
QEVTAPAPAACQILKERGLRPYLLIHDGVRSEFDQIDTSNPNCVVIADAGESFSYQNMNNAFQVLMELEKPVLISLG
KGRYYKETSGLMLDVGPYMKALEYACGIKAEVVGKPSPEFFKSALQAIGVEAHQAQ

FIG. 12 aagaactttaaaaatcacctagtgtgtggcccggcacggtggctaacgcctgtaatcccagcactttgagatgctga
ggcaggtggatcacgaggtcaggagatcgagaccatcctggataacacggagaaacccggcgctgaggagcag
ggccgggcgccATGGCCACGTGGGGCAAGCGGCTGGCTGCTGCGGAGGTGCTGCTTGACATCTCGGGCGTGCTG
TACGACAGCGGCGGCGGCGGGCCACGGCCATGCGCGGCCATGCGGCCATGCCGCGGTGGCCAGCTTCAGAGCGTTCCGGCT
GAAGGTGAGGTTCTGCACCAACGAGTCGCAGAAGTCCCGGGCAGAGTCGGTGGGGCAGCTTCAGAGGCTGGGATTTG
ACATCTCTGAGCAGGAGGTGACCGCCCCGGCACCAGCTGCCTGCCAGATCCTGAAGGAGCGAGGCCTGCCGACATAC
CTGCTCATCCATGACGGAGTCCGCTCAGAATTTGATCAGATCGACATCCAAACTGTGTGGTAATTGCAGA
CGGAGGAGAAAGCTTTTCTTATCAAAACATGAATAACGCCTTCAGGTGCTCATGAGCTGGAAAAACCTGTGCTCA
TATCACTGGGAAAAGGGCCCAGTGACGAGCACCATCCGGAAGTGAAGGCTGATGGGTACGTGGACAACCTGCAGAG
GCAGTGGACCTGCTGCTGCAGCACGCCGACAAGTGAtggcctcctgggagagcccgcctcctccacccctgcct
cctccacccctgcctccccctgcctccccctcacctgcccagtgcccagaccaaccaaggccctgacagcctgcttctgcc
tctgccctgcatgggcaggcagtttgttccctaccggtggcctgctccccgtccccgtgcctgacttcagctccct
gtagtgaagtccaggagggtgggacaggcctgtcaggcctcactaacagattcagggcactaccacctcctcagactctt
atgggctttaaatgcagtaaactccacctaaccagaacccgagggcctcctatgcacagatctttgcagccaggcaagtcagcc
tgcatttcagtgaagagcctggaagaaaccagggagaccactgtgcccacccgggcactgtgaaggctcctgttttttctatcctcc
tccctgcgactgcccaaggcacactgccaccacaggtactttctggaccactgctggacagactggacagtgagaact
cagtcaccttttgcagacaaagaccaggggcagctcccgagggcactgtgaaggctcctgttttttctatcctcc
gtagcctctgcgtccaaggcacacaggtactttctggaccactgctggacagactggacagtgagaact
tgtgcaggaggaaactaacagttcagtaaactctgccttgaccagcagccttt

FIG. 13

```
aagaactttaaaaatcacctaggtgtgggccggcacggtggctaacgcctgtaatcccagcactttgagatgctga
ggcaggtggatcacgaggtcaggagatcgagaccatcctgataacacggagaaaccccgtcgagtgaggagcag
ggccgggcgccatggccaccgtggggcggcggcgcacggccatcgccggctggctgccgcggtgctgcttgacatctcgggcgtgctg
TACGACAGCGGCGGCGGGGGCGGCGCCAACGAGTCGCAGAAGTCCCGAGCAGAGCTGGTGGGGCAGCTTCAGAGGCTGGGATTTG
GAAGGTGAGGTTCTGCACCAAGGAGGTGACCGCCCGGCACCACCAGCTGCCTGCCAGATCCTGAAGGAGCGAGGCCTGGCGACATAC
ACATCTCTGAGCAGGAGGTGACCGCCCGGCACCACCAGCTGCCTGCCAGATCCTGAAGGAGCGAGGCCTGGCGACATAC
CTGCTCATCCATGACGGAGTCCGCTCAGAATTTGATCAGATAACGCCTTCCAGGTGCTCATGGAGCTGGAAAAACCTGTGCTCA
CGCAGGAGAAAGCTTTTCTTATCAAAACATGAATAACGCCTCTGGCCTGATGCTGGACGTTGGTCCCTACATGAAGGCGCTT
TATCACTGGGAAAAGGGCGTTACTACAGACCGAGTGGTGGGAGAAGCCTTCTCCTGAGTTTTCAAGTCTGCCCTGCAAGCGAT
GAGTATGCCCTGTGGCATCAAAGCCGAGGTGGTGGGAGAAGCCTTCTCCTGAGTTTTCAAGTCTGCCCTGCAAGCGAT
AGGAGCGGAAGCCCACCAGGCCGTCATGATTGGGACGATATCGTGGGCGACGTGCGGCGGTGCCAGCGGTGTGGAA
TGAGAGCGCTGCAGGTGCGCACCGGGAAGTTCAGGCCACCCAGTGACGAGCACCATCCGGAAGTGAAGGCTGATGGACTC
TTTGCATTTCAGTGAAgagcctggaagaaaaccagggcctccatgcacagatcttgcagcccagaaccaagtcag
cctccctgcgactgcccaggcacactgcccacccccgaaacaatgccagcccgtgctgctttctatcct
cccagtcacctttgcagacaaagaccagggcagctcccgagggcactgtgaaggtgaggtgaaaggcactgaaggtgaagga
ctgtagcctctgcgtcaaggcacacaggtacttctctgaccactgctgacagactgtgaaggtgtcatgcccgg
tgtgtgcaggaggaaactaacagttcagtaactctgccttgaccagcagcctttt
```

FIG. 14 aagaactttaaaaatcacctagtgtgtggccggcacgtggctaacgcctgtaatccagcactttgagatgctga
ggcaggtggatcacgaggtcaggagatcgagaccatcctgataacacggagaaaccccggagctgaggagcag
ggccgggcgccATGGCCACCGTGGGGCGGGGCGGCACGGCTGGCTGCCTGCGTGCCGGGGTGCTGCTTGACATCTCGGGCGTGCTG
TACGACAGCGGCGGCGGGCGGCACGAGTCGCGACAAGTCCGGGCAGAGTCCGGGTGGAGGCGGTGGCGGGGCGGTGGTGGGGCAGCTTCAGAGGCTGGATTTG
GAAGGTGAGGTTCTGCACCAACGAGTCGCGACCCCCGGCACCAGTGCCTGCCAGATCCTGAAGGAGGAGGCCTGCGACCATAC
ACATTCTGAGCAGGAGGTGACCGCCCCGGCACCAGTGCCTGCCAGATCCTGAAGGAGGAGGCCTGCGACCATAC
CTGCTCATCCATGACGGAGAGTCGCTCAGAATTTGATCAGATCGACACATCCAACCCAAACTGTGTGGTAATTGCAGA
CGCAGGAGAAAGCTTTTCTTATCAAAACATGAATAACGCCTTCCAGGTGTCTCATGGAGCTGGAAAAAACCTGTGCTCA
TATCACTGGGAAAAAGGGCGTTACTACAAGGAGACCTCGGCCTGATGCTGGACGTTGGTCCTACATGAAGGGCTT
GAGTATGCCTGTGGCATCAACAAGCCGAGGTGGTGGGGAAGCCTCTCCTGAGTTTTTCAAGTCTGCCCTGCAAGCGAT
AGGAGTGGAAGCCCACCACCCAGGCCCGTCATGATTGGGACGATATCGTGGGACGCACGATCGACCTGCCAGCCGGTGTGGAA
TGAGAGCGCTGCAGGTGCGCACGGGAAGTTCAGGCCGACCAGTGAACTGAGCCGTGTGTGATGCTTGCCTGGGGGTCGGTGT
TTCCTGGCCCTGCGGGGTGCCCTGTCTCTGGCTGGAGTTCAGGCCGACCAGTGAACTGAGCCGTGTGTGATGCTTGCCTGGGGGTCGGTGT
TGCCTAGagtgaggaatgacctccttcaccctggctcctccggcagcctggccactttccagcatgtggaggggg
ccgggccctggcagagacggtgtggaaccgccggccgcatgcggggctggagttcggggctgccaatgggctaagg
cctgttcaacacatgtcgcggaactgtcgtgaaaaagactcaggaccacaggtccggggtgctccaggggt
ctttcccaccgaggctggagtggagtgagcagcagcctaggcccagagcagcacacctcccaggctcggaggactgccaggccagg
caaccgtgaaggtagcaggtgggggtgaggggaggacaggcctctcgggctcacccttatgaaaactcaattg
caccttccagtctaggcccacacagtaccaagccctggggtcaatgtacccacttatgaaaactcaattg
gcttagtgcaacaaggtatttgtggtctcacatgtccccagccaccaccaggcctgctcacggaaccgcatctct
tccattgcagctcacttgcaggtggcaggtgtccccagccaccaccaggcctgctcacggaaccgcatctct
gcctgcagaaaaggccacagactcagactggcagagacttagccggacaggaacaggggcgcagtctccgtccc
accaaaccctaaccaggcccacagagaacacggacgttgtgccagacggaggacggatgccagcgagggttccatgtcctca
ctgccgacaaggctggaactgggcaagtgaagcagagcctccacgtcagatgtgagcgccacggccaggtga
ctgcagttcttccctccttccgttcggcttgagccctgagtcaggatcggaaggctgaggctgacctgtgccgct

FIG. 15A

```
gtcctggtgggtctgtcctgctggtcggttcctgcccctctcggggaggttggctggctggcaggtggaaagc
ctcctgtgttcacctcagggcagaggtggggacacagggcgggacgggcgagtgtggtgccccctctgggtgggtgc
tcttggtccgcctcccgtgccagagtgcgtgtcaacagttccagctgccctcagaactgtcctggtttaggaggt
gaacacggggcagcctacattctacgtgttttttttaacattataaaagcagcatgtgttattacaggaaattta
acagaagtatataaaagaaaccagaagtca
```

FIG. 15B aagaactttaaaaatcacctagtgtgtgggcccggcacggtggctaacgcctgtaatcccagcactttgagatgctga
ggcaggtggatcacgaggtcaggagatcgagagaccatcctgataacacggagaaacccgcggagctgaggagcag
ggccgggcgccatggcacggtggggcgggcggcacggccatcgccggctcggtggaggcggtggcagagcagctttgacatctcggggctgctg
tacgacacagcggggcgggcggcacggccatcgccggctcggtggaggcggtggcagagcagctttgacatctcggggctgctg
gaaggtgaggttctgcaggaggtgaccgccccggcaccagtgcctgccagatcctgaaggagGAGCCTGCGACCATAC
acatctctgagcaggaggtgaccgccccggcaccagtgcctgccagatcctgaaggagGAGCCTGCGACCATAC
ctgctcatccatgacggagtccgctcagaatttgatcagatgacacatccaaactgtggtaattgcaga
cgcagagaaagcttttctatcaaaacatgaataacgcctccaggtcctgatgcctgacgttggtccctacatgaaggcgctt
tatcactggaaaagggttactacaaggagaccctctggcctgatgcctgacgttggtccctacatgaaggcgctt
gagtatgcctgtgtggcatcaaagccaccaggccgtcatgattgggacgatatcgtgggcgacgtcggcggtgccagcggtgtggaa
aggagtggaagccaccaggtgccaccggaagttcagtgccagctggagtcattattcaccttccttccaggggg
tgagaccgctgcaggcggctgccaccggaagttcagtgccagctggagtcattattcaccttccttccaggggg
atgaccaccattctcattctgtttgttctttttgtgttcttctgttgttcttaaatcaaagagcag

FIG. 16 aagaactttaaaaatcacctaggtgtgtggccgggcacggtggctaacgcctgtaatcccagcactttgagatgctga
ggcaggtggatcacgaggtcaggagatcgagaccatcctgatacacggagaaccccgtcggagctgaggagcag
ggccgggcgccatggcacccgtgggggcggcaagcggctggctgcctgccgtgggggtgctgcttgacatctcgggcgtgctg
tacgacagggcggggcggggcggcacggccatcgccgcctcggctcggtggaggcggtggcccagagctgaaagacttcccggct
gaaggtgaggttctgcaccaacgagtcgcagaagtcccgggcagagctggtgggcagcttcagagggctggattttg
acatctctgagcaggaggtgaccgccccccgctcagaatttgatcagatcgacacatccaaccaaactgtgtaattgcaga
ctgctcatccatgacggagtccgctcagaatttgatcagatgaataaacatgaataacgcctccagttggcctgatgtggaaaacctgtgctca
cgcaggagaaagcttttctttatcaaaacatgaataacgcctccaggtgctctgatgtggaagctggtccctgctacatgaaggcgctt
tatcactgggaaaaggcgttactacaaagccgaggtgtgggaagccttctctgagttttttcaagtctgccctgcaaggcgat
gagtatgcctgtgtggcatcaaaagcccaccagccgtcatgattggggacgatatcgtgggcgagcgtcggcggtgccagggtgtggaa
aggagtggaagcccaccagccgctcaacacgtgttgcaaggcacgtgctctggacctggtgctcacacgtgctcttctcc
tgagagcgctgcagagccgtcaacacgtgttgcaaggcacgtgctctggacctggtgctcacacgtgctcttctcc
caagacactccctgAagcgcgttcccca

FIG. 17

```
aagaactttaaaaatcacctagtgtgtgggccgggcacggtggctaacgcctgtaatcccagcactttgagatgctga
ggcaggtggatcacgaggtcaggagatcgagaccatcctgatacacggagaaacccggcgagctgaggagcag
ggccgggcgccATGGCACCGTGGGGCACGGGCGGGCACGGCAAGCGGCTGGCTGCCTGCCGCGGGGTGCTGCTTGACATCTCGGGCGTGCTG
TACGACAGCGGCGGGGGGGCGGGCACGGCCATCGCCGCCGGCTCGGTGGAGGCGGTGGCCAGAGCGGTGAGAGCTGGTGGGGCAGAGCTGGTGGGGCAGCTTCAGAGGCTGGATTTG
GAAGGTGAGGTTCTGCACCAGAGTGCCCCCGGCACCAGTGCCTGCCAGATCCTGAAGGAGGCCTGCGACCATAC
ACATCTCTGAGCAGGAGGTGACCGCCCCCGGCACCAGTGCCTGCCAGATCCTGAAGGAGGCCTGCGACCATAC
CTGCTCATCCATGACGGAGTCCGTCGCTCAGAATTTGATCAGATCGACACATCCAACCAAACTGTGTGGTAATTGCAGA
CGCAGGAGAAAGCTTTTCTTATCAAAACATGAATAACGCCTTCCAGTGCTCATGGACGTTGGTCCCTACATGAAGGCGCTT
TATCACTGGGAAAAGGGCGTTACTACAAGGAGACCCTCTGGCCTGATGCTGGAGCTTTTTTCAAGTCTGCCCTGCAAGGAT
GAGTATGCCTGTGCCATCAAAGCCGAGGTGGTGGGGAAGCCTTCTCCTGAGTTTTTTCAAGTCTGCCCTGCAAGGAT
AGGAGTGGAAGCCACCAGTTACTTTCAGTATGAaagcaagaagcagaaatgcctgcggctttttcctgagttttttgc
tgcttctctgaaagataagaagaattgacaagtcctatcagtgttaatatatctcactggcaagacagtgtaacagc
aagattacaacaatatggaggaaataataaagtcactcattttgcacctttata
```

FIG. 18

Aagaactttaaaaatcacctagtgtgtgggccgggcacgtgtggctaacgcctgtaatcccagcactttgagatgctga
ggcaggtggatcacgaggtcaggagatcgagaccatcctgatacacggagaaaccccggcggagctgaggagcag
ggccgggcgccATGGCACCGTGGGCACGGCCAAGGCGCTGGCTGGCGTGCGCGGGGTGCTGCTTGACATCTCGGGCGTGCTG
TACGACACAGGGCGCGGCGGCGGCACGGCCATCGCCGGCTCGGTGGAGGCGGTGGCCAGACTGGCGAAGGTTCCCGCT
GAAGGTGAGGTTCTGCACCAACGAGTCGCAGAAGTCCCGGCAGAGCTGGTGGGCAGCTTCAGAGGCTGGGATTTG
ACATCTCTGAGCAGGAGGTGACGCCCCGGCACCAGTCCTGCCAGATCCTGAAGGAGGAGGCCTGCACCATAC
CTGCTCATCCATGACGGAGTCCGCTCAGAATTTGATCAGATGACACATCCAACCAAACTGTGTGGTAATTGCAGA
CGCAGGAGAAAGCTTTTCTTATCAAAACATGAATAAGCCTTCCAGGTGCTCATGGACGTCCTAAgtggggctgccgttggct
TATCACTGGGAAAAGGCATCCACGGGTTCCTCTTTGTGGCTAGAACATTCACGTCCTAAgtggggctgccgttggct
gggttaaaccagtaaccagtaacaggagagaaatacgtcgcatctctagtgtgtggagattaccgggcctttatattaa
aaaaaattttaagtgcttat

FIG. 19

```
tgagaacccaggctcgctggatgtgtcctcctcctcctcctctgcaagctggtgggaagccctgcca
aagcgcacaagacccctttcacacagcaggggcacaagtcttcgaggcagagtcgcctgcagtggg tgggtggaaggg
tgcgcccagaccccaagaatcgcccgcctctccaagaccatccctggtcgctgcggccagtgacgagcacatccga
agtgaaggctgatgggcacttcctgccctgccctgtctctggctgagctgatgagccgtggtgtgatg
cttgcctgggggtcggtgttgctagaagtgaggaATGACCTCCTTCACCCCTGGCTCCTTCCGGCAGCCTGGCCAC
TTCCAGCATGTGGAGGGGCCCGGAGCCCTGGACCCTGTGGAACAGCGGTGTGGAACACGGTGTGTGGAACAGCCGGGCATGCGGGGCTGGAGTTCGG
GGCTGCCAATGGGCTAAGGCCCTGTGTTCAACACATGTCGCGGAGTGAGCAGCATGTGAAAAAAGACTCAGGACCAGGT
CCGGGGTGCTCCCAGGGGTCTCTTTCCCACCGAGGCTGGGAGTGAGCAGCTAGGCCCACACCTCCCAGGCT
CGGGAGCTGCCAGGCCAGCAACCGTGAAGGGTAGCAGGGTGGAGGGTGGAGGGAGGAGACAGGAGAGCAGGCCTCT
CGGGCTCACCCACCCTTGCACCTTCCAGCTCTCAGGCCCACACAGTACCAAGCCTGGGCTCAATGTACCACTTAT
GAaaactcaaticaaattggcttagtgcaacaaggtatttgtggtctcacatgacttgaacatccaggcctggctg
tcacgggaaccgcatctcttcccattgcagtcagtgcaggtggcgggatgtccccagccagccaccgacgtcccctg
cctgctccgcaacccagggcctgcagaaaagggcccacgagactcagactggcagaacagcgcttaggcgaccaggaaca
gggcgcagtctccgtcccaccaaaccctaaccagcaagctgggaactgggccaagtgaagcagagccctccacgtvgccagatgtga
gcgaggtccatgtcctactgccgacaagctgactgcagttctctcccttccctccgttccagttcagatcgaaaggctga
gcgccaccggcccaggtgactgcagttcttcctctccgttccgttcgtcttgaggcctcgcagaggatcggggaggttggctgg
ggcctgacctggttgccgctgggttccgcgtcgttcacctcagggcagaggtggggacaggggggacagggggcgagtgtggt
cagtggcaggtggaaagcctcctgtgttcacctcagggcagaggtggggacacaggggggacaggggcgagtgtggt
gccctctggttggttaggaggtgaacacacggggcagctacattctacgtgttttttaacattataaaagcaggatg
ctgtcctggttaggaggtgaacacacggggcagctacattctacgtgttttttaacattataaaagcagcatg
tgttattacaggaaatttaacagaagtatataaaagaaaccagaagtca
```

FIG. 20

MTSFTPGSFRQPGHFQHVEGARALAETVWNRRPHAGLEFGAANGLRPCVQHMSRNCREKKTQDHRSGVLPGVFPTEAGSEQQPRPSHTSQARELPGQATVKGSRVGGGGEDRESRPLGPHPPLHLPALGPTQYQALGSMYHL

FIG. 21

```
catgacggagtccgctcagaatttgatcagatcgacacatccaacccaaactgtgtggtaattgcagacgcaggaga
aagcttttcttatcaaaaacatgaataacgccttccaggtgctcatggagctggaaaaacctgtgctcatatcactgg
gaaaaggagccgctcaacacgtgttgcaaggcacgtgctctggacctggtgctcacacgtgtcttctcccaagaca
ctccctgaagcgcgttcccaggagctggaaggggataacgcaggccagtgacgagcaccatccggaagtgaagg
ctgatggtgaagagcctggaagaaaccaggggcctcctatgcacagatcttgcagcccagaaccaagtcagcttcc
ctgcgactgccagcacactgccatcaccccgaaacaatgccagcccgtgcttttctatcctcccag
tcaccttgcagacaaagaccaggggcagctcccgagggcactgtgaaggctcccatgccacacagtgagaactgta
gcctctgcgtccaaggcacacagggtacttttctggaccactgctgacagactgaaggtcatgcccggtgtgt
gcaggagaaactaacagttcagtaaactctgccttgaccagc
```

FIG.22

```
tgtgccattggcgatgcggggaggctggcccatcgaaggctggtggactggtggagactcctgtcctgctcag
cactaggcctgcagcagacaccatgagcccaaacttcccaagccctccagtccacaagatgtgtctgcgg
acgtgctcgtgagagaaagccagatggcagccagcagtcccagcaccattcagtgccccgcttctcagacaag
gaaactgaggccagaaagccaggtggccaggagctggcttcccatcctcctgtgggcccactgcagtgc
CCATGGGCCGGGCTGATATTACCCAGAGCTTCGAGAGTCTCACGGGTGCGAGTAATTTAGGCTGCATGGACACAAGC
TGCTGGCTTGAGTGCGCCCCGTTATGAATGTGTGTGGGTCTGTGCCCTTTCATGTCTGCCACAGGCCCACGAGTG
TGCTGAAAGGGAAGGACACGGCCAAGGGCCATGGTGGACAGGAGAACCTTCTTGGGGGTTCGGTGGTGTCCTTGACC
CCACTCTGACTGAGCACTGCCCCAAGGCACTGCCATTCCAGGCCCCCTTCCCTGAGCCTCCCACCCAGGCCCACCC
ACCTGCTGGGTCCTCCCACCTGCGGGGCCCGCCATGGGGGTCACCATGCGAGTCTCACCATGCAGGGTCACCACAC
GAGTCTCACCATGCAGGGTCACCACGCGAGTCTCACCATGCGGGGTCACCATGTGGGGTCACCA
TGCGGGGCTCACCATGTGGGGGCTTCAGGAGCTTGCTGAgcacccccaccgtcactcctccctgggtctgt
aagcctccctgagcagctcccagctccagcctgctgcctttccacttcctggcagtgaggtctcctgggtgcc
ttctctcagcccttgggatgtttttttgtgagaaggggaggctttgatgtgtggagcatctgtagtgccactcca
gtggcttcacaggagcagcaggctgttgttctgagctgtcgcccgtgttgccccatacctggggcacacaccactgccc
gcctccctccccccaagtggtgggtggacccctgctgagaccctgctgagaccctgggaagagacggaggatgaaattgttgccagata
tgggccgtgcagctgctatgaagagtgtgccatgccgtgagactgcatgctgggagaatcctgggagaggtcataactgcttggacagtcatgtcctcagag
gtccatttgttgttctgagaccaaggtgttctgacttgccagaggtcataactgcttggacagtcatgtcctcagag
tacagaaaagtgagaccaaggtgttctgacttgccagaggtcataactgcttggacagtcatgtcctcagag
cccacgtttgctgacccagtgcagctctcacagctcctgcagccgtggctggcagaggaggaagcac
ttcctgggattatgtgcctcctgacatttcaaggcccttcatttctctaaatatttgaggagtttgaattatttt
tagttgaccctcaaggatcagagaataagctttgcagcaacgttgcagatgggcttcttctagcagagagtggtta
ttcgggcctcttattgagagagaatcgggtgattgaggaaatcgggtgtcctgagcataccagaggacccccaa
gttttcctgtgctcgtctgccatcaggaaaccaaatgactcccctcgtcctgagctctccagggtggacctg
gaatgcttaagggagcaatgcatatctttaagatgagcacagtcccggaccactcgagccaaggccacgt
```

FIG.23A cctgctcagggcactttcgggcctcagtttcctatctcttaaaatggacagagttggccggtgaggtggccctgcct
gtaatcccagcactttggaggccaaggctggcagattgcttgagccaggagtttgaagccagctgggcaacatg
gcgaaacccatctctactacaagtacaaaaattggccgggcatgtgtgctcatgtcttgtaatccagcactttgg
gaggcaaggagcggatcacttgaggccagaagctcgagaccgcctctactaaaatacaaaaattagccaggcg
tggtggctcacgcctgtaatctcagctactcggtggctgaggcaggagaatcactgaacctggaagtagaggtt
gcagtgagctgagatcgtgccactgcactctagcctgggcgacagagcaaaaccctgtctc

FIG.23B

MGRADITRDFGALTGASNLGCMDTSCWLESPRYECVWVCAPFMCCHRAHECAEREGHGQGAMVDRRPSWGFGGVLDP
TLTEHCPKALPFOAPFPEPPTPGPPTCWVLPPAGPAMRGHHASLTMQGHHTSLTMQGHHASLTMQGHHAGSPCGVTM
RGSPCGASGAC

FIG.24

```
tttttttttttttctgcttatatagtttattcaatgcaaaataacctcaccagtttactgaggtgctgaccatgt
ccagcgaccaaatacgcctgtaaactgaaattcggttgctgaccattccagcctcagcttcctcactggcaccagg
gggacagcactccatctgtgggtgtctcttctctcATGGCTGTGTGTGTGGGTGTCTCTCTGTCTGGGT
GTCTTTGGCATCTGTGGGTATCTCTCTGTCTGTGGGTATCTCCCATCTGTGGGTGTCCATCTCTGTCTTGG
GTGTCTCTCTTGTGAGTGTCTCTCCTCGTGTCGTGGGTATCTCTCCCTGTCTGTGGGTGTCTGTTGGCTTCCCACTT
TCTCTGTCTGTGGGTGTCTCTCCTGTCTGTGGGTATCTCTCCCTGTCTGTGGGTGTCTGTTGGCTTCCCACTT
GTGGGTCTTGCAGGTCGGTCACGCTCCAGACCTTTAGGCCGCAGCCTGCCAGTCTCCAGACCGCTGTGACATGGGT
AGCAGACACGCTCTCCAGGGCAGATGGTGGTAATCGCAGAGATTCGGATCCCCATGTGGGTGAGGTACCAGTAGA
AATGTCTCCAGCAAACTCCTTCCTGCAACCTCAGGACTCGAGAGACCTGAGCCTTCATGACGTGAAGGTTGGGC
ACATTCTCATCTGCCAGCTCCGGGTCTTAGGCAGGTGGACATTCTTCTTGGACTACGGTGACTCCCTCCTTAAAAAGG
AGTTCATAAatagcaatctggttcttcttaggcatcaacatctcgagctgtagggtccaggtccgggctgaaa
gcatgattttttctaactgatctctgctgatggcatctagatgttcctggttttttcaccataccagggctgtat
gagcatctggtgcatttcggatgacgtccagatacagttacagaacgagtatttttgaggttcttgaggcatgt
tgccaagttgttccagaaagctgcacagttctgcacagactatttcgcacagcctagaattcacagggtctgcacaa
cctagagttctggaatcacagggttctgcacacaacctagagttctgcacagcctagaatcacagggtctgcacagcct
aatcacaggttctgcacactagaatcacagggttctgcacagcctagaatcacagggttctgcacagcctagagttctgcacagct
tctgcacagctagaatcacacagggttctgcacagcctagaatcacagggttctgcacagcctagaatcacagggtctgcacagcct
agagttttgaatcacacacagtgtgggaattccgaggcggttggcggaggaagtgtttccatctcttggtgcttttgcttctg
cacagggttctacacgtaagtgtgggaattccgaggcggttggcggaggaagtgtttccatctcttggtgctttgttgccc
gatctcatgaaggcgtccactgcctctgcttgctgtacggagcagctgatggaaccgacagggaggggactttttatctgcc
gtgacagcgctcactgcctctgcttgctgtacggagcagctgatggaaccgacagggaggggactttttatctgcc
attggccactgccacacactttgtgtacccgtttttgtgtaccggagccacaggagaataagctgctgtcccccagccattgagtgctgat
ttgctgttttgcaagtgggtgttgaagccacaggagatgaaataagctgctgtcccccagccattgagtgctgat
aggatcaggagtgccagttggtggtgctgacccagacccctgtgcgttaacctctaagctacattctagaagcagac
```

FIG. 25A ttttgccacacaagccttaaatgtgggctggggacagtgctcacgcgtaatcccagcactttggggacaa
ggtgggcagatccctgaggcaggggtttcaagacaggctggccaacatggtgaaacctgtctctactaaaaata
caaaaattagccaggtgtggtggtgcgtgcctatagtcccagctactcgggaggctgacgcatgagaattgcttgaa
cctgggaggcagaggttgcagtaagtcgcgcattgcgcactcagcctgggcgacagagcaagactccatct
cgaaaaaacaacaaaaccttaaatgtattttgaggctgtgtttaaaatggggatatttttacacaaatatccag
atttctgattcttttgaagaatcagaagatctgacaatacggagcctcacattcctgcacacacagcagccatcgc
tggagccactgcctccattagttgtgtgccattgaattactgcagacccccactcctcctgtcgtccctgtctccagaccacaga
gttagttgtcattgatcgtgtgtgccattgttgtttttttcaaagtagagaagtactttctcacgtgtctctatc
aaaatggacaagtgaaagatgtttcaagaaatgaaaagatttctttttagtgacaaaaaatttctagtatgtttc
tcatataaataaaatgtcctgtatgtcaggttcctcagagaagcccgaagctacaggatacaggatatagatgtag
agagattgtggagctgtgtgtgctgtcggtcgagggacttgcagggcaggctgggactcaggaggatgcgcagc
agagtcgtaaggctgtgtgtgctgtcggtcgagggaaggtcagtcttgtctttgttaaagcctgcaactgg
ttggatggtgtccaccacattgcgaaggaatgtactctcctcagttcaccgattaaatgttaatctcatcc
aaaacaccttcagaaacatccagataatgtttgacacatatctggcacgtggccagccagttgacata
ttaattaaccctttgtagtcccttttaaacttacacccattggccttttgagtcaccaaacacctcactagaacaagca
acctggcctcttaactcatttacccgggctgacccattagttaacactttttcttaaagatgtctcatgctgacttcgtggc
taatgaagagctctgctgtaattcgtaattgttaacactttttcttaaagatgttgagctgagttcgagaccagcctgg
acacgctataatcccagcactttggggggctgagatgagaggaagaaaaagaaaagtcgtctcataattattaaaaaccactattcc
gcagcatgtaagaattccgtctctcacaaaaaaaagaaaaagaaaaaagtgtctcataattattaaaaaccactattcc
agatcatggataataatagtcagaacaggtatattgttg

FIG. 25B

MAVCLWVSLSVGCLSPSVGISLCLWVSLPSVGVHLCLWVSLFVSVSVCGCLCLWVSLCECPCECLCLWVSLLVCGY
LSLSVGVSVGFPTCGSCRSVTLQTFRQPASLQTAVAWGSRHALQGQMVIAEILDPHVGEVPVEMSPGKLLPATSG
PERLPGLHDVKVGHILICQLRVLGRWTFFLATVTPSLKRSS

```
Genecarta
h5173309
h5194531
h5197955
h4565014
```

(Genecarta) tgcattcggctgacaga (h5173309) gcatgagggggaggaatcactgatgacaggcactggcctgcccagctgggggcctttgtttattcatttggtgggca
gcatgagggggaggaatcactgatgacaggcactggcctgcccagctgggggcctttgtttattcatttggtgggca
(h5194531) gca cttcctgggtgctgctctgggtcaggcctgtgggggggaccactgagggcaggaaacctggcctgtccctccagga
cttcctgggtgctgctctgggtcaggcctgtgggggggaccactgagggcaggaaacctggcctgtccctccagga
cttcctgggtgctgctctgggtcaggcctgtgggggggaccactgagggcaggaaacctggcctgtccctccagga
(h5197955) ctgagggcaggaaacctggcctgtccctccagga agcgaagtcaacactggcacctgcagatgaagtggcagagcagccccagctttgatggcatggggtggttggggg
agcgaagtcaacactggcacctgcagatgaagtggcagagcagccccagctttgatggcatggggtggttggggg
agcgaagtcaacactggcacctgcagatgaagtggcagagcggccccagctttgatggcatggggtggttggggg
agcgaagtcaacactggcacctgcagatgaagtggcagagcagccccagctttgatggcatggggtggttggggg cacattctgcatgctcagaagagagagcaactcgccctgtggaaggagcatacagtgggagatggggacaggccag
cacattctgcatgctcagaagagagagcaactcgccctgtggaaggagcatacagtgggagatggggacaggccag
cacattctgcatgctcagaagagagagcaactcgccctgtggaaggagcatacagtgggagatggggacaggccag
cacattctgcatgctcagaagagagagcaactcgccctgtggaaggagcatacagtgggagatggggacaggccag
(h4565014) tacagtgggagatggggacaggccag tgacgagcaccatccggaagtgaaggctgatgggtacgtggacaacctcgcagaggcagtggacctgctgctgcagc
tgacgagcaccatccggaagtgaaggctgatgggtacgtggacaacctcgcagaggcagtggacctgctgctgcagc
tgacgagcaccatccggaagtgaaggctgatgggtacgtggacaacctcgcagaggcagtggacctgctgctgcagc
tgacgagcaccatccggaagtgaaggctgatgggtacgtggacaacctcgcagaggcagtggacctgctgctgcagc
tgacgagcaccatccggaagtgaaggctgatgggtacgtggacaacctcgcagaggcagtggacctgctgctgcagc acgccgacaagtgatggcctcctgggagagccccgctcctccacccctgcctctcctccacccctgcctcccctcc
acgccgacaagtgatggcctcctgggagagccccgctcctccacccctgcctctcctccacccctgcctcccctcc
acgccgacaagtgatggcctcctgggagagccccgctcctccacccctgcctctcctccacccctgcctcccctcc
acgccgacaagtgatggcctcctgggagagccccgctcctccacccctgcctctcctccacccctgcctcccctcc
acgccgacaagtgatggcctcctgggagagccccgctcctccacccctgcctctcctccacccctgcctcccctcc accctgcctctcctccaccgccaggagagcccacctcctccacccctgcctctcctccacccctgcctccct
accctgcctctcctccaccgccaggagagcccacctcctccacccctgcctctcctccacccctgcctccct
accctgcctctcctccaccgccaggagagcccacctcctccacccctgcctctcctccacccctgcctccct
accctgcctctcctccaccgccaggagagcccacctcctccacccctgcctctcctccacccctgcctccct
accctgcctctcctccaccgccaggagagcccacctcctccacccctgcctctcctccacccctgcctccct ccacctgccccagtgcccagaccaaccaaggccctgacagccctgccttctgccctctgccctgcatgggcaggcat
ccacctgccccagtgcccagaccaaccaaggccctgacagccctgccttctgccctctgccctgcatgggcaggcat
ccacctgccccagtgcccagaccaaccaaggccctgacagccctgccttctgccctctgccctgcatgggcaggcat
ccacctgccccagtgcccagaccaaccaaggccctgacagccctgccttctgccctctgccctgcatgggcaggcat
ccacctgccccagtgcccagaccaaccaaggccctgacagccctgccttctgccctctgccctgcatgggcaggcat

FIG. 30 (cont.)

```
ttgttccctacctgggtggcctgctccctgcctgggccctgacttcagctccctgtagtgaagtccaggacggtgg
ttgttccctacctgggtggcctgctccctgcctgggccctgacttcagctccctgtagtgaagtccaggagggtgg
ttgttccctacctgggtggcctgctccctgcctgggccctgacttcagctccctgtagtgaagtccaggagggtgg
ttgttccctacctgggtggcctgctccctgcctgggccctgacttcagctccctgtagtgaagtccaggagggtgg
ttgttccctacctgggtggcctgctccctgcctgggccctgacttcagctccctgtagtgaagtccaggagggtgg gacaggcctgtcaggcctctgggaatctcccaaatcccagaactcaccactcaccatgggcctttaaatgcagtaaa
gacaggcctgtcaggcctctgggaatctcccaaatcccagaactcaccactcaccatgggcctttaaatgcagtaaa
gacaggcctgtcaggcctctgggaatctcccaaatcccagaactcaccactcaccatgggcctttaaatgcagtaaa
gacaggcctgtcaggcctctgggaatctcccaaatcccagaactcaccactcaccatgggcctttaaatgcagtaaa
gacaggcctgtcaggcctctgggaatctcccaaatcccagaactcaccactcaccatgggcctttaaatgcagtaaa ctccacctaaccagattcaggggcactatgcccactgctcctcttcagactctttgcatttcagtgaagagcctgg
ctccacctaaccagattcaggggcactatgcccactgctcctcttcagactctttgcatttcagtgaagagcctgg
ctccacctaaccagattcaggggcactatgcccactgctcctcttcagactctttgcatttcagtgaagagcctgg
ctccacctaaccagattcaggggcactatgcccactgctcctcttcagactctttgcatttcagtgaagagcctgg
ctccacctaaccagattcaggggcactatgcccactgctcctcttcagactctttgcatttcagtgaagagcctgg aagaaacccaggggcctcctatgcacagatcttgcagcccagaaccaagtcagcctcctgcgactgcccaggcaca
aagaaacccaggggcctcctatgcacagatcttgcagcccagaaccaagtcagcctcctgcgactgcccaggcaca
aagaaacccaggggcctcctatgcacagatcttgcagcccagaaccaagtcagcctcctgcgactgcccaggcaca
aagaaacccaggggcctcctatgcacagatcttgcagcccagaaccaagtcagcctcctgcgactgcccaggcaca
aagaaacccaggggcctcctatgcacagatcttgcagcccagaaccaagtcagcctcctgcgactgcccaggcaca ctgccaccaccccaccccgaaacaatgcagcccgctgcttttctatcctcccagtcacctttgcagacaaaga
ctgccaccaccccaccccgaaacaatgcagcccgctgcttttctatcctcccagtcacctttgcagacaaaga
ctgccaccaccccaccccgaaacaatgcagcccgctgcttttctatcctcccagtcacctttgcagacaaaga
ctgccaccaccccaccccgaaacaatgcagcccgctgcttttctatcctcccagtcacctttgcagacaaaga
ctgccaccaccccaccccgaaacaatgcagcccgctgcttttctatcctcccagtcacctttgcagacaaaga ccaggggcagctcccgagggcactgtgaaggctcccatgccacacagtgagaactgtagcctctgcgtccaaggcac
ccaggggcagctcccgagggcactgtgaaggctcccatgccacacagtgagaactgtagcctctgcgtccaaggcac
ccaggggcagctcccgagggcactgtgaaggctccatgccacacagtgagaactgtagcctctgcgtccaaggcac
ccaggggcagctcccgagggcactgtgaaggctccatgccacacagtgagaactgtagcctctgcgtccaaggcac
ccaggggcagctcccgagggcactgtgaaggctccatgccacacagtgagaactgtagcctctgcgtccaaggcac acagggtactttctggacccactgctggacagacttgaaggtgtcatgcccggtgtgtgcaggaggaaactaacagt
acagggtactttctggacccactgctggacagacttgaaggtgtcatgcccggtgtgtgcaggag
acagggtactttctggacccactgctggacagacttgaaggtgtcatgcccggtgtgtgcaggaggaaactaacagt
acagggtactttctggacccactgctggacagacttgaaggtgtcatgcccggtgtgtgcaggaggaaactaacagt
acagggtactttctggacccactgctggacagacttgaaggtgtcatgcccgtgtgtgcaggaggaaactaacagt tcagtaaactctgccttgaccagcagccttt
tcagtaaactctgccttgaccagca          aaaaaaaaaaaaaaaaaaaaa
tcagtaaactctgccttgaccagca          aaaaaaaaaaaaaaaaaaaaa
tcagtaaactctgccttgaccagca          aaaaaaaaaaaaaaaaaaaaa
```

DEP2 AND ITS USES IN MAJOR DEPRESSIVE DISORDER AND OTHER RELATED DISORDERS

The subject application is a Continuation-In-Part of U.S. patent application Ser. No. 11/412,184, filed on Apr. 26, 2006 now abandoned, which is hereby incorporated in its entirety by reference.

Sequence Listing

The instant application contains a Sequence Listing which has been submitted in ASCII format via EFS-Web and is hereby incorporated by reference in its entirety. Said ASCII copy, created on Jun. 25, 2012, is named 8108USP1.txt and is 322,526 bytes in size.

BACKGROUND INFORMATION

Mood disorders, of which major depressive disorder is the most common, affect one person in five during their lifetime. The World Health Organization estimates that depression is currently the fourth most important worldwide cause of disability-adjusted life year loss, and that it will become the second most important cause by 2020 (See, Murray C J L and Lopez A D, The Global Burden of Disease: A Comprehensive Assessment of Mortality and Disability From Disease, Injuries, and Risk Factors in 1990 and Projected to 2020, volume 1. World Health Organization. Cambridge Ma.: Harvard University Press. 1996.). Pharmaceutical treatment of depression is frequently inadequate. In randomized clinical trials of the current best treatments, one-third of patients or more do not achieve remission, even after several months of treatment (See, *Journal of the American Medical Association*, 286: 2947-55 (2001); *Biological Psychiatry*, 48:894-901 (2000)). Even when today's drugs do help patients achieve remission from their depression, the onset of action is over a period of weeks and there appears to be an increased risk of suicide during initial antidepressant therapy, although this risk may be less than that just prior to therapy initiation (See, *Neuropsychopharmacology*, 31:473-492 (2006)). Further, there are high recurrence rates—approximately 85% of patients who achieve remission will suffer another episode of major depression (See, *American Journal of Psychiatry*, 156:1000-6 (1999)). Finally, currently available antidepressants are associated with side effects that lead some patients to stop taking their medications at risk of sinking back (further) into depression, and to morbidity in others (See, *New England Journal of Medicine*, 353:1819-34 (2005)).

The currently available antidepressants work primarily by increasing the activity of certain neurotransmitters, serotonin and norepinephrine, in synapses. Some medications (such as monoamine oxidase inhibitors) inhibit the degradation of these molecules, others (such as selective serotonin reuptake inhibitors and dual serotonin/norepinephrine reuptake inhibitors) decrease removal of neurotransmitters from the synaptic space, and some medications (such as receptor antagonists) stimulate norepinephrine release or inhibit negative feedback of serotonin signaling. Because these medications are all based on a single principle, the strength and range of their efficacy is similar. The improvements of the last half century have involved the development of safer and more tolerable drugs. However, despite this, today's drugs are neither completely safe nor completely tolerable for many patients.

Thus, there is considerable need for new drugs that are effective in a broader range of patients (particularly for patients whose depression is resistant to available pharmaceuticals), that have a faster onset of action, that are safer and more tolerable, or that complement the efficacy of existing drugs. It is possible, but unlikely, that further improvement in any of these dimensions will be achieved through development of additional serotonergic or noradrenergic agents. Therefore, alternative pharmacological approaches must be developed and pursued.

Part of the challenge in developing new drugs lies in the complexity of demonstrating efficacy of a major depression treatment. For example, the development of novel antidepressants is constrained by the limited understanding of depression's etiology. Because of this, there are relatively few pharmacological targets that can be considered for antidepressant development. Thereupon, there is a need for the identification of drug targets for depression. Genetic linkage can open new windows for the development of novel depression drug targets. Specifically, if a genetic variant is identified as being linked to depression in families, the gene in which that variant occurs is likely to be involved in the etiology of disease. Such a gene can be a target for the development of novel antidepressants. Additionally, such a gene can lead to the identification of previously unknown physiological pathways that may be modulated for effective therapy of depression.

Several genes have been identified or proposed as factors for depression or related phenotypes. Among these, most have been associated with disease in population studies of candidate genes selected on the basis of existing hypotheses about the etiology of depression. Many of these genes relate to serotonin or norepinephrine. Examples include: (1) associations of a HTR1A (serotonin receptor 1A) promoter variant with depression, suicide, bipolar disorder, panic disorder with agoraphobia, neuroticism and anti-depressant response; (2) associations of the HTT (serotonin transporter) promoter short allele with depression, suicide, depressive behavior response to tryptophan depletion, bipolar disorder antidepressant-induced mania and lesser anti-depressant response; and (3) association of a variant in HTR2C (serotonin receptor 2C) with both recurrent major depression and bipolar disorder and with major depression.

Thereupon, as evidenced by the above, there is a need in the art to identify proteins and genes associated with the pathophysiology of depression that are proteins and genes that relate to other than serotonin or norepinephrine. Such proteins and genes would be useful in the diagnosis of depression or a related disorder, and in the development of new drugs that could be used to treat patients suffering from depression or a related disorder.

SUMMARY OF THE INVENTION

In one embodiment, the present invention relates to an isolated nucleic acid molecule or fragment thereof comprising a nucleotide sequence having at least 90% identity to: (i) SEQ ID NO:2, (ii) nucleotides 352 to 771 of SEQ ID NO:2; or (iii) nucleotides 812 to 1162 of SEQ ID NO:2 or (iv) a complement comprising a nucleotide sequence having at least 90% identity to: (i) SEQ ID NO:2, (ii) nucleotides 352 to 771 of SEQ ID NO:2; or (iii) nucleotides 812 to 1162 of SEQ ID NO:2. The present invention also encompasses a purified or isolated protein encoded by the above nucleic acid molecule or fragment thereof.

In another embodiment, the present invention relates to a purified polypeptide or fragment thereof comprising an amino acid sequence having at least 90% identity to: SEQ ID NO:3 or SEQ ID NO:4.

In yet another embodiment, the present invention relates to a vector comprising:

a) an isolated nucleic acid sequence comprising a nucleotide sequence having at least 90% identity to: (i) SEQ ID NO:2, (ii) nucleotides 352 to 771 of SEQ ID NO:2; or (iii) nucleotides 812 to 1162 of SEQ ID NO:2 or a complement comprising a nucleotide sequence having at least 90% identity to: (i) SEQ ID NO:2, (ii) nucleotides 352 to 771 of SEQ ID NO:2; or (iii) nucleotides 812 to 1162 of SEQ ID NO:2; operably linked to b) a regulatory sequence.

Additionally, in yet another embodiment, the present invention relates to a host cell comprising the above-described vector.

In still yet another embodiment, the present invention relates to a non-human transgenic animal. In one aspect, said non-human transgenic animal comprises:

a) an exogenous and stably transmitted nucleic acid comprising a nucleotide sequence of SEQ ID NO:2 (or any one or more of the sequences described above); or b) a knock-out of a nucleic acid comprising a nucleotide sequence of SEQ ID NO:2 (or any one or more of the sequences described above).

In another aspect, said non-human transgenic animal comprises:

a) an exogenous and stably transmitted nucleic acid having a nucleotide sequence selected from the group consisting of: SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 and SEQ ID NO:33, with the proviso that said animal does not comprise an exogenous and stably transmitted nucleic acid having a nucleotide sequence of SEQ ID NO:2; or b) a knock-out of a nucleic acid comprising a nucleotide sequence selected from the group consisting of: SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 and SEQ ID NO:33, with the proviso that a nucleic acid having a nucleotide sequence of SEQ ID NO:2 is not knocked out.

In yet another embodiment, the present invention relates to a method of modifying or altering the expression of SEQ ID NO:2 in a cell or animal. The method involves the steps of:

a) exposing said cell or administering to said subject a nucleic acid molecule, wherein said nucleic acid molecule modifies or alters the expression of SEQ ID NO:2; and b) modifying or altering the expression of SEQ ID NO:2.

In the above-described method, the nucleic acid molecule can be an antisense molecule, a small interfering RNA, a co-suppression RNA, an aptamer, a ribozyme or a triplexing agent.

In yet another embodiment, the present invention relates to a method of modifying or altering the expression of a nucleic acid sequence having a nucleotide sequence selected from the group consisting of: SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 and SEQ ID NO:33 in a cell or animal, with the proviso that the expression of a nucleic acid having the sequence of SEQ ID NO:2 is not modified or altered. The method involves the steps of:

a) exposing said cell or administering to said subject a nucleic acid molecule, wherein said nucleic acid molecule modifies or alters the expression of a nucleotide sequence selected from the group consisting of: SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 and SEQ ID NO:33; and b) modifying or altering the expression of SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33.

In the above-described method, the nucleic acid molecule can be an antisense molecule, a small interfering RNA, a co-suppression RNA, an aptamer, a ribozyme or a triplexing agent.

In yet another embodiment, the present invention relates to a method of determining a genotype of a subject at a polymorphic site in nucleotides 1 to 316 of SEQ ID NO:2 in a test sample. The method involves the steps of:

a) obtaining a test sample comprising DNA of a subject;

b) analyzing the test sample for at least one polymorphic site in nucleotides 1 to 316 of SEQ ID NO:2;

c) identifying the allele(s) present at said polymorphic site in said test sample; and d) determining the genotype of a subject based on the identification of the allele(s) at said polymorphic site in said test sample.

The above-described method can further involve the step of analyzing the test sample(s) for a C-G polymorphism at position −1019 in a human serotonin receptor 1A (HTR1A) gene.

The analyzing performed in the above-described method can be accomplished using direct sequencing, polymerase chain reaction, ligase chain reaction, a fragment length polymorphism assay, a single strand conformation polymorphism analysis, a heteroduplex assay, hybridization, Taqman®, Molecular Beacon, Pyrosequencing, a microarray, Southern blotting, an Invader assay, a single base extension assay, or mass spectrometry.

In still yet another embodiment, the present invention relates to a method of determining a genotype of a subject at nucleotides 77402 or 79906 of SEQ ID NO:1 in a test sample. The method involves the steps of:

a) obtaining a test sample comprising DNA of a subject;

b) analyzing the test sample for at least one polymorphic site selected from the group consisting of nucleotides 77402 and 79906 of SEQ ID NO:1;

c) determining the allele(s) present at said polymorphic site in said test sample; and d) determining the genotype of a subject based on the identification of the allele(s) at said polymorphic site in said test sample.

The above-described method can further involve the step of analyzing the test sample(s) for a C-G polymorphism at position −1019 in a human serotonin receptor 1A (HTR1A) gene.

The analyzing performed in the above-described method can be accomplished using direct sequencing, polymerase chain reaction, ligase chain reaction, a fragment length polymorphism assay, a single strand conformation polymorphism analysis, a heteroduplex assay, hybridization, Taqman®, Molecular Beacon, Pyrosequencing, a microarray, Southern blotting, an Invader assay, a single base extension assay, or mass spectrometry.

In still yet another embodiment, the present invention relates to a method of identifying a subject having major depression or a related disorder, or at risk of developing major depression or a related disorder. The method involves the steps of:

a) obtaining a test sample subject comprising DNA of a subject;

b) analyzing the test sample for at least one polymorphic site in SEQ ID NO:1;

c) identifying at least one allele at said polymorphic site; and d) identifying whether said subject has major depression or a related disorder or is at risk of developing major depression or a related disorder based on the allele(s) identified at said polymorphic site(s) in said test sample.

The above-described method can further involve the step of analyzing the test sample(s) for a C-G polymorphism at position −1019 in a human serotonin receptor 1A (HTR1A) gene.

The analyzing performed in the above-described method can be accomplished using direct sequencing, polymerase chain reaction, ligase chain reaction, a fragment length polymorphism assay, a single strand conformation polymorphism analysis, a heteroduplex assay, hybridization, Taqman®, Molecular Beacon, Pyrosequencing, a microarray, Southern blotting, an Invader assay, a single base extension assay, or mass spectrometry.

In still yet another embodiment, the present invention relates to a method of providing a prognosis for or predicting a response to treatment for a subject having major depression or a related disorder. The method involves the steps of:

a) obtaining a test sample comprising DNA of a subject;

b) analyzing the test sample for at least one polymorphic site in SEQ ID NO: 1;

c) identifying at least one allele(s) at said polymorphic site; and d) providing a prognosis for and predicting the response to treatment for a subject having major depression or a related disorder based on the allele(s) identified at said polymorphic site(s) in said test sample.

The above-described method can further involve the step of analyzing the test sample(s) for a C-G polymorphism at position −1019 in a human serotonin receptor 1A (HTR1A) gene.

The analyzing performed in the above-described method can be accomplished using direct sequencing, polymerase chain reaction, ligase chain reaction, a fragment length polymorphism assay, a single strand conformation polymorphism analysis, a heteroduplex assay, hybridization, Taqman®, Molecular Beacon, Pyrosequencing, a microarray, Southern blotting, an Invader assay, a single base extension assay, or mass spectrometry.

In still yet another embodiment, the present invention relates to a method of detecting or quantifying an mRNA which comprises nucleotides 1 to 316 of SEQ ID NO:2 in a test sample. The method involves the steps of:

a) obtaining a test sample subject comprising mRNA of a subject;

b) analyzing the test sample for a mRNA comprising at least 15 contiguous nucleotides of nucleotides 1 to 316 of SEQ ID NO:2; and b) detecting or quantifying said mRNA in said test sample.

The above-described method can further involve the step of analyzing the test sample(s) for an mRNA transcribed from a human serotonin receptor 1A (HTR1A) gene.

The analyzing performed in the above-described method can be accomplished using reverse transcription, quantitative polymerase chain reaction, cDNA microarrays, or Northern blotting.

In still yet another embodiment, the present invention relates to a method of identifying a subject having major depression or a related disorder, or at risk of developing major depression or a related disorder. The method involves the steps of:

a) obtaining a test sample subject comprising subject mRNA;

b) analyzing the test sample for at least one mRNA transcribed from SEQ ID NO:1; and c) identifying whether said subject has major depression or a related disorder or is at risk of developing major depression or a related disorder based on the presence, absence or amount of at least one of the mRNAs recited in step b) in said test sample.

The above-described method can further involve the step of analyzing the test sample(s) for an mRNA transcribed from a human serotonin receptor 1A (HTR1A) gene.

The analyzing performed in the above-described method can be accomplished using reverse transcription, quantitative polymerase chain reaction, cDNA microarrays, or Northern blotting.

In the above-described method, the mRNA transcribed from SEQ ID NO:1 can have the nucleotide sequence of: SEQ ID NO:2, SEQ ID NO:5, SEQ ID NO:6, SEQ ID NO:7, SEQ ID NO:8, SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33.

In still yet another embodiment, the present invention relates to a method of providing a prognosis for or predicting a response to treatment for a subject having major depression or a related disorder. The method involves the steps of:

a) obtaining a test sample comprising mRNA of a subject;

b) analyzing the test sample for at least one mRNA transcribed from SEQ ID NO:1; and c) providing a prognosis for and predicting the response to treatment for a subject having major depression or a related disorder based on the presence, absence or amount of at least one of the mRNAs recited in step b) in said test sample.

The above-described method can further involve the step of analyzing the test sample(s) for an mRNA transcribed from a human serotonin receptor 1A (HTR1A) gene.

The analyzing performed in the above-described method can be accomplished using reverse transcription, quantitative polymerase chain reaction, cDNA microarrays, or Northern blotting.

In the above-described method, the mRNA transcribed from SEQ ID NO:1 can have the nucleotide sequence of: SEQ ID NO:2, SEQ ID NO:5, SEQ ID NO:6, SEQ ID NO:7, SEQ ID NO:8, SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33.

In still yet a further embodiment, the present invention relates to a method of detecting or quantifying the amount of a protein having an amino acid sequence selected from the group consisting of: SEQ ID NO:3 and SEQ ID NO:4 in a test sample. The method involves the steps of:

a) obtaining a test sample subject comprising at least one polypeptide of a subject; and b) detecting or quantifying the amount of a protein having an amino acid sequence selected from the group consisting of SEQ ID NO:3 and SEQ ID NO:4 in said test sample.

The above-described method can further involve the step of detecting or quantifying the amount of a polypeptide encoded by a human serotonin receptor 1A (HTR1A) gene.

The analyzing performed in the above-described method can be accomplished using ELISA, RIA, Western blotting, fluorescence activated cell sorting or immunohistochemical analysis.

In still yet a further embodiment, the present invention relates to a method of identifying a subject having major depression or a related disorder, or at risk of developing major depression or a related disorder. The method involves the steps of:

a) obtaining a test sample comprising at least one polypeptide of a subject;

b) analyzing the test sample for at least one polypeptide translated from SEQ ID NO:1; and c) identifying whether said subject has major depression or a related disorder or is at risk of developing major depression or a related disorder based on the presence, absence or amount of at least of the polypeptides recited in step b) in said test sample.

The above-described method can further involve the step of analyzing the test sample(s) for a polypeptide encoded by a human serotonin receptor 1A (HTR1A) gene.

The analyzing performed in the above-described method can be accomplished using ELISA, RIA, Western blotting, fluorescence activated cell sorting or immunohistochemical analysis.

In the above-described method, the polypeptide translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet a further embodiment, the present invention relates to a method of providing a prognosis for or predicting a response to treatment for a subject having major depression or a related disorder. The method involves the steps of:

a) obtaining a test sample comprising at least one polypeptide of a subject;

b) analyzing the test sample for at least one polypeptide translated from SEQ ID NO:1; and c) providing a prognosis for and predicting the response to treatment for a subject having major depression or a related disorder based on the presence, absence or amount of at least one of the polypeptides recited in step b) in said test sample.

The above-described method can further involve the step of analyzing the test sample(s) for a polypeptide encoded by a human serotonin receptor 1A (HTR1A) gene.

The analyzing performed in the above-described method can be accomplished using ELISA, RIA, Western blotting, fluorescence activated cell sorting or immunohistochemical analysis.

In the above-described method, the polypeptide translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a kit. In one aspect, the kit can comprise:

a) at least one reagent for determining a genotype of a subject at a polymorphic site in SEQ ID NO:1 in a test sample; and b) instructions for determining the genotype of the subject.

In another aspect, the kit can comprise:

a) at least one reagent for determining a genotype of a subject for a C-G polymorphism at position −1019 in a human serotonin receptor 1A (HTR1A) gene;

b) at least one reagent for determining a genotype of a subject for a polymorphic site in SEQ ID NO:1, in a test sample; and c) instructions for determining the genotype of the subject.

In another aspect, the kit can comprise:

a) at least one reagent for determining a genotype of a subject at nucleotide 77402 of SEQ ID NO:1 in a test sample; and b) instructions for determining the genotype of the subject.

In another aspect, the kit can comprise:

a) at least one reagent for determining a genotype of a subject at nucleotide 79906 of SEQ ID NO:1 in a test sample; and b) instructions for determining the genotype of the subject.

In another aspect, the kit can comprise:

a) at least one reagent for determining a genotype of a subject for a C-G polymorphism at position −1019 in a human serotonin receptor 1A (HTR1A) gene;

b) at least one reagent for determining a genotype of a subject for a polymorphic site at at least one of nucleotides 77402 or 79906 in SEQ ID NO:1, in a test sample; and c) instructions for determining the genotype of the subject.

In still yet another aspect, the kit comprises:

a) at least one reagent for detecting or quantifying an mRNA transcribed from SEQ ID NO:1 in a test sample; and b) instructions for detecting or quantifying the mRNA transcribed from SEQ ID NO:1 in the test sample.

In still yet another aspect, the kit comprises:

a) at least one reagent for detecting or quantifying an mRNA from a serotonin receptor 1A (HTR1A) gene in a test sample;

b) at least one reagent for detecting or quantifying an mRNA transcribed from SEQ ID NO:1, in a test sample; and c) instructions for detecting or quantifying the mRNA from a serotonin receptor 1A (HTR1A) gene and the mRNA transcribed from SEQ ID NO:1 in the test sample.

The mRNA transcribed from SEQ ID NO:1 in the above kits in can have the nucleotide sequence of: SEQ ID NO:2, SEQ ID NO:5, SEQ ID NO:6, SEQ ID NO:7, SEQ ID NO:8, SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33.

It still yet another aspect, the kit comprises:

a) at least one reagent for detecting or quantifying a polypeptide translated from SEQ ID NO:1 in a test sample; and b) instructions for detecting or quantifying the polypeptide translated from SEQ ID NO:1 in the test sample.

In still yet another aspect, the kit comprises:

a) at least one reagent for detecting or quantifying a polypeptide encoded by a serotonin receptor 1A (HTR1A) gene in a test sample;

b) at least one reagent for detecting or quantifying a polypeptide translated from SEQ ID NO:1, in a test sample; and c) instructions for detecting or quantifying the polypeptide encoded by a serotonin receptor 1A (HTR1A) gene and the polypeptide translated from SEQ ID NO:1 in the test sample.

The polypeptide translated from SEQ ID NO:1 in the above-described kits can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of screening a composition for the ability to bind to a protein translated from SEQ ID NO:1. The method involves the steps of:

a) exposing said protein to a composition for a time and under conditions sufficient for said test composition to bind to said protein to form protein/composition complexes; and b) detecting presence or absence of said complexes, wherein the presence of said complexes indicates a composition having the ability to bind to said protein.

The presence or absences of the complexes in the above-described method can be detected using mass spectrometry. Additionally, a composition identified pursuant to the above-described method as having the ability to bind to a protein translated from SEQ ID NO:1 can be used to treat major depression or a related disorder in a subject.

In the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of detecting binding of a composition to a protein translated from SEQ ID NO:1. The method involves the steps of:

a) subjecting said protein to nuclear magnetic resonance and recording the resulting spectrum;

b) subjecting said protein to nuclear magnetic resonance in the presence of said composition and recording the resulting spectrum; and c) detecting the difference between said spectrum of step a) and said spectrum of step b) and comparing said difference to a control, said comparison indicating whether said composition binds to said protein.

A composition identified pursuant to the above-described method as having the ability to bind to a protein translated from SEQ ID NO:1 can be used to treat major depression or a related disorder in a subject.

In the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of identifying the structure of a composition bound to a protein translated from SEQ ID NO:1. The method involves the steps of:

a) exposing said protein to a composition known to bind to said protein; and b) observing the resulting X-ray diffraction pattern of said resulting bound composition of step a), said diffraction pattern indicating the structure of said composition.

Additionally, a composition identified pursuant to the above-described method as having the ability to bind to a protein translated from SEQ ID NO:1 can be used to treat major depression or a related disorder in a subject.

In the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of screening a composition for the ability to modulate the activity of a protein translated from SEQ ID NO:1. The method involves the steps of:

a) providing a composition;

b) exposing the protein to a substrate for sufficient time and conditions to allow the substrate to react with the protein in order to produce a reaction product or complex;

c) exposing the protein to the composition; and d) measuring said reaction product or complex, wherein a decreased or increased amount of said reaction product or complex, as compared to the amount of reaction product or complex produced in the absence of said composition, indicates a composition having the ability to modulate the activity of said protein.

In the above-described method, a protein translated from SEQ ID NO:1 having an amino acid sequence selected from the group consisting of SEQ ID NO:10, SEQ ID NO:13, SEQ ID NO:15, SEQ ID NO:17, SEQ ID NO:19, SEQ ID NO:21, SEQ ID NO:23, SEQ ID NO:25 and SEQ ID NO:27 may be capable of modifying the phosphorylation of the substrate. Additionally, the substrate can be selected from the group consisting of: phosphohistidine, phospholysine, phosphodiimide, pyrophosphate and a peptide or protein phosphorylated on histidine or lysine.

Furthermore, a composition identified in the above-identified method as having an ability to modulate the activity of a protein can be used to treat major depression or a related disorder in a subject.

Moreover, in the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of screening a composition for the ability to modulate the activity of a protein translated from SEQ ID NO:1. The method involves the steps of:

a) providing a composition;

b) simultaneously exposing the protein to the composition and to a substrate, wherein the protein is exposed to the substrate for sufficient time and conditions to allow the substrate to react with the protein in order to produce a reaction product or complex; and c) measuring presence or absence of said reaction product or complex, wherein a lack of said reaction product or complex indicating a composition having the ability to modulate the activity of said protein.

In the above-described method, a protein translated from SEQ ID NO:1 having an amino acid sequence selected from the group consisting of SEQ ID NO:10, SEQ ID NO:13, SEQ ID NO:15, SEQ ID NO:17, SEQ ID NO:19, SEQ ID NO:21, SEQ ID NO:23, SEQ ID NO:25 and SEQ ID NO:27 may be capable of modifying the phosphorylation of the substrate. Additionally, the substrate can be selected from the group consisting of: phosphohistidine, phospholysine, phosphodiimide, pyrophosphate and a peptide or protein phosphorylated on histidine or lysine.

Furthermore, a composition identified in the above-identified method as having an ability to modulate the activity of a protein can be used to treat major depression or a related disorder in a subject.

Moreover, in the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of screening a composition for the ability to modulate activity of a protein translated from SEQ ID NO:1, in a cell. The method involves the steps of:
   a) exposing said cell to said composition; and
   b) measuring the amount of activity of said protein in said cell, wherein a decreased or increased amount of activity of said protein, as compared to a cell which has not been exposed to said composition, indicates a composition having the ability to modulate the activity of said protein.

A composition identified in the above-identified method as having an ability to modulate the activity of a protein can be used to treat major depression or a related disorder in a subject.

In the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of screening a composition for the ability to modulate expression of a protein translated from SEQ ID NO:1, in a cell. The method involves the steps of:
   a) exposing said cell to said composition; and
   b) measuring the amount of said protein in said cell, wherein a decreased or increased amount of said protein, as compared to a cell which has not been exposed to said composition, indicates a composition having the ability to modulate the expression of said protein.

A composition identified pursuant to the above-described method as having an ability to modulate the expression of the protein can be used to treat major depression or a related disorder in a subject.

In the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of screening a composition for the ability to modulate the level of expression of a protein translated from SEQ ID NO:1. The method comprises the steps of:
   a) exposing an in vitro transcription and translation system comprising a regulatory sequence from SEQ ID NO:1 functionally connected to the open reading frame for a detectable protein, to a composition for a time and under conditions sufficient for said test whether said composition modulates the level of expression of the detectable protein; and
   b) detecting the level of expression of the detectable protein, wherein a reduction or an increase in the level of expression of the detectable protein indicates that said composition has the ability to modulate the level of expression of a protein translated from SEQ ID NO:1.

A composition identified pursuant to the above-described method as having an ability to modulate the level of expression of the protein can be used to treat major depression or a related disorder in a subject.

In the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of treating major depression or a related disorder in a subject in need of said treatment comprising the step of administering a composition identified as modulating the activity of a protein translated from SEQ ID NO:1, to said subject, in an amount sufficient to effect said treatment.

The composition administered to a subject pursuant to the above-described method can: (a) inhibit or reduce the activity of the protein; (b) increase the activity of the protein; or (c) decrease the activity of the protein.

A protein translated from SEQ ID NO:1 and that can be used in the above-described method can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of treating major depression or a related disorder in a subject in need of said treatment comprising reducing the amount of a protein translated from SEQ ID NO:1 in said subject, to a level sufficient to effect said treatment.

In the above-described method, the reduction can result from complete binding or partial binding of a composition to said protein. A protein translated from SEQ ID NO:1 and that can be used in the above-described method can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of treating major depression or a related disorder in a subject in need of said treatment comprising increasing the amount of a protein translated from SEQ ID NO:1, to a level sufficient to effect said treatment.

In addition, the above-described method can involve administering to said subject a therapeutically effective amount of a protein translated from SEQ ID NO:1. A protein translated from SEQ ID NO:1 and that can be used in the above-described method can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of treating major depression or a related disorder in a subject in need of said treatment comprising the step of administering a composition identified as modulating the level of expression of an mRNA molecule transcribed from SEQ ID NO:1 to said subject, in an amount sufficient to effect said treatment.

In the above-described method, an mRNA molecule transcribed from SEQ ID NO:1 can have the nucleotide sequence of SEQ ID NO:2, SEQ ID NO:5, SEQ ID NO:6, SEQ ID NO:7, SEQ ID NO:8, SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33.

In still yet another embodiment, the present invention relates to a method of determining the therapeutic activity of a composition used to treat major depression or a related disorder. The method involves the steps of:

a) determining the amount of a protein translated from SEQ ID NO:1, in a test sample from a subject treated with said composition; and b) comparing the amount of said protein in said test sample with the amount of protein present in a test sample from said subject prior to treatment, an equal amount of said protein in said test sample of said treated subject indicating lack of therapeutic activity of said composition and a changed amount of said protein in said test sample of said treated subject indicating therapeutic activity of said composition.

In the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of determining the level of therapeutic activity of a composition used to treat major depression or a related disorder. The method involves the steps of:

a) determining the activity of a protein translated from SEQ ID NO:1, in a test sample from a subject treated with said composition; and b) comparing the amount of activity of said protein in said test sample with the amount of activity of protein present in a test sample from said subject prior to treatment, an equal amount of activity of said protein in said test sample of said treated subject indicating lack of therapeutic activity of said composition and a changed amount of activity of said protein in said test sample of said treated subject indicating therapeutic activity of said composition.

In the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of determining the level of in vivo activity of a composition used to treat major depression or a related disorder comprising the steps of:

a) determining the amount of a mRNA molecule transcribed from SEQ ID NO:1, in a test sample from a subject treated with said composition; and b) comparing the amount of said mRNA molecule in said test sample with the amount of mRNA molecule present in a test sample from said subject prior to treatment, an equal amount of said mRNA molecule in said test sample of said treated subject indicating lack of therapeutic activity of said composition and a changed amount of said mRNA molecule in said test sample of said treated subject indicating therapeutic activity of said composition.

In the above-described method, an mRNA molecule transcribed from SEQ ID NO:1 can have the nucleotide sequence of SEQ ID NO:2, SEQ ID NO:5, SEQ ID NO:6, SEQ ID NO:7, SEQ ID NO:8, SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33.

In still yet another embodiment, the present invention relates to a method of determining presence or absence of activity of a composition used to treat major depression or a related disorder. The method involves the steps of:

a) observing phenotype of a subject according to a method validated as a measure of major depression or a related disorder;

b) administering said composition to said subject for a time and under conditions sufficient for said composition to bind to, inhibit, increase or reduce the activity of, or increase or reduce the amount of a protein translated from SEQ ID NO:1;

c) repeating step a) with said subject of step b); and d) comparing said phenotype of step a) and said phenotype of step c), a difference in step c) as compared to step a) indicating presence of activity of said composition and the lack of a difference indicating absence of activity of said composition.

In the above-described method, a protein translated from SEQ ID NO:1 can have an amino acid sequence selected from the group consisting of SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

In still yet another embodiment, the present invention relates to a method of determining presence or absence of activity of a composition used to treat major depression or a related disorder comprising the steps of:

a) observing phenotype of a subject according to a method validated as a measure of major depression or a related disorder;

b) administering said composition to said subject for a time and under conditions sufficient for said composition to increase or reduce the amount of a mRNA molecule transcribed from SEQ ID NO:1;

c) repeating step a) with said subject of step b); and d) comparing said phenotype of step a) and said phenotype of step c), a difference in step c) as compared to step a) indicating presence of activity of said composition and the lack of a difference indicating absence of activity of said composition.

In the above-described method, an mRNA molecule transcribed from SEQ ID. NO:1 can have the nucleotide sequence of SEQ ID NO:2, SEQ ID NO:5, SEQ ID NO:6, SEQ ID NO:7, SEQ ID NO:8, SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33.

BRIEF DESCRIPTION OF THE FIGURES

FIG. 1 shows the genomic DNA sequence comprising DEP2 (SEQ ID NO:1). The capital letters show the open reading frame for human phospholysine phosphohistidine inorganic pyrophosphate phosphatase (Lhpp) protein. Red text indicates single nucleotide polymorphisms. The bold underlined portions are forward primers. The bold italic underlined portions are reverse primers. The italic portions are repeat regions. The beginning portion of the sequence before the gap is disclosed as SEQ ID NO: 70.

FIG. 2 shows the nucleic acid sequence of DEP2-1 (SEQ ID NO:2). The nucleic acid sequence contains two (2) coding regions, each of which are shown in capital letters.

FIG. 3A shows the amino acid sequence of the Dep2-1a protein encoded by one of the coding regions of the nucleic acid shown in FIG. 2 (SEQ ID NO:3).

FIG. 3B shows the amino acid sequence of the Dep2-1b protein encoded by the second coding region of the nucleic acid shown in FIG. 2 (SEQ ID NO:4).

FIG. 4 shows the nucleic acid sequence of a naturally occurring splice variant of DEP2-1 (SEQ ID NO:5). The coding regions are shown in capital letters. The amino acid sequences of the proteins encoded by each of the coding regions is the same as shown in SEQ ID NOS: 3 and 4.

FIG. 5 shows the nucleic acid sequence of a naturally occurring splice variant of DEP2-1 (SEQ ID NO:6). The coding regions are shown in capital letters. The amino acid sequences of the proteins encoded by each of the coding regions is the same as shown in SEQ ID NOS: 3 and 4.

FIG. 6 shows the nucleic acid sequence of a naturally occurring splice variant of DEP2-1 (SEQ ID NO:7). The coding region is shown in capital letters. The amino acid sequence of the protein encoded by the coding region is the same as shown in SEQ ID NO:4.

FIG. 7 shows the nucleic acid sequence of a naturally occurring splice variant of DEP2-1 (SEQ ID NO:8). The coding region is shown in capital letters. The amino acid sequence of the protein encoded by the coding region is the same as shown in SEQ ID NO:4.

FIG. 8 shows the reference nucleic acid sequence of LHPP (SEQ ID NO:9). The coding region is shown in capital letters.

FIG. 9 shows the amino acid sequence of the Lhpp protein encoded by the nucleic acid shown in FIG. 2 (SEQ ID NO:10). A polymorphic amino acid has been found to exist at amino acid 94 where arginine is replaced by glutamine (see the underline).

FIG. 10 shows a naturally occurring splice variant of LHPP (SEQ ID NO:11). The coding region is shown in capital letters. The coding region encodes a protein that is identical to SEQ ID NO:10.

FIG. 11 shows a naturally occurring splice variant of LHPP (SEQ ID NO:12). The coding region is shown in capital letters.

FIG. 12 shows the amino acid sequence of the variant Lhpp protein encoded by the nucleic acid shown in FIG. 5 (SEQ ID NO:13).

FIG. 13 shows a naturally occurring splice variant of LHPP (SEQ ID NO:14). The coding region is shown in capital letters. The amino acid sequence of the variant Lhpp protein encoded by the nucleic acid is shown in SEQ ID NO:15.

FIG. 14 shows a nucleic acid sequence of a naturally occurring splice variant of LHPP (SEQ ID NO:16). The coding region is shown in capital letters. The amino acid sequence of the variant Lhpp protein encoded by the nucleic acid is shown in SEQ ID NO:17.

FIG. 15 shows a nucleic acid sequence of a naturally occurring splice variant of LHPP (SEQ ID NO:18). The coding region is shown in capital letters. The amino acid sequence of the variant Lhpp protein encoded by the nucleic acid is shown in SEQ ID NO:19.

FIG. 16 shows a nucleic acid of a naturally occurring splice variant of LHPP (SEQ ID NO:20). The coding region is shown in capital letters. The amino acid sequence of the variant Lhpp protein encoded by the nucleic acid is shown in SEQ ID NO:21.

FIG. 17 shows a nucleic acid of a naturally occurring splice variant of LHPP (SEQ ID NO:22). The coding region is shown in capital letters. The amino acid sequence of the variant Lhpp protein encoded by the nucleic acid is shown in SEQ ID NO:23.

FIG. 18 shows a nucleic acid of a naturally occurring splice variant of LHPP (SEQ ID NO:24). The coding region is shown in capital letters. The amino acid sequence of the variant Lhpp protein encoded by the nucleic acid is shown in SEQ ID NO:25.

FIG. 19 shows a nucleic acid of a naturally occurring splice variant of LHPP (SEQ ID NO:28). The coding region is shown in capital letters. The amino acid sequence of the protein encoded by the nucleic acid is shown in SEQ ID NO:29.

FIG. 20 shows a nucleic acid sequence of DEP2-2 (SEQ ID NO:26). The coding region is shown in capital letters.

FIG. 21 shows the amino acid sequence of the Dep2-2 protein encoded by the nucleic acid shown in FIG. 20 (SEQ ID NO:27).

FIG. 22 shows a nucleic acid sequence of DEP2-3 (SEQ ID NO:30).

FIG. 23 shows a nucleic acid of AK127935 (GenBank: AK127935) (SEQ ID NO:31). The coding region is shown in capital letters.

FIG. 24 shows the amino acid sequence of the Dep2-4 protein encoded by the nucleic acid shown in FIG. 23 (SEQ ID NO:32).

FIG. 25 shows a nucleic acid of AW867792 (GenBank: AW867792) (SEQ ID NO:33). The coding region is shown in capital letters.

FIG. 26 shows the amino acid sequence of the Dep2-5 protein encoded by the nucleic acid shown in FIG. 25 (SEQ ID NO:34).

FIG. 30 shows a sequence alignment of DEP2-1 sequences either predicted by a bioinformatic algorithm (Genecarta (SEQ ID NO:71)) or determined experimentally by direct sequencing of cloned cDNAs h5173309(SEQ ID NO:72), h 5194531(SEQ ID NO:73), h5197955 (SEQ ID NO:74) and h4565014(SEQ ID NO:75. Arrowheads indicate major transcription start sites determined by RLM-RACE. A single nucleotide polymorphism is indicated by an underlined base in the h4565014 sequence. The last line of sequence was found, downstream of a polyadenylate tract, in h4565014 and does not match DEP2.

DETAILED DESCRIPTION OF THE INVENTION

Definitions

Figure 27:
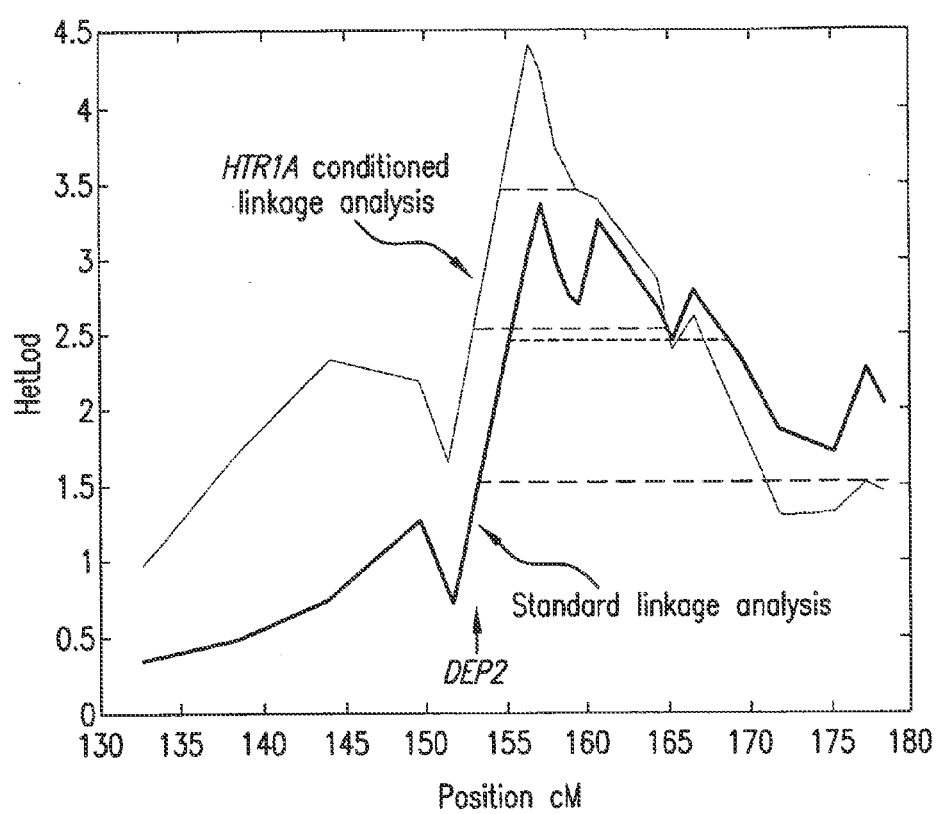
FIG. 27 shows the genetic evidence on chromosome 10 for linkage of a gene to major depressive disorder. The lower, curved line and lower, two horizontal lines show evidence from standard linkage analysis. The green lines show evidence from serotonin receptor 1A-conditional linkage analysis. The dotted horizontal lines indicate the extent of the linkage region as defined by a drop of one unit in the heterogeneity LOD score. The dashed horizontal lines indicate the extent of the linkage region as defined by a drop of two units in the heterogeneity LOD score. The right side of the figure represents the telomere of chromosome 10. The approximate location of DEP2 is represented by an arrowhead.

As used herein, the singular forms "a," "an" and "the" include plural reference unless the context clearly dictates otherwise. Unless defined otherwise, all technical and scientific terms used herein have the same meaning as commonly understood to one those of skill in the art to which this invention belongs.

As used herein, the term "allele" refers to a particular form of a nucleic acid, either DNA or RNA, wherein different alleles of a nucleic acid differ in sequence, by either change or insertion/deletion, at one or more nucleotides at a polymorphic site.

"cDNA" refers to a DNA that is complementary to and synthesized from a mRNA template using the enzyme reverse transcriptase. The cDNA can be single-stranded or converted into the double-stranded form.

As used herein, the term "coding sequence" or "coding region" refers to a nucleic acid sequence that codes for a specific amino acid sequence.

As used herein, the term "complementarity" refers to as the degree of relatedness between two nucleic acid segments. It is determined by measuring the ability of the sense strand of one nucleic acid segment to hybridize with the antisense strand of the other nucleic acid segment, under appropriate conditions, to form a double helix. A "complement" is defined as a sequence which pairs to a given sequence based upon the canonic base-pairing rules. For example, a sequence A-G-T in one nucleotide strand is "complementary" to T-C-A in the other strand.

In the DNA double helix, wherever adenine appears in one strand, thymine (uridine in RNA) appears in the other strand. Similarly, wherever guanine is found in one strand, cytosine is found in the other. The greater the relatedness between the nucleotide sequences of two nucleic acid segments, the greater the ability to form hybrid duplexes between the strands of the two nucleic acid segments.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity" between two amino acid sequences is defined as the presence of a series of exactly alike or invariant amino acid residues in both sequences.) The definitions of "complementarity", "identity" and "similarity" are well known to those of ordinary skill in the art.

As used herein, the term "DEP2" refers to a gene on human chromosome 10q26.2 that has been statistically linked and associated with major depression, and that is believed to be within the 159 kb sequence comprising SEQ ID NO:1. Transcripts that arise from DEP2 include: (a) LHPP (SEQ ID NO:9) (See, Yokoi et al., J Biochem 133:607-14 (2003)); (b) naturally occurring splice variants of LHPP (SEQ ID NO:11, SEQ ID NO:12, SEQ ID NO:14, SEQ ID NO:16, SEQ ID NO:18, SEQ ID NO:20, SEQ ID NO:22, SEQ ID NO:24 and SEQ ID NO:26; (c) DEP2-1 (SEQ ID NO:2); (d) naturally occurring splice variants of DEP2-1 (SEQ ID NO:5, SEQ ID NO:6, SEQ ID NO:7 or SEQ ID NO:8); (e) DEP2-2 (SEQ ID NO:28); (f) Dep2-3 (SEQ ID NO:30); (g) GenBank sequence AK127935 (SEQ ID NO:31); and (h) GenBank sequence AW867792 (SEQ ID NO:33). Proteins that are encoded within DEP2 include: (a) Lhpp (SEQ ID NO:10) (See, Yokoi et al., J Biochem 133:607-14 (2003)); (b) naturally occurring protein variants of Lhpp (SEQ ID NO:13, SEQ ID NO:15, SEQ ID NO:17, SEQ ID NO:19, SEQ ID NO:21, SEQ ID NO:23, SEQ ID NO:25 and SEQ ID NO:27); (c) Dep2-1a and Dep2-1b (SEQ ID NO:3 and SEQ ID NO:4, respectively); (d) Dep2-2 (SEQ ID NO:29); (e) Dep2-4 (SEQ ID NO:32); and (f) Dep2-5 (SEQ ID NO:34).

As used herein, the term "DEP2 transcripts" refers to the group of transcripts arising in whole or in part from SEQ ID NO:1, including but not limited to: LHPP and naturally occurring splice variants thereof; DEP2-1 and naturally occurring splice variants thereof; DEP2-2; DEP2-3; GenBank sequence AK127935 and GenBank sequence AW867792. As used herein, the term "DEP2 proteins" refers to the group of proteins encoded in whole or in part from one or more DEP2 transcripts, including but not limited to: Lhpp and naturally occurring protein variants thereof; Dep2-1a; Dep2-1b; Dep2-2; Dep2-4 and Dep2-5. As used herein, the terms "DEP2 polymorphic sites" or "DEP2 polymorphisms", used interchangeably, refer to polymorphic sites found within SEQ ID NO:1, or if outside of SEQ ID NO:1, within a DEP2 transcript.

As used herein, the term "DEP2-1" refers to a messenger RNA shown in SEQ ID NO:2 and in FIG. 2, and DNA sequences that functionally regulate expression thereof. Experimental evidence that DEP2-1 messenger RNA is a naturally occurring transcript is disclosed herein. As shown in FIG. 2, DEP2-1 messenger RNA has 2 exons. Of these, an exon comprising nucleotides 1-315 of SEQ ID NO:2 was not previously known to be in any naturally occurring transcript. In addition, three naturally occurring polymorphic sites in nucleotides 1-315 of DEP2-1 messenger RNA are disclosed herein: (a) 135T>C, (b) 209A>G and (c) 241G>A.

As used herein, the terms "Dep2-1a" and "Dep2-1b" refer to proteins shown in SEQ ID NO:3 and in FIG. 3A, and in SEQ ID NO:4 and in FIG. 3B, respectively. These proteins may be encoded from DEP2-1 as well as naturally occurring splice variants thereof.

As used herein, the term "DEP2-2" refers to a messenger RNA shown in SEQ ID NO:28, and DNA sequences that functionally regulate expression thereof.

As used herein, the term "Dep2-2" refers to a protein shown in SEQ ID NO:29. This protein may be encoded from DEP2-2.

As used herein, the term "DEP2-3" refers to a messenger RNA shown in SEQ ID NO:30, and DNA sequences that functionally regulate expression thereof.

As used herein, the term "Dep2-4" refers to a protein shown in SEQ ID NO:32. This protein may be encoded from SEQ ID NO:31.

As used herein, the term "Dep2-5" refers to a protein shown in SEQ ID NO:34. This protein may be encoded from SEQ ID NO:33.

As used herein, the phrase "effective amount" or a "therapeutically effective amount", which are used interchangeably herein, when used in connection with an active agent (such as a drug) is meant a nontoxic but sufficient amount of the active agent to provide the desired effect. The amount of active agent (such as a drug) that is "effective" will vary from subject to subject, depending on the age and general condition of the individual, the particular active agent or agents, and the like. Thus, it is not always possible to specify an exact "effective amount." However, an appropriate "effective amount" in any individual case may be determined by one of ordinary skill in the art using routine experimentation.

As used herein, the phrase "encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

As used herein, the term "exon" refers to a portion of the gene sequence that is transcribed and is found in the mature messenger RNA derived from the gene, but is not necessarily a part of the sequence that encodes the final gene product.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target transcript. "Co-suppression" refers to the production of sense RNA transcripts capable of suppressing the expression of identical or substantially similar foreign or endogenous genes (U.S. Pat. No. 5,231,020).

As used herein, the term "fragment" of a nucleic acid sequence refers to a contiguous sequence of approximately at least 6 nucleotides, preferably at least about 8 nucleotides, more preferably at least about 10 nucleotides, and even more preferably at least about 15 nucleotides, and most preferable at least about 20 nucleotides identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, and "N" for any nucleotide.

As used herein, the term "gene" refers to a nucleic acid sequence that undergoes transcription as a result of the activity of at least one promoter. A gene may encode for a particular polypeptide, or alternatively, code for a RNA molecule. A gene includes one or more exons and one or more regulatory or control sequences and may include one or more introns. The phrase "target gene" as used herein, refers to a nucleic acid sequence, such as, but not limited to, a nucleic acid sequence of interest that encodes a polypeptide of interest or alternatively, a RNA molecule of interest. The term "target gene" can also refer to a gene to be identified or knocked-out according to the methods described herein.

As used herein, the term "genotype" refers to the identity of alleles present in a subject or in a test sample.

As used herein, the term "genotyping" refers to the process of determining the genotype of a subject.

As used herein, the terms "homologous", "substantially similar" and "corresponding substantially" are used interchangeably. They refer to nucleic acid or protein fragments wherein changes in one or more nucleotide bases or amino acids does not affect the ability of the nucleic acid or protein fragment to mediate gene expression or produce a certain phenotype. These terms also refer to modifications of the nucleic acid or protein fragments of the instant invention such as deletion or insertion of one or more nucleotides or amino acids that do not substantially alter the functional properties of the resulting nucleic acid or protein fragment relative to the initial, unmodified fragment. It is therefore understood, as those skilled in the art will appreciate, that the invention encompasses more than the sequences exemplified herein.

As used herein, the term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences).

"Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, *Appl. Math.*, 2:482 (1981), by the algorithm of Needleman & Wunsch, *J. Mol. Biol.*, 48:443 (1970), by the method of Pearson & Lipman, *Proc. Natl. Acad. Sci.*, (USA) 85:2444 (1988) and by computer programs which implement the relevant algorithms (for example, Clustal Macaw Pileup (which is publicly available on the Internet; Higgins et al., *CABIOS*. 5L151-153 (1989)), FASTDB (Intelligenetics), BLAST (National Center for Biomedical Information; Altschul et al., *Nucleic Acids Research*, 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

As used herein, the term "isoform" refers to a particular form of a protein, wherein different isoforms of a protein differ in sequence, by either change or insertion/deletion, or covalent modification at one or more amino acids.

As used herein, the terms "isolated" or "purified", used interchangably, when used in connection with biological molecules such as nucleic acids or proteins means that the molecule is substantially free of other biological molecules such as nucleic acids, proteins, lipids, carbohydrates or other material such as cellular debris and growth media. Generally, the term "isolated" or "purified" are not intended to refer to a complete absence of such material or to absence of water, buffers, or salts, unless they are present in amounts that substantially interfere with the methods of the present invention.

As used herein, an "isolated nucleic acid fragment or sequence" is a polymer of nucleic acid (RNA or DNA) that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, the term "Lhpp" refers to an enzyme known as phospholysine phosphohistidine inorganic pyrophosphate phosphatase, and the term "LHPP" refers to the corresponding messenger RNA, and DNA sequences that functionally regulate expression thereof. Lhpp was originally purified from swine brain in 1957 (See, Seal et al., *J Biol Chem* 228:193-9 (1957)), and subsequently has been purified from several additional mammalian sources (See, Felix et al., *J Biochem* 147:111-8 (1975); Yoshida et al., *Cancer Research* 42:3256-31 (1982); Hachimori et al., *J Biochem* 93:257-64 (1983); Smirnova et al., *Arch Biochem Biophys* 287:135-40 (1991); Hiraishi et al., *Arch Biochem Biophys* 341:153-9 (1997)). The enzyme has been characterized in vitro as efficiently catalyzing the hydrolysis of P—N bonds in phosphohistidine and phospholysine, and less efficiently catalyzing the hydrolysis of P—N or P—O bonds in imidodiphosphate and pyrophosphate, respectively. Lhpp may be a protein histidine or lysine phosphoamidase, i.e., an enzyme that modifies the N-linked phosphorylation state of other proteins. The human LHPP has been cloned. Functional human Lhpp enzyme has been purified following heterologous expression in *E. coli* (See, Yokoi et al., *J Biochem* 133:607-14 (2003)). The nucleic acid sequence of LHPP messenger RNA is shown in SEQ ID NO:9 and in FIG. 8. The amino acid sequence of Lhpp is shown in SEQ ID NO:10 and in FIG. 9. As shown in FIG. 1, LHPP messenger RNA has 7 exons. The locations of these exons are provided below in Table A.

TABLE A

| Exon | Start in SEQ ID NO: 1 | End in SEQ ID NO: 1 |
|---|---|---|
| 1 | 3001 | 3163 |
| 2 | 25305 | 25492 |
| 3 | 29588 | 29741 |
| 4 | 38127 | 38190 |
| 5 | 39202 | 39294 |
| 6 | 58346 | 58437 |
| 7 | 154430 | 155313 |

In addition, there is a naturally occurring polymorphic site in Lhpp (R94Q) in which amino acid 94 is either arginine or glutamine in the two naturally occurring isoforms. In the corresponding naturally occurring polymorphic site in LHPP messenger RNA (281G>A), base 281 of the open reading frame is either guanine or adenine in the two naturally occurring alleles. Further, Lhpp is encoded from a naturally occurring splice variant of LHPP that is shown in SEQ ID NO:11 (See FIG. 10).

As used herein, the term "locus" refers to a location on a chromosome of a nucleic acid molecule corresponding to a gene or a physical or phenotypic feature, where physical features include polymorphic sites.

As used herein, the term "major depression or a related disorder" refers to any Mood Disorder or Anxiety Disorder described in the Diagnostic and Statistical Manual (DSM-IV-TR, American Psychiatric Association, 2000). Mood Disorders include, but are not limited to, Depressive Disorders (DSM-IV-TR 296.2x, 296.3x, 300.4, 311), Bipolar Disorders (DSM-IV-TR 296.0x, 296.40, 296.4x, 296.5x, 296.6x, 296.7, 296.89, 301.13, 296.80) and Mood Disorder Not Otherwise Specified (DSM-IV-TR 296.90). Anxiety Disorders include, but are not limited to, Panic Disorders (DSM-IV-TR 300.01, 300.21), Phobic Disorders (DSM-IV-TR 300.29, 300.22, 300.23), Obsessive-Compulsive Disorder (DSM-IV-TR 300.3), Post-Traumatic Stress Disorder (DSM-IV-TR 309.81), Acute Stress Disorder (DSM-IV-TR 308.3), Generalized Anxiety Disorder (DSM-WV-TR 300.02) and Anxiety Disorder Not Otherwise Specified (DSM-IV-TR 300.00). Extensive lists of symptoms and diagnostic criteria for each of these disorders are found in the DSM-IV-TR sections cited above.

As used herein, the terms "modulates" "modulation" or "modulating" as used interchangeably herein, refer to both upregulation (for example, activation or stimulation (for example, by agonizing or potentiating)) and downregulation (for example, inhibition or suppression (for example, by antagonizing, reducing, decreasing or inhibiting)).

As used herein, the term "naturally occurring" refers to a DNA molecule, a messenger RNA, a protein, an allele, an isoform, a polymorphic site, a splice variant or a protein variant, wherein the existence in nature of said DNA molecule, messenger RNA, protein, allele, isoform, polymorphic site, splice variant or protein variant is supported by either (a) direct experimental evidence or (b) algorithmic assembly from a database of nucleic acid or protein sequences. Alleles, isoforms, polymorphic sites, splice variants and protein variants might also be created by experimental manipulation.

As used herein, the term "naturally occurring splice variant of DEP2-1" includes but is not limited to the sequences shown in SEQ ID NO:5, SEQ ID NO:6, SEQ ID NO:7 and SEQ ID NO:8.

As used herein, the term "naturally occurring splice variant of LHPP" includes but is not limited to the sequences shown in SEQ ID NO:12, SEQ ID NO:14, SEQ ID NO:16, SEQ ID NO:18, SEQ ID NO:20, SEQ ID NO:22, SEQ ID NO:24 and SEQ ID NO:26. As used herein, the term "naturally occurring protein variant of Lhpp" includes but is not limited to the sequences shown in SEQ ID NO:13, SEQ ID NO:15, SEQ ID NO:17, SEQ ID NO:19, SEQ ID NO:21, SEQ ID NO:23, SEQ ID NO:25 and SEQ ID) NO:27.

As used herein, the phrase "3' non-coding sequences" refer to mRNA sequences located downstream of a coding sequence.

As used herein, the term "non-human animal" includes all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus.

Mice are often used for transgenic animal models because they are easy to house, relatively inexpensive, and easy to breed. However, other non-human transgenic animals may also be made in accordance with the present invention such as, but not limited to, primates, mice, goat, sheep, rabbits, dogs, cows, cats, guinea pigs, rats, zebrafish and nematodes. Transgenic animals are those which carry a transgene, that is, a cloned gene introduced and stably incorporated which is passed on to successive generations.

As used herein, the term "nucleic acid" refers to a polymeric form of nucleotides of any length, either ribonucleotides or deoxyribonucleotides. This term includes double- and single-stranded DNA, as well as double- and single-stranded RNA. It also includes modifications, such as methylation or capping and unmodified forms of the polynucleotide. The terms "polynucleotide," "oligomer," "oligonucleotide," and "oligo" are used interchangeably herein.

As used herein, the phrase "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Polymerase chain reaction ("PCR") is a technique used to amplify DNA millions of fold, by repeated replication of a template, in a short period of time. (Mullis et al., *Cold Spring Harbor Symp. Quant. Biol.* 51:263-273 (1986); Erlich et al., European Patent Application No. 50,424; European Patent Application No. 84,796; European Patent Application No. 258,017; European Patent Application No. 237,362; Mullis, European Patent Application No. 201,184; Mullis et al., U.S. Pat. No. 4,683,202; Erlich, U.S. Pat. No. 4,582,788; and Saiki et al., U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

As used herein, the term "polymorphic site" refers to a nucleic acid sequence comprising one or more consecutive nucleotides that differ between alleles, or to a protein sequence comprising one or more consecutive amino acids that differ between isoforms.

As used herein, the term "polymorphism" refers to a sequence variation observed in a subject at a polymorphic site. Polymorphisms include nucleotide or amino acid substitutions, insertions and deletions and may, but need not, result in detectable differences in gene expression or protein function.

The terms "polypeptide" and "protein" are used interchangeably herein and indicate at least one molecular chain of amino acids linked through covalent and/or non-covalent bonds. The terms do not refer to a specific length of the product. Thus peptides, oligopeptides and proteins are included within the definition of polypeptide. In addition, protein fragments, analogs, mutated or variant proteins, fusion proteins and the like are included within the meaning of polypeptide.

As used herein, the term "primer" refers to an oligonucleotide, whether naturally occurring, such as in a purified restriction digest, or produced synthetically, which is capable of acting as a point of initiation of synthesis when placed under conditions in which synthesis of a primer extension product that is complementary to a nucleic acid strand is induced (such as in the presence of nucleotides and an inducing agent such as DNA polymerase and at a suitable temperature and pH). Primers can be single or double stranded. If double stranded, the primer is first treated to separate its strands before being used to prepare extension products. The exact length of the primers will depend on many factors, including temperature, source of primer and the use of the method. Primers preferably have a length of at least 10 contiguous nucleotides. For example, primers can have a length of 10 contiguous nucleotides, 15 contiguous nucleotides, 20 contiguous nucleotides, 25 contiguous nucleotides, etc.

As used herein, the term "probe" refers to an oligonucleotide, whether naturally occurring, such as in a purified restriction digest, produced synthetically, recombinantly or by polymerase chain reaction amplification which is capable of hybridizing to another oligonucleotide or nucleic acid of interest. A probe may be single-stranded or double-stranded. Probes can be labeled with a detectable label so as to make said probe detectable in a detection system. The detectable label used is not critical.

As used herein, the term "promoter" refers to a DNA sequence capable of controlling the transcription of a RNA. Promoters may be derived in their entirety from a native gene, or be composed of different elements derived from different promoters found in nature, or even comprise synthetic DNA segments.

As used herein, the term "protein variant" refers to a polypeptide that is encoded from a splice variant, wherein two protein variants differ in the inclusion/exclusion of one or more blocks of consecutive amino acids.

The terms "recombinant construct", "construct", "expression construct" and "recombinant expression construct" are used interchangeably herein. These terms refer to a functional unit of genetic material that can be inserted into the genome of a cell or expressed in vitro using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

As used herein, the term "regulatory sequences" refers to a DNA or RNA sequence capable of controlling the expression of a RNA or protein. Regulatory sequences may include, but are not limited to, promoters, translation leader sequences, introns, and polyadenylation recognition sequences.

As used herein, the phrase "RNA transcript" or "RNA molecule" as used interchangeable herein, refers to the product resulting from RNA polymerase-catalyzed transcription of a DNA sequence. "Messenger RNA (mRNA)" refers to the RNA that is without introns and that can be translated into protein by the cell.

As used herein, the phrase "sense RNA" refers to RNA molecule that includes the mRNA and can be translated into protein within a cell or in vitro. As used herein, the phrase, "antisense RNA" refers to an RNA molecule that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. As used herein, the phrase, "functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

As used herein, the term "single nucleotide polymorphism" or "SNP" refers typically, to a specific pair of nucleotides observed at a single polymorphic site. In some cases, which are rare, three or four nucleotides may be found.

As used herein, the term "splice variant" refers to a particular form of a messenger RNA, wherein two splice variants share either (a) a transcriptional start site or (b) an open reading frame, but differ in the inclusion/exclusion of one or more exons.

As used herein, the term "subject" refers to an animal, preferably a mammal, including a human or non-human. The animal can be a domesticated or non-domesticated animal.

As used herein, the term "treating" refers to reversing, alleviating, inhibiting the progress of, or preventing at least one overt symptomatic manifestation of the disorder or condition to which such term applies, or one or more symptoms of such disorder or condition. The term "treatment" as used herein, refers to the act of treating, as "treating" is defined herein. For the present invention, the term "treat" means to alleviate or eliminate one or more symptoms, behavior or events associated with a depressive disorder.

DEP2-1 Transcripts and Proteins Encoded Thereby

In one embodiment, the present invention relates to the discovery of a novel transcript of DEP2, named DEP2-1. FIG. 2 illustrates the isolated nucleic acid sequence for DEP2-1 (SEQ ID NO:2), which is 1198 base pairs in length. Nucleotides 1 to 316 of SEQ ID NO:2 comprise an exon that was not previously known to be in any naturally occurring transcript of DEP2. The remaining portion of SEQ ID NO:2 (from nucleotides 317 to 1198) are shared with LHPP and naturally occurring splice variants thereof, and correspond to nucleotides 882 to 1760 of SEQ ID NO:9. DEP2-1 was initially assembled using Genecarta software (Compugen, Tel Aviv, Israel) from publicly available expressed sequence tags ("ESTs"). Specifically, the proprietary algorithms identified that certain ESTs (GenBank accession numbers BI669229, BI489679, BI756098, Z44231, R15274, R11923, BX952014, BI754006, H51555, H51378 and BG397886) each comprised of sequences from within both nucleotides 1-316 and nucleotides 317-1198 of SEQ ID NO:2. These two sequence blocks are not contiguous in the human genome, implying that SEQ ID NO:2 is a spliced transcript. To confirm that DEP2-1 is a naturally occurring transcript, four IMAGE clones (h5173309, h5194531, h5197955 and h4565014, corresponding to BI489679, BI756098, BI754006 and BG397886, respectively) were completely sequenced in both directions (see Example 5). The contiguous sequence of nucleotides 19-1198 of SEQ ID NO:2 was thereby confirmed. IMAGE clones h5173309, h5194531 and h5197955 are from brain, and include only sequences shown in SEQ ID NO:2. Among the ESTs that assembled to form DEP2-1, all were from brain except for BG397886, which was from a tonsillar primary B cell line. IMAGE clone h4565014 corresponds to BG397886. The sequence of this clone included nucleotides 299-1198 followed by a polyadenine tail and a further 77 nucleotide sequence that did not match DEP2. Further, a single nucleotide polymorphism (1142G>A) was discovered at nucleotide 1142 of SEQ ID NO:2. Rapid amplification of cDNA ends was performed to determine the 5' end(s) of DEP2-1 (see Example 6). These experiments identified two 5' ends in human spinal cord RNA, at nucleotides 1 and 75 of SEQ ID NO:2. Two series of PCR experiments were also performed to determine whether the first exon (nucleotides 1-315) of DEP2-1 is included in additional transcripts with upstream exons (see Example 7). The first experiments used forward primers in an upstream exon of LHPP and reverse primers in the first exon of DEP2-1. The second experiments used forward primers in an upstream exon of LHPP and reverse primers in a downstream exon of LHPP. No sequence from the first exon of DEP2-1 was amplified in either set of experiments. In total, these experimental results demonstrate that DEP2-1 is a naturally occurring transcript, that it is not an alternative splice variant of LHPP, and thus does not encode a naturally occurring protein variant of Lhpp.

The isolated nucleic acid sequence of DEP2-1 has two coding regions, which are each illustrated in capital letters in FIG. 2. The first coding region (nucleotides 352 to 771 in SEQ ID NO:2) may encode for the protein, referred to herein as Dep2-1a, shown in FIG. 3A (SEQ ID NO:3). Dep2-1a is 140 amino acids in length. The second coding region (nucleotides 812 to 1162 in SEQ ID NO:2) may encode for the protein, referred to herein as, Dep2-1b, shown in FIG. 3B (SEQ ID NO:4). Dep2-1b is 117 amino acids in length.

In addition, naturally occurring splice variants of DEP2-1 have been identified by the inventors of the present invention. These transcripts were assembled using Genecarta software (Compugen, Tel Aviv, Israel) from publicly available expressed sequence tags ("ESTs"). These splice variants of the DEP2-1 are shown in SEQ ID NO:5, SEQ ID NO:6, SEQ ID NO:7 and SEQ ID NO:8. SEQ ID NO:5 is also shown in FIG. 4 and is 1092 base pairs in length. The coding regions are shown in capital letters in this figure. The first and second coding regions encode for Dep2-1a (See, FIG. 3A (SEQ ID NO:3)) and Dep2-1b (FIG. 3B (See, SEQ ID NO:4)). SEQ ID NO:5 was assembled on the basis of three ESTs (BG759116, BF976531 and BQ706325), all of B cell origin. SEQ ID NO:6 is shown in FIG. 5 and is 1022 base pairs in length. The coding regions are shown in capital letters in this figure. The first and second coding regions encode for Dep2-1a (See, FIG. 3A (SEQ ID NO:3)) and Dep2-1b (FIG. 3B (See, SEQ ID NO:4)). SEQ ID NO:6 was assembled on the basis of two ESTs (BI226948 and BE396637), both from a Burkitt's lymphoma cell line. SEQ ID NO:7 is shown in FIG. 6 and is 1186 base pairs in length. The coding region is shown in capital letters in this figure. The coding region encodes for Dep2-1b (See, FIG. 3A (SEQ ID NO:4)). SEQ ID NO:7 was assembled on the basis of a single EST (CF454636), from the peripheral nervous system. SEQ ID NO:8 is shown in FIG. 7 and is 1005 base pairs in length. The coding region is shown in capital letters in this figure. The coding region encodes for Dep2-1b (See, FIG. 3B (SEQ ID NO:4)). SEQ ID NO:8 was assembled on the basis of a single EST (BE560698), from a Burkitt's lymphoma cell line.

The ESTs described in the preceding paragraph were used to assemble the 5' ends of the variant DEP2-1 transcripts. None of these ESTs contain the entire transcript sequence. In all cases, the 3' end of each of these transcripts is common to all these sequences as well as to LHPP as well as to some of the splice variants thereof and can be found in multiple ESTs. These ESTs are listed below in Table B.

TABLE B

| GenBank Accession | Tissue Source (If Specified) |
|---|---|
| AA292585 | Ovarian tumor |
| AA308083 | Colon L KM12C (HCC) metastasis into mouse (liver) |
| AA379353 | Skin |
| AA379626 | Skin |
| AA635531 | Normal prostate |
| AA669836 | Bone Marrow stroma |
| AA677990 | Liver and spleen |
| AA725685 | |
| AA912377 | Dorsal root ganglion |
| AI086359 | Pooled human melanocyte, fetal heart, and pregnant uterus |
| AI139589 | Placenta |
| AI97875 | Anaplastic oligodendroglioma |
| AI221142 | Pooled |
| AI272203 | Oligodendroglioma |
| AI361781 | B-cell, chronic lymphotic leukemia |
| AI378120 | B-cell, chronic lymphotic leukemia |
| AI420571 | Prostate |
| AI439876 | Lymphoma, follicular mixed small and large cell |
| AI475774 | B-cell, chronic lymphotic leukemia |
| AI492345 | Kidney |
| AI565021 | Well-defferentiated endometrial adenocarcinoma, 7 pooled tumors |
| AI582637 | Kidney |
| AI598057 | Adenocarcinoma |

TABLE B-continued

| GenBank Accession | Tissue Source (If Specified) |
|---|---|
| AI805094 | Prostate |
| AI972592 | Prostate |
| AW139347 | |
| AW301045 | Moderately differentiated adenocarcinoma |
| AW511836 | Moderately-differentiated endometrial adenocarcinoma, 3 pooled tumors |
| AW512618 | Lymphoma, follicular mixed small and large cell |
| AW954516 | |
| BE675320 | B-cell, chronic lymphotic leukemia |
| BF740030 | Kidney |
| BF949274 | Nervous_normal |
| BF986056 | Placenta_normal |
| BF986061 | Placenta_normal |
| BG027502 | Osteosarcoma, cell line |
| BG150734 | Normal epithelium |
| BI819728 | Pooled brain, lung, testis |
| BQ644034 | Hepatocellular carcinoma, cell line |
| BU539737 | Adenocarcinoma, cell line |
| BU683755 | Primary lung cystic fibrosis epithelial cells |
| BU753421 | Placenta |
| BX096697 | Well-differentiated endometrial adenocarcinoma, 7 pooled tumors |
| BX330376 | Placenta |
| BX361464* | Placenta |
| BX423161 | Adult brain |
| CD631211 | |
| CD631212 | |
| CK823134*^ | Islets of Langerhans |
| CN265311 | Embryonic stem cells, embryoid bodies derived from H1, H7 and H9 cells |
| N38886 | Multiple sclerosis lesions |

*Reverse direction EST sequence also present in the public domain
^Two additional sequences from the same clone are also present in the public domain.

It should be noted that the present invention also encompasses isolated nucleotide sequences (and the corresponding encoded proteins) having sequences comprising, corresponding to, identical to, or complementary to at least about 90% identity to SEQ ID NO:2. (All integers (and portions thereof) between 90% and 100% are also considered to be within the scope of the present invention with respect to percent identity.) For example, the present invention encompasses an isolated nucleic acid or fragment thereof comprising (a) a nucleotide sequence having at least 90% identity to SEQ ID NO:2; or (b) a complement comprising a nucleotide sequence having at least 90% identity to SEQ ID NO:2. Such sequences may be derived from any source, either isolated from a natural source, or produced via a semi-synthetic route, or synthesized de novo.

The invention also includes a purified polypeptide that has at least about 90% amino acid similarity or identity to the amino acid sequences of SEQ ID NO:3 or SEQ ID NO:4 of the above-noted proteins which are, in turn, encoded by the above-described nucleic acid sequences.

The present invention also encompasses an isolated nucleic acid sequence which encodes a polypeptide having the amino acid sequence of SEQ ID NO:3 or SEQ ID NO:4.

Once DEP2-1 or any naturally occurring variants thereof have been isolated, they may then be introduced into either a prokaryotic or eukaryotic host cell through the use of a vector or construct. The vector, for example, a bacteriophage, cosmid or plasmid, may comprise a nucleic acid sequence having a nucleotide sequence of SEQ ID NO:2, or nucleotides 352-771 or 812-1162 thereof, as well as any regulatory sequence (such as, but not limited to a promoter) which is functional in the host cell and is able to elicit expression of the protein encoded by the nucleotide sequence. Alternatively, the vector may comprise a complement comprising a nucleotide sequence of SEQ ID NO:2 or nucleotides 352-771 or 812-1162 thereof, as well as any regulatory sequence. The regulatory sequence (for example, a promoter) is in operable association with, or operably linked to, the sequence of SEQ ID NO:2, or nucleotides 352-771 or 812-1162 thereof. Examples of promoters that can be used include LTR or the SV40 promoter, the E. coli lac or trp, the phage lambda P sub L promoter and other promoters known to those of skill in the art. Additionally, nucleic acid sequences which encode other proteins, oligosaccharides, lipids, etc. may also be included within the vector as well as other regulatory sequences such as a polyadenylation signal (for example, the poly-A signal of SV-40T-antigen, ovalalbumin or bovine growth hormone). The choice of sequences present in the construct is dependent upon the desired expression products as well as the nature of the host cell.

Once the vector has been constructed, it can be introduced (namely, transformed or transfected) into host cells, such as mammalian (such as, but not limited to, simian, canine, feline, bovine, equine, rodent, murine, etc.) or non-mammalian (such as, but not limited to, insect, reptile, fish, avian, etc.) cells, using any method known to those of skill in the art including, but not limited to, electroporation, calcium phosphate precipitation, DEAE dextran, lipofection, and receptor mediated endocytosis, polybrene, particle bombardment, and microinjection. Alternatively, the vector can be delivered to the cell as a viral particle (either replication competent or deficient). Examples of viruses useful for the delivery of nucleic acid include, but are not limited to, lentivirus, adenoviruses, adeno-associated viruses, retroviruses, herpesviruses, and vaccinia viruses. Other viruses suitable for delivery of nucleic acid sequences into cells that are known to those of skill in the art may be equivalently used in the present invention.

The engineered host cells can be cultured in conventional nutrient media modified as appropriate for activating the promoter sequences, selecting transfected cells, etc. The culture conditions, such as temperature, pH and the like, are those previously used with the host cell selected for expression, and will be apparent to those of skill in the art.

The engineered host cells containing the incorporated vector(s) can be identified using hybridization techniques that are well known to those of skill in the art or by using the polymerase chain reaction to amplify specific polynucleotide sequences. If the nucleic acid sequence transferred to the cells produces a protein that can be detected, for example, by means of an immunological or enzymatic assay, then the presence of recombinant protein can be confirmed by performing the assays either on the medium surrounding the cells or on cellular lysates.

Non-Human Transgenic Animals

In another embodiment, the present invention relates to non-human transgenic animals that contain the transcripts that arise from DEP2 as well as methods of making said animals. Specifically, the nucleic acid sequences that can be used in said non-human transgenic animals include: (a) LHPP (SEQ ID NO:9); (b) naturally occurring splice variants of LHPP (SEQ ID NO:11, SEQ ID NO:12, SEQ ID NO:14, SEQ ID NO:16, SEQ ID NO:18, SEQ ID NO:20, SEQ ID NO:22, SEQ ID NO:24 and SEQ ID NO:26; (c) DEP2-1 (SEQ ID NO:2); (d) naturally occurring splice variants of DEP2-1 (SEQ ID NO:5, SEQ ID NO:6, SEQ ID NO:7 or SEQ ID NO:8); (e) DEP2-2 (SEQ ID NO:28); (f) Dep2-3 (SEQ ID NO:30); (g) GenBank sequence AK127935 (SEQ ID NO:31); and (h) GenBank sequence AW867792 (SEQ ID NO:33).

A variety of methods can be used to create the non-human transgenic animals. For example, the generation of a specific alteration of a nucleic acid sequence of a target gene is one approach that can be used. Alterations can be accomplished by a variety of enzymatic and chemical methods used in vitro. One of the most common methods uses a specific oligonucleotide as a mutagen to generate precisely designed deletions, insertions and point mutations in a target gene. Secondly, a wildtype human gene or humanized non-human animal gene could be inserted by homologous recombination. It is also possible to insert an altered or mutated (singly or multiply) human gene as genomic or minigene constructs.

Additionally, non-human transgenic animals can also be made wherein at least one endogenous target gene is "knocked-out". The creation of knock-out animals allows those of skill in the art to assess in vivo function of the gene that has been "knocked-out". The knock-out of at least one target gene may be accomplished in a variety of ways. One strategy that can be used to "knock-out" a target gene is by the insertion of artificially modified fragments of the endogenous gene by homologous recombination. In this technique, mutant alleles are introduced by homologous recombination into embryonic stem ("ES") cells. The embryonic stem cells containing a knock out mutation in one allele of the gene being studied are introduced into a blastocyst. The resultant animals are chimeras containing tissues derived from both the transplanted ES cells and host cells. The chimeric animals are mated to assess whether the mutation is incorporated into the germ line. Those chimeric animals each heterozygous for the knock-out mutation are mated to produce homozygous knock-out mice. A second strategy that can be used to "knock-out" at least one gene involves using siRNA and shRNA and oocyte microinjection or transfection or microinjection into embryonic stem cells as described further herein.

The present invention contemplates that the somatic and germ cells of said non-human transgenic animal comprise an exogenous and stably transmitted nucleic acid sequence of SEQ ID NO:2 (DEP2-1). Additionally, the present invention further contemplates that the somatic and germ cells of the transgenic animals comprise an exogenous and stably transmitted nucleic acid sequence having a nucleotide sequence selected from the group consisting of: SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 and SEQ ID NO:33, with the proviso that its somatic and germ cells do not comprise an exogenous and stably transmitted nucleic acid having a nucleotide sequence of SEQ ID NO:2. The methods for creating such transgenic animals will be discussed in more detail below.

The present invention further contemplates non-human transgenic animals wherein a nucleic acid comprising a nucleotide sequence of SEQ ID NO:2 (DEP2-1) is knocked out in said animal. Additionally, the present invention contemplates a non-human transgenic animal wherein a nucleic acid having a nucleotide sequence selected from the group consisting of: SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 and SEQ ID NO:33 is knocked out, with the proviso that a nucleic acid sequence of SEQ ID NO:2 is not modified or altered. The methods for creating such "knock-out" animals will be described in more detail below.

To create a non-human transgenic animal containing an exogenous and stably transmitted nucleic acid of a target gene or other nucleic acid sequence, a nucleic acid sequence of interest can be inserted into a non-human animal germ line using standard techniques of oocyte microinjection or transfection or microinjection into embryonic stem cells. Alternatively, if it is desired to knock-out or replace an endogenous gene, homologous recombination using embryonic stem cells or siRNA or shRNA using oocyte microinjection or transfection or microinjection of embryonic stem cells can be used.

For oocyte injection, at least one nucleic acid sequence of interest that is operably linked to the promoter can be inserted into the pronucleus of a just-fertilized non-human animal oocyte. This oocyte is then reimplanted into a pseudopregnant foster mother. The liveborn non-human animal can then be screened for integrants by analyzing the animal's DNA (using polymerase chain reaction for example) such as from the tail, for the presence of the polynucleotide sequence of interest. Chimeric non-human animals are then identified. The nucleic acid can be a complete genomic sequence injected as a YAC or chromosome fragment, a cDNA, or a minigene containing the entire coding region and other elements found to be necessary for optimum expression.

Retroviral or lentiviral infection (See, Lois C, et al., *Science*, 295:868-872 (2002) (which teaches methods for transgenics using lentiviral transgenesis)) of early embryos can also be done to insert an altered gene. In this method, the altered gene is inserted into a retroviral vector which is used to directly infect mouse embryos during the early stages of development to generate a chimera, some of which will lead to germline transmission (Jaenisch, R., *Proc. Natl. Acad. Sci. USA*, 73: 1260-1264 (1976)).

Homologous recombination using embryonic stem cells allows for the screening of gene transfer cells to identify the rare homologous recombination events. Once identified, these can be used to generate chimeras by injection of at least one non-human animal blastocyst and a proportion of the resulting animals will show germline transmission from the recombinant line. This gene targeting methodology is especially useful if inactivation of the gene is desired. For example, inactivation of the gene can be done by designing a polynucleotide fragment which contains sequences from an exon flanking a selectable marker. Homologous recombination leads to the insertion of the marker sequences in the middle of an exon, inactivating the gene. DNA analysis of individual clones can then be used to recognize the homologous recombination events.

Alternatively, "knock-out" of a target gene can be accomplished using siRNA or shRNA. In one strategy, oocyte microinjection can be used as described herein. Specifically, at least one nucleic acid sequence of interest that expresses at least one RNA molecule that is siRNA or shRNA, and that is operably linked to at least one promoter (such as a RNA pol III dependent promoter), is prepared using the methods described herein. This nucleic acid is introduced into a non-human animal fertilized oocyte, preferably by injection. The fertilized oocyte is then allowed to develop into an embryo. The resulting embryo is then transferred into a pseudopregnant female non-human animal and then allowed to give birth. Liveborn non-human animals are then screened for chimeric animals that contain the nucleic acid by obtaining a sample and analyzing the animal's DNA (using techniques such as polymerase chain reaction) and such chimeric non-human animals are identified. When these non-human animals are treated with an inducing agent, transcription is induced, the siRNA or shRNA expressed, and the target gene is repressed or "knocked-out". In the absence of the inducing agent, the gene is not repressed or "knocked-out".

In a second strategy, microinjection of embryonic stem cells can be used as described herein. Specifically, at least one nucleic acid sequence of interest that expresses at least one RNA molecule that is siRNA or shRNA, and is operably linked to at least one RNA pol III dependent promoter sequence of the present invention, is prepared using the methods described herein. This nucleic acid is introduced into non-human animal embryonic stem cells which can be used to generate chimeras by introducing these embryonic stem cells, preferably by injection, into at least one non-human animal blastocyst. The resulting blastocyst is then implanted into a pseudopregnant female non-human animal and then allowed to give birth to a chimeric non-human animal. PCR can be used to identify the animals of interest. Liveborn non-human animals are then screened for chimeric animals that contain the nucleic acid by obtaining and analyzing a sample of said animal's DNA (using techniques such as polymerase chain reaction) and such chimeric non-human animals are identified. This chimeric non-human animal can then be used in breeding to produce a transgenic non-human animal that stably contain this nucleic acid within their genome. As with the previous method, when these non-human animals are treated with an inducing agent, transcription is induced, the siRNA or shRNA expressed, and the target gene is repressed or "knocked-out". In the absence of the inducing agent, the gene is not repressed or "knocked-out".

Methods of making transgenic animals are described, for example, in Wall et. al., *J Cell Biochem.*, 49(2):113-20 (1992); Hogan, et al., "Manipulating the mouse embryo", *A Laboratory Manual.* Cold Spring Harbor Laboratory Press, Cold Spring Harbor, N.Y. (1992); in WO 91/08216 or U.S. Pat. No. 4,736,866 the disclosures of which are hereby incorporated by reference in their entirety.

Method of Modifying or Altering Expression of Nucleic Acid Molecules

In another embodiment, the present invention relates to methods of modifying or altering the expression of nucleic acid sequences. The present invention contemplates that the nucleic acid sequence whose expression is modified or altered is SEQ ID NO:2. The present invention further contemplates that the nucleic acid sequence whose expression is modified or altered is a nucleic acid having a nucleotide sequence of at least one of SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33.

Methods for modifying or altering the expression of a nucleic acid sequence are well known to those skilled in the art. Specifically, said methods involve exposing a cell or administering to a subject (such as a transgenic non-human animal (for example, a transgenic non-human animal having at least one nucleic acid molecule knocked-out)) containing a nucleic acid whose expression is to be modified or altered at least one nucleic acid molecule. The methods described herein could be useful, such as in transgenic non-human animals (such as in transgenic non-human animals having at least one nucleic acid molecule knocked-out), as animal models for major depression or a related disorder. Nucleic acid molecules such as antisense molecules, aptamers, triplexing agents, ribozymes, siRNA, or co-suppression (co-suppressor) RNA can be used in said methods.

An antisense molecule, aptamer, triplexing agent, ribozyme or siRNA are DNA, RNA or chemically modified or hybrid sequences thereof of varying length that are single or double stranded. These nucleic acid molecules are complementary to a target nucleic acid sequence, such as a mRNA of a nucleic acid (a) having a nucleotide sequence of SEQ ID NO:2; or (b) of at least one of SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33, and can be a coding sequence, a polynucleotide sequence comprising an intron-exon junction, a regulatory sequence, such as a promoter sequence, or the like. The degree of complementarity is such that the nucleic acid molecule can interact specifically with the target nucleic acid sequence in a cell. Depending on the total length of the nucleic acid molecule, one or a few mismatches with respect to the target nucleic acid sequence can be tolerated without losing the specificity of the nucleic acid molecule for the target sequence. Thus, a few mismatches, if any, would be tolerated, for example, in an antisense molecule containing, for example, 20 consecutive nucleotides, whereas several mismatches will not affect the hybridization efficiency of an antisense molecule that is complementary to a full length of a target mRNA encoding a protein (such as, Dep2-1a, Dep2-1b, Dep2-2, Dep2-4 or Dep2-5). The number of mismatches that can be tolerated can be estimated, using well known formulas for determining hybridization kinetics (See, Sambrook et al., *Molecular Cloning: A Laboratory Manual,* $2^{nd}$ Edition (1989)) or can be determined empirically using methods known in the art, particularly by determining that the presence of the antisense molecule, aptamer, triplexing agent, ribozyme or siRNA in a cell modifies or alters (such as by decreasing) the level of expression of the target sequence in a cell.

A nucleic acid molecule useful as an antisense molecule, aptamer, triplexing agent, ribozyme or siRNA can reduce or inhibit translation or cleave a target nucleic acid, thereby reducing or inhibiting the amount of the protein encoded by said target nucleic acid in a cell. For example, an antisense molecule can bind to an mRNA to form a double stranded molecule that cannot be translated in a cell. Antisense oligonucleotides of about 15 to 50 consecutive nucleotides are preferred since they are easily synthesized and can hybridize specifically with a target nucleic acid, although longer antisense molecules can be used. When the antisense molecule is contacted directly with a target cell, it can be operatively associated with a chemically reactive group such as, but not limited to, iron-linked EDTA, which cleaves a target RNA at the site of hybridization. A triplexing agent, in comparison, can stall transcription (Maher et al., *Antisense Res. Devel.*, 1:227 (1991); Helene, *Anticancer Drug Design,* 6:569 (1991)). Aptamers adopt highly specific three-dimensional conformations that enable them to bind to a specific location on a molecule whose activity is being affected. Methods for making antisense molecules, aptamers and triplexing agents are well known in the art.

A ribozyme is a catalytic RNA molecule that cleaves RNA in a sequence-specific manner. Ribozymes that cleave themselves are called cis-acting ribozymes, while ribozymes that cleave other RNA molecules are called trans-acting ribozymes. Nucleic acids molecules can encode ribozymes designed to cleave particular mRNA transcripts, thus preventing expression of a polypeptide. A ribozyme sequence can have a sequence from a hammerhead, axhead, or hairpin ribozyme, and may be modified to have either slow cleavage activity or enhanced cleavage activity. For example, nucleotide substitutions can be made to modify cleavage activity (see, e.g., Doudna and Cech, *Nature,* 418:222-228 (2002)). Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678. Hammerhead ribozyme sequences can be embedded in a stable RNA such as a transfer RNA (tRNA) to increase cleavage efficiency in vivo (Perriman, R. et al., *Proc. Natl. Acad. Sci. USA,* 92(13): 6175-6179 (1995); de Feyter, R. and Gaudron, J., *Methods in Molecular Biology*, Vol. 74, Chapter 43, "Expressing Ribozymes in Plants", Edited by Turner, P. C, Humana Press Inc., Totowa, N.J.).

siRNA useful in the present invention can be obtained, for example, using an in vitro transcription system or can be synthesized chemically, and can be contacted with cells (or administered to a subject) as RNA molecules. siRNA also can be expressed from an encoding nucleic acid, which can be contacted with cells (or administered to a subject). siRNAs can be designed using techniques well known to those skilled in the art.

Another nucleic acid molecule that is useful in the present methods also can be a co-suppression RNA that reduces or inhibits transcription of a target nucleic acid, such as a nucleic acid (a) having a nucleotide sequence of SEQ ID NO:2; or (b) of at least one of SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33. A co-suppressor RNA, like an siRNA, comprises (or encodes) an RNA comprising an inverted repeat, which includes a first oligonucleotide that selectively hybridizes to the target nucleic acid or gene and, in operative linkage, a second oligonucleotide that is complementary and in a reverse orientation to the first oligonucleotide. In comparison to an siRNA, which comprises a functional portion of a transcribed region of the target nucleic acid or target gene and reduces or inhibits translation of RNA transcribed from the nucleic acid or gene, a co-suppressor RNA comprises a functional portion of a transcriptional regulatory region of the target nucleic acid or gene (namely, a promoter region) and reduces or inhibits transcription of the nucleic acid or gene. Methods for making co-suppression RNA are well known in the art.

Polymorphism Detection/Genotyping

In another embodiment, the present invention relates methods of genotyping one or more subjects. The information obtained from the genotyping of subjects can be used in a variety of different ways. For example, the genotyping of subjects can be used to diagnose those subjects suffering from major depression or a related disorder or at risk of developing major depression or a related disorder, provide a prognosis for or predict or diagnose a response to treatment for a subject suffering from major depression or a related disorder, or identify subjects for selection or inclusion in a clinical trial for treating major depression or a related disorder. Additionally, genotypes can be used to analyze the results of a clinical trial for subjects being treated for major depression or a related disorder. Specifically, the relationship the genotypes of subjects and the clinical outcome of said subjects can be determined.

Genotyping involves obtaining a test sample from said subject(s). The subject may or may not be experiencing any symptoms of major depression or a related disorder at the time the test sample is obtained. In this embodiment, a test sample is any biological sample which contains the DNA of the subject. Test samples can be prepared using techniques well known to those skilled in the art such as by obtaining a specimen from an individual and, if necessary, disrupting any cells contained therein to release DNA. Examples of test samples include, but are not limited to, whole blood, serum, plasma, cerebrospinal fluid, sputum, bronchial washing, bronchial aspires, urine, lymph fluids, and various external secretions of the respiratory, intestinal and genitourinary tracts, tears, saliva, milk, white blood cells, myelomas and the like, etc.

Once the test sample(s) is obtained, it is analyzed, using routine techniques known in the art, in order to determine the presence or absence of specific sequences (alleles) for: (a) at least one polymorphic site in nucleotides 1 to 316 of SEQ ID NO:2; (b) a T-C polymorphism at position (nucleotide) 136 of SEQ ID NO:2; (c) a A-G polymorphism at position 210 of SEQ ID NO:2; (d) a G-A polymorphism at position 242 of SEQ ID NO:2; (e) at least one polymorphic site selected from nucleotides 77402 and 79906 of SEQ ID NO:1; (f) at least one polymorphic site in SEQ ID NO:1; or (g) any combinations of (a)-(f). Additionally, the test sample may optionally be further analyzed for a C-G polymorphism at position –1019 of a human serotonin receptor 1A gene ("HTR1A"). For example, the identification of at least one polymorphic site at nucleotide 38048, 77402 or 79906 in SEQ ID NO:1 in combination with the identification of a C-G polymorphism at position –1019 of a human serotonin receptor 1A gene in a test sample obtained from a subject may indicate that the subject is at risk of developing major depression or a related disorder.

The genotype of the subject can be determined based on the combination of sequences present at one of more polymorphic sites. Once the genotype of the subject has been determined, then further determinations can be made, such as, diagnosing whether the subject has major depression or a related disorder or is at risk of developing major depression or a related disorder, providing a prognosis for or predicting the response to treatment for a subject having major depression or a related disorder, determining whether the subject should be selected for inclusion in a clinical trial for treatment of major depression or a related disorder, or analyzing the relationship between genotypes of subjects and their clinical outcome. Additionally, if the test sample is also analyzed for the presence of sequences at a C-G polymorphism at position –1019 in the HTR1A gene, then the genotype(s) at one or more polymorphic sites in DEP2 may be used in combination with the genotype at HTR1A to make further determinations, as elaborated above.

As briefly discussed above, techniques for identifying the presence or absence of at least one sequence (allele) at a polymorphic site in a test sample are well known in the art and include, but are not limited to direct sequencing, amplification, fragment length polymorphism assays, mobility based assays, hybridization assays and mass spectroscopy. These techniques will be discussed briefly below.

Direct Sequencing

The presence or absence of a sequence at a polymorphic site may be determined by direct nucleotide sequencing. Methods for direct sequencing are known in the art. For example, following amplification of the DNA from the test sample, the DNA can be sequenced using manual sequencing techniques, such as those that employ radioactive marker nucleotides, or by automated sequencing. The results of the sequencing can be displayed using any suitable method known in the art. The sequence is examined and the presence or absence of a given sequence at a polymorphic site is determined.

Amplification

The presence or absence of a sequence at a polymorphic site may be determined using amplification techniques, such as PCR. PCR involves the use of primers to amplify a region of a DNA sequence from the test sample containing the polymorphic site of interest. The design of primers is well known to those skilled in the art. For example, primers can be designed that hybridize only to a portion of SEQ ID NO:1 or a portion of SEQ ID NO:2 (hereinafter "the wildtype"). If these wildtype primers result in a PCR product, then the subject has the wildtype allele (namely, SEQ ID NO:1 or SEQ ID NO:2). Similarly, primers can be designed that hybridize only to a portion of SEQ ID NO:1 or a portion of SEQ ID NO:2 containing a variant sequence at one or more polymorphic sites (hereinafter "the variant"). If these variant primers result in a PCR product, then the subject has the variant allele (namely, SEQ ID NO:1 or SEQ ID NO:2). The presence of an amplification product only when wildtype primers are used, or only when variant primers are used, indicate a homozygous wildtype or variant genotype, respectively. The presence of an amplification product when either wildtype or variant primers are used indicates a heterozygous genotype. Amplification methods other than PCR can be used. Such methods include strand displacement, the QB replicase system, the repair chain reaction, ligase chain reaction, rolling circle amplification and ligation activated transcription.

Fragment Length Polymorphism Assays

The presence or absence of sequences at a polymorphic site may be determined using a fragment length polymorphism assay. In a fragment length polymorphism assay, a unique DNA banding pattern based on cleaving the DNA at a series of positions is generated using an enzyme (such as, but not limited to, a restriction endonuclease). DNA fragments from the test sample containing a variant sequence will have a different banding pattern than DNA fragments generated from the wildtype.

For example, sequences at a polymorphic site can be detected using a restriction fragment length polymorphism assay ("RFLP"). The region of interest in the DNA is first isolated using PCR. The PCR products are then cleaved with restriction enzymes known to give a unique length fragment for a given variant sequence. The restriction-enzyme digested PCR products are separated and detected (such by gel electrophoresis) and visualized (such as, but not limited to, by ethidium bromide staining). The length of the fragments is compared to molecular weight markers or fragments generated from wildtype and variant controls (for example, vectors containing the wildtype and variant sequences, respectively).

Sequences (alleles) at a polymorphic site can also be detected using a CLEAVASE fragment length polymorphism assay ("CFLP"; Third Wave Technologies, Madison, Wis.; See, U.S. Pat. No. 5,888,780). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated using routine techniques known in the art, such as by PCR. Next, DNA strands are separated by heating. The reactions are cooled to allow intrastrand secondary structure to form. The PCR products are then treated with the CLEAVASE I enzyme to generate a series of fragments that are unique to a given wildtype or variant sequence. The CLEAVASE enzyme treated PCR products are separated and detected (such by gel electrophoresis) and visualized (such as, but not limited to, by ethidium bromide staining). The length of the fragments is compared to molecular weight markers or fragments generated from wild-type and variant controls.

Mobility Based Assays

The presence or absence of a sequence (allele) at a polymorphic site may be determined by a single strand conformation polymorphism assay ("SSCP"). In this technique, PCR products from the region to be tested are heat denatured and rapidly cooled to avoid the reassociation of complementary strands. The single strands then form sequence dependent conformations that influence electrophoretic mobility. The different mobilities can then be analyzed by electrophoresis.

Alternatively, the assessment of a polymorphism may be by a heteroduplex assay. In this analysis, the DNA sequence to be tested is amplified, denatured and renatured to itself or to known wildtype DNA (namely, from SEQ ID NO:1 or SEQ ID NO:2). Heteroduplexes between different alleles contain DNA "bubbles" at mismatched basepairs that can affect electrophoretic mobility. Therefore, electrophoresis can be used to indicate the presence or absence of wildtype and variant sequences.

Hybridization Assays

The presence or absence of a sequence (allele) at a polymorphic site can be detected in a hybridization assay. In a hybridization assay, the presence or absence of a given sequence (allele) is determined based on the ability of the DNA from the test sample to hybridize to a complementary DNA molecule (such as, but not limited to, a probe). The hybridization of a probe to DNA from the test sample is subsequently detected. Detection of hybridization only to a wildtype probe, or only to a variant probe, indicate a homozygous wildtype or variant genotype, respectively. Detection of hybridization to both wildtype and variant probes indicates a heterozygous genotype. A number of hybridization assays using a variety of technologies for hybridization and detection are available. Examples of some of these assays are provided below.

Solution Based Detection

The presence or absence of polymorphisms can be determined using any solution based detection techniques known in the art. An example of such a technique that can be used is TaqMan® (Applied Biosystems, Forest City, Calif.; see, Holland et al; *Proc. Natl. Acad. Sci. USA* 88:7276-7280 (1991); and Gelmini et al. *Clin. Chem.* 43:752-758 (1997)). TaqMan® allows for the real-time quantification of PCR. TaqMan® probes are widely commercially available, and the TaqMan® system (Applied Biosystems) is well known in the art. TaqMan® probes anneal between the upstream and downstream primer in a PCR reaction. They contain a 5'-fluorophore and a 3'-quencher. During amplification the 5'-3' exonuclease activity of the Taq polymerase cleaves the fluorophore off the probe. Since the fluorophore is no longer in close proximity to the quencher, the fluorophore will be allowed to fluoresce. The resulting fluorescence may be measured, and is in direct proportion to the amount of target sequence that is being amplified.

Another technique that can be used is a Molecular Beacon (See, Tyagi et al., *Nat. Biotechnol.* 14:303-308 (1996); and Tyagi et al., *Nat. Biotechnol.* 16:49-53 (1998)), the beacons are hairpin-shaped probes with an internally quenched fluorophore whose fluorescence is restored when bound to its target. The loop portion acts as the probe while the stem is formed by complimentary "arm" sequences at the ends of the beacon. A fluorophore and quenching moiety are attached at opposite ends, the stem keeping each of the moieties in close proximity, causing the fluorophore to be quenched by energy transfer. When the beacon detects its target, it undergoes a conformational change forcing the stem apart, thus separating the fluorophore and quencher. This causes the energy transfer to be disrupted to restore fluorescence. Any suitable fluorophore known in the art can be used. For example, fluorophores that can be used include, but are not limited to, FAM, HEX®, NED®, ROX®, Texas Red®. Quenchers that can be used include, but are not limited to, Dabcyl and TAMRA.

Another technique that can be used is Pyrosequencing™ (Pyrosequencing, Inc. Westborough, Mass.). This technique is based on the hybridization of a primer to a single stranded, PCR-amplified, DNA template in the presence of DNA polymerase, ATP sulfurylase, luciferase and apyrase enzymes and the adenosine 5' phosphosulfate ("APS") and luciferin substrates. In the second step, the first of four deoxynucleotide triphosphates ("DCNTP") is added to the reaction and the DNA polymerase catalyzes the incorporation of the deoxynucleotide triphosphate into the DNA strand, if it is complementary to the base in the template strand. Each incorporation event is accompanied by release of pyrophosphate ("PPi") in a quantity equimolar to the amount of incorporated nucleotide. In the last step, the ATP sulfurylase quantitatively converts PPi to ATP in the presence of adenosine 5'-phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device ("CCD") camera and seen as a peak in a Pyrogram™. Each light signal is proportional to the number of nucleotides incorporated.

Detection of Hybridization Using Reverse Solid Phase Detection

The presence or absence of polymorphisms can also be determined using reverse solid phase detection, such as, but not limited to, a microarray, such as a DNA chip assay. In a DNA chip assay, a series of probes are affixed to a solid support. The probes are designed to be unique to a given polymorphism. The DNA obtained from the test sample is contacted with the DNA "chip" and hybridization is detected. Any DNA "chip" assay known in the art can be used in the methods of the present invention. For example, the DNA chip assay can be a GeneChip assay (Affymetrix, Santa Clara, Calif.; See, U.S. Pat. No. 6,045,996). The GeneChip technology uses miniaturized, high-density arrays of probes affixed to a "chip." Alternatively, a DNA microchip containing electronically captured probes (Nanogen, San Diego, Calif.; See, U.S. Pat. No. 6,068,818) can be used. Also, a "bead array" can also be used (Illumina, San Diego, Calif.; See WO 99/67641 and WO 00/39587). Illumina uses a BEAD ARRAY technology that combines fiber optic bundles and beads that self-assemble into an array.

Solid Phase Detection

In solid phase detection, hybridization of a probe to the sequence of interest, such as a polymorphism, is detected directly by visualizing a bound probe by using Southern blotting. In this technique, genomic DNA is isolated from a subject. The DNA is then cleaved with a series of restriction enzymes that cleave infrequently in the genome and not near any of the markers being assayed. The DNA is then separated (such as, but not limited to, by agarose gel electrophoresis) and transferred to a membrane. At least one probe which has been labeled with, for example, a radioactive, fluorescent or enzymatic label, specific for the polymorphism being detected is allowed to contact the membrane under a condition of low, medium, or high stringency conditions. Unbound probe is removed and the presence of binding is detected by visualizing the labeled probe.

Enzymatic Detection of Hybridization

The presence or absence of polymorphisms can be detected using an assay that detects hybridization by enzymatic cleavage of specific structures ("INVADER assay", Third Wave Molecular Diagnostics, Madison, Wis.; See, U.S. Pat. No. 6,001,567). The INVADER assay detects specific DNA and RNA sequences by using structure-specific enzymes to cleave a complex formed by the hybridization of overlapping probes. Elevated temperature and an excess of one of the probes enable multiple probes to be cleaved for each target sequence present without temperature cycling. These cleaved probes then direct cleavage of a second labeled probe. The secondary probe can be 5'-end labeled (such as, but not limited to, with fluorescein) that is quenched by an internal dye. Upon cleavage, the dequenched fluorescein labeled product may be detected using a standard fluorescence plate reader.

The INVADER assay detects specific mutations and SNPs in unamplified genomic DNA. The isolated DNA sample is contacted with the first probe specific either for a SNP or wild type sequence and allowed to hybridize. Then a secondary probe, specific to the first probe, and containing the fluorescein label, is hybridized and the enzyme is added. Binding is detected using a fluorescent plate reader and comparing the signal of the test sample to known positive and negative controls.

Hybridization of a bound probe can be detected using a TaqMan® assay using the techniques described previously herein.

In still further embodiments, polymorphisms are detected using any single base extension ("SBE") methods known in the art (See U.S. Pat. Nos. 5,888,819 and 6,004,744). For example, a shifted termination assay ("STA") can be performed. The STA method involves designing a detection primer that is complementary to a target DNA. The detection primer is labeled with any detectable label known in the art. The 3'-terminal of detection primer ends at the base just before the target base. The detection primer hybridizes to the target nucleic acid sequence. When performing a primer extension reaction, if the first base is the target base, a primer extension reaction will be terminated at the target base position without incorporating any of the labeled nucleotides. No color reaction will be detected. If the target base is changed by any type of mutation, including point mutation (SNP), deletion, insertion, and translocation, a primer extension reaction will continue through the target base position, and multiple labeled nucleotides will be incorporated into the extended detection primer. A strong color reaction will be observed. A STA can be performed on a DNA sequence or using fluorescence polarization.

Another SBE that can be performed is a SNP-IT primer extension assay (Orchid Biosciences, Princeton, N.J.; See, U.S. Pat. No. 5,952,174). In this assay, SNPs are identified using a specially synthesized DNA primer and a DNA polymerase to selectively extend the DNA chain by one base at the suspected SNP location. DNA in the region of interest is amplified and denatured. PCR is then performed using miniaturized systems called microfluidics. Detection is accomplished by adding a label to the nucleotide suspected of being at the polymorphic site. Incorporation of the label into the DNA can be detected by any method known in the art.

Mass Spectroscopy

The presence or absence of polymorphisms can be detected using a MassARRAY system (Sequenom, San Diego, Calif.; See, U.S. Pat. No. 6,043,031). DNA is isolated from test samples using routine procedures known to those skilled in the art. Next, specific DNA regions containing the polymorphism of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization-Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than 0.0001 second, enabling samples to be analyzed in a total of 3-5 second including repetitive data collection. The SpectroTYPER software then calculates, records, compares and reports, the genotypes at the rate of three seconds per sample.

Kits

The present invention also provides kits that enable or allow for the detection of a genotype of one or more subjects. These kits are useful for diagnosing those subjects suffering from major depression or a related disorder or at risk of developing major depression or a related disorder, providing a prognosis for or predicting a response to treatment for a subject suffering from major depression or a related disorder, identifying subjects for selection or inclusion in a clinical trial for treating major depression or a related disorder, or for analyzing the relationship between genotypes of subjects being treated for major depression or a related disorder and their clinical outcome.

The kits can be produced in a variety of ways. For example, the kits contain at least one reagent useful for detecting (a) at least one polymorphic site in SEQ ID NO:1; (b) at least one polymorphic site in nucleotides 1 to 316 of SEQ ID NO:2; (c) a T-C polymorphism at position 136 of SEQ ID NO:2; (d) a A-G polymorphism at position 210 of SEQ ID NO:2; (e) a G-A polymorphism at position 242 of SEQ ID NO:2; (f) at least one polymorphic site in SEQ ID NO:1; (g) a polymorphic site in nucleotide 77402 of SEQ ID NO:1; (h) a polymorphic site in nucleotide 79906 in SEQ ID NO:1; or (i) any combinations of (a)-(h). Additionally, any of the kits described above in (a)-(i) can further contain at least one reagent useful for detecting a C-G polymorphism at position −1019 in a human serotonin receptor 1A gene. Examples of the at least one reagent that can be included in the kits described herein are one or more primers for amplifying the region of DNA containing the polymorphic site or one or more probes that bind to or near the polymorphic site. In addition, the kits can further contain (a) instructions for determining the genotype of a subject; (b) ancillary reagents such as buffering agents, nucleic acid stabilizing reagents, protein stabilizing reagents, and signal producing systems (such as, but not limited to, fluorescence generating systems); or (c) positive and/or negative control(s). The kit may be packaged in any suitable manner, typically with the elements in a single container or various containers as necessary.

RNA and Protein Detection and Quantification Assays

In another embodiment, the present invention relates methods for detecting or quantifying mRNA or protein in a test sample obtained from one or more subjects. The information obtained by detecting or quantifying mRNA or protein in a test sample obtained from a subject can be used in a variety of different ways. For example, the presence, absence or amount of mRNA or protein detected or quantified in subjects can be used to diagnose those subjects suffering from major depression or a related disorder or at risk of developing major depression or a related disorder, provide a prognosis for or predict or diagnose a response to treatment for a subject suffering from major depression or a related disorder or identifying subjects for selection or inclusion in a clinical trial for treating major depression or a related disorder. Additionally, the presence, absence or amount of mRNA or protein can be used to analyze the results of a clinical trial for subjects being treated for major depression or a related disorder. Specifically, the relationship between the presence, absence or amount of the mRNA or protein detected or quantified in the test samples and the clinical outcome of said subjects can be determined.

The methods described herein involve obtaining a test sample from said subject(s). The subject may or may not be experiencing any symptoms of major depression or a related disorder at the time the test sample is obtained. In this embodiment, a test sample is any biological sample which contains the RNA or protein of the subject. Test samples can be prepared using techniques well known to those skilled in the art such as by obtaining a specimen from an individual and, if necessary, disrupting any cells contained therein to release RNA or protein. Examples of test samples include, but are not limited to, whole blood, serum, plasma, cerebrospinal fluid, sputum, bronchial washing, bronchial aspires, urine, lymph fluids, and various external secretions of the respiratory, intestinal and genitourinary tracts, tears, saliva, milk, white blood cells, myelomas and the like, etc.

Once the test sample(s) is obtained, it is analyzed, using routine techniques known in the art, in order to determine or quantify the presence, absence or amount of: (a) at least one mRNA which comprises nucleotides 1 to 316 of SEQ ID NO:2; (b) at least one mRNA transcribed from SEQ ID NO:1; (c) at least one protein having an amino acid sequence of SEQ ID NO:3 or SEQ ID NO:4; (d) at least one polypeptide translated from SEQ ID NO:1; or (e) any combinations of (a)-(d). Additionally, the test sample may optionally be further analyzed for the presence, absence or amount of mRNA transcribed from the HTR1A gene or a polypeptide translated from the HTR1A gene.

As discussed above, once a test sample is obtained, it can be analyzed, using routine techniques known in the art for the presence, absence or amount of at least one mRNA transcribed from SEQ ID NO:1. Examples of mRNAs transcribed from SEQ ID NO:1 include, but are not limited to, SEQ ID NO:2, SEQ ID NO:5, SEQ ID NO:6, SEQ ID NO:7, SEQ ID NO:8, SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33. Alternatively, the test sample can be analyzed for the presence, absence or amount of at least one polypeptide translated from SEQ ID NO:1. Examples of polypeptides translated from SEQ ID NO:1 include, but are not limited to, SEQ ID NO:3, SEQ ID NO:4, SEQ ID NO:10, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:32 and SEQ ID NO:34.

Once the presence, absence or amount of a mRNA or a protein as specified in (a)-(e) above has been determined or quantified in a test sample, then further determinations can be made, such as, diagnosing whether the subject has major depression or a related disorder or is at risk of developing major depression or a related disorder, providing a prognosis for or predicting the response to treatment for a subject having major depression or a related disorder, determining whether the subject should be selected for inclusion in a clinical trial for treatment of major depression or a related disorder, or analyzing the relationship between the frequency of presence or relative amounts of at least one mRNA or polypeptide in subjects, and their clinical outcome. Additionally, if the test sample is further analyzed for the presence, absence or amount of mRNA transcribed from the HTR1A gene or a polypeptide translated from the HTR1A gene, the information pertaining to mRNA(s) or polypeptide(s) transcribed or translated from DEP2 may be used in combination with the information pertaining to mRNA(s) or polypeptide(s) transcribed or translated from HTR1A to make further determinations, as elaborated above.

For example, a test sample can be obtained from a subject. The test sample can then be analyzed using routine techniques known in the art, in order to determine or quantify the presence, absence or amount of (a) at least one mRNA which comprises nucleotides 1 to 316 of SEQ ID NO:2; (b) at least one mRNA transcribed from SEQ ID NO:1; (c) at least one protein having an amino acid sequence of SEQ ID NO:3 or SEQ ID NO:4; (d) at least one polypeptide translated from SEQ ID NO:1; or (e) any combinations of (a)-(d). If, for example, the presence of (a) at least one mRNA which comprises nucleotides 1 to 316 of SEQ ID NO:2; (b) at least one mRNA transcribed from SEQ ID NO:1; (c) at least one protein having an amino acid sequence of SEQ ID NO:3 or SEQ ID NO:4; (d) at least one polypeptide translated from SEQ ID NO:1; or (e) any combinations of (a)-(d) is detected, then a diagnosis can be made for said subject related to major depression or a related disorder or related to risk of developing major depression or a related disorder. This information can also be useful for providing a prognosis for or predicting the response to treatment for a subject already diagnosed as suffering from major depression or a related disorder. Moreover, this information can be used to determine whether or not the subject should or could be selected for inclusion in a clinical trial for treatment of major depression or a related disorder. Further, the frequency of presence of: (a) at least one mRNA which comprises nucleotides 1 to 316 of SEQ ID NO:2; (b) at least one mRNA transcribed from SEQ ID NO:1; (c) at least one protein having an amino acid sequence of SEQ ID NO:3 or SEQ ID NO:4; (d) at least one polypeptide translated from SEQ ID NO:1; or (e) any combinations of (a)-(d) can be used to analyze the results of a clinical trial for subjects being treated for major depression or a related disorder. Specifically, the relationship between the presence of said mRNA, protein, polypeptide or combinations thereof in the test samples and the clinical outcome of said subjects can be determined. Similarly, any of the above further determinations might be made on the basis of absence of: (a) at least one mRNA which comprises nucleotides 1 to 316 of SEQ ID NO:2; (b) at least one mRNA transcribed from SEQ ID NO:1; (c) at least one protein having an amino acid sequence of SEQ ID NO:3 or SEQ ID NO:4; (d) at least one polypeptide translated from SEQ ID NO:1; or (e) any combinations of (a)-(d), or on the basis of detection or quantification that an amount of: (a) at least one mRNA which comprises nucleotides 1 to 316 of SEQ ID NO:2; (b) at least one mRNA transcribed from SEQ ID NO:1; (c) at least one protein having an amino acid sequence of SEQ ID NO:3 or SEQ ID NO:4; (d) at least one polypeptide translated from SEQ ID NO:1; or (e) any combinations of (a)-(d), is within a certain range.

Techniques for identifying the presence, absence or amount of mRNAs or proteins in a test sample are well known in the art. For example, techniques for identifying the presence, absence or amount of mRNAs include, but are not limited to, reverse transcriptase, cDNA microarrays, quantitative PCR and Northern blotting. Techniques for identifying the presence, absence or amount of proteins include, but are not limited to, ELISA, RIA, Western blotting, fluorescence activated cell sorting and immunohistochemical analysis. These techniques will be discussed briefly below.

RNA Techniques

Reverse transcriptase can be used to prepare a cDNA by used of an oligo dT primer which is annealed to the poly A sequence of the RNA. Examples of reverse transcriptases that can be used include, but are not limited to, ImProm-II Reverse Transcriptase (Promega, Madison, Wis.) and BD Powerscript Reverse Transcriptase (BD Biosciences, Franklin Lakes, N.J.). Methods for using reverse transcriptases to prepare and obtain cDNA molecules are well known in the art and are described in Sambrook, J. et al., *Molecular Cloning: A Laboratory Manual,* 2nd edition, Cold Spring Harbor Press, Cold Spring Harbor, N.Y. (1989).

A cDNA microarray is an array of multiple cDNA molecules, fixed in addressable locations (such as on a chip assay), to which complementary nucleic acids in applied samples may hybridize (see Hegde et al., *Biotechniques* 29(3):548-562 (2000)). cDNA microarrays provide for qualitative and quantitative analysis of mRNA expression of the molecules contained in the array.

Quantitative PCR allows for the direct monitoring of the progress of a PCR amplification as it is occurring, without the need for repeated sampling of the reaction products. In quantitative PCR, the reaction products may be monitored as they are generated and are tracked after they rise above background but before the reaction reaches a plateau. The number of cycles required to achieve a chosen level of fluorescence varies directly with the concentration of amplifiable targets at the beginning of the PCR process, enabling a measure of signal intensity to provide a measure of the amount of target DNA in a sample in real time. Quantitative PCR according to the present invention may be performed on any suitable instrument, including, but not limited to, Mx4000 or Mx3000P (Stratagene, La Jolla, Calif.), ABI7700 or ABI7000 (Applied BioSystems Inc., Foster City, Calif.), M J Opticon (MJ Research, Watertown, Mass.), iCycler (Bio-Rad, Hercules, Calif.), RotorGene 3000 (Corbett Life Sciences, Mortlake, NSW, Australia), and the SmartCycler (Cepheid, Sunnyvale, Calif.).

In solid phase detection, hybridization of a probe to the sequence of interest, such as an RNA, is detected directly by visualizing a bound probe by using Northern blotting. In this technique, RNA is isolated from a subject. The RNA is then cleaved with a series of restriction enzymes that cleave infrequently in the genome and not near any of the markers being assayed. The RNA is then separated (such as, but not limited to, by agarose gel electrophoresis) and transferred to a membrane. At least one probe which has been labeled with, for example, a radioactive, fluorescent or enzymatic label, specific for the polymorphism being detected is allowed to contact the membrane under a condition of low, medium, or high stringency conditions. Unbound probe is removed and the presence of binding is detected by visualizing the labeled probe.

Protein Techniques

ELISA involves the fixation of a test sample containing a protein substrate of interest to a surface such as a well of a microliter plate. A substrate specific antibody coupled to an enzyme is applied and allowed to bind to the substrate. Presence of the antibody is then detected and quantitated by a colormetric reaction employing the enzyme coupled to the antibody. Enzymes commonly in ELISAs include, but are not limited to, horseradish peroxidase and alkaline phosphatase. If well calibrated and within the linear range of response, the amount of substrate present in the sample is proportional to the amount of color produced. A substrate standard is generally employed to improve quantitative accuracy.

Another technique that can be used is a radioimmunoassay ("RIA"). One version of RIA involves the precipitation of a desired substrate (such as a protein of interest) with a specific antibody and detectably labeled antibody binding protein (the antibody binding protein can be labeled with any detectable isotope known in the art) immobilized on a precipitable carrier, such as, but not limited to, agarose beads. The number of counts in the precipitated pellet is proportional to the amount of substrate present in the test sample. In an alternate version of RIA, a labeled substrate (such as a protein of interest) and an unlabelled antibody binding protein are employed. A test sample containing an unknown amount of substrate is added in varying amounts. The decrease in precipitated counts from the labeled substrate is proportional to the amount of substrate in the added sample.

Western blot involves separation of a substrate (such as a protein of interest) from another protein by means of an acrylamide gel followed by transfer of the substrate to a membrane (such as, but not limited to, nylon or PVDF). The presence of the substrate is then detected by antibodies specific to the substrate. The antibodies are then detected by antibody binding reagents. Antibody binding reagents may include, but are not limited to, protein A or other antibodies. The Antibody binding reagents may labeled with a detectable label as described previously herein. Detection may be by autoradiography, calorimetric reaction or chemiluminescence. Western blotting allows for both the quantitation of an amount of substrate and a determination of the substrate's identity by a relative position on the membrane which is indicative of a migration distance in the acrylamide gel during electrophoresis.

Fluorescence activated cell sorting ("FACS") involves detection of a substrate (such as a protein of interest) in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis involves detection of a substrate (such as a protein of interest) in situ in fixed cells by substrate specific antibodies. The substrate specific antibodies may be enzyme linked or linked to fluorophores. Detection is by microscopy and subjective evaluation. If enzyme linked antibodies are employed, a calorimetric reaction may be required.

Kits

The present invention also provides kits that enable or allow for the detection or quantification of (a) at least one mRNA which comprises nucleotides 1 to 316 of SEQ ID NO:2; (b) at least one mRNA transcribed from SEQ ID NO:1; (c) at least one protein having an amino acid sequence of SEQ ID NO:3 or SEQ ID NO:4; (d) at least one polypeptide translated from SEQ ID NO:1; or (e) any combinations of (a)-(d) in one more subjects. These kits are useful for diagnosing those subjects suffering from major depression or a related disorder or at risk of developing major depression or a related disorder, providing a prognosis for or predicting a response to treatment for a subject suffering from major depression or a related disorder, identifying subjects for selection or inclusion in a clinical trial for treating major depression or a related disorder, or for analyzing the results of a clinical trial for treating major depression or a related disorder relationship.

The kits can be produced in a variety of ways. For example, the kits contain at least one reagent useful for detecting or quantifying the presence, absence or amount of: (a) at least one mRNA which comprises nucleotides 1 to 316 of SEQ ID NO:2; (b) at least one mRNA transcribed from SEQ ID NO:1; (c) at least one protein having an amino acid sequence of SEQ ID NO:3 or SEQ ID NO:4; (d) at least one polypeptide translated from SEQ ID NO:1; or (e) any combinations of (a)-(d). Additionally, any of the kits described above in (a)-(e) can further contain at least one reagent useful for detecting or quantifying the presence, absence or amount of the presence, absence or amount of mRNA transcribed from the HTR1A gene or a polypeptide translated from the HTR1A gene. Examples of the at least one reagent that can be included in the kits described herein are a reverse transcriptase, one or more primers for amplifying cDNA or at least one antibody. In addition, the kits can further contain (a) instructions describing how to detect or quantify the presence, absence or amount of at least one mRNA or at least one protein in a test sample; (b) ancillary reagents such as buffering agents, nucleic acid stabilizing reagents, protein stabilizing reagents, and signal producing systems (such as, but not limited to, fluorescence generating systems); or (c) positive and/or negative control(s). The kit may be packaged in any suitable manner, typically with the elements in a single container or various containers as necessary.

Screening Assays and Methods of Treatment

In another embodiment, the present invention relates to methods (also referred to herein as "screening assays" or "screening methods") for identifying compositions, namely candidate or test compounds or agents (such as, but not limited to, small molecules, antibodies, nucleic acids, peptides, peptidomimetics, or other drugs), which: (a) bind to a protein translated from SEQ ID NO:1; (b) modulate the activity or expression of a protein translated from SEQ ID NO:1 (such as by inhibiting, reducing or decreasing the activity, reducing or decreasing the expression, or by stimulating or increasing the activity, or stimulating or increasing the expression, of the protein); or (c) modulate the expression of an mRNA molecule transcribed from SEQ ID NO:1 (such as by reducing or decreasing the expression or by stimulating or increasing the expression. Since genetic linkage between DEP2 and major depressive disorder has been established, it is thought that compositions identified pursuant to the screening methods described herein may be useful in treating major depression or a related disorder.

Examples of proteins translated from SEQ ID NO:1 include, but are not limited to, (i) Lhpp (SEQ ID NO:10), (ii) naturally occurring protein variants of Lhpp (SEQ ID NO:13, SEQ ID NO:15, SEQ ID NO; 17, SEQ ID NO:19, SEQ ID NO:21, SEQ ID NO:23, SEQ ID NO:25 and SEQ ID NO:29); (iii) Dep2-1a (SEQ ID NO:3); (iv) Dep2-1b (SEQ ID NO:4); Dep2-2 (SEQ ID NO:27); (v) Dep2-4 (SEQ ID NO:32); and (vi) Dep2-5 (SEQ ID NO:34). Examples of RNA molecules transcribed from SEQ ID NO:1 include, but are not limited to, SEQ ID NO:2, SEQ ID NO:5, SEQ ID NO:6, SEQ ID NO:7, SEQ ID NO:8, SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33.

As will be discussed in more detail herein, the present invention includes a method of determining whether a composition, identified in accordance with the methods described herein, is a potential therapy for major depression or a related disorder by initially administering the composition to a mammal (for example, an animal model). One may then monitor for major depression-related symptoms of the animal or the level or activity of a protein translated from SEQ ID NO:1 in the test subject. A decrease in the appearance of such symptoms indicates the potential suitability of the composition of interest in the treatment of major depression or related disorders. Such a finding in an animal model would then lead to use of the composition in human clinical trials.

Suitable animal models for such experiments include, but are not limited to, behavioral despair or mouse forced swim test (*Arch. Int. Pharmacodyn.* 229:327-336 (1977), *Psychopharmacology* 94:147-160 (1988)); tail suspension test (*Psychopharmacology* 85:367-370 (1985)); elevated plus maze test (*Psychopharmacology* 92:180-185 (1987)); open field test (*Behav. Brain Res.* 134:49-57 (2002)); dark-light transitions test (*Pharmacol. Biochem. Behav.* 15:695-699 (1981)); Irwin test (*Brain Res.* Vol. 835:18-26 (1999); Psychopharmacology 147:2-4 (1999)); inescapable stress test (learned helplessness) (Seligman and Maier, *J. Exp. Psychol* 74:1-9, (1967)); chronic mild stress (Ducottet et al., *Prog. Neuro-Psychopharmacol. Biol. Psychiatry* 27:625-631 (2003); Kopp et al., *Behav. Pharmacol.* 10:73-83 (1989)); and novelty-suppressed feeding model (Bodnoff et al., *Psychopharamcology* 97:277-279 (1989)).

The present invention additionally relates to the compositions identified by use of the above screening methods as well as to methods of using these compositions in the treatment of major depression or a related disorder. More specifically, once a composition of interest has been identified, the composition may be used in clinical trials to determine whether it actually alleviates the symptoms of major depression or a related disorder or at least decreases the severity thereof.

Also, it is submitted that the proteins described herein may be used to characterize the physical properties of compositions which may be used to ultimately treat major depression or a related disorder and thus in the "design" of such compositions. Thus, based upon such properties, one may design a composition or compound that has the ability to have a significant degree of binding affinity to a protein translated from SEQ ID NO:1, thereby modulating the activity of the protein. Such a composition or compound could then be used in the treatment of major depression or a related disorder.

Furthermore, one may detect binding of a test composition to a protein translated from SEQ ID NO:1 by subjecting the protein to, for example, nuclear magnetic resonance ("NMR") alone and in the presence of the composition. Characteristic changes in the NMR spectrum of the protein may then allow one to determine whether and how the composition has bound to the protein. This procedure may be repeated for a series of compounds, enabling discovery of relationships between compound structure and binding to the target protein. This iterative process is known as "structure-activity relationships by NMR" or "SAR by NMR" (Shuker et al., *Science* 274:1531-1534 (1996); SAR by NMR is described in U.S. Pat. Nos. 5,891,643, 5,989,827, 5,804,390, 6,043,024 and 6,897,337).

Similarly, one may identify the structure of a composition bound to the protein by x-ray diffraction techniques. By iterative operation of this technique, one may optimize lead compositions or compounds so as to develop the most efficacious therapeutic compositions or compounds for the treatment of major depression or a related disorder.

One method of identifying compositions that modulate the amount or activity of a protein translated from SEQ ID NO:1 or that modulate the expression of an mRNA molecule that is transcribed from SEQ ID NO:1 is a reporter gene assay. It is well known to those skilled in the art that a reporter gene assay may be carried out in an intact cell transfected with the reporter gene construct, in extracts from a cell transfected with the reporter gene construct, or in a cellular extract (for example, reticulocyte lysate) to which the reporter gene construct is added. It is further recognized that reporter gene assays may be carried out using cells or extracts that naturally contain a protein translated from SEQ ID NO:1 or an mRNA molecule transcribed from SEQ ID NO:1, cells into which a vector for the expression of a protein translated from SEQ ID NO:1 or an mRNA molecule transcribed from SEQ ID NO:1 that has been transfected (transiently or stably), or extracts to which a purified or partially purified amino acid translated from SEQ ID NO:1 or an mRNA molecule transcribed from SEQ ID NO:1 is added. In the present invention, it is preferred that a protein translated from SEQ ID NO:1 or an mRNA molecule transcribed from SEQ ID NO:1 be purified from a human cell or tissue, or from expression in an heterologous system. Further, it is also well known in the field that reporter gene assays may be conducted in cells or extracts that are of human origin, or that come from a different mammal or organism. It is additionally recognized that there are many regulatory sequences (such as promoters) that can be used to initiate transcription in a reporter gene construct, and that the choice of a regulatory sequence may be determined more by the particular cell or extract in which the assay will be conducted. It is still further well known that there are a variety of reporter genes that are amenable to screening assays, including high throughput screening assays. Examples of reporter genes include those which are themselves fluorescent, luminescent or have easily detected spectral characteristics (for example, a green fluorescent protein), as well as those having well-characterized fluorescent, luminescent or calorimetric substrates (for example, beta-galactosidase, luciferases). It is finally recognized that certain cofactors may be added as purified or partially purified components to a reporter gene assay. A discussion of reporter systems can be found in *Current Protocols in Pharmacology* (2003), Units 6.2.1-6.2.11, Wiley & Sons, Inc.

An additional embodiment of reporter gene assays involve the use of at least one substrate for a protein translated from SEQ ID NO:1. The substrate can be added before the protein is exposed to the test composition or simultaneously with the test composition, provided that the protein is exposed to the substrate for a time and under conditions sufficient to allow the protein to react with the substrate in order to produce a reaction product. Any substrate wherein the phosphorylation of said substrate is capable of being modified by a protein translated from SEQ ID NO:1 can be used in the reporter gene assays described herein. Proteins translated from SEQ ID NO:1 that can be used to modify the phosphorylation of said substrate, include, for example, proteins having an amino acid sequence selected from the group consisting of: SEQ ID NO:10, SEQ ID NO:13, SEQ ID NO:15, SEQ ID NO:17, SEQ ID NO:19, SEQ ID NO:21, SEQ ID NO:23, SEQ ID NO:25 and SEQ ID NO:27. Examples of substrates that can be used include, but are not limited to, phosphohistidine, phospholysine, phosphodiimide, pyrophosphate or any peptide or protein that is phosphorylated on a histidine or a lysine. For example, a reporter gene assay for screening a composition for the ability to inhibit activity of SEQ ID NO:10, SEQ ID NO:13, SEQ ID NO:15, SEQ ID NO:17, SEQ ID NO:19, SEQ ID NO:21, SEQ ID NO:23, SEQ ID NO:25 and SEQ ID NO:27 can be performed. The method involves exposing a protein to a test composition and then measuring the presence or absence of a reaction product or complex. The lack of a reaction product or complex indicates that the composition has the ability to inhibit the activity of the protein. Prior to exposing the protein to the test composition, a substrate can be added to the protein. Alternatively, the substrate can be added when the protein is exposed to the test composition.

An additional substrate that can be used is a radioactive enzyme substrate. In such an embodiment, the reporter gene encodes an enzyme (for example, chloramphenicol acetyltransferase) having a substrate that is readily separated from the corresponding reaction product. This type of radioactive detection assay may be utilized in order to identify a compound that binds to or modulates a protein translated from SEQ ID NO:1 or that modulates the expression of an mRNA molecule transcribed from SEQ ID NO:1. It is well known to those skilled in the art that the separation and detection of radioactive compounds may be accomplished by a variety of chromatographic and other methods. A discussion of radioactive reporter gene assays can be found in *Current Protocols in Pharmacology* (2003), Units 6.4.1-6.4.11, Wiley & Sons.

An additional assay that may be used to detect a composition or compound having the ability to modulate the activity or expression of a protein translated from SEQ ID NO:1 or modulate the expression of an mRNA molecule transcribed from SEQ ID NO:1 is the scintillation proximity assay. This assay is based upon the binding of a radiolabeled tracer to a protein translated from SEQ ID NO:1 or an mRNA molecule transcribed from SEQ ID NO:1 that has been exposed to the composition or compound of interest. The scintillant is incorporated into small fluoromicrospheres to which target macromolecules (for example, proteins or mRNAs) attach. If a radioactive molecule (for example, $^3H$) binds to the target, it is brought close enough to the bead to stimulate the scintillant to produce light. On the other hand, unbound radioactivity is not detected if the bead is outside the distance subatomic particles produced by the decay are likely to travel. Thus compositions or compounds that bind to a protein translated from SEQ ID NO:1 or an mRNA molecule transcribed from SEQ ID NO:1 may be detected by changes in the amount of scintillant-emitted light. A discussion of scintillation proximity assays can be found in *Current Protocols in Pharmacology* (2003), Unit 9.4.9-9.4.10, Wiley & Sons, Inc.

Another assay which may be utilized in the identification of compositions that affect the binding or that modulate a protein translated from SEQ ID NO:1 to mRNA is a filter binding assay. An example of the filter binding assay that may be utilized for a protein translated from SEQ ID NO:1 involves immobilization of an RNA molecule (for example, all or part of an mRNA transcribed from SEQ ID NO:1) on a solid support, exposure of the immobilized RNA to a protein translated from SEQ ID NO:1 in the absence or presence of compositions thought to bind or inhibit protein translated from SEQ ID NO:1, and quantitation of a protein translated from SEQ ID NO:1 on the solid support. It is well known to those skilled in the art that the solid support may be a nitrocellulose or other filter, or any of a variety of beads or microparticles. It is further recognized that a protein translated from SEQ ID NO:1 used in the assay may be purified from an heterologous expression system, and will advantageously be tagged such that it can be detected using commonly available reagents. For example, a protein translated from SEQ ID NO:1 may be a fusion to a 'tag' sequence expressed in *E. coli* (Tateiwa et al., *Journal of Neuroimmunology* 120:161-69 (2001)). Compositions that bind to or inhibit a protein translated from SEQ ID NO:1 may be identified by a increase or reduction in the amount of a protein translated from SEQ ID NO:1 on the solid support, relative to a reaction in which no test compound was added.

Another type of assay that may be useful to screen for compositions that bind to protein translated from SEQ ID NO:1 is a fluorescence polarization assay. This method detects molecular interactions and is based on the concept that fluorescent molecules excited by light polarized in one plane will emit a fluorescent signal again in a polarized manner. The rotational relaxation time is proportional to the molecular volume if other physical variables are unchanged. Thus, when binding to a larger molecule restricting rotation and tumbling, the emission remains polarized, such polarization can be calculated and is directly proportional to the fraction of bound ligand. Change in fluorescence polarization thus accounts for the ratio of bound versus total ligand. For a protein translated from SEQ ID NO:1, one embodiment of a fluorescent polarization assay would involve a fluorescently labeled polynucleotide comprising all or part of a nucleic acid of SEQ ID NO:1, SEQ ID NO:2, SEQ ID NO:5, SEQ ID NO:6, SEQ ID NO:7, SEQ ID NO:8, SEQ ID NO:9, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:31 or SEQ ID NO:33. Compositions that bind to a protein translated from SEQ ID NO:1 may be detected by a reduction of fluorescent polarization attributable to the labeled polynucleotide. A discussion of fluorescent polarization assays can be found in *Current Protocols in Pharmacology*, (2003), Units 9.4.12-9.4.13 Wiley & Sons, Inc.

Another type of assay that may be used to screen for compositions that bind to a protein translated from SEQ ID NO:1 is the spin-screening assay. This method detects molecular interactions, and is based on the concept that the sedimentation rate of molecules or molecular complexes in solution depends on mass and shape. In particular, the sedimentation rate of a small molecule alone is expected to be substantially different from that of the same small molecule bound to a macromolecule. Thus, when a directional force is applied (for example, by spinning a solution at high speed in a centrifuge), small molecules that bind to a protein translated from SEQ ID NO:1 can be readily separated from other small molecules in a mixture that do not. Separation of bound from unbound small molecules can also be accomplished by including a size exclusion filter within the centrifuge tube, such that unbound small molecules pass through the filter but bound small molecules do not. It is recognized by those skilled in the art that molecules separated in this fashion can be identified by a variety of spectroscopic and other methods. In one embodiment, a spin-screening assay includes detection by mass spectrometry.

In another embodiment, the present invention relates to methods of determining the in vivo activity of a composition identified as a potential therapy for the treatment of major depression or a related disorder. These methods involve obtaining at least two (2) test samples from a subject, preferably a human, being treated for major depression or a related disorder. A first test sample can be considered to be a test sample that is obtained at a period in time before the subject has begun a course of treatment with the test composition. Alternatively, a first test sample can also be considered to be a test sample obtained at a period in time during which a subject has been receiving a course of treatment with the test composition. A second test sample can be considered to be a test sample that is obtained at a period in time that is subsequent to the obtaining of the first test sample. For example, the second test sample can be obtained after a period of time has elapsed after the subject has begun an initial course of treatment with the test composition (meaning that the subject had not previously received the test composition prior obtaining the first test sample). Alternatively, if a subject has been receiving treatment with a test composition, a first test sample can be obtained from said subject. After a period of time has elapsed (for example, three (3) months) during which said subject is still being treated with the test composition, a second test sample can be obtained from said subject. A discussion of what constitutes a test sample and examples of test samples has already been provided previously herein and is incorporated herein by reference.

Once the test samples are obtained, they are analyzed, using routine techniques known in the art (which have been discussed previously herein), to determine or quantify the: (a) amount or activity of a protein translated from SEQ ID NO:1; or (b) amount of mRNA transcribed from SEQ ID NO:1, in each of the test samples. The amount or activity of a protein translated from SEQ ID NO:1 or the amount of mRNA transcribed from SEQ ID NO:1 that was detected or quantified in each of the test samples is compared. If, for example, the amount or activity of protein or the amount of mRNA determined or quantified in the second test sample (which was the test sample obtained after the subject began a course of treatment with the composition) is the same (namely, equal) as the amount or activity of protein or the amount or activity of mRNA determined or quantified in the first test sample (which was the test sample obtained from the subject prior to undergoing said course of treatment with the composition), this indicates that the composition lacks therapeutic activity. In contrast, if the amount or activity of the protein or the amount of mRNA determined or quantified in the second test sample has changed, namely, has increased or decreased, when compared to the amount or activity of the protein or the amount of mRNA determined or quantified in the first test sample, this indicates that the composition possesses some type or degree of therapeutic activity.

In addition, in yet another embodiment, the present invention relates to methods for determining the presence or absence of activity of a composition identified pursuant to the screening methods described herein that is being used to treat a subject suffering from major depression or a related disorder. The method involves observing the phenotype of said subject prior to the subject being administered the test composition ("first visit"). For example, observation of the subject's phenotype should be based on a method that has been validated as a measure of major depression or a related disorder. Such validated methods include, but are not limited to: the Hamilton depression rating scale (Hamilton, *J. Neurol. Neurolsurg. Psychiatry* 23:56-62 (1960), Schedule for affective disorders and schizophrenia (Spitzer and Endicott, Schedule for affective disorders and schizophrenia, lifetime version. New York, N.Y.: New York State Psychiatric Institute, Biometrics Research. 1975), Montgomery-Åsberg depression rating score (Montgomery, Br. *J. Psychiatry* 134: 382-389 (1979)) and the Structured clinical interview for DSM-IV (First et al., *Structured Clinical Interview for DSM-IV*. Washington, D.C.: American Psychiatric Press 1997). After observation, the subject is administered the test composition for a time and under conditions that are sufficient for the composition to either: (a) bind to, inhibit, increase, decrease or reduce the amount of a protein translated from SEQ ID NO:1; or (b) increase or reduce the amount of a mRNA molecule transcribed from SEQ ID NO:1. After the subject has been administered the test composition for a time and under the conditions described above, the phenotype of the subject is again observed, preferably, using the same validated method as was used to establish the initial phenotype. Observable improvement in the phenotype of the subject at the second observation compared to the first observation indicates that the composition has some type or degree of therapeutic activity. A lack of observable differences in the phenotype of the subject at the first observation compared to the second observation indicates that the composition does not possess therapeutic activity. The steps of observing the phenotype of the subject and administering the composition to said subject can be repeated for as long as the treating physician deems necessary. The physician may then compare the phenotype of the subject between any pair of observations to judge whether the composition has some type or degree of therapeutic activity. In one aspect of this embodiment, commonly used in clinical research, the phenotype observed at the time of the last administration of the test composition is referred to as the "last visit". Eventually, the phenotype of the subject prior to initiation of treatment is compared with the phenotype of the subject at the last visit. Observable differences in the phenotype of the subject prior to initiation of treatment compared to the last visit indicates that the composition possesses some type or degree of therapeutic activity. A lack of observable differences in phenotype of the subject prior to initiation of treatment compared to the last visit indicates that the composition does not possess any type of therapeutic activity.

In another embodiment, the present invention relates to the compositions identified by methods described herein in the prevention of major depression or a related disorder or the treatment of major depression or a related disorder. More specifically, the present invention contemplates a method for at least substantially preventing in a subject major depression or a related disorder by administering to a subject in need of treatment thereof, a therapeutically effective amount of at least one composition that has been identified by the hereinbefore described methods that: (a) modulates the activity of a protein translated from SEQ ID NO:1; (b) reduces the amount of a protein translated from SEQ ID NO:1; (c) increases the amount of a protein translated from SEQ ID NO:1; or (d) modulates the level of expression of an mRNA molecule transcribed from SEQ ID NO:1. Administration of a prophylactic composition can occur prior to the manifestation of symptoms characteristic of major depression or a related disorder.

Additionally, the present invention further contemplates a method of treating a subject suffering from major depression or a related disorder by administering to a subject in need of treatment thereof, a therapeutically effective amount of at least one composition that has been identified by the hereinbefore described methods that: (a) modulates the activity of a protein translated from SEQ ID NO:1; (b) reduces the amount of a protein translated from SEQ ID NO:1; (c) increases the amount of a protein translated from SEQ ID NO:1; or (d) modulates the level of expression of an mRNA molecule transcribed from SEQ ID NO:1.

By way of example, and not of limitation, examples of the present invention shall now be given.

EXAMPLE 1

Identification of Genetic Linkage and Association Between DEP2 and Major Depressive Disorder Genetic linkage between DEP2 and major depressive disorder was established in a pedigree-based study in the Mormon population of Utah. The ascertainment and characteristics of a majority of these pedigrees has been described (Abkevich et al., *Am. J. Hum. Genet.* 73:1271-1281 (2003)). In the study described herein, a total of 93 pedigrees that contain a minimum of four females affected with major depressive disorder (DSM-IV-TR sections 296.2x or 296.3x) were selected for genetic analysis. These pedigrees comprised 744 affected females.

Affected individuals were genotyped and genome-wide linkage analysis was performed as described (Abkevich et al., op. cit.). Two meaningful differences between the present study and our previously published work are: first, that additional pedigrees were ascertained; second, that the definition of affected status was different as it did not include bipolar disorder in this study.

Using a dominant genetic model and considering only females with major depressive disorder as affected, evidence of linkage on chromosome 10 at marker D10S1676 was observed (heterogeneity LOD score (HLOD) 2.4). Upon genotyping of additional markers in the 26 centimorgan ("cM") interval between D10S2322 and D10S1700, the linkage evidence increased to a peak HLOD of 3.4 at D10S214 (FIG. 27 and Table 1).

The serotonin receptor 1A (Htr1a) is a therapeutic target in the management of depressive and anxiety disorders (Barnes and Sharp, *Neuropharmacology* 38:1083-1152 (1999)). A common polymorphic site in the corresponding gene (HTR1A) has been described, such that the 1019$^{th}$ nucleotide upstream of the transcriptional start site naturally occurs as either cytosine or guanosine (Wu and Comings, *Psych. Genet.* 9:105-106 (1999)). Results of in vitro experiments suggest that the variant allele (–1019G) prevents binding of a transcriptional repressor, resulting in enhanced Htr1a expression (Lemonde et al., *J. Neurosci.,* 23:8788-8799 (2003)). Either the –1019G allele or homozygous –1019GG genotype has been associated with depression, suicide, bipolar disorder, panic disorder with agoraphobia, neuroticism and decreased anti-depressant response (Arias et al., *Mol. Psych.* 7:930-932 (2002); Strobel et al., *J. Neural Transm.,* 110-1445-1453 (2003); Lemonde et al., *J. Neurosci.,* 23:8788-8799 (2003); Rothe et al., *Int. J. Neuropsychopharmacol.* 7:189-192 (2004); Huang et al., *Int. J. Neuropsychopharmacol.* 7:441-451 (2004); Serretti et al., *Int. J. Neuropsychopharmacol.* 7:453-460 (2004); Lemonde et al., *Int. J. Neuropsychopharmacol.* 7:501-506 (2004); Arias et al., *J. Psychopharmacol.* 19:166-172 (2005)).

In the Utah population, HTR1A allele –1019G and genotype –1019GG were 1.1- and 1.3-fold over-represented among individuals affected with major depressive disorder compared to unaffected individuals (one-tailed p=0.05 and 0.02, respectively). Hence, linkage analysis was stratified according to HTR1A –1019 alleles. That is, only individuals with major depressive disorder, and also carrying one or two copies of the HTR1A –1019G risk allele, were considered affected. In a genome-wide HTR 1A-conditional linkage analysis using a dominant genetic model and also restricted to female sex, the observed evidence of linkage on chromosome 10 strengthened to a peak HLOD of 3.1 at D10S1222. Upon inclusion of additional marker data in the 26 cM interval between D10S2322 and D10S1700, the linkage evidence increased to a peak HLOD of 4.4 at D10S575 (FIG. 27 and Table 1).

The conditional linkage method improved upon the previously performed traditional linkage analysis in three ways. First, as noted above, it revealed stronger evidence supporting linkage of a dominant gene to major depressive disorder in females on chromosome 10 in the vicinity of D10S575. Second, it narrowed the linkage region (as defined by a drop of HLOD of either 1 or 2 from the peak value), such that the location of the linked gene was better defined. Third, and most importantly, it revealed linkage evidence in a distinct subset of pedigrees. Further investigation of those pedigrees was crucial to the discovery of DEP2 as a gene linked to major depressive disorder.

As a next step to identify a gene linked to major depressive disorder, each gene in the conditional linkage region was resequenced in representative affected females from each of sixteen pedigrees. These pedigrees were selected on the basis of having a familial HLOD of at least 0.4. Among these pedigrees, six had not shown linkage evidence without stratification on the basis of HTR1A alleles. The frequencies of variant alleles among the 22 chromosomes that segregated with major depressive disorder within these pedigrees was compared to the frequencies among 60 control chromosomes. For seven single nucleotide polymorphisms ("SNPs") within SEQ ID NO:1, statistically significant frequency differences were observed. Additionally, a statistical trend was observed for an eighth SNP in SEQ ID NO:1 (Tables 2 and 3). Two pairs of these SNPs (DEP2.0001 and DEP2.0002, DEP2.0004 and DEP2.0005) were in complete linkage disequilibrium with each other. Between these markers, only DEP2.0002 and DEP2.0004 are described further. One SNP in each of six other genes in the linkage region showed statistically significant frequency differences between the 22 chromosomes that segregated with major depressive disorder within these pedigrees and the set of 60 control chromosomes (Table 3).

For three of six tested SNPs in SEQ ID NO:1, statistically significant frequency differences were also observed between the 22 chromosomes that segregated with major depressive disorder and an independent set of 180 control chromosomes (Table 4). None of the six tested SNPs from other genes showed statistical significance in this test. For five of the six tested SNPs in SEQ ID NO:1, statistically significant frequency differences were also observed between the 22 chromosomes that segregated with major depressive disorder and a third independent set of 708 control chromosomes (Table 5).

To confirm the relationship between DEP2 genotypes and major depressive disorder, genetic association studies comparing genotype frequencies between individuals affected with major depressive disorder (not ascertained on the basis of familial history of disease) and healthy controls were performed in two populations. Consistent with the dominant linkage model, DEP2 genotypes were grouped into dichotomous variables such that carriers of a DEP2 risk allele (heterozygous or homozygous) were compared to non-carriers. Following the conditionality of DEP2 linkage on carriage of the HTR1A –1019G allele, this genotype was similarly included in statistical models as a dichotomous variable. Sex and all first-order interaction terms between genotypes or between genotype and sex were also included in statistical models. Non-significant terms (p>0.05) were sequentially dropped from statistical models using a backward elimination process.

In the Mormon population, DEP2.0004 (odds ratio for the T allele 1.40, 95% confidence interval 1.00-1.94) and DEP2.0007 (odds ratio for the A allele 2.03, 95% confidence interval 0.99-4.48) were associated with major depressive disorder (Tables 6 and 7). For each marker, the frequency of DEP2 allele carriage was highest among –1019G-positive cases, and approximately equal among all other groups. Additionally, the same DEP2 alleles were both linked to and associated with major depression in the Mormon population. There was also a significant DEP2.0004 genotype-by-sex interaction. In an Ashkenazi Jewish population, DEP2.0004 (odds ratio for the T allele 0.59, 95% confidence interval 0.35-0.99) and DEP2.0006 (odds ratio for the A allele 0.43, 95% confidence interval 0.24-0.75) were associated with major depressive disorder (Tables 8 and 9). For each marker, the frequency of DEP2 allele carriage was lowest among −1019G-positive cases, and approximately equal among all other groups. There was no association of DEP2.0006 in the Mormon population (Table 10), or of DEP2.0007 in the Jewish population (Table 11), with major depressive disorder.

The DEP2 polymorphisms associated with major depressive disorder differ between Mormon and Jewish populations, and opposite alleles at DEP2.0004 were associated with major depressive order between the two populations. This sort of situation is not unusual in psychiatric genetics, in fact it has been observed for most of the genes that have been linked to schizophrenia (Harrison and Weinberger, *Mol. Psych.* 10:40-68 (2005)). The most parsimonious explanation for these results is that functional alleles of DEP2 arose on different haplotypes in the Mormon and Jewish populations.

TABLE 1

| Microsatellite Marker | HLOD | Conditional HLOD |
|---|---|---|
| D10S1656 | 0.8 | 1.9 |
| D10S2322 | 0.7 | 1.9 |
| D10S575 | 3.1 | 4.4 |
| D10S214 | 3.4 | 4.2 |
| D10S1703 | 2.9 | 3.8 |
| D10S1782 | 2.7 | 3.6 |
| D10S1222 | 2.7 | 3.5 |
| D10S1727 | 2.7 | 3.5 |
| D10S1676 | 3.3 | 3.6 |
| D10S1439 | 2.7 | 3.1 |
| D10S1134 | 2.5 | 3.0 |
| D10S1248 | 2.8 | 2.3 |
| D10S505 | 2.4 | 1.6 |
| D10S1770 | 1.9 | 1.6 |
| D10S1651 | 1.8 | 1.7 |
| D10S590 | 1.7 | 1.7 |
| D10S212 | 2.3 | 1.9 |
| D10S1711 | 2.0 | 1.8 |
| D10S1700 | 2.0 | 1.8 |

TABLE 2

| Marker Name | Alleles | Location in SEQ ID NO: 1 |
|---|---|---|
| DEP2.0001 | C, T | 2955 |
| DEP2.0002 | A, C | 3005 |
| DEP2.0003 | C, A | 33241 |
| DEP2.0004 | C, T | 38048 |
| DEP2.0005 | G, A | 38215 |
| DEP2.0006 | G, A | 77402 |
| DEP2.0007 | G, A | 77333 |
| DEP2.0008 | C, T | 79906 |

TABLE 3

| Marker Name | Linked Chromosomes | Control Chromosomes | P |
|---|---|---|---|
| DEP2.0001 | 10/22 | 5/60 | 0.0004 |
| DEP2.0002 | 10/22 | 5/60 | 0.0004 |
| DEP2.0003 | 10/22 | 12/58 | 0.02 |
| DEP2.0004 | 13/22 | 17/60 | 0.02 |
| DEP2.0005 | 13/22 | 17/60 | 0.02 |
| DEP2.0006 | 14/22 | 25/60 | 0.09 |
| DEP2.0007 | 4/22 | 1/60 | 0.02 |
| DEP2.0008 | 3/22 | 0/60 | 0.02 |
| rs1466361 | 17/22 | 34/58 | 0.05 |
| rs3740013 | 14/22 | 20/60 | 0.003 |

TABLE 3-continued

| Marker Name | Linked Chromosomes | Control Chromosomes | P |
|---|---|---|---|
| rs4462251 | 12/22 | 18/58 | 0.05 |
| rs1063536 | 6/22 | 2/60 | 0.004 |
| rs3781412 | 15/22 | 25/60 | 0.007 |
| rs1436803 | 7/22 | 6/60 | 0.009 |

TABLE 4

| Marker Name | Linked Chromosomes | Control Chromosomes | P |
|---|---|---|---|
| DEP2.0002 | 10/22 | 45/176 | 0.07 |
| DEP2.0003 | 10/22 | 32/178 | 0.01 |
| DEP2.0004 | 13/22 | 61/178 | 0.03 |
| DEP2.0006 | 14/22 | 73/178 | 0.07 |
| DEP2.0007 | 4/22 | 4/178 | 0.006 |
| DEP2.0008 | 3/22 | 6/174 | 0.07 |
| rs1466361 | 17/22 | 103/176 | 0.11 |
| rs3740013 | 14/22 | 75/176 | 0.07 |
| rs4462251 | 12/22 | 86/178 | 0.65 |
| rs1063536 | 6/22 | 21/174 | 0.09 |
| rs3781412 | 15/22 | 106/178 | 0.50 |
| rs1436803 | 7/22 | 25/176 | 0.06 |

TABLE 5

| Marker Name | Linked Chromosomes | Control Chromosomes | P |
|---|---|---|---|
| DEP2.0002 | 10/22 | 105/356 | 0.15 |
| DEP2.0003 | 10/22 | 121/684 | 0.003 |
| DEP2.0004 | 13/22 | 184/686 | 0.002 |
| DEP2.0006 | 14/22 | 251/696 | 0.01 |
| DEP2.0007 | 4/22 | 17/696 | 0.003 |
| DEP2.0008 | 3/22 | 20/708 | 0.03 |

TABLE 6

| HTR1A | | DEP2.0004 T+ | | Males | | Females | |
|---|---|---|---|---|---|---|---|
| Genotype | Status | Number | % | Number | % | Number | % |
| G+ | Case | 197/342 | 58 | 69/113 | 61 | 128/229 | 56 |
|  | Control | 85/182 | 47 | 42/101 | 42 | 43/81 | 53 |
| CC | Case | 33/77 | 43 | 20/37 | 54 | 13/40 | 32 |
|  | Control | 28/62 | 45 | 11/31 | 35 | 17/31 | 55 |

TABLE 7

| HTR1A | | DEP2.0007 A+ | |
|---|---|---|---|
| Genotype | Status | Number | % |
| G+ | Case | 29/347 | 8 |
|  | Control | 7/183 | 4 |
| CC | Case | 3/77 | 4 |
|  | Control | 3/63 | 5 |

TABLE 8

| HTR1A | | DEP2.0004 T+ | |
|---|---|---|---|
| Genotype | Status | Number | % |
| G+ | Case | 51/132 | 39 |
|  | Control | 35/64 | 55 |

TABLE 8-continued

| HTR1A | | DEP2.0004 T+ | |
|---|---|---|---|
| Genotype | Status | Number | % |
| CC | Case | 29/50 | 58 |
| | Control | 13/21 | 62 |

TABLE 9

| HTR1A | | DEP2.0006 A+ | |
|---|---|---|---|
| Genotype | Status | Number | % |
| G+ | Case | 71/132 | 54 |
| | Control | 49/65 | 75 |
| CC | Case | 34/50 | 68 |
| | Control | 17/22 | 77 |

TABLE 10

| HTR1A Genotype | Status | Number | % |
|---|---|---|---|
| | | DEP2.0006 A+ | |
| G+ | Case | 122/347 | 35 |
| | Control | 75/183 | 41 |
| CC | Case | 27/77 | 35 |
| | Control | 27/63 | 43 |
| | | DEP2.0007 A+ | |
| G+ | Case | 10/132 | 8 |
| | Control | 4/65 | 6 |
| CC | Case | 1/50 | 2 |
| | Control | 3/22 | 14 |

EXAMPLE 2

Detection of a Brain-Specific DEP2 Transcript by Northern Blotting

Northern blotting was performed using a probe from the 3' UTR (nt. 1295 to 1713) of LHPP (SEQ ID NO:9) on a multi-tissue blot containing poly(A) RNA from the following human tissues: brain, placenta, skeletal muscle, heart, kidney, pancreas, liver, lung, spleen, and colon. The probe used is within sequences that are common to SEQ ID NO:2, SEQ ID NO:5, SEQ ID NO:6, SEQ ID NO:7, SEQ ID NO:8, SEQ ID NO:9, SEQ ID NO:11, and SEQ ID NO:12.

Methods

The pre-made poly(A) RNA Northern blot was product #3140 from Ambion (Austin Tex.). PCR was conducted to amplify a product that lies entirely in the 3' UTR of SEQ ID NO:9 (nucleotides 1295 to 1713).

```
Forward    GAATCTCCCAAATCCCAGAACTCA (SEQ ID NO: 68)
primer:

Reverse    ACACCGGGCATGACACCTTCAAGT (SEQ ID NO: 69)
primer:
```

The DNA product was labeled using an ArnbionStrip-EZ DNA kit (Ambion, Austin Tex. and [α-32P] dATP. The blot was hybridized overnight at 42 degrees Celsius in ULTRAhyb Ultrasensitive Hybridization Buffer (Ambion, Austin Tex.). The blot was washed 2×15 minutes at low stringency (2×SSPE, 0.1% SDS) and 2×15 minutes at high stringency (0.1×SSPE, 0.1% SDS). All procedures were carried out per the manufacturer's instructions.

Results

Figure 28:
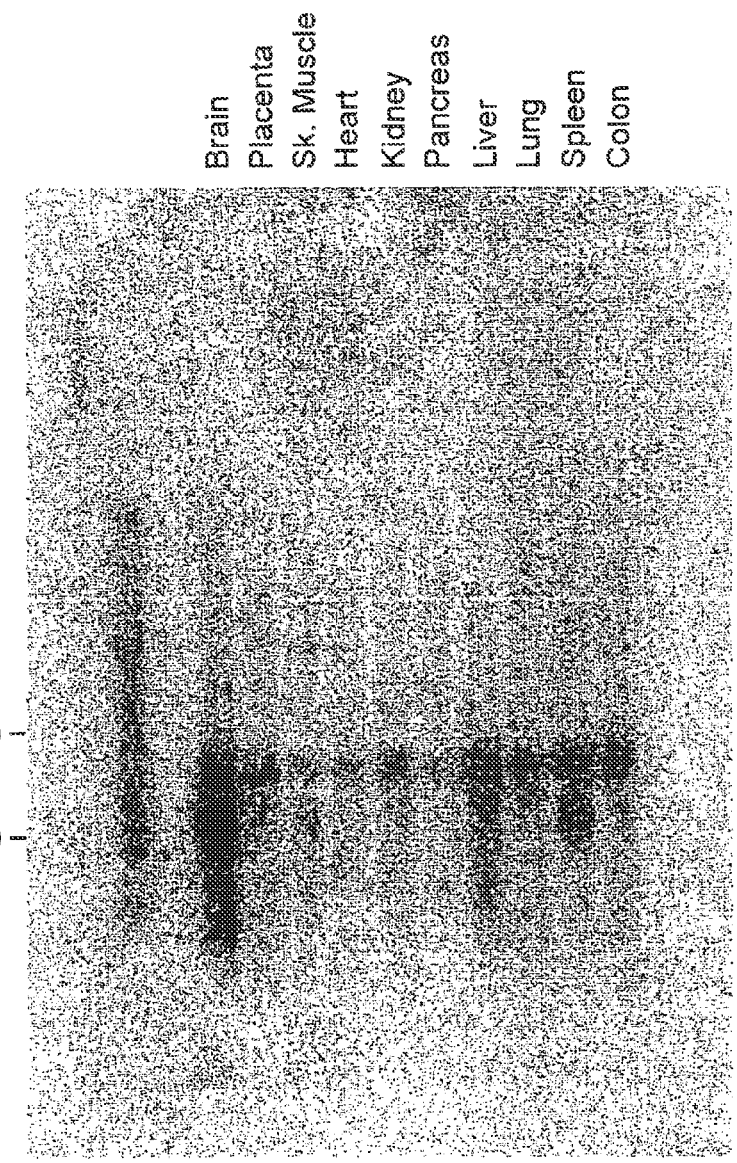
FIG. 28 shows a Northern blot probed with a polynucleotide complementary to SEQ ID NO:2, SEQ ID NO:5, SEQ ID NO:6, SEQ ID NO:7, SEQ ID NO:8, SEQ ID NO:9, SEQ ID NO:11 and SEQ ID NO:12.

FIG. 28 shows the existence of at least two DEP2 transcripts. An approximately 1.7 kb transcript was present in approximately equal abundance across all tissues tested. An approximately 1.1 kb transcript was very abundant in brain and observed at low levels in skeletal muscle and lung.

Conclusion

The 1.7 kb transcript is consistent with LHPP (SEQ ID NO:9) in the literature (Yokoi et al, J Biochem 133:607-613 (2003)). The existence of a novel DEP2 transcript of approximately 1.1 kb was established. Furthermore, this transcript appears to be most abundant in brain.

EXAMPLE 3

Observation of Enhanced DEP2 Transcript Expression on Microarrays

Probe sets within DEP2 are present on Affymetrix U133 Plus and U13; Av2 microarrays. These probe sets are annotated as recognizing LHPP, however they are within sequences that are common to SEQ ID NO:2, SEQ ID NO:5, SEQ ID NO:6, SEQ ID NO:7, SEQ ID NO:8, SEQ ID NO:9, SEQ ID NO:11, and SEQ ID NO:12.

Methods

Datasets from microarray experiments that had been conducted for unrelated purposes were mined to learn additional information regarding the expression level of DEP2 transcripts in normal human tissues. An alpha value of 1E-12 was used for statistical significance.

Results

Data from Affymetrix U133 Plus and U133Av2 microarrays are shown in Table 11 and Table 12, respectively. Results considered statistically significant are in boldface type.

TABLE 11

| Tissue type | Intensity | p-value |
|---|---|---|
| spinal cord(BD) | 1192.5 | 0 |
| univ ref(BD) | 658.0 | 4.10E−30 |
| brain(AM) | 616.6 | 1.00E−27 |
| brain(AM) | 604.8 | 5.88E−39 |
| Caudate nucleus(AM) | 592.9 | 5.61E−45 |
| basal ganglia(AM) | 508.4 | 1.74E−39 |
| hippocampus(AM) | 388.4 | 8.36E−25 |
| brain(AM) | 323.4 | 1.61E−16 |
| brain(BD) | 230.5 | 7.06E−20 |
| hypothalamus(AM) | 228.9 | 8.77E−17 |
| cerebellum(BD) | 198.0 | 4.54E−16 |
| Adrenal gland(BD) | 172.3 | 6.39E−09 |
| univ ref(S) | 153.5 | 1.94E−07 |
| salivary gland(BD) | 148.9 | 0.00013 |
| salivary gland(BD) | 128.9 | 7.24E−08 |
| prostate(BD) | 107.1 | 4.30E−05 |
| testis(AM) | 105.1 | 0.000276 |
| retina(BD) | 103.0 | 0.00229 |
| ileum(AM) | 100.8 | 0.000296 |
| pericardium(AM) | 93.5 | 0.000186 |
| lymph node(AM) | 90.6 | 2.71E−05 |
| Thyroid gland(BD) | 87.8 | 2.28E−06 |
| kidney(AM) | 87.4 | 0.00573 |
| Trachea(BD) | 86.2 | 4.03E−06 |
| aorta(AM) | 84.3 | 0.000571 |
| colon proximal(AM) | 81.8 | 1.23E−05 |
| liver(BD) | 77.5 | 2.72E−06 |
| prostate(BD) | 73.7 | 0.02 |
| Thyroid(AM) | 71.0 | 0.00019 |
| fetal liver(BD) | 68.6 | 0.000435 |
| kidney(BD) | 67.5 | 0.000257 |
| right atrium(AM) | 66.2 | 0.03 |

TABLE 11-continued

| Tissue type | Intensity | p-value |
| --- | --- | --- |
| colon distal(AM) | 65.3 | 0.000397 |
| testis(BD) | 59.5 | 0.000539 |
| Thymus(BD) | 55.1 | 0.00131 |
| spleen(AM) | 54.5 | 0.00491 |
| Vena cava(AM) | 53.2 | 0.05 |
| jejunum(AM) | 47.5 | 0.02 |
| uterus(BD) | 46.9 | 0.00417 |
| pancreas(BD) | 46.2 | 0.03 |
| bone marrow(BD) | 45.9 | 0.05 |
| Bladder(AM) | 41.2 | 0.00923 |
| Left ventricle(AM) | 39.2 | 0.15 |
| left atrium(AM) | 37.8 | 0.13 |
| duodenum(AM) | 35.0 | 0.04 |
| Thymus(BD) | 35.0 | 0.12 |
| placenta(BD) | 34.3 | 0.01 |
| prostate(BD) | 34.1 | 0.03 |
| right ventricle(AM) | 31.3 | 0.14 |
| heart(BD) | 30.8 | 0.08 |
| lung(BD) | 29.4 | 0.04 |
| bone marrow(BD) | 25.6 | 0.04 |
| breast(AM) | 24.8 | 0.09 |
| Skeletal muscle(BD) | 15.5 | 0.16 |
| stomach(AM) | 14.8 | 0.25 |
| ovary(AM) | 14.4 | 0.21 |
| pancreas(AM) | 8.7 | 0.37 |
| fetal brain(BD) | 7.4 | 0.32 |

(AM) = purchased from Ambion (BD) = purchased from BD Biosciences (S) = purchased from Sigma

TABLE 12

| Tissue type | Intensity | p-value |
| --- | --- | --- |
| Frontal cortex | 897.9 | 0 |
| Thalamus | 806.1 | 0 |
| Basal ganglia | 634.7 | 0 |
| Temporal cortex | 348.3 | 0 |
| Occipital cortex | 294.6 | 0 |
| Parietal cortex | 274.8 | 0 |
| Medulla | 257.9 | 0 |
| Cerebellum | 253.1 | 0 |
| Universal 1 | 83.2 | 0.02 |
| Heart | 47.5 | 0.22 |
| Stomach | 42.2 | 0.05 |
| Prostate | 34.2 | 0.08 |
| Universal 2 | 0.7 | 0.49 |
| Pancreas | −20.7 | 0.7 |

All RNAs were purchased from Ambion.

Conclusion

Based on observation of statistically significant intensity data for every central nervous system sample examined (except a single fetal brain sample), and lack of statistically significant intensity data for any other sample examined, it appears that DEP2 transcripts are preferentially expressed in the central nervous system. Because the microarray probe sets are complementary to sequences common to several naturally occurring DEP2 transcripts, attributing intensity data from these probe sets specifically to LHPP may be misleading.

EXAMPLE 4

Tissue Distribution of DEP2 Transcripts

The tissue distributions of human DEP2 transcripts were determined using quantitative reverse transcription polymerase chain reaction (QPCR). Assays were conducted for each DEP2 transcript for which there was more supportive evidence (bioinformatic or experimental) than a single expressed sequence tag. Because of the linkage and association of DEP2 to major depressive disorder, there was particular focus on the distributions of these transcripts in the brain.

Methods

Human total RNAs were purchased from either Ambion, Inc. (Austin, Tex.) or BD Biosciences (Franklin Lakes, N.J.).

Reverse transcription and PCR were conducted using the Invitrogen Platinum Thermoscript One Step System qRTPCR kit following the manufacturer's instructions. 50 ng DNAse-treated total RNA was used as a template for each reaction. All Ct readings were normalized to 28S rRNA. A dilution series of Universal Human Reference (BD Biosciences) was used to generate a standard curve for these analyses. Relative expression levels were determined by the Relative Standard Curve Method described in the ABI Prism User Bulletin Number 2 with 28s rRNA assayed as an endogenous control for each sample. Equivalent reverse-transcription efficiency was assumed for gene-to-gene comparison in the absence of quantitative standards such as purified RNA transcripts.

Figure 29:
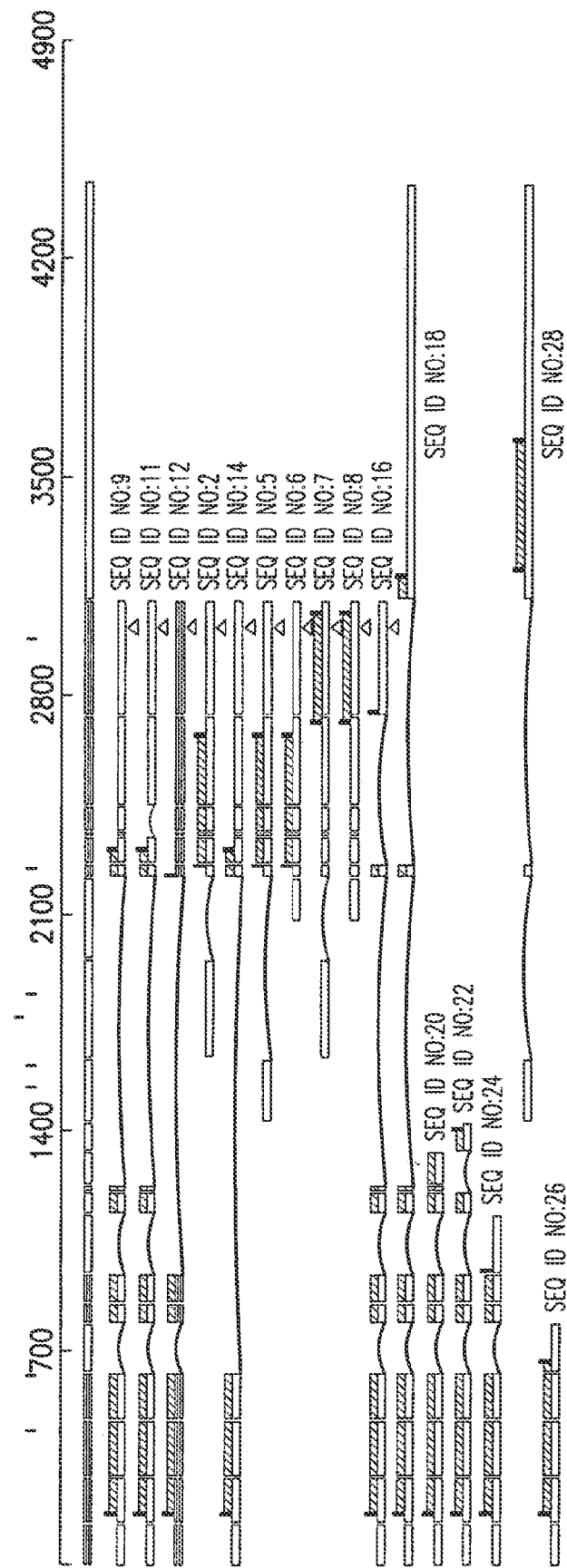
FIG. 29 is a schematic representation of certain naturally occurring DEP2 transcripts and proteins. This figure was created using Genecarta software (Compugen, Tel Aviv, Israel). Dark lines represent transcripts and light lines represent coding regions. Transcripts shown include LHPP and naturally occurring variants thereof, DEP2-1 and naturally occurring variants thereof, and DEP2-2. DEP2-3, for which all supportive evidence has been generated, is not shown. AK127935 and AW867792, which share no exons in common with LHPP or DEP2-1, or naturally occurring variants thereof, are not shown. Although SEQ ID NO:2, SEQ ID NO:5 and SEQ ID NO:6 each contain the coding regions for both Dep2-1a and Dep2-1b, only the 5'-most (Dep2-1a) is associated with those transcripts in this figure. The location of Dep2-1b is associated with SEQ ID NO:7 and SEQ ID NO:8.

A schematic of DEP2 transcripts is shown in FIG. 29.

The following primers and probe were used for amplification and detection of DEP2-1 mRNA (SEQ ID NO:2). These primers and probe do not discriminate against a naturally occurring splice variant of DEP2-1 (SEQ ID NO:7).

```
Set 1 (inter-exon)
                                           (SEQ ID NO: 35)
5'-CACGTACCCATCAGCCTTCAC-3'

(SEQ ID NO: 36)
5'-CCTGTGGAAGGAGCATACAGT-3'

(SEQ ID NO: 37)
5'-\56-FAM\CCCAGTGACGAGCACCATCCGG\36-TAMSp\-3'
(probe)

Set 2 (intra-exon)
                                           (SEQ ID NO: 38)
5'-CAACACTGGCACCTGCAGAT-3'

(SEQ ID NO: 39)
5'-CCACCCCATGCCATCAA-3'

(SEQ ID NO: 40)
5'-\56-FAM\AAGTGGCAGAGCAGCCCCCAGC\36-TAMSp\-3'
(probe)
```

The following primers and probe were used for amplification and detection of a splice variant of DEP2-1 (SEQ ID NO:5).

```
                                           (SEQ ID NO: 35)
5'-CACGTACCCATCAGCCTTCAC-3'

(SEQ ID NO: 41)
5'-CCCGCCTCTCCAAGACCAT-3'

(SEQ ID NO: 37)
5'-\56-FAM\CCCAGTGACGAGCACCATCCGG\36-TAMSp\-3'
(probe)
```

The following primers and probe were used for amplification and detection of a splice variant of DEP2-1 (SEQ ID NO:6). These primers and probe do not discriminate against another naturally occurring splice variant of DEP2-1 (SEQ ID NO:8).

```
                                        (SEQ ID NO: 35)
5'-CACGTACCCATCAGCCTTCAC-3'

(SEQ ID NO: 42)
5'-GGTACACTCATGTCCCCACCAT-3'

(SEQ ID NO: 37)
5'-\56-FAM\CCCAGTGACGAGCACCATCCGG\36-TAMSp\-3'
(probe)
```

The following primers and probe were used for amplification and detection of LHPP mRNA (SEQ ID NO:9).

```
                                        (SEQ ID NO: 35)
5'-CACGTACCCATCAGCCTTCAC-3'

(SEQ ID NO: 43)
5'-GCGCACCGGGAAGTTCAG-3'

(SEQ ID NO: 37)
5'-\56-FAM\CCCAGTGACGAGCACCATCCGG\36-TAMSp\-3'
(probe)
```

The following primers and probe were used for amplification and detection of a splice variant of LHPP (SEQ ID NO:12).

```
                                        (SEQ ID NO: 44)
5'-TGCAAGCGATAGGAGTGGAA-3'

(SEQ ID NO: 45)
5'-GGTTGTCCACGTACCCATCAG-3'

(SEQ ID NO: 46)
5'-\56-FAM\CCCACCAGGCCCAGTGACGAGC\36-TAMSp\-3'
(probe)
```

The following primers and probe were used for amplification and detection of a splice variant of LHPP (SEQ ID NO:20).

```
                                        (SEQ ID NO: 47)
5'-GCGCACCGGGAAGTTCAG-3'

(SEQ ID NO: 48)
5'-TGAAGAACAAAACAGAATGAGAATGTG-3'

(SEQ ID NO: 49)
5'-\56-FAM\CCAGCTGGAGTCATTTATTCACCTTCCTTCC\36-
TAMSp\-3' (probe)
```

The following primers and probe were used for amplification and detection of a splice variant of LHPP (SEQ ID NO:24).

```
                                        (SEQ ID NO: 50)
5'-CCACCAGTTACTTTCAGTATGAAAGCA-3'

(SEQ ID NO: 51)
5'-TATCCTTTCAGAGAAGCAGCAAAAAC-3'

(SEQ ID NO: 52)
5'-\56-FAM\CAGAAATGCCTGCGGCTTTTCCTG\36-TAMSp\-3'
(probe)
```

The following primers and probe were used for amplification and detection of DEP2-2 (SEQ ID NO:28).

```
                                        (SEQ ID NO: 53)
5'-CGCCCCAGACCCAAGAATC-3'

(SEQ ID NO: 54)
5'-CAGGAAGTGCCCATCAGCCT-3'

(SEQ ID NO: 55)
5'-\56-FAM\CCCGCCTCTCCAAGACCATCCCT\36-TAMSp\-3'
(probe)
```

The following primers and probe were used for amplification and detection of Dep2-3 (SEQ ID NO:30).

```
                                        (SEQ ID NO: 56)
5'-AGCACCATCCGGAAGTGAAG-3'

(SEQ ID NO: 57)
5'-GCTGCAAGATCTGTGCATAGGA-3'

(SEQ ID NO: 58)
5'-\56-FAM\CTGATGGTGAAGAGCCTGGAAGAAACCCA\36-
TAMSp\-3' (probe)
```

The following primers and probe were used for amplification and detection of AK127935 (SEQ ID NO:31).

```
                                        (SEQ ID NO: 59)
5'-CAATTTAGGTCGCTGCTATGGA-3'

(SEQ ID NO: 60)
5'-TGGTGACTCAAAGGCCTAATGG-3'

(SEQ ID NO: 61)
5'-\56-FAM\CCTGGCCTCTTAACTCATTTACCCGGG\36-TAMSp\-
3'
```

The following primers and probe were used for amplification and detection of AW867792 (SEQ ID NO:33).

```
                                        (SEQ ID NO: 62)
5'-TGGAGGCAGCCTCGCTTTA-3'

(SEQ ID NO: 63)
5'-TTGGAGGAAGAGTTCTCATGCA-3'\

(SEQ ID NO: 64)
5'-\56-FAM\CCCGCAGAACCTCCACGCTGTT\36-TAMSp\-3'
```

Cycle threshold (Ct) values were qualitatively interpreted as follows:

Ct>35 probably noise

Ct=30-35 possibly low abundance transcript, reliability assessed by shape of Ct curve Ct=25-30 moderate abundance transcript Ct=20-25 high abundance transcript Ct<20 very high abundance transcript Results Observed Ct values are shown in Table 13. For SEQ ID NO:5, only inter-exon results are shown.

TABLE 13

| | SEQ ID NO: | | | | | | | | | |
|---|---|---|---|---|---|---|---|---|---|---|
| | 2 | 5 | 9 | 12 | 20 | 24 | 28 | 30 | 31 | 33 |
| Adrenal gland (MP) | 27.41 | 38.66 | 23.27 | 22.54 | 25.68 | 30.16 | 38.01 | 27.7 | 26.68 | 26.64 |
| Amygdala (AM) | 20.48 | 32 | 22.91 | 21.83 | 26.78 | 30.47 | 38.93 | 27.12 | 27.93 | 27.15 |
| Basal ganglia (AM) | 19.8 | 36.52 | 22.84 | 21.02 | 26.54 | 30.86 | 37.54 | 26.82 | 27.87 | 26.67 |
| Brain (AM) | 19.82 | 31.78 | 22.86 | 21.34 | 26.37 | 30.34 | 36.91 | 26.36 | 27.31 | 26.75 |
| Brain (MP) | 24.5 | 37.02 | 22.91 | 21.99 | 26.01 | 29.9 | 40 | 26.22 | 26.21 | 25.7 |
| Caudate nucleus (AM) | 20.36 | 33.16 | 22.58 | 21.05 | 25.52 | 29.79 | 36.34 | 26.69 | 25.92 | 25.63 |
| Fetal brain (AM) | 26.24 | 31.91 | 23.97 | 22.83 | ND | ND | ND | ND | ND | ND |
| Fetal liver (MP) | 31.03 | 40 | 40 | 23.53 | 33.18 | 31.48 | 39.34 | 29.88 | 30.27 | 29.93 |
| Globus pallidus (AM) | 17.54 | 32.81 | 22.59 | 21 | 26.23 | 30.74 | 40 | 25.71 | 26.99 | 26.52 |
| Heart (AM) | 30.96 | 40 | 26.49 | 25.12 | 40 | 31.59 | 39.7 | 32.78 | 32.72 | 29.93 |
| Heart (MP) | 29.59 | 34.83 | 23.87 | 24.38 | 31.43 | 30.17 | 38.33 | 30.14 | 28.71 | 28.33 |
| Hippocampus (AM) | 21.09 | 32.7 | 22.58 | 21.22 | 26.2 | 30.17 | 40 | 26.47 | 27.03 | 26.21 |
| Hypothalamus (AM) | 19.83 | 28.99 | 22.43 | 20.23 | 26.66 | 30.43 | 33.54 | 25.85 | 27.42 | 26.86 |
| Kidney (AM) | 31.94 | 32.1 | 23.38 | 21.81 | 31.6 | 30.06 | 35.26 | 29.37 | 30.24 | 29.38 |
| Kidney (MP) | 27.93 | 38.31 | 22.51 | 21.31 | 26.64 | 30.96 | 39.4 | 26.67 | 27.54 | 27.62 |
| Liver (AM) | 30.01 | 40 | 23.8 | 22.48 | 32.56 | 32.36 | 40 | 29.74 | 30.65 | 29.51 |
| Liver (MP) | 30.12 | 40 | 23.67 | 22.41 | 29.47 | 31.65 | 40 | 27.96 | 28.59 | 28.12 |
| Lung (AM) | 40 | 32.29 | 25.44 | 25.11 | 33.74 | 32.6 | 39.22 | 32.82 | 31.34 | 29.92 |
| Lung (MP) | 28.01 | 36.39 | 24.55 | 23.66 | 28.05 | 31.7 | 37.84 | 28.46 | 28.39 | 28.21 |
| Medulla (AM) | 18.77 | 40 | 22.5 | 21.2 | 26.17 | 30.87 | 40 | 25.52 | 27.09 | 26.5 |
| Orbital frontal cortex (AM) | 18.84 | 30.1 | 22.47 | 20.92 | 25.86 | 30.12 | 35.83 | 25.65 | 26.96 | 25.94 |
| Peripheral leukocytes (BD) | 25.15 | 29.52 | 24.18 | 23.35 | 27.4 | 31.12 | 31.81 | 27.7 | 27.09 | 27.52 |
| Placenta (MP) | 29.52 | 40 | 25.02 | 24.75 | 33.54 | 31.93 | 38.76 | 35.4 | 29.48 | 28.93 |
| Pons (AM) | 19.05 | 38.91 | 22.25 | 20.7 | 26.34 | 30.59 | 40 | 25.05 | 27.54 | 26.94 |
| Prefrontal cortex (AM) | 20.25 | 37.69 | 22.59 | 21.34 | 26.06 | 30.06 | 40 | 26.66 | 27.15 | 26.04 |
| Prostate (MP) | 28.26 | 33.94 | 24.84 | 23.54 | 28.4 | 31.48 | 34.97 | 29.31 | 28.3 | 28.09 |
| Salivary gland (MP) | 29.25 | 31.94 | 25.1 | 24.14 | 31.38 | 31.47 | 34.7 | 29.37 | 29.39 | 29.02 |
| Skeletal muscle (MP) | 30.18 | 40 | 26.01 | 25.27 | 40 | 33.16 | 40 | 30.85 | 30.33 | 29.51 |
| Small intestine (AM) | 28.42 | 36.4 | 24.03 | 23.19 | 30.37 | 31.34 | 39.58 | 29.81 | 29.4 | 29.17 |
| Spinal cord (AM) | 18.12 | 31.91 | 21.89 | 20.59 | 27.21 | 31.32 | 37.64 | 24.45 | 27.67 | 26.99 |
| Spinal cord (MP) | 22.88 | 37.62 | 22.34 | 21.29 | 27.4 | 31.32 | 39.49 | 24.74 | 27.56 | 27.32 |
| Spleen (MP) | 28.97 | 27.06 | 25.32 | 24.34 | 30.36 | 32.28 | 29.81 | 29.17 | 28.68 | 28.91 |
| Testis (MP) | 25.85 | 40 | 22.65 | 21.96 | 24.48 | 27.75 | 40 | 26.53 | 24 | 25.04 |
| Thalamus (AM) | 19.81 | 40 | 21.81 | 20.5 | 26.29 | 30.09 | 40 | 26.28 | 27.33 | 26.48 |
| Thymus (MP) | 26.57 | 28.63 | 24.44 | 23.52 | 27.08 | 30.48 | 31.79 | 29.56 | 27.04 | 27.26 |
| Thyroid gland (MP) | 27.56 | 32.25 | 22.87 | 21.72 | 26.23 | 30.05 | 35.03 | 26.86 | 26.96 | 27.28 |
| Trachea (MP) | 27.85 | 31.73 | 24.44 | 23.53 | 28.36 | 31.18 | 34.36 | 28.83 | 28.2 | 28.12 |
| Uterus (MP) | 28.04 | 40 | 24.54 | 23.79 | 28.84 | 32.16 | 40 | 29.17 | 28.3 | 28.31 |

(AM) = purchased from Ambion
(BD) or (MP) = purchased from BD Biosciences
ND = not done
Data for SEQ ID NO: 2 are from primer/probe set 1.

DEP2-1 (SEQ ID NO:2) was detected as a very high or high abundance transcript in all central nervous system samples tested (Ct range 17.5-24.5) except for fetal brain (Ct 26.2), and as a moderate or low abundance transcript in other tissues (Ct range 25.2-31.9) except for lung (Ct 40). Similar results were obtained using a second set of primers and probe within the first exon of DEP2-1 (nucleotides 1-316 of SEQ ID NO:2).

A splice variant of DEP2-1 (SEQ ID NO:5) was reliably detected in spleen, thymus, hypothalamus and peripheral leukocytes (Ct range 27.1-29.5).

A splice variant of DEP2-1 (SEQ ID NO:6) was not reliably detected (not shown).

LHPP (SEQ ID NO:9) was detected as a high or moderate abundance transcript in all samples tested (Ct range 21.8-26.5) except fetal liver (Ct 40). Expression in central nervous system was in general slightly higher than in other tissues.

A splice variant of LHPP (SEQ ID NO:12) was detected as a high abundance transcript in all samples tested (Ct range 20.2-25.2). Expression in central nervous system was in general slightly higher than in other tissues.

A splice variant of LHPP (SEQ ID NO:20) was detected as a moderate abundance transcript in all central nervous system samples tested (Ct range 25.5-27.4), as well as in several other tissues.

A splice variant of LHPP (SEQ ID NO:24) was detected as a moderate abundance transcript in a few samples, and as a low abundance transcript in all others.

DEP2-2 (SEQ ID NO:28) was detected as a low abundance transcript (smallest Ct 29.8).

Dep2-3 (SEQ ID NO:30) was detected as a moderate abundance transcript in all central nervous system samples tested (Ct range 24.4-27.1), as well as in several other tissues.

AK127935 (SEQ ID NO:31) was detected as a moderate abundance transcript in all central nervous system samples tested (Ct range 25.9-27.9), as well as in several other tissues.

AW867792 (SEQ ID NO:33) was detected as a moderate abundance transcript in all samples tested (Ct range 25.0-30.0). Expression in central nervous system was in general slightly higher than in other tissues.

Conclusions

SEQ ID NO:2, SEQ ID NO:5, SEQ ID NO:9, SEQ ID NO:12, SEQ ID NO:20, SEQ ID NO:24, SEQ ID NO:28,

SEQ ID NO:30, SEQ ID NO:31 and SEQ ID NO:33 are naturally occurring transcripts arising from DEP2 (SEQ ID NO:1). Some of the signal observed for SEQ ID NO:5 may be attributable to SEQ ID NO:7, see Examples 5-7 below for independent experimental evidence that SEQ ID NO:5 is a naturally occurring transcript arising from DEP2. Failure to detect SEQ ID NO:6 (or SEQ ID NO:8, which would be amplified and detected by the same primer/probe set) cannot be taken as evidence that it is not a naturally occurring transcript arising from DEP2, without use of a positive control to ensure that the assay worked. Expression of transcripts arising from DEP2, relative to 28S rRNA, was generally higher in the central nervous system than in other tissues. The difference between central nervous system and other tissues was strongest for DEP2-1 (SEQ ID NO:2).

EXAMPLE 5

Establishing the Sequence of DEP2-1

DEP2-1 (SEQ ID NO:2) which is a novel sequence that has never been described previously, comprises distinct protein coding capacity for Dep2-1a (SEQ ID NO:3) and Dep2-1b (SEQ ID NO:4), and is highly and preferentially expressed in the central nervous system. These characteristics make it of particular interest as a candidate to explain the linkage and association of DEP2 to major depressive disorder. DEP2-1 clones were sequenced to establish whether the sequence predicted by mining EST sequence databases was correct.
Methods
IMAGE clones h3175509, h5194531, h5197955 and h4565014 were obtained from the American Type Culture Collection ("ATCC"), P.O. Box 1549, Manassas, Va. 20108. DNA sequencing was performed using standard methods well known to those practiced in the art.
Results
Aligned sequences of the four IMAGE clones and the sequence predicted by Genecarta software from EST sequences are shown in FIG. 30. Clone h4565014 contains sequence, downstream of a polyadenylate tract, that does not match DEP2.
Conclusion
The full-length sequence of DEP2-1 has been established. A novel single nucleotide polymorphism has been identified.

EXAMPLE 6

Characterization of the 5' Ends of DEP2-1 by RLM-RACE

RNA ligase-mediated rapid amplification of cDNA ends (RLM-RACE) was performed on a pool of human spinal cord RNA to determine the 5' ends of DEP2-1 (SEQ ID NO:2).
Methods
Human spinal cord total RNA (#636554 (also called 64113-1)) was obtained from BD Biosciences Clontech (Palo Alto, Calif.). The FirstChoice RLM-RACE kit and was purchased from Ambion (Austin, Tex.). The following gene-specific RACE primers were used.

```
5'RACE gene specific outer primer:
TCTCCCACTGTATGCTCCTTCCA      (SEQ ID NO: 65)

5'RACE gene specific inner primer:
CTCTGCCACTTCATCTGCAGGT       (SEQ ID NO: 66)
```

Figure 31:
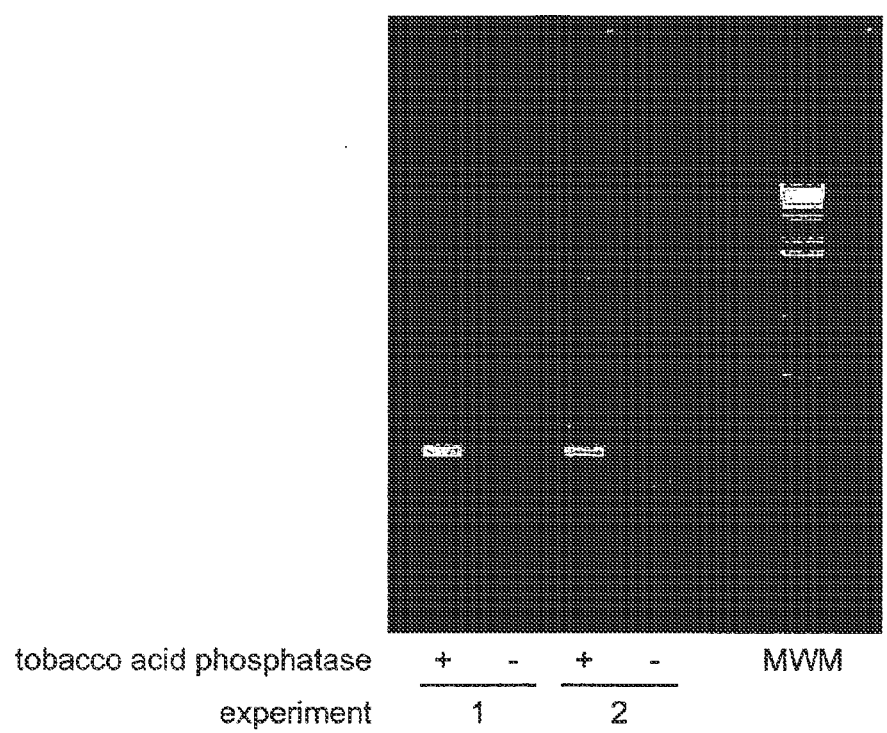
FIG. 31 shows RLM-RACE results. MWM=molecular weight markers.

RLM-RACE was performed using 10 μg human spinal cord total RNA according to manufacturer's instructions, except as noted below. Total RNA was treated with calf intestine alkaline phosphatase to remove free 5'phosphates from molecules such as rRNA, fragmented mRNA, tRNA and contaminating DNA (this step entailed treatment with 3 μL calf intestine alkaline phosphatase (CIP) for 1.5 h at 37° C.). Full length mRNA molecules that contain a 5' methylated guanosine (CAP) should not have been affected by this treatment. The RNA was then treated with tobacco acid pyrophosphatase to remove the CAP structure from full length mRNA, leaving a 5'phosphate. An RNA adapter oligonucleotide was ligated to full-length mRNA using T4 RNA ligase. The adapter could not ligate to dephosphorylated RNA molecules since they lacked a 5'phosphate. A random-primed reverse transcription reaction and nested PCR (using gene-specific inner primers) was then used to amplify the 5'ends of a specific transcript. As a negative control, RNA was treated with calf intestinal alkaline phosphatase but not with tobacco acid pyrophosphatease, such that T4 RNA ligase should have had no substrate to ligate to the RNA adapter oligonucleotide. RLM-RACE products were separated by electrophoresis, extracted from the gel, purified, and sequenced using standard methods well known to those practiced in the art.
Results
RLM-RACE was performed on 2 different lots of human spinal cord mRNA, with identical results (FIG. 31). Two bands (approximately 168 and 243 nucleotides) were observed using tobacco acid pyrophosphatase-treated RNA. These were not observed in negative control reactions.
Sequencing revealed 5'cDNA ends at nucleotides 1 and 76 of SEQ ID NO:2 (FIG. 30). Clean splices at the junction between the 5'RACE Adapter and the mRNA were not observed. This suggests that there was a mixed population of DNA within a single band on the gel, and that transcription initiation may also occur within a few bases upstream or downstream of the major transcription start sites.
Conclusion
Two major transcription start sites of DEP2-1 have been identified.

EXAMPLE 7

Characterization of the 5' Ends of DEP2-1 by Exon-Bridging PCR

Two exon-bridging RT-PCR experiments were conducted to learn whether DEP2-1 was a naturally occurring splice variant of LHPP, or only originates from one or more distinct transcriptional start sites. In a first experiment, PCR was conducted using a reverse primer within the first exon (nucleotides 1-316) of DEP2-1 (SEQ ID NO:2) and a forward primer within an upstream exon of LHPP (SEQ ID NO:9). This PCR was designed to amplify any transcript originating from the LHPP transcription start and comprising exon 1 of DEP2-1. In a second experiment, PCR was conducted using a forward primer within an upstream exon of LHPP and a reverse primer in the exon common to LHPP and DEP2-1. This PCR was designed to amplify any transcript containing both exons of DEP2-1 as well as upstream sequences from LHPP.
Methods
cDNA was prepared from 3 different lots of human spinal cord mRNA (BD Biosciences Clontech) using the SuperScript III First Strand Synthesis System (Invitrogen, Carlsbad, Calif.). The following primers were used.

Experiment 1

Forward:  TGCAAGCGATAGGAGTGGAA    (SEQ ID NO: 44)

Reverse:  CCACCCCATGCCATCAA       (SEQ ID NO: 39)

Experiment 2

Forward:  TGCAAGCGATAGGAGTGGAA    (SEQ ID NO: 44)

Reverse:  CACGTACCCATCAGCCTTCAC   (SEQ ID NO: 67)

PCR, electrophoresis and sequencing were performed using standard methods well known to those practiced in the art.

Results

Figure 32:
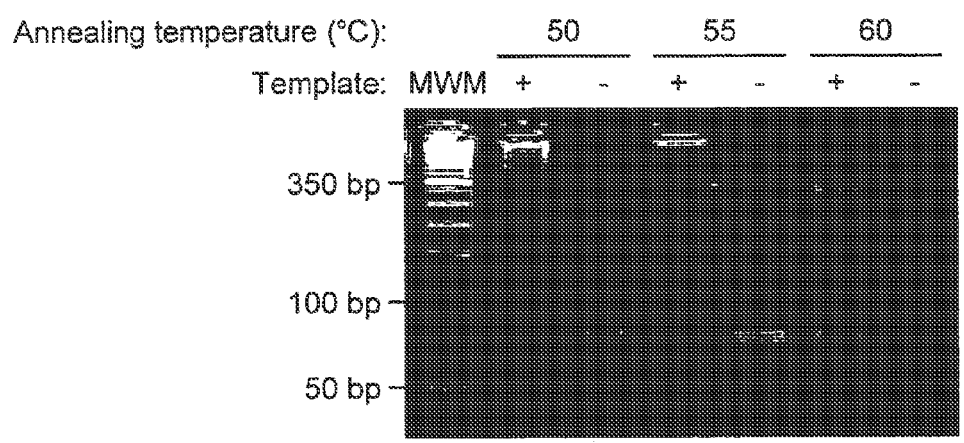
FIG. 32 shows the results of exon bridging PCR experiment #1 in Example 7. The lower band between 50 and 100 nucleotide markers are primer dimers.
Figure 33:
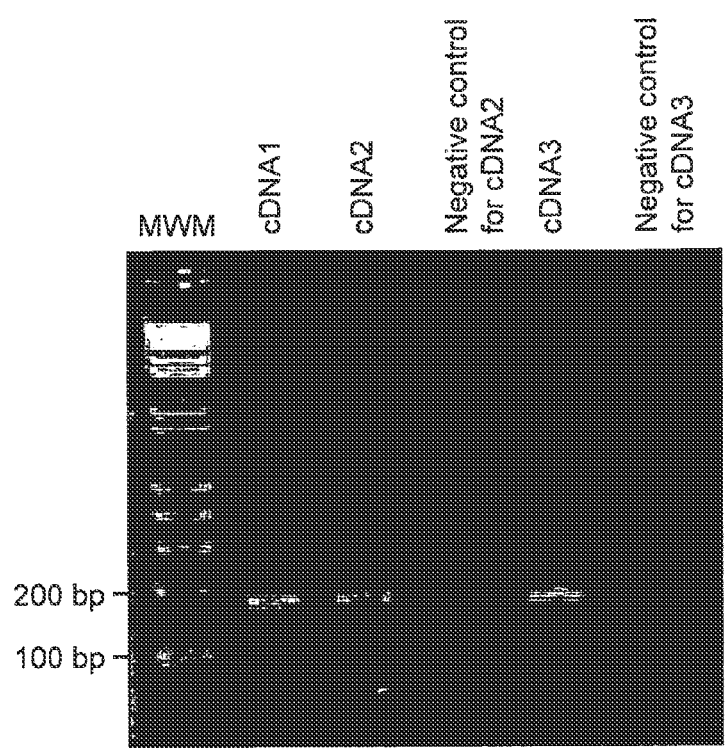
FIG. 33 shows the results of exon bridging PCR experiment #2 in Example 7. Negative controls are reactions in which no reverse transcriptase was added.

In experiment 1, products were observed following PCR and agarose gel electrophoresis (FIG. 32). These were weak and not consistently observed. Sequencing revealed that these were PCR artifacts not containing any sequence from SEQ ID NO:2. In experiment 2, products were observed following PCR and agarose gel electrophoresis (FIG. 33). This was expected, as the primer pair used amplifies LHPP (SEQ ID NO:9). No sequence from exon 1 (nucleotides 1-316) of SEQ ID NO:2 was detected in these products.

Conclusion

DEP2-1 and LHPP do not share a transcriptional start site.

EXAMPLE 8

Expression of LHPP, a Naturally Occurring Splice Variant Thereof, and DEP2-1, in Human Neuronal and Glial Cell Lines To establish feasibility of cell-based assays to screen for compositions that modulate the activity or expression of DEP2 products, quantitative PCR ("QPCR") experiments were conducted to detect expression of DEP2-1 (SEQ ID NO:2), LHPP (SEQ ID NO:9) and a naturally occurring splice variant thereof (SEQ ID NO:12).

Methods

Cells of six ATCC cell lines (SH-SY5H, SK-N_SH, LN18, H4, Ntera2 and U87MG) were suspended in RNALater (Ambion, Austin Tex.). Total RNA was isolated from each cell line using TRIZOL reagent (Invitrogen, Carlsbad Calif.) and purified using RNeasy columns (Qiagen, Valencia Calif.). Reverse transcription and PCR conditions were done as described in Example 4.

Results

Observed Ct values are shown in Table 14.

TABLE 14

| | SEQ ID NO: | | |
|---|---|---|---|
| | 2 | 9 | 12 |
| SH-SY5H | 40 | 40 | 40 |
| SK-N_SH | 31.71 | 24.82 | 23.65 |
| LN18 | 31.02 | 25.16 | 24.01 |
| H4 | 30.04 | 25.79 | 24.72 |
| Ntera2 | 29.35 | 24.91 | 23.76 |
| U87MG | 31.57 | 27.19 | 26.17 |

Conclusions

Cell-based assays to screen for compositions that modulate expression of SEQ ID NO:2, SEQ ID NO:9 or SEQ ID NO:12, or that modulate expression or activity of the corresponding proteins Dep2-1a (SEQ ID NO:3), Dep2-1b (SEQ ID NO:4) or Lhpp (SEQ ID NO:10), may be feasible using five of the six tested cell lines.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An isolated nucleic acid molecule selected from the group consisting of:
   (a) a nucleic acid consisting of nucleotides 352 to 771 of SEQ ID NO: 2;
   (b) a nucleic acid consisting of nucleotides 812 to 1162 of SEQ ID NO: 2;
   (c) the complement of (a), wherein the complement is identical in length to (a); and
   (d) the complement of (b), wherein the complement is identical in length to (b).

* * * * *

SEQUENCE LISTING

<160> NUMBER OF SEQ ID NOS: 82

<210> SEQ ID NO 1
<211> LENGTH: 159047
<212> TYPE: DNA
<213> ORGANISM: Homo sapiens

<400> SEQUENCE: 1

```
gtagatttgc tataacaggc tgaaagctca gtcagtggtg tatgcttcct ggcacactat    60
ggtgttcatg tgccacctgg ctagctctgg cccaaaagat gcaaatgaga gtccattgga   120
tcagggttct gggaaagctt ttgctttctg ggtataaagg gtcagactca gctgtcacat   180 gcccttttt cttttctttc ccctccttcc tgcctgaaat gcagtcatga tgcctcgggt   240
ggagcaggaa tcttgctagc gtgaggagca ggccacatgc tgagagagtg gtggagcaga   300
aagcaggagg cagcctgatg gtcctgggag ctgttgtccc atccaggatt tcctccctct   360
tggcttcttg atatatgagg aaaagtaaaa tctgatttgg ttgggcaact atggctgggt   420
ttctgttaca tgtagccaaa tgcaacccta acatagacaa tgccctacac tcattgcatc   480
ccaagaaaag cctggaattt tcagatcaag ttttagccta tcagtggccc acacttagag   540
acttgccaca tttttcaggt gagggacctg gatccctgta tttgtttctt gtcactactg   600
caagaaatta ccatatactt agtggcttaa acaacagat ttattattat agttctggag    660
gtaagaagtc ctaaacttga agtaccagca gggctgcatt ccttctggag gctctagggg   720
agaatccaat tctttgcctt ttttagcttc cagaggccac ctgcatttct tggctcatgg   780 ccccttgta ttcaaggcca gtagcacggt atcttcacac ctctctctct gacctctgct   840
tctgctgtca cacctccttc tctgactctg actctctcct gcttccctct ttcccttatg   900
aggactcatg tcattatact gggcccacct ggaccatcca ggataatctc cctacaggag   960
cataggctct gcaagatcta agtccttttt gccatgtcag gtaatatatt tagaggttgt  1020
ggggattggg aggtggacat ctcaaggggg cactattctg tctactgtag tcgtagaaat  1080
gaaaagggac ttgcccaaga gtacccacag agctgactga aaagaaacaa ctatgggtag  1140
gctcacacca ctggcagaag caccccttt cctcctcctt ggcatgaagc taaagcccag   1200
ccattctcca aggtccattt caggctgccc ctgcccagaa gccacagctg ccctcctagg  1260
cctgcagagg tcatcctctt gactgtgtct gtgtcactca ttgccacttg gcacacattt  1320
ggtcagcagt cgtgaaggtc ttccattgtt ctctgcccag tcttgatcct ggaaggcaag  1380
gatcacaccc tagaactttt ttgtgcccac tgcacagagt agggtctcaa tacgtgtacg  1440
gttcatgatg ttcctagcag attctccaaa ctgactcact cagcccctgg aacactaaaa  1500
actgcatttc ccagactcct ttgcagcgtg ggctaggttc caccaagcca gacacagtga  1560
aagtgagtgg gtggccacag gtggagggca cagtggtgga tatgttttgt tcttttgggg  1620
gcagctatgc tgggggctgc actaagtgat ggggcagtgg tcccaatgga gtagtaaaat  1680
taagtgtttc tcgtggctgc atggctcctg gctgtgtagg acttagaccc gtcatctgta  1740
agctccttca cctcatgtaa acaaaacccc tctagctgga gtggtgtcta ttgtctgcga  1800
ctaagaaccc ttatataagg tatactactc cccaacccca ttagtggaaa tcccaaaggg  1860
taggaactgt attttatttc acttgtaaac agctccccta gtaagcatgt caacaaaata  1920
tacacaattc attgaacccc ataacatttc aacgaattcc tcatcctttc tgtgaatcaa  1980
gagcctgaaa agaaatggtg aaataatatg atcctctctt ctttgaaagc tcaaagctat  2040
gttggaccag aagtaaagtg ttctcgtttc tatttaataa cttgaaaggt tccgaggggc  2100
cattgaggaa actcctccct tttaatatca atgtgtattt attgcaaaaa taatgtagca  2160
tcgagtggta ttttatagct tatccaaaaa cctcctgggt ttaacgcatt gtgatagtcc  2220
cgttttcttc tcagcccagg tcctatgcat cctcatctat gcagggctgt tatctgcata  2280 taatttttt tttttttaag acaaagtctt gctctgtcgc cccggctgga gtgcagtggt  2340
```

```
gcaatctcgg ctcactgcaa cctccgcctc ccaggttcaa gcggttcttc cgcctcagcc    2400
taccgagtag ctgggactac aggcatgcgc caccacacct aggtgatttt tgtatttta     2460 gtagagacag gggtttcacc atgttgacca ggctggtctc gaactcctga tctcaagcga    2520
tccacccgcc tcagcctccc aaagtgctgg gattacaggc ataagccact acgcccggcc    2580
tcaattttgt attgtacttt tcttcttt ctttaataga gacagggtct cactatgttg      2640
actaggttgg tctagaactc ctgggcacaa gctgtccgcc cgcttctgcc tcccaaagtg    2700
ctgggattgc aggcgtgaac caccgcccct ggctacaggt gccttcttgt ctcaatttgc    2760
ctttgacctt tcttagggac ttgttttctg cttttcctgc tctttgtccg ctgatctcct    2820
gggaagaaag cttccgaaaa ggacaccgtt tcaggggcga gtgacgccgg ggtgcccagg    2880
ccgcgcccca gttccgggtt tgcacccggt cttcttgccc tgccccgccc gcggactac    2940 agttcccagg cgcccctgcg cggccgcggc gccggcgccg gcgtcggttg ggacgcggag    3000
gcggagctga ggagcagggc cgggcgccat ggcaccgtgg ggcaagcggc tggctggcgt    3060
gcgcggggtg ctgcttgaca tctcgggcgt gctgtacgac agcggcgcgg gcggcggcac    3120
ggccatcgcc ggctcggtgg aggcggtggc caggtgagtg ggccccggga cgccgctggg    3180
gccgccgagc tctaagctca gcccgctccc tggctgccgg caggggcgg ggcggcaggg     3240 ggcggggccg cggcgcaggc cccgcctcgg tctcccctt cccacccggg tgcgcgcaca     3300
gtgctgacca cggacgaccc cactgttgcc cccggcgagc accaggactc tgctggttag    3360
ggctgcgcgg tcagacaggg cggccacctg gtacgtgcgc tgctgagcgc ttgacctgcg    3420
gccagtctga attgagatgt gctgtaagcg taaaatgcat accgattaac aagacttagc    3480
cgggcgcggt ggctcgcatc tgtgattcta gcacttgcag aggcagagga gggaggatcg    3540
cttgaggcta gggggttgga gaccaccctg gcaacatag ggagaccccg tctctgccaa     3600
aaatttaaaa attagccggg tgtggtggtg cacgcctgta ggcccagcca cttgggaggc    3660
tgaggcagga ggatcgcttg agcccaggag gtcaaggcta cagtgagctg tgatcacccc    3720
actgtactct agcctggact gcagagcgag acggtctcat aaacaaaacc cccaaaaaca    3780
ccagacttcg tgagtaaaat gtaaaataaa aacatgaaaa tgggttatgt tgtttgcctg    3840
ttgaaatgat atactttttg tttgttttgt tttgttcttt tcagatggag tcttgctctg    3900
tcgcccaggc tggagtgcaa tggcacgatc tcggctcact gcaacctccg cctcccgggt    3960
gcaagtgatt ctccccttc aggctcccga gtagctggga ttacaggcac ccgccatcat     4020
gcccagttac tttttttatt tgttttgttt gagacggagt tttgctcttg ttgcccaggc    4080
tggaatgcag tggtgcaatc tctgctgact gcaaccgccg cctcccaggt tcaagcgatt    4140
ctcctgcctc agcctcctga atagctggaa ttacaggcat gtgccaccac acccggctaa    4200
ttttttgtat tttagtaga cggggtttt caccatgttg ggcaggctgg tctctaactc      4260
ctgacctcag gtgatccacc tgcctcggcc tcccaaagtg ctgggattat aggcgtgagc    4320
cacatgccca gttgataata tttttaatat actgttttag gttaaaatat ttgaaattaa    4380 gtatacctttt ttttttaac ttttgttaat gtgcttatta gaaaacttta aattaccttt    4440
gtggctctca ttataattct gttggactgc attggtttag gtgagaggag gaggaagaga    4500
acatcgtgcc agccaagact tgaccatgag gacactttt tttttttgag acagttttgc     4560
tcttgttgcc caggccggag tgcagtggcg ccatctgggc tcactgcaac ctctgcctcc    4620
caggttcaag tgattctcct gcctcagcct cccaagtatc tgggattaca ggcacccgcc    4680
accacgccca gctaattttt gtattttgg tagacatggg gtttcaccat actggctagg     4740
```

```
ctggtctcga actcctgacc tcaactgatc cacctgcctg ggccttctaa agtgctggga    4800
ttacaggcgt gagccaccgc acctggctga cactttTctt tgtataattT tTTttttTga    4860
gacaaggtct cattatgttg ccagggtggt cttgaactcc ttggctcagg cagtcctcct    4920
gccttggtct cccaaagtgc taggattaca ggcatgagcc accacacctg gcctaatttt    4980
ttttTctTTT TTTTTTTTTT TTTTtgagac aaggtcttac tttgccaccc aggctggagt    5040
gcagtggttc aatctcactg caacctctac ctcaagggct caagagatcc tcccacctca    5100
gcctcccaag tagctggaac tacaggcacg tgccaccatg cccagctaat tTTTttgtgt    5160
tTTTtgtaga gatggggttt tgccatgttg cccaggccgg tcttgaactc ctgggctgaa    5220
gtgatctgcc tgcctcagct cccagagttc tgggattaga ggtgtgagcc actgtggcca    5280
gccagaagga cactttcagt agcatggttg gcaccactgg acctgggctt tgtaaggcct    5340
cctgttggca tcccaggtca gcactgccat gtgttgatag cagccgggaa agggctaact    5400
gccaggactt ggcctcccgg agtcactagc tgaggcaccc tggcttggta gcctgatgtc    5460
actgggactc aatataccta tctgtaggtg gcaattaact gagtctcttg gtccttctta    5520
gagaccccat tctaccaatc tgcatgtctg atgtctggga gctgctgaga taataggggac    5580
ccaaacggtc ccgcatagtg aagccggagg tgtttgggag gctgggaact gggaacaggg    5640
agacttggct tccaggagca agcacaaagg gcagcccaga cctaggacac tccgctgggt    5700
cctgggtctg ctctcagtgt tggctgaagt tcagggttaa gtgcattcct gaccttattc    5760
tccattactc caaagcttta gactagctca gtcacagatg agagcattct gtgagtggca    5820
ctggtgggaa tccagcagag ggctctgggc agtgttttgg ggtgaagtgg gcctcatctg    5880
gggagcagga agccagagct caatgctgtg actggggcag gcaaggcctc atgggagacc    5940
ctgccactca ttgcttgcgg aagatacatt tgacattatc taccagtggt tccacttctg    6000
agaatttgtc cttgtctcat gcgtgagaaa tgacatgagt acaaggtcat tcctggcagt    6060
acctTTtaaa tagcaaaaga ctggaaacag ctcagatacc catcagtagg ggagtattag    6120
ggtctgatgt gtggagggga gagggacagt aaagctgcag gcacacaggt aaatcatcct    6180
cacaggtggg cacacgggta aagcgcatca tcacaggtag gcctaagggg tgtgaagacg    6240
ggagggtact gagagtgtga tggacgaggg tggcctgtgc tagagagggg gtcgggacag    6300
ctctgaggag aaggcactgg acagacccgg agggataaga gggaactgtc tgcaggaaga    6360
ggcggaggaa gcgcattcca ggcagaagga atggtagctg caaagacctc aggaagagag    6420
cacttggcga gttcgagggc gtggggtggg ggagtgggta caccaggcag gaacttgagg    6480
ggcacggaga ggtgtccgga ctttatcctg agtggcagga agtcagtgaa gactctagat    6540
aggcatatca tgtggtctga tTTatatgtt ttaaagaaat acaaatgtaa aaagtgagac    6600
atacaagtca aatgaaagca agggagattt cctTTgaaac cttggagaga aggccTTTac    6660
atccaggcct tgaaatctag aaagcaaaaa caacgaacaa gcagcccaat agcaatatga    6720
gcaaaagatg caaacaggtc atggaagagg aagtgagaga ggctccgcct tactcaaata    6780
agaggtgtgt gatctcggct cactgcagcc tctgcctcct gggttcaagc cactcttgtg    6840
cctcagcctc ctgagcagct gggactacag gcatatgcca ccgtgcccag ctaaTTTTtg    6900
gtatTTTTag tagaggcagg atTTTaccat gatggccagg ctggtcccga actcctggct    6960
tcaagtgatt cacccacctt ggcctcccaa ggtgctggga tcacaggcgt gagccactgc    7020
gcccagcctg agaaatgcaa atTaaaacta tatcaagctg ccctgTTTca tcaaTTTgac    7080
```

```
aaaattggcc aaaatccaaa agtttgagaa cactttctct gtgagagttt gtggaaacag   7140
accctgccac acattgcttg cagaagatac atttgacatt atctaccagt ggttgcgctt   7200
ctgagaattt gtcctatctc gtgtgagaaa ggacacaagt acaaggtcat tcctggcaat   7260 gcctttaaa tagcaaaaga ctggaagcag ctcagatatc catcagtagg ggagttttag   7320
ggtctgtctg tttatacagc agaataacat gcagtgtaag aaggaatgag taccttgtct   7380
atagacatat tactagtgga gacagcaagc acacagcagg atgcacggtg cgctgtttct   7440
ggtatagaaa atgcagaaat gcaagaatgt atttctcctg ctgtgtttgc ataaagacac   7500
tggaaggacg caggctgctt cagagtctgg gaagagctgg aggataagga agtgggggc   7560 cactgtgtgg ttggagacag ggtaggagaa agactcttca ctgtataact ttgtatacca   7620
acgtttttgt ttttgttttt gaaacagagt gttgctctgt cacccagatt ggagggcagt   7680
ggtgcaattt tggcttactg taacctctgc ctcctgggtt caagtgatta tcctgcctca   7740
gcctcccgag tagctgagat tacaggcacc tgccaccatg cctggctaat ttttgtattt   7800
ttagtagaga tgggttttg ccacattggc caggctggtt cgaactcct gacctcatgt   7860 gatctgccca ccttggactc ccaaagtgct gggattacag gtgtgagcca ccgcgcccag   7920
cctgcatatc attttaaga ttttaaact atgtgaatgt gttttctatt caaaatatta   7980
caattcaaat attaaattga atattaaat tcaaatatt aacgtctggg cacagtggct   8040
catacctgta atcccagcac tttgggaggc tgaggtaga aggattgaga ccagcctggg   8100
caacacagcg agacccccat ctctacaaaa aatacaaaaa ttagccgggc atggtggtgc   8160
acgcctgtag tcccaactac ttgggaggct gaggcaggag aactgcctga gcccaggagt   8220
ttgaggctgc cgtgagctat gaatgtgcta ctgcactcca gcctgggtga cagagtgaga   8280
ctctaaaaaa aaaaaccatt gtttttaaa taaaatattt caaggagatc tctctggctg   8340
cagtgtggag aacaggctgg cagtagggca ggaggtgggg gggcttggac tgggtagaag   8400
gcaatggaga tgggaggaa ggcatgaatt aaagaggtgt tttggaagca ggacctatgg   8460
gacctgcgga catacggggt attgtggggg tcagggagaa cttgaaataa agggtggttt   8520
ccggtgtctg actggaacag ctggcagggt ggagagggg cagggagggg gtcatggggc   8580
gggaaccatg atggctcatg atgtatgtca agttcctggc ctggtgtttg gcacacagta   8640
gacccacaac agtgtaacat taaagaccac tttcttttct ttttcttttt tttttttttt   8700
tgagacagga tcttgatctg tctcccaggc tggagtgcag tgacacaatc acggctcact   8760
gcagccttga cctcctccta ggctcaaaaa aatctttcta cccaagtttc ccagatagct   8820
gggactacag gtatacctcc acatgcaggt ttttcttttg tgtgtgtgtg tgtttttgt   8880 tgttgttgtt gttgttgttt tgagacagtc tcactctgtc tcccaggctg gagtgcagtg   8940
gtatgatctc ggctcactgc agcctccgcc tcctgggttc aagggattct cctgcctcag   9000
agtagctggg attacaggtg cctgccacca tgcctggtta atcatttgta tttttagtag   9060
agacggggtt tcaccatgtt gaccaggctg gtctcaaact cctgacctca agtgatccac   9120
tcgcctgggc ctcccaaagt gctgggatta caggcatgag ccaccatgcc cagcccccaa   9180
gggacagttt gagccctggt ctgcccaacc cagaccccta cttggaatcc ttcagggaga   9240 aggggtgtt gggaaatgtc acaggcttct ctaacagctt attttgagca gatgacccc   9300 acgtgatata gaactgtcca acaaacgtgc agattccagg ttgtgacatt ggaaagggtt   9360
ctgttaactt ctctggggttc tgggttggtg tcttctgact gattgattgc caggagggtt   9420
ttgtttggat ttgctttggc tcctgcagat ttatctagct gggggtgtct ctggtagcag   9480
```

```
ctatactgta tacatctaac agcaatgtaa taacaatccc gaaatacacc acagcctgtt   9540
atgtagctgg gagaggctaa aatctccctt cccaaaagca tatgggatta tttttggtga   9600
ggggacatca cacccgtgat atgggaggtt ttgttattgt gctgtctgtg ggcctgcaga   9660
accgatggcc tggtctctca accccatggg cttcccatgc cataggacca agtcccatg   9720
tcctgccttg tccacgagga ccttctcaac tgacctttgt ggcctcttcc actggccccc   9780
agttacacag acttcttggt ggggttttca ctgaaggggc cgctgagctg tccagcaccc   9840
acaaacctgt ttccgcccac accagcgtgc ccttcggctc tcggcagacc ttggcagggc   9900
cccctttcagc ctttctgttg cttttaaggc gcaaggcccc tccactctgg cccagtgcct   9960
ctggggccag atcatcaccc tcagggcccg ggaagctccg tacaccctcc ctcgcatgcc  10020
tgtgggctc gtggcagatg cccagagtgg ctgcgaaggt ggtgcaggaa acgccccctc  10080
caggaaagtg tgcctgcttt tggaattttc cctggggatt ttccagagat gcaggacacc  10140
tgttttcctc gcctggtgat tgagccggga agccttcatg gagcaggccc tacttgccca  10200
ggtgaagtct gtgtggcctg cagccacggg ggcgagtggc cctgcgcctt tcatgctgtg  10260
gcctccttga tatgtacagc ctgctttgaa gtcctgcagg agctcaaagg aagttcctgg  10320
ggtgagacca gccgccgcag agggaaaagt gtgattggag tggggtgggg ggtcttaggg  10380
ttggcagggg gaacacatgc ctccgtggca gctcccggca ccatgggctc cctggcagca  10440
tcgtccgttc tctgagcctg cgaggggcga cacactgtca ccattcttct tcttggattt  10500
tctgtgatga tgggtcctcc gattttattg agggccacgg agcacggggg aagtagaagc  10560
tcaacttttt aaaataatat ccacagcaac agcagtcacc ccgcatcgag ggaggcctgt  10620
cgtgcgccag gcaggtgctt aaccacccac cttcccttca caccagcccc tgaggtgggg  10680
ggggcttcct ctttttcaaag tgaggaccaa aaatcggaga gattcaggaa ctggcagaag  10740
tagaaaatgt tgccgagccc tcattaaaga tgcatgcaca cacacacatt cgttcattta  10800
ttcctttttt attttttttt cattcattca ttcctttact catacactca acaagcaaac  10860
attgagtgcc tctgctgtac taaagacacc atcctaggcc ctggggatgt gcagcagtga  10920
acaggtggag ccgatgctgc agtcatgggg gaccagcagg cgacagcgtg cactcgggaa  10980
ggctagagca tctgagacac gcagtgaggt ggggagccct gggctgggta cctggcctcg  11040
cagatcccat ggcgagggag ctgggattgg aggatgctga gcgagccagc caggcaggca  11100
tctgggctaa gagcatccca gatgaaggag caggaggccc aaacctctga ggccacactg  11160
gtgctgctgc ccaggcaggg cccacttgct gctctaggac ttgtgggtgg gcgtggtcac  11220
aggccggagg acatctgtaa ccggccgtgt ccccccaaca ggccctttat tgaagccctt  11280
tcatgggcgg attgggttcc ccgaggggag ccattcagag gcagggccca gcacagcgag  11340
gggtgcagag gccggcctcg ggccctggg cctatggctg ggaggcatct gcatgtgaaa  11400
gggggtgggc atttactgca tcctgtcttg ggccactaaa gcacatctgc tgggcccagc  11460
ccaggcccgg ctcggcgttt ttggagccgg cggaaggaag aagacttggc ccagggcagc  11520
ctcataaagc aattcccacc caggaccgcc ccgatcgatc ggcctggtgc tgtggagcca  11580
ggcccacagc ccttccgtcc agtagcacct ctcaatcccc tgtgtgtctg ggtgccttcg  11640
ggatcctgat aaaacgtagg tgcctcctag taggtctgga acagcgaagg ccagggccag  11700
gggatctttg aagtccagct ggtcctggca ccccagtatc ccctccttca tgcccggctt  11760
ccctggtacc atccagccct agggacacag gtccctggga gtagcagcaa tagtaacaac  11820
```

```
aacaacaaca acaacaacaa caacaacaat aataataatg taggctgtgg gcctgggctg    11880
gaacttcatc tctattgcct catccaaccc ccacacgcgg tgtggcacct gccggagggg    11940
tctggcagga cattgtaggg agagggccat ttgtttgcat ttgtttaagc caacaggagt    12000
tttcctgatg caacctggac cttggacaag gggtgtttgt cgagaacgtg ctgtcgtcac    12060
ctgtggtccc atttgctgtc aggaggtgaa gcactttgtc ttcagagatg ggagccggtg    12120
ctctttcacc ctgggttctg tgatttcagc tgtcatttca acattttaag tttcataaga    12180
aataggtggc ctccttatgt aaacattctc accagcctgt gaatatacag agtgaaaagt    12240
ccaagtcctc catcctcgac caagtcccag tgacttcccc agggtgacac aatacatcct    12300
tttccttcgt attcctcaaa agcacagagg attttgagat gcagccttcc ctgactcttg    12360
tccagttctg cgggcacctg ccccatcact cttgaatgcc accgcccac cattgcccaa     12420 ggcatgtgtt tggttagtca caggtcactg gaggctggag accccttgca ggtccccggg    12480
ccaggagttt tgaattcttt gtagcctcag agcacttatc caaccaaatg aaattttgag    12540
tagaactcca aaattatata tatataatat atatattttat atattatata tatttttata   12600
tattatatat atttatatat ttatatatat ttatatatta tatatatttta tatttttata   12660 tatatttata tattatatat atttatatat ttatatatat ttatatatat tttatatata   12720
tttatatata tataaatttt tttatatttta tatattttt atatatttat atatattaca   12780 tatatttttta tatttttatat atatttatat atgtatttat atatatgtat atttatatat   12840
atttgtatat atatttatgt atatttatat atatttgtat atatatttat gtatatatat   12900
atttgtatat atatttgtat atatatatat ttatatataa atatttatga gaacagtgtt   12960
tgaatagtat attattttta atagggatgg gatcttaata tattgcccag gctggtctca    13020
aactcctggc ctcaaggagt cctcctgcct cagcctaccc agtagctggg attataggtg    13080
tgtgccaccg tgtctagctc agaatggaat atgttttctg tgttcaaatt tataatgttt    13140
gttctgaggt caactgatga gaatgatgga agtgttttta tgaataacaa tgttgggctg    13200
ggtgcagtgg ctcacgcctg taatccctgc actttgggag gccaaagcgg gcagatcaca    13260
taaggtcagg agtttgagac cagcctggcc cacatagtga aaccccgtc tttactaaat    13320 atacaaaaat cagctgggtg tggtgttgtg cgcctgtaat cctagctact gggaggctg    13380 aggcgtgaga attgcttgaa cccgagaggc agaggctggg gtgagccaag attgtgctac    13440
tgcaccccag cctgggagac acagcaagac tctgtctcaa aaaaaatgtt gaggtctgca    13500
gcagtgaacc acacaacaca gtttatatgc ttagaagttt atgtgagtgc tggaagcgag    13560
cttattagga gggatgagtg aatgttttct ggtttatcca gacttcagac tgttagacag    13620
ctatgaaaga atgacttcgc tctgtttggt gctgacatta gtttatatga tatgagtgct    13680
gtatatacca agtgaaaaag ctgtagaata atgtgtataa acttactttt tttttttttt    13740
ttgagacgca gtctcgctct gtcacccagg ctggagtgca gtggtgcgat ctcagctcac    13800
tgcaaccttg gcctcccggg ttcaagcgat tctcctcctc agcctcctga gtagctggga    13860
ctacaggcgc ctgccaccac gtctggctaa cttttgtatt tttagtagag acggagtttc    13920
actatgttga ccaggctggt tttgaactcc tgacctcagg tgatccgccc gcctcagctt    13980
cccaaagtgc tgggattaca ggcgtgagcc actgcgccca gcctaaactt ccattttgt     14040 taagagaaaa caaggaaac acaaccaccc ccgtatatct ggggtagagt cataatagaa     14100
tcacaaactt gaactgtatg gaagagact gaggaaaatc tgatggctgc ttgaaagctt     14160
tcccgtggct ctgctggcag gagtaaggtc tgcttctcag tttctgatct cagccttggt    14220
```

```
gggcggggt  caccctgtga  aaatcaaggg  cagccagggt  gggtctggca  caggattatt   14280
ggtttaccct  gcaggtgctg  cctctggttg  gaagcccttg  gccaattaca  agggagtgt   14340 ggcacaagtt  acaaagctca  tgaatggagt  cctgcccta   cccccagtgc  cccacaacgt   14400
gcaagaagcc  atattggcaa  agcagtgcca  cacctgccca  ctgtggtgtg  cagggtgatt   14460
tcccaggccc  ccggcaacag  gcacgttgct  gtccagcttg  tagaggagga  acttaaggtt   14520
cacagaagtg  ataggactta  ttcagacacc  ttttgagggg  gactgagggc  tgctgcttct   14580
gccagggcag  gcaccacctc  ttacctgttg  caaagcttaa  tcctgtcaca  gaaagtgcca   14640
ggtgtcagct  ctagtgtgag  agcgtgggtt  tccaatccca  gctctgcccc  atagttgcca   14700
tgtggcctca  aggaagtccc  ttagcgttcc  gtcaccccat  tatggctgca  gctcaagggc   14760 cccagttcc   tatgtgtaat  tcctgtaccc  aggctgcaag  aattaagtga  aatattttct   14820
cttaaaccaa  tgtttgggtg  gggcgaggcg  actcatgcct  gtaatcccag  cactttggga   14880
ggccgaggca  agtggatcac  ctgaggtcag  gagttcaaga  ccagcctggc  caacatggtg   14940 aaacccccgtc  tcactaaaaa  tataaaaaaa  ttagctgggt  gcagtggttt  gcacctctaa   15000
taccaactac  tcaggagact  gaagaatcac  ttgaacctgg  gaggcggagg  ttgcagtgag   15060
ctgagattgc  accactgcac  tccagcctgg  gcaataccag  cgagactcgg  tctcaaaaaa   15120
gcaaaaacaa  acaaaagcca  acgttttcct  ttttttttaa  gttttgttt   tcttttcctt   15180 tttaccttaa  actatcagga  gataaaagcc  aacgttttac  ttattccata  tctaggagct   15240
aaaggagcat  tttgttgttg  aagggtcaaa  taattttgaa  gagtgggttg  ctttgccctt   15300
tttttttttt  tttttttttt  tttgagacag  gtctcactt   tgtcacctag  gctggagtgc   15360
agtggcacaa  tcttggctca  ctgcagcctc  gacctcctgg  gctcaagcga  tcctttcacc   15420
tcagccccca  aagtagctga  gactacaagt  gcacaccact  gcacctggcc  aatttttgta   15480
tttttagtac  agacaaggtt  ttgccacgtt  gcccaggctg  gtcttgaact  ccagagctca   15540
acggatctgc  ccacctcagt  ctcccaaagt  gttgggatta  caagtatgaa  ccaccgtgcc   15600
cggccatatg  aagtcttgta  gttgttgaac  tcggtgtaca  tgctaaacca  aagcacacag   15660
ttctgctcaa  ggagctgtat  tttccacatc  tgtttgtatt  ttcatgaagc  caacataaaa   15720
ggattctcat  cccagttctg  tccctagaca  agtcactgaa  cccctccaaa  ccacaggtcc   15780
catctccaaa  cagcaggtcc  catctctaaa  ccacaggtcc  catctccaaa  ccacaggtcc   15840
catctgtaaa  tggaaacatg  aacccacctc  tcagactgtc  aagaggattc  gatgtgaaca   15900
tgccgttggg  gctcggtgga  ggaggagcca  gtcaccgggc  gctgctgtag  ccactgctgg   15960
ggctcagttc  accctgggct  ccctgctggt  gtaaacttc   ccctctttct  aaaggtgccc   16020
ctgggcgata  cactctgggc  tcctcctgct  ggcctcctc   ccagggcacc  tggcttcctc   16080
tcagaatgta  cctgccccaa  cagtgggttt  gtcagagacg  tggttgtcat  tgtcaccacc   16140
acagcaatta  ctgccattta  tttagtattt  gaaatgtgcc  aggtgcttct  catgtctttt   16200 tttttgaaa   tggagtctcg  ctctgtcgcc  caggctggag  tgcagtggtg  ccatctcagc   16260
gcactgcaac  ctctgccacc  caggttctag  tgattctcct  gcctcagcct  cctgaatagc   16320
tgggattaca  ggtgtgcacc  accacaccca  gctaactttt  gtattttaaa  tagagatggg   16380
gtttcactgt  gttgttcgcc  atgttggcca  ggctggtctc  aaactcctga  cctcaagtga   16440
cccacccgcc  ttggcctccc  aaagtgctgg  ggattacagg  catgagccgg  tggtcaggag   16500
ttcgagacca  gcctggccaa  catggtgaaa  ccccatctct  actaaaaata  caaaaataa   16560
```

```
gctgggcata gtggcgggtg cctgtaatcc cagctacttg ggaggctgag gcaggaggat    16620
cacttgaacc tgggaggcag aggttgcagt gagccaagat catgccactg cactccagcc    16680
tgggtgactg agtgagactc cgtctcaaaa ataaaataaa ataaaaaata aataatatga    16740
tcttcatgac agccctgtcc agtagctact gttggtgcct cattttacag gtgaggaaac    16800
tgaggttgca gagggttagg tgacaagcca cagtcataca gggaggaggt gtgtctgctt    16860
cccgagctga gctcccacct tacttacagg ggcctggcct ttgtcccctg cagccaccat    16920
ggccctcagg gacgtcgggc tgctgctgag gctcctaggc tgaggagtgg aagaaaggag    16980
ccaggatccc cacccctcac ccccacatgc cacgaggcat ttcctgtccc tctgggcctt    17040
agtatccccc tctgtgaaat gagacactcg ggctgtgtgg tctccaaagt ctctggctgc    17100
cgattcccat gtacttcatt ctaaattgcg tttattgatt cctgggacat cgatgcttgt    17160
gggatcaaca tgtccctgtg atctgggctc cgtggcacag gcacttcaga gaacactcta    17220
gatgggagtt ctgccggcag gtgaggaggc gcaggtacgg gagggtgtgc tgcgtgtttt    17280
ataagtgccc tagctggggg ccggcccccag cttgacctca ttgccgtccc gctaaggtga    17340
ctgcccagct gacccagacc aggaggccca gctaggtccc agctcctgcg tcactgtgtc    17400
tcttctctcc attcaaactt tggactctga tgactcaagg ctctgtgcag gtgctcaaca    17460
gcgtctagtg gacctgttgc cctggccggt cagctggaag gaggagcaag tgcaggaggc    17520
tcagctggag ccagtgtgag gccgtgccct gtgccagggg cccgtggcat ctctgctgtg    17580
cccagccttt acctcgtctc cttcatggca gccctggaga gctggaaggc tgggcaccac    17640
catcacccat cactgtttat ggctcgggtt ccaagactcc accagcctgg tgcgcgcgcc    17700
agggtgggaa gccagacccc acgcccaggg gacagatgcc gatctgttgc tgctcctacc    17760
tgcaggtggt cccccagccc aagctggtgt gcttcatggt gcagggcacg gggtgggctc    17820
atgcgcacat cagtgtgggc gtccccgggg catatgtgaa taactgtatt tttctattga    17880
aaaaacaact ctgctctgct tacggggctc ctgcttgacc ttctgttttg gaaaattgga    17940
tttttggagg aaatcagcac cttgtgggtt tcaattctcc aaacatgcgt gttcaatctc    18000
cattgctttc caaaggggga gcgactgaag atctgaaaat tagacagtgg ctagcactgc    18060
ccagaggccc cgttattaaa aacatttcaa ggccgggtgc cggtggctta cgcctgtaat    18120
cccagcactt tgggaggctg agactggcgg atcacgaggt caggagttca agaccagcct    18180
agccaacata gcgaaacccg tctactaaaa atacaaaaat tagctgtgca tggtggcacg    18240
cgcctgtagt cccaactact cgggaggttg aggcaggaga atcgcttgaa cctgggaggc    18300
agaggttgtg gtaagttgag attgtgccac tgcactccag cctgggcaac ggagtgagac    18360
tctgtctcaa aacaaaaaca tttcatgcca gtggcattgc tgagggcctg gggctggtgc    18420
tgcacctgca tctcttttca ctacaacccc cggggaaggg ggtggtcaat gtcctttccc    18480
ctctctgagg aaactgaggc attgagcttg tatttctctg cactggttcc catttcagta    18540
gtaataggga ccctccagca caccaggtga tgtctgcaat gtggcccag aggcaggagc    18600 aggctgggag ttaggaggct gaagcctgat gtggggagc gctgccccc aaccccactc    18660 cctgggaacc aaccctccac ccctttgccc tgctgcctcc acaccccttt cctctggctg    18720
tgaatttctc cattaccaag tgggcccgtc agatctggaa cttgggtcag ttaggtgctt    18780
ctcccagtaa agcacctact gtgctgggta ctgggtactg tgcccggtag atttttgggca    18840 ggattctaga gagcatctgg caaagttgct gcaggaaagg gccagtcact gcctgccagt    18900
ctcggcccct gtgaatgcac gagttgacat ttctcaaatt ccagcctcac tttgtgggcc    18960
```

```
aggcagccct tctgacctat gagctgccaa actgagcctt ttgatgacac tgccccgag   19020 gattccctgc agccctatgt cctcctgagc acctggtggc ccctctgtgg cctccgagac   19080
cctggcctgg gtgctcactg cccctcatcc ctacacagga gatgctgggg tgactcctct   19140
gttggtaaac caaggctctg gttgctgagg atggggctgg tcctgcgcca gggtgccccc   19200
aggtgctgat cttggctcca ctgtggttgg gcaccaggca tggcagaggt gctgagcaga   19260
caaaaccctg ccctcccaag ccccgggctt gcagaggagg caggaggagg gaggtggtga   19320
tgtcaggacc agagcagcac caagggctgt gtgggcgcag ctcggaggat gggatctggc   19380
tgggtgcatg gctgtggggc ctccaggagg aagaggtgta tgaaccctgc tttgtaggat   19440
gatcagggtc aggccccagg ggagcatgaa agcaaagact cagggtgcta tgagggcctc   19500
tgggtcacac gaaggtgacc agtaccgggg ctagagggca gggggcccag ctgggagggg   19560
ctcatgctgc ccttttcctg aggcccctg ctgcctgccc agtctcccct ccgagggatc   19620
ccattctccc tccagcctca ggaccctcgg cggtccccag agggctagct attgagctgt   19680
cccaaggtca ctcaggatgt ccaataattg tcctaacagt ttacctgctg tggaacagta   19740
atgagagggt tttcattatt tgcgggtgag cgctcctggc agatgccaac agccagcaga   19800
tgtggagagt ccgaggtgat ttgtaagggc cggttcatct gatgcacggt aattgccccg   19860
ggcgatgttg tcactcagag gctcgtcctg gcctgctgag atgaggtaaa ggtcagttca   19920
aagatccagt ttgggccagg cgcggtggct caggccgggt gccatggctc acgcctgtaa   19980
ttccagcact ttgggaggcc gaggcaggtg gatcactgga gattgggagt tcaagaccag   20040
cctgggcaac atggtgagac cccgtctcta ctaaaaatat aaaaattagc cgggcatggt   20100
ggtgggcacc tgtaatccca gctactcggg agactgaggc aggagaattg cttgaaccca   20160
ggaggcggag gttgcagtga gctgagattg tgccattgca ctccagcctg gctgacagag   20220
tgagactctg tctcaaaaaa aaaaaaaaaa agatccagtt tggctacagg aagtgggagc   20280
aaatccccac tcccatggga ctcctgggga ggaggcagcg tgctgaggtg ggggccatgg   20340
tctcagaggg gctatctggc agccaggacc ctgcagaagg ccccttcccc caaggttctt   20400
gggtggtggg gtgggaacag cccatcccag agctgggctt gtccttcttt gcaggggctc   20460
tttgtacagc tctctgcaag ccttgctggg gtcctggagc cgcacctgac tagggctttc   20520
ctgatatttt ggaattcttg tacttcatgc ctcccaaggc ttagtctgtg acatctggtg   20580
gcaggcccca cggagggatg acaagggttt gcttccttag ctgtcctagt cggcctgggc   20640
tgccataaca agtgccattg actggggact tcaacagcag acgtttattt tttcacagtt   20700
ctggaggctg gaaggctgat atcagggggt cggcatggcc agtttctggt gaggcccctt   20760
ttctgggctt gtaagcaggt gccggcttgc tgtgtgctca catggcctct ttgtgcattc   20820
atgagggtgc tctctggtgt ctcttcctcc taggacactg atcctgtcat gtgggagtcc   20880 caccccttatg ccttcatttc acctgaatta ctccacaaag gccctgtctc cagatgcagt   20940
cacattgggg gttaggactc cccatctggg ctcacaggcc ttgctgctta caagctgtgt   21000
gaccttggtc aggtctctgt ctcctggggc ctccatcttc tcctttctag agtggagata   21060
atggttcttg cctcataggc tcgtttaccc agtgggtacg acttactgag ggccacctga   21120
cagccaggca cctgggcctt ggggatgtcc attagggaca gcaaataccT tgggcacgag   21180
gacaaaatca gatcatggat cctgagtgac accaccgtcc ttacccagat gcaaggctca   21240
gtataatgtt gtattaatat tttactcttt aaacaatagt gcctactttc tttattttca   21300
```

```
gtaatttaaa ataaggaaga ggcaacctgg ggctggtccc tggtggtcag aatgggtctc   21360
tggtgacggc tcaaaggggg gtgtggtccg gggcgcagaa ggacagaacc caatgggagc   21420
ggacttaccc cagcatttca catccgattt ttcagggata gatttcgtct ctaaaactag   21480
cacttgatat tataagagca tataggctga atgaacttat attgctattt cagaggaggc   21540
cagtggctta agagtcccaa agtgagttct gtgacttact catgtttcat ccacatctga   21600
agttgtgttt ggaataacag atgtgaggca ctgtcatctc actgtcacat cgattgctca   21660
ctgttctgag aaggtcacat catcattcat tagcaataat tagtcccagg ggaccccctg   21720
cacttcttca ctcaactgct ccattaactt gggtgcaaat cacacgttcc aggtgccaat   21780
caatggagat ctatccataa tgtacaaggt gacgctatta gttacaatat attaactgcc   21840
taatttaaaa ataaaactat ctttatgaag ggcaattaac cactaagtgt aattgataat   21900
tcataaacct ctgattagga aagacaaata ataagaaagg aatgaatcac ccatcctatt   21960
gaagaagacg ttgccagcct ctggtctgca ttcactatgt ggtcagcaga tctacagatt   22020
tcttcctaaa ttgcacctgt cagctccagg gctgggggtc tggaggctca tttcagtgca   22080
gaaacatgtg ttttcaccac tgaagcctgt ctgtttctgt tgggggttat aaggaggctg   22140
caggctcagg acaccctcag ggaagtagtg ggtgaggtca tttagacttc tcagtcagtc   22200
agtcattcag caaatgttaa tgggggattg tggagtgcca agccctgtgg gaagccctgg   22260
ggatgccgtg gagacccgaa tagattcatc cctgaactcc tggagctcgt aggccagtga   22320
gaaagacaat tgcgtaaatc agatgattgg agacactggt tagtgttaca aacaaaaact   22380
gacagagaca gggcggaggc aatggcacac tggatggtgg gaggaaggga cattggcctg   22440
agtcctgcca ccttttttgta gtagctgtca ctaccactca tggctgtatt tggggccctc   22500
tctcactggt ggggaatcgt gcctggctta tctgcccccct ttttttttttt ttttttttttt   22560 gcgacagagt ctcactgtgt gacccaggct ggagggcagt ggcttgatct tggctcactg   22620
tgacctccac ctcctgggtt caagagattc ttctacctca gcctcccgag tagctaggac   22680
tacaggtgcc cgccaccaca cctggctaat tttttttggt attttttagta cagacaggat   22740 ttctccatgt tgaccaggct gatctcaaac tcctgccctc aagtgatcca cccacctcga   22800
cctcccaaag tgctggggtt acaggactga gccaccatgc tctgccttat ctgccctctc   22860
agtggtcctc cactccagcc tcatttcctg gctccacctt ccacataccc cacgctgctc   22920
gagttctttc tatccgagag ggtggggcca gtgcacacct gcctgtgcgc aaggtgggtg   22980
gcccttccca ccacctggcc tgcccttccc tgccatctcc ttgtccgtcc ctcaggtctc   23040
cagttgggcc tgaatcccca gtcttttaag accccacact gggctgtgtc ctttcccac   23100 tatgtgggag agctccagga gtgctgattt cctgttcctg actccactgt gtgtagatat   23160
cagctccatc tccaaagtct caggctcaag agcggaacag aaagcccttg acatttctgg   23220
gattcagtcc ctcacccata acatggataa attacattca cactgggttc agtttgagtt   23280 gagttttttag ttgggtctca cttgctcaga tggaagttga tttcaagccg tagttctagt   23340
aactgggttg aatctgcgtg tattcatttc attgggccac atctgtaaac agaacttgag   23400
cacatgcctc ctctctatgt gtgttttcta taaattttaa attattcatt taacactatt   23460
gcttaggtta taaaaaatac acaacttgaa agaataggtg aagagccaag atgtctgcat   23520
ctttggagat cagtggaatg tgtgtgtttc gggacctgtc tgagaacagt gccagatgca   23580
attagcatgg ctgattaatt ttactagggt ttcttaaaag tgcctccgg cccttgggct   23640 tgcagcttga tgtctttttcc acgagtccac actgcagctc catgcagatg tcaaatatga   23700
```

```
ccgctgcctt gttggggccg gtttgtccag gaagggatct tgtgatcttg gcgagggagc    23760
caggtcctgc ctgtcaccct cccccaggt ctgagtgacc caccccgcct gcctctgtag    23820
gttcctctag cacgctcggg tcccttcctg gtgggcgcca ggtcctccag cctcctctcc    23880
ctgcacagaa gcaccacacc ctggccctct ctcttgcttc cccagggagg cctcccctga    23940
ccttcctacc ccaccttgtc accctctgtc tgctcaccct gtttatattc tgcatagcgt    24000
ctctctcttc tcagtcacaa attgcccttc ctttgcaggg tctcttgttc ctattccaac    24060
ctcctcctat tccaacctgg atggtggcct ggagatcagg gaactttttcc atgctcacga    24120 ctacagctct gtgcaccagg ccagtgccag gcacgtagta ggcgctcagt gacagtttgc    24180
agaagggtgg atgttacttc atttggtgcg ttctgagaac ttgcccaggt gcagcctgga    24240
ttcgcgggtc tcctatgaag tcaggaggga agaagctcgg tgccgccggc cagtggcagc    24300
atcctgaagt tcatgagacc tccaggctgg gtttgggcag ggtccacgtc ctgtctgtcc    24360
atcccggaat gttggtgtcc ctgatgactt tggcaaacct ttctccattg acagtgatga    24420
gaagacaaac ctgtctcggg ccatctgcct ttgtacttttt gggaagtat ggatccagag    24480 ttagtaaggc gtggacgtgt gcagctcact tgcaagtgga aatgccaaat gtggtggaaa    24540
gggacagaga aatagctgtg gacattcaga ggtggcccct agccaggctg agcaggattg    24600
tggagaggag gtattgcatg gatctcaggg gctgggtaga agtggccagg caggtgggcc    24660
aggcacggtg gctcacacct gtaatcccag cactttggga cacctgaggt caggagttcg    24720
agaccagcct tgctaacata gtgaaacccc atctgtacta aaatacaaa aaattagcca    24780 ggtatgatgg caggcgcctg taatcccagc tgctctggag gctgaggcag gagaatcgct    24840
tgaatctggg aggcggaggt tgcagtgagc tgagatcatg ccactgcact ccagcctggg    24900
cgacaagagc gagactccat ctcaaaaata aagaaataaa aaaaataaag aagtggcaca    24960
ggtagagagg cggggggaca gagttgcatt ccaggcaagg ggagaggcaa tgaaaagggg    25020
ggtcaggtgg ggaacctcgg ggagcctcag gtgtatgaag tccagtgagg atggaaaaga    25080
gttgtcgggg cgtggtatgg gggtcctctg agaagggatc tgcttcagct cagaaatccc    25140
agcctgaaca catcctggat cagccaggac ccctcagg gctcgcagtg gcctagtctg    25200
ctctgggctt tgctggatgc ccttcgagaa tcaccgcgca acctccttca gaggcccaac    25260
actccacgtg ctgacttccc gggcctgtgt ctccctgcc gcagactgaa gcgttccgg    25320 ctgaaggtga ggttctgcac caacgagtcg cagaagtccc gggcagagct ggtggggcag    25380
cttcagaggc tgggatttga catctctgag caggaggtga ccgccccggc accagctgcc    25440
tgccagatcc tgaaggagcg aggcctgcga ccataccctgc tcatccatga cggtaggcct    25500
gtcggacacc aggacctcac gggggtgaaa gctccccttt cccagggtgg gggctgtgca    25560
gagagcctct ttcactgggc caaaccactg actgagctag gccaccaaca ctcatgggtt    25620
gggggtaaaa acctcatggg acttcctgct ggggctggg ggcaggttag gacccagctc    25680
tgtccattcc ttggcctcac accagagggt ccttagagca ggttctggat ggctcctggg    25740
aggaaaatcc taggctctct ttcctgatct aggatggacc aagcggccag ggaattgtca    25800
aggtggcgga gttctagctc ctgttgagaa agagacagag agagagagag agagagagag    25860
agaaaatgag aatgagaatg aatgaatata aatgagaagc tacattgagg tccatagctt    25920
ctaacgtctg gcaccatagc cttcaactat gtgaaaacca gccctgctct ttggaacagt    25980
ttgcaaatgg cgtaggaaca aggtttgcat cctgatttta gtctgaatgc aagaacagac    26040
```

```
agccccttgg accctcagtg gggaggtttt cttggaatga agcagaagga acaatattac    26100
tggtgcctcc tgaatattta aaaagaagag acattagcaa ttccagacac ttctccattg    26160
gtccactgca ccttcttcct tcctctgcac ttgatatttt tagttttaca aactgctagg    26220
cagaggcaaa catggttttt tcctttccag ggcaaggtgg gggctctcaa gaagtggcgg    26280
gtgctccctg gaaagcctag atgtcgactt catagccctg gtgccagtta agggtgacag    26340
gcctggcctt tagaaatcat gtttctcaaa attccttctc tgtaatctag gatccctgct    26400
agtgccttta gaacatggtc ttcaaagaaa gaagatttaa gaaaaatatc ttgccccacc    26460
ctccagaaaa gggttgctgg acccgggagt ggagctggaa gaagccagca ggagagggaa    26520
gtgggcatcc gcttggaggg tggccttggc cagtgaatca gacaagcaga cggcaaagct    26580
gggaggctga agggaggatg aatgcccttc ctcagctgta atcctgcatc cgtgttttca    26640
ataactagac ccttgttttc agacttggaa ttttttttt cagtcattgg tggatttttct    26700 gtctaacatt ttatgaaaat ttcaagcat ccaacaaagt tcaaataatt tttacttgga    26760
atagttttgg tttttttttt ggagacagag tcttgctctg tcacccaggc tggagtacaa    26820
cagtggtgtg atcttggctt cctgtgactt ccgcttccct ggttcaagcg attcttctgc    26880
ctcagccccc caagtagctg gggttacagg tgtgtgccac cacgcccgcc taattttgt     26940 attttagta gagatggggt ttcaccatgt tggccaggct cgtcttaaac tcctgacctc    27000
aggtgatcca cccaccttgg cctcccaaag tgctgggatt acaggcgtga gccaccgcct    27060
ccggtcttac ttggcatagt tttatacct tcacctagat tgtcaatgac atttttgat    27120 attttcttca ctttatatcc atccatccct ccgtctgtct atccatgtta ttatttagat    27180
gcatttccga gtaaaatgca gacacgggta tactccccta tacacttcag catatcattg    27240
gagtttggta tttgtttacg gttttttcctg tttgatgtaa aatttacata caatgaaatg    27300
tacacacgtc aagtgtactt ttgctgagtt ttgacatatg catgcaccca tggaacccaa    27360
ccccgtgaag agctagacca tcaccatcac tgacagctct gacagctacc tcgcaccttg    27420
cccaggtggt cttcacccct tgtcccctta gaggcaacca ctgtttggat tttttccgtt    27480
ataaataagt tttcctattc tagaattta tgtaaataga atcatacagt atataattgt    27540 gctgggcct ccagtgctac ccccaggctg aatgattcat tagcaggact cacagaactt    27600
agaaaaggta ttacactccc agttagactt attactgtga aagaataaag attaaattca    27660
gcgaagagag gagacacatg gggcaaagtc taggagaaga caggcatgaa cttccagttg    27720
tcccttcgaa atggagtcct actgggcaca cttgattctc ccagcgatga tgtgtgacaa    27780
cacatgggaa gcattggcca ccagggaagc tcactggagc ctcagtgtcc agggtttttg    27840
tgtagacatt agcaccctgtg tgactgactt tagcgactca gtctccagcc ccacagagtc    27900
caaactgata cagctgggcc agggccgcag ggatacagaa acaggtgttc actgtaagcc    27960
aagctgttag cgtaaatgat ctggtcagac tgagagagca gggcccgagg ccttgagcat    28020
acaaaacccc ttatcaggta gaacattgca gtggctcaga ggttatctcc caggagccag    28080
tcctgaagac aggccttttt tggaatgtac agggtttgag caacctagtc ctgctgagtt    28140
aaccctttcc gtcacagtag tcttttgtgt aaggcttctt ttacccaacg taatgttttt    28200
gagactcatc catattattg catgtatcag cagtgttgtt cattttatt gcagaatagt    28260 attccattga gtgaacagac cacagtttat ccattcacat gttgttgata cctggattgt    28320
gaccagtttc agtctattat gagcaaatct gctatgaaca ttcttacaca gttcttttgg    28380 gtaaataccct agcagcgaaa ttactgggtc atagggtaca tgtatgttca cctttgtaaa    28440
```

```
attctgccag accttttttt cagagggatt gcaatatttt acacgtcctc catctgctgc   28500
agctgttcag tatcctcacc agaccttggt gttatcagtc tttttaattc tcaccattct   28560
ggtgggtatg aaatcgtatc tcattgtgta tttcagtttc tttctttctt tttttttttt   28620
tttttttgaga cagagtctcg ctctgttgcc caggctggaa tacagtggtg caatctcagc   28680
ccactgcaac ctctgcctct cgggttcaag tgattctact gcctcagact cctgagtagc   28740
tgagattaca ggcggccgcc accgtgccgg gctgattgtt gtattttag tagagatggg   28800
attttgacca tgttggccag gctggtctcg aactcctgaa ctcaggcgat ccgcccacct   28860
tgacctccca aagtgctggg attacaggca tgagccaccg cacctggcct cagtttcttt   28920
tcaatttaga aaggtcaaca tctagtccta agagagatga cagcatgttt cttctaggat   28980
ctgaaaacac agatccaatg atttgatgta tccttgcaaa ttttcctatt ttaatttaaa   29040
atgggggaag acaaagaagg agaaggagga agagagtttc ctaagggagc tggtgaactg   29100
gacctgtggg gatggaattc tgcttttttct tcaggacata tgtgtggggt tgcctgaaat   29160
gtgtcaacgg ttcttacagt ttgggaccag tagtgccaac cctccaaggc ttgtgcagcc   29220
ccatttcctc ctgctgcagg ctctcagtgt ctttctgagca gatttccctt ctcagtagca   29280
aagctgtggg tttcctgcct gcgatagtga cctcagggag ctcctggggc tgatgtggta   29340
ttgggatgga gggtcctggg tgtgtccacc tttctcctca taagccctct ctgaggagcc   29400
gaattccctc ctctgtcaaa taggaataac ccttctgtgt ctacctccca tggcagctgt   29460
gatgatcaga aagaaatgca tctgagaaag ggggaggaca tgtgaaaggt gtccctggta   29520
ggagatgggg aggtaggcca tgtcctccca gggctccgtg gcactctgtc tctctctctc   29580
tttccaggag tccgctcaga atttgatcag atcgacacat ccaacccaaa ctgtgtggta   29640
attgcagacg caggagaaag cttttcttat caaaacatga ataacgcctt ccaggtgctc   29700
atggagctgg aaaaacctgt gctcatatca ctgggaaaag ggtaagttgg ctccagggag   29760
agtcatttct cggtgcttta gatgatgctg tgccagtctc caacttgcgg aatcaggcag   29820
agaaggatgc agaaggggag gtgggaggag caccggtgat cttcttttcc ctccctttt   29880
catgctttct ctcttcattt ctttattcct ctcctttaat catttcttta ggaaatagga   29940
acactgtctt caggagctgg ttgatcaagc ttccatgtgg agtctagact agaagagggc   30000
gtcattgcag agggagaccc tctggagatc tcagaggcca agtgttgatt gtcccaagtt   30060
tagagcaaag aaggagaagg tgcatttgca taggatgtag cagggtgttg gagaatgctc   30120
tcaagggttg tctaattagt aaaacatagg cttgagggcc tacccagtct gggcaccgac   30180
agtctctggc cacagatcac tgtctctgtg aagttgtgat tttgtgatca gtgttttgtc   30240
tgagccttta gcacatgcct tgccatctct ttcttaaaca aaacagtgtt ggttattttt   30300
aacattttc ttacactgag atagcacatg ttcattgaag aaaaattaga caatacagat   30360
gagcaaaaga agaaaccaga aagtattttt agtcccactg cacgaggaaa acacctgtcc   30420
ctattttggt gtatgtcctt gcaagtggct tcctgtgcga atagactatt atggatggag   30480
atgttcacag catcgatgtc acacttgacc ttgttttgtc atctgttttt tattgttcac   30540
caaacaatat ttgtgactga cttagcatgc agcaaatgga tatgtcttgg ggcatggtta   30600
tctatggtgt ggctatcttg tatatatata tattttttaa gactgagtct cgctctgtca   30660
cccaggctgg agtgcagcgg cgtgatctcg gctcgctgca acctctccct cccgggttca   30720
agcgattctc ctgcctcagc ctcctgagta gctgggacta caggcgcccg ccaccatccc   30780
```

```
agctaattttt tatatttttg gtagaggcgg ggtttcacca tgttggccag gatggtctca   30840
atctcctgac cttgtgatcc gcccgccttg gcctcccaaa gtgctgggat tacaggcatg   30900
agccaccgcc cccaacctct tgtaattttt ttcttttttt ttttttctgc ttataagttt   30960
attcaatgca aaataaccct caccagtttt actgaggtgg ctgaccatgt ccacgaccaa   31020
atacgcctgt aaactgaaat tcggttgctg acccattccc agcctcagct ttctcactgg   31080 caccagggg acagcactcc atctgtgggt gtctctttct ctctatggct gtctgtctgt   31140
gggtgtctct ctctgtctgt gggtgtcttt cgccatctgt gggtatctct ctctgtctgt   31200
gggtatctct cccatctgtg ggtgtccatc tctgtctttg ggtgtctctc tttgtgagtg   31260
tctctgtctg tggttgtctc tgtctgtggg tgtctctctg tgagtgtccc tgtgagtgtc   31320
tctgtctgtg ggtgtctctc ctcgtctgtg ggtatctctc cctgtctgtg ggtgtctctg   31380
ttggcttccc cacttgtggg tcttgcaggt cggtcacgct ccagaccttt aggccgcagc   31440
ctgccagtct ccagaccgct gtggcatggg gtagcagaca cgctctccag gggcagatgg   31500
tggtaatcgc agagattctg gatccccatg tgggtgaggt accagtagaa atgtctccag   31560
gcaaactcct tcctgcaacc tcaggacctg agagactgcc tggccttcat gacgtgaagg   31620
ttgggcacat tctcatctgc cagctccggg tcttaggcag gtggacattc ttcttggcta   31680
ccgtgactcc ctccttaaaa aggagttcat aaatagcaat ctggttcttc ttaggcatca   31740
acatctctgc agctgtaggg tccaggtccg gggctggaaa gcatgatttt tttctaactg   31800
atctctgctg atggcatcta gattgttcct ggttttcac cataccaggg ctgtgatgag   31860
catcttggtg catttcggat gacgtctcca gatacagtta cagaacgagt attttttgagg   31920 ttcttgaggc atgttgccaa gttgtttcca gaaagctgca cagacttatt ctgcacagcc   31980
tagaattcta gaatcacagg gttctgcaca acctagagtt ctggaatcac agggttctgc   32040
acagctagaa ttctagaatc acagggttct gcacagctag aattctagaa tcacagggtt   32100
ctgcacaacc tagagttctg gaatcacagg gttctgcaca gcctagagtt ctggaatcac   32160
agggttctgc acagctagaa ttctagaatc acagggttct gcacagccta gagttctgga   32220
atcacagggt tctgcacagc ctagagtttt ggaatcacag ggttctgcac agctagaatt   32280
ctagaatcac agggttctgc acagctagaa ttctagaatc acagggttct acacagctag   32340
aattctagaa tcacaggctc ccaggggttgc aaggacactt tggagtgtct acctcagcat   32400
ctcatgaagt gtgggaattc cgaggcggtg gcggaggaag tgttttccat cttcggtgct   32460
ttcgttgctt ctggtgacag cgctcactgc ctctgcttgc tgtacgggac cagctgatgg   32520
aaccgacagg gagggacttt ttatctggcc attggccact gccacacact ttgtgtaccc   32580
cgttttgtgt aattctgact acaaccttgt gggatctagg caggtcattg ctgttttgca   32640
agtggggttg ttgaagccac aggagatgaa ataagctgct gtcccccagc cattgagtgc   32700
tgataggatc aggagtgcca gttggtgtgg ctgaccccag accctgtgcg tgttacctct   32760
aagctacatt ctagagcaga ctttttgccc acacaagcct taaatgtggg ctggggacag   32820
tggctcacgc cggtaatccc agcactttgg gaggacaagg tgggcagatc acctgaggcc   32880
aggggttcaa gaccaggctg gccaacatgg tgaaaccctg tctctactaa aaatacaaaa   32940
attagccagg tgtggtggtg cgtgcctata gtcccagcta ctcgggaggc tgacgcatga   33000
gaattgcttg aacctgggag gcagaggttg cagtaagtca agactgcgcc attgcactct   33060
agcctgggcg acagagcaag actccatctc gaaaaaaaca acaaaacctt aaatgtattt   33120
ttgaggctgt gtttaaaaat ggggatattt tacacaaaat atccagattt ctggattctt   33180
```

```
ttgaagaatc agaagatctg acaatacgga gcctcacatt cctgcacaca cagcagccat    33240
agctggagcc actgcctcca ttagtttgaa tttactgcag accccactcc tccctgtcgt    33300
ccctgtctcc agaccacaga gttagttgtc attgatcgtg tgccatttgt tgttttttc     33360 aaagtagaga agtacttctt cacgctgtgt ctctatcaaa aatggacaag tgaaagatgt    33420
ttcaagaaat gaaagatttt ttttagtgac aaaaaatttc tagtatgttt ctcatataaa    33480
taaaatgtgt cctgtatgta gtcagggttc ctcagagaag cccgaagcta caggatatag    33540
atatgtagag agattgtgga ggcttggcga gtccaaaatc tgcagggcag ggctggcagg    33600
ctagggactc aggaatgcgc gcagcagagt cgtaaggctg tgtgctggtg ggattcttgc    33660
tcggggaagg tcagtctttg ttcttgtaaa gcctgcaact ggttggatgt ggtccaccca    33720
cattgcggaa gggaatgtac tctcctccta gttcaccgat ttaaatgtta atctcatcca    33780
aaaacacctt cacagaaaca tccagaataa tgtttgacca catatctggg caccgtggcc    33840
cagccaagtt gacatattaa attaacccct gtagtcccct tttaaactta cacccattgc    33900
aatttaggtc gctgctatgg agcaagccac agaacctggc ctcttaactc atttacccgg    33960
gctgacccat taggccttg agtcaccaac acctcactag agaacaagca taatgaagaa    34020
gctctgctgt aattcgttaa tgttaacact tttttcttta aagatgtctc atgctgagct    34080
tcgtggcaca cgcctataat cccagcactt gggaggctg agatgagagg atggcttgag    34140
ctcagaggtt cgagaccagc ctgggcagca tagtaagatt ccgtctctac aaaaaagaaa    34200
agaaaaaaag ttgtctcata attattaaaa accactattc cagatcatgg ataataatag    34260
tcagaacagg tatattgttg aaaagaaaa aaaaaaaccg gaagcagtcg ctttcagctt     34320
tgtaataccg cagcaaatgt catagtagac aaggttttt taaagtagg agattagtgg      34380 cgtctctgct gatgggggtt ctgggtgttt aaaaaccaga gaaggaacc ggcggttta     34440 gggactaggt cccagcttct caggacagcc tgaggacccc ccgagagctg ccatcaccat    34500
gccgtcctcg gctgtgggtc actgctggtg aggtccatcc tgcactgcgg gacacagggg    34560
cacaggctga gcggtgccca ccaaggaggc aggagcagcg ggtggaggcg ccggggcaga    34620
ctgtccctct cctggaaatg gagtgattta catttggcat ctgtttggac cccagagtgg    34680
gaattggctt tgtaatttct tctgtcatgc cgctctcaga aaattaagct gtttacccga    34740
cagactatgg aaggttaacg gctcttctgg gaaaggtcaa gtggtcattt gcagggaggc    34800
tgtgctgaat aatctgaaac ggcagaagaa taaagcataa aatcgcatct gactcctcct    34860
cccgggcttc ccccttcct tccagcatcc acgggttcct ctttgtggct agaacattca     34920
cgtcctaagt ggggctgccg ttggctgggt taaaccagta accagtaaca ggagaaatac    34980
gtcgcatctc tagtgtgtgg agattaccgg gcctttatat taaaaaaaaa ttttaagtgc    35040
ttatatttgc tctgtctcta aaaatgttt ccaggtaaca gttggcctca agatgccttt     35100 ttgttttct gaatgaataa ggaataaaga aaaattctgg gcactataaa atcaagccca     35160
gattcagttt tttaaaaaat aaacgttaaa gtttctcatt ttgatttctg gaagttcgtg    35220
ttctccttgg actctaaaga ttagcatgca aagacaaggt tttgattgtg tattttcagt    35280
tgcacgttca gttttttaa aatcccatcc aggactaaat ttaaacataa gaaaatccag     35340
gtttctttcg ctttcgaaga ggctgcaggg aacttgaggc cagaggaagt ggcgccgcgt    35400 gggtccccttt aggaggtttt gccagatgat gggaggtgct tgctcccgtc cacccaacct   35460
ctagctcctc cagccggccc cagggtagct gagggacagg ggtctgggcc cagaagcccc    35520
```

```
cagaatcctc agctccaaac agagctgtac ctgtcgcaat ggagtagttt tgttgatttc    35580
aggttttctt ttgttgctgg gtaagcattt cctgtgtggg gtatattctt tcctccgtcc    35640
tggcttactt ccacacatca cttcattagg gaggccctcc ctacccacct cgatgccctc    35700
cttctcctgg cacaggtggg caggagggga cgagggtcat ggcctttgag ggcctgcaga    35760
gggccttgcc tgtggtggcg tggccaccct ggtcctcagc agggtgctca gtggattcca    35820
aggtgctccc tggacccgga cctccccttc acttcctttt agctcaggtc tcagcttttcc   35880 atgcctctgc tgcctccctg aacccagcct gtccccgcc ctgttcaagc agactgcccc     35940 tccctgggt cctgcccttt aaagtttgtc tgtgggcttc tttgcttccc caccagactg     36000
tgagtccctg tggagcaggc tggggctggg agtatccctg agtcctgcaa agggctgtgg    36060
agcatctggg atcgttaatg ccaaggggga ccaaggtaac ctgggccatt tgcagcacca    36120
gccagtgcag gccccaggac ccggtgtccc ctcactgttt cctgagaact ctggacccca    36180
ctaaggaaac catcagacca aagtagctga ttgtccaact gggaaaaaga aaaagcagta    36240
cttttttagg ccatgtaaat gcaaaatata catttgaagt ctgcgtttaa gacatgaact    36300
tagagatttc taagcctgtt tttggggtc actctaaaag ggagggcatt ttcaggtccc     36360
ccctctgtga gcattcacag catcccagcc agcctgtatc cctgtgccgt gaccccagag    36420
cacagagcct cagaggctgt ggaacaggcc tggggttcac gtggagagtc ccaagcccac    36480
gtcatgacag gagatgccca caccttcaac aaacagactc caagctccaa agctgcctaa    36540
caggagtggc aggggacca gccctggcaa ggcccaggtt tggctgaagc ccgtacctgc     36600
agcccagctt gtaagtttag ccgggaagca tctgaggcag gcagtggagg acgcacaggg    36660
gtgagcggtt catctcacag gtgtggctgg gtgcctgcta cagcttcaag gcatcaggtg    36720
gggcagaaag ggacaggcag ggtgcccagg agtggcggag ctggaggaag ggcacagccc    36780
cagggcagct cccgaggagc tcagttctca caccccaggt ggtcacagaa cacatttcag    36840
cccccaaatt gaacagggct gtgttcattt tttccttccc ccagctcatc ttattgcttg    36900
tgtcagcctg ggtgaaaggt tatttataat aatattctcc tgtctcatct gggcagcttc    36960
tgcatggaag gtaccgagtt aataactttg catgcgttat tttgttcaag cttcacagca    37020
atccgtgagg taggtattgt ttgttgttcg ttttgcccat tttacagatt aggaaactga    37080
ggcccacagg cgtaagcaac ccaaagtcac accgttagaa ggcagtgaga tctgaatgct    37140
caagtcagca tgcgctcttc ttccctctcg ttttctgcat acgtgctttc tccacgtctc    37200
ccatatcgta agggcatggc aggaggagag ggaaactgat gtgatggtgg atggcaaaac    37260
attttagtgg ttccaagaat caagccccct tgtgtattct tggcttcaa tgaactgcgt     37320 cttcagagca gcgcaggtta aaccactttc tcgcctcatt gtagtcaatt ggcttagttc    37380
agccagagcc aggtctggcc caccatgtgt ctggactgtg agtgccttga ggctcagtgt    37440
gacgcgatcg tagggtgagc ctggccgggc tgcagccagc caccaagcca gccctgggct    37500
caaagagcag tgaggccatt ttgagagagg aatgctccct cgtgcagagc ctgtctccac    37560
ctccatgaga cgggaaggaa cagttgtctt ctcataaaag catctggcgc ccatgaaacc    37620
tggcacctcg cttgacctcc ggctaacggg atgcggcagg gtgctgtgga actaatggag    37680
ttctcttctt cagccagcaa ttaggggtta attattagca attagggtt cgccacatac      37740 cccgtggacc tgctgttcct tcccaggaca caggtcactt gtcattctct gtgttagcaa    37800
ctgaaaccgt ctgccttctg ggtccccgt taatcattgc agcagggtcc ccacgagtct     37860
gacagcaggg ttgcgttctg tgcgacctgt ggcatccctg gagctgctgg ctgctgcgct    37920
```

```
cgccccactg ggtgtggcgg cctgccgccc ggctctgtgg tgctggtccc ctgcggtcat   37980
tctcagcgta gcgcctggac tgcccctcag ccgcggcttg gctctgcagc cagcgggaca   38040
ggcccggtgc tcagctcccg atacttagca tcctgcggtc agctcccgt gctcagcatc    38100 ccgtgctccg ttctgctctc tcctaggcgt tactacaagg agacctctgg cctgatgctg   38160
gacgttggtc cctacatgaa ggcgcttgag gtaccagccc tggttctgtc ccaaactctc   38220
ttcagacctc agggcacctg ggactttttg ggtctttgtt gagaagaggc tgtgcttaat   38280
taacgtacaa atggcctttt gggcttccac aaaggctgcc ttcctattct gggctcccct   38340
ggccgggccc tcgggccctc aggccctcag ctgtcctcct ccctccccat ctctcccttc   38400
ccatccttcc catcctcccc atcctcccca tcctccccat cctccccatc ctccccatcc   38460
tccagtgggc gcagcccccc ctgccgcgcg tggaccctgc cgctctccca gctgctctct   38520
gccacactcc tctcgggctt gtggcttctg tatcagtgct gaccaccgct ctcattcctg   38580
accctgggca tctgcagcac ctcaagcttg acgggtcctc actggcctcc ttcctgactt   38640 cccctttcagt ttccaaggcc atctgtggcc aggcctccgg gtgggctcc cctgggtcca    38700 ctctggccca ggtccatta gctgccccag gtcagcctca catcccgtcc catcctcaca    38760
gctgcagccc ctcctgcctg cctgccgtca ggtgggaggg agaggcagac gagcagatgg   38820
agccctgtga tgagctgcga gtgggcaggg gagaagaggg ggagaaggga tgagaggacg   38880
gaattgcagg cgagtgagca gagcactgct ctgctggccc ttgggagccc tgtagttttg   38940
ccagctcttg gatgccttct gctgtgggta ggcctttgag tggatggcag ggtgcctggt   39000
gctaggggac ctgagtgacc cgggcagccc tttctggagt tgtgaggctc ctgcctgtga   39060
gatgagttct caggcccaca gcatcctgct tcttcaaggc ccttgactct tgggggcaca   39120
tttgggacag tgtttccgtg gctgggcata cacctgttcc ttgatcccaa acttatgcca   39180
tgtccctctc tcttttccca gtatgcctgt ggcatcaaag ccgaggtggt ggggaagcct   39240
tctcctgagt ttttcaagtc tgccctgcaa gcgataggag tggaagccca ccaggtaggt   39300
tggcgccttg tgaagtgggt caggggaggc agccccgtca gggaggccct ggagcttgga   39360
atggattaca ggactcaggc agcctgtggg gttggcagg cagccaagcg tgggctccct    39420
gtgaaagctg acctggctgg gaaggagggg gaagacagca aacgaaatcc actgaatagt   39480
ttcaaccgtg aagttacttt cagtatgaaa gcaagaagca gaaatgcctg cggcttttcc   39540 tgagttttg ctgcttctct gaaaggataa gaattgacaa gtcctatcag tgtgttaata    39600
tatctcactg gcaagacagt gtaacagcaa gattacaaca atatggagga aataataaag   39660
tcactcattt tgcgaccttt atattttgac tattttggga tagattgcct ttcaaacttc   39720
caaattttag aaaggaaaaa gaatcggtta tgatttatt gtctacacct accccaaccc    39780
taagtgagtc tggcttcgtc ctccagtggg ttttctttc ttttctttt ttttttttt      39840 ttttttttga gccaatgtct ccatttgtca ccctggctag agtgcagtgt agtggcacag   39900
tcatggctca ctgcagcctg gacctcccag gctcaagcga tcctgccatc tcagtgcccc   39960
cttaaccccc ttactaacca ggcccccccc ccgccaaccc caactgagta gctgggacta   40020
caggtatatg ccaccacgcc tggcaaactt ttttttttt ttttgagac agagtctcac     40080 tctgtcaccc aggctggagt gcagtggcgc tgtctcggct cactgcaacc tccacctcct   40140
gggttcaagc aattcttctg cctcagcctc ctgatgagct gggactacag gtgtgcacca   40200
ccacaccagc taatttttta ttttagtag agacagggtt tcaccatgtt ggccaggctg   40260
```

```
gtctcaaatt cctgacctca ggttatctgc ccgccttggc ctctcaaagt gctgggatta   40320
caggtgtgag ccaccatgcc cagcccccggc taacttttgt attttccata gagatggggt   40380
tttgccatgt tgcccaggct ggttttaaac tcctagctca agccgtcctc ctgcctcggc   40440
ctcccaaagt gctgggatta caggcatgag ccaccaacac acagccccct ccagcaggtt   40500
ttctgaaaga ttgtaaggaa tagtgggcag ccggcatgga ggctgacgcc tgtagtccca   40560
acactttggg aggctgaggc aggtggatca cttgaggtca ggagtttgag accagcctgg   40620
ccaatgtgat gaaaccccat ctctactaaa aatacagaaa aacaaaaaaa attagctggg   40680
cgaggtggtg catgcctggt aatcccagct acttgggaag ctgagggatg agaattgctt   40740
gaacctggga ggcagaagtt gcagcgagcc gagatcatgc cactgcactc cacctgggtg   40800
atagagtgag actccttctt taaaaaaaag aaaaagaaa cagagtccac agctgcccca   40860
ggctgtcctg ctgcctcctc agaagtgggc agcagaagca tgggttgggg gtccctcagg   40920
tgtcaagcct ggtgcatgtt tcccctgtgt gcatttcggt ccagaacact ggtgcctcat   40980
ggtgctttga gaaagatggc ccaaagctgc caaaatctag acactgcacc tgcacctgcc   41040
ctgagatcca tagagatgtc agaagatgca ggctgtctgg agtccccaga aaacacctgg   41100
gaaatgtcac attagtctgt tgagaaggaa aggtttgtgt tttgaatgag tgagaactgc   41160
agcaataaat aacctggctt tttactacct tgcttcatag ggcagaattt cttttttat   41220 tagagatttc aaacatacag aaaagtagag agaatgatac agacacccca ttatatccat   41280
catccagctt cagtggttaa gattttgcca cattcctttc ttctatcctc tttttttcc   41340 ttttaaaaaa tttactggct gggtgtggtg gcccacgcct gtaatcccag cactttggga   41400
ggctgaggca ggtggatcac ctgaggtcag gagttcaaga ccagcctggc caacatggtg   41460
aaaccccgtc tctactaaaa tataaaaatt agccgggtgt ggtggtatgc acctgtaatc   41520
ccagctactc aggaggctga ggcaggagaa ttgcttgagc ccaggaggtg gaggttgcag   41580
tgagccgaaa ttgtgccact gcattccagc ctgggcgaca gagtgagact ctatttccaa   41640
gtaatagtaa tagtaatgat aataataaat ttacttattt ttttgcttca tattttaaag   41700
caaatctcaa ttgtatcctt tcatgttgta gcatgacatt taaaaatcac gattttgga   41760 tgtaaataca atacattaaa actcctaaca tggccaacag gcatacaaaa agatactcaa   41820
tatcatcatt catcaggaaa tgcagatcaa aactccagtg agataccact tcacactaag   41880
atgactgtat agttaaaaaa aaaaatagaa aataacaagt gttggcaagg atgtagagaa   41940
attggaaccc ttctctattg ctgctgggaa ggtgaaatga caatgctgcc acggaaagcc   42000
acttggtggt tcctcaaagt taaacataga atttgccgta tgactcagca acccatttcc   42060
aggtctatac ccagaagaac tgaaacacgt gttcaaacaa aaacttgtac acagatattc   42120
atagcagctc catacacaat agccaaaagg taaaaaagc caagataccc gcccatcaac   42180
tgatgaaagg ataaccaaat gtggtatgtc catacagtgg aatattattc agccataaag   42240
aggaatgaag ttctgacaca tgctacagtg tagatgaacc ttggtagcat tatgctaagt   42300
gaaggaagcc aaaacacaaa ggacacatat tgtattcttc catgtatagc aaatgtctag   42360
aatgggcaaa tccatagaga tggaaggag attagtggtt ggcaggggtc gggtgcaggg   42420
gaatggggag tgcagcttca gggtacgagg tctccttttg ggatgataca aatattctgg   42480
aactgggccg ggcacagcag ctcacacctg taaccacagc actttgggag gctgaggagg   42540
gtgaatcact tgaggtcagg agttcgagat cagcctggcc aacatggtga aaccccgtct   42600
ccactaaaaa tacaaacatt agccagacgt ggtggtgtgc acctataatc ctagccactc   42660
```

```
gggaggctga ggtgggagaa ttgcttgaac ccaggaggtg gagattgcag tgagccgaga    42720
tcgtgcaact gtgctccagc ctgggcgaca gagccagact ctgtcttaaa aaaaaaaaaa    42780
aaaaaaagaa aaatattctg gaactggaca gtgatgatgg tggcacgacg ttctgaatgt    42840
gctcgatgcc agtgaattga atactctggt cacggtcata aattttatgt aatgtgtatt    42900
ttaccacaat aaacatttta aaaccaccta aaaaattaac agtgattttt gttagtatta    42960
tttaatagca acccatattt aaatttcctt gactgtctca gaaatgctct tttaccgttg    43020
atctgttgga atccaatctg aagaagctcc gtgacttgtg tgtcgttttt atgttttctg    43080
agcctctctt tttagccctc catcatagaa catttgaaat atctatgtca gtagagaggg    43140
cagctcaggg aactcctagg tacccatcac tgtgctttaa taattatcaa ctaataacca    43200
ctttaaaatt gttttcaact tttcattttg aagtaacttg acactcacaa aaagttgcaa    43260
acatagtaca aaatgttcac gtgtaccgtt cagcagcttc cccatcatca tcgagcagtg    43320
ataaaaccgg gaaatcaaca ctggcacaag gcggttagct aacctagaga gcttattcag    43380
acaccaccag tcatcccact catggctttc tggggacacg ttgcatgtag cagtcatgac    43440
cctagtgtcc tttatctgtg aactctgatc acctgttgag gaggtgtctt ccagagttct    43500
ctactgtcat tgctatttgt ccctttcagt aattatcttt tttttttttga gacggagtct    43560 cgctgtgtca cccaggctgg agtgcagtgg cgctgtctca gctcactgca agctccgcct    43620
cctgggttca cgccattctc ctgcctcagc ctcccaagta gctgggactg caggcgcccg    43680
ccaccatgcc tgagtaattt ttgttttttgt attttttagta gagatggggc ttcaccatgt    43740
tagccaggat ggtctcgatc tcctgacctc gtgatctgcc cgcttcggct cccaaagtgc    43800
cgggattaca gacgtgagcc accacgccca gcctttttt tttttttttt tttttttgag    43860
caggaatctc atcctgtcac ccaggctgga gtacaatagc atgatctcag ctcactgcaa    43920
cctcctccac ctcctgggtt caagtgattc tcctgcctca gcctcctgag tagctgggat    43980
tacaggcacc tgccaccaag cccggctaat ttttgtattt ttagtagaga cagggtttct    44040
ccatgttggc caggcttgtc ttgaactcct gacctcaggt gatctgcctg ccttggcctc    44100
ccaaagtgct gggattacaa gcgtgagcca ctgcatccaa ccctaataag tatcttgtgg    44160
gaaagttctt tgacactatg taaatattct ctttctgatc attagttcta attttggcat    44220
ctcttgataa ttcttttatt tttttatttt ttgagacaga gtttcactcc tgttgcccag    44280
gctggagtgc agtggtgcct gggctcacca caacccccctc ctcctgggtt caagcaattc    44340
tcctgcctca gcctcttgag tagctgggat tacaggcatg tgccaccacg cccatctaat    44400
tttgtgtttt tagtagagac ggggtttctc catgttggtc aggctggtct caaactctca    44460
atctcaggtg atccgcccgc ctcggcctcc caaagtgctg ggattacagg catgagccac    44520
cacatccggc cttcattggt gtattttatg tgtgcccaa gacatttctt cttccagtat    44580
ggtgcaggga agccaaaaga tcggacaccc ctgctctaga ggtttatgac caaaatactg    44640
tatttaaagc tgctgggaat aattctttttt tgtgggtggt attccccccaa gtggacgctc    44700 tttgaattca ttttcatttt gatgtttagg gaattggctt aacatttaca tttgttttgt    44760
agttatgtaa aacatttata tggttctaaa atcaaatcca caaagcaaga catattcaaa    44820
gaagtccaac ttcttttcct tctatttgt ttttacctgt ctctggtagg tagccatgtt    44880
tataaatatt aaagctataa atattttata aatattatag cttttttttat ttaaaaaata    44940 agcaactatg tatatatttg tattcccctc ataggatgaa tttaagagac aaattctcaa    45000
```

```
aataatgtgt tttatatata gagagaaagg ctaatgcttt aagtttaaaa atcagtattt    45060
aaaagtttat aagtaggctg ggcatggtgg ctcacacctg taatctcagc actttaggag    45120
tccaaggagg gcggatcacc tgaggtcaga agttccagac cagcctggcc aacatggcaa    45180
aaccccatct ctactacaaa tacaaaaatt agccgggcct ggcagcaggt gcctgtaatc    45240
ccagctactc aggaggctga ggtgggagaa tcacttgaac ccaggaggcg gaggttacag    45300
tgagccgaga tcctgccact gcactccagc ctgggtgaca gagtgagact ctgtctcaaa    45360
aaataaaata aaataatata agtggtatga tcacaaccat ctcaaacagc cccttcccc     45420 cgacccaaaa cccaaacaaa aacaaaaccc tgccactgcc tggaaaataa gacctggcca    45480
ggtgccatgg ctcacgcctg aaatcccagc actttgggag gccgaggtgg gcaggtcatt    45540
agagcccaaa agtttgagac cagcctgggc aacacggaaa aaccccgtct ctacagaaaa    45600
aatgcaaaaa aaaaaaaaag gcagatgtgg ttgcatgtgc ctatggttcc agctacttgg    45660
ggggctgagg tgggcagatt gcttgggccc aggaggttga ggttgcagca agctgagatt    45720
gcaccactgc actccagcct gggcaactga gcgagaccct gtctcaaaaa aaaaaaaata    45780
ggaaagcaag aaggaaggaa ggaaagaagg aaggaaggag ggaaggggaa gggaagagag    45840
gggaggagac gagactggct gtccagatgg cattgctggt gatatttgga tggtctgacc    45900
ttgggtggtc tccctgcctt tttcttgtgg cattttcagt tattttcaca gtcagcttcc    45960
ttcacatttc gaatgagata cagcccacct caccgccgaa agaagacccc tcatgggggt    46020
ctggtgaatc tgggtttgtc gttttcggat gctggggcag tgcgtctggg agggagcggg    46080
gctgtggatt cctggtgggt caccgtggct gcttgaggct ttggtccctg ccgctgccat    46140
ccaccctgag catctgtggc cctggagagc gaaagacttg tttcctctgg tggctccgag    46200
catatgtggc aaagctgtgt cttatttacc tcccacatca tcatcctctc ctaccctcat    46260
atgacatttc tgcctgtccc cttgacagtg gagtagcagc tgcatgttcc gaacgtcccc    46320
accctgccat tttcctaaaa tgctcactaa cgttatttga ctctcaggat gtgtagacat    46380
tttaaagctg tatttcaaga taaggccatt tcaaatgaac tgtgtcttat gcacagggta    46440
ataattctct gttcctggct ttttattttt taatgaaaaa tgcctgcaag gacctctctt    46500
gctgctgaat gccaggctgt ggcaaaacctt aaattttttcc agctgcttta atcaataaag    46560
ttatcaccag tcatttccct tgatcactgc tgcttcccga gaccctgacc tgcttcttgc    46620
tgctgagttt tcagtctgca ctcagaatag atataactcc ccaaatccaa ttttcatttt    46680
aacctttcct cagtggccta gaaatcacag attgctggta ttatgctaat agattggaaa    46740
ttcaaacctc ttagaggcaa cctggccctt tctaggattc agtaataagg caaagaataa    46800
cataccttaa aggttacttc tagaaatatc taattctcac ggtttaagct tctgaatcag    46860
tggatggttt tatagcttca tatgagcacc caagtgatgt gaaggttttg gcagttctcc    46920
atcatcataa gaagttctgt gggatgcaaa tcctgcaggt ttagtggaga ttgagactgt    46980
tcaaaccaga gcacttagtt atatgtgaca gccaagaacc ctcgcctgga ggggcccgtt    47040
tcacaggtga ggagcctgaa gcttagagat gaaacacctt gtcataggcg ctttgcattc    47100
ccaccatgag gttaagacag gatttctcag gctgggcgca gttgctcaca cctgtaatcc    47160
cagcactttg ggaggccgag gtgggtggat cacgagccca ggagttcgag accagcctgg    47220
gtaacatggt gaaaccctgt ctctacaaaa aaatacaaaa attaactggg catggtggct    47280
ggcacatgcc tgtggtccca gctgctcagg aagctgacgc acgagattcg cttgaatctg    47340
ggaggcaggg gttgcagtga gccaagatgg taccactgta ctctaggctg gacaagagag    47400
```

```
taagaccttg tctcaaaaaa aacaacaaac ccccccccca ccccgcggtt tctcaacctc    47460
gacacttggt gtttttggac tgggtcattt tgtggtgagg ggatgtccta tgcattgtag    47520
ggtgctaaac agcatcccac tgtccgccca ctacatggga ccaccccctt cccaagctgt    47580
gaaaccaaaa ttgtctgtag acattgccag atgtgccctg gggagaaccg cagcattaag    47640
cggtattaag agaacggtta cggagaactc tagtactgaa cccaagatta ctttgccaat    47700
gaggagtgaa gccaggcacc aaaccatcgt cttccagccc cgtccagtgc tctttgccat    47760
agcccaactc tcaggagga ccagcggtgc agcagaattt cttagggagg tggggagggt    47820
agggaggatt tcaggttggg gggtaggaa gatttcaggt tggcgggtag ggaagatttc    47880
aagtggggtg ggtaaggagg atttcaggtt ggggggtagg gaagatttca gtggggtgg    47940 gtaaggagga tttcaggttg ggggggtag ggaggatttc aggtgggggg gtagggagga    48000
tttcaggtag ggggtaggga ggatttcagg tggagaggta gacaggattt caggttgggg    48060
ggtagggagg atttcaggtt gggggtaga caggatttca ggtgggggg tagggaggat    48120 ttcaggtggg cgggtagaca ggatttcagg tgagggggt agggaggatt tcaggtcggg    48180
gggtagacag gatttcaggt gaggggta gggaggattt caggtgtagg ggtagacagg    48240
atttcaggtg ggggggtagg gaggatttca ggtgcagggg tagacaggat tcaggtcgg    48300 ggggttagag aggatttcag gtggggggt aggcaggatt tcaggtcagg gggatagaca    48360
ggatttcagg tggggggata gggaagattt caggtgtgga gggtaggcag gatttcaggt    48420
cgggggggta gacaggattt caggtgggg ggtagggagg atttcaggtg tggagggtag    48480
acaggatttc aggtggggg gtaggagga tttcaggtgt ggagggtaga caggatttca    48540 ggtggggga tagggagtat ttcaggtggg gagggtaggg aggatttcag gtgtggaggg    48600
tagacaggat ttcaggtggg gggataggga ggatttcagg tgtggaggt agacaggatt    48660 tcaggtgggg ggatagggag tatttcaggt gggagggta gggaggattt caggtgtgga    48720
gggtagacag gatttcaggt ggggggatag ggagtatttc aggtgtggag ggtagacagg    48780
atttcaggtg tggagggtag acaggatttc aggtggggg ataggagta tttcaggtgg    48840 ggagggtaga caggatttca ggtgtggagg gtagacagga tttcaggtgg ggggtaggg    48900 aggatttcag gtgtggaggg tagacaggat ttcaggtggg gggatagga gtatttcagg    48960 tggggggggt agggaggatt tcaggtgtgg agggtagaca ggatttcagg tggggggta    49020 gggaggattt caggtggggg ggtaggcagg atttcaggtc gggggggtag acaggatttc    49080
aggtggggag ggtaggcatg agggctgcag tgatcttcat ggctcgcacc ctcagaactg    49140
cctgtgaaaa atgggggtga ggtttgcagg cttatccaga ggcctggcca tataaactca    49200
aaggtgccct accatttcgt tccctgattc tcagggcatc agtcctgact ataggggtct    49260
ggggacagtc tgtaccccta ggggaggct ggtgagtggg gagtacatgt ctgtccacat    49320
gggggccact ccgcccagt tctttctgct gtggcctccc tccccatgg gtgtttccac    49380 tgaggcctcc ccacgaactc tgttggctga gccccacctc ccagccgtgg gcattttctt    49440
tggattgtca gtgtgggat gaccctgctc aactcctgac tgggagcagg ctggcctgct    49500
gggccgtgcc cacttccagc actgaaagaa tgggcccagg acggggtca gccctcctgc    49560 agccctggtt tgaattggaa actctgtcca ccgatgcctg gcacctggca cctagccctg    49620
cagctgtggg tctgaaactg acgggagttg caggagcttc cggccctggc tttgtctttg    49680
tgatgtgtcc tagtcataag gtgctctgag acctcatggc ttagttttcc ttcagagttt    49740
```

```
tttctcccttt ggaggctttt tttttttttt aagtagatttt tatttcttc tcaaaacaca  49800 agtatttaaa atatctgatt atgaagcaac tcatgctcat taaggagct aagaaaaatt  49860 caggaaagta caagaagaaa agaaaccact catttcacca gcccagaata acacaaatca  49920
tgcttgatct tgccaatttt ttgtgtctat atatacattt ttaacacaaa attgggataa  49980
tcttgtatct gctgtttgaa atctgagttt tcccccttaa tatcctattg gggacaattt  50040
ttgttaactt atattttagg ttcagggata cgtgtgcagg tttgtgatac aggtacattg  50100
tgtgtcttgg gggtttggtg tgcagattat tttgtcctcc aggtcataag cctagtacct  50160
gttggggtag tttttcaatc ctcaccctcc tcccaccctc caccctcagg taggccctgg  50220
tatctgttgt tgccctgtgt ccatgtgtat tcagtattta gcccccactt ataagtgcaa  50280
acacacagta tttggttttc tgttcctgca ttagtttgct taggataatg gcctccagtt  50340
ccatccctgt agctgcaaac gacatgacct tgttcttttt taggggacag ctgtctttgt  50400
gcttattgaa gcactttaac gaagcagttt tcacagctgc atactattcc actgttcaga  50460
ctcccgtcat attcttgacc atttcctatt gatggagatg aggctgcttc cagtttcgct  50520
cttgtgcgta accctgatga acacatcttg tatgtacatc ctcttgtaca tttctaatta  50580
tttgctccaa atcctagtgg tgtggctggg aggctgtgat gcatgttgct tatttctgtt  50640
tcagaaaggt gtgtccgttc accttcctga cctgctgcgt atacagatgc ttgtttcccc  50700
acatccttac caaacaccatg atttctgact tttttttttt aaagtggtct ttgagttttg  50760
ctgttagtct tgttccttat gaaggtgtcc gaccacagtg gcaattactc agcattgcac  50820
tgtctccagg tctctgtggg agcctgggtt cctttggggc ctggattcag gctcatcct  50880 agagtgagct gtcatctcag ggcatctccc tggggatat gtgcaccca gagctgcagt  50940 tacagacact gagctcactc caccttcacc acccagccct gctgcttccc gcctaatcc  51000 tcctggcaga gccctggat aaggaaaata tttgtgaacc acggaagctc tttggtgctg  51060
gaattttgca ctccaaagca tcgccgcctg ttagatgatg tttccctcca gcacctagga  51120
cactgaagag gagaccaggg caggcaggca gatgcgtaag agggaggatt gactgctgta  51180
gcacccgacc caggacacct gcctctggga ctgtggcgcc tccatccggc tctctggatc  51240
ctgggttctg gggggtccga ccttttcattt tttttctccgc ctcacacccc accatgtcgt  51300
gtctgaaagg aagcgaagcc cagccctggc aggtggagta ttttttattc ccctgacagc  51360
gcacctcctg acctctatct tcttgccagt gattttttaa atcctaaatg atttggcaat  51420
aattgctcct ccttgcgtga ttattgccct tcaccgatag taaatctggg aatcccctgg  51480
ggtcctgagc gcactttggt atgcggagcc cacaagctgg cctggacagg catcactgct  51540
ccaggcagct gtgcacccag ccggccctgg cgtcccggcc ccagcctcc gcctccctcg  51600 ccgacagctt cccggggctc tgcctggagg cagcctcgct ttatcccgca gaacctccac  51660
gctgttcctg catgagaact cttcctccaa gagaccacgt tcctctggtc ctgtctccgt  51720
gggccacatc cacaaatgtt ccagcccagg aagaaccaag tctgtattct gggagggaaa  51780
cctgtgtgct gtctggtttt gtatgtggga ggagcatgca cacagtttca ttttccccgg  51840
aagcatggag gtgtaggatg acatgtaata tttggaagac ccattgcatt tccaaggaac  51900
cttctagcag gatggccctg gagtctctgg cagcagtgga catggtcctg aattggagtg  51960
ctgtgaatgt tcactgctga cctcacggtt tgaagacaat tccttgagaa gggcagaggg  52020
gacccgaata cggggggctct ggccggccct gctgccagat gccagcagcc gtgggggctt  52080 gccccggccag ccctggcttt tcccaaccct cagagtgccc cttgtgcatg cagcagacac  52140
```

```
tggtgctggt cccattcccg ggagcacgcg gtgccactgg ctgtgtcttg cctggccagg    52200
tgttggtttg atagactcga aaacctcatt tggatttggc aggattttcc ctaacatcag    52260
tcattctgga aaaaacactt tgaattttta ccatatctgg gtattttttac catatctggg    52320 tacttgccac tagctctatt tacttcacgt ttcttaaaat tgattcattt tattacttaa    52380
ataaatgtat tttaaaagga acttttgatg actactataa atggaaaacc agaatctctc    52440
acttaccata atagattaat ctaaaaataa agaccacatg attacattaa aatgtatgtc    52500
cttgctctgc ctggagtcaa atagtatgtc acccgtgtgc atgacacact ctgggaagca    52560
caggggtggg tggaggaaag atcagagaaa atccgtggaa agtatgaagt agagagcacc    52620
acaccaggaa gacgtggttt tatttcagta cctcatgtct cgcggtggct tgcggctacc    52680
agtaactggc agaattctca acattgtggc cctcagccac ctcctccgag ctctctctca    52740
gcaccaccat ccgccgtggc ttctctgagg gaggcccctc tggcctctgc ttgactatga    52800
tacatgtcga gtccatgccg agtggcagaa aagctccgtt ttcagctgaa actacctccc    52860
tggcctcagg gggcctcatt ggctctgtct ttgtactttc tcaatggctc ctgatgattc    52920
cttggttatc tgaaggcctg tttgggagac ggttcccagg acagttgctt caggcttata    52980
tgtgtgtgct ttctggaatt cacagcatgg cgtgccctgg tgagtggtgg ggagatgggt    53040
agtgaacacg tgtggtagcc cctgctgggc gtgtcccacc tgtcctccat gtcctacaac    53100
ctggttggcc cctttgctt gtcagagcaa agctcagaac ctcacctcct ctgggaggcc    53160
tttcctgacc acccacaagc ccagtaggtc aggaggtcag gcctcacagc ctcctgtgtg    53220
ttatcccagg ccctgatgat gagactgtgg aattacctga ttaatgtctg tctttagcac    53280
ttgtcgtgag ctccgtaagt gctgggactg catgtgtctg attcacactg tgtgcccact    53340
gcctggcctg gcactggcct gcgaaggcct agggcaaagg tatcaagtaa ccagggcaag    53400
ggtgcctgtt gcaggtcggg ggcctctctg atgtggtgag atagggaatt tcctcaacga    53460
aacatttcct catgtttctg tttcctttgt aacatgttta ggccgggcgc ggtggctcac    53520
acctgtaatt ccagcacttt gggaggctga ggcaggtgga tgacttggtc aggagatcaa    53580
gaccatcttg gttaacacgg tgaaacccccg tctctactaa aaatacaaaa caaacagcgg    53640
ggcatggtgg cagccgcctg taatcccagc tactcaggag gctgaggcag gagaatggcg    53700
tgaacctggg aggcggagct tgcagtgagc cgagatcgcg ccactgcact ccagcctggg    53760
tgacagagcg ggactccgtc tcaaaaaaaa aaaaaaaaa aaaagtttta ggtaatgtat    53820
tatgtcctgg ccctgtgctg ggtgcttcac taagatgatt tcctttaaac gccacacctg    53880
ttatacccat tttacagatg gaggtggagg ctggcccaag gtcacacagc cagcaaacag    53940
gagagctggg atctccaccc cactgctcta gctcagcgtg agacaggagt gagtctgtgc    54000
atctgctggc cacatcgggc ccgccccctc tttctgtggt cccttcccc cagatggaga    54060 gcaaattcca cctggacccg tccttgcagg cagagtccaa atctatggga cacacactca    54120
gtaagactcc cctggcttgg gcatgcttca tagtcatcgt ttcattttgt cttgattttg    54180
gtttgtgtat ttatcggtta gcccctctta gcatctgaat tccagtgaga agacatgtag    54240
tttgtttgtt tgtttgtttg tttgtttgtt ttaagacaga gttttgctct tctcgcccag    54300
gctggagtgc aatggttgca atcttggctc attctcctgc ctcagcctcc caagtagctg    54360
ggattacagg catccgccac catgcctggc taattttttg tatttttaata gagacggggtt    54420 tcaccatgtt gcccaggctg gtctggaact cctgggctca agtgatctgc ctccctcggc    54480
```

```
ctcccacagt gctggaatta caggcatgag tcactgcgcc cagcttttaa tcagattttg    54540
gagtagggga gtgagaggag ctggttggtg gtggttttt ttctttaaa attattatta     54600 cttttttttt ctttaaaatt attattactt tttttttttt tttttttga gaccgagtct    54660 cactccatcg cccatgctgg agttcagtgg cacaatctca gctcactgca acctccacct   54720
cccaggttca agcaattcgt gtgcctcagc ctcccgagta tctgggatta caggtgcatg    54780
ccgggctaat ttgtatattt ttagtgaaga ctggtttcac tatgttggcc aggctggtct   54840
cgaactcctg acctcaagtg atccacccgc ctcagcctcc caaagtgctg ggattatagg    54900
tgtgtgctac cactcccagc tgttttttct ttaaattaca tatatttatt tatattaaaa   54960 aaaaaaaag agcatgagtc catttaagca ataacacatg ttaatgtggc aaaaggagac    55020
ccacaaatga ctgacgtttc agccacactg gcgaggactg tatgactccc tccactctat   55080
gtaggtgacc aatgggaagt cttgtttgcg cctcataagt gtgtccagac acagccagcc    55140
gtgccgtaat gcagagcact cagctgctca agacacattt gctgagcgtc aaccaagtgc   55200
cagttgtcaa cccagattcc ttgtcctgaa ggagctccta cttctggaag ggtgggatga    55260
gcagagtcca ttatgctgca ctatgacacg gtggcacca gggtgtgatc ccagagtgct    55320
ttgggagagc cacacaaccc agcctggggg cagaggaaag tggtggtca ccagagctga    55380 gtcctgaagg cctggggga attagccagc agaggaggga ggtgagcagg cagaaggtca    55440
gcacgtgccc acaaggtaat ttctggtgt tgatgtgtat ttccagctat tgtcattttc    55500
ccttcgccca aaggacttct tctacatttc ttgtagggta gatctcttgg tgatgaatta   55560
tttccgcttc ggatgtctga aatatcttta tttcatcttc attttggaaa gatattttg    55620 ctgggtacag aattctagat gggcagtttt ttcttttact gcttaaaaga cggcactcca   55680
cagtcttctc acttgcattg tttccaacaa gaaatctaac gtcttaatct tcgttttctct  55740 gtacataaca tgtctctttt gtctgactgt tttataagat tttctccttg tcactggctt   55800
tgagcaattt gattatgatg tgccttaata cagttttctt tgtgtttctt gtgtttggtg   55860
ttcattggga tcttggatct gtggatttat tatttttatc aagtttggaa aagtttcagt    55920
cactatttct tcaaatatat ttatgtcttc tctcatctca ctttttttt ttttaatcta    55980 atttagagac agggtcttgc tctgtcgctc aggctggagt gcagtggcac aaacacagct    56040
cactgcagtc tcaaactccc gggctcaagt gatcctccca cctcagtctc ccaagtagct    56100
gggactacag gcgtgcgcca ccacatctgg ctaattttt aaattttat agagacaggg     56160 tcttgcggtg ttgcctaggc tggccttgga ctcctgggct caagtgatcc tcccacctca   56220
gccttccaca gtgctaggat gataggtgtg agccactgtg ccccagctca tctcactttg   56280
aggaactcta attgcgtgta catcaggccg cttgaagttg tgccatagct cactgatgct   56340
ctgttcattt ttgaaaataa ttttttctgcc tctgtttcat tttgggcagt ttctattgcc   56400
atgtctccag gttcattcat cttttcctct gcggtatctc ttctggcatt aatcccaccc   56460
agtgtatttt gatccctgac attgtagttt tcatctctag aagcttggtt tggattttt    56520 cttttatctt ccatttctct acttttggaa cacatgaaat accattacaa gggctgactg    56580
aatgctctcg tctgctcatt ctcacctctc tgtcagttct ggctcagttt ggataaactc    56640
atctttctcc tccttctgca tgatactttc cttctttgca cgtctgatca ttttttattg    56700
ggtgccagac gtgatcaatt ttaccttctt tttgggtgct ggatattttt gtgtgcccat    56760
aaagaatttc gaactttgtt gtgggatgca gttaaattac ttgaaaacag tttgatcctt    56820
ccagatcttg ctgttaagat ttgggggcag caccagagca gggttgccct gggtgaatca    56880
```

| | |
|---|---|
| ttcctcatag tgaagccagc ggcttctgag atcgcactca atgccctgtg catcgtgagt | 56940 |
| gagctttccc agcctggctg gtggggacat aacgcagtcc tgcgtgagac acaggcaccg | 57000 |
| ttttccctag ttatttggtg tgattctttc ccaggctcag ggagtttcct ccctcacgtg | 57060 |
| tgctggcagt ggtctgctga gtacttgagg ggaccctcca cgatctccac agctctttct | 57120 |
| ccatgcagcc ttctcctctc tgattccctg tcctgtggac tctgctcctg ggtctcccca | 57180 |
| gaatcctagc tttgtctccc cagttcaggg atcctactgg gctctacctg ggtttccctt | 57240 |
| ggtattagtc agcccagtct gtcatacaaa acaccacaga ctgtgtggat tcaacagcag | 57300 |
| aaactttttt tctcactgtt ctggaggctt gaagcctgag atcagggtgc agcaagtcc | 57360 |
| ggtttctggt gagggctctc ttcccagctt gtagatggcc gccttcttgc agtgtcctcc | 57420 |
| catggcctct cctctgtgct tgcatggaga gggcactcca gtgcctcttc ctctggtaag | 57480 |
| gacagcagtc ccatcagatc agggcccccct ctgacctcat tcgcccttaa agaattacct | 57540 |
| ccttacaggc cctgtctcca aatacagtca cgctgcgggc tagtgaattt gtggggaca | 57600 |
| cacttgagtt cacagcaccc ctcctgtgtc cacagtctgg aagcatcgaa ggcagtaggc | 57660 |
| tgggggcagt cacaggagcc acctcatttg tttcctgcgt ctcagaagtc attgtccttc | 57720 |
| gttgcttgat gtccggtgtc ctgaaagctg ttggttcata atttggtttt ctggttttt | 57780 |
| caggtgagag agtttatccc agaggctagt ttttgaaatg atacccaggc tgtgagcatt | 57840 |
| tcctctgtgt gtgtgtgaat tttggtttgt atatattatt ttgttttaa ggcaataccct | 57900 |
| tcaccattga agcaaaacc tatataaagc aaaacttaca aagatttgcc agagatttgc | 57960 |
| ttcactttca tggaatcaag ggcaaataac caggttacag agtctttagg gtcaggtgaa | 58020 |
| atttagcctg tgttccagca gaggccagac agcgttcagc atccccgcac gtccttgggg | 58080 |
| cgccaaatca ctttgacgtc tgctgattga tttcaaattg cacagatata tactgttcaa | 58140 |
| agctgtggcc tacgggggca gtgtgagata tattcaaggt gggttgactt ttaatcaata | 58200 |
| cgatgacaat attatcttgt ttaatttgta tgatggtggt tgtaaacatc aaatcaagcc | 58260 |
| atttattatg tcaaaaaaag atgaaggagc ccgggaataa aactctcctg acatcacttc | 58320 |
| tgagcgtatt tcactgccgt gacaggccgt catgattggg gacgatatcg tgggcgacgt | 58380 |
| cggcggtgcc cagcggtgtg gaatgagagc gctgcaggtg cgcaccggga agttcaggtc | 58440 |
| agtgccagct ggagtcattt attcaccttc cttccagggg atgaccacat tctcattctg | 58500 |
| ttttgttctt caaaataaag gggatattct ttccaaatca aagagcagta tgtgggcatt | 58560 |
| cactatcttg tatgtaatgg acctctaaga acagggctga gtggtctttt atagcagaca | 58620 |
| gtgataaagt agagtggctt ttgatacagg gtctgggttt tggaatggcg tgcagtgcag | 58680 |
| agagaaataa gcaaaggcac tatccatcct ggcggcggcc caccagggag ttgggccgaa | 58740 |
| tttgtgctgc tgtcccttttg gcaatttgat cagaccctgc actacggcag ttacagctgt | 58800 |
| gggcactcag cccccttggac agcctccctc tccttttgtt cactttctcc actctgtaag | 58860 |
| acacagagag cctggagacg acagagggtt gctcaggcat gccctggagc agaacctcca | 58920 |
| tctcaagaag aaggttgtgt tttatttgct ggcaaaagtc tgcctggtct ggagcagctg | 58980 |
| tcaggggttg ggagctccca ggcatgtgga gggccctgtg gtacccaagc tccagctcgc | 59040 |
| ctggtcatcg agaggatctt ggacatcaga gtgttgcctt gccttatgct agatggtttc | 59100 |
| gattgtggcc attcagagaa agtacatctt tgcagatgct ggggagactt ggttgaaaca | 59160 |
| tggttacctg gaggtacttg gatttggggt gggggcagtt acatttgtcc tgagagatct | 59220 |

```
gcttaggcag gaccagagaa gacagatcag agggcccgac cgtcgctctg aagtctctcc   59280
tgcgggttgg gagctgtggc tgagtgcgag gtgagtgagg aaggctcagc gcacctgggt   59340
ccagggtcag gaagttggtc ccttccagct acctcccaga ccctcccagg cttcccccga   59400
cgtgtatgac atatgggcct tctttctttc ttgaagttgg gttttgtggc tccccttggt   59460
taggcctggc ctaagggagt gagggagacc ccactcacaa gccacaggaa cgttttttc    59520
caagagacca gccaggggtc ccccagtccc caatcctgcc tttcctgcaa aggtcgcaga   59580
gcctggtctt gctgctgctc ccaggcgagg ggctctccgc tgacagcgga cctcggggcc   59640
ctatagttga tgccgggtgc tgcctggcgt cagccgtcag gagcccagcc cggcgcccca   59700
tgcgtctcag ggcacacctg tgacccgtga gcacaagtga cacctccctg cttgggagca   59760
cagcggtgtg gctcggcagg aggtggaaag ggagaaccgt actgtgttgt gtactgggct   59820
tcttccagtt ccttggagga gaaacatgtc tgtcctgaat gccacctcag ttggggtctt   59880
tctggccagc ccaggccagg tgcccctata aactgagaat gggcctctga agaaggcccc   59940
ccacagccca cgaatgcagg tgggcacgag ggaggctgtg cccaccctac gccagcaagg   60000
gttggtgctt ttcagattcc ggttacctgc atgctattta agaagagta cgaggtgggc    60060
atccccatg acactgtctc ccggagagag agaaactctg tttttttgtt tttgtttttg    60120
ttttttgag acagagtctc cctctgtcgc ccaggctgga gtacagaggt gcgatcgatc    60180
tcagctcact gcaacctccg cctcccaggc tcaagtgatt ctcctgcctc agcctcccga   60240
gtagctggga ctacaggtgt gcaccaccac gcctggctag ttttgtatt tttagtggag    60300
acggggtttc accatgttgg ccaggctggt ctcgaactcc tgacctcagg cgaaccaccc   60360
gcctcttcct ccggaagtgc tgggattata cgcgtgagcc accgcgcccg gccccagaga   60420
gagaaactcc atcaacagtt tgccgaatcc ttccacactg ccttctctgc atagataaac   60480
agactggtaa tattttggtt ttttcttttt ataaaatgg gatgatattg ttttgcagcc    60540
tccttttcc ttgaacactg ttttatggcc tctttctaca agtgtcttca taatgatttt    60600
tttggtaatt tttaaaattt cagtagtttt tggagaacag gtggtgtttg gttacatgca   60660
taagttcttt agtggtgatt tctgagattt tggtgcaccc atcacccgag cagtatacac   60720
tgtacccagt gtgtagtctt ttatttctca cctacctccc acccttcccg gcaagccccc   60780
aaagtccatt gtattatttt tatgcctttg cgtcctcata acttagctcc cacttataag   60840
tgagaacata cagtgtttgg ttttccagtc ctgagttacc tccattcctt gaggtctcca   60900
actccatcta ggtttgctgt taatgccatt atttcgttcc ttttatggc taagtagtat    60960
tccatggtgt atatgtacca cattttttt ctttgtttct ttctttttt ttctttgaga     61020
tagagtcttg ctctgtcacc caggctggag tgcagtggcg cagtctcggc tcactgcaag   61080
ctccgcctcc cgggttcacg ccattctcct gcctcagcct cccaagtagc tgggactaca   61140
ggcgcccacc accacgcccg gctaattttt tggtattttt agtagagacg gcgtttcacc   61200
atgttagcca ggatggtctc gatctcctga ccccgtgatc tgcccacctc ggcctcccaa   61260
agtgctagga ttacaggtgt gagccaccgc gcccggcctc tttcttttt ttttaacttt    61320
taagttcagg gtacatgtg caggttcatt acataggtga acatgtatca tgggggttta    61380
ttgtacagat tatttcatca ctcagatatt aaacctagta cccattagtt attttcctg    61440
atcctctccc tcctcccctc ttcaccctcc aacaggcccc agtgtgtgtg ttatcctgtg   61500
tatccatgtg ttcagatgct gtaggaaagg aatcagtgta gtgccgggca cacagcaagc   61560
cctcagcaaa tggccagggt ggggagcacg tgcggccact actgtccata tccatccgta   61620
```

```
tccatgcata tccatccata tccaccaagc tccagacatg gagtcacctg cctccattga    61680
agaggatggg acttagccca tttgttccta acgagattta aaatgtcaga ccttttgatt    61740
tgtttgtaag gatgcaaatc tgcctttgtt aacatgcagg acaaagggag aagagtgtta    61800
gcttggctaa ggtagggacc cagtcgctgg gggaggccac atgggcatca aaggaggtgg    61860
ggctctgcgt gtgtaggtgt gccccagtta aagggatggg aggtctccca gccattggtg    61920
actctctgga gctgcactgt cagacacagt agcggcgagc cgcagggggt gacttgtagc    61980
tcgcccacag tgagacgtgc aggaagtgta aaatacacac tggatttcag agactgggtg    62040
gggagaaagg attgtgaaag agctcatgag tattttttta tatcggctgc atgttgaaat    62100
gctgatattt cgtgttaatt tcacccattt atttaaattt ttgttaacgt ggctactaga    62160
aaaggttcgc tggcttctgc aggagtgttg gtggccccag gtggcagctg ccctcctcct    62220
gcactgtccc cttctccctc cagatggtac tcttggtaca cagatacact gaaatgctgg    62280
aggggcgtgg ggtcctggat gagtggctga tggggcctcg ctctctggag ggctgttttg    62340
ggactggaat tgcctgcgtg gtgctcccta tggatgtgtg gccagcctgg ggccagcaca    62400
cagcctctgg agtcagccgg gcacctgccg ctgggccggc atcccttcct tccaggaaat    62460
acccccagcc aggctctatg gagcagcacc tcgcccttcc agggccaccc ccagccctct    62520
ggcacctcag cacggcccca ttctgcacag cggtgagccc cccaggggca gcagctgtgt    62580
ctcctctgca gctgaggcat gtcgtcgcaa ccctgtgctg agcctctcct ctcctgcaag    62640
tggcccaaag aggcctcaac aggggccaat gaccactgga tgggtcagct gggcatcaga    62700
aggccttcca ggctctgtcc tctgttggtg gccttggcgg aaatgggaga atgaaggggg    62760
aggaggggtg gccttgtcct gggcccaggt ggcagagagc cctgcagtga gtaactgcgc    62820
tcacacttgg tttgaggcca gggcagcatg gggaggccgt ccaggctggg gcagctggcg    62880
ggtgggggca gcggtcagtc ctgccagtca ctggcaccag gaaggggggag aagccagagg    62940
gatgactgag gcctcccact ggtcctgctg tgggacgtgc cctcagccaa ggtcttctag    63000
tacggagcac gcacacgtgc acgcacttac acgtacacac acacacacac acaattgttt    63060
ctgaggcagc tgtcaggagt ctgagaggcc gagaggtggc tgaggagtgg gattcggccg    63120
ctgactggca gtgagatctc cttgtcacct tagatgtatc catttctctt gttttcatta    63180
taaaatggcc caaagagagt gaagcctcgg ggttgggaga gattgcaggt ggcttagctc    63240
tggagggaaa gttttgcagg gcctgctccc caggaaagca tcatccccgg gcagggtgt    63300
ctggagcttg gcccaacagg gctgcccaag agccctggac agggaagcac aaagctttct    63360
tttcatacct gctccctgtg gaaatcctgc ccagccaggg ggcggccctc acctggctgg    63420
caggtaaagg ccttctgggt gttccctgcc tgccctgttc ccaggactcc tggcgcattg    63480
gacatggctg ctcccccaga ctcctcgagg tccatccag ccacagcgtt cctgctgccc    63540
aggccctgga caacagtgtc tcctccgtgg ggggtcctgt gccatgggtg gcaaatcctc    63600
atgatgccat gagtcctgca gccccagagg gtgctgctgc cctgccgtga gaggcttttt    63660
cagatgggac agctaggacc ttggccaagg ccacctggca aggttttaca gaagctggac    63720
tggaacctgg ccgcccccag tccctgggc gggtgctttt cctgcacttt tccctggtag    63780
aatgtcctgc ccttggggcc acattttgca gcagtcacag ggcctggcct cactccaggg    63840
ctccatgttt ggatgcgagg cccagtgggt aagtgcactg ctgcccacgc ccccccccaa    63900
gcactgtctg ctcctccctg cttgcctgcc tgtcaaggca gccctcatct tccttggagg    63960
```

```
atgggnctgg gctgggagcc tgcgccctcc cattctgaca aatgagtaga gggaagggac    64020
gttttgccca gttccaaggt gccctctctg tcctcagtgg agaaggaaga gccgctggca    64080
catctgagcc acagacccct cctgcctctt atatcccac caacctgtgt tcctgtggac     64140
atgccagaaa ccaggccgtg tggcctctca ccacccatc actctgttcg ctgttccacg     64200
ccacaccctg cagccaccac ccagtcaaag gcgccactgc ctgggaagcc cctgcgctag    64260
tcctggtgct gctgtgtaaa taagccgcg atgcggagct cgcctctggt cttctcttat     64320
tgtttaccca aggctggcag atgttttata agccccgaac gttcttgaca aacagtttgc    64380
ccttcggaga gggaaagttt cctggaccgt gattcccgac atcctgcaag gtcccttcta    64440
gctgtggcct gggtgctgaa ggggtttccc cccagtgggg tggccagccg atctaggatt    64500
ccagccgcct tgcacaaagc tggaagacga ggggctgcag ggtgcatggc tgtggagctg    64560
gctgcgtcgg gagggagagt gccccacgc ctggcctttg accttggaag cggctgccgt     64620
caaagcagca gcttgtcctg ggtcttccca gacttcgcag tgacggattt cagagtgttt    64680
cctgttacga gaaggctgtg gattcgcttt ggaacatgac agattttct tctgtgctac     64740 gtggagtgtg agggaaggaa gtgaaactgg tgttaatttt tcagcagtca catgtcaaag    64800
tgagtggcta gcaagcaggg gggtccaggc tgtggtggcc ctggtcagcc ttccaggagt    64860
caggaccctc ctgctgccct cctgtgtaaa cagaccagcc agggcaatcc gagccagccc    64920
cggtggagag aaagggccag tgctgggctt ggagctcac cccaagttcc tcgggtactc     64980
atcctggcag tgcagggaag ggcaccggga acaggcctgt ggaaaaatcc actgtgcaat    65040
gagtccgtga atcccagaca tcctctcagc agccctctgg tcctgcccgg atagaggct     65100 gtggcttctg gtgtaggtgg gcacttctgg gctcagaggg gtcatttagc tcacctgagg    65160
tcacacggag tgggacccac cccaatttaa gcctgtacac ttttttcttt tgtctctttt    65220
ggtaacagct ttattgagaa atcactccca cgctgtataa ctcagtggtt ttcatacatt    65280
cacagagctg tgcagtcgtc accacaattt tataacattt catcaccca aaaagaagcc     65340 tcaaatcgtt tagctattat tagcaaagac cccccacatt ccacccagcc ccagacaatc    65400
actaatctac tttatgtcat actttctttc ttttgttttc attttttttt tttttttttt    65460
gagacagagt ctcactctga cagccaggct ggagtgcagt agcatgatct ggctcacta     65520 caacctccgc ctcccaggtt caagcgattc tcctgcctca gcctcccaag tagctgggat    65580
tatagccacg caccaccatg cccaactaat ttatgtattt ttagtagaga tggggtttca    65640
ccacgttggc caaactggtc tcaaactcct gacctcaaat gatcccccg ccttgacctc     65700 ccaaagtgct gggattacag gcatgagcca ccgtgtctgg ccttatgtca tacttttcatt   65760 tgaaaaattt agaaaaatta aattggccca ggagtttgag accagcctgg gcaacatagc    65820
gagacctcat ttctattaaa aatcaaaatt agccaggtgt ggtgacaccc acctgtggtc    65880
ccagctactc gggaggctga ggcaggagga tctcttaaac ccaggaggtc cacgaggctg    65940
cagtgagctg tgatcatacc actgcacttc agcctgggtg acagagcaag accttgtctc    66000
aaaaagaaat ttttttaaat tgtggtaaaa tatatataac ataaaatatg ccattaaaca    66060
attgtgatgt gaagtgaata aaatttgaat acacagcata atgaataaca aagcaaacac    66120
tctaaggtca agaattagga ggctatcagc tccccagaag acctagtccc tgattgacat    66180
gcccagtcct gcagaggcgg ccccgccttg ccgtgggcac agtggccgcg gtgactgggc    66240
ctgctttctt ctcccacatg gctggcttcc ctccaacatg gcgctggctc ttccttctct    66300
gacctttatc caagtggaat cgcacactgt accgttgagc tgtggcttgt tcatcgtgtc    66360
```

```
ctctgtggct ccaacacccc tctctgcccg tccctcagag ggaacatctg ggtgggtccc    66420
agtttggccc ttctgcactg gctgccagga atgttctggt ttttgtctcc tggacacatg    66480
ggcgtgagtc cttctggggc ggatctgctg atagatggca gtgctgggtc atggaggagc    66540
atatgttcaa cttgaccaga tgaggccaga cgggtttatg cccccaccac gggggaccc     66600 tgttgctccc cgccccgacc atcacgagct gttctgggag ggaggcccat gttcttccca    66660
gtttacggtc ctgggaggtt tctggacatt gtcagcatgt ggcagtcccg gacgctgggc    66720
ctcctgagag agtggggagg agacccgagg cggaggcgag tgtgtgaaag gaggctggtg    66780
gggtccacat ggctcagcag gtgaacatgg ggtttccagg ggcagacacc ccatcgtggc    66840
ccccatggct ttggttgggg cagcatcagc ttcctcctct gctgggtttc ctgccttctg    66900
ttggctgctg gggcagggga acaggattg ggaacagtca ccctctctgg tactgaccct     66960
cattagcatt cttggttcct gagcaaggct gcttcatgtc cagggcaaga ggggaaagat    67020
gttaaaacct gaaccccect gctgggcttg gtgccgcctg tggaaaaacc ggtgggctga    67080
gggctggggg gctctgagct gaggaagggg gtcccaggtg gaggccggga ggtggctgca    67140
gagtgaggcc acaaggcctg ggggttggcc cagaaggtag gaccctgta ggcagcctcc     67200 caacccagg aatttgcctc ttgggaacgt gcaggtccct cgagggtcct ggaaggcgct     67260
ggagtggtgg gacagggatt gagggagcgt cagcagggcc ctctcttctc cctagagccg    67320
ctcaacacgt gttgcaaggc acgtgctctg gacctggtgc tcacacgtgc tcttctccca    67380
agacactccc tgaagcgcgt tccccaggag ctggaagggg gataacgcag gtatgcctca    67440
tggcggggcc agtgctcatg cttacacaca ctcagcctca gctcgtctac accctgcaac    67500
agcccagaga agccaccccgc cttcttaccc ctaccattta gatttgcaaa tggaagctca    67560
gagaggtgaa gtaacttgcc caaggccaca cagcctacca gtgtcagaat cgggattcga    67620
acccacctct gcctgactcc aaggcctgtg cccctgaaca ttctcaagcc acccccaat     67680 tagccaagtg ttgctggagc tctgagcagg ggccgggcct cacaaaacaa tagtagccag    67740
tgtgggggct cacaggactg gtcagctccc gccctccccc gctttggccc cctccacaca    67800
cacacgacct gctgctgagc tggacataag caggacctgg ctctggggc ttctgaccta     67860 gggcaggccc tgaagttggt cattagaccc cacccaccca cctgagagcc tggcggagat    67920
gtgacaggtg acagcccccag aagtcccatc gttgctgcct ttgtggttaa agtccgctga    67980
acccaagcgc tctcttcccc tccagtgtgt ggtggggagg tggggagggg acccaggcag    68040
atctgggaag ccgtggccag gccgcagcaa gcagggggaag aaggggcccg cagtgaactt    68100
gcagcaggag ctgtggccac cgtcctagcc aggccggcca cctgcccaaa atgttctcta    68160
accttaacat gaacctgggc cacttgggct ctgctggatg cccccagggc tgccagagcc    68220
tgcccgccac agagcccctc tgagacctgg agtctcacct gagccctctc gctgcccaca    68280
gggctggcct ctgcctttcc gctgctgctc tgcggctcgg ggacacggcc agggctggtg    68340
gcgcttacag cccagggggca ggggagggca catcccccac agcattcacc attgctgctg    68400
tgttctgatg catcagggaa tctgcatttt tgacccttt g attgctacat ctttttccagc    68460 ctggaaaagt gaagaaggaa ggaaggggg ctcagaggcc cctgactcct gtccttgcag     68520
gcacagctgg acgcagttct tattttcaac catcttgcag cagtggtttt atttgtgcac    68580
aggttcctct gtgtcatggg tgggtcccag gatgtgaacc cggtgtgctc ctctagctcc    68640
actgtcctca ggttggggac agccagggac aaggcccccct actccagctc caaacgtagt    68700
```

```
tccaggctgg ggtgccctttt gcccaggccc agcctggtag ccccgggtgc tctccctgac   68760
ttttcatgag cccgggggct gaaaccagag cagcagggag acagaaaagc ccagccccac   68820
cctccagagg gggagtccag ctgcccggag accccaagag cactgccaga atctgggtat   68880
gagacccagt cccctgccgc gtgctaacca tgtaaccttg acgtgatct ctttgtgctt    68940
ttttttttt gttttttct ttttgagatg cggtcttgtt ctgtttccta ggtgggagtg     69000
cagtggcacc atcatggccc actgcagcct ggaactcctg gcacaagtg attctcccgc    69060
ctcagcctcc caaatagctg gaaacaggt ttatgccacc acgcccaact aattttttaaa   69120
tttttttataa agatggagtc tccctgtgtt gcccagcctc ctgggctcaa gtgatctccc  69180
cgccttggcc tcccaaagtg ctgggattac ccggcttgag catgatcttt ttgccttgct   69240
tggctctggg tttcctcatg tgtcaagtgg ggctgagccc cagctgtgtg ggctgaacag   69300
gggagggtta agctcggccc ctagagtgag gccccgccat ggtggtggct cccgtatggc   69360
atatttccct aacggttccc atttggtctg tcctgctaga ccaggctggt gggacgtaca   69420
ctgactctgg ggttctgtcc accccgtggg tgtggtccac cacatggtca tggtggcttt   69480
ctagggtaga cttgaccttc cccactgcct ttatttattt atttattatt ttatttttttt  69540
ttgaaacgga gtcttgctct gttgcccagg ctggagtgca atggtgcgat cttggctcat   69600
tgcaacctcc gcctcccggg ttcaagggat tctcctgcct cagccttcca agtagctggg   69660
aatacagatg tctgccacca cacccggcta attttttgtat ttccactaga gacggggttt   69720
cgccatgttg gccaggctgg tcttgaactc ctgacctcag gtgatctgcc cacctcagcc   69780
tcctaaagtg ctgggattag aggcgtgagc cacagtgcct ggccttcccc actgccttta   69840
aaatctctat ggtccccact gcccacggga ggaggcccaa ccctgtcctc tgttagtccc   69900
ctggtccccg tagatattta ccaagcacct actatggcca ggcgctgttg aggatgtggg   69960
ggatcgagtg aatgtggcag gtgtcccctg ccctctaggg ctgttcttcc ttctagggag   70020
ggaggttcaa gcccctctcc tgatgcccag ctggcctccc agcgtcaggg atctctgctc   70080
tgttggtccc ctggagtggc cctggggcca ccacataaca cttttgtaag aataagagtt   70140
atttttatg gcacaatcgc ccctgccctg ggtttgtgaa tttgggggat tctttttttt    70200
tttttttttt tttttgagac agagtcttgc tctgtcgccc aggctggagt gcagtggtgt   70260
gatctcggct cactgtaagc tccgcctccc gggttcatgc cattctcctg cctcagcctc   70320
ctgaatagct gggactacag gcacccacca ctaccatgcc cagctaattt ttttgtattt   70380
ttagtagaga cggggtttca ctgtgttagc caggatggtc tcaatctcct gacctcgtga   70440
tctgcccacc tcggcctccc aaagtgctgg gattacaggt gttggggat tcttaaggaa    70500
aaccacctga aagtgcgggg ttattaaaaa cagaaaccaa cccatgcacc caccactcac   70560
gagcagccca cacagctccc acctgaccag ggctccccct tctcatgggt gagtgaaagt   70620
tgctgaaaat aggcctcctg gtgaggaacc tcccagccag ccctgtcagt ggcactgagg   70680
ctgctctccg actgtggcat ccccccatgtc tgtcctcatt actgagcaaa aatttgtgca   70740
gaggagtgct ctacactttc caagggttta atccaggagc tgagggccag gggctccatg   70800
actgtagact caacatcctg ggccacagcc atccgtgagg gggaggacga ggggccacgc   70860
cctgcactct gtcccagcat cccctctccc tggagccatg cagagatggc ctcatttcat   70920
cccacactca catgcgggtc ctagacacca gctcatgcac atacacacac acacacacgc   70980
acacacacac acacacacat gcgcacatgc acccacgcac tctctttgcc tgtgggaggg   71040
caggatccca gctgccccag cggggaaggg gtgtggggaa tcagccctgc agatgcggtg   71100
```

```
tgaggggcag acatggcatg ctggtctttg gcagtgtggt cccaagtggg ggcggctgga    71160
gaggtgcctt gccacagggc ccaggccacc cgcatgcatc ccatgaggcc gtccaagccc    71220
gtctgccctg catcagagag gacacgccaa tgcggggagg gaggaacctg gtgaagccag    71280
gagcggtggg cagggggccag caaggatccc caggccccca gggcagtgtg catccggcct   71340
tcttgcatgc ccacctggca tcctgcctgc cgcctcctgc ctcccgcccc acccctcctg    71400
cgtcccagcc tggtggacct ctcagggttc actctcattt cctcctcccc acgccacctg    71460
ctcgggccac aagagggcgc cttgctgcca gggatgggac aggccgggcc tgctggagcc    71520
agggccgatg cacgcacagc tacatacact cacccgggcc cacgtgtgct cacgaggggc    71580
ccccataccc acacgatccc gcatccacat gtgcgcacgc caggccccac aggttctcag    71640
gcccaggcca cacatccaca ggtgcccact ctcatgctgg cctcatagtg catgcacaca    71700
cacacacaca cacacatata catacactca cgcccagacc cccccacgcc ccaggccaca    71760
catgtgggcc tgctcacacc ccactcattc cctcccagat gccgcaccac ccccatgccc    71820
tgtgtgccct ctgcctctcg ggccctggg  gccccagctc aagaaccac  gggcttgctt    71880 tagccaggct tccacaagcc tgcccattcc tcaggacact gaccctctcc tctgccaccc    71940
ttcacgggtg cagacgatga gcatggagaa caccacagcg cacagggccg agggccacca    72000
tcagagtctc ctgcagccct ggattccctg ggcctgaagc aggcagagcg gccaaggtag    72060
cctcatcagc ctcaccagcc cgtccttctt gtctccctgg caccttgtca gagagaggcc    72120
taagaacacg ctctgggcat tggggggcctc ccagtgttcc ctgcgagttt ggagaggcca    72180
ggtccctggg atgaggacac gcccacccgc caagctcccc tcctgccagt cccacctgga    72240
gcctttatgc atgctgtctg cgcccttcac ctgtcccacc acctcttctt tggcctgcct    72300
ggatcctgcc atatcctcaa ggccttccct ggtgatggaa ttccagagtc ctcccaattg    72360
caagggcctg agggatccgc tgccctccaa ccccacaccc cgtctcaagg tcatgtgcta    72420
atcccgtgca agctggggtg tgggctggct gccatgtcaa gctcgtttct gttgtaccca    72480
aaacacagtc tcacctccag aagaattacc tggcactccc tggagttccc gcagccttct    72540
cattttcaaa taatttttca gatttccaga atagaaagaa attccataca cccttctccc    72600
agagacagac cccattcaag ctttgccaat cattccatga actcctctag agaggggaag    72660
acccagtccg gggccaggca gctctctctg gtctctctgg actccgtcct ggagcacttc    72720
cctgtcctcg cctcagttct cacagattgc cagttttgaa gattacgaga cagtcatttt    72780
gtgtggtgtt ttctcatgat acaacccaag ttacgcgttt ggggctagca ttgcttagaa    72840
gtggtgctgt gcttgttctc ataggcatgt aatgttggtt tgcccaaata ttgctgatgt    72900
taaccttgac ctcttgttta atggcaacca cataatgtgt ttttcccctt tgtgattgat    72960
acgtatttgt ggggagatgc tttgaggtga tgcgatgtcc cactttcatc tgccagtttt    73020
agtgtccctt agtatttctt gtttgaatga atgatttcta tgatggtcgc caaataactc    73080
catcattctt ccttgtattt actcctggtg ttttacttta aggaaagatg ttctcttctt    73140
tccactgatt gatgtatgcc agtgtgggct cgtggcttcc tatgtaattc agtgggttat    73200
cgtctgttaa ccgtcatcac tgggatattc agatggtccc cgacgcaggc actggcagcc    73260
ccttcaggct ggccctgtga cctttcggca catcctcacc gttctttgag cccttccttg    73320
cattttggcc caaaaagatg tttcaggttc atttgttcag tctttgcttc agccctggaa    73380
tcggccattt ctccaaggag ccccagttcc ttccagtgga gggcactgtt tagaatctca    73440
```

```
gcccagggcc ccaggtgtgc ttgtgttgtc tctgggcatt gctgctcagg ccctggcggt    73500
ggacagaggt aggaaagatg cgcatggtat gcaggtgtga cacacacatg cgtccatgct    73560
taccctaccc acctggacct gcccaaaagc ccgagctcac agcagtgcct ccgattccag    73620
tccagcagca cagggttcct tctcacctca tgcctttaca cgttcatgcc ttccttccac    73680
agcagggaga agcctggctt cctcattctc tctccatctg cttatcgctc tatcccatgt    73740
agagccaagt ccctgacctt gcctgtggtg gacactctgc gtttgttaaa ctgaataaca    73800
acaatcctcc ctattgggag aaaccttttc agcttcccag gccatttctg catttgtggt    73860
tctcttccaa gcctcttggg taggcataga aagtcttctc tgttttccag ggaagctgca    73920
gactcaccca gcatcaccca gctggtaagg gtgtagcagg acagtgccag catgtctgtc    73980
ccaactgtcc ctatggcccc tatggaagat tagctatgtg gtggcaaagt gtcccgagga    74040
aggggcattc tgggatgttc aggtgctcga ctgggctggg acttgtactt tggaaatgag    74100
aagaagccca ggctcaaatc tttgccccac tgcttgctgg caggaagacc actgagcctc    74160
agttttctca tctgtaaaat ggacttattt tggacttact tcccaggtat cctcagcacc    74220
tttattacag gagctccatt aatacatggc tgcaggaggt agttcaggga agcaatggga    74280
gtggaatgct gggtgcatca cggcctgggg ttgtcagcct ggcctctgca ggcatctgag    74340
atattcctga gggcagattc agccaggcca cacttctgg atagaaccac agggccataa    74400
actgagacca ttgagggaga ctgcttggct tggaaaactc gcccagggac catgtgctct    74460
gatttgcaaa atgcaccccc cagagcggct tcctgccttc actttgtgca gagttggggg    74520
cggcaggggc gtgggggtt ggatggacca tgtcacccaa aagtttgtgt cctcggatgg    74580 ggagggaga gcgtctgccc aagcacagcc tggaggcttc ccttacttcc gatgaccttg    74640
tggcagtcag tgtcacccgg acagagtgtg gcacgccttg ggaccagcc cctcccagaa    74700 ggataggcgc ttgattggaa acgttgactt ttcatttaaa taagtaaagg tcaaggccta    74760
ctgcatggcg aggaggagat ggctcttccc tgcctctgtc ctcccttacc cccgtgtgag    74820
tggacaaacc ccccgtcctc acccaggtgg cccgcttctg ccacccgcac tatatccaag    74880
acacagccca gctttgcagg cacttgccgt gtgctccgca gtgtgcaggg tgatgagatg    74940
aacaagacca tgtggcctga agggtcccac gctgcagagg gccccagccc agggccagac    75000
cccaagtgtg tgcctggagt gactcagggg tgcgcgagga ggactcagtg ggatatggaa    75060
tgcaggggct gaggcatagg gagtgacaca ggggctcagg gctttcccat gagtcgaggc    75120
tcattgggtt ggcagggacc acatctgccc tggtcgatgc cctgcccatg caggctctaa    75180
cggcagagtt tggggattgg ggcggggat gcagggggcc tggggtgggg agcttggggg    75240
cagtgggcca gcaaagcag agcccttgc tgtgttggaa accctcaga ggccctaggc    75300 gtgataagtg agtgtgacgc aggagagtct ctctgcatgg gccacccaca attgcagaga    75360
agacgccctg catgtcatag gcttggcggc ccatgccggg aatttggcat ggccgtcttt    75420
cctccggtgc tggggagctc agcagctgga ggcagatgct ggattgtctt tctctaccgc    75480
agcagggcag gtagcttgtc ttttagtttg ttttgttagt ctcctgtatc tgtgactctg    75540
cagagagcca acggcaggaa gagggcagca ccggcacgtc ggaggccgag gacgcttag    75600 acgggaggtc cggaggctct cagcctgacc agccctggcc tagggccggg gaaaggcctg    75660
ggctttgggg tcaagggcag gggatgagat ctcagaccca cgacctaacc attgacctgc    75720
ctgggccact tcacccctgc atgcttcctt ccctgtctgt aaaagcggat cacgtgaggg    75780
gccttgcagg aagctctgag gcccagtgag gcccccggga gacaggcgag accgctgtga    75840
```

```
gcgcccgtcc ttcccgcccg gtgcctggca ggttcctatg cgctctcggg gcttcgggct    75900
ggggccctgc tgcggcgagg ggggtgctcc ccaggctggc gctgtcggtg gtgtggcttt    75960
ggctgacacg aggtggagag gatcttgttg acctgaccgt ataaagtagc agtgaggcct    76020
tacaagtagt tctaggcctg gaaaggaaag ggaaagaaag agcaatggaa tctggtattt    76080
tctcaggtgt cctggactcc atctgaaaga tttcgccatg ggaaacattc cttcctgggt    76140
cctcggcgcc tattgttaca gcacgcaggc acccgggctg tggcctaggg gtgaaacctc    76200
tctcgattgt gtggccatag gtggttactt aacttctctg tgcctcagcg ttgccactgt    76260
gtgtggcgat agcaacatgt cttcttccta aggttgttgg gaaaacactg atcgcaacag    76320
tgacagatgc aggacccact ccaccagaaa ttgttccatg agcttgttta cccaccagac    76380
gcctgtatga gagagaactg acatcgtcct cactttgcag agaggttaag taacttgcct    76440
aaggtcacac agcctttgaa ccctgggagt cgaactccgt catctatgct ctgaaccact    76500
ctgccacatg tggtggttac tgtcagttcc atttgtttcc acacagcttt aagttagtcc    76560
tgtggtttgc ttttatttta tttttaagac atggtcttgc tctgtcaccc aggctggagt    76620
gcagtggtgc aatcatagct cactgcagcc tcgacttctg atgagattct cgcatctcag    76680
cctcccaagt agccgggact ataggcacat gccacaatgc ctggctaatt aaaaaaacat    76740
tttttttttt tttgtagaga caaagctgtt gctatgttgc ccaagctggt cttaaactcc    76800
tggcctcaag tgattctccc acatcgggat cccaaagtgc tggaattagc ttggcgtgag    76860
ccgccatgcc tggcctagtc tggtgggtgt ttaaaccttg ctggcctttta ggggtgcatg    76920 ctgtgaagac ctgtgggcca gaggccaggt atcaggagga gacactcagg cctgttgaat    76980
cagctcagtg ccacagggct gcaagagcag ctgcttcagg ctcctcaggc cgtgggcccc    77040
tgagcaccag ttctgctctg ctccctcagg ggaactgggg agatcaaggt ggggcccctg    77100
gacctcccct aattcagcca gagaagctct catctcttcc ggggtcccag gcaggattcc    77160
cctgggctgg ggtgggaggt tctgctgctt taaaaccact ggaaaggctt gagaaccagt    77220
gatcttctgc cctgttacag acgcggaagc cggggtggag caggcctgta aggtggggc    77280 tggggccggc actgggtccc cgggcttttc caccccctgcc gcgtgtgcgt gcagactggc    77340
cctgcggtcc atgggcttgg gcctgccttt tggcttgctc ccgagtattt tgcccagagg    77400
ccttgtggct ttcagggatg ctgtctgggg ctggaagtca gtccttgttt tgtcctggca    77460
gtagtcagca ggagggagaa gaagggggtta acctgtctgg aaccaggaaa gaggaagcgg    77520
tagtgttccc gcatgcagtc ccaaatagac tcctgctcct gctccgaggc caccccagcc    77580
aggctggatg gaagctcccc ggctgggcca ttgttccggc ccctctccct ccaccctgag    77640 aaagcccca gccggtggg tcagggcagg acatggacag gccaaggctt tgggctccag    77700
ggaggccaag ctgctggggc ccagagaccc tgctgtgtat cccagagcca gagaagaacc    77760
tccctgaggg ctctgtgagc cagagggctg ggggatgtca agacacaggc agggcaggc    77820 tgcaaggtta gagtgagggg aggggtacct ggtgccattt tggaagggac ccctgaaggc    77880
aggaagcagg acagaccccc cgccattggc agaagacctc tggaatcctg agatacttaa    77940
attccctgcg gcagctccaa gcctaggaa ccagacagat cggggaggat tggctagaac    78000
agtgcatcct ggtgggtcgt gttgaagct ctctgaggtc cctctgctgc tgagagatga    78060
aggaatggag ccctggctct gctgtgggat gccaggctgc ccaggctccc cgacctctcc    78120
agcaacaaaa atcataaaca cagcatatgt aatatataaa taataaaagt aacagccatc    78180
```

```
ttttcagaat aatctagcac ttagaatgtg ctagggaaca tacaagcact tttctcctta    78240
tttacagtaa gccttaaggt aaatttcatc atctccagat tttaagtaaa gaatttgaga    78300
atcagagaca ttcacagcaa cctggtgcac ccggagcctg gctgacccca gcaccgctgc    78360
tggcggcccc acctcactcg cccagtctcc ctgcttcccc agccaccgtc cagctacctc    78420
gagagatcct gggagcatgg tgattgtggg gtgcatgggg gcccgtgagc tgttgggggt    78480
gtcagggttc tgcccgtgag atcctccttg ttgccagaca tgaggacctg gactggcagc    78540
tgtgggtggc ctcatgaatc agggatcaga gatagcgggc agcaggcggg cccagcccgg    78600
agcaagctgt gccattggcg atgcggggag gctggcccca tcgaaggctg gtgggactgg    78660
tggagactcc tgtccactgc tcagcactag gcctgcagca gacaccatga gccccaaact    78720
tcccaaagcc cttccccagt cccacaagat ggtgtctgcg gaccgtgctc gtgagagatg    78780
gcagccaggc agtccccaca gggcacccat tttcagctgc ccccgcttct cagacaagga    78840
aactgaggcc agaaagccag gtggcccagg agctggcttc cccatttcct gctcctgtgg    78900
gccccactgc agtgccatg ggccgggctg atattacccg agacttcgga gctctcacgg     78960
gtgcgagtaa tttaggctgc atggacacaa gctgctggct tgagtcgccc cgttatgaat    79020
gtgtgtgggt ctgtgcccct ttcatgtgct gccacagggc ccacgagtgt gctgaaaggg    79080
aaggacacgg ccaaggggcc atggtggaca ggagaccttc ttgggggttc ggtggtgtcc    79140
ttgacCCCAC tctgactgag cactgcccca aggcactgcc attccaggcc ccttccctg     79200 agcctcccac cccaggccca cccacctgct gggtcctccc acctgcgggg cccgccatgc    79260
ggggtcacca tgcgagtctc accatgcagg gtcaccacac gagtctcacc atgcagggtc    79320
accacgcgag tctcaccatg cagggtcacc atgcgggtc accatgtggg gtcaccatgc     79380
ggggctcacc atgtggggct tcaggagctt gctgagcacc ctccccaccc acggtcactc    79440
tccctggggt ctgtaagcct ccctgggcct gagcagctcc cagccttgct gctgcctttc    79500
cacttcctgg cagtgaggtc tcctgggtgc cttctctcag ccctttggga tgttttttgt    79560
gaggaaggga ggctttgatg ctgtggagca tctgtagtgc ccactccagt ggcttcacag    79620
gagcagcagg ctgtttgttc tgagctgttc caccttgtgc ctgccagagg ggagatagtg    79680
gacaggcctc cctccccccca agtggtgggg tggaccccct gcccgctgtg gccccatacc    79740
tgggggccac acaccactgc cctgggccgt gcagctgcta tgaagagtgt gctgctgaga    79800
ccctggaaga gacggaggat gaaattgtgt tgccagatag tccatttgtt gttctgagac    79860
tcgcatgcct gggagaatcc tgggaattaa ctagctcctt ctctcccatc ccattttaca    79920
gaaaagtgag acccaaggtg gtttctgact tgcccagagg tcataactgc ttggacagtc    79980
atggtcctca gagcccacgt ttgctgacca gtgcaggctc tcacagccac tcagctcctg    80040
cagccgtggc gtggcagagg agggaagcac ttcctgggat ttatgctgcc tccctgacat    80100
ttcaaggccc ttcatttctc taaatattgg aggagttgaa ttattttag ttgagcctca    80160 agggatcaga gaataagctt gcagcaacgt tggcagatgg gcttcttcta gcagagagtg    80220
gttattcggg gcctcttatt gagagaatcg ggtgatttga ggaaatctgg ggtgtcctga    80280
ggcataccag aggaccccca agttttttcct gtggctcgtc tgccatcagg aaaccaaaat    80340
gactcccctc gtcctgagct ctccagggtg tggacctgga atgcttaagg ggaggcaatg    80400
gcatatcttt aagatgagca cagctccgga gccactcgag cacccaaggc cacgtcctgc    80460
tcagggcact tcgggcctca gtttccttat ctttaaaatg gacagagttg gccgggtgag    80520
gtggccctgc ctgtaatccc agcactttgg gaggccaagg ctggcagatt gcttgagccc    80580
```

```
aggagtttga agccagcctg ggcaacatgg cgaaacccca tctctactac aagtacaaaa   80640
atttggccgg gcatggtggc tcatgcttgt aatcccagca ctttgggagg ccaaggagag   80700
cggatcactt gaggccagaa gctcgagacc gcctctacta aaaatacaaa aattagccag   80760
gcgtggtggc tcacgcctgt aatctcagct actcgggtgg ctgaggcagg agaatcactt   80820
gaacctggga agtagaggtt gcagtgagct gagatcgtgc cactgcactc tagcctgggc   80880
gacagagcaa aaccctgtct caaaaaaaaa aaaaaaatt agtcaggcat ggtggcacac   80940
acctgtagtc ccagctactc aggaggctga ggtgggagga ttgtttgagc ccagaaggtt   81000
gaggctgcat tgagctgaga ttgcaccact gcactccagc ctgggcgaca gagcgagacc   81060
ctgtctcaaa aaataaaat agacataata agagtaccta ccacctacgg ctggggagac   81120
cagaatgaga tatcctgcca aaagcactca ccgcacttcc tggcacacag caagggttca   81180
gcagttaccc gcttctgctc attttcttgg tgttctcatc agtatgatta tttagggaaa   81240
cttgggtccc cagataaccg tggggagggg agggtttacc tgcaggtgcc ctggcccagc   81300
cgttcatgca gcgccgtgct gtttctgtgt ctgtgcgctt cggtggagat gctgtgggtg   81360
ggtgggcagg tgtgccttgt gctgtggcct cccgagacaa ggagggctcc cacctaagca   81420
gggtcctgca gcccaggcac atagccctgc cctggccctc caggtccaca cggctgtggg   81480
ttcccaccag ggggcggcag ggacttgcgg ccggggaccc agcctggttt ctcccgcttt   81540
gcttcgtggc caggctaggg ccagggggc tgcgcaggat ggggccttt caccactgcc    81600 tggagccgct cgcccaccaa ccccactgac ggctctcagt ttcccttttcc ccgagcgccc   81660 ttcaccctga ggcacagcac agcctcgtgc tcctggcccc actggcctgc tcccttaagc   81720
tgagttttgc ctttgcagtt tgagtgacat ttttgctggg gatccggggc tgctcggggt   81780
ggcctcgcac acccctgcac tttggctgcc tggaacgtgg cttggggttc acggtgctcc   81840
atggtttgac tcacaggcag ggttccagca gcagcagaga gaaagagcat cttctccagc   81900
cggccctaca gaggccccgg gaccccaaag gctgcactga ggtggccacc aaaaccaggg   81960
ggcagagtcc tcctaagttc tggccctaga tctaggctcc agatctcccg ggagttggat   82020
ccagaggaac ctgggctcac ttcttttagca ggttctggac acacgatgcc tttagggct    82080 caagaaaatg tttaatttat tttaaaatta gaaggaaaat atctctggaa catttagggc   82140
caaagaaaat gttttaatgt ttttttctcac tttagaaata ataattcaaa aatccattaa   82200
attatttaac agcttttta atggaggaag gggcccccca aatcacaaag tggccctggg    82260
ccctgggatg gccggaggag agcctgccat acccacgcag tgtgcctgag tcctggagtg   82320
cgatgtattc tgagccaccc agaatggtga gtcaccaaga ggcagcttgg aggtgggccg   82380
ctgcccctgc acactgtgct tgggggacac agccgacacg accagcctgc agtaccagga   82440
tagacaattt gggctggagc caaacttgat cagagggagg ctgactttat cgagggctgc   82500
tttgtggcgg gcgttcattg tggaaagagc ccaggaagga gctctctgcc ttgcaagaac   82560
attgcctgtg gctcaaaatg gccacatggg atgcagttcc tgaggtggca gaagagccag   82620
cctctgctag ccccagacct aacggagttg cggctcatgg ccaccctgag gaattccacc   82680
tgggcgtttg gtgtccctag catatctcga atggcaggct gaggctcgaa agtctcatgc   82740
ctgtctgcag gaccccgcg tgagcctggg accacccgtg gggacagtgt gtgtctaggc    82800
aaatgccttg ggcactcgag ggggcactga ggccctggag ggcttctgtg ggtgggagtt   82860
cccatgacgt catccctcag tacaagctac gagggcttct tagaacacgc tggacactgg   82920
```

-continued

```
ggagggctct aatggtattt gcacaaattt gcaatgttgg agaccagagt ggagtgggct    82980
gggcgggcca ggccccggcc cagatggggt gacctttcct tcaccccctac ttccccactg   83040 caagggtgct gcctccccag ctcctacctg gggagatgct gacatctggt cattcgcaga   83100
gtgccctgtg cccacatgct gtccctgtcc agacatgaaa cggacagcag gagggggctt   83160
tgaggggtct ctcctgagac acctctccag ctgaggctcc tggagttgga agccctgca    83220 gactcggtgg ctgcctcacc aaaggctcca tctgcatttg cccccatgac cttcccactg   83280
tgcctgggac cgcagttaga gctgaccagc acctgggca gtctgggtc tggggctggc     83340 gttcgggcca gcatggaaca cagatgcctt cagtggctct ggtgggcacg ggcttgcac   83400 agatcggact gtgaccccag gctgtgggac tcagccacca agcgccttca cttatttact   83460
gaccttgaag ttatccagca cttatgtgtt tacagatacc tgcacaacag ccagagaggt   83520
acgaatacat ctccacctac aggtgagggc acagagaggt taggacccac ctgaggggat   83580
gcagccagca ggtgggactt gggccctggc agtctgtttc cagcctgtgt gctcaggtcc   83640
agggtctccc tgggactgga gagggcgctg ggggaatgga gccgcctcct gcatcagagc   83700
ttctcctgct ccagttcagc ctgcagctct cctgcatccc caggtgggga ccagagagag   83760
gggcaggctg gtaccagcct gggggagggg gcagttacca gaagaccttg gtccccatcc   83820
cagccctgtg caccctgggg cccagccagg ctggaggccc attttttccca gaagcccacc   83880 tctctgcctc cttccagggg ctcacccgc cctgctgcct cttcttgatc gcctccttgc    83940
ccctactctc ccctctgccc tctcgcctcc cctcacgttc atgggttttt gtggacgcgc   84000
ctgcctgcct ttcatcagtg gtgtccagcc gtctccctga ccgaggctga gggtcctgca   84060
catctaggcc ccgtcacggt cgttctcccc ggtccctgcc tgcccatggc tcttgccaca   84120
gtggggatgc agcagctctg ggttgagtgt ctgtcgttgc ccctgcactg cgtgtgccct   84180
gtgagtgggg gctgctgtgc cacacctcac tgccacccat gcccatctca gggtgtgggc   84240
ccagcgggtc ctcaggctgt acctgtcagg gggctggata cctggacagg gccttgtccg   84300
agggttgact gggagagaaa atgcccccgt tccagctcgg gcagtacaag ccttcatcct   84360
cccagactcc acctccctgg ctgctccttc ctgtatggcc cccacagggg ttggcagggc   84420
gcactcccca gagggacagg agtttgtggc caacctgagg gtagacactg cctgtcctcc   84480 agaccctag acaccccgg tcggcccagg tgcggggtct gcccgcatcc cacagccatc     84540
tttccagcga ggacagtgca ggcgcaggtg gctgtaccgt ggctgcggtg atgtgctgac    84600
tgggaacggc agaggtgccc tgggaaggcg gaggtctggg agcccacaa gggctgagcc    84660 ttggggcctc aaaacaggga gtcttctctg ggctcagggc ctttctggag atgggacttc   84720
taggttgcca gggccactag ccgtgaggag ttcagctgcc catggtggcg gcggctgggc   84780
tgtatcttgc acttctcagc tgtgtggagg ggtccgtggg gcctgtctgg gcccagcaca   84840
gcagcgcaca gaaagccac tttatatatt tgggattcta ttaatccttc tagtttgtac    84900 atttttatg gcaccttcaa ttttttttctt ttaaaaatta atatattttt ttttctgata   84960
atataagaaa tgcatgcctt ctttggaaaa tacagaaaat cacaaagaaa ataatccaca   85020
atcccacctt ccaaaggaa ccacagttag cattttgttc agcctgtttt ttaaaaaaca    85080
aacaaacaaa aaatgcatac taaaagcaac gatttataaa ctgtggttgt agagttaagc   85140
tcatacccag agttgccggc atctcaccag ttcctctcct gggacagtga ttgtgccttc   85200
ccagagctgc cgcaccctgg cctcgcagcc aagcctggtg acagcagtgg ggtgaccctg   85260
cgaggcccct cggatggctg atgctgagag cccagcagag ctggaggggg taggggcagc   85320
```

```
ctccccagga ctgatctgac agacgggtat gtgcctcacc cggcatcacc caccggggag   85380
gcctccgtcc gccccccatgc agtcatgctg ggtcccccca tctcgtgtct tctggggaat   85440
ggagcggaag acctcccctc tctggaacca ggggtgggag ggactgtgct ccccagaatg   85500
aatattcctt ggctgtgggt gagcctgcca gcccagagtc cccaggggtc aggagcagac   85560
tggcaggggc catggcaacg actgggacac ctggggagcc aggtgtccag gcaggctcca   85620
gtgtccactc ccaacaagta tggggcattg agatcctggg tggatcacag gggagcaggc   85680
gtgctcaagc tgacacagcc caagctgtct ttattcacca ccagacccga atccacctct   85740
gggccaacag tctcaccctg caggaggcct ggcacctgtg tttgtatttt atcaccatga   85800
ggttgtgtgg gctgctgaga gcgtgtgcag agctctgggc acaagcctcg gctctgtggc   85860
cggctgagtg gccgggcctc ggtgttctcg tctctgaagt ggggagaagg ctgccccccgt   85920 cacgggacct cacagtgtta gatgagattg cagatgcgat gaggtggggg cccagcaggc   85980
ctgctcaggg cgtggctgtc cctcctggtg cagacaccat cacgtggaag gcgatcacat   86040
cgagtgttct ggccactgtg gcgcgagtgc atatgtgcgc agggctgtgc atgggcggcc   86100
tgggttgggc ttccttttctc ggcttgtctg ggaggacggt ggctcccagt gggtgtctcc   86160
ctgtctctgc cccactctga ggatgtgggt gctttgagct gagtgaagga ggaacttctc   86220
taggagagag ctctgcctgc cacctccctg gtgcccccgc ccccagagca gagctgtcct   86280
tacagggcca cagcctctgc tggccccgaa gccccctttgc agtgaagggg ggctcctgtg   86340
tgcggctccc tccagatgga caaaaaccag gtttggatgc cggggcctcg gctgagtccc   86400
tcgcttctct aagcattcct ttcctcgtct ggaaagtggg ggtgtagtat tgtgcgaacc   86460
tcccaggcca tccaggatg aactgagatc atgcccataa catagacttc cgcctggtcc   86520
ctgctcagag ctccccgaat ggtcattgcc acatctaaac aaattttttct ttcagctggg   86580 ggtgctggcg gcccctgcag cggtgcccac ggcagcccat gcacccaggc aggaagctgc   86640
tttgtgcagg agggtctttg tgcaggggca gtgtgggcga gcctggcagc ctcctgagcg   86700
gcaggactat gcaggcgcct tattgagctg tcagcggctg gcagctgctc ccaggtagca   86760
ggaagaaggg ccgagctcca cgtgggcatg aaaggcccag cgggtgtgtc aggggcgggg   86820
gtggggtgga agtgttagtg cgaatgtgag tgtgtgtgca cgcttgcagg ataaagatga   86880 gttttttaaaa tgtgtctcct gtggttttttg attttttttaa tctttcccaa aatcaataca   86940
aacaaaccac aggcataatt tgggtctgta aaggccgacg ctgtcattct gctgcaagag   87000
ggagggaagt tcagttgggg ggaaaatgca gcgcttttgc tgtcattaag tccaatggtg   87060
gctggcgaca gtcacggcgc tggtggagct cagagcagag gtgggagggg tggtattgac   87120 cagggcgtgtg tgtttccggt gtgtgatgtg agaacccagg gctcgctggg atgctgtcct   87180
ccctccctcc ctccctctgc caagctggtg ggaaggccct tgccaaagcg cacaagaccc   87240
cttcacacag caggggcaca agctcttcga ggcagagtcg cctgcaggtg gggtggaagg   87300
ggtgcgcccc agacccaaga atcgcccgcc tctccaagac catccctggc tgctggtgag   87360
cagggtagga gggttgttgg cacctgctgt ggccggggcc gtgccaggtc tgtacacatt   87420
gtgctctttg ctgggtggca gccaccacgt attctcaagg gcctgtgcta ggcctctggc   87480
gggccctggg ttgttcccctt ccttatgagc tcccattatt aactaaagaa gacactgaat   87540
gatctcatgt ggttgtatgt ttttttgttt ggttgtttgt ttttttgaga cggagtctca   87600
ctctgtcgcc caggctggag tgcagtggcg cgatctcggc tcactgcaag ctctgcctcc   87660
```

```
tgggttcaca ccattctcct gcctcaccct cccgagtagc tgggactaca ggtgcctgcc    87720
accacgcccg gctaattttt tgtatttttg tattttagt agagatgggg tttcaccatg    87780
ttagccagga tggtcttgat ctcctgacct catgatccgc ccgcctcagc ctcccaaagt    87840
gctggaatta caggcgtgag ccaccgcgcc cgcctcatgc ggttgtatct tggtgggtaa    87900
ggcaggtctt tctatgaccc acctgccagc ctcatcatcc gtgctcccca cctcaccatg    87960
catgcttcgg ttgctgtttg tccacaggcg tacttacttt gttttatatc agttttaga    88020 tacaaaaata gtacaggtag aattcggtat tctacatttt cagggaatat cacatcacac    88080
acacgctgct ctttcactat ggttttcatg ttttctgcac ctctcccgct cttaacccgc    88140
ctcccaccca gatttagctc tgttaaccct tcaggcttct ttttctgcac acacacacgc    88200
acacgcgcgc acacacacag gaggttgtcc tgtttggttt ttagaaatgg aattgtcctg    88260
ttcctctttg caccttgctc atttcacttc atggtgcgtc ccagatacca cttctaagt    88320 caccggcaga agcaggacct tgtgcttcct gatggctgtg agctgtcgtg gcggcacacc    88380
tgtcctcggt gtggagttcc agttcattcc tgcagtcccc tgttaacaga tgtttagact    88440
gtttcccttt ttttcccttt tcattacaaa caaaaaaaat tgctttctta aacttattt    88500 catgttttta aactttctaa tttctcataa atatttcaac tttagattct gtgagtgagt    88560
ctattagtgt caggctttgc agaggaaagg aaagttctag aagagtctgc agctcgttct    88620
cccaccccct gcccccagtg tccacccaca gaggtgtgag catgcaaata gggtgagctt    88680
ctgtctcccg tctcttgggt gtcttttcca cctggggcct ccctgggggcc atgctggggg    88740 agtgaaaggc ccctccctgg aagcccgagg cccctggcct ggatgctgta gcttgcctga    88800
aagcggagga attctggctg cctggtggag gtcggggctg gcctgcacc gccaggagaa    88860 gcagtctgag gagggctgc tcaggctgga cccagccctg accagcgggg ccatcgggcg    88920
tcctgggccc tggcaggatg tcgttccagt gatacagcac ttccttgctt ctaaactgct    88980
gagtggtcag tgtcggttat cagctgtcca catatattgc ataatctcag atgctggctt    89040
gtaacagtga gtggaggtgg gtggccacac tgtccctta gaataatcca catggccctg    89100
tccaggcagg gcagcctctg ggctcccgcc caccgcctga tgcccctgtg cctggtgagc    89160
ctgggccggg gtgtgtttgc tgtggatggg tgtgttccga gttctccggt cagcaagctc    89220
cctttgtctc taggggagtt cctgggaggt aaagggagc cttttcaagc cacaagatca    89280
cccagaaaac ctacgtaagc actaaagttc agaaaaatcc agccagcctt ggagctgggg    89340
agactgcttc ccttggggcc cggccactcc agagccattt ccgtgatggt aaaatgagtg    89400 ggggcccat gctgcctctg cctcctgtga acgccatcct ctggttcttc accttcaggc    89460
tcccgcatga gctgggtggt tggtgttaac tcctctcttc tctctttcta cccggaaccc    89520
cctgcccaga gctccaggga gctccaccat agccagtaga gggagggctc tgtttacctc    89580
cttccaagtt cccaattttg ctctactgat ttttgtctgc ggtgcataat caatcagcct    89640
ggaccccaga gaggccttct gtcgaggtgg gtgggtctca gaacggcagg ctgctccccc    89700
tcctacctcg gggccccac tgtgcacctg cagctgaggc atgttttctg gggttcctgg    89760
ctttggcctg cacggctggg tgggaggagg gcatggaggg tgatgctgct cactgagcag    89820
ggcctgcttt gaccacctcg ggatcaagag tcctgttaga tgcccaggta gagacccttg    89880
ctgggcgggc aggtggatct tcgagaatgg agctccgagg gacaggttgg ctgatctcag    89940 tgaacctga ggcttcccca aggccataca gcttgtctgg cagagcctca gcaggagccc    90000
gggtccccgg acaccgaggc tagctctttc tgctgtggcc ttctcacaga ccaaggtggg    90060
```

```
atcgcagcct tggtagcctt gaagtctccc taacctggca agacagtgga aaggggggac    90120
agccagcggg acattccact gtagaataaa tacatgcatg gcaaaacact tgacatctat    90180
taacttctaa gtggcaagag tgattcttgt ggttagacct gaatgggaac ttgtaagtct    90240
aaagtgaaaa tctaattaga ttttttcccac aaaacaattt tccgcaacgc attgtggaca    90300
taaaggtttg atgaatgtat agccaggcac agtggctcac atctgtattc ccaacacttt    90360
gggaggccaa ggcaggagga ttgcttgagc acaggatttg agaccagcct gggcaacata    90420
gtgagactct gtctctataa aaaaataaat tagcagggca tgacggtgta cacctgtagc    90480
cccagctact cgggaggctg aggcaggagg atcacttgag ctcaggagtt cgaggttgca    90540
ccatgattac acctgtgagt agccatgcac tccagcctgg acaacacagc aagaccctgt    90600
ctcaaaaaaa aaaaaaagat ttggccaatg aattttatca gctaaactgg gatatttaag    90660
agaaaggaag gaactcctaa tttctgagcc ctggttctga aaaagctttc ttttttcttt    90720
cttcacttta gtcttgttag caaaaccttta acagttcata gaagaaatca ttttttactt    90780
ttttcccctt aatctgagca caacatctgg ggttgccatg gtggtccatt ggtggtgatt    90840
tgcaggacgg gaccttacat ctggggaagg ggctgccagg ctgggcctgc ctctggccct    90900
gtgggcatgg ccggggtggg catggccggg aaaggcatgg cctccagaat cagaggcctg    90960
ggttgaatcc tggctgagtg cctagtgggg cactttggga caaatgacca cctttctgag    91020
ccttgctttt ctcatctgta aatgggggtg gcaatgccta cttagttgaa tgttaaataa    91080
aatgaagtcg tgtctgtgaa gcacctggca tggtaatcgg tggccgtgag gatgacgctg    91140
gcctcgcagg gactgggtgg cacaggtgtc ctgaccttgg catgcagggt ggatgggcca    91200
ggcttccagc cagtgctgga tctcagaggc ccaggggtta gagaactaag gcctccgag    91260 ccaggctcct cgttgcaaat ggacttctct cctttgcgtg ctgtgaactg ggcgtgaaca    91320
cctcctgtga tggggagctc actccttgcc gagggagcct ggtaagctgc cggcacagtc    91380
atcctcatac cctctctcct gacctgtgtc ttatggcctc tgccccagg cagctgcggg    91440 gcaggggct ggggtgaccc ccgtcttggt tgttgagccc ttccactagc tggagggtga    91500
ctgtcccccc ttctcccccg acacaaggca cagccttct tgtggctgtc aggagagagg    91560
gcctgtcctc ctttgcgccc acgctgcccc tgcgccttgt ggcactgcat tcaaagtgag    91620
tgcgcctgct tttgttttctt cctaggactt ctgaaaacgt gtgggtgggg gagggtgtgg    91680
agggttcgtg caccgggtgg tgtggctgca gtggcgtggg aggcggcccc agaggggcag    91740
aggcgcagtg tgtttatgtg cacagggccg ttcccttcct gtccctcatg tgaacaccag    91800
tgtacaaatg tgtgcacaca ggcgtgtccc ccgtgccttt tccctacctt ggctgatcgt    91860
ggggaagata gactcacttc ccctctccag gcggcgattc cggaaaggag gctctggaat    91920
gccagctggg ggcagggaag ccagggcagc caggagggac ctagcaggcc cacagaggtc    91980
tgggacagct gagccctcct gcccacggcc ctgccatccc tgtgtgtccc caaggtaacg    92040
tccaagctct gcagcaggga ccagccctgg gtcccacaga ggaggctggt ccaggtggtg    92100
gactagagct ccgcttgtgc cagcctaggt gcagaggccc ggcccagccc ttcctaacct    92160
tgccgtcctg ggcagctgt tcggtctctg cgtgcctgtt tctacacaac ccatctgtaa    92220
aatggggcca tgggagccac cacctccccc aggcctgtcg ccatcactgg cacctccacc    92280
agcattagca ccagtgtctc catgaagttg gggttcctgg ggagatggct ccccccagcc    92340
tcgcctcctc cctgcctcag agactgcgca gaaggagggc agctgggctg atgagcaact    92400
```

```
cgcctggggc cccagagagg cccgatccca tcccgctggg gcacgcccca ggtccaagcc   92460
tgtctgggca ccccccaggg c tctggactca cctccacccc tccctctgca tccttggtgg   92520
tgacaccatc agcaagtttg gcaccccggg ccctcacact gaccccagca ccccttcccc   92580
aggctctggt ggactccttg ctcacgctgc ctgctctgca gggtggggc ggggggcag   92640 agcctgccag cccctcccac acttccctca ccagatcaca ggaccctcgg ggtggaggct   92700
ggtgcgtggg gaggtaaggg tcaggtggtg ggaggccatc ctcagcaggg gtcccagagt   92760
gggagaccca gagctttagg accccaccat gcggaggggc cagggtccct gggatgggga   92820
gaggcctcag ccagggtgag cagaagagct gcagcccctg agaccgcgg gcttggccgg   92880 ccccccggga agaagaccca cagctgggag ggcagttcat gcagggcacc ctcccctcca   92940
cctgccggcc ttggggagca ccaggcaagg ctccctgggg agcagggctg ccacctctga   93000
cctcgctcca gcctgacctc accacggagg cgcacgcagg atgtccgcag gcccccgggt   93060
ggcagcttcc tacagtgctt ttccaccagg gaccgtgctg aggcccaggg ccctgagacc   93120
ctcaggccca tcacagcctc cccactgagc acaggcacgt ccatcccctc cccttctcca   93180
cctgtcacct gtctgtcttc caggcttcgt gggacttccc agtgccccat tcctgcttgt   93240
cagaagaggg gctgggagaa tggcaggcc tggcactcca ggctgcccct gcctcctgc   93300 gctcttgccc tccagccttt ccccaccctg gaagtgagtt catgatgtta atggcagcag   93360
cagccatggt gcaccaggca ctctgctaag cactttatgt acattcttaa attaccggat   93420
ccccattacg gaaacggagt cttaggttga aaaactactt gaccaaggtc atcccagctg   93480
taagtggcag agcaggccct gaatccaggc aacccaggct gatcaccacc ctgccaccac   93540
ccacccctct ctcacataca ggctctaggc ctcctgtcta tactggaatc cccacagca   93600 gatccacatg gagctgtcta aagaagcacc tgccctccc ccagacaagg caagaaagcc   93660
atctctacct ggagggagag cagtgagggg catcattaat gggctgttgg gtgtcctgat   93720
ttctttgaga gaagacgagc tgagcaggca cagctcttaa tcctccagcc actgccccc   93780 aggctggggc ctgccagccc ccgcccctgt agtcatttct aaatcgggtc tagatggact   93840
ggacgcgtgg ctgccagaga ccatttgaac cccctacctc caaattcccc aaggtccccg   93900
cctgcaaagg accagcccca gcatgaggcc ctgaaagtgg caacatttca atagcctatc   93960
ctggacaatc aggacgatcc ctttactaat ttatatgcta tacgtttggg gtttaattgg   94020
agcgtaattg taatccatat gctgttaagg taattacact tataaaccta atataatcca   94080
tagatcaatg ggtttggagc taattaaggc aaccgtaatt aacatttacc aaaaaccttg   94140
caattactgg aatatccttt aagctggcct tccgagctga taatgagcgc cgctcagcgc   94200
tccgcggcct cctagcgtgt ctttattctg cacaagggg ccttctgggg acctcgatgt   94260
tgggagggca gtcagtgcct gcttttagca cccagggact ctgatcaggg acccagctga   94320
tgagtggcag caccatggga agccaggtcc ctgtgacttg gccatcccca gaacacggct   94380
gattttctgg ctcaatagac tcagcctgac aaagggaac ttgagaaag agaacaagaa   94440 atccatatgc tgagctggga cagaacccaa gtggggttct catgtgggga gcatatgggg   94500
ctttcctcct gccacccccc tgcacctgca gccaggatgc acctgagctc ggactgccct   94560 gaaacccag gaaaatccca acagcggcac catagggcca ggattacagc cattcttttt   94620
tttttttttt tttttttttt ttgagacgga gtctcgctct gtcgcccagg ctggagtgcc   94680
gtggcacaat ctcagctcac tgcaagctcc gcctcccggg ttcacgccat tctcctgcct   94740
cagcctcccg agtagctggg actacaggtg cccgccacca cgcctggcta atttttttgta   94800
```

```
tttttttagta gagacagggt ttcaccgtgt tagccaggat ggtctcgatc tcctgacctt   94860
gtgatccgcc cgcctcggcc tcccaaagtg ccgggattac aggcgtgagc caccacgccc   94920
ggcctacagc cattcttgaa tgttgtatga ctcccggtga tattgtcacc ttgggagctg   94980
cacagagacc tcccccgggc caggcccctc ctctgtctgc agaaggaggt aaggggccca   95040
ccacatctgt cttaccacag gctaagctgt tggcatctgt tcttttcctg ctccaggagg   95100
gacagagccc ccctgttgtc cttgcgcac catgctctgg gaactgggcg ctcctgtgga    95160
cagctccatg tgagtcttct tcgagagact ccactgcaga tagaagaagg cctcgagcct   95220
gtagttgcgg ggcggtggtc agcctgggct gcctggattc agctcctgct ctgacattta   95280
cagctgggac gacctgggcc aggtagaggt ttttcaacct aagactcagt ttattatgta   95340
tttattcatt tattcatttt atttatttat tgacagggtc ttgctctgtc acctaggctg   95400
gagtgcagtg gtgcaatcat ggctcactgc agccttgacc ttctggactc aagtgatcct   95460
cccacctccg cctcctgggt aggatgcatg cctgaggtgg gactactggc atgcaccacc   95520
acaccggcta gttttttaaaa ttcttgcaga gacagggtct ccctgtgtgg cccaggctgg   95580
tcttgaactg ggctcaagtg atcctcctgc cttggccttc caaaatactg ggattacagg   95640
catgagccac tacacccggc ctggactcag tttctataat gggatatggc agtttaataa   95700
tgtgcatgca gtgcttagcc tagtgcccgg tgcagagcca ctgcttcatt aatgctgctg   95760
ctgctgtcct tgtcatctct atcattgaca gccctagacg agctgaaggg gtgggcccag   95820
gtgggagggg ccaggtgggc ggggccaggt gggctgtctg cacctcgctt actcctgggt   95880
gggctgttag cttggcgggt cccagggctc acttttgccc catcatcatt tctgtacact   95940
ttttccatct ctgggcctta gggccttcc aaagactttg caactctggc agatatttct    96000
agacagaatt aggttcttta acgaaggaat gaggcaaatg tggacaggag attgttcata   96060
attgcggctg tcatttattg agcacctgct gtgtgctctt agcctctggg ctaaacactg   96120
cacagacata attcactgat tgccaacagc agctttatgc ggctggcatt ttagtctcac   96180
tttagggtga ggaaactgag gctcagagag gctgaatcac tggtttgagt acgtccagcg   96240
agagggcagc tgggccagga tttgaagcca gccattctca acaccactgt gctctctgcc   96300
tcccgagtgg aggccctgac ccctttgctc tcttcctggg tgggccagtg gggatgggtg   96360
aggggtgagt gtgtcaatgt ttccctcagc ccagtagtgg agaacaggca gggtgggcga   96420
actcctggct ggaccacagc cacaggcctg caggaggcac ccttgccagg gcgagtgagc   96480
actgtagtct gggagaccct agagtgagat ggggctcta caaggcacag ctcctccctg    96540
gaggaaggga ggaagggagg gtccctgcct tacagggcct ggccctcccc acttgtccaa   96600
agcccggctg ggtcctggtg tgtcagcgct ttgcagtaca ccctgtgcta cccacccaac   96660
ctgtgtcccc gtctgatctc cctggaccct cccacagcct gggaagggtc cccagctgt    96720 gaggtcagca tgggggacct tgctctgcag agggcacctg tagggctggc cttattggag   96780
tccctccttt ctaggcccac agtcctgcgc tgcctggtgt gcggggcctg aatgtcattg   96840
tttcatatat tttatctgat tttctagttg ctttaaggta ctttgtctat cttgactgtt   96900
aggctcttta ttttttcaaaa aaaaattcaa tataatagtt tgcattttt cttattgata    96960 ataaaaccac tgacattatt gagctcttgt tctgggctca gttctgcccc gagctgtttg   97020
tacatgttac cttgctgaac ctgcacccaa gtcctcaggc catattcccc cttacagatg   97080
aatgaagtca ctgcccgag gtcacacagc tgggacgtag tgcaaccagg ctgggcccta    97140
```

```
gctggttgac cccagtgccc actatttatt tggtgcttac atgcactggc tcattttgtc    97200
tctacagcct tgcaaaggcc acagttatga gatggcagag gtggtattca aattcaggcc    97260
cctaaacttg tgtctgtgtt ccctcttgaa aacttcagta aactgaagaa gtgaaaggca    97320
gagggtaaac caccgaccag cccaccatcc agaggtgacg gtgacctctg atgccgctgg    97380
gtgtccacct tccaaactgt gtgcacaaat gtgtcctctg tgttctagtc cacaggtgag    97440
gtcaggagca caggctgttt tgggacatct cttcccagtg cccagttcca gaacaccctt    97500
ccaaaccacc gtgcattctc cggggccatc gttttaatgg ctgcaccctg ctcccgcgtg    97560
tggacgcatc ctaaacagtc ccttagtatt atggttagat gctccatgtg tttccaattc    97620
ttcattattg taaacccaac tgcattgctc atccttgtag catagctttg cacttatttt    97680 ggattttttgc tttaagataa cttctcacac atggaattgc tgggtcaaag ggtatgcaaa    97740
attctaaggt gtttggtact tctgcagaat tctccctcca gacatcaagt tgctctccca    97800
tctgcactgt ggataattct gcaactctcg acaccctcac caacaaataa caccgaggac    97860
tagcagtgtc attttttaaaa cgcgcctcca tcaatgggaa aagaatggga tcttctttga    97920
ttgataatga gactaaaggc ttttttctgtc ttcctcagtc gctgatattt gtttcttcta    97980
taaattgcat attcatatcc tttctcagtc ttttttgtat gttttttaaa cgaaggctct    98040
tctttaatgg gaaatctgca tttcatcaaa gatggagcgc agagtctgtg gttcatttat    98100
tctctggaga agatgcttct tttttgttct ctaaccaatc agagaccagc ctgaagatgc    98160
tagcaaatta atttcaggcg cacgagacag gcggtcggtg ctcatgagga tcctggctga    98220
ggaaatcaca ttttagtccc aactcctcga agtgttgagg ccgcctggag tccacgcgga    98280
ccagggttca aatccccact cggccacttc ctagcagcat gactttggga tgtccctcag    98340
ccatcagaga cttcactttc tgggctgtac catgaggtgt tggtgtgcag tttaaaggaa    98400
gtttggacgg ctgtggtgtg gatagttctg agtgctcagt aggcagacct ggttttgagc    98460
tgatagagaa ggcccacgcg aacgggcaga gctgggcctc gccagggcct ggcactcagt    98520
agtgctcacc aaatgcctgt tgcacaaggg atggtgccca ggtaacctgg gtgagctaca    98580
aaccagagcc gctggacgag ttccaaaggg aactcgggcg cactagcccc ctttgtttgt    98640
gtttggagtg ggagtcaccg tatagcttta tttgattact ttttacccaa atccccatat    98700
cctcaggaat tcaaggacaa ggatacataa caaaatgatt tttgtctcag agtaaatcac    98760
agtccacttg gaaaatctcc atcctagagg agggtgaggg tgcaggtctt ggggtgaggc    98820
tggggatgaa gcctcccatg actttgtggt taccctgctg gtgggctcac tccctgcagg    98880
gccattggtg gagtcacatg atgccaggca aggctggcca agcagggtac agagcacact    98940
gggggaggga tggctgcaca ggcgtggacc gtggggatc cagggtaggg atcccacctg    99000
ggggtcttgg gctgagtggt ggagcgtgtt gcctgaacac atgagcccgt ggacatctag    99060
tgagcttagg gcatggcagg ggtggggtgc gttgcctgca gcctggggcg gcctcggctc    99120
cttcatgtca gcgcgtcctg acaccgtgac actgcgcatg gtcacatgga gcctgtcctc    99180
ttgtatctgc ttcatctctg gctttcctgt ccatctgcct ggtgctttgg agggtgtacc    99240
aggctgtgag ggagaagcag ccacgtggct ccgtttttctt gtgctgcagc tgggccagca    99300
gatctagggg aaaggccact tcctagtggc ctttctggtg ggagggagtc atagtgatga    99360
gtctggaagc tgagccctgg cttgggagca gctggaaagg ctgcctgtgg cctccctgag    99420
tggacgtcct ctagcagttg ttcagcctcc ctgtccccag ccagccacca cctagttggc    99480
actcccagtg ggccccacga gccgcgtgtt gctatgcaca gcccttacga gaatcccact    99540
```

```
ttccagatga gggcgacagg aggaggaagc atcactcact tgcccaaggt cccaccggca   99600 agggggctctg agtctggacg tggccctctg agctgctctg tccccgcttg gcgttggagc   99660
gtctcagcct ctcccaagag tgtgtgccct tgtgtcgctg gttcagaagc cagaaggctt   99720
ccaggggcag acctaggcag aagccctgag tgggcatcct ggtcagccct gtggggttg    99780 ggggccagtg ggcaggggca ctcaccatgc tacccaaccc cccatggcac ccccaatgtg   99840
gaacgcacgg gctcaggact cacttttatt ttggtagagc ttggagtccc catttccatg   99900 tttttgttttt ctttacagtc ccagtgtcaa gcttagtagg acacagatgt ctcagcaaac  99960
aaaactagga gccatccgag caggccctg cggccatatg cattcccatg cgtagcgaaa   100020
ccaggccctc ttgccaagca ctctttggga ggatatttgg aaaaaatgtc aaggcattca   100080
tttttctctc gacttttct gttggaatcg tggggcctta acactggaag taaaaggagt    100140
tataagacac agctggcttc ctgcacccgg gacagcccca gtggccaggc ctggccctat   100200
tctcccatct ggccctcggt ggtttctgca gaggttacca tgcacaaggg ccaggccgcg   100260 gccccacct atgtgcaaag aagttggcaa tgatgtccag gtagcaggtg cagcgggcaa    100320
ggtttctacc cccaggctag ttaaggacac aggagactcg aggagggaga ggaccagcag   100380
aggacactct atgggggtgg cttctggcaa aacagtgcta tctgaagatg agtttgaagt   100440
taggaatgtt tgctgagttg gcctggatat tggaagtgcc ctttcttttg agcccctttgg  100500 ctctcttggc gttgaccatc tgctggtgga acatgggtgg gctcccagag cacctgcccc   100560
tgtggtgtat accagctgga tctcagctac acctacggac ctgcactggt atagatttgg   100620
gtcccaggtt ccccaccagg ggcctggctg gcttccccag gtccacaccc ttccagcgaa   100680
gtcacatcac aagttgtgtg gaaatggagg tcaccaccct ggccacagag gtgaggctgg   100740
tgaggcccag agtgtacctg ttggggatgc tgcaacactt ggaaatccgg ctgcccgagg   100800
ctggaagccg tcttgctgcg tatgtcacgt aggataatga gtggactctt ttctcagtcc   100860
tggaggactt cctcggccag tctggagtaa gccatggctg gggagatcag ttcttggaag   100920
tgctgggttt tcctgcatct ttggtccttt ggtggcacag gccttccctt gcaggccttt    100980
ggcacctgtc tgggggtgtgt gccattggct cagtagccca tgggcagtaa gttccgtgga   101040
atcaggcaca ttttcagcca gcgctgccaa gtgctccctg caatggtgtt gccacctgag   101100
gtgccaccca aagcagaaaa ccctgggggct gggcaagaca gcagctttca ggagctggga  101160
ggaggcatca tttccacttt ccaggccctg cgatctggtt tgtagcctgt accagggcac    101220
tggagtcctg ccttggcaca gctcatggtc tagaggaata acctcaggtc caggtgagac   101280
actcagcctg tgatggcttc atatggtcac tacgttgttg tatatggaga gaggactctt   101340
tcttggtttt aaattttgtt tttaatttta taaatgtaat atattcacat ggaaatttg    101400 gaaattataa acaatcaaaa agaagcagct aaaaaaagtc ctttcataat ccaccggcaa   101460
catcagttaa catgtggcat atttccttcc cgtctcctcc actcccattt tttttggact   101520
tcttaaacat aattgagatt gtgttttatg tacaattta tagcatgtac ttgttagctt    101580
tgaaacagac ccatctgcgt ttgcaatttg gcctgcaggg aaaagaccag attgctgagt    101640
cttagctaaa gctgtgggag aaggaaatct aaaaataccc tcctcgttgg cctgctcagg   101700
gagcgccgtg gcctcttgtt ctcctccctg tcagtacagc agaattagcc atgactcaga   101760
gtgggtctcc gtggtgattc tgcctctaga gaacatgccg tgctcccgac gtcaggctca    101820
caggtgagcg ggggcactag ccggggacga ggggctggag cctggccggc caaactacag   101880
```

-continued

```
agggqcctgg ggtttggctc ctgccggagg agccctctca gggctctccg gggtcttctg 101940
cagagcgaac actttgaggg gagcatctgt cagagacaca tgatgcttct tcacccaaag 102000
ccccaccctg gctgcaagag gagaaaatca aaccgtgaa gagcatttta gagacttcca 102060
cttccagcaa gatggagcag aagtgccttt ccctattcct cctgccaagt gcaatgaaaa 102120
accctggacg tcagttatga acaaacaga agaggctgaa aggaagagag gagaaggcag 102180
actgaccagg gacctcagga cctggggatc agtggagggg tgaattccct gggtttcctt 102240
tgtgccttgc acatctcaga cgtggagctg aagaagccag caagagcctc tgcagaagcc 102300
tgctctccct ggctgaagga ccaagccagg ggcacctggc gagacagaaa catttaggc 102360
aataactgtg gtactccagc caaacaccac agaaaaccct gtggcccct cagctactcg 102420
tgccagcaag ggctcagcag ggatcctgga ccaaaacact gaccaggctg aaatgagccc 102480
ctaccactgg gggtgtcaga aaggccaag gagggagcca ggagcagggt gggaatgagg 102540
tcccccagct ggagcatcag tggagaccac atggtaagcc tgtgcttccc ctagtcagtg 102600
gtgacaagac atcccttccc ctcccactgg acgggcagca tcatactgaa gagtcaggac 102660
ttcatcgcca ctcagaggtt acaaggctat ccgcccccc cacaacagtg acaatggagc 102720
ccgcatggga cacagtaatg agggattcct gcacctccca accaggggaa aacttcctcc 102780
ttgaagagca gtaatgagag cacctccccc acctcagtgt cagcagaggc caagtgggga 102840
acctggacgt ccacccccacc caagcagaat aaggcagcac taccctcttc ccctgcctga 102900
gttgtgtcca gagaaggcca ctgaaaggga aggttaaat aagactcaga gtctcacacc 102960
acacacccaa aatgtccagc ttgtggtaca aaaccacctg tcatgctaag aaccaaggaa 103020
accccaacat gaataagaag agaagaccaa cagacaccag cactgagatg acacagatgt 103080
cagggcaaag actaaaacag ctactggaaa aatgcttcaa ccagcaattg caaatatgct 103140
caaaacaaat gacaaagtag aaagtctcag caaagaaata aagatacag ggccaggtac 103200
ggtggctcat gcctgtgatc ccagcacttt gggaggctga ggtcggtgga tcacttgagc 103260
ccaggagttt gagaccagac ctgggcaaca cagggagacc ttgtctctac aaaaattaaa 103320
aaattagctg agcatggtgg cacacacctg tagtctcagc tacttaggag gctgaggtgg 103380
gaggatcacc tgagcctgaa aggtcaaggt tgtagtgagc tgagatcacg ccactgcact 103440
ccagtctggg caacagggtg agaccctgtc tcaaacaaac aaacaaacaa acaaataaat 103500
agaagataca atgaagagcc aaatgaaaat tttagaactg aaaatacag tagccaaaat 103560
agaaaactcc atggatgggt ttgacagcag aatcaagggg acagaggaaa gagtctgtga 103620
acttgaaggc aggaaaatag agatgaccca atcagaacag agaaaaata gactgaaaag 103680
aatgaacaga catttcacca aagatgatat ccaaatagca aataagcaca taaaaagatg 103740
tcatgagtca ctagggtaac gcaatttaaa gccacaatga gacatcacta cacacctatc 103800
agaatggcta aaataggcca ggcgtggtgg ctcacagctg taatcccagc attttggaag 103860
gctaaggtgg gtggatcact tgaggccagg agctcgagaa cagcctggcc aacatggcaa 103920
aaccctgtct ctattaaaaa tataaaaatt acctaggcat gatggtgctc gcctgtaatt 103980
ccagctactt gggaggttga ggtgggaaga tcacttgaac tggggaggca gaggttgtag 104040
tgagccgaga tcatgccact gcacctcagc ctgggcgaca aaacaagaaa gataccatct 104100
aaaaaaaaaa agaaaaaaaa aagaatgac taaaataaaa aatgccgatg agaacagtga 104160
gaatctgaat cactcagaca ttgctggtga aaggtaaaa tgatacaaat gctctgaaa 104220
atagcttggc agtgtcttaa aactctaaat gtaaaactgt cacatgactc agccatggta 104280
```

```
ctcctgggca gttatcagag aaatgaaaaa ttataattta cacaaaaacc tatacacaaa    104340
tgttcgttgc agttttattg ataatagccc caaactagaa gcaatccagg tgtccttcag    104400
tgggtgacga gaggaactac atccatgtca tgcaatagta ctcagcaata aaaagaaaca    104460
atctctctct ctcttttct tttttttttt ttttgcataa aatccagatc ctgcagaaaa    104520
aagaaacaaa tttgatactc acaatgactt ggatggactc ccagtgaaaa aagcctatcc    104580
caaaaggtta tgtactttct gattccatgt atagaacatc ctcaaaatga caaaattcta    104640
tcatgcaaaa cagatactgt tggatggggt ggggcggggc aggagggcag tgggcgtggc    104700
tataaagagc agcctgaggg gtcctggtgg tgatggaaag cttctttatt tcactgtatc    104760
aatgtcaatt gttgactttg atattgttct atagttttgc aatatattac tgttaagaga    104820
aactgagtca gtggcgttct tacaactgca tgtgaatctc caattagccc caaattaaaa    104880
gtttactaaa gcaacaattg aacaagaaaa agaaaagcct ttgtacctag caacccagaa    104940
tgcctatgat aagtggcagg agctgatgac aggcgttctt ggttcagaac aatgacaact    105000
ctgggacaag catgccgctg ggagaaagag accaggagct gcacagccag acagatgctt    105060
ttgcagtggg atggcagtgg ggagttggaa tggttcatca tttactttt atatttaaca    105120 cttttttttt taagagatgg aatgctctgt cacccaggct ggagtgcagt ggtatgatcg    105180
tggctcactg caacttcgaa ctcctgggct caagcgatcc tcccacctca gcctcctgag    105240
tggctggacc tacaggtgca cattgaagca cccagctgat ttaaaaaaaa atttttttt    105300 ttttttgag acggagtctc gctctgtcac ccaggctgga gtgcagtggc gcgatcttgg    105360
ctcattgcaa cctccacctc ccaggttcaa gtgattctcc tgcttcagcc tcccgagtag    105420
ctgggactac aggcacgcag caccacaccc agctaatttt ttgtattttt agtagagaca    105480
gggtttcacc atgttaccca agatggtctc aatctcctga tctcgtgatc tgcccacctt    105540
ggcctcccaa agtgctggga ttgcaggcgt gagccaccgc gcccggccaa ttttttttt    105600 tatagagacg agtctcactg tggtgcccag gctggtcttg aactcctggg ctcaagtgat    105660
cctcccactt cagcctctca aagtgctggg attacaggtg tgccccaccg tgccagcct    105720 cggattgtca tttagcggtc tgtctgaaca tcagtctcct gacgtccttc ctacagatat    105780
gaacagagcc cctgctaggc atgagtattc ggagcataag ctcctggttc cccagtgaga    105840
gacggatgtg taaggaggca gtctcagggt aggatgttga gtctgggctg gggacagtgc    105900
actgtgccgt ggaattatgg agagtttttc ctcctatctc taagtccaat gtgtggcatg    105960
gttatattac atttttagga tggaaaagtt ataccatata tttaaatgaa ttaacagcat    106020
ttgcaatgat ctggatgaga ttggagacta ttattctaag tgaagtaact caggaatgga    106080
aaaccaaaca tcttatgttc tcactgatat gtgggagcta agctatgaag acgcaaaggc    106140
atgagaatga tacagtggac tttgggggact tggaggaaga gtgggaggga acgaggtgtc    106200
cttgtccagc aagcgctctg tgtgaggctc catgcatctt tatgcattct gctctgatgt    106260
ttgcaaacac gacgcccggc aataagtgag gccccctga ggtactcaag gggcttcact    106320
cgccgaagct cccctcccca cagcaacctg agcttctgca aaagctgaga agcacgcatg    106380
agaagggcac ctcccctgct tggaaataat ttttggttg cagtaggggg ttttgtttgt    106440
tgtttgttgc ttgctgctcg ctagcttgtt cttgcagaag gaagagctgg tctcctttgc    106500
catcccttac tgagggtcga gaaatacaga caggtgtctt caggctctcc gtgcaggcca    106560
tagtccccaa gaattcactt gtgagcctct gtggcagttt atgttgagga ttaggtttag    106620
```

```
tttggggaga ggaggatcca tggagctggg gttccagatt tgatgtctaa ttttagaaag 106680
gacactattt ttaaatcaat agctgtgcag cctagcatat cactctgacc ctgtgccctt 106740
aagggacgca ctggggagga cattgttcag gacggagcct gacaagaaag gaatgctacc 106800
ccacgccgtg cgccccaggc ggccactgtc gtccaagaat ttccaggtct tttctggtat 106860
cacttcttgg cacaggcgga agaagccatg ttcccatcgt cccaacatgc agctggggac 106920
ctggagaccg ctttggcctt tctcaaggtc acaggaaggc aggggaagg ctggcgaggg 106980
ccctgtggat ccgccctgct ccagcccggc gtcgggttac agcagtgggg acaggagggg 107040
gaaggggtgt cactgcagga gctaaggaga aatccagggt tgacaccctc agaaactgga 107100
gaagaccaag aaagcagagc ggagagtgcc ccctgcagtc cgcagagggc cttgccgag 107160
gtgggcctgg agccgtcgcc gtaccctgg gtggcccgca aggccaggct tggctgcctg 107220
gcaatgtttg ttgtgggcag ttgccatgcc actccggcgg cagcaagagc agggacaggt 107280
gtggcagagc ccggtggttc cagcccagcc tggcctccca gcatcacctt ctccagttac 107340
ttgaagtggg ccaggtcctg gagaccgggc gtgtggttat gggctctcca gattcttggc 107400
gccttcctga ttgcaggagt ctggttggca tcatgggacc cctgggagac tcactttcag 107460
gaggggttgt cctttccccc ctgggggaca cactctgctt acttgtcccc tgggagcgct 107520
gggcagggag actgcaggtg ccagccactc ctgcagcttc tgcccagcct cctctggtgt 107580
cctctgcact gtcaccaagc catggcctca agcaacttgt gggtgcctgt gatttaggcc 107640
ttggggtgtt ggagcctgct tggacccact ggcaggagtc agttgtgatg tcttttgcca 107700
gctctcttct gtagcttgaa attggccacg gtggaagtat ttacaccatg gaagttggca 107760
aatgcacgga cccagcaccc ctaccccatc ccggagagcc agttaccagc acacgtctgc 107820
cttttgggt cttttgtgca ggactgatgg atggagtcgc agcagacact tggcctggcc 107880
actgtgaggc tgtgtggtgg gaggtcgggg gcacctgaga cagagggagg aggctgagag 107940
tctgaggggg cagccagggc tggagggcca tttgggattc tgttggattt ccctgcactt 108000
tgtccagggg cagaagcctc cctcccaagg tcaggcccca tttctagccg tgctggtcgc 108060
acatccctgt gagcagggt gcagaagaga aatggtccct caggagcccc acacccgctc 108120
ccatccagct ctcctccaga tgacatctcc aggcactggg accccacaga ggcaggccct 108180
gctcagcctg cagagctccc ggtggagagg gagggcgggg gtccaggtgg cctgaggaga 108240
ggggtgcagg ccagctgagg gggctcccag aactccacga gctcagagac gggctcttgc 108300
ccttgcagcc ccatccttgg gatgcccag cccttcatcc agacctctgc tgtgattgtg 108360
tcaggacctg tccctgcagt ggactggaag ctccaggtgg gcaggccttg ccgtggtcac 108420
ctgtgtccac aggcctgggc agagcaaact gatgagtgtc tactaaatca gagagaagac 108480
acaaccaggg agcgagtgca cgcccgggcc gaccagggct gcgggcatca tatcccgctc 108540
agccgctgcc tgccctccac gcgccctgg ctgcctctct cagcctcggc ccctccact 108600
catgagtggg aataaataag agagtagaaa acgtaagtga ggttcttgtc tggccgcccg 108660
gctcatagca atgtttaata gatagtaact ggtgttatga ctgaagacgt cctttgtggg 108720
ctattggagt tcttaatatc cccgagtaac cacagggcaa cgctctggct tgacaagggg 108780
cggcactgct ggtcagcagc ccagccagcc gcagcggcca cttgtgttcc cagctgtggc 108840
ttgtgatcta tggtcgactg agctgttact ctcctcggtt agacacgcat atgcacacac 108900
atgcacactc atgtacttac acatgtgcac gcgcatgcaa cgcacaaaca catggacaca 108960
catgcgcatg catgcacaca ctgtacccac gtgcacacac gagtgcacag acacgagggc 109020
```

```
tcactgtgat ctgctctaat gcatggtctt aatagctata taatattcca cggttctttt 109080
ttctttcttt cctttttaag atggagtctc gctctgtcgc caggctggag tgcagtggcg 109140
cgatctcggc tcactgcaac ctccgcctcc cgggttcaag cgattctcct gcctcagcct 109200
ccttagtagg gggggactac aggcgcgtgc caccacgccc ggctaatttt tgtattttt 109260 cagtagagac ggggtttcac cgtgttggct aggatggtct ccatctctcg acctcgtgat 109320
ccgcccgcct cagcctccca aagtgctggg ataacaggtg tgagccacca tgcccggctg 109380
gttcttattt ctttaatttt attgaagaat aacatacctc cggagccgtg tgcatatcat 109440
aagggtacaa tttgatatac tttcatggag tgaaatacat ccctgaaacc agctccggat 109500
cgagaagcag gacatttccc accctcttct tgcccttgc ctgcaacccc catcccggg 109560 gtgaccattc cccggcctct gccccggga cagttttgtt cgctcctttg ctttatggag 109620
gtgaaaccgc gcgatgaggc cccttcgag tctggctgct tttgcttagc cctgcgcttg 109680
tgagatccct ccgcggtggc gtggagaggt gtggccactt cccgcttcgt ggcaagtcgt 109740
gttctgccat ttctccgaat accgatggag gcttaccgtg ctggaccatg gaatggggtc 109800
tggaatgttc tcatacaggt cctgtggtgc aatgggcgtg tgctggcact gggattctgt 109860
gtctaatgct cttcatccta gacctgtgag aggagactgt tgtccccagg gcagtgagga 109920
ggaggccagc tttggagtgg tcaccctcac ctcgccgtta cacacgtcac ttcatttaat 109980
ttttaaacaa cagtcctgct gccggtggcc ttttctgtgt gctatagaag tgagagcagg 110040
tgcctgggga cacttggagg cccccctagg tttgtctgta atgagcttgt gctggcgact 110100
ggcatgttct gtccccccca cggctcccag cgtgctccca gcgccctccc acagctttag 110160
gcaattaaga cacgggcttg gagtggccat tgcaggacct gctggtaatg ggggtgaggg 110220
gtaagctttg tttccaaggc aggtctgtgc cctggggtct tgtcccctc cacatgcaca 110280 ctgcctgggt ggggctcatt cctgcgggta aggcccggga tcaggaatgg ctgtctttct 110340
tctgcccaga gggagctgct tgtggcttga ggtggccctg agactgtgag acaggccact 110400
gggaggccca ggctctagca aaagtgggga tttttttctc tccctagttt tggatcaggt 110460
ttttgaggtt gtgcaaacgt aggaatgagg cctttcaccc cgtcagttgt ctgtcgggct 110520
gtgtcgcaca gtggcccctc gggacagcct acagagctgc tgtctcttcc aggcattgct 110580
gcagggcctg ctgtctctgc tgtcctgggc caggcgctga gttctgtcgc ggaaagtctg 110640
agggcagagc tgggagggca gcgtttccaa agcaaatgga aaaggcaaac gggaacgtgg 110700
cgggcagggt gggcagggca gcctggaaac acccttttgtc ccatgcagct cattcactcg 110760
gccaggattt gccgagtggc ttactgcact ctgtggccct gaaccagggc tgggggatct 110820 caggggacatg tgtgtccaca gagatggtca cctgccacct ccaccatcac agatgccatg 110880
aaggctgtga agggaaacag acctgtaagg cagcggagcc gagatggggt tgatgagtgt 110940
caccagtcac aagcaaggtg tctctgttct ctcttctaca tgttgatcga ggtataaaac 111000
ccaggaaagg acatcaagtg tacagtttga atttttgcac acacgtacac ccgtgtaacc 111060
cccacacaga tcaagatgta gaacattcca gcacccagaa gtttcccgt gccccttccc 111120 agtcagaccc cccgacccca ggtcacccct gccctgactt gcagtgtaga gctcaccgg 111180 ccacttcctc ttttgcccac agcaggtgag gagggccttc tactgggaaa aactgtgact 111240
attaatttag gttaaaaatg tattggtaac aggcagatct ggccagtccc tcctggctt 111300 caatctcctt ggtagcttcc aggattactc ttaggaggga ctggaggaaa agcccctctc 111360
```

```
tgtccccatg gcacccacag tgaccgtcac agccctcctc tgggccctca ctgccaccag    111420
tggactcact gtctccctct gccctgtgca cagcttctta atttgggtcc ctctggttta    111480
gctcagtgca gccagaattc acccagtgcc tatgtgagtc gggcactggg ctggcccagg    111540
ggcctttgga atgaagggga cagtcggtga gctgaggttg tccccaaatc agaggtgtga    111600
ccctatgagc agccaggttt ttaattttgt aattgagata ttcacatgcc atacaattcc    111660
tcttaaaata cacaattcag tggtctttag gtttttaata tattcacaat gctgtgcaac    111720
tatcacctct aattccagaa tattctgtca ctccaaagag aaaccctgta cccattagca    111780
gtgacttccc actccccaca cccccagccc ctagcagcct ccagcctctt tcaatctctg    111840
tggattcgcc cgctctgggc atttcatgta aatggaatca gacgatacat ggtcttttgt    111900
gtctgactcc attcactttg cttaatgtct tgaccgttca tctgtgttac ggtgtgtatc    111960
agagtttcac ttcttttttgt ggctgagtaa tattccacta tgtggatagg ccacattttg    112020
ttgatctgtt atcagctgat ggacatttgg attgcttcct gatatggttt ggctgcatcc    112080
caacccaaat ctcgtctcga attcccatgt gttgtgggag gtaattgaat cacggggca    112140 ggtcttcccc atgttgttct gttctggtga tagtgaatta gtctcacaag atcagatggt    112200
tttaaaaagc ggagttgccc tgcacacgct ctcttctctt gtctgccgcc atgtgagaca    112260
tgcctttcac cttctgccgt gacggtgagg cctccccagt cacgtggaac tgtaagtgca    112320
ttaaacctct ttcttttgta aactgcccag tctctctggt atgtctttat cagcagtgtg    112380
aaaacggact gatacacttc cactttttgg ctattgggaa tagtggtgct gtgaacacta    112440
atgtataggt ttttgtgtgg acacgtttcc agttgtcttg gatatatacc tagttgtgga    112500
attcctggct catgtggtaa ttcatgtttta acttttttgag taacgagcgg ccattttttaa    112560 agactggata ggaatatgta aggaagaaag taaatttatt cacttccgtt caggaaattt    112620
acctaccaaa caacatgctg aatgggaacc tttaggggct tggctgaatg ccctgcaca    112680 aggtgtccag gatgcactgc ctaaaagctg tggaccctgt gcctgggagg aggaccagca    112740
aagggcagag ccccccgtgt ttcagatgga aaggttaagt aatgtgactc tggtaatgca    112800
gtccagttca tttatgagat catggacctc ttatactaca gactttttgt gttttttttgc    112860 tgagtctttt gctccctaac cgtgttccct ggctggccac cctgccagca ccacgctggt    112920
cctcaggaag catcatcagt cagagacaca ggcctttgct gtggcctcac atgctagcag    112980
aggaagatag acaacatggc gatggatgag gaagttgggt tgtctgtaag aggatgagaa    113040
gggctgtcat taaacaggtg ggttcaggtg ggtctcattg aaccatgaga tttgaaccaa    113100
gacctagggg ggtgagtgag gggttgggga agggagatta atgcgagttc tggggaagga    113160
acattccagg tgaggaaaca gccactgcag agcccttgg gtgttggagg aagacactca    113220
ggtggctgga ggggtagggg aagcattggc agggagaggc cagggctggc aggcctgccg    113280
aaggctttgc ttctcttctg ccaggctggc catcacgggc cttgcacaga agagagcaat    113340
gacctgcctt caggtttcaa aaggtccctc tggccgctgt ttgagagaag gtcacagtgg    113400
gatgagggca gagcaggggg actgctcagg aggcttttgc agtaaccgac ggagtggtgg    113460
cggtcactgg caccgagaag tgtacatgct gcaaagaaaa tactctgttc aggagaccag    113520
gtgcggtggc tcacgcctgt aatcccagca ctttgggagg ccgaggtggg tggaccactt    113580
gaggtcagga attcgagacc agcctggcca atatgctgaa accctgtcaa tactaaagat    113640
acaaacatta gctgggcgtg gtggtgggtg cctgtaatcc cagctgctcg ggaggctgag    113700
gcaggagaat cgcttgaacc caggaggtgg aggttgcagt aaaccgagat cacgccattg    113760
```

```
cactccagcc tgggcgacag agcgagactc catctcaaaa aaagaaagaa agtaagaaag    113820
gaaaggaaag aaaagaaaaa aaagaaggaa gggagggagg aaggaaggga gggagggaga    113880
aaggaggaag ggagggaggg aggaagaggg gaggtgggga gggctctgtt cacataataa    113940
agaaatccag aggtttgacc atgggcgtca tttcatcact gcacttggca gaggtcatcg    114000
ctgctgctcc catccagctc agtcctgtgg tccctgtcgt gtgtagaaac acatactctg    114060
tacgttgctg ggatcatagc agaatatcag ctccaccaat cctggttcct caatggcgac    114120
acccacgcac tcagggcatg tatcagtgtg catggagttg cctcgcgttc aactgcgtgg    114180
tgtgggtaac gcagttgtgc cattgtgtgt ctcacaattc ccagactggt aaataatgtt    114240
gcttctagtt ttttgctact taagcagtgt cacagtgaac attcttttat aaacgtgttt    114300
gtgttttaaa aataagctta ttttggaata atttcatatg tacagaaaag ttatggagtt    114360
aggatgtttt catccactct tcatccagtt tcctctgtga cacctcaca catctgtggt    114420 acatttgtta caaccaagaa actgacattg gtacccacac tattcatgag accagact     114480 ttatttggat ttttttcttt ttgagatggg gtcttactct gtcattcagg ctggagtgca    114540
gtggcacaga tcatagctca ctatagtctc cacctcaagt gatcctcccg cctcagcctc    114600
ccaagtaggt gggagtacag gtgcacgccc ccacacccag ctaatttttt atttttgta    114660 gagacagggt ctcactgtgt tgcccaggct ggtcttgaac tcctgacctc aaaggatcct    114720
cctgccttgg cctcccaaag tgctgggatt acaggcatga accactatat ccagtcttta    114780
tttgattttt actacaaaca tatgcttctg tatacttgtg tgactatttg tttaaggtac    114840
agtccctgaa gtgggattgc cgtgcctgat ccttgctgcc acatcatcat cccataggg    114900 acagggcccc actgtccccc atcactgaac agtgtgccca ggtgagatca tggacttggg    114960 cccctaggc cagcccagtc tctttgcagc caaggaaagt gaggcttagc tgtcggggc     115020 tgtgggggga tgcagcttgc cacacttgac acccaaacgc tgattttgtt tacatgagac    115080
tcaggtccga gtttatgtct gagacctggg aatcaaaaag ccacccccac agcctccagg    115140
gacctggctc cctggagcc accgtgctgc cccacaggtg tcacccatgg aggctgcagg    115200
agcacctggc gtggtccagg ggacacgaag ccctggtgct ggctcctccc aacgcccctg    115260
tgagttctgc ctcccataga ccacatgtgt catctgcgtg cacatgtgtg aaacccgaaa    115320
gacaagcaga tgagacccgc ctgccaaaat atttgctgcc gcgcagaaca gtaagtcgtt    115380
tttgacatat ggatctcagc gcgcagccac agcaaacagg cagcgtggcg ctgaggggca    115440
caggtttgct gggggggcgtg agccgggagc atcgccagca gcaggctcgc cccctgcga    115500 gggcgcgcac ggattcgctc gccaccaaga gcagggcccc aagagggcc ctcggcatag    115560 tcccctcgag tccccagaac ttcacaggca gagagcctgg ctcgaggatg ggcgggagct    115620
cagtctggct ttgatctgcg ggaggtgttg tgtgcagaag ctgtgggcac cggggctgc    115680 agagcttcag acctggagcc tgctcccagg gccgatctga accggcacc tgtgctgacc    115740 caagggtcaa ccaaagtcct gagtttggtg gcgccgaggg aggggagtgg tcgcatccca    115800
ccgggtgcct ggaatggtgc tggaggaggc agcatctgat ttgggccccg tagggccaga    115860 gggggggattt gtagggacag agcaggaggg agtggagctg aggctgggg agggcatggt     115920 cggaggtcca gaggtgggag aggggccgcc atcctgaagc acacccctcc tcgtcttcct    115980
gaggcctcca tcccttcctg atcttccagg tcatgggctc caggcttggg cccactgctg    116040
tccttctcca ctctctcccc agggaaccca cctgggttgt ggccttaaac ccagccagat    116100
```

```
gatgcttctc cagcctctgc ctcctgccgg gccctcccct gagctcagaa gctgccatca   116160
gtagccatgc aacctccccc ttgccatcat gaagtatctc aaacttggca gcctcgaaac   116220
agagcccttg gggagtttaa gcagaaacag aatattttg catagtctta aagtaattcc    116280
ccccaccccc aaatattgag caattacaaa gggcaaaata ggaagtttac ggtggagaat   116340
cctggtggac acagccttgg ccaggtgatc aaggttcatg tcaccagtca tgaagcggcg   116400
tgcaccctg gtgtgctgag aagggcagct tacctcctgc aggtgccctt gcccaacgc    116460
accactcagc ctaaccatgg ggagcatccg acaaaaccaa gctgtccgca tctccaagga   116520
caggcacact ggggcttagg gcttcagtgg gggcggaggt acagttcact ccctaatacg   116580
ccatttactt ggagaagccc tctccagctg cctgaggcag aagcacccgg ttctctctct   116640
gcaggaccccc tgctttgttc ttcctaggat gcgtcagccc ctgattttcc atgacagtcc   116700
cctgtgccca tgtcctgcag cctctcctgg gggcaggagc tacagggttt cttgactcct   116760
acctcagcac tttggtccaa gctctgagca gagacctctg taggcgtctg caggactggc   116820
tggcccttgt gtctgtcttt cccctcgtcc tggccccctt tgtccactcc tgcaccagct   116880
tccctggacc cactgccact gcgtcacgtg gtcggatctg tgtccctgc actctcacca    116940
cctccaactt gcatcccggt cccccacacc ctgacccca aaggcattgt gcatgtggat    117000
gagtgagtga aggaaaggct ggcgtgttgg gtgtgcgagg tcgcaggggc atgaggtgcc   117060
tggacgcag agagccaggg ctgggtgagg acctgggtgc caggtcgggg gtctgggcag    117120
cctggtggcc ccctgaaaac gttcacatcc cttgggcct gctgtgatac atactaatca    117180
gtgcttcatg agaaaggtat gagccgaaag aaatgggggt tcccactgga ttggtcgttt   117240
ctgcattgtc cggagctctc agacctggtt tcttaaccac tgtgttcact gaacaccccg   117300
ggcttgatca gctgctgagg gtgacttcac atgagattat aattgtactg cctaatagag   117360
tgctcacaca tgttaaaact acctggcagg caggagtgag aatacagctt tcccagaaac   117420
gtgttcaaag aaaaacccat taccaacccg gcagaacata aagtactagt gtgggggtatg    117480
aggcagcatg tgggggcgct ggggtggcag cagggccaga ccccacttca ggggttgccc    117540
ccaggacccc ccttgcggta cccgtatatc ccaccccag actcctttcc atgagctgct    117600
cccagacccc ctcatatcca tcctgcctcc agaacccta tatcttgctc ccactcccta     117660
ccatatgctg ttcccagacc ccctccatg gcctgcccc agatcccct ttgctgccac       117720
ccctatatct taccccagac tcccccatat ctcgccccca gaccctcctc catggtctgc   117780
ccccaggcct gctggtaata tgggatacag aggtctcctc actgcacaca caaaactcct   117840
tccctgagcg agggataggc agagctgagg gcggggtac tgggggggctg aggggggttc    117900
tttagggcag gagttacctg ccctgtagac ggggagacca cattagtgtt tgtgcaaagc   117960
cctgccctcg tgcacctgtc cttccgtagc ccacgatacc tcatccagcc cgggcccgtg   118020
ggtgggctgc tgagcacccg accacagcca ggcctccatg tgccactgtc aaggggactt   118080
ggcccgccat gatcctgagt gcacaggtac attgctccgc cctctcaaca gccacgaccc    118140
agaaataaag taggcactgt aatttgcatt ttgaggataa ggaaaccgaa taatagagtc   118200
tactgagcgc atactcagtc tttccagacc ctagaaagta ggtaccattg tcatcctcat   118260
ttcagagcta ggagagcaga ggccagacag gttccatagc ctgctcaggt gggtccgtgc   118320
tggaccagga aagggccag gtaggctgat gggtcctgag cttgtgctcc cgaccgccag    118380
gctgtgtgtc tgatggccga ggccagggtg gctcagccaa gccagccaa cccaagacta    118440
gaccatcccc agcgtccacc ccagcctcct gggcacaggg gtcacctccc acccctggcc   118500
```

```
cacccataca gccttttccc atctaaccct ttctttaaag gaaggcatcc cttggaatga   118560
gtccaccctg agattttatg gatccaaaga aaaaacttaa ttagctgcat aaactgtcag   118620
ttgagactct ccagaggaca cacctccggc tttcaggttc cccagggaat ctgaggctct   118680
gaggcaggtg gacagccagg tccctcttta cccagcacca ggtaacctta gaggcctggc   118740
cctgccttcc tcattttgaa atgtcaccct gtggtcatct ctccttccct gatgtgaagc   118800
agtgaccagt tctgccccat cctacacatg tgtgcacaca tacatgcaca catgtgtaaa   118860
tacacatgca tgcacatgca tatgtgtgca cacatatgca cataccttca ccttcctatc   118920
cctccccagg ggaaggcctt ccttggggct gcccctcctc cactctggca gcattgggac   118980
ttgaatcttg tggccccgtc acaactgtac tcagctactc cagctccttg tgtgacctct   119040
cagcccccag gctctgagct acctgaggtg aggtggggcc acactggtcc ccacctcggt   119100
gcagcacaca cagccccatc ctgggagtgc cacccaggtt tcctctaact gtgctttcca   119160
agggctggaa ggacctcttc ctctatgcca ggtgtgctag agtggcccca gccgagaacc   119220
tgactgggac caagccccag gacagtggtc aggcacacac ctgagtcgct cttcctccca   119280
tagacacatt tggagttccc actgccttcc taggccccac cacatgctgt cacctccagg   119340
aagccttcac aggttgctcc ctgctgatag ccttgacctg cttcccaggg catttgcaag   119400
ggagtagaac gaagaccaag tccgtgcagg ggctgctggc tctgtgctca gcacacgccc   119460
cgtgaccacc tcagggcgg ctctgcgagt ccccacttga caggtgagcc acagggccac   119520
aggcatggct tggggtcctc tgcggagccc gatgtgtcac tggccctcac gtgtccttct   119580
ccgatctgct cactcattca tccattcatt tattcagcag gggttcttga gtgtctctga   119640
ggtggagcgt ctgctgtgaa ggactggcgg gacgcaaacg gttaccactg gtgtgacggg   119700
ctctgatcag gaggcacagg gtgttgggga gctcagaggg tgacatctca ccctgccttg   119760
gccagtgtgg gagggagagg gttcaggag gatgtaactg tgtgtgtggc aggtgctgtg   119820
gtggcacaga gctgagggga cataggcaca gttgctggat gcagggctta caccgcgcca   119880
cgcgtcagaa gctagcaggg gctgagcagc atctctgccc tccccgcttg cacccccacc   119940
atccagtgca gcccagcacc tagggggcat ggggccagtg cctggcacat tttgtcctga   120000
ctgtggaaaa aagctcttca cagccctgag tgctgcttta gctttggctc cacccatctt   120060
aggctgctca gaggcctcag gcctccctgg agggccagaa gggattccca ggggcaggat   120120
agcacggacg gggggtccg ctgtgtaagc ctgggaaatt ctggctgctt gaagctggca   120180
cactcccctg aggctgttcc aggcacagtc actgggtctc cccgtcgaag tggctctaag   120240
gcaggtcttc ccggttacca gcaagcagat acatgttgta acgggctgag agtgggtgtg   120300
tatctcatat tccccagagg agcttacgga cagcccctct ttaaggaaca tctcccggcc   120360
cgagcgttct gagcgccctc tgagcaggca gcccaccacc ggggcgctgg ccagtctgag   120420
tcagtcctgc ctgggaggca gtcaactctg ggaaggcag aagaatcaca gcactgagtg   120480
ccgtccagtt tccctcaac tatattcgcg gacacggcgc caacagggga aaacttacat   120540
agcacctatt cattctgagg cctggccggc ctctggaaat cagcatttca gtgttggcca   120600
ggaaggaggc cagaactgtg ctgtagcatt tcaatgtatg gctgtcccac aatttatatt   120660
ccagtcccct gatgatggac atgtaggcgg tttccagttt ttttcatgat cacagatcac   120720
acttctgtga acagctctgg atgtgtctcc ttgtgcaaat atggtgctag gtgttcttca   120780
gagcattttt ctccaaactt gccgggtaat atggtcacct tggggagttt gttaaatata   120840
```

```
catatttcca ggtctgctct ggtgggtctg atatttggag ccaggaatct tttctttctt    120900
ttaacagata cttaagtgat tcctgtggtc caggaagttt tgcaagctct gatgcagaag    120960
agctcgctgg agcaaacatg tatgttctgt tttactaatt agatatacgc tgttgatgac    121020
tccaaagtgg acgtgccatt tctgtcccct ccagcagtag gaaagaatcc cattatccca    121080
catcctggcc agttcttggt attgtgagat tttttttaaac ttcttctctt aagactatga    121140
tggtatttg ttgtaatata atccacattt tctatattat tactgtgctt gagcacttct    121200
tcaaatgttt gatgaccttg accattgaaa cttccttttt gtgaattacc tattcatatc    121260
ctttgtagct tcactgtgga atgcttgtta ctgatttgta gccattcttt atacatttca    121320
ctcccactcg tttgtcagtt atatgtggtg cacacatctg ctcccagtct gtggtttgtc    121380
tttccacttt gtttatggcc tcttattggg acacagtttt aaattaaaat ataatcagat    121440
gtattaatca tgatgttgta gtttgtgcat tttctatctt gtctaagaaa ttcatccctc    121500
tccttgttat acttagaaag aaggatattc tacattctcc ttcaggagtt ctaaagattt    121560
gctttgcaca ttcaggttcc aaatctactt gaatttgact tgtgtatatg gtgtgaggta    121620
gggatttgat tttatttct atgtggataa cagttgttcc attatcactt ttgagtagtc    121680
cacctttttct ctcactgact tataatgcca cctctgtcat gtcagctttt catatttatc    121740
agttcctgtt aaatgtatct ttaaagcttt attgagacat aattcacatg atacaattta    121800
cccatctaaa gtgaataatt aatgttttta ttatattcat acaccatcgc tatcagtcaa    121860
ttttagaaca ttttctttt tttttctt tttttttttt tgagatggag tcttgctgtt    121920
gtcacccagg ctagagtgca atggcacaat cttggctcac tgcaacctct gcctcctggg    121980
tttaagcact tctcctgcct cagcctcctg agtagctggg attacaggca cccgccacca    122040
cacccagcta atttttgtat ttttagtaga cacggggttt cgccatgttg gccaggctgg    122100
ttttgaactc ctgatcttgg gtcttgggat ccacccgcct tggcctccca agtgctggg    122160
attacagacg taagccacca tgcccggcta ttttcattac ccccaaataa accttgtacc    122220
ctttagttac ctcctcatct ctgtaaccct aagcaaatac tcatctgctt tctgcctttg    122280
tgggtttccc tgttctaaat attttttatg aatggagtca tatagtatgt ggcccttttct    122340
gtcttctttt actctgcgtg ttttcaaggt tcatccatgt tgtagcatgt atcaggactt    122400
catttctttt tatggctgaa taatgctcca ctgtatggat agaacacagt tatttattca    122460
ttcctgtgtt agtgtatatt tgggttgttt ctgcctttgg ctattgtgag taatgctgct    122520
ataaggattc atgggcaagt ttttgtgtgg acataggtct tcatttctct tgaatatatg    122580
cctaaggagt ggaattgctg ggtcacgtgg tatctatttt taatcacttg aggaattgcc    122640
agactattca aaagcagctg caccatttta tgccattta cattcccacc agtagtgtat    122700
gagggctgat ttatctatgt ccttaccaac gcttcttatc tgactgttta attctagcca    122760
ttctagtggc tggtgaagta ctatctcatt cagatttgg tttgcaattc cctacaatga    122820
tgactagtga tgtcaggcat ctttcttgt acttattggc cacctgtatg tcttccttgg    122880
agaaatgtct attcaaattt tttgcacaat tttaatacat acatatatgt atatacacac    122940
acacacacac acacattttt tcttttaaaa cagattctgc tttgtcggcc aggctggagt    123000
gcagtggcac aatcttggct tactgcaagc tccgcctcct gggttcatgc cattctcctg    123060
cctcagcctc ccaagtagct gggactacag gtgcccacca ccacacccag ctaatttttt    123120
gtattttta gtagagatgg ggtttcacca tgttagccag gatggtctcg atctcctgac    123180
ctcgtgatcc acccaccttg gcctcccaaa gtgctgggat tacaggtgtg agccaccgca    123240
```

```
cctggcctat ttatatatat atttttaaaa gtcaggatct ctgtcaccta ggctggagtg   123300
cagtggcaca atcacagctc actgcaacct tgaactcctg ggctcaaacc atccttctgc   123360
ctcagtctct caagtagcta ggactacagg tatgcaccac cattcttggt gaattttat   123420
ttttattttt atagagatgg gatcttgcta tgttgctcaa gctggtctca aactcttagc   123480
ctcaagcaat cctcctggct aggcccctca aagtgttggg attataggtg tgagccacca   123540
catctagcct cctttgcaca ttttaaaagt ggattagttg ccttttatc attgagttgt    123600
aagagttgtt tatatattct ggatataagg cctttatcaa atatatgatt tacaggtaca   123660
gttgacccctt gaataacatg ggagttaagg gtgcttgctg cctatgcagt agaaaatctg  123720
tatataccctt tgacttcccc aaaatttaac tacagatacc ctgctgttga ctggaagact  123780
tactgaaaac ataaacaatt ggttaacaca tattttgtgt atgtattaca ccctatattc   123840
ttacaataaa ggaagccaga gaaagaaaa tttaagaaaa gcataagggg ctgggtgtgg    123900
tggctcacac ctgtaatccc agcactttag gaggccgagg caggtggatt gcttgagctc   123960
aggagttcaa gaccagcctg gcaacatgg tgaaaccttg tctctattca aaaaaaaaaa    124020
agaagaagaa aatatattta ctgttcatga agcagaagtg aatcatcatg aaggtcttta   124080
tcttcattgt cttcacattg agtaggatgt gagtaggctg aggaggtgga agaagaggag   124140
ggttggtctt gctgtctcaa ggtggcagag gtagaagaaa aactgcatat aagtgggccc   124200
atgcagttca aacccagttg ttaagggtca actgtatttt ctcatatttt gtgggttgtc   124260
ttttcatttt cttgatgttg tttttttaaag cataaaagtt tttaaagttt tgatgaagtc   124320
catttgatct tttattttct cttgttgctt atagttttgg tggcatatct aagaatcctt   124380
tgataaatct gaagccatgt agattttaccc ctgtgttttc tcctaagaat tatatattct  124440
tagctgtaac agataggttt ttgatacatt gttaattcac ttttgcatat ggtgtgaggt   124500
aagggtacaa cttctgttct tttgcatggt gctatccagt tgtcccagca gcatttgttg   124560
aaggctattc tttccccttt gaatggtcat ggcacacttg tcaaaaatca gttgaccatt   124620
gtagtaggct gttcttgcac tgctataaag aaatacctga gcctgggtaa ttttataagaa 124680
aagaaactta aatggcttac agttctgtag gttgcacaga aagtaaagca gcatctgctt   124740
ctgggaagcc tcaggaagct tccaatcaca gtggaaggca aagcaggagt aggcatctca   124800
catggcgaga atgggagcaa gagtggtagg ggtgccgtat acttctaaat gaccagatct   124860
catgagaact tactcactat cgcaaatatg gcaccaagcc ctgagagatc tgccccatga   124920
cccaaacacc tcccaccatg ccccacctct agcatggagg attacaattc aacgtgagat   124980
ttgggtgggg acaaatattc aaactaaagc aaccatacac acaaagtttt atttccagat   125040
ttacagttct attgcattga tcactgacat gattactgtt cctttgtagt aagttttgaa   125100
attaggaagt atgaatcttc ctactttgta cttcttttc tagatcattt tggctattct    125160
gggtccttta taattccata tgaattttag attcagcttg tcaatttcaa caataagtc    125220
agctgggatt ctgaaggggg ttgtgtcaca tccgtagccc aatttgggga gtgtcttagt   125280
ccatttgtgc tgctataaca aaatacctga aagtgggtaa tctataaata agagaaattt   125340
agcttgggca acatagggag accccatctc tgaaaaaaaa aaaaattagg catggtggcg   125400
tgcacctgta gtctcagcta ctcaggaggc tgaggtggga gaatcacttg agcccaggag   125460
gtcaaggcag cagtgaacca tgatccacta ttgcattcca gcctgggcaa cagagcgaga   125520
ctctgtctca aaaaaaaaaa aaaaagaaa aagaacagca atttatttcc tcacggttct    125580
```

```
ggagctggga attccaatat caaggcactg gtaggttggt gtctggtgag tgctactctg   125640
tgctttcaag atggtgcctc ttggtttgtc ctcacgtggc gaaggaggga aaggagaaac   125700
agggacgaac agtgttcata gcagctcttt tatttataaa ttgctaatcc tgttcatgag   125760
agcagagccc tcatgactga atcacctcct aaaggcccca cctcgaaata ctatcacgtt   125820
gctggtttag tttcaataca tgaattctgg ggggacattc agaccgtagc agggagcgtt   125880
gccatcttaa caatattaag tattttgctc catgaacatg ggatgctttt ctgtttattt   125940
agatcttctt taatttcttt taacaagtat cattaatcca aaaatctgaa atctggtatg   126000
ctccaaaacc tgaaactttc tgagcactaa catgacagca acagtggaaa attccacccc   126060
tgtcctcacg cgatgggtcg cagtcaaaac ccaatcaaaa ccttgtttca tgcacaaaat   126120
tatttaaaat tttgtataat taccctcagg ctatgtgtct aagcatatat gaaacacaaa   126180
ttttatgttt agatttgggt cccatcccca agatatctca tgtatatgca aatattccag   126240
aatcaaaaaa tatatataga gagaaatttg aaacacttt ggtcccatgc attttggata    126300
agggattctt tacttgtatt ttgtagtgtt cacaatataa actataatat aatacaaaca   126360
atataagcta aaatataaaa tttgcacttc cgttgtcaaa tttactactg agtattttat   126420 tcttttttgag ctaccataaa tgggactgca ttcctgttag attttttctt tctttctttt   126480
ttaagaaatg gagacttagg ccaggagcgg tggctcgtgc ctataatccc agcagtttgg   126540
gaggccgagg cgggcagatt gcctgagttc aggagtttga ccagcctg gcaacacag     126600 tgaaaccccg actctactaa aatacaaaaa attagccagg catggtggct ggcgcctgta   126660
gtcccagcta ctcaggaggc tgaggcagga gaattgcttg aacccaggag atggaggttg   126720
cagtgagctg agatcgcgcc atcacactcc agtctgggcg acagaacgag actctatctc   126780
taaaaaaaaa aaagaaaaag aaaaaaaaga aaagataagg agccttgctg tgttgctcag   126840
gctgacctca aactcctggg ctcaagtaat ccttctgcct cagcctcccg agcagcaagc   126900
agggaccgag cagcagggac cataggagta tgtcactgtg cctggctaga tgtgtgtgtt   126960 ttctttttttt ggagatagag tcttgctctg tccaggctgg agtgcagtgg cacaatcttg   127020
gctcactgca acctctgccg cctgggttta agtgattctc ctgcctcagc tccggagta   127080 gctgggacta gctgtgtg ccaccacacc cagctaattt ttatatttttt agtagaggcg    127140 gggttttcca tgttggccag gctggtctca aactcctgaa ctcaagtggt ctgcctgcct   127200
tgacctccca aagtgctggg attacaggcg tgagccacac tacacccggc ctagatatgt   127260
ttctaaaaca acattgtgta ggaaatttttt cttaggctgg ttcaaggcta acatgctgaa   127320
ggtcccaggt agtgaagcag gtgaaccctg aaggaccgtg cccctcccac acccacccta   127380
gcagctgttc cacattgtag atggatccct gcgtccctac attgtcacct ttctgtctaa   127440
atgagaggtg gggagaagga ggggtgaaga ccaatgaggt tagtcacctc aagggtggg    127500 gccggtgcag agaaagatgg gaactgttcc ctagtcctct tccttctgga gttgggaggg   127560
ggaaatagcc ctgccccaac atgtgatcca gcatggacta tggtcagtta caaatatgag   127620
tgagccaggc cctgccctg aaggacctcc cagatttgtg gggaagacac aaactcagca    127680
cagaatggaa aggggcctgg ggacacagtg ctgtgccgag cttggaattt gtttcatgaa   127740
gggacagcca gcagtgtctg tgcaggtcca gggaggctcc acaggggaag tgagatttga   127800
gctgaggctt gaaagaaagg tggaccgaga ggagacgact ttccagggca ggaagtggcc   127860
tgcacagagg ccccgaggcg agaaggacca caactctcct gtggacctcc tctttgtacg   127920
atcagtttta attacgcaaa aaaattatgc agttaaagct ttgctcattt aaacagacct   127980
```

```
tccctggatt aagagtaatt aggttttatt gtcattgtct tgaaaattgc cttgccatgg  128040
acctgtgaac acagaattat ttatatatgt gtgcatagaa atcatctcat ggatttttt   128100 ttaactgaga tgaacttggg ggattttaaa ggtaacaaac aaccccttct ggctggtgtg  128160
ggggaagccc taatttgtag tgcttgctac tttttttttt ttttttttt  ttgagacagt  128220 gttttgctct cgtcacccag gctagagtgc aacggcacaa tcttcactca ttgtaaaacc  128280
tccgtctccc gggttccagc gattctcctg cctcagcctc ccgagtagct gggattacag  128340
gcacctgcca ccacacccgg ctaattattt ttgtattttc agtagagatg gggtttggcc  128400
atgttggcca ggctggtctc gaactcctgg cctcaagtga tccgcccgcc tcagcctccc  128460
aaagtgctgg gattgcaagc ataagccacc gcgcccggcc tccactttct gtggtgtaaa  128520
tattcctacc atggctgatt tcctctgggg aagccatgtc ccctccactt ctaccttcat  128580
ggtctttgct tgtttatttt caaatgtggc ccaaatccac cctgaggcag gcgcagtggc  128640
tcacgtctgt aatcccagca ctttgggagg ccgagacggg cggatcacct gaggtcgaga  128700
gtttgagcca gcctgactaa cacggggaaa ccccgtctct actaaaaaca caaaaattag  128760
ccaggcatgg tggcacactc ctgtaatccc agccactcgg gaggctgagg caggagaatc  128820
gctggaacct aggaggtgga gattgcagtg agccaagatc atgccactgc actccagcct  128880
gggagacaca gccagactcc atctaaaaaa aaaaaaaaa  aaaaaaaaa  accaaaaaaa  128940 cccaccctga gtttaaaaga aaaaggctaa gaaatgcttg ctgggctgtc tcaggggtgg  129000
cagtggagct cccgtgcctc ccacagatga ggacgtggag gccctggccg agtgctgaat  129060
gcaggttggg ggacagggct gccggcctct gtaaggatgg ggaccccaga cccacccggt  129120
ggagctgggg ctgaaggccg tgataaacac agcctcaccc tggcattgcc cacctccact  129180
ggccaccagc tttgacggac agccccactg ccactgcccc tctccaggca ggccacattc  129240
acaggtgttc tgtacagaga gcagaagttt gagaaaacgt gacccactga acagacactt  129300
gctgaggccc gggggcttca tgtgtcaggc ccagaggtgg ccacaggcac aacacgcgtc  129360
cctcagcctt gccacctctg ctgccctcca aggtgccctg ggtccagctg gccagaagca  129420
ctgctttctg gagcagccac ttatgctttt acttttttct cttctttttt tttttaagac  129480
tgagtcttgc tctgttgccc aggctggagt gcagtggcac aatcttggct cactgcattc  129540
tccagttcaa gtgattctcc tgcctcagcc tcctgagtag ctgagattac aggcatctgc  129600
caccatgccc ggctaatttt tgtattttta gtagagatgg aatttcgcca tgttgaccag  129660
actagtcttg aactcctgac cccaagtgat ccgcccgccc aaagtgctgg gattacaggc  129720
gtgagccaca gtgcccggcc cagctttttc attttgaaat caatacaagt ttttacagat  129780
gtctgcaaaa aatatccata ttgatggatc ctggctcctc agaatctgag gttttacaa   129840 atgtctgcaa aaaatatcca tattgatgga tcctggctcc tcagaatctg aggtgacagc  129900
agcttgcaga ggacactgct cccccaacac tgccttccaa gggagacatg ccctacccca  129960
aggcctccct tgtcccctcc ctcctctgac agtcaggtcc aggggtcct  ggagagggca  130020 ctggcccacc ctccacacat gttgcacagt gccctgggaa tgaggaagga agggcaaagg  130080
ttagggaaaa ccagacgtca gtttcttgac cagccacagc cggtgcagcg cggttattta  130140
tagccctggt ggagcgccca taaatcaagg cttccccag  cagcgcggct gtgagggctc  130200
cgagatgatc tcatggtgcc cctcccttga accatcccag agaaaggagg cctgtcacct  130260
tcaaggacca atgcttctgc cgggactcaa gcagaacctg ttcctgctgc tgcaaggttt  130320
```

```
acaggcagcc ttggggacag tccgtgcaga aatgtcagga gccttttcct gcataaggca   130380
tctcagagct tatagcacct ccttggcggt ggccgtgctc gcagcctgat acatgggacc   130440
tctgtctcac ttgcagtgtg caccgcaggt cctaattcct tatctgttcc aaccacaaaa   130500
gcttccactg ctggatggag ccctgttatc attcaggctt ctgagccacc tggaaggcaa   130560
aggcctctct gtgaaaatga aaacttggct ttaaaaagct ggcatgggct cagccatgga   130620
gttgcttaga tgtagttcac aatctcgcag acccacggca ggattccacc aggagaagg    130680 tcctggaggt ggccatgggg ctcagcagaa tgagccggga ggagcaggac tgttgacacg   130740
agagcagggg tcaggctcag tgcacaggtc ccagtgtgca gagctcaccc ggccccagct   130800
ttcatcaccc atctgagatc ggcctccttc actcctgttc tctgggactt ccttgtgtgt   130860
tagagactcg agcaagaccc tttcttgtct atccccggac ggacccgcct ttcccgcatc   130920 tctggggtg aggtcggctc tcgttcaggc ctgcagggtc cctggtgccg cagcccctct    130980
ggttggaagg cccctgcgt gcagcccgt cctccagccc cgctcggctc tgaatgagtt     131040
cattatgtct cagcgcgccc tggccgcag gctggcagtt cttcgggctg gcggggctcg    131100
ggagctgtca gcctgccaaa tccagttgtt tgacttcatg tttcaaggcc aaatcctttc   131160
aggaaagttc tctccatccc accactccac cgccccccgc ccttagaaaa ataaatgcgt   131220
gattgactgg ctttgcaggt tttttatcca tcgttctttc caaagaatag tgtgaacagc   131280
tcattcgatt cgttcatgtg acgtcctccc tctcccaatc cctgtctctc tctctccttc   131340
cacagccaca tgaaattgaa gtgggagaac atggtgtgtg agcattattg ggggtggggt   131400
gcggagcagg cactggcttt ggttgaggtc tgcaaaggaa agcaccccca ctgccaggct   131460
gctcaggagt ggctcccacc ctcgactgcg gggaagtgct ggaaccctcc gcacgagggc   131520
aacctttctt gggctctgaa ggcgcctctc atcctctgag ccaagaagac ttctgaccca   131580
gaattctgag ttgagttccg acgcaggcgt gggcgatggt gagcaactcc aggctacccc   131640
gagaaagccg ctgtgtgacc ccattagggg acttggctct cctgccaagc ccccacccag   131700
cacctgtccc ttgtgtcatg actggacttg ttacttctag cccaggagct ccaggtgaag   131760
gggactgtgt tggtcctgtc tgcccaggac tctccccacc cgcacagtgt acctgtccca   131820
cagtggcacc aacaaggctc agctgagccc ttgccagagg agacacggtg ggcaccagcc   131880
ccagcgctgc cacctgcctg cctcctctgc caccgaggga agccatgtcg ccttcctgag   131940
cctgcttctc tgtccacaaa acaaagacta gataattaga gtgcacactt ggagggacag   132000
gatggcttcg tatccatctg gctgtgccct gtaactcaag ggatgggact gtgtcattgg   132060
taaacactgc aacaggcctc cttttccagga aacaggatcc ctgtctcaga cagaagcagt   132120
ctcgcccatc ctggggcctg agagcatcat tcctttgtga gactcaaatg tgaggaattc   132180
ctgtttcctc aagtctgtgt ggggagtgca gagcagccct ctgaggggt agcgtgtgca    132240 ggaaataagc cggggggaag ggggcaccgc gggtgggtgt taactgctgc ttcgggtcc    132300 agtcctgtta atgaaagcag gggtgaggca agcggggaag actctctgta cctgatcagt   132360
ggcatgtgtg tggctccagc cggcatggcc tgagctgccg gtgagggaga ggcctcaggg   132420
agaaaagaca aaagctgggg tgccctgaa ggtggggcag agctgggca gtcagggct      132480 cttccacagg tgcaggcctg gtgctggagg acacagtcca taccacctcc aaccccacc    132540 acctcccctg ccatggacag tgtggggcag gctcctgagg atgaggcagc ctgacccta    132600 cccctgggct gtcccccga ctcctggttt tctctggaagc ctggggttcc aggccatgca   132660
ggtagagaac aacaggttta ggacaaagtc attgtggaca ctgaggccca gaaaagggac   132720
```

```
ttgcccaagg ccacacagca ggtggccagc actgtgtccg tgtctctgtt attccttcct 132780
ctgcttgctt tgggtttatt ttgtgctcct tttctacttc cttaagatgg gagcttcagt 132840
gatcaatttc agatctttcc tctcttctaa caagcatttg gtactatgaa tttccctctg 132900
aatcctgctt cagctgcatc ccaacttctg ataccaggta ggagtaattg ttctaagctc 132960
cgcagctgac tacagagagc ggccacattt gagaaacatt ctcatctctc tgatcttggg 133020
tctctgacaa tggagctagc aacacttcct ggttttaagg gctctgagga gcaaattaga 133080
ctgtctggtg gtgaagaact tgtttagga acaatttaag atgccaacag gttcatctgc 133140
tctcctgcct ccttctcccc accttgtaac acccctaga caagtcagca ctcaagttta 133200
tatggacaaa taagcaagta aaattagtta ggaaatcaaa tattgggagtt ggggaacaat 133260
aagagaaggc aagccctatg ggatggtaaa ctgcagtata aagccccatt tgctggcaca 133320
gtgtggtctg gcctgtgact aggtgaggga cagtgcgggg tggcctgcct gcatatgcca 133380
ggttctgtgt atcacatctc tcaccaggaa ggcaaaacct ggcagatggc acccgggcct 133440
gatggctcct caaccctctc agcaccccaa agagggaagt cccatcaccc tcactcaccc 133500
agccccgggc tggccctgtc agctctcgaa ctgcagcata cccgagctct taaagcacac 133560
tggacctagg gctcaggttt gagctttcat gatgagaccc tgaggtcact ggcggggaaa 133620
atgagtcact ggggcattcc ccgaacttgg gaaaagccct gacccagaa tcctgagcct 133680
aaattgctgc caagttcccg atttcccttc cagtcctcag tttcccttc tctccggcac 133740
cctcctgagg accactgagc cccaaccacc accatgccca tggctggtgc ccaggaggtg 133800
ggagctgtgg agctgcctcc aggccttccc ggaggcccca tggctgtctt acttggtttg 133860
tggcttccca gtaaacggtg ggacaggacc agggtctgag gaaaagcaaa gcagtgttga 133920
cagagtgtcc tggagggcag cttgtctccc tggcctggag atgaaaactg aagaaaacaa 133980
gattccgtct aggaatcgtc cagggcgcgg cagcccgcca ggagcccggg cagcttggat 134040
ggggtccctg tgggcacaat cggcccagtg tggggcgcac cgccccaggc aggctggcgt 134100
cccgggggcc agaatgaatg gaccctcact gggccgcttt gacagtttat gaggtgatga 134160
cgttgcagct atgattgatg aggtggcctc agtcggcgtt tcggggaacc gggtacaagt 134220
tgctagggaa atacagggg agggtgctgc cctccccact ggcccgctct gggtccctgt 134280
gctatgcctc agtctcccca tctgtgtgga ggaactgatg aagacagcac atgccccctg 134340
ccctggtccc tggattgcaa gtccagacag aagagagcgt cctgggaagc cagctgagag 134400
cacctctttc tctttgggtc ctgcagcccg tgggtgcag ggcggtaacc ccatctgccc 134460
agaaccaggc tgcgctctcg ggagggaaac agactcttat cctcttaggt acagcctccc 134520
tggccgcctc ggatgagcat ctgccctcc cgggcctcag tttccacacc tgagatggga 134580
gaggttgcat cctaaaggcc ctccatctct caggttgggg gatcactctt gtttccctgc 134640
agttgtttcc agcattagag tcacactggg gtccttgttc tagcccccgt gtgttggctg 134700
catgacccga actttactcc catgtcctcc tcttgggggt gtgacatgag gtcttcccca 134760
agtggccccg agtgaggcac caccatggac ctgatgggca gatcccccag ggcactctat 134820
ccagagggtg gtggacccaa acgcgacgtc cccagtggcg gtggctgagg agagggggttga 134880
gggcgaggac cagctctggg cagtctccag gtcatgcgcg tttgacgcag gaggttttgc 134940
cggcgccagg ggctccctcg gctgaccgag ggtgtccctt actccataag gtactgatat 135000
ggtctgcgga gcaggtggca tttgccatgc ctgccctgct tgggtatttg gccccagggc 135060
```

```
cagggctgtc cctcccacag ctattgaaca ccaggtcctt gctgcgtctg gctgggctgc   135120 agaatacect tgacctttca gcatcctcag tacctctgtg gagtgctgcc atgaccaaac   135180
tagagactgt tattattacg cacattttaa gacagcatcg gccggacgtg gggggctccc   135240
accagcactt tgggaggctg aggcaggcgg atcacttgag gtcaggagtt caacaccagc   135300
ctggccaaca tggggaaacc ctgtctctac taaaaataca aaaaaactag ctgggcatga   135360
tggtgcatgc ctataatccc agctactcag gaggcggagg caagagaatc acttgaacct   135420
aggaggcaga ggttgtagtg agccaagatc atgccattgc actccagcct gggcggcaga   135480
gtgagactcc atctcaaaaa aaaaaaaaaa aaaaaagac agcatcactg tagccaaggg    135540
aacttaaaag aaaaagtgc atgtttagac agttgttcat ttcctccagt ttcctgccag    135600 ccccettctg tagctgtggg cacgtgcaca tataagtctt ctctttctca ccctgctcat   135660
tgttcatagc tgcataatat tttacagagc agataaactc tgccggcctt aactactccc   135720
agggtcgaac gtctccttt ctatcgtaaa tatctctgca attcctatag ctttttcct      135780 tcaattcagt aaactttttt tttttttta atttgagatg gagtctcact ctgtcaccca    135840
ggctggaatg cagtggtgtg atctcagctc actgcaacct ctgcctcctg ggtccaagca   135900
attctcctgc ctcagcctcc tgagtagctt ggaaaacagg catgcaccac cacacccggc   135960 taattttgt attttttagt agagagggt ttcaccatgt tggccaggct ggtcttgaat     136020
gcctgatctc gagtgatcca cctgcctcag cttcccaaag tgctgggatt acaggcatga   136080
gccaccgcac ccagcccctt tgctcttcct ttgtcttctg ccatgattgt gaggcctccc   136140
cagccatgtg gagttgtgag tccattaaac ttctttcctt taaacattac ccagtctcag   136200
gtatgtcttc attagcagca tgaaaacaga ctaatacacc atgtcattta atgaggctgg   136260
gcctgcctct ttctgatgga atgaactctc cccaggtgac agcctctggt cccctctgcc   136320
tttggagtga cttctcctgc atgggggttc tgggcagggt tgggggtga acactggaga    136380 gggatcagtc ccagctctgt tcttccccac ccgctgcaac ctggttgggg acgcgaggag   136440
ggcacccagc aggctgccag ggggaggagg agggactgca gtctgggccc agagcccggt   136500
tgtcccccat ggagccacac agcaggcacc tcagagtttg catccattgg agatggccag   136560
gagtctgctc gtgtgggaag aatggcttct gagcgccaag gtagcctgtg ctggagcctt   136620
ggctgccata gaaggccatt cacgtccctc acacccggc ctgtgctgct gggaaggctg     136680
tcactcctaa acagttatct gcttctgtgt taacctacag ggattccctc tttgctttgg   136740
ctgccaggga actcaaagct aagttttttc gctcacattc ccaggcttct ggtgtagata   136800
tctcctttct tccttactgt ggtttctgag ccatctggtg tagatatctc ccttcttcct   136860
tactgtggtt tctgagccac cctgcaaact tcctctgcat ctgtcccagt acaaatatca   136920
ctgtgtgccc ttctaggcta tctgggacac ttaaaaataa ataaataaag acatctgtct   136980
gaggcttaac ttgcatatag caaagtgcat gaatctgaag tgtgtggctg atgaatctgt   137040
acacaccgct ctccctgcac agccacccag atgaagacga ggagcacctc caataccecaa 137100 gcctccctcc acccagtcaa cactcttctc cagagggagc tagcccgtgc cttcaccccc   137160
gtcttctgcc tgacggtaaa cttgaggtga atgggctcct acccatgaac acccaccgtt   137220
catttcatcc gtgttgttct gtgcagccag actccatcct acggcatccg tgggtgatgt   137280
ttcatcacga ggctggacca cgatgtgttt atcatgtcac tgttgctgtc acatgggctg   137340
tttctggctt ggggtcctta tgaacagagc tgatcagaac atatctgtcc atggctcttg   137400
gtggacatag cctcatttca tgtgtgtgac tcaggagtga ggttgctggg tcccgcggca   137460
```

```
ttcatgtgtt tagtgtagga gactcttgcc aaacatttct ccagagtgtc tgatgtacca   137520
tgttgcgctc ccgccagcct cgctgagttc ccatagcacc atgtcttctg cagcacacga   137580
tgtggccgga cctctccacg ctggccattc aggtggacgt ggagcggtgt catttccttc   137640
ctgagggggcc tgcatgaatc ccttttaggt ggaacacaca cagagtgggc cggcgctcat   137700
aagcagtccc gtgtgaatcc ttggagagct gtggaggtag cacagctgca tctctaggtt   137760
ggggccactc ttttcttgga acaagagccc taaacgtggg accctaaaca acacccaggg   137820
aggagcagcc tggcctatga gcaggggac accatgaagc tgggtggacg ggtggggagg   137880
cccgacttta agggacctgc ttcctaagca aacaggccag gacagaggct gcaggtataa   137940
gccctgccct gccaccatga tggtgaatat gaggtgtcaa cctgattgga ttgaaggatg   138000
cctagatggc tggtaaagtt ttgtttctgg ctggttaagt gtgtctgtga gggtgttgcc   138060
agaggagact gactttgag tcggtggacc gggtgacgga gacccaccct ccgtgtgggt   138120
gggcaccatc tcatcggctg tccttgtggc tggaacaaag cagatggagg aaggtgggaa   138180
gactttgttt gctgggtctt ctggctttca tccgtctccc gtgctggatg cttcctgctc   138240
tgggacatca gactccaggt tctttgacct ttggactctg gtttagctgg agctctcggg   138300
aggtgtcggc ttccctactt tgaggatttt tggactcgga cttggccatt accagcttct   138360
ctcttcccca gcttgcgtac ggtctgtcgt gggacccgcc tagtgatcgt gtgagccagt   138420
tctccctaat aaactcccct tcatgtatag acatggatcc tatgagtctt ttccctctgg   138480
ggagccctgc ctaacacagt ggcatagagc tccaggcagg cccctcacct ggccttcagc   138540
ttcagttctt ttgcctactg ggctgaatat tggtgtcacc acccaggata gcaagtcccc   138600
atcagtgtca ctgccacctg tcgaagagat cccccagccc agcactcggg tctgtgagtg   138660
gcagtggaga tgacactagg ctctaagtag tggggctgcg tgactccagc gcccctagga   138720
ccagcaaggg cacccagagc actgtgggag gactggtgcc gcctccctgc ccccctgctt   138780
tctcctgggc cactgggcta gacatggggc ctccctgccc ccatgtggtt tggcctgaaa   138840
aagagaggag gtggggtggc acttctgggg cagcccagag tgagtgccct gccctgagcc   138900
cagcgtgtgc cctgcctgtg cccctgggtg ggggtgcat acagacctcg gggggatctg   138960
gccgttggag tgcgcactgg gagggacgga gtcagctctt tttaatctaa acacacacca   139020
ggtgcttaac gtgtttttat caaaatatca agcacagctg caagaggctg ctctgctcca   139080
aggccctacg cccaggcccg tccctctgcc aaagcgagcc ttttaggtga gccctgccgg   139140
ccacctgcta gcccaggccc cggctcctgg tgggccctgg accaggctgc aagcatatcc   139200
aagtgcatgg cagtgagacg tccaggcctc ccagccccaa ctctgagcct ccgttgggtc   139260
agtggtaaga tgggggcagtg gcacctacct ccccggctgc tgtgaaaacc aagtgagcgg   139320
aagcatggca gcccctcacc aggtccccag tgggaggact ctcaatgatt ggcactgcca   139380
ggagtaatgt tatgagagga gcgtcccatc agcctggagg ggacacaggc tgggtcagca   139440
cccacagggg cttccgcttc tctgtctcag ggggtccagg gtggcccctt gccactggtc   139500
cccaggcaca gccgctacac aggtgcctct gcagggtctg ggagtcagct gtccagggcc   139560
tgcttggcca ccgcagggca ggagtgtggc actgtgagcc tggtggcctg gctgggcgtg   139620
gccttgaggt tctattgata acccccatggg gaaagccccc ctgaggtgct tgggcatcgg   139680
acctgcccac catctcctga ggtggggcct gctctccaga cagtcaggtc agcatggagtt   139740
cccatgaggc cagggccagc acgaggaatt gctgggagcg gtccatccac ccatccgtcc   139800
```

```
gtccatccat ccatccatcc atccatccct atccacctgt ccaccctgat gcagttcctg    139860
ccatccacgt gtccatctgt ctacccgtac acctgttcat ccccatccat ccatccccct    139920
gtccatccct gcccattcat ccaccctgat gcagcgcctg ctacccaccc ttctctgtcc    139980
atccccatcc atccatctct gtccatccat ctgtccacct gtccatcccc ctatccatcc    140040
ctgtccattc gtccacccat ccaccctgat gcagcacctg ccatccaccc ttttctgtcc    140100
atccccgtcc atccatctcc atctatccat ctctgtcctt ccatctccat ctatccatct    140160
ctgcccatcc atccatccat ccatccatcc acctgtccat ccccatccat ccatccctgt    140220
ccatccatcc actcatccac cctgatgcag tgcctgccgt ccacccttct ctgtccattc    140280
ccatccatcc atccatgtcc atccatccat tcattgccca tctgtccact cacccatcca    140340
ctcatcccac ccaccccatcc atccacccat ccgtccccag ccatccatcc tcctgtccat    140400
ccctgtgcat gcatcatcct tccaactgtc tgtttgtcca ttcccatcca tctatccacc    140460
catccaccca ggcgagcacc tgccatgccc acgacctgca ccatctcggt gaatctccat    140520
cgtagcccca ggaggggctc ttttcagctg cactttcagg atgagagaag ggaggctctg    140580
agtggccatt tgcccaaggt cacacagagc tcagggccag cgcttcccat ggccaaagcc    140640 caggcccccct ctgccagtcc cgcctccagg cttgcaggtg gagcagccag gggttccgta    140700
ctccctgcca ggcagctgcc agccctcccc gctcccctct cagttcctca gcctggctat    140760
gggaggccca agtcccacgt gtcactgaaa ttcgggaggc ctggctctca aagctttctg    140820
tacaaaacaa ggagaaaaag agaagccact tttgctgtct ggacatgctg tgggtgtcct    140880
ggggaatgtg ctgcccact gcttgggccc tgacttggag tgcccaggag ctgcgtctgc    140940
actgtggctt gaaccgagtg tcgtgctctg tggacagagc catccactct gggggtgctc    141000 gtccatggc actgtcagcc cccattctgg aaggtcccaa ctgggtcccc caggcctgtg    141060
tcccagagac cttccaggtc ttcattcact gatcatgcat ttattttggg ggtaggatag    141120
gtcctgaaga ccacagggca gggatctctg agttgggct tttgcggagt gagggagtga    141180
gagggtgttc caggcagagg aggtggcaga gaaaggcacc aagtgaggca ggggcagttg    141240
gggacatgag tgctcgggag cggggagagg gggcagctgg tgggtaagca gaggccagct    141300
ccaaggcccc cctgtgggcc acattaggga gacagggtct ggccttgttg gtagcgcggc    141360
ccctcgcagt gatgggtccc ctgtcagacc tccaggatcc tgggttgctg gtttggcgca    141420
gccccggctt ctgtgagctt tgtttctgt tactggcacc tgcagctctt cctaggcccc    141480
tgccctgggg cactggtgcc tgcttcgcca aaggcacaga gggctgcagg cgactggggc    141540
agggtggggg gctcgcctct tagggctcag cttcactggc cagaaacagg gctggctcga    141600
tctgggtgtt ggcctgggtg gggtggccag catgcccaca cctctcagtc tggatgtggg    141660
gagaggttgt tccatccagg gcagttggtc tccagaagga aattctctgt atctgggtgc    141720
tgcaacctag gtgcccgggg tctcacgcag tggggcctcc ccggaggagg tgaagtgcat    141780
gtggcccctc gtgctggatg gagctggact ctagggagga ccaggagggt gagctcaggc    141840
cagggcgcca aggccctgag ccccagggc ctgcctgtct gcccatcatt cctccactca    141900
tggggaggga ctgcccccca gcccagattt ctaggagggc cgaggctcac aggaagccaa    141960
tgccaggcga taacccacag tccccagtgg tcagtaggaa ggaggctgcc tgcttgtgtg    142020
ctcattagga gccaaggcca tgaggccact aacggaatgt ccctgatctc agggatctca    142080
gtgtggaggt ggcagcacac aggtaaccaa acaattgtgg cagattgatg ggtgctttga    142140
tggggtccac acagttaccg tggagtgcag agtgggcacc taactgagga ggcaagggtt    142200
```

```
ggagggagga aggtttcagg gaagacttcc tggaggaggt gacttgttct tagggaatga 142260
ggcccaggga gctaaagctt tagggcaggg cagcagattc agagacaccc ccaggggtag 142320
ggggaagtgc actagagtga cgtgtgcctg gcgtgggaac agggagacat tagagaatag 142380
tgggagtgtg gcaggctggg cccgccttgc cccttttcaag gaagcagctg ccgcgtcaca 142440
cgctgcagcg cagtgctgcc catggtttgt cggcccatat tgtgggatct ttcagatttt 142500
ctcaagaagc caggtttcca gctcctaggt ttgaaaagtt ctatgtgcgc ttgaccgggg 142560
ggccttacgt acgtgaattg ggtgagggcc tgagacaggc gggtgagcac ttgccccaca 142620
ctccagccag gattgggggt tcaaggtacc gcatttgcca cgtgagggag tctctggaga 142680
ccaccaaccc gctggtgggc ggccaagcgt caccaccagt ccctctcagt gcgtcccacc 142740
tctgttctca gcccctgcgg tgcccgcagt cagtggggca gtgagaaccg cgcaggaaat 142800
agctggcgcc atggtgtcgg ttctggttga cagagtgcca cctggctaaa cccagccgta 142860
aataagcccc gtttcctccc tgtggacaga gactggtggg tgccaaggtt cacggcaaaa 142920 accсcttcccc gccaggcccc actgctctct gcctggctgg cacacgccct tgcctcaggc 142980
ctggctcccc gggtcctgtt gaccaccagg ctgcagatcc caaggaatgc aggcatctgg 143040
gtggccccac gtggagcacc agccatgggg aggccgtggg ctaccaggcc ctgcgtgcac 143100
tcgcagcatg caccactcct tctccaggtc ccgttgacct ccatgtgtgc tgtgccccgt 143160
cctccgctgc actgcctctt cgtagtgccc cagctccatc cggggtgggtgggg tgggagtgga 143220 gacccctgcc tacaggcctc cgggtctagc cagagtcaac cagcccacca gagacaccca 143280
gatgcaggct atgccccacg tgcccaggga ggatctgctg acgtgagccc agatttcgat 143340
tcttgtgcga gggagacgaa ccaggtttaa accсccagctc tgccacttct ggctgtgact 143400
ttgagcatgg ctgttcatct ctgggggtct ctctcctcat ctcagagaag cagatcatgg 143460
tgcgcacccc atggcgcgct gtgcagagca catagagacg ccaccacag ctggcttact 143520 gcagaggtgt gggcccattg tggtatcgct gatgtcctgg aggccacaag tctgctagct 143580
agaggagcct cacctgcatc ccgggggcctg cccactggct ggtggagagc tctgggttgt 143640
gggcagcagg caggcctatt tccagtgagt ctgtggctcc tgggggtgtg tgagacccttg 143700 ggcagatccc ttcctgtgcc tcggtttacc cactagggct cagagccctg ggggactggc 143760
tcagtgagtg cctccttctg cgaggagaga cttttgtcct tactagccag aggacaggtc 143820
agccggggca ggctctgggc cctgggcacc acccactgga aggaaagggg gttcagttag 143880
cccagccctg ccccccaatg gaagaaaatt ggggttcagt tagcccagcc ctgccccacc 143940
ccagctcttc acacatccag atccagatgg gggccagacc accaggagac tgtaaggatc 144000
caaggccgag gggcaggaga cgcagtgcgc ccctctccta tttctgggtt gcaaccgccc 144060
acacatgtgc acacagggaa gatgtctctt ttggttgggg ggcacaggac cccacctcac 144120
tcttagctct gagacaccct tgtcaggcct cctggacagg tggagggac agggcaggg 144180 gggtgtggc cagctgcagt ccctgggagg ggtactgggg ctgggccagg ccagggcagg 144240
acagagttgg ggaatccagg cccctcacca ttgccctggc tctttgtatg tagtgctgcc 144300 tgcgggcgg agcctagctg gacacctgca gtgcgctcat gcccagcctc tgtgggtgtc 144360
tggctcaccc cacgtgggag gaaggcgggc acgggtggtt tgggctgggc aggcccagcc 144420
cgggtgcaca gctttctcat ccacacacac attccatgtg tagggctca ggggagggg 144480 tcacctcctc cctccccacc cctccttgtt acagaggagc agatggccaa acggatgggg 144540
```

```
gacaagcacc tgacagggcc actgctcctg ctctcagctg ggccagtggg aaagggagct   144600
tggcacctcc aagggaggtc ccagccaggg gaagtgtgtc cccatccctg ctctggtccc   144660
caggccagag aggtgaggga cccagagagg cccaggatga ggactccttc agtcctgggt   144720 tttttgtttgg attttttttt tctgccaagt gacttcaaag ccgcccgaga aggtcctgta   144780
tgtgtgagca ggttgggcaa ggggagggcg ggtctccaag ctgggagcct cctcgcggcc   144840
ctcgcctcgg cactgatgtg gccctggacc ctccggtccc tccaggccac ccttcgtgcc   144900
aggacccagc tggcttcaat ggcaggaggt gccctgggct ggagggtccc cacgctgggc   144960
tccggggctc caggttgact cagcagtccc caggcctgtg ggcagagctg gcctgggagg   145020
acacgggcct gagggctgag caatccctga gtgagaacag gtagctgagg ctggagcctg   145080
tgtcccccag gcagctgcta aggcccgggc ctggggctgg agtgctgggc tcaggtgcca   145140
tgtgagctct ttgcaggcag ggaccaggtc agagtccttt gtgtgcctct tgaccccccag  145200 gtcctgggag aagaggggct tgggaggcct tggctggatg cacaggctcc atgggaagga   145260
gctcctgctc gggtttcttt gtaagcagca cgacatggca ccttcccaga ggtacatggg   145320
tctgggcatg tcattccccg acctgcttcc agaacccagg ggacggaggt cggagcagcc   145380
tgcctgagat ctgtggccat ctccactccg ccacccagct accccgtaag gaggccaccg   145440
accctcgggc acctgccagg gacccagctc aggccaggtc acgggctgga tgtgggatgt   145500
tctgggcctt ctgcccacct cactgggccc cagcaagctg ctgtcctgag ggtggccgtg   145560
ctgggccagc acgtggacag cagggaaccc catgggcaca ggcctagtgt gtgtgatgta   145620
ccggtgcaga ccatctgata agcagccttc agagaagctg cgggtgtgca ggtggaggca   145680
gacctcccag ctgcatcctc caggcacttg ccagggtcag gctctggtga acacccttct   145740
agaaataacc ccccaggccc ccgggggtct tgggctcctg gggttctgat ggaaggatgc   145800
cccttgcccg gcctcactac ctccacctca tgaatcaccc tctgtccttg tcctgcaagt   145860
ctgtcggcac agccgagctg gcgtcaccct ctgatgccag tgcccagatc cctgaattca   145920
ctgggcagcc gccccctgca cctggctccc agccactgcc tttccaaagc aaatggggac   145980
agggatacct gcccctccct gggtaggcag ctgttgcggc ctccagttgt gagagtctct   146040
gccccaccct gccccttccc ctgcccctgc agggtagaga ggaggcgggt gggccaccga   146100
ctgggagtcc cggcagctc aggtcccta agagccctc ggggagaggc cgcacccgtc    146160
tcccttggtc agtgttcccc aggaggcggt gctggcctgc gtgtgccctg gaggaggcgg   146220
cagggagact ggcctcatgg ggctctttg ctggggcctg gccaccattt tccttcgatt    146280
ggtacaaaga ctgtccctgt gaagctggcc aggcccagg cacagaaccg ccttgttttc    146340
tgcctctcac tcacccgttc cctgcattcg gctgacagag catgagggg aggaatcact    146400 gatgacaggc actggcctgc ccagctgggg gcctttgttt attcatttgg tgggcacttc   146460
ctgggtgcct gctctgggtc aggcctgtgg gggggaccac tgaggcagg aaacctggcc    146520 tgtccctcca ggaagcgaag tcaacactgg cacctgcaga tgaagtggca gagcagcccc   146580
cagctttgat ggcatggggt ggttgggggg cacattctgc atgctcagaa gagagagcaa   146640 ctcgcccctgt ggaaggagca tacagtggga gatggggaca ggtgagtggg gtcttgaaac   146700
gtgaacagga gtttgcaggt ggagcaggtt tcaagagcat tccagggcac agcatgggca   146760
atggcaggga gagctgggat gtctgaagag cagcagccca gacactgagt ggctggcgag   146820
gcgagggagg tccgcaggtg gggcccagtc aggatggact catctgccat gctgaggagc   146880
caggctatga tgtgggcaat agggagccac agcagtttac acaggggagg cgggagcagc   146940
```

```
tgagcattta gggaagccac tctggctgca aaagaggaga gggggccagg caggagggag   147000
agccagtgga gggggagggg gaagggga ggaacaggct tcagcagaag acctcctgcc   147060 ttcaagggc ccgggtcacc ctgtgggttc cggtggttaa ggccagcctc ctggtcctgc   147120
agccacatgc ctcccagctg tgtgcctccg cttctacctc cgaaacccgg gcagcaggac   147180
ccaccctgca ggctcctgcg caaggatggg ggaggtacct ggagggccca ccccacatca   147240
gaagcaggtc ctcagccaga gacgcccaaa tgcagcccga ggaggctgc ccccaggaga   147300 ggagaggaga acccgcagcc gccccgcagg cgcctgggga aatcactcac tgctcccacc   147360
tcccagccag gccccgaggg ccaggcactc tggcttagtg aagaagccac ccagcaaagg   147420
cctggtgtct ccacaccatt ctcgggggga cagcagcaag gacgatggac gggagcagtg   147480
ctcagcctta acgtccctgt ttccggaagc gtccctgccc cgctcagtcc tgccccactc   147540
cctctcccat cagtgccctc agactccagg cccttttctt tctttcccag cagtgctgac   147600
aactgtgagt gtggaactgg actgtgaacc ctggagggca gatggtggag gtgggagggg   147660
gcagggccag cgccagggtg agctgcaggg tccccaggtg caggggaaac gccaacttcg   147720
tgtgcagtct tgcctctttt gtttcgtttc agagtggccc ccagagccaa gcccatgct   147780 accttacaga tgaggaaact gaggctcggg caggtgaaga gaccggcct gggccatgca   147840 ctttttggg gacagagcag ggtgctcagc tgtctggggg cctgggctgg gcctgggca   147900 gggggaggag cagcgctgtg accccacgg ggagccgtca gccaggcccg tagccaggga   147960
agggcggagg ggcttaacgc aggcccacat ggccaggaca cagaaccgtg ggggcagccc   148020 cagccctttcc ctgcctgtta caggcccctg cccctgttcc tgtgtcccat gcctgtcccc   148080
tccctccatg tgtctgtctc tactcgcctg ccctctctct gccctcttt ctctgcttca   148140 tcctctttt ccgtttctgc ctgtctcatg gttcttcctg tccctgccct ccctccctcc   148200
gtgtgtggcc gtgtctctct gtctgtctct tcctcctcct ccagctctgt cccagtaggg   148260
ccactccggg caggatggtc tgcggcccct cctgcttcac cctctccgct ctgtaccac   148320 tgccgaggac acacctttgc tgggtttctt ggttcagctt ttgtaccgtg acatctctga   148380
ggtccacagg tcacagggca ctggccagtg tggggcaggg actcctcctg cccaggccat   148440
tggacaaagc agagctgctt caggggcttt ggggccacca ggccaggaac aggtcccctc   148500
ctgcctaccc cagctcctg ggagacacag cccacagcag cgtcacgtaa ttaagacata   148560
aaagtccacg atttccgctg cgtgtgggca aacaccggcc gggtgctaat gcaatcctt   148620 cttttagtgg attcttgaat ttaaatgata tgtaattaaa cataattagc cacggacgcc   148680
attcggctag gtacacgtgc ggagtggggc tggccggatt ctcattacaa agcgtcatct   148740
tctatgggga gacctcttgt tccctctcgg ggctggttgc ttttgcctgg acaataagcc   148800
tggccccagg gcacctgggg aaggtgtcca aggaggggt cctgggggcc agtccccgg   148860 gggctcggat gatgaatcat gggcggtgtt tgctggaaga atttttgttc cgcttcgggc   148920
aacaaggaac ccaaacctct cactgttgtg gggagaaaag ttgaaaatca gatgggaact   148980
ggctgcggta ccagagagga cgtcagaccc gggccgcggc ctcagccccc gactccttgt   149040
aagcgtgggc tgggtgcaca cgtggcggct gcgagcagtg ctttggagct catctcccca   149100
gaccctagtg ggagctgagg gcagcctggc agggctgatg caggcccatg cacacaggcc   149160
aggcagaggt gagaccaggg aatagaagcg ttgcaggggc agaggcagg aggggcaga   149220 gcctcggcgt aggagtgagc ctactggtcc ttcccgcagg caccctccct agtgccaggt   149280
```

```
ctgctgggac tccaggctgt tggtatgccc cctagggtcc tgcttggagc ctttctgacc    149340
ctcctgatcc agtgcctgtg ccgggcttcc tccccactca ccctgtcctc cctgtgccc     149400
atgtagccca cacatcagtg tgtccgtccg tctgcctgtc tgcccccac  cagcctgtgt    149460
gcccagggga aggctcaagg ccggtcatgc tctacctccc tggccagccc agccccagcc    149520
cacggtgcat tccctggaca ggattgctga gttttccatt ttagccacaa cagcgcccac    149580
acccgcgcca accaacctgt ccttgccacg aatattggct cctgccctcc tcatgggagc    149640
ccatggtgca tgctattatg acctcggtct agaggcaggg acaccaaggc acagggcctt    149700
agggaagttg cctgaggtca cgtggctggt aggggcgga  gccagcttta tcctcatggc    149760
acagatgagg aaactgaggc agagaggtgt tttgccaggg ggctgattta ctgagctagc    149820
cagccgttct ggttttgtct ctgtctcgct cagagggacc cccaccccac ccacctgcct    149880
acccagcttg ccgtgtcctc ggccagggcc agcagtctca gaggtagagc tgctgagaga    149940
agcctgtcat ctgtcctcca agagggatct gagtaagccg gagagcatca gcagcctcaa    150000
ggggaccttg gaccctgcc  cacctttcat tctgtaccag gcagggtgt  gtctgcacag    150060
cctggagcca ggtgtggctg cagccccag  gaagacaggg ccaaccctgc ccagcccaga    150120
gcagccgcat ctctgcagca gcggtgcact tgagtggaag cactggcttc caagagtaa    150180
gagcttgaga aggggcctgt ccagagccct gggggacggt ggacaggcca gcccagggt    150240
ccaggccttt cctgtagggg ccgaatcgtt accacttcag gctctgccag cttccatttg    150300
gtctctcttg catattactc tcttcttttt acccccttt  aaaaatataa agacaggccg    150360
caggtaggat ttggccctct ggcctacaca atagcaactg tgagcattat atgtggcttc    150420
tctttctttt tgagactctc atctgtcacc caggttggaa tgcagtggtg tgatcacggc    150480
tcaccacagc ctcaacctcc caggctcagg tgatcctccc acctcagcct cccaagtagc    150540
tgggactaca ggcgcctgcc actacacctg gctgattttt gtacttttt  gtagagatag    150600
ggtttcacca tgttgcccag gctggtcttg acctcctggg ctcaagcaat cctcctgcct    150660
tagcctccca aagtgctagg atgacaggcg tgagctacca cgcccggccc atatgtggct    150720
ttttaattaa attttttgagg tataacatta gtaaagtgct ctaaaagtga agaataggat    150780
gttagcccca cccaggtcaa gatctagaac attcctggca cccctattca ccttttccgtt   150840
aggaagctgc cgtcccaccc tctgtcacta gtctgccttt gccagctctg gagctctctg    150900
taagtcagtc ctgctgtgtg tattcctcga gtctggcctc agttgctctt caggtctggg    150960
gctcaccccc attgccgcgg caggaactca ccccagattg agccgttgtg gagtattcca    151020
gtgtgcaatt ctgccgtggt ctgttttccc atcctccccc tggcgggcat tgtccagtg     151080
tttgactttt gctattgcaa ctaaagctgt gtggagcagt gtgcctttgg tgaacgtgcc    151140
tttggtgaac gtgaggatgc atttctgctg tgtacatact taggagtggg actgcagggt    151200
tgcaagtgga tatcaacacg cagttttcca atgtggcccg taccatagaa ggcctcgtgg    151260
tgatgccgag tccatattcc agcactgacg caggattgcg tggtgccaag tcctatttc     151320
agcactgacg caggatcacg catgtcttca atgcccctct cctagatcgt agacaccctg    151380
tgtggcatca cagaatgaca cacacaagac aagaggcctc taaagccctg acactgacac    151440
gggttgttct tgctggggtt gctaatggag cgggtgcggg tgtgggtgcg ggtgaggtg     151500
ctgatggagc gggtgagggt gcggtgagg  tgctggtgg  agcgggtgag ggtgcgggtg    151560
agggtgctgg tggagcgggt gagggtgagg gtgagggtgc tgatgcagcg ggtgaggtg     151620
agggtgaggg tgagggtgct gatggagcgg gtgagggtga gggtgttgac ggagcgggtg    151680
```

```
agggtgcggg tgagggtgct gatggagcgg gtgagggtgc gggtgagggt gctggtggag    151740
cgggtgcggg tgcgggtgca ggtgagggtg ctgatggagc gggcgagggt gagggtgagg    151800
gtgctgatgg agcgggtgag ggtgcgggtg agggtgctgg tggagcgggt gcgggtgcgg    151860
gtgcaggtga gggtgctgat ggagcgggcg agggtgaggg tgagggtgct gatggagcgg    151920
gtgagggtgc gggtgagggt gctgatggag cgggtgaggg tgcgggtgag ggtgctgatg    151980
gagcgggtga gggtgagggt gagggtgagg gtgttgacgg agcgggtgag ggtgagggtg    152040
agggtgctga tggagcgggt gagggtgagg gtgagggtgc tgatggagcg ggcgagggtg    152100
agggtgaggg tgctgatgga gcgggtgagg gtgcgggtga gggtgctggt ggagcgggtg    152160
agggtgttaa tgaagcgggt gcgggtgagg gtgctgatgg agcgggtgcg ggtgaggggg    152220
ccgcatactc atcccttgc ctggtccccc aggctcctac tttggtgtgt gctcattcag    152280
gagcagcaga gtggccgtgc ttgggacggc cagccaagcg atccccactg gtactggcat    152340
ctgtaggtgc ccctgcttgg agcgggtgct ggcaactgcc ctttgctgga aggggcagca    152400
atgtccagca gtggtggaag ctctcgaaag aacacagggc tgggagtaga actcagtcag    152460
atcccagctc tgctctccct gctgtgtgac ctatagcaag tctctgaacc tttctgagct    152520
gtttcctcac ctgttcaaga tggggtgac cacttcttcc ttggaggatg aagggagag    152580 ggatgtgagg ctcgtgagtg ctgtgctcgg agactgtgca ggaggggaag cggccgtagc    152640
cccatacaag caggtgggca aggaagtggg ggcgctggag gggcttaggg gacaagggt    152700 tctgtccttg ggacctggac aagagccaaa aggtataccc tcacagtcac aggggagccc    152760
acactgccct cccctcccag ggactgcccc tgtggccccc gtccaggtcc acagcctcag    152820
cagtccctga gggccaggag gtagcctcca ggccactggg ctgagaaccc ttaaaagaaa    152880
aagcccccct gcccatgaca gtcattttag ggtcaagaaa gcccttttgca gaaaccaaac    152940 cctttgaaag ggccaacacg gcttttagat gacgtgagaa ccaacttcaa gcacttcctc    153000
tcagaccagg gtggcagctt ccaaagtggg ggcgctgctg ccgggagact gtggtttccc    153060
tgcttctcag ggagcttggg ccaggccgtg gggagatcca agcaacatgt ccctcggtag    153120
tggtaggttt gcagacgggc cgctccccac ttcctgccaa gctccagcgg cacctctgtg    153180
ggtgcaaggc tgtggggagg ggccttctgg ctcacagccc tccaggctgc ccacagcccc    153240
taggatgagg tgccacttcc tcaaatgact gtcaagactg ggatggggc cgggcacggt    153300 ggctcactcc tgtaatccca gcactttggg aggctaaggc gggcaaatca cttgaggtca    153360
ggagtcggag accggcctgg ccaacatggc gaaaccctat ctctacacta aaaaatacaa    153420
aaaaagccgg gcgtggtggc gggtgcctgt agtcccagct actcaagagc cgaggcagga    153480
gaatcgcttg aaactgggag gcagaggttg cagtgagcca agatcgcacc attgcactcc    153540
agcctgggca acagagtgac acttggtctc aaaaaaataa aaaataaaaa aggctctgga    153600
tgtctccacg aacccacctg accccttcct gctcctgggg ctctcctctc cacccacgt    153660 gtctacccgt agctcctgcc tgccttcagg actcagccca cagcccctc cacaaagtcc    153720 cctggcaggg cccggaggcc tctgcactgt ctcatggctt cattcctgtg tcctcagcat    153780
ccagtgagac ctcaggagat gcctggggaa tggctgaagg ctttggagag gttgctgccc    153840
ccagaatccc agccagaggg cagtttatcc aggagcccgg tgcctcctct gttgggtggg    153900
cgtggcctca gagggcacca accagaagac acatgctgtc actgacatgc gggccccag    153960 cgttagggca ggcaggagct ccgagtctct accccagctg tccccacagt gcacatggac    154020
```

```
taggctcctc ccacggggca ctaggccagg ccaggggtgt ggggtgagcc cctggggagc  154080
ccagagcagg gtacactcat gtccccacca tccaaggtga gatgtctgtg ctggaggccc  154140
agagggagct gggccggctg tcactccacc acaaggctga gcaggctccc cagtgggaga  154200
caggtttggg gaggtgtcca ggttgagggc acagtcagga ggggccatgt gtgcctgagt  154260
agggcagggg gaggaggggg atggccagtg gccacgggcc aggctgcctg gcaggacctg  154320
gaggtttcct caagctaagg ccaggcccat gttagatgct gggagggtgg gtgtggctgc  154380
agaggggtca gcgtgggggc actgactaac ctccggccat cctctccagg cccagtgacg  154440
agcaccatcc ggaagtgaag gctgatgggt acgtggacaa cctcgcagag gcagtggacc  154500
tgctgctgca gcacgccgac aagtgatggc ctcctgggag agccccgcct cctccacccc  154560
tgcctctcct ccacccctgc ctcccctcca cccctgcctc tcctccaccc gccaggagaa  154620
gccccacctc ctccacccct gcctctcctc caccctgcc tccctccac ctgccccagt  154680 gcccagacca accaaggccc tgacagccct gccttctgcc ctctgccctg catgggcagg  154740
catttgttcc ctacctgggt ggcctgctcc cctgcctggg ccctgacttc agctcccgt   154800 agtgaagtcc aggagggtgg gacaggcctg tcaggcctct gggaatctcc caaatcccag  154860
aactcaccac tcaccatggg cctttaaatg cagtaaactc cacctaacca gattcagggg  154920
cactatgccc actgcctcct cttcagactc tttgcatttc agtgaagagc ctggaagaaa  154980
cccaggggcc tcctatgcac agatcttgca gcccagaacc aagtcagcct ccctgcgact  155040
gcccaggcac actgcccacc accccacccc cgaaacaatg ccagcccgct gcttttcta   155100 tcctcccagt caccttttgca gacaaagacc aggggcagct cccgagggca ctgtgaaggc  155160
tcccatgcca cacagtgaga actgtagcct ctgcgtccaa ggcacacagg gtactttctg  155220
gacccactgc tggacagact tgaaggtgtc atgcccggtg tgtgcaggag gaaactaaca  155280
gttcagtaaa ctctgccttg accagcagcc tttgactcag gctttgactg ctaggaagaa  155340
ccgtatgggg gaggccacca gcagggtctg ggccactgtc tctagtcctg ccttatgctt  155400
gagccactga atatcagagg tgcgagggac aagggccctg aaacacctca cctgctccag  155460 cccttcact tagcagatgg ggaaactgag gcccagaggg gccagtgagc tgctgttggc   155520
cctatctgga acgaggcagt ccagggcaaa ctttggcact gccttcccta acggaacagc  155580
ctgtggcctg ggggtggtga gctttgcttt cccgaccaag ggcgcggcgg ccttcccaca  155640
ggggccctgg gaacaaatca ctcataactg aagtttcagg tttcagaatc agtcagctga  155700
acagataact tgattgctcc atttctcccc aaatcagttc agaagctact gataaccctt  155760
gagagactgc ttctttattt tatttattta ttattatttt tgaaatggag ttttgctttc  155820
gttgcccagg ctgagggca ctggcgtgat ctcagctcac tgcaacctcc gcctcctggg  155880
ttcaagctat tctcccgcct cagcctcccg agtagctggg attataggtg cccgccacca  155940
cgcctggcta attttttgta ttttagtag acagggtt tcaccatgtt ggtcaggctg     156000
gtctcgaact cccaacctca ggtgatccgc ccacctcggc cttccaaagt gctggtatta  156060
caggcatgag ccactgcgcc cggcctggag agcgcttctt atgagagaag ccatgggtct  156120
ccggagcagg atttccacca catgaaggtg gacgataaga aagtgtggga cccacgccgg  156180
ggaggggcaa gtacagcccc cgcaaggccg cccattaaat caggattggg ggaaacggtg  156240
acagtctttt cagcaagatg agaggccacc agccgggcca gtgtcactgg atttgaggga  156300
gggccatttg gccccttagt tggaaaatat gcagatggct ggctccttga tggagtcccc  156360
tgatggcagc tccttaggag acaatacagg acgttcaggc ggcggctgca gttcagtggc  156420
```

```
agcctggagg ggctgtgcgt gatgccgggc tgtgcgtgat gccgggctgt gggtgatgcc  156480
atgctgtgcg tgatgccggg tttgtgggtg atgccgagtt tgtgggtgat gccgggctgc  156540
gggtgatgcc gggctgtgcg tgatgccggg tttgtgggtg atgccgggct gtgcgtgatg  156600
ccgggtttgt gggtgatgcc gggctgcggg tgatgccggg ctgtgcgtga tgccgggctg  156660
cgggtgatgc cgggctgcgg gtgatgccgg ggctgtgtgt gatgccgggt tgtgtgtga   156720 tgccgggctg tgcgtgatgc cgggctgggg gtgatgccgg gctgtgcgtg atgccgggct  156780
gtgcgtgatg ccaggctgtg cgtgatgccg gtttgtttgt aggtctttag ttttttcttt  156840
cttttgtgtt taatggggaa gcttcccgcc aagacagcaa cccctctggg ggaaggagtt  156900
caagctgaga cctcttttt tttttttttg agacggagtc tcgctctgtc gcccaggctg  156960
gggtgcagtg gccaatctcg gctcactgca aactccgcct cccgggttca ccatttcc    157020 ctgcctcagc ctcccgagtg gctgggacta caggtacctg ccaccacgcc cagctaattt  157080
tttgtatttt ttagtagaga cagggtttca ccgtgctagc caagatggtc tcgatctcct  157140
gaccttgtga tccgcctgcc tcggcctccc aaagtgctga gattacaggc gtgagccact  157200
gcgcccagcc gagacctcct ctttcaagtt gctacccagg agtggggtgc cagagggac   157260 agcccctgga ggtgcagccc cctgctttgt tggggcggga gcatgccacc ctctgagccg  157320
cggtgggctc agtgaagtgg gtgttgtcat ccttcccact gcacgggtct agagtctggg  157380
gtgcggtgag ctcgcggctt gctgagggcc aacagttagt gaggggtgga gctgcgactt  157440
gcaggaaggt ccagccccgc ctcccaggcc ctttctagcc ccttctgttg ccgtgctgct  157500
tcccacccct gcctggaatc tcctgtgggg ggacgcatgt ggtggcccct gtggctgact  157560
ttccggctga gccagggcac cagtgtcctc actctagaga tgagctcttc tgaggggtga  157620
ggtccagcca cacctgtggt ggggtggtgt agcccgagcc tgttaccccg tctataaaac  157680
agagggattc acttcttta caggcacttc ctggccctgc ggggtgccct gtctctggct   157740
ggagctgatg agccgtggtg tgatgcttgc ctggggggtcg gtgttgccta gaagtgagga  157800
atgacctcct tcacccctgg ctccttccgg cagcctggcc acttccagca tgtgagggg   157860 gcccgggccc tggcagagac ggtgtggaac cgccggccgc atgcgggct ggagttcggg    157920 gctgccaatg ggctaaggcc ctgtgttcaa cacatgtcgc ggaactgtcg tgaaaaaaag  157980
actcaggacc acaggtccgg ggtgctccca ggggtctttc ccaccgaggc tgggagtgag  158040
cagcagccta ggcccagcca cacctcccag gctcgggagc tgccaggcca ggcaaccgtg  158100
aagggtagca gggtggggg tggaggggag gacaggggaga gcaggcctct cgggcctcac  158160
ccacccttgc accttccagc tctagggccc acacagtacc aagccctggg ctcaatgtac  158220
cacttatgaa aactcaattc aaattggctt agtgcaacaa ggtatttggt ggtctcacat  158280
gacttgaaca tccaggcctg gctgtcacgg gaaccgcatc tcttcccatt gcagctactt  158340
ggcaggtggc gggatgtccc ccagccaccg acgtccccct gcctgctccg caaccccagg  158400
gcctgcagaa aaggcccacg agactcagac tggcagagac ttaggcggac caggaacagg  158460
ggcgcagtct ccgtcccacc caaacccctaa ccagagagaa cacggcacgt tgtgccagac  158520
ggaggacgga tgccagcgag gtccatgtc tcactgccg acaaggctgg gaactgggcc    158580
aagtgaagca gaggcctcca cgtcagatgt gagcgccacc ggcccaggtg actgcagttc  158640
ttccctcctt ccgttcggct tgagccctcc agaggatcgg aaaggctgag gcctgacctg  158700
gtgccgctgt cctgggtggg tctgtcctgc tggtcggttc ctgccctct cggggaggtt    158760
```

-continued

```
ggctggcagc tggcaggtgg aaagcctcct gtgttcacct cagggcagag gtggggacac      158820
agggcgggac gggcgagtgt ggtgcccctc tggggtgggt gctcttgggt ccgcctcccg      158880
tgccagagtg cgtgtcaaca gttccagctg cccctcagaa ctgtcctggt ttaggaggtg      158940
aacacacggg gcagcctaca ttctacgtgg ttttttttaac attataaaag cagcatgtgt     159000
tattacagga aatttaacag aagtatataa aaagaaacca gaagtca                   159047
```

<210> SEQ ID NO 2
<211> LENGTH: 1194
<212> TYPE: DNA
<213> ORGANISM: Homo sapiens
<220> FEATURE:
<221> NAME/KEY: CDS
<222> LOCATION: (351)..(410)
<220> FEATURE:
<221> NAME/KEY: CDS
<222> LOCATION: (414)..(587)
<220> FEATURE:
<221> NAME/KEY: CDS
<222> LOCATION: (591)..(686)
<220> FEATURE:
<221> NAME/KEY: CDS
<222> LOCATION: (693)..(770)
<220> FEATURE:
<221> NAME/KEY: CDS
<222> LOCATION: (811)..(849)
<220> FEATURE:
<221> NAME/KEY: CDS
<222> LOCATION: (853)..(1062)
<220> FEATURE:
<221> NAME/KEY: CDS
<222> LOCATION: (1066)..(1071)
<220> FEATURE:
<221> NAME/KEY: CDS
<222> LOCATION: (1075)..(1161)

<400> SEQUENCE: 2

```
attcggctga cagagcatga gggggaggaa tcactgatga caggcactgg cctgcccagc        60
tgggggcctt tgtttattca tttggtgggc acttcctggg tgcctgctct ggtcaggcc       120 tgtgggggg accactgagg gcaggaaacc tggcctgtcc ctccaggaag cgaagtcaac       180
actggcacct gcagatgaag tgcagagca gcccccagct ttgatggcat ggggtggttg       240 ggggcacat tctgcatgct cagaagagag agcaactcgc cctgtggaag gagcatacag       300
tgggagatgg ggacaggccc agtgacgagc accatccgga agtgaaggct gat ggg        356
                                                         Asp Gly
                                                           1 tac gtg gac aac ctc gca gag gca gtg gac ctg ctg ctg cag cac gcc        404
Tyr Val Asp Asn Leu Ala Glu Ala Val Asp Leu Leu Leu Gln His Ala
          5                  10                  15 gac aag tga tgg cct cct ggg aga gcc ccg cct cct cca ccc ctg cct        452
Asp Lys     Trp Pro Pro Gly Arg Ala Pro Pro Pro Pro Pro Leu Pro
     20                  25                  30 ctc ctc cac ccc tgc ctc ccc tcc acc cct gcc tct cct cca ccc gcc        500
Leu Leu His Pro Cys Leu Pro Ser Thr Pro Ala Ser Pro Pro Pro Ala
 35                  40                  45 cag gag agc ccc acc tcc tcc acc cct gcc tct cct cca ccc ctg cct        548
Gln Glu Ser Pro Thr Ser Ser Thr Pro Ala Ser Pro Pro Pro Leu Pro
50                  55                  60                  65 ccc ctc cac ctg ccc cag tgc cca gac caa cca agg ccc tga cag ccc        596
Pro Leu His Leu Pro Gln Cys Pro Asp Gln Pro Arg Pro     Gln Pro
             70                  75                  80 tgc ctt ctg ccc tct gcc ctg cat ggg cag gca ttt gtt ccc tac ctg        644
Cys Leu Leu Pro Ser Ala Leu His Gly Gln Ala Phe Val Pro Tyr Leu
         85                  90                  95
```

```
ggt ggc ctg ctc ccc tgc ctg ggc cct gac ttc agc tcc ctg tagtga       692
Gly Gly Leu Leu Pro Cys Leu Gly Pro Asp Phe Ser Ser Leu
    100             105                 110 agt cca gga ggg tgg gac agg cct gtc agg cct ctg gga atc tcc caa       740
Ser Pro Gly Gly Trp Asp Arg Pro Val Arg Pro Leu Gly Ile Ser Gln
115             120                 125 atc cca gaa ctc acc act cac cat ggg cct ttaaatgcag taaactccac         790
Ile Pro Glu Leu Thr Thr His His Gly Pro
            130                 135 ctaaccagat tcaggggcac tat gcc cac tgc ctc ctc ttc aga ctc ttt gca     843
                     Tyr Ala His Cys Leu Leu Phe Arg Leu Phe Ala
                         140                 145 ttt cag tga aga gcc tgg aag aaa ccc agg ggc ctc cta tgc aca gat       891
Phe Gln     Arg Ala Trp Lys Lys Pro Arg Gly Leu Leu Cys Thr Asp
                150                 155                 160 ctt gca gcc cag aac caa gtc agc ctc cct gcg act gcc cag gca cac       939
Leu Ala Ala Gln Asn Gln Val Ser Leu Pro Ala Thr Ala Gln Ala His
        165                 170                 175 tgc cca cca ccc cac ccc cga aac aat gcc agc ccg ctg ctt ttt cta       987
Cys Pro Pro Pro His Pro Arg Asn Asn Ala Ser Pro Leu Leu Phe Leu
    180                 185                 190 tcc tcc cag tca cct ttg cag aca aag acc agg ggc agc tcc cga ggg      1035
Ser Ser Gln Ser Pro Leu Gln Thr Lys Thr Arg Gly Ser Ser Arg Gly
195                 200                 205                 210 cac tgt gaa ggc tcc cat gcc aca cag tga gaa ctg tag cct ctg cgt      1083
His Cys Glu Gly Ser His Ala Thr Gln     Glu Leu     Pro Leu Arg
                215                 220 cca agg cac aca ggg tac ttt ctg gac cca ctg ctg gac aga ctt gaa      1131
Pro Arg His Thr Gly Tyr Phe Leu Asp Pro Leu Leu Asp Arg Leu Glu
225                 230                 235                 240 ggt gtc atg ccc ggt gtg tgc agg agg aaa ctaacagttc agtaaactct        1181
Gly Val Met Pro Gly Val Cys Arg Arg Lys
                245                 250 gccttgacca gca                                                       1194

<210> SEQ ID NO 3
<211> LENGTH: 140
<212> TYPE: PRT
<213> ORGANISM: Homo sapiens

<400> SEQUENCE: 3

Met Gly Thr Trp Thr Thr Ser Gln Arg Gln Trp Thr Cys Cys Cys Ser
1               5                   10                  15

Thr Pro Thr Ser Asp Gly Leu Leu Gly Glu Pro Arg Leu Leu His Pro
            20                  25                  30

Cys Leu Ser Ser Thr Pro Ala Ser Pro Pro Leu Pro Leu Leu His
        35                  40                  45

Pro Pro Arg Arg Ala Pro Pro Pro Pro Leu Pro Leu Leu His Pro
    50                  55                  60

Cys Leu Pro Ser Thr Cys Pro Ser Ala Gln Thr Asn Gln Gly Pro Asp
65                  70                  75                  80

Ser Pro Ala Phe Cys Pro Leu Pro Cys Met Gly Arg His Leu Phe Pro
                85                  90                  95

Thr Trp Val Ala Cys Ser Pro Ala Trp Ala Leu Thr Ser Ala Pro Cys
            100                 105                 110

Ser Glu Val Gln Glu Gly Gly Thr Gly Leu Ser Gly Leu Trp Glu Ser
        115                 120                 125
```

```
Pro Lys Ser Gln Asn Ser Pro Leu Thr Met Gly Leu
    130                 135                 140
```

```
<210> SEQ ID NO 4
<211> LENGTH: 117
<212> TYPE: PRT
<213> ORGANISM: Homo sapiens

<400> SEQUENCE: 4
```

```
Met Pro Thr Ala Ser Ser Asp Ser Leu His Phe Ser Glu Glu Pro
1               5                   10                  15

Gly Arg Asn Pro Gly Ala Ser Tyr Ala Gln Ile Leu Gln Pro Arg Thr
                20                  25                  30

Lys Ser Ala Ser Leu Arg Leu Pro Arg His Thr Ala His His Pro Thr
            35                  40                  45

Pro Glu Thr Met Pro Ala Arg Cys Phe Phe Tyr Pro Pro Ser His Leu
        50                  55                  60

Cys Arg Gln Arg Pro Gly Ala Ala Pro Glu Gly Thr Val Lys Ala Pro
65                  70                  75                  80

Met Pro His Ser Glu Asn Cys Ser Leu Cys Val Gln Gly Thr Gln Gly
                85                  90                  95

Thr Phe Trp Thr His Cys Trp Thr Asp Leu Lys Val Ser Cys Pro Val
                100                 105                 110

Cys Ala Gly Gly Asn
            115
```

```
<210> SEQ ID NO 5
<211> LENGTH: 1092
<212> TYPE: DNA
<213> ORGANISM: Homo sapiens

<400> SEQUENCE: 5
```

```
tgagaaccca gggctcgctg ggatgctgtc ctccctccct ccctccctct gccaagctgg     60
tgggaaggcc cttgccaaag cgcacaagac cccttcacac agcagggggca caagctcttc    120
gaggcagagt cgcctgcagg tggggtggaa ggggtgcgcc ccagacccaa gaatcgcccg    180
cctctccaag accatccctg gctgctggcc cagtgacgag caccatccgg aagtgaaggc    240
tgatgggtac gtggacaacc tcgcagaggc agtggacctg ctgctgcagc acgccgacaa    300
gtgatggcct cctgggagag ccccgcctcc tccaccctg cctctcctcc acccctgcct    360
ccctccacc cctgcctctc ctccacccgc ccaggagagc cccacctcct ccacccctgc    420
ctctcctcca ccctgcctc ccctccacct gccccagtgc ccagaccaac caaggccctg    480
acagccctgc cttctgccct ctgcctgca tgggcaggca tttgttccct acctgggtgg    540
cctgctcccc tgcctgggcc ctgacttcag ctccctgtag tgaagtccag gagggtggga    600
caggcctgtc aggcctctgg gaatctccca atcccagaa ctcaccactc accatgggcc    660
tttaaatgca gtaaactcca cctaaccaga ttcaggggca ctaatgccca ctgcctcctc    720
ttcagactct ttgcatttca gtgaagagcc tggaagaaac ccaggggcct cctatgcaca    780
gatcttgcag cccagaacca agtcagcctc cctgcgactg cccaggcaca ctgcccacca    840
ccccaccccc gaaacaatgc cagcccgctg cttttttctat cctcccagtc acctttgcag    900
acaaagacca ggggcagctc ccgagggcac tgtgaaggct cccatgccac acagtgagaa    960
ctgtagcctc tgcgtccaag gcacacaggg tactttctgg acccactgct ggacagactt   1020
gaaggtgtca tgcccggtgt gtgcaggagg aaactaacag ttcagtaaac tctgccttga   1080
```
ccagcagcct tt                                                          1092

<210> SEQ ID NO 6
<211> LENGTH: 1022
<212> TYPE: DNA
<213> ORGANISM: Homo sapiens

<400> SEQUENCE: 6
ctccgagtct ctaccccagc tgtccccaca gtgcacatgg actaggctcc tcccacgggg        60
cactaggcca ggccagggt gtggggtgag cccctgggga gcccagagca gggtacactc       120
atgtccccac catccaaggc ccagtgacga gcaccatccg gaagtgaagg ctgatgggta      180
cgtggacaac ctcgcagagg cagtggacct gctgctgcag cacgccgaca agtgatggcc      240
tcctgggaga gccccgcctc ctccaccct gcctctcctc caccctgcc tccctccac        300
ccctgcctct cctccacccg cccaggagag ccccacctcc tccacccctg cctctcctcc      360
accctgcct ccctccacc tgccccagtg cccagaccaa ccaaggcct gacagccctg        420
ccttctgccc tctgccctgc atgggcaggc atttgttccc tacctgggtg gcctgctccc      480
ctgcctgggc cctgacttca gctccctgta gtgaagtcca ggagggtggg acaggcctgt      540
caggcctctg ggaatctccc aaatcccaga actcaccact caccatgggc ctttaaatgc      600
agtaaactcc acctaaccag attcaggggc actatgccca ctgcctcctc ttcagactct      660
ttgcatttca gtgaagagcc tggaagaaac ccaggggcc cctatgcaca gatcttgcag       720
cccagaacca agtcagcctc ctgcgactg cccaggcaca ctgcccacca ccccaccccc      780
gaaacaatgc cagcccgctg ctttttctat cctcccagtc acctttgcag acaaagacca     840
ggggcagctc ccgagggcac tgtgaaggct cccatgccac acagtgagaa ctgtagcctc     900
tgcgtccaag gcacacaggg tactttctgg acccactgct ggacagactt gaaggtgtca     960
tgcccggtgt gtgcaggagg aaactaacag ttcagtaaac tctgccttga ccagcagcct    1020
tt                                                                   1022

<210> SEQ ID NO 7
<211> LENGTH: 1186
<212> TYPE: DNA
<213> ORGANISM: Homo sapiens

<400> SEQUENCE: 7
tgcattcggc tgacagagca tgagggggag gaatcactga tgacaggcac tggcctgccc      60
agctgggggc ctttgtttat tcatttggtg ggcacttcct gggtgcctgc tctgggtcag     120
gcctgtgggg gggaccactg agggcaggaa acctggcctg tccctccagg aagcgaagtc     180
aacactggca cctgcagatg aagtggcaga gcagccccca gctttgatgg catgggggtgg    240
ttgggggca cattctgcat gctcagaaga gagagcaact cgccctgtgg aaggagcata     300
cagtgggaga tggggacagg cccagtgacg agcaccatcc ggaagtgaag gctgatgggt     360
acgtggacaa cctcgcagag gcagtggacc tgctgctgca gcacgccgac aagtgatggc    420
ctcctgggag agccccgcct cctccacccc tgcctcccct caccccctgc ctctcctcca    480
cccgccagg agagcccac ctcctccacc cctgcctctc ctcaccccct gcctcccctc     540
cacctgcccc agtgcccaga ccaaccaagg ccctgacagc cctgccttct gccctctgcc    600
ctgcatgggc aggcatttgt tccctacctg ggtggcctgc tccctgcct gggcctgac     660
ttcagctccc tgtagtgaag tccaggaggg tgggacaggc ctgtcaggcc tctgggaatc    720
tcccaaatcc cagaactcac cactcaccat gggcctttaa atgcagtaaa ctccacctaa    780

```
ccagattcag gggcactatg cccactgcct cctcttcaga ctctttgcat ttcagtgaag      840
agcctggaag aaacccaggg gcctcctatg cacagatctt gcagcccaga accaagtcag      900
cctccctgcg actgcccagg cacactgccc accaccccac ccccgaaaca atgccagccc      960
gctgcttttt ctatcctccc agtcaccttt gcagacaaag accaggggca gctcccgagg     1020
gcactgtgaa ggctcccatg ccacacagtg agaactgtag cctctgcgtc caaggcacac     1080
agggtacttt ctggacccac tgctggacag acttgaaggt gtcatgcccg gtgtgtgcag     1140
gaggaaacta acagttcagt aaactctgcc ttgaccagca gccttt                    1186
```

<210> SEQ ID NO 8
<211> LENGTH: 1005
<212> TYPE: DNA
<213> ORGANISM: Homo sapiens

<400> SEQUENCE: 8

```
ctccgagtct ctaccccagc tgtccccaca gtgcacatgg actaggctcc tcccacgggg       60
cactaggcca ggccaggggt gtggggtgag cccctgggga gccagagca gggtacactc       120 atgtccccac catccaaggc ccagtgacga gcaccatccg gaagtgaagg ctgatgggta      180
cgtggacaac ctcgcagagg cagtggacct gctgctgcag cacgccgaca agtgatggcc      240
tcctgggaga gccccgcctc ctccacccct gcctcccctc cacccctgcc tctcctccac      300
ccgcccagga gagccccacc tcctccaccc ctgcctctcc tcaccctg cctcccctcc       360 acctgcccca gtgcccagac caaccaaggc cctgacagcc ctgccttctg ccctctgccc      420
tgcatgggca ggcatttgtt ccctacctgg gtggcctgct ccctgcctg ggccctgact       480 tcagctccct gtagtgaagt ccaggagggt gggacaggcc tgtcaggcct ctgggaatct      540
cccaaatccc agaactcacc actcaccatg gccttaaa tgcagtaaac tccacctaac        600
cagattcagg ggcactatgc ccactgcctc ctcttcagac tctttgcatt tcagtgaaga      660
gcctggaaga aacccagggg cctcctatgc acagatcttg cagcccagaa ccaagtcagc      720
ctccctgcga ctgcccaggc acactgccca ccacccacc cccgaaacaa tgccagcccg      780 ctgcttttc tatcctccca gtcacctttg cagacaaaga ccaggggcag ctcccgaggg      840
cactgtgaag gctcccatgc cacacagtga gaactgtagc ctctgcgtcc aaggcacaca      900
gggtactttc tggacccact gctggacaga cttgaaggtg tcatgcccgg tgtgtgcagg      960
aggaaactaa cagttcagta aactctgcct tgaccagcag ccttt                     1005
```

<210> SEQ ID NO 9
<211> LENGTH: 1765
<212> TYPE: DNA
<213> ORGANISM: Homo sapiens
<220> FEATURE:
<221> NAME/KEY: CDS
<222> LOCATION: (166)..(975)

<400> SEQUENCE: 9

```
aagaacttta aaaatcacct aggtgtgggc cgggcacggt ggctaacgcc tgtaatccca       60
gcactttgag atgctgaggc aggtggatca cgaggtcagg agatcgagac catcctggat      120
```

```
aacacggaga aaccccggcg gagctgagga gcagggccgg cgcc atg gca ccg tgg      177
                                                 Met Ala Pro Trp
                                                  1
```

```
ggc aag cgg ctg gct ggc gtg cgc ggg gtg ctg ctt gac atc tcg ggc       225
Gly Lys Arg Leu Ala Gly Val Arg Gly Val Leu Leu Asp Ile Ser Gly
 5                  10                  15                  20
```

| | | |
|---|---|---|
| gtg ctg tac gac agc ggc gcg ggc ggc ggc acg gcc atc gcc ggc tcg<br>Val Leu Tyr Asp Ser Gly Ala Gly Gly Gly Thr Ala Ile Ala Gly Ser<br>25 30 35 | 273 | |
| gtg gag gcg gtg gcc aga ctg aag cgt tcc cgg ctg aag gtg agg ttc<br>Val Glu Ala Val Ala Arg Leu Lys Arg Ser Arg Leu Lys Val Arg Phe<br>40 45 50 | 321 | |
| tgc acc aac gag tcg cag aag tcc cgg gca gag ctg gtg ggg cag ctt<br>Cys Thr Asn Glu Ser Gln Lys Ser Arg Ala Glu Leu Val Gly Gln Leu<br>55 60 65 | 369 | |
| cag agg ctg gga ttt gac atc tct gag cag gag gtg acc gcc ccg gca<br>Gln Arg Leu Gly Phe Asp Ile Ser Glu Gln Glu Val Thr Ala Pro Ala<br>70 75 80 | 417 | |
| cca gct gcc tgc cag atc ctg aag gag cga ggc ctg cga cca tac ctg<br>Pro Ala Ala Cys Gln Ile Leu Lys Glu Arg Gly Leu Arg Pro Tyr Leu<br>85 90 95 100 | 465 | |
| ctc atc cat gac gga gtc cgc tca gaa ttt gat cag atc gac aca tcc<br>Leu Ile His Asp Gly Val Arg Ser Glu Phe Asp Gln Ile Asp Thr Ser<br>105 110 115 | 513 | |
| aac cca aac tgt gtg gta att gca gac gca gga gaa agc ttt tct tat<br>Asn Pro Asn Cys Val Val Ile Ala Asp Ala Gly Glu Ser Phe Ser Tyr<br>120 125 130 | 561 | |
| caa aac atg aat aac gcc ttc cag gtg ctc atg gag ctg gaa aaa cct<br>Gln Asn Met Asn Asn Ala Phe Gln Val Leu Met Glu Leu Glu Lys Pro<br>135 140 145 | 609 | |
| gtg ctc ata tca ctg gga aaa ggg cgt tac tac aag gag acc tct ggc<br>Val Leu Ile Ser Leu Gly Lys Gly Arg Tyr Tyr Lys Glu Thr Ser Gly<br>150 155 160 | 657 | |
| ctg atg ctg gac gtt ggt ccc tac atg aag gcg ctt gag tat gcc tgt<br>Leu Met Leu Asp Val Gly Pro Tyr Met Lys Ala Leu Glu Tyr Ala Cys<br>165 170 175 180 | 705 | |
| ggc atc aaa gcc gag gtg gtg ggg aag cct tct cct gag ttt ttc aag<br>Gly Ile Lys Ala Glu Val Val Gly Lys Pro Ser Pro Glu Phe Phe Lys<br>185 190 195 | 753 | |
| tct gcc ctg caa gcg ata gga gtg gaa gcc cac cag gcc gtc atg att<br>Ser Ala Leu Gln Ala Ile Gly Val Glu Ala His Gln Ala Val Met Ile<br>200 205 210 | 801 | |
| ggg gac gat atc gtg ggc gac gtc ggc ggt gcc cag cgg tgt gga atg<br>Gly Asp Asp Ile Val Gly Asp Val Gly Gly Ala Gln Arg Cys Gly Met<br>215 220 225 | 849 | |
| aga gcg ctg cag gtg cgc acc ggg aag ttc agg ccc agt gac gag cac<br>Arg Ala Leu Gln Val Arg Thr Gly Lys Phe Arg Pro Ser Asp Glu His<br>230 235 240 | 897 | |
| cat ccg gaa gtg aag gct gat ggg tac gtg gac aac ctc gca gag gca<br>His Pro Glu Val Lys Ala Asp Gly Tyr Val Asp Asn Leu Ala Glu Ala<br>245 250 255 260 | 945 | |
| gtg gac ctg ctg ctg cag cac gcc gac aag tgatggcctc tgggagagc<br>Val Asp Leu Leu Leu Gln His Ala Asp Lys<br>265 270 | 995 | |
| cccgcctcct ccaccctgc ctctcctcca ccctgcctc cctccaccc ctgcctctcc | 1055 | |
| tccacccgcc caggagagcc ccacctcctc caccctgcc tctcctccac ccctgcctcc | 1115 | |
| cctccacctg ccccagtgcc cagaccaacc aaggccctga cagccctgcc ttctgccctc | 1175 | |
| tgccctgcat gggcaggcat tgttccta cctgggtggc ctgctcccct gcctgggccc | 1235 | |
| tgacttcagc tccctgtagt gaagtccagg agggtgggac aggcctgtca ggcctctggg | 1295 | |
| aatctcccaa atcccagaac tcaccactca ccatggggcct ttaaatgcag taaactccac | 1355 | |
| ctaaccagat tcaggggcac tatgcccact gcctcctctt cagactcttt gcatttcagt | 1415 | |

```
gaagagcctg gaagaaaccc aggggcctcc tatgcacaga tcttgcagcc cagaaccaag    1475
tcagcctccc tgcgactgcc caggcacact gcccaccacc ccaccccga aacaatgcca     1535 gcccgctgct ttttctatcc tcccagtcac ctttgcagac aaagaccagg ggcagctccc    1595
gagggcactg tgaaggctcc catgccacac agtgagaact gtagcctctg cgtccaaggc    1655
acacagggta ctttctggac ccactgctgg acagacttga aggtgtcatg cccggtgtgt    1715
gcaggaggaa actaacagtt cagtaaactc tgccttgacc agcagccttt               1765
```

<210> SEQ ID NO 10
<211> LENGTH: 270
<212> TYPE: PRT
<213> ORGANISM: Homo sapiens

<400> SEQUENCE: 10

```
Met Ala Pro Trp Gly Lys Arg Leu Ala Gly Val Arg Gly Val Leu Leu
 1               5                  10                  15

Asp Ile Ser Gly Val Leu Tyr Asp Ser Gly Ala Gly Gly Thr Ala
             20                  25                  30

Ile Ala Gly Ser Val Glu Ala Val Ala Arg Leu Lys Arg Ser Arg Leu
         35                  40                  45

Lys Val Arg Phe Cys Thr Asn Glu Ser Gln Lys Ser Arg Ala Glu Leu
     50                  55                  60

Val Gly Gln Leu Gln Arg Leu Gly Phe Asp Ile Ser Glu Gln Glu Val
 65                  70                  75                  80

Thr Ala Pro Ala Pro Ala Ala Cys Gln Ile Leu Lys Glu Arg Gly Leu
                 85                  90                  95

Arg Pro Tyr Leu Leu Ile His Asp Gly Val Arg Ser Glu Phe Asp Gln
            100                 105                 110

Ile Asp Thr Ser Asn Pro Asn Cys Val Val Ile Ala Asp Ala Gly Glu
        115                 120                 125

Ser Phe Ser Tyr Gln Asn Met Asn Asn Ala Phe Gln Val Leu Met Glu
    130                 135                 140

Leu Glu Lys Pro Val Leu Ile Ser Leu Gly Lys Gly Arg Tyr Tyr Lys
145                 150                 155                 160

Glu Thr Ser Gly Leu Met Leu Asp Val Gly Pro Tyr Met Lys Ala Leu
                165                 170                 175

Glu Tyr Ala Cys Gly Ile Lys Ala Glu Val Val Gly Lys Pro Ser Pro
            180                 185                 190

Glu Phe Phe Lys Ser Ala Leu Gln Ala Ile Gly Val Glu Ala His Gln
        195                 200                 205

Ala Val Met Ile Gly Asp Asp Ile Val Gly Asp Val Gly Gly Ala Gln
    210                 215                 220

Arg Cys Gly Met Arg Ala Leu Gln Val Arg Thr Gly Lys Phe Arg Pro
225                 230                 235                 240

Ser Asp Glu His His Pro Glu Val Lys Ala Asp Gly Tyr Val Asp Asn
                245                 250                 255

Leu Ala Glu Ala Val Asp Leu Leu Leu Gln His Ala Asp Lys
            260                 265                 270
```

<210> SEQ ID NO 11
<211> LENGTH: 1669
<212> TYPE: DNA
<213> ORGANISM: Homo sapiens

<400> SEQUENCE: 11

```
aagaacttta aaaatcacct aggtgtgggc cgggcacggt ggctaacgcc tgtaatccca      60
gcactttgag atgctgaggc aggtggatca cgaggtcagg agatcgagac catcctggat     120
aacacggaga accccggcg gagctgagga gcagggccgg gcgccatggc accgtggggc      180
aagcggctgg ctggcgtgcg cggggtgctg cttgacatct cgggcgtgct gtacgacagc     240
ggcgcgggcg gcggcacggc catcgccggc tcggtggagg cggtggccag actgaagcgt     300
tcccggctga aggtgaggtt ctgcaccaac gagtcgcaga agtcccgggc agagctggtg     360
gggcagcttc agaggctggg atttgacatc tctgagcagg aggtgaccgc cccggcacca     420
gctgcctgcc agatcctgaa ggagcgaggc ctgcgaccat acctgctcat ccatgacgga     480
gtccgctcag aatttgatca gatcgacaca tccaacccaa actgtgtggt aattgcagac     540
gcaggagaaa gcttttctta tcaaaacatg aataacgcct tccaggtgct catggagctg     600
gaaaaacctg tgctcatatc actgggaaaa gggcgttact acaaggagac ctctggcctg     660
atgctggacg ttggtcccta catgaaggcg cttgagtatg cctgtggcat caaagccgag     720
gtggtgggga agccttctcc tgagtttttc aagtctgccc tgcaagcgat aggagtggaa     780
gcccaccagg ccgtcatgat tgggacgat atcgtgggcg acgtcggcgg tgcccagcgg     840
tgtggaatga gagcgctgca ggtgcgcacc gggaagttca ggcccagtga cgagcaccat     900
ccggaagtga aggctgatgg gtacgtggac aacctcgcag aggcagtgga cctgctgctg     960
cagcacgccg acaagtgatg gcctcctggg agagccccgc ctcctccacc cctgcctccc    1020
ctccacctgc cccagtgccc agaccaacca aggccctgac agccctgcct tctgccctct    1080
gccctgcatg ggcaggcatt tgttccctac ctgggtggcc tgctcccctg cctgggccct    1140
gacttcagct ccctgtagtg aagtccagga gggtgggaca ggcctgtcag gcctctggga    1200
atctcccaaa tccagaact caccactcac catgggcctt taaatgcagt aaactccacc     1260
taaccagatt caggggcact atgcccactg cctcctcttc agactctttg catttcagtg    1320
aagagcctgg aagaaaccca ggggcctcct atgcacagat cttgcagccc agaaccaagt    1380
cagcctccct gcgactgccc aggcacactg cccaccaccc cacccccgaa acaatgccag    1440
cccgctgctt tttctatcct cccagtcacc tttgcagaca aagaccaggg gcagctcccg    1500
agggcactgt gaaggctccc atgccacaca gtgagaactg tagcctctgc gtccaaggca    1560
cacagggtac tttctggacc cactgctgga cagacttgaa ggtgtcatgc ccggtgtgtg    1620
caggaggaaa ctaacagttc agtaaactct gccttgacca gcagcccttt               1669
```

<210> SEQ ID NO 12
<211> LENGTH: 1673
<212> TYPE: DNA
<213> ORGANISM: Homo sapiens
<220> FEATURE:
<221> NAME/KEY: CDS
<222> LOCATION: (166)..(795)

<400> SEQUENCE: 12

```
aagaacttta aaaatcacct aggtgtgggc cgggcacggt ggctaacgcc tgtaatccca      60
gcactttgag atgctgaggc aggtggatca cgaggtcagg agatcgagac catcctggat     120
aacacggaga accccggcg gagctgagga gcagggccgg gcgcc atg gca ccg tgg      177
                                                  Met Ala Pro Trp
                                                   1 ggc aag cgg ctg gct ggc gtg cgc ggg gtg ctg ctt gac atc tcg ggc       225
Gly Lys Arg Leu Ala Gly Val Arg Gly Val Leu Leu Asp Ile Ser Gly
 5              10                  15                  20
```

| | | |
|---|---|---|
| gtg ctg tac gac agc ggc gcg ggc ggc ggc acg gcc atc gcc ggc tcg<br>Val Leu Tyr Asp Ser Gly Ala Gly Gly Gly Thr Ala Ile Ala Gly Ser<br>              25                      30                 35 | 273 |
| gtg gag gcg gtg gcc aga ctg aag cgt tcc cgg ctg aag gtg agg ttc<br>Val Glu Ala Val Ala Arg Leu Lys Arg Ser Arg Leu Lys Val Arg Phe<br>        40                      45                      50 | 321 |
| tgc acc aac gag tcg cag aag tcc cgg gca gag ctg gtg ggg cag ctt<br>Cys Thr Asn Glu Ser Gln Lys Ser Arg Ala Glu Leu Val Gly Gln Leu<br>              55                      60                 65 | 369 |
| cag agg ctg gga ttt gac atc tct gag cag gag gtg acc gcc ccg gca<br>Gln Arg Leu Gly Phe Asp Ile Ser Glu Gln Glu Val Thr Ala Pro Ala<br>     70                      75                      80 | 417 |
| cca gct gcc tgc cag atc ctg aag gag cga ggc ctg cga cca tac ctg<br>Pro Ala Ala Cys Gln Ile Leu Lys Glu Arg Gly Leu Arg Pro Tyr Leu<br>85                      90                      95                 100 | 465 |
| ctc atc cat gac gga gtc cgc tca gaa ttt gat cag atc gac aca tcc<br>Leu Ile His Asp Gly Val Arg Ser Glu Phe Asp Gln Ile Asp Thr Ser<br>              105                    110                    115 | 513 |
| aac cca aac tgt gtg gta att gca gac gca gga gaa agc ttt tct tat<br>Asn Pro Asn Cys Val Val Ile Ala Asp Ala Gly Glu Ser Phe Ser Tyr<br>            120                    125                    130 | 561 |
| caa aac atg aat aac gcc ttc cag gtg ctc atg gag ctg gaa aaa cct<br>Gln Asn Met Asn Asn Ala Phe Gln Val Leu Met Glu Leu Glu Lys Pro<br>      135                    140                    145 | 609 |
| gtg ctc ata tca ctg gga aaa ggg cgt tac tac aag gag acc tct ggc<br>Val Leu Ile Ser Leu Gly Lys Gly Arg Tyr Tyr Lys Glu Thr Ser Gly<br>        150                    155                    160 | 657 |
| ctg atg ctg gac gtt ggt ccc tac atg aag gcg ctt gag tat gcc tgt<br>Leu Met Leu Asp Val Gly Pro Tyr Met Lys Ala Leu Glu Tyr Ala Cys<br>165                     170                    175                 180 | 705 |
| ggc atc aaa gcc gag gtg gtg ggg aag cct tct cct gag ttt ttc aag<br>Gly Ile Lys Ala Glu Val Val Gly Lys Pro Ser Pro Glu Phe Phe Lys<br>                185                    190                    195 | 753 |
| tct gcc ctg caa gcg ata gga gtg gaa gcc cac cag gcc cag<br>Ser Ala Leu Gln Ala Ile Gly Val Glu Ala His Gln Ala Gln<br>            200                    205                    210 | 795 |
| tgacgagcac catccggaag tgaaggctga tgggtacgtg acaacctcg cagaggcagt | 855 |
| ggacctgctg ctgcagcacg ccgacaagtg atggcctcct gggagagccc cgcctcctcc | 915 |
| accccctgcct ctcctccacc cctgcctccc ctccacccct gcctctcctc acccgccca | 975 |
| ggagagcccc acctcctcca ccctgcctc tcctccaccc ctgcctcccc tccacctgcc | 1035 |
| ccagtgccca gaccaaccaa ggccctgaca gccctgcctt ctgccctctg ccctgcatgg | 1095 |
| gcaggcattt gttccctacc tgggtggcct gctcccctgc ctgggccctg acttcagctc | 1155 |
| cctgtagtga agtccaggag ggtgggacag gcctgtcagg cctctgggaa tctcccaaat | 1215 |
| cccagaactc accactcacc atgggccttt aaatgcagta aactccacct aaccagattc | 1275 |
| aggggcacta tgcccactgc ctcctcttca gactctttgc atttcagtga agagcctgga | 1335 |
| agaaacccag gggcctccta tgcacagatc ttgcagccca gaaccaagtc agcctccctg | 1395 |
| cgactgccca ggcacactgc ccaccacccc accccgaaa caatgccagc ccgctgcttt | 1455 |
| ttctatcctc ccagtcacct ttgcagacaa agaccagggg cagctcccga gggcactgtg | 1515 |
| aaggctccca tgccacacag tgagaactgt agcctctgcg tccaaggcac acagggtact | 1575 |
| ttctggaccc actgctggac agacttgaag gtgtcatgcc cggtgtgtgc aggaggaaac | 1635 |
| taacagttca gtaaactctg ccttgaccag cagccttt | 1673 |

<210> SEQ ID NO 13
<211> LENGTH: 210
<212> TYPE: PRT
<213> ORGANISM: Homo sapiens

<400> SEQUENCE: 13

```
Met Ala Pro Trp Gly Lys Arg Leu Ala Gly Val Arg Gly Val Leu Leu
1               5                   10                  15

Asp Ile Ser Gly Val Leu Tyr Asp Ser Gly Ala Gly Gly Thr Ala
            20                  25                  30

Ile Ala Gly Ser Val Glu Ala Val Ala Arg Leu Lys Arg Ser Arg Leu
        35                  40                  45

Lys Val Arg Phe Cys Thr Asn Glu Ser Gln Lys Ser Arg Ala Glu Leu
    50                  55                  60

Val Gly Gln Leu Gln Arg Leu Gly Phe Asp Ile Ser Glu Gln Glu Val
65                  70                  75                  80

Thr Ala Pro Ala Pro Ala Ala Cys Gln Ile Leu Lys Glu Arg Gly Leu
                85                  90                  95

Arg Pro Tyr Leu Leu Ile His Asp Gly Val Arg Ser Glu Phe Asp Gln
            100                 105                 110

Ile Asp Thr Ser Asn Pro Asn Cys Val Val Ile Ala Asp Ala Gly Glu
        115                 120                 125

Ser Phe Ser Tyr Gln Asn Met Asn Asn Ala Phe Gln Val Leu Met Glu
130                 135                 140

Leu Glu Lys Pro Val Leu Ile Ser Leu Gly Lys Gly Arg Tyr Tyr Lys
145                 150                 155                 160

Glu Thr Ser Gly Leu Met Leu Asp Val Gly Pro Tyr Met Lys Ala Leu
                165                 170                 175

Glu Tyr Ala Cys Gly Ile Lys Ala Glu Val Val Gly Lys Pro Ser Pro
            180                 185                 190

Glu Phe Phe Lys Ser Ala Leu Gln Ala Ile Gly Val Glu Ala His Gln
        195                 200                 205

Ala Gln
    210
```

<210> SEQ ID NO 14
<211> LENGTH: 1516
<212> TYPE: DNA
<213> ORGANISM: Homo sapiens
<220> FEATURE:
<221> NAME/KEY: CDS
<222> LOCATION: (166)..(726)

<400> SEQUENCE: 14

```
aagaacttta aaaatcacct aggtgtgggc cgggcacggt ggctaacgcc tgtaatccca      60
gcactttgag atgctgaggc aggtggatca cgaggtcagg agatcgagac catcctggat     120
aacacggaga aaccccggcg agctgagga gcagggccgg cgcc atg gca ccg tgg      177
                                              Met Ala Pro Trp
                                              1 ggc aag cgg ctg gct ggc gtg cgc ggg gtg ctg ctt gac atc tcg ggc      225
Gly Lys Arg Leu Ala Gly Val Arg Gly Val Leu Leu Asp Ile Ser Gly
5               10                  15                  20 gtg ctg tac gac agc ggc gcg ggc ggc acg gcc atc gcc ggc tcg          273
Val Leu Tyr Asp Ser Gly Ala Gly Gly Thr Ala Ile Ala Gly Ser
            25                  30                  35 gtg gag gcg gtg gcc aga ctg aag cgt tcc cgg ctg aag gtg agg ttc      321
Val Glu Ala Val Ala Arg Leu Lys Arg Ser Arg Leu Lys Val Arg Phe
        40                  45                  50
```

```
tgc acc aac gag tcg cag aag tcc cgg gca gag ctg gtg ggg cag ctt        369
Cys Thr Asn Glu Ser Gln Lys Ser Arg Ala Glu Leu Val Gly Gln Leu
            55                  60                  65 cag agg ctg gga ttt gac atc tct gag cag gag gtg acc gcc ccg gca        417
Gln Arg Leu Gly Phe Asp Ile Ser Glu Gln Glu Val Thr Ala Pro Ala
        70                  75                  80 cca gct gcc tgc cag atc ctg aag gag cga ggc ctg cga cca tac ctg        465
Pro Ala Ala Cys Gln Ile Leu Lys Glu Arg Gly Leu Arg Pro Tyr Leu
85                  90                  95                 100 ctc atc cat gac gga gtc cgc tca gaa ttt gat cag atc gac aca tcc        513
Leu Ile His Asp Gly Val Arg Ser Glu Phe Asp Gln Ile Asp Thr Ser
                105                 110                 115 aac cca aac tgt gtg gta att gca gac gca gga gaa agc ttt tct tat        561
Asn Pro Asn Cys Val Val Ile Ala Asp Ala Gly Glu Ser Phe Ser Tyr
            120                 125                 130 caa aac atg aat aac gcc ttc cag gtg ctc atg gag ctg gaa aaa cct        609
Gln Asn Met Asn Asn Ala Phe Gln Val Leu Met Glu Leu Glu Lys Pro
        135                 140                 145 gtg ctc ata tca ctg gga aaa ggg ccc agt gac gag cac cat ccg gaa        657
Val Leu Ile Ser Leu Gly Lys Gly Pro Ser Asp Glu His His Pro Glu
    150                 155                 160 gtg aag gct gat ggg tac gtg gac aac ctc gca gag gca gtg gac ctg        705
Val Lys Ala Asp Gly Tyr Val Asp Asn Leu Ala Glu Ala Val Asp Leu
165                 170                 175                 180 ctg ctg cag cac gcc gac aag tgatggcctc ctgggagagc ccgcctcct            756
Leu Leu Gln His Ala Asp Lys
                185 ccaccctgc ctctcctcca ccctgcctc cctccaccc ctgcctctcc tccaccgcc          816 caggagagcc ccacctcctc cacccctgcc tctcctccac cctgcctcc cctccacctg       876 ccccagtgcc cagaccaacc aaggccctga cagccctgcc ttctgccctc tgccctgcat      936
gggcaggcat tgttcccta cctgggtggc ctgctccct gctgggccc tgacttcagc         996 tccctgtagt gaagtccagg agggtgggac aggcctgtca ggcctctggg aatctcccaa      1056
atcccagaac tcaccactca ccatgggcct ttaaatgcag taaactccac ctaaccagat      1116
tcaggggcac tatgcccact gcctcctctt cagactcttt gcatttcagt gaagagcctg      1176
gaagaaaccc aggggcctcc tatgcacaga tcttgcagcc cagaaccaag tcagcctccc     1236
tgcgactgcc caggcacact gcccaccacc ccacccccga acaatgcca gcccgctgct      1296 ttttctatcc tcccagtcac ctttgcagac aaagaccagg ggcagctccc gagggcactg     1356
tgaaggctcc catgccacac agtgagaact gtagcctctg cgtccaaggc acacagggta     1416
ctttctggac ccactgctgg acagacttga aggtgtcatg cccggtgtgt gcaggaggaa     1476
actaacagtt cagtaaactc tgccttgacc agcagccttt                           1516

<210> SEQ ID NO 15
<211> LENGTH: 187
<212> TYPE: PRT
<213> ORGANISM: Homo sapiens

<400> SEQUENCE: 15

Met Ala Pro Trp Gly Lys Arg Leu Ala Gly Val Arg Gly Val Leu Leu
1               5                   10                  15

Asp Ile Ser Gly Val Leu Tyr Asp Ser Gly Ala Gly Gly Thr Ala
            20                  25                  30

Ile Ala Gly Ser Val Glu Ala Val Ala Arg Leu Lys Arg Ser Arg Leu
        35                  40                  45
```

```
Lys Val Arg Phe Cys Thr Asn Glu Ser Gln Lys Ser Arg Ala Glu Leu
     50                  55                  60

Val Gly Gln Leu Gln Arg Leu Gly Phe Asp Ile Ser Glu Gln Glu Val
 65                  70                  75                  80

Thr Ala Pro Ala Pro Ala Ala Cys Gln Ile Leu Lys Glu Arg Gly Leu
                 85                  90                  95

Arg Pro Tyr Leu Leu Ile His Asp Gly Val Arg Ser Glu Phe Asp Gln
                100                 105                 110

Ile Asp Thr Ser Asn Pro Asn Cys Val Val Ile Ala Asp Ala Gly Glu
                115                 120                 125

Ser Phe Ser Tyr Gln Asn Met Asn Asn Ala Phe Gln Val Leu Met Glu
    130                 135                 140

Leu Glu Lys Pro Val Leu Ile Ser Leu Gly Lys Gly Pro Ser Asp Glu
145                 150                 155                 160

His His Pro Glu Val Lys Ala Asp Gly Tyr Val Asp Asn Leu Ala Glu
                165                 170                 175

Ala Val Asp Leu Leu Gln His Ala Asp Lys
                180                 185

<210> SEQ ID NO 16
<211> LENGTH: 1287
<212> TYPE: DNA
<213> ORGANISM: Homo sapiens
<220> FEATURE:
<221> NAME/KEY: CDS
<222> LOCATION: (166)..(936)
<220> FEATURE:
<221> NAME/KEY: CDS
<222> LOCATION: (940)..(948)

<400> SEQUENCE: 16
aagaacttta aaaatcacct aggtgtgggc cgggcacggt ggctaacgcc tgtaatccca         60
gcactttgag atgctgaggc aggtggatca cgaggtcagg agatcgagac catcctggat        120
aacacggaga acccccggcg gagctgagga gcagggccgg gcgcc atg gca ccg tgg       177
                                                    Met Ala Pro Trp
                                                      1 ggc aag cgg ctg gct ggc gtg cgc ggg gtg ctg ctt gac atc tcg ggc         225
Gly Lys Arg Leu Ala Gly Val Arg Gly Val Leu Leu Asp Ile Ser Gly
  5              10                  15                  20 gtg ctg tac gac agc ggc gcg ggc ggc ggc acg gcc atc gcc ggc tcg         273
Val Leu Tyr Asp Ser Gly Ala Gly Gly Gly Thr Ala Ile Ala Gly Ser
                 25                  30                  35 gtg gag gcg gtg gcc aga ctg aag cgt tcc cgg ctg aag gtg agg ttc         321
Val Glu Ala Val Ala Arg Leu Lys Arg Ser Arg Leu Lys Val Arg Phe
             40                  45                  50 tgc acc aac gag tcg cag aag tcc cgg gca gag ctg gtg ggg cag ctt         369
Cys Thr Asn Glu Ser Gln Lys Ser Arg Ala Glu Leu Val Gly Gln Leu
         55                  60                  65 cag agg ctg gga ttt gac atc tct gag cag gag gtg acc gcc ccg gca         417
Gln Arg Leu Gly Phe Asp Ile Ser Glu Gln Glu Val Thr Ala Pro Ala
     70                  75                  80 cca gct gcc tgc cag atc ctg aag gag cga ggc ctg cga cca tac ctg         465
Pro Ala Ala Cys Gln Ile Leu Lys Glu Arg Gly Leu Arg Pro Tyr Leu
 85                  90                  95                 100 ctc atc cat gac gga gtc cgc tca gaa ttt gat cag atc gac aca tcc         513
Leu Ile His Asp Gly Val Arg Ser Glu Phe Asp Gln Ile Asp Thr Ser
                105                 110                 115 aac cca aac tgt gtg gta att gca gac gca gga gaa agc ttt tct tat         561
Asn Pro Asn Cys Val Val Ile Ala Asp Ala Gly Glu Ser Phe Ser Tyr
```

```
Asn Pro Asn Cys Val Val Ile Ala Asp Ala Gly Glu Ser Phe Ser Tyr
            120                 125                 130 caa aac atg aat aac gcc ttc cag gtg ctc atg gag ctg gaa aaa cct      609
Gln Asn Met Asn Asn Ala Phe Gln Val Leu Met Glu Leu Glu Lys Pro
        135                 140                 145 gtg ctc ata tca ctg gga aaa ggg cgt tac tac aag gag acc tct ggc      657
Val Leu Ile Ser Leu Gly Lys Gly Arg Tyr Tyr Lys Glu Thr Ser Gly
150                 155                 160 ctg atg ctg gac gtt ggt ccc tac atg aag gcg ctt gag tat gcc tgt      705
Leu Met Leu Asp Val Gly Pro Tyr Met Lys Ala Leu Glu Tyr Ala Cys
165                 170                 175                 180 ggc atc aaa gcc gag gtg gtg ggg aag cct tct cct gag ttt ttc aag      753
Gly Ile Lys Ala Glu Val Val Gly Lys Pro Ser Pro Glu Phe Phe Lys
                185                 190                 195 tct gcc ctg caa gcg ata gga gtg gaa gcc cac cag gcc gtc atg att      801
Ser Ala Leu Gln Ala Ile Gly Val Glu Ala His Gln Ala Val Met Ile
            200                 205                 210 ggg gac gat atc gtg ggc gac gtc ggc ggt gcc cag cgg tgt gga atg      849
Gly Asp Asp Ile Val Gly Asp Val Gly Gly Ala Gln Arg Cys Gly Met
        215                 220                 225 aga gcg ctg cag gtg cgc acc ggg aag ttc agg ccc agt gac gag cac      897
Arg Ala Leu Gln Val Arg Thr Gly Lys Phe Arg Pro Ser Asp Glu His
230                 235                 240 cat ccg gaa gtg aag gct gat gga ctc ttt gca ttt cag tga aga gcc      945
His Pro Glu Val Lys Ala Asp Gly Leu Phe Ala Phe Gln     Arg Ala
245                 250                 255 tgg aagaaccca ggggcctcct atgcacagat cttgcagccc agaaccaagt           998
Trp
260 cagcctccct gcgactgccc aggcacactg cccaccaccc cacccccgaa acaatgccag   1058 cccgctgctt tttctatcct cccagtcacc tttgcagaca agaccagggg gcagctcccg   1118 agggcactgt gaaggctccc atgccacaca gtgagaactg tagcctctgc gtccaaggca   1178 cacagggtac tttctggacc cactgctgga cagacttgaa ggtgtcatgc ccggtgtgtg   1238 caggaggaaa ctaacagttc agtaaactct gccttgacca gcagcctttt              1287

<210> SEQ ID NO 17
<211> LENGTH: 257
<212> TYPE: PRT
<213> ORGANISM: Homo sapiens

<400> SEQUENCE: 17

Met Ala Pro Trp Gly Lys Arg Leu Ala Gly Val Arg Gly Val Leu Leu
1               5                   10                  15

Asp Ile Ser Gly Val Leu Tyr Asp Ser Gly Ala Gly Gly Gly Thr Ala
            20                  25                  30

Ile Ala Gly Ser Val Glu Ala Val Ala Arg Leu Lys Arg Ser Arg Leu
        35                  40                  45

Lys Val Arg Phe Cys Thr Asn Glu Ser Gln Lys Ser Arg Ala Glu Leu
    50                  55                  60

Val Gly Gln Leu Gln Arg Leu Gly Phe Asp Ile Ser Glu Gln Glu Val
65                  70                  75                  80

Thr Ala Pro Ala Pro Ala Ala Cys Gln Ile Leu Lys Glu Arg Gly Leu
                85                  90                  95

Arg Pro Tyr Leu Leu Ile His Asp Gly Val Arg Ser Glu Phe Asp Gln
            100                 105                 110

Ile Asp Thr Ser Asn Pro Asn Cys Val Val Ile Ala Asp Ala Gly Glu
```

```
                115                 120                 125
Ser Phe Ser Tyr Gln Asn Met Asn Asn Ala Phe Gln Val Leu Met Glu
    130                 135                 140

Leu Glu Lys Pro Val Leu Ile Ser Leu Gly Lys Gly Arg Tyr Tyr Lys
145                 150                 155                 160

Glu Thr Ser Gly Leu Met Leu Asp Val Gly Pro Tyr Met Lys Ala Leu
                165                 170                 175

Glu Tyr Ala Cys Gly Ile Lys Ala Glu Val Val Gly Lys Pro Ser Pro
            180                 185                 190

Glu Phe Phe Lys Ser Ala Leu Gln Ala Ile Gly Val Glu Ala His Gln
        195                 200                 205

Ala Val Met Ile Gly Asp Asp Ile Val Gly Asp Val Gly Gly Ala Gln
    210                 215                 220

Arg Cys Gly Met Arg Ala Leu Gln Val Arg Thr Gly Lys Phe Arg Pro
225                 230                 235                 240

Ser Asp Glu His His Pro Glu Val Lys Ala Asp Gly Leu Phe Ala Phe
                245                 250                 255

Gln

<210> SEQ ID NO 18
<211> LENGTH: 2264
<212> TYPE: DNA
<213> ORGANISM: Homo sapiens
<220> FEATURE:
<221> NAME/KEY: CDS
<222> LOCATION: (166)..(1005)

<400> SEQUENCE: 18
aagaacttta aaaatcacct aggtgtgggc cgggcacggt ggctaacgcc tgtaatccca      60
gcactttgag atgctgaggc aggtggatca cgaggtcagg agatcgagac catcctggat    120
aacacggaga aaccccggcg agctgagga gcagggccgg cgcc atg gca ccg tgg      177
                                                Met Ala Pro Trp
                                                  1 ggc aag cgg ctg gct ggc gtg cgc ggg gtg ctg ctt gac atc tcg ggc      225
Gly Lys Arg Leu Ala Gly Val Arg Gly Val Leu Leu Asp Ile Ser Gly
  5                  10                  15                  20 gtg ctg tac gac agc ggc gcg ggc ggc acg gcc atc gcc ggc tcg          273
Val Leu Tyr Asp Ser Gly Ala Gly Gly Thr Ala Ile Ala Gly Ser
                 25                  30                  35 gtg gag gcg gtg gcc aga ctg aag cgt tcc cgg ctg aag gtg agg ttc      321
Val Glu Ala Val Ala Arg Leu Lys Arg Ser Arg Leu Lys Val Arg Phe
                 40                  45                  50 tgc acc aac gag tcg cag aag tcc cgg gca gag ctg gtg ggg cag ctt      369
Cys Thr Asn Glu Ser Gln Lys Ser Arg Ala Glu Leu Val Gly Gln Leu
             55                  60                  65 cag agg ctg gga ttt gac atc tct gag cag gag gtg acc gcc ccg gca      417
Gln Arg Leu Gly Phe Asp Ile Ser Glu Gln Glu Val Thr Ala Pro Ala
     70                  75                  80 cca gct gcc tgc cag atc ctg aag gag cga ggc ctg cga cca tac ctg      465
Pro Ala Ala Cys Gln Ile Leu Lys Glu Arg Gly Leu Arg Pro Tyr Leu
 85                  90                  95                 100 ctc atc cat gac gga gtc cgc tca gaa ttt gat cag atc gac aca tcc      513
Leu Ile His Asp Gly Val Arg Ser Glu Phe Asp Gln Ile Asp Thr Ser
                105                 110                 115 aac cca aac tgt gtg gta att gca gac gca gga gaa agc ttt tct tat      561
Asn Pro Asn Cys Val Val Ile Ala Asp Ala Gly Glu Ser Phe Ser Tyr
            120                 125                 130
```

-continued

| | | |
|---|---|---|
| caa aac atg aat aac gcc ttc cag gtg ctc atg gag ctg gaa aaa cct<br>Gln Asn Met Asn Asn Ala Phe Gln Val Leu Met Glu Leu Glu Lys Pro<br>     135                   140                   145 | 609 |
| gtg ctc ata tca ctg gga aaa ggg cgt tac tac aag gag acc tct ggc<br>Val Leu Ile Ser Leu Gly Lys Gly Arg Tyr Tyr Lys Glu Thr Ser Gly<br>150                   155                   160 | 657 |
| ctg atg ctg gac gtt ggt ccc tac atg aag gcg ctt gag tat gcc tgt<br>Leu Met Leu Asp Val Gly Pro Tyr Met Lys Ala Leu Glu Tyr Ala Cys<br>165                   170                   175               180 | 705 |
| ggc atc aaa gcc gag gtg gtg ggg aag cct tct cct gag ttt ttc aag<br>Gly Ile Lys Ala Glu Val Val Gly Lys Pro Ser Pro Glu Phe Phe Lys<br>                  185                   190               195 | 753 |
| tct gcc ctg caa gcg ata gga gtg gaa gcc cac cag gcc gtc atg att<br>Ser Ala Leu Gln Ala Ile Gly Val Glu Ala His Gln Ala Val Met Ile<br>                200                 205                210 | 801 |
| ggg gac gat atc gtg ggc gac gtc ggc ggt gcc cag cgg tgt gga atg<br>Gly Asp Asp Ile Val Gly Asp Val Gly Gly Ala Gln Arg Cys Gly Met<br>215                   220                   225 | 849 |
| aga gcg ctg cag gtg cgc acc ggg aag ttc agg ccc agt gac gag cac<br>Arg Ala Leu Gln Val Arg Thr Gly Lys Phe Arg Pro Ser Asp Glu His<br>    230                   235                   240 | 897 |
| cat ccg gaa gtg aag gct gat ggg cac ttc ctg gcc ctg cgg ggt gcc<br>His Pro Glu Val Lys Ala Asp Gly His Phe Leu Ala Leu Arg Gly Ala<br>245                   250                   255               260 | 945 |
| ctg tct ctg gct gga gct gat gag ccg tgg tgt gat gct tgc ctg ggg<br>Leu Ser Leu Ala Gly Ala Asp Glu Pro Trp Cys Asp Ala Cys Leu Gly<br>                  265                   270               275 | 993 |
| gtc ggt gtt gcc tagaagtgag gaatgacctc cttcacccct ggctccttcc<br>Val Gly Val Ala<br>            280 | 1045 |
| ggcagcctgg ccacttccag catgtggagg gggcccgggc cctggcagag acggtgtgga | 1105 |
| accgccggcc gcatgcgggg ctggagttcg gggctgccaa tgggctaagg ccctgtgttc | 1165 |
| aacacatgtc gcggaactgt cgtgaaaaaa agactcagga ccacaggtcc ggggtgctcc | 1225 |
| cagggtctt tcccaccgag gctgggagtg agcagcagcc taggcccagc cacacctccc | 1285 |
| aggctcggga gctgccaggc caggcaaccg tgaagggtag cagggtgggg ggtgagggg | 1345 |
| aggacaggga gagcaggcct ctcgggcctc acccacccct gcaccttcca gctctagggc | 1405 |
| ccacacagta ccaagccctg ggctcaatgt accacttatg aaaactcaat tcaaattggc | 1465 |
| ttagtgcaac aaggtatttg gtggtctcac atgacttgaa catccaggcc tggctgtcac | 1525 |
| gggaaccgca tctcttccca ttgcagctac ttggcaggtg gcgggatgtc ccccagccac | 1585 |
| cgacgtcccc ctgcctgctc cgcaaccca gggcctgcag aaaaggccca cgagactcag | 1645 |
| actggcagag acttaggcgg accaggaaca ggggcgcagt ctccgtccca cccaaaccct | 1705 |
| aaccagagag aacacggcac gttgtgccag acggaggacg gatgccagcg agggtccatg | 1765 |
| tcctcactgc cgacaaggct gggaactggg ccaagtgaag cagaggcctc cacgtcagat | 1825 |
| gtgagcgcca ccggcccagg tgactgcagt tcttccctcc ttccgttcgg cttgagcccct | 1885 |
| ccagaggatc ggaaaggctg aggcctgacc tggtgccgct gtcctgggtg gtctgtcct | 1945 |
| gctggtcggt tcctgcccct ctcggggagg ttggctggca gctggcaggt ggaaagcctc | 2005 |
| ctgtgttcac ctcagggcag aggtgggac acagggcggg acgggcgagt gtggtgcccc | 2065 |
| tctggggtgg gtgctcttgg gtccgcctcc cgtgccagag tgcgtgtcaa cagttccagc | 2125 |
| tgcccctcag aactgtcctg gtttaggagg tgaacacacg gggcagccta cattctacgt | 2185 |
| ggttttttta acattataaa agcagcatgt gttattacag gaaatttaac agaagtatat | 2245 |

```
aaaaagaaac cagaagtca                                              2264
```

<210> SEQ ID NO 19
<211> LENGTH: 280
<212> TYPE: PRT
<213> ORGANISM: Homo sapiens

<400> SEQUENCE: 19

```
Met Ala Pro Trp Gly Lys Arg Leu Ala Gly Val Arg Gly Val Leu Leu
1               5                   10                  15

Asp Ile Ser Gly Val Leu Tyr Asp Ser Gly Ala Gly Gly Thr Ala
            20                  25                  30

Ile Ala Gly Ser Val Glu Ala Val Ala Arg Leu Lys Arg Ser Arg Leu
        35                  40                  45

Lys Val Arg Phe Cys Thr Asn Glu Ser Gln Lys Ser Arg Ala Glu Leu
    50                  55                  60

Val Gly Gln Leu Gln Arg Leu Gly Phe Asp Ile Ser Glu Gln Glu Val
65                  70                  75                  80

Thr Ala Pro Ala Pro Ala Ala Cys Gln Ile Leu Lys Glu Arg Gly Leu
                85                  90                  95

Arg Pro Tyr Leu Leu Ile His Asp Gly Val Arg Ser Glu Phe Asp Gln
            100                 105                 110

Ile Asp Thr Ser Asn Pro Asn Cys Val Val Ile Ala Asp Ala Gly Glu
        115                 120                 125

Ser Phe Ser Tyr Gln Asn Met Asn Asn Ala Phe Gln Val Leu Met Glu
    130                 135                 140

Leu Glu Lys Pro Val Leu Ile Ser Leu Gly Lys Gly Arg Tyr Tyr Lys
145                 150                 155                 160

Glu Thr Ser Gly Leu Met Leu Asp Val Gly Pro Tyr Met Lys Ala Leu
                165                 170                 175

Glu Tyr Ala Cys Gly Ile Lys Ala Glu Val Val Gly Lys Pro Ser Pro
            180                 185                 190

Glu Phe Phe Lys Ser Ala Leu Gln Ala Ile Gly Val Glu Ala His Gln
        195                 200                 205

Ala Val Met Ile Gly Asp Asp Ile Val Gly Asp Val Gly Gly Ala Gln
    210                 215                 220

Arg Cys Gly Met Arg Ala Leu Gln Val Arg Thr Gly Lys Phe Arg Pro
225                 230                 235                 240

Ser Asp Glu His His Pro Glu Val Lys Ala Asp Gly His Phe Leu Ala
                245                 250                 255

Leu Arg Gly Ala Leu Ser Leu Ala Gly Ala Asp Glu Pro Trp Cys Asp
            260                 265                 270

Ala Cys Leu Gly Val Gly Val Ala
        275                 280
```

<210> SEQ ID NO 20
<211> LENGTH: 992
<212> TYPE: DNA
<213> ORGANISM: Homo sapiens
<220> FEATURE:
<221> NAME/KEY: CDS
<222> LOCATION: (166)..(960)

<400> SEQUENCE: 20

```
aagaactta  aaaatcacct  aggtgtgggc  cgggcacggt  ggctaacgcc  tgtaatccca     60
gcactttgag  atgctgaggc  aggtggatca  cgaggtcagg  agatcgagac  catcctggat    120
```

```
                                                                              -continued aacacggaga aaccccggcg gagctgagga gcagggccgg gcgcc atg gca ccg tgg               177
                                                  Met Ala Pro Trp
                                                   1 ggc aag cgg ctg gct ggc gtg cgc ggg gtg ctg ctt gac atc tcg ggc                 225
Gly Lys Arg Leu Ala Gly Val Arg Gly Val Leu Leu Asp Ile Ser Gly
 5              10                  15                  20 gtg ctg tac gac agc ggc gcg ggc ggc acg gcc atc gcc ggc tcg                     273
Val Leu Tyr Asp Ser Gly Ala Gly Gly Thr Ala Ile Ala Gly Ser
                25                  30                  35 gtg gag gcg gtg gcc aga ctg aag cgt tcc cgg ctg aag gtg agg ttc                 321
Val Glu Ala Val Ala Arg Leu Lys Arg Ser Arg Leu Lys Val Arg Phe
            40                  45                  50 tgc acc aac gag tcg cag aag tcc cgg gca gag ctg gtg ggg cag ctt                 369
Cys Thr Asn Glu Ser Gln Lys Ser Arg Ala Glu Leu Val Gly Gln Leu
        55                  60                  65 cag agg ctg gga ttt gac atc tct gag cag gag gtg acc gcc ccg gca                 417
Gln Arg Leu Gly Phe Asp Ile Ser Glu Gln Glu Val Thr Ala Pro Ala
    70                  75                  80 cca gct gcc tgc cag atc ctg aag gag cga ggc ctg cga cca tac ctg                 465
Pro Ala Ala Cys Gln Ile Leu Lys Glu Arg Gly Leu Arg Pro Tyr Leu
85                  90                  95                 100 ctc atc cat gac gga gtc cgc tca gaa ttt gat cag atc gac aca tcc                 513
Leu Ile His Asp Gly Val Arg Ser Glu Phe Asp Gln Ile Asp Thr Ser
                105                 110                 115 aac cca aac tgt gtg gta att gca gac gca gga gaa agc ttt tct tat                 561
Asn Pro Asn Cys Val Val Ile Ala Asp Ala Gly Glu Ser Phe Ser Tyr
            120                 125                 130 caa aac atg aat aac gcc ttc cag gtg ctc atg gag ctg gaa aaa cct                 609
Gln Asn Met Asn Asn Ala Phe Gln Val Leu Met Glu Leu Glu Lys Pro
        135                 140                 145 gtg ctc ata tca ctg gga aaa ggg cgt tac tac aag gag acc tct ggc                 657
Val Leu Ile Ser Leu Gly Lys Gly Arg Tyr Tyr Lys Glu Thr Ser Gly
    150                 155                 160 ctg atg ctg gac gtt ggt ccc tac atg aag gcg ctt gag tat gcc tgt                 705
Leu Met Leu Asp Val Gly Pro Tyr Met Lys Ala Leu Glu Tyr Ala Cys
165                 170                 175                 180 ggc atc aaa gcc gag gtg gtg ggg aag cct tct cct gag ttt ttc aag                 753
Gly Ile Lys Ala Glu Val Val Gly Lys Pro Ser Pro Glu Phe Phe Lys
                185                 190                 195 tct gcc ctg caa gcg ata gga gtg gaa gcc cac cag gcc gtc atg att                 801
Ser Ala Leu Gln Ala Ile Gly Val Glu Ala His Gln Ala Val Met Ile
            200                 205                 210 ggg gac gat atc gtg ggc gac gtc ggc ggt gcc cag cgg tgt gga atg                 849
Gly Asp Asp Ile Val Gly Asp Val Gly Gly Ala Gln Arg Cys Gly Met
        215                 220                 225 aga gcg ctg cag gtg cgc acc ggg aag ttc agg tca gtg cca gct gga                 897
Arg Ala Leu Gln Val Arg Thr Gly Lys Phe Arg Ser Val Pro Ala Gly
    230                 235                 240 gtc att tat tca cct tcc ttc cag ggg atg acc aca ttc tca ttc tgt                 945
Val Ile Tyr Ser Pro Ser Phe Gln Gly Met Thr Thr Phe Ser Phe Cys
245                 250                 255                 260 ttt gtt ctt caa aat aaagggata ttctttccaa atcaaagagc ag                          992
Phe Val Leu Gln Asn
                265

<210> SEQ ID NO 21
<211> LENGTH: 265
<212> TYPE: PRT
<213> ORGANISM: Homo sapiens
```

<400> SEQUENCE: 21

Met Ala Pro Trp Gly Lys Arg Leu Ala Gly Val Arg Gly Val Leu Leu
1               5                   10                  15

Asp Ile Ser Gly Val Leu Tyr Asp Ser Gly Ala Gly Gly Gly Thr Ala
            20                  25                  30

Ile Ala Gly Ser Val Glu Ala Val Ala Arg Leu Lys Arg Ser Arg Leu
        35                  40                  45

Lys Val Arg Phe Cys Thr Asn Glu Ser Gln Lys Ser Arg Ala Glu Leu
50                  55                  60

Val Gly Gln Leu Gln Arg Leu Gly Phe Asp Ile Ser Glu Gln Glu Val
65                  70                  75                  80

Thr Ala Pro Ala Pro Ala Ala Cys Gln Ile Leu Lys Glu Arg Gly Leu
                85                  90                  95

Arg Pro Tyr Leu Leu Ile His Asp Gly Val Arg Ser Glu Phe Asp Gln
            100                 105                 110

Ile Asp Thr Ser Asn Pro Asn Cys Val Val Ile Ala Asp Ala Gly Glu
        115                 120                 125

Ser Phe Ser Tyr Gln Asn Met Asn Asn Ala Phe Gln Val Leu Met Glu
130                 135                 140

Leu Glu Lys Pro Val Leu Ile Ser Leu Gly Lys Gly Arg Tyr Tyr Lys
145                 150                 155                 160

Glu Thr Ser Gly Leu Met Leu Asp Val Gly Pro Tyr Met Lys Ala Leu
                165                 170                 175

Glu Tyr Ala Cys Gly Ile Lys Ala Glu Val Val Gly Lys Pro Ser Pro
            180                 185                 190

Glu Phe Phe Lys Ser Ala Leu Gln Ala Ile Gly Val Glu Ala His Gln
        195                 200                 205

Ala Val Met Ile Gly Asp Asp Ile Val Gly Asp Val Gly Gly Ala Gln
        210                 215                 220

Arg Cys Gly Met Arg Ala Leu Gln Val Arg Thr Gly Lys Phe Arg Ser
225                 230                 235                 240

Val Pro Ala Gly Val Ile Tyr Ser Pro Ser Phe Gln Gly Met Thr Thr
                245                 250                 255

Phe Ser Phe Cys Phe Val Leu Gln Asn
            260                 265

<210> SEQ ID NO 22
<211> LENGTH: 952
<212> TYPE: DNA
<213> ORGANISM: Homo sapiens
<220> FEATURE:
<221> NAME/KEY: CDS
<222> LOCATION: (166)..(936)

<400> SEQUENCE: 22
aagaacttta aaaatcacct aggtgtgggc cgggcacggt ggctaacgcc tgtaatccca      60
gcactttgag atgctgaggc aggtggatca cgaggtcagg agatcgagac catcctggat     120
aacacggaga aaccccggcg gagctgagga gcagggccgg cgcc atg gca ccg tgg     177
                                                Met Ala Pro Trp
                                                1 ggc aag cgg ctg gct ggc gtg cgc ggg gtg ctg ctt gac atc tcg ggc     225
Gly Lys Arg Leu Ala Gly Val Arg Gly Val Leu Leu Asp Ile Ser Gly
 5                  10                  15                  20 gtg ctg tac gac agc ggc gcg ggc ggc ggc acg gcc atc gcc ggc tcg     273
Val Leu Tyr Asp Ser Gly Ala Gly Gly Gly Thr Ala Ile Ala Gly Ser
                25                  30                  35

```
gtg gag gcg gtg gcc aga ctg aag cgt tcc cgg ctg aag gtg agg ttc    321
Val Glu Ala Val Ala Arg Leu Lys Arg Ser Arg Leu Lys Val Arg Phe
        40                  45                  50 tgc acc aac gag tcg cag aag tcc cgg gca gag ctg gtg ggg cag ctt    369
Cys Thr Asn Glu Ser Gln Lys Ser Arg Ala Glu Leu Val Gly Gln Leu
                55                  60                  65 cag agg ctg gga ttt gac atc tct gag cag gag gtg acc gcc ccg gca    417
Gln Arg Leu Gly Phe Asp Ile Ser Glu Gln Glu Val Thr Ala Pro Ala
        70                  75                  80 cca gct gcc tgc cag atc ctg aag gag cga ggc ctg cga cca tac ctg    465
Pro Ala Ala Cys Gln Ile Leu Lys Glu Arg Gly Leu Arg Pro Tyr Leu
85                  90                  95                 100 ctc atc cat gac gga gtc cgc tca gaa ttt gat cag atc gac aca tcc    513
Leu Ile His Asp Gly Val Arg Ser Glu Phe Asp Gln Ile Asp Thr Ser
                105                 110                 115 aac cca aac tgt gtg gta att gca gac gca gga gaa agc ttt tct tat    561
Asn Pro Asn Cys Val Val Ile Ala Asp Ala Gly Glu Ser Phe Ser Tyr
        120                 125                 130 caa aac atg aat aac gcc ttc cag gtg ctc atg gag ctg gaa aaa cct    609
Gln Asn Met Asn Asn Ala Phe Gln Val Leu Met Glu Leu Glu Lys Pro
                135                 140                 145 gtg ctc ata tca ctg gga aaa ggg cgt tac tac aag gag acc tct ggc    657
Val Leu Ile Ser Leu Gly Lys Gly Arg Tyr Tyr Lys Glu Thr Ser Gly
        150                 155                 160 ctg atg ctg gac gtt ggt ccc tac atg aag gcg ctt gag tat gcc tgt    705
Leu Met Leu Asp Val Gly Pro Tyr Met Lys Ala Leu Glu Tyr Ala Cys
165                 170                 175                 180 ggc atc aaa gcc gag gtg gtg ggg aag cct tct cct gag ttt ttc aag    753
Gly Ile Lys Ala Glu Val Val Gly Lys Pro Ser Pro Glu Phe Phe Lys
                185                 190                 195 tct gcc ctg caa gcg ata gga gtg gaa gcc cac cag gcc gtc atg att    801
Ser Ala Leu Gln Ala Ile Gly Val Glu Ala His Gln Ala Val Met Ile
        200                 205                 210 ggg gac gat atc gtg ggc gac gtc ggc ggt gcc cag cgg tgt gga atg    849
Gly Asp Asp Ile Val Gly Asp Val Gly Gly Ala Gln Arg Cys Gly Met
                215                 220                 225 aga gcg ctg cag agc cgc tca aca cgt gtt gca agg cac gtg ctc tgg    897
Arg Ala Leu Gln Ser Arg Ser Thr Arg Val Ala Arg His Val Leu Trp
        230                 235                 240 acc tgg tgc tca cac gtg ctc ttc tcc caa gac act ccc tgaagcgcgt    946
Thr Trp Cys Ser His Val Leu Phe Ser Gln Asp Thr Pro
245                 250                 255 tccccca                                                            952

<210> SEQ ID NO 23
<211> LENGTH: 257
<212> TYPE: PRT
<213> ORGANISM: Homo sapiens

<400> SEQUENCE: 23

Met Ala Pro Trp Gly Lys Arg Leu Ala Gly Val Arg Gly Val Leu Leu
1               5                   10                  15

Asp Ile Ser Gly Val Leu Tyr Asp Ser Gly Ala Gly Gly Thr Ala
            20                  25                  30

Ile Ala Gly Ser Val Glu Ala Val Ala Arg Leu Lys Arg Ser Arg Leu
        35                  40                  45

Lys Val Arg Phe Cys Thr Asn Glu Ser Gln Lys Ser Arg Ala Glu Leu
    50                  55                  60
```

```
Val Gly Gln Leu Gln Arg Leu Gly Phe Asp Ile Ser Glu Gln Glu Val
 65                  70                  75                  80

Thr Ala Pro Ala Pro Ala Ala Cys Gln Ile Leu Lys Glu Arg Gly Leu
                 85                  90                  95

Arg Pro Tyr Leu Leu Ile His Asp Gly Val Arg Ser Glu Phe Asp Gln
            100                 105                 110

Ile Asp Thr Ser Asn Pro Asn Cys Val Val Ile Ala Asp Ala Gly Glu
        115                 120                 125

Ser Phe Ser Tyr Gln Asn Met Asn Asn Ala Phe Gln Val Leu Met Glu
    130                 135                 140

Leu Glu Lys Pro Val Leu Ile Ser Leu Gly Lys Gly Arg Tyr Tyr Lys
145                 150                 155                 160

Glu Thr Ser Gly Leu Met Leu Asp Val Gly Pro Tyr Met Lys Ala Leu
                165                 170                 175

Glu Tyr Ala Cys Gly Ile Lys Ala Glu Val Gly Lys Pro Ser Pro
            180                 185                 190

Glu Phe Phe Lys Ser Ala Leu Gln Ala Ile Gly Val Glu Ala His Gln
        195                 200                 205

Ala Val Met Ile Gly Asp Asp Ile Val Gly Asp Val Gly Gly Ala Gln
    210                 215                 220

Arg Cys Gly Met Arg Ala Leu Gln Ser Arg Ser Thr Arg Val Ala Arg
225                 230                 235                 240

His Val Leu Trp Thr Trp Cys Ser His Val Leu Phe Ser Gln Asp Thr
                245                 250                 255

Pro

<210> SEQ ID NO 24
<211> LENGTH: 979
<212> TYPE: DNA
<213> ORGANISM: Homo sapiens
<220> FEATURE:
<221> NAME/KEY: CDS
<222> LOCATION: (166)..(801)

<400> SEQUENCE: 24
aagaacttta aaaatcacct aggtgtgggc cgggcacggt ggctaacgcc tgtaatccca      60
gcactttgag atgctgaggc aggtggatca cgaggtcagg agatcgagac catcctggat     120
aacacggaga acccccggcg gagctgagga gcagggccgg gcgcc atg gca ccg tgg    177
                                               Met Ala Pro Trp
                                                 1 ggc aag cgg ctg gct ggc gtg cgc ggg gtg ctg ctt gac atc tcg ggc      225
Gly Lys Arg Leu Ala Gly Val Arg Gly Val Leu Leu Asp Ile Ser Gly
  5                  10                  15                  20 gtg ctg tac gac agc ggc gcg ggc ggc ggc acg gcc atc gcc ggc tcg      273
Val Leu Tyr Asp Ser Gly Ala Gly Gly Gly Thr Ala Ile Ala Gly Ser
                 25                  30                  35 gtg gag gcg gtg gcc aga ctg aag cgt tcc cgg ctg aag gtg agg ttc      321
Val Glu Ala Val Ala Arg Leu Lys Arg Ser Arg Leu Lys Val Arg Phe
         40                  45                  50 tgc acc aac gag tcg cag aag tcc cgg gca gag ctg gtg ggg cag ctt      369
Cys Thr Asn Glu Ser Gln Lys Ser Arg Ala Glu Leu Val Gly Gln Leu
     55                  60                  65 cag agg ctg gga ttt gac atc tct gag cag gag gtg acc gcc ccg gca      417
Gln Arg Leu Gly Phe Asp Ile Ser Glu Gln Glu Val Thr Ala Pro Ala
 70                  75                  80 cca gct gcc tgc cag atc ctg aag gag cga ggc ctg cga cca tac ctg      465
Pro Ala Ala Cys Gln Ile Leu Lys Glu Arg Gly Leu Arg Pro Tyr Leu
```

```
ctc atc cat gac gga gtc cgc tca gaa ttt gat cag atc gac aca tcc        513
Leu Ile His Asp Gly Val Arg Ser Glu Phe Asp Gln Ile Asp Thr Ser
            105                 110                 115 aac cca aac tgt gtg gta att gca gac gca gga gaa agc ttt tct tat        561
Asn Pro Asn Cys Val Val Ile Ala Asp Ala Gly Glu Ser Phe Ser Tyr
        120                 125                 130 caa aac atg aat aac gcc ttc cag gtg ctc atg gag ctg gaa aaa cct        609
Gln Asn Met Asn Asn Ala Phe Gln Val Leu Met Glu Leu Glu Lys Pro
            135                 140                 145 gtg ctc ata tca ctg gga aaa ggg cgt tac tac aag gag acc tct ggc        657
Val Leu Ile Ser Leu Gly Lys Gly Arg Tyr Tyr Lys Glu Thr Ser Gly
    150                 155                 160 ctg atg ctg gac gtt ggt ccc tac atg aag gcg ctt gag tat gcc tgt        705
Leu Met Leu Asp Val Gly Pro Tyr Met Lys Ala Leu Glu Tyr Ala Cys
165                 170                 175                 180 ggc atc aaa gcc gag gtg gtg ggg aag cct tct cct gag ttt ttc aag        753
Gly Ile Lys Ala Glu Val Val Gly Lys Pro Ser Pro Glu Phe Phe Lys
            185                 190                 195 tct gcc ctg caa gcg ata gga gtg gaa gcc cac cag tta ctt tca gta        801
Ser Ala Leu Gln Ala Ile Gly Val Glu Ala His Gln Leu Leu Ser Val
        200                 205                 210 tgaaagcaag aagcagaaat gcctgcggct tttcctgagt ttttgctgct tctctgaaag      861
gataagaatt gacaagtcct atcagtgtgt taatatatct cactggcaag acagtgtaac     921
agcaagatta caacaatatg gaggaaataa taaagtcact cattttgcga cctttata       979

<210> SEQ ID NO 25
<211> LENGTH: 212
<212> TYPE: PRT
<213> ORGANISM: Homo sapiens

<400> SEQUENCE: 25

Met Ala Pro Trp Gly Lys Arg Leu Ala Gly Val Arg Gly Val Leu Leu
1               5                   10                  15

Asp Ile Ser Gly Val Leu Tyr Asp Ser Gly Ala Gly Gly Gly Thr Ala
            20                  25                  30

Ile Ala Gly Ser Val Glu Ala Val Ala Arg Leu Lys Arg Ser Arg Leu
        35                  40                  45

Lys Val Arg Phe Cys Thr Asn Glu Ser Gln Lys Ser Arg Ala Glu Leu
    50                  55                  60

Val Gly Gln Leu Gln Arg Leu Gly Phe Asp Ile Ser Glu Gln Glu Val
65                  70                  75                  80

Thr Ala Pro Ala Pro Ala Ala Cys Gln Ile Leu Lys Glu Arg Gly Leu
                85                  90                  95

Arg Pro Tyr Leu Leu Ile His Asp Gly Val Arg Ser Glu Phe Asp Gln
            100                 105                 110

Ile Asp Thr Ser Asn Pro Asn Cys Val Val Ile Ala Asp Ala Gly Glu
        115                 120                 125

Ser Phe Ser Tyr Gln Asn Met Asn Asn Ala Phe Gln Val Leu Met Glu
    130                 135                 140

Leu Glu Lys Pro Val Leu Ile Ser Leu Gly Lys Gly Arg Tyr Tyr Lys
145                 150                 155                 160

Glu Thr Ser Gly Leu Met Leu Asp Val Gly Pro Tyr Met Lys Ala Leu
                165                 170                 175

Glu Tyr Ala Cys Gly Ile Lys Ala Glu Val Val Gly Lys Pro Ser Pro
            180                 185                 190
```

```
Glu Phe Phe Lys Ser Ala Leu Gln Ala Ile Gly Val Glu Ala His Gln
    195                 200                 205

Leu Leu Ser Val
    210

<210> SEQ ID NO 26
<211> LENGTH: 1590
<212> TYPE: DNA
<213> ORGANISM: Homo sapiens
<220> FEATURE:
<221> NAME/KEY: CDS
<222> LOCATION: (344)..(769)

<400> SEQUENCE: 26
tgagaaccca gggctcgctg ggatgctgtc ctccctccct ccctccctct gccaagctgg      60
tgggaaggcc cttgccaaag cgcacaagac cccttcacac agcagggggca caagctcttc     120 gaggcagagt cgcctgcagg tggggtggaa ggggtgcgcc ccagacccaa gaatcgcccg     180
cctctccaag accatccctg ctgctggcc cagtgacgag caccatccgg aagtgaaggc      240
tgatgggcac ttcctggccc tgcggggtgc cctgtctctg gctggagctg atgagccgtg     300
gtgtgatgct tgcctggggg tcggtgttgc ctagaagtga gga atg acc tcc ttc       355
                                              Met Thr Ser Phe
                                                1 acc cct ggc tcc ttc cgg cag cct ggc cac ttc cag cat gtg gag ggg       403
Thr Pro Gly Ser Phe Arg Gln Pro Gly His Phe Gln His Val Glu Gly
  5                  10                  15                  20 gcc cgg gcc ctg gca gag acg gtg tgg aac cgc cgg ccg cat gcg ggg       451
Ala Arg Ala Leu Ala Glu Thr Val Trp Asn Arg Arg Pro His Ala Gly
                 25                  30                  35 ctg gag ttc ggg gct gcc aat ggg cta agg ccc tgt gtt caa cac atg       499
Leu Glu Phe Gly Ala Ala Asn Gly Leu Arg Pro Cys Val Gln His Met
             40                  45                  50 tcg cgg aac tgt cgt gaa aaa aag act cag gac cac agg tcc ggg gtg       547
Ser Arg Asn Cys Arg Glu Lys Lys Thr Gln Asp His Arg Ser Gly Val
         55                  60                  65 ctc cca ggg gtc ttt ccc acc gag gct ggg agt gag cag cag cct agg       595
Leu Pro Gly Val Phe Pro Thr Glu Ala Gly Ser Glu Gln Gln Pro Arg
     70                  75                  80 ccc agc cac acc tcc cag gct cgg gag ctg cca ggc cag gca acc gtg       643
Pro Ser His Thr Ser Gln Ala Arg Glu Leu Pro Gly Gln Ala Thr Val
 85                  90                  95                 100 aag ggt agc agg gtg ggg ggt gga ggg gag gac agg gag agc agg cct       691
Lys Gly Ser Arg Val Gly Gly Gly Glu Asp Arg Glu Ser Arg Pro
                105                 110                 115 ctc ggg cct cac cca ccc ttg cac ctt cca gct cta ggg ccc aca cag       739
Leu Gly Pro His Pro Pro Leu His Leu Pro Ala Leu Gly Pro Thr Gln
            120                 125                 130 tac caa gcc ctg ggc tca atg tac cac tta tgaaaactca attcaaattg         789
Tyr Gln Ala Leu Gly Ser Met Tyr His Leu
        135                 140 gcttagtgca acaaggtatt tggtggtctc acatgacttg aacatccagg cctggctgtc     849
acgggaaccg catctcttcc cattgcagct acttggcagg tggcgggatg tcccccagcc     909
accgacgtcc ccctgcctgc tccgcaaccc cagggcctgc agaaaaggcc cacgagactc     969
agactggcag agacttaggc ggaccaggaa caggggcgca gtctccgtcc cacccaaacc    1029
ctaaccagag agaacacggc acgttgtgcc agacggagga cggatgccag cgagggtcca    1089
tgtcctcact gccgacaagg ctgggaactg ggccaagtga agcagaggcc tccacgtcag    1149
```

```
atgtgagcgc caccggccca ggtgactgca gttcttccct ccttccgttc ggcttgagcc   1209
ctccagagga tcggaaaggc tgaggcctga cctggtgccg ctgtcctggg tgggtctgtc   1269
ctgctggtcg gttcctgccc ctctcgggga ggttggctgg cagctggcag gtggaaagcc   1329
tcctgtgttc acctcaggc agaggtgggg acacagggcg ggacgggcga gtgtggtgcc    1389
cctctggggt gggtgctctt gggtccgcct cccgtgccag agtgcgtgtc aacagttcca   1449
gctgcccctc agaactgtcc tggtttagga ggtgaacaca cggggcagcc tacattctac   1509 gtggttttttt taacattata aaagcagcat gtgttattac aggaaattta acagaagtat  1569
ataaaaagaa accagaagtc a                                             1590
```

<210> SEQ ID NO 27
<211> LENGTH: 142
<212> TYPE: PRT
<213> ORGANISM: Homo sapiens

<400> SEQUENCE: 27

```
Met Thr Ser Phe Thr Pro Gly Ser Phe Arg Gln Pro Gly His Phe Gln
1               5                   10                  15

His Val Glu Gly Ala Arg Ala Leu Ala Glu Thr Val Trp Asn Arg Arg
            20                  25                  30

Pro His Ala Gly Leu Glu Phe Gly Ala Ala Asn Gly Leu Arg Pro Cys
        35                  40                  45

Val Gln His Met Ser Arg Asn Cys Arg Glu Lys Lys Thr Gln Asp His
    50                  55                  60

Arg Ser Gly Val Leu Pro Gly Val Phe Pro Thr Glu Ala Gly Ser Glu
65                  70                  75                  80

Gln Gln Pro Arg Pro Ser His Thr Ser Gln Ala Arg Glu Leu Pro Gly
                85                  90                  95

Gln Ala Thr Val Lys Gly Ser Arg Val Gly Gly Gly Glu Asp Arg
            100                 105                 110

Glu Ser Arg Pro Leu Gly Pro His Pro Pro Leu His Leu Pro Ala Leu
        115                 120                 125

Gly Pro Thr Gln Tyr Gln Ala Leu Gly Ser Met Tyr His Leu
    130                 135                 140
```

<210> SEQ ID NO 28
<211> LENGTH: 791
<212> TYPE: DNA
<213> ORGANISM: Homo sapiens
<220> FEATURE:
<221> NAME/KEY: CDS
<222> LOCATION: (166)..(672)

<400> SEQUENCE: 28

```
aagaacttta aaaatcacct aggtgtgggc cgggcacggt ggctaacgcc tgtaatccca    60
gcactttgag atgctgaggc aggtggatca cgaggtcagg agatcgagac catcctggat   120
aacacggaga aaccccggcg gagctgagga gcagggccgg cgcc atg gca ccg tgg    177
                                                Met Ala Pro Trp
                                                1 ggc aag cgg ctg gct ggc gtg cgc ggg gtg ctg ctt gac atc tcg ggc     225
Gly Lys Arg Leu Ala Gly Val Arg Gly Val Leu Leu Asp Ile Ser Gly
5                   10                  15                  20 gtg ctg tac gac agc ggc gcg ggc ggc acg gcc atc gcc ggc tcg          273
Val Leu Tyr Asp Ser Gly Ala Gly Gly Thr Ala Ile Ala Gly Ser
                25                  30                  35
```

```
gtg gag gcg gtg gcc aga ctg aag cgt tcc cgg ctg aag gtg agg ttc      321
Val Glu Ala Val Ala Arg Leu Lys Arg Ser Arg Leu Lys Val Arg Phe
         40                  45                  50 tgc acc aac gag tcg cag aag tcc cgg gca gag ctg gtg ggg cag ctt      369
Cys Thr Asn Glu Ser Gln Lys Ser Arg Ala Glu Leu Val Gly Gln Leu
             55                  60                  65 cag agg ctg gga ttt gac atc tct gag cag gag gtg acc gcc ccg gca      417
Gln Arg Leu Gly Phe Asp Ile Ser Glu Gln Glu Val Thr Ala Pro Ala
 70                  75                  80 cca gct gcc tgc cag atc ctg aag gag cga ggc ctg cga cca tac ctg      465
Pro Ala Ala Cys Gln Ile Leu Lys Glu Arg Gly Leu Arg Pro Tyr Leu
 85                  90                  95                 100 ctc atc cat gac gga gtc cgc tca gaa ttt gat cag atc gac aca tcc      513
Leu Ile His Asp Gly Val Arg Ser Glu Phe Asp Gln Ile Asp Thr Ser
             105                 110                 115 aac cca aac tgt gtg gta att gca gac gca gga gaa agc ttt tct tat      561
Asn Pro Asn Cys Val Val Ile Ala Asp Ala Gly Glu Ser Phe Ser Tyr
                 120                 125                 130 caa aac atg aat aac gcc ttc cag gtg ctc atg gag ctg gaa aaa cct      609
Gln Asn Met Asn Asn Ala Phe Gln Val Leu Met Glu Leu Glu Lys Pro
             135                 140                 145 gtg ctc ata tca ctg gga aaa ggc atc cac ggg ttc ctc ttt gtg gct      657
Val Leu Ile Ser Leu Gly Lys Gly Ile His Gly Phe Leu Phe Val Ala
150                 155                 160 aga aca ttc acg tcc taagtggggc tgccgttggc tgggttaaac cagtaaccag      712
Arg Thr Phe Thr Ser
165 taacaggaga aatacgtcgc atctctagtg tgtggagatt accgggcctt tatattaaaa    772 aaaaattta agtgcttat                                                  791

<210> SEQ ID NO 29
<211> LENGTH: 169
<212> TYPE: PRT
<213> ORGANISM: Homo sapiens

<400> SEQUENCE: 29

Met Ala Pro Trp Gly Lys Arg Leu Ala Gly Val Arg Gly Val Leu Leu
 1               5                  10                  15

Asp Ile Ser Gly Val Leu Tyr Asp Ser Gly Ala Gly Gly Thr Ala
             20                  25                  30

Ile Ala Gly Ser Val Glu Ala Val Ala Arg Leu Lys Arg Ser Arg Leu
         35                  40                  45

Lys Val Arg Phe Cys Thr Asn Glu Ser Gln Lys Ser Arg Ala Glu Leu
 50                  55                  60

Val Gly Gln Leu Gln Arg Leu Gly Phe Asp Ile Ser Glu Gln Glu Val
 65                  70                  75                  80

Thr Ala Pro Ala Pro Ala Ala Cys Gln Ile Leu Lys Glu Arg Gly Leu
                 85                  90                  95

Arg Pro Tyr Leu Leu Ile His Asp Gly Val Arg Ser Glu Phe Asp Gln
             100                 105                 110

Ile Asp Thr Ser Asn Pro Asn Cys Val Val Ile Ala Asp Ala Gly Glu
         115                 120                 125

Ser Phe Ser Tyr Gln Asn Met Asn Asn Ala Phe Gln Val Leu Met Glu
     130                 135                 140

Leu Glu Lys Pro Val Leu Ile Ser Leu Gly Lys Gly Ile His Gly Phe
145                 150                 155                 160

Leu Phe Val Ala Arg Thr Phe Thr Ser
                 165
```

<210> SEQ ID NO 30
<211> LENGTH: 659
<212> TYPE: DNA
<213> ORGANISM: Homo sapiens

<400> SEQUENCE: 30

```
catgacggag tccgctcaga atttgatcag atcgacacat ccaacccaaa ctgtgtggta    60
attgcagacg caggagaaag cttttcttat caaaacatga ataacgcctt ccaggtgctc   120
atggagctgg aaaaacctgt gctcatatca ctgggaaaag gagccgctca acacgtgttg   180
caaggcacgt gctctggacc tggtgctcac acgtgctctt ctcccaagac actccctgaa   240
gcgcgttccc caggagctgg aaggggata acgcaggccc agtgacgagc accatccgga   300
agtgaaggct gatggtgaag agcctggaag aaacccaggg gcctcctatg cacagatctt   360
gcagcccaga accaagtcag cttccctgcg actgcccagg cacactgccc atcaccccac   420
ccccgaaaca atgccagccc gctgcttttt ctatcctccc agtcacccttt gcagacaaag   480
accaggggca gctcccgagg gcactgtgaa ggctcccatg ccacacagtg agaactgtag   540
cctctgcgtc caaggcacac agggtacttt ctggacccac tgctggacag acttgaaggt   600
gtcatgcccg gtgtgtgcag gaggaaacta acagttcagt aaactctgcc ttgaccagc    659
```

<210> SEQ ID NO 31
<211> LENGTH: 2294
<212> TYPE: DNA
<213> ORGANISM: Homo sapiens
<220> FEATURE:
<221> NAME/KEY: CDS
<222> LOCATION: (311)..(805)

<400> SEQUENCE: 31

```
tgtgccattg gcgatgcggg gaggctggcc ccatcgaagg ctggtgggac tggtggagac    60
tcctgtccac tgctcagcac taggcctgca gcagacacca tgagcccaa acttcccaaa   120
gcccttcccc agtcccacaa gatggtgtct gcggaccgtg ctcgtgagag atggcagcca   180
ggcagtcccc acagggcacc catttttcagc tgccccgct ctcagacaa ggaaactgag   240
gccagaaagc caggtggccc aggagctggc ttccccattt cctgctcctg tgggccccac   300
```

```
tgcagtgccc atg ggc cgg gct gat att acc cga gac ttc gga gct ctc       349
          Met Gly Arg Ala Asp Ile Thr Arg Asp Phe Gly Ala Leu
            1               5                  10 acg ggt gcg agt aat tta ggc tgc atg gac aca agc tgc tgg ctt gag      397
Thr Gly Ala Ser Asn Leu Gly Cys Met Asp Thr Ser Cys Trp Leu Glu
 15                  20                  25 tcg ccc cgt tat gaa tgt gtg tgg gtc tgt gcc cct ttc atg tgc tgc      445
Ser Pro Arg Tyr Glu Cys Val Trp Val Cys Ala Pro Phe Met Cys Cys
 30                  35                  40                  45 cac agg gcc cac gag tgt gct gaa agg gaa gga cac ggc caa ggg gcc      493
His Arg Ala His Glu Cys Ala Glu Arg Glu Gly His Gly Gln Gly Ala
                 50                  55                  60 atg gtg gac agg aga cct tct tgg ggg ttc ggt ggt gtc ctt gac ccc      541
Met Val Asp Arg Arg Pro Ser Trp Gly Phe Gly Gly Val Leu Asp Pro
             65                  70                  75 act ctg act gag cac tgc ccc aag gca ctg cca ttc cag gcc ccc ttc      589
Thr Leu Thr Glu His Cys Pro Lys Ala Leu Pro Phe Gln Ala Pro Phe
         80                  85                  90 cct gag cct ccc acc cca ggc cca ccc acc tgc tgg gtc ctc cca cct      637
Pro Glu Pro Pro Thr Pro Gly Pro Pro Thr Cys Trp Val Leu Pro Pro
```

```
                95                    100                  105
gcg ggg ccc gcc atg cgg ggt cac cat gcg agt ctc acc atg cag ggt         685
Ala Gly Pro Ala Met Arg Gly His His Ala Ser Leu Thr Met Gln Gly
110                 115                 120                 125 cac cac acg agt ctc acc atg cag ggt cac cac gcg agt ctc acc atg         733
His His Thr Ser Leu Thr Met Gln Gly His His Ala Ser Leu Thr Met
                130                 135                 140 cag ggt cac cat gcg ggg tca cca tgt ggg gtc acc atg cgg ggc tca         781
Gln Gly His His Ala Gly Ser Pro Cys Gly Val Thr Met Arg Gly Ser
                145                 150                 155 cca tgt ggg gct tca gga gct tgc tgagcaccct cccacccac ggtcactctc         835
Pro Cys Gly Ala Ser Gly Ala Cys
        160                 165 cctggggtct gtaagcctcc ctgggcctga gcagctccca gccttgctgc tgccttccca       895
cttcctggca gtgaggtctc ctgggtgcct tctctcagcc ctttgggatg ttttttgtga       955
ggaagggagg ctttgatgct gtggagcatc tgtagtgccc actccagtgg cttcacagga      1015
gcagcaggct gtttgttctg agctgttcca ccttgtgcct gccagagggg agatagtgga      1075
caggcctccc tcccccaag tggtggggtg accccctgc cgctgtggc cccatacctg         1135 ggggccacac accactgccc tgggccgtgc agctgctatg aagagtgtgc tgctgagacc      1195
ctggaagaga cggaggatga aattgtgttg ccagatagtc catttgttgt tctgagactc      1255
gcatgcctgg gagaatcctg ggaattaact agctccttct ctcccatccc attttacaga     1315
aaagtgagac ccaaggtggt ttctgacttg cccagaggtc ataactgctt ggacagtcat      1375
ggtcctcaga gcccacgttt gctgaccagt gcaggctctc acagccactc agctcctgca      1435
gccgtggcgt ggcagaggag ggaagcactt cctgggattt atgctgcctc cctgacattt      1495
caaggcccTt catttctcta aatattggag gagttgaatt atttttagtt gagcctcaag      1555
ggatcagaga ataagcttgc agcaacgttg gcagatgggc ttcttctagc agagagtggt      1615
tattcggggc ctcttattga gagaatcggg tgatttgagg aaatctgggg tgtcctgagg     1675
cataccagag gacccccaag ttttttcctgt ggctcgtctg ccatcaggaa accaaaatga    1735
ctcccctcgt cctgagctct ccagggtgtg gacctggaat gcttaagggg aggcaatggc     1795
atatctttaa gatgagcaca gctccggagc cactcgagca cccaaggcca cgtcctgctc     1855
agggcacttc gggcctcagt ttccttatct ttaaaatgga cagagttggc cgggtgaggt     1915
ggccctgcct gtaatcccag cactttggga ggccaaggct ggcagattgc ttgagcccag     1975
gagtttgaag ccagcctggg caacatggcg aaacccccatc tctactacaa gtacaaaaat    2035
ttggccgggc atggtggctc atgcttgtaa tcccagcact ttgggaggcc aaggagagcg     2095
gatcacttga ggccagaagc tcgagaccgc tctactaaa aatacaaaaa ttagccaggc      2155
gtggtggctc acgcctgtaa tctcagctac tcgggtggct gaggcaggag aatcacttga     2215
acctgggaag tagaggttgc agtgagctga gatcgtgcca ctgcactcta gcctgggcga     2275
cagagcaaaa ccctgtctc                                                 2294

<210> SEQ ID NO 32
<211> LENGTH: 165
<212> TYPE: PRT
<213> ORGANISM: Homo sapiens

<400> SEQUENCE: 32

Met Gly Arg Ala Asp Ile Thr Arg Asp Phe Gly Ala Leu Thr Gly Ala
1               5                   10                  15
```

```
Ser Asn Leu Gly Cys Met Asp Thr Ser Cys Trp Leu Glu Ser Pro Arg
            20                  25                  30

Tyr Glu Cys Val Trp Val Cys Ala Pro Phe Met Cys Cys His Arg Ala
        35                  40                  45

His Glu Cys Ala Glu Arg Glu Gly His Gly Gln Gly Ala Met Val Asp
    50                  55                  60

Arg Arg Pro Ser Trp Gly Phe Gly Gly Val Leu Asp Pro Thr Leu Thr
65                  70                  75                  80

Glu His Cys Pro Lys Ala Leu Pro Phe Gln Ala Pro Phe Pro Glu Pro
                85                  90                  95

Pro Thr Pro Gly Pro Pro Thr Cys Trp Val Leu Pro Ala Gly Pro
                100                 105                 110

Ala Met Arg Gly His His Ala Ser Leu Thr Met Gln Gly His His Thr
            115                 120                 125

Ser Leu Thr Met Gln Gly His His Ala Ser Leu Thr Met Gln Gly His
        130                 135                 140

His Ala Gly Ser Pro Cys Gly Val Thr Met Arg Gly Ser Pro Cys Gly
145                 150                 155                 160

Ala Ser Gly Ala Cys
                165

<210> SEQ ID NO 33
<211> LENGTH: 3350
<212> TYPE: DNA
<213> ORGANISM: Homo sapiens
<220> FEATURE:
<221> NAME/KEY: CDS
<222> LOCATION: (192)..(776)

<400> SEQUENCE: 33
tttttttttt ttctgctta taagtttatt caatgcaaaa taaccctcac cagtttttact   60 gaggtggctg accatgtcca cgaccaaata cgcctgtaaa ctgaaattcg gttgctgacc  120
cattcccagc ctcagctttc tcactggcac caggggggaca gcactccatc tgtgggtgtc  180
tctttctctc t atg gct gtc tgt ctg tgg gtg tct ctc tct gtc tgt ggg  230
            Met Ala Val Cys Leu Trp Val Ser Leu Ser Val Cys Gly
             1               5                  10 tgt ctt tcg cca tct gtg ggt atc tct ctc tgt ctg tgg gta tct ctc  278
Cys Leu Ser Pro Ser Val Gly Ile Ser Leu Cys Leu Trp Val Ser Leu
         15                  20                  25 cca tct gtg ggt gtc cat ctc tgt ctt tgg gtg tct ctc ttt gtg agt  326
Pro Ser Val Gly Val His Leu Cys Leu Trp Val Ser Leu Phe Val Ser
30                  35                  40                  45 gtc tct gtc tgt ggt tgt ctc tgt ctg tgg gtg tct ctc tgt gag tgt  374
Val Ser Val Cys Gly Cys Leu Cys Leu Trp Val Ser Leu Cys Glu Cys
             50                  55                  60 ccc tgt gag tgt ctc tgt ctg tgg gtg tct ctc ctc gtc tgt ggg tat  422
Pro Cys Glu Cys Leu Cys Leu Trp Val Ser Leu Leu Val Cys Gly Tyr
        65                  70                  75 ctc tcc ctg tct gtg ggt gtc tct gtt ggc ttc ccc act tgt ggg tct  470
Leu Ser Leu Ser Val Gly Val Ser Val Gly Phe Pro Thr Cys Gly Ser
    80                  85                  90 tgc agg tcg gtc acg ctc cag acc ttt agg ccg cag cct gcc agt ctc  518
Cys Arg Ser Val Thr Leu Gln Thr Phe Arg Pro Gln Pro Ala Ser Leu
 95                 100                 105 cag acc gct gtg gca tgg ggt agc aga cac gct ctc cag ggg cag atg  566
Gln Thr Ala Val Ala Trp Gly Ser Arg His Ala Leu Gln Gly Gln Met
110                 115                 120                 125
```

| | |
|---|---|
| gtg gta atc gca gag att ctg gat ccc cat gtg ggt gag gta cca gta<br>Val Val Ile Ala Glu Ile Leu Asp Pro His Val Gly Glu Val Pro Val<br>                    130                        135                      140 | 614 |
| gaa atg tct cca ggc aaa ctc ctt cct gca acc tca gga cct gag aga<br>Glu Met Ser Pro Gly Lys Leu Leu Pro Ala Thr Ser Gly Pro Glu Arg<br>              145                        150                        155 | 662 |
| ctg cct ggc ctt cat gac gtg aag gtt ggg cac att ctc atc tgc cag<br>Leu Pro Gly Leu His Asp Val Lys Val Gly His Ile Leu Ile Cys Gln<br>        160                        165                        170 | 710 |
| ctc cgg gtc tta ggc agg tgg aca ttc ttc ttg gct acc gtg act ccc<br>Leu Arg Val Leu Gly Arg Trp Thr Phe Phe Leu Ala Thr Val Thr Pro<br>175                        180                        185 | 758 |
| tcc tta aaa agg agt tca taaatagcaa tctggttctt cttaggcatc<br>Ser Leu Lys Arg Ser Ser<br>190                        195 | 806 |
| aacatctctg cagctgtagg gtccaggtcc ggggctggaa agcatgattt ttttctaact | 866 |
| gatctctgct gatggcatct agattgttcc tggttttttca ccataccagg gctgtgatga | 926 |
| gcatcttggt gcatttcgga tgacgtctcc agatacagtt acagaacgag tatttttgag | 986 |
| gttcttgagg catgttgcca agttgttccc agaaagctgc acagacttat tctgcacagc | 1046 |
| ctagaattct agaatcacag ggttctgcac aacctagagt tctggaatca cagggttctg | 1106 |
| cacagctaga attctagaat cacagggttc tgcacagcta gaattctaga atcacagggt | 1166 |
| tctgcacaac ctagagttct ggaatcacag ggttctgcac agcctagagt tctggaatca | 1226 |
| cagggttctg cacagctaga attctagaat cacagggttc tgcacagcct agagttctgg | 1286 |
| aatcacaggg ttctgcacag cctagagttt tggaatcaca gggttctgca cagctagaat | 1346 |
| tctagaatca gggttctg cacagctaga attctagaat cacagggttc tacacagcta | 1406 |
| gaattctaga atcacaggct cccagggttg caaggacact tggagtgtc tacctcagca | 1466 |
| tctcatgaag tgtgggaatt ccgaggcggt ggcggaggaa gtgttttcca tcttcggtgc | 1526 |
| tttcgttgct tctggtgaca gcgctcactg cctctgcttg ctgtacggga ccagctgatg | 1586 |
| gaaccgacag ggagggactt tttatctggc cattggccac tgccacacac tttgtgtacc | 1646 |
| ccgtttttgtg taattctgac tacaaccttg tgggatctag gcaggtcatt gctgttttgc | 1706 |
| aagtgggtt gttgaagcca caggagatga ataagctgc tgtcccccag ccattgagtg | 1766 |
| ctgataggat caggagtgcc agttggtgtg gctgacccca gaccctgtgc gtgttacctc | 1826 |
| taagctacat tctagagcag acttttttgcc cacacaagcc ttaaatgtgg gctggggaca | 1886 |
| gtggctcacg ccggtaatcc cagcactttg ggaggacaag gtgggcagat cacctgaggc | 1946 |
| caggggttca agaccaggct ggccaacatg gtgaaaccct gtctctacta aaaatacaaa | 2006 |
| aattagccag gtgtggtggt gcgtgcctat agtcccagct actcgggagg ctgacgcatg | 2066 |
| agaattgctt gaacctggga ggcagaggtt gcagtaagtc aagactgcgc cattgcactc | 2126 |
| tagcctgggc gacagagcaa gactccatct cgaaaaaaac aacaaaacct taaatgtatt | 2186 |
| tttgaggctg tgtttaaaaa tggggatatt ttacacaaaa tatccagatt tctggattct | 2246 |
| tttgaagaat cagaagatct gacaatacgg agcctcacat tcctgcacac acagcagcca | 2306 |
| tcgctggagc cactgcctcc attagtttga atttactgca gaccccactc ctccctgtcg | 2366 |
| tccctgtctc cagaccacag agttagttgt cattgatcgt gtgccatttg ttgttttttt | 2426 |
| caaagtagag aagtacttct tcacgctgtg tctctatcaa aaatggacaa gtgaaagatg | 2486 |
| tttcaagaaa tgaaaagatt ttcttttttag tgacaaaaaa tttctagtat gtttctcata | 2546 |
| taaataaaat gtgtcctgta tgtagtcagg gttcctcaga gaagcccgaa gctacaggat | 2606 |

-continued

```
atagatatgt agagagattg tggaggcttg gcgagtccaa atctgcagg gcagggctgg    2666 caggctgggg actcaggaat gcgcgcagca gagtcgtaag gctgtgtgct ggtgggattc    2726
ttgctcgggg aaggtcagtc tttgttcttg taaagcctgc aactggttgg atgtggtcca    2786
cccacattgc ggaagggaat gtactctcct cctagttcac cgatttaaat gttaatctca    2846
tccaaaaaca ccttcacaga aacatccaga ataatgtttg accacatatc tgggcaccgt    2906
ggcccagcca agttgacata ttaaattaac ccttgtagtc cctttttaaa cttacaccca    2966
ttgcaattta ggtcgctgct atggagcaag ccacagaacc tggcctctta actcatttac    3026
ccgggctgac ccattaggcc tttgagtcac caacacctca ctagagaaca agcataatga    3086
agaagctctg ctgtaattcg ttaatgttaa cacttttttc tttaaagatg tctcatgctg    3146
agcttcgtgg cacacgccta taatcccagc actttgggag gctgagatga gaggatggct    3206
tgagctcaga ggttcgagac cagcctgggc agcatagtaa gattccgtct ctacaaaaaa    3266
gaaaagaaaa aaagttgtct cataattatt aaaaaccact attccagatc atggataata    3326
atagtcagaa caggtatatt gttg                                            3350
```

<210> SEQ ID NO 34
<211> LENGTH: 195
<212> TYPE: PRT
<213> ORGANISM: Homo sapiens

<400> SEQUENCE: 34

```
Met Ala Val Cys Leu Trp Val Ser Leu Ser Val Cys Gly Cys Leu Ser
1               5                   10                  15

Pro Ser Val Gly Ile Ser Leu Cys Leu Trp Val Ser Leu Pro Ser Val
            20                  25                  30

Gly Val His Leu Cys Leu Trp Val Ser Leu Phe Val Ser Val Ser Val
        35                  40                  45

Cys Gly Cys Leu Cys Leu Trp Val Ser Leu Cys Glu Cys Pro Cys Glu
    50                  55                  60

Cys Leu Cys Leu Trp Val Ser Leu Leu Val Cys Gly Tyr Leu Ser Leu
65                  70                  75                  80

Ser Val Gly Val Ser Val Gly Phe Pro Thr Cys Gly Ser Cys Arg Ser
                85                  90                  95

Val Thr Leu Gln Thr Phe Arg Pro Gln Pro Ala Ser Leu Gln Thr Ala
            100                 105                 110

Val Ala Trp Gly Ser Arg His Ala Leu Gln Gly Gln Met Val Val Ile
        115                 120                 125

Ala Glu Ile Leu Asp Pro His Val Gly Glu Val Pro Val Glu Met Ser
    130                 135                 140

Pro Gly Lys Leu Leu Pro Ala Thr Ser Gly Pro Glu Arg Leu Pro Gly
145                 150                 155                 160

Leu His Asp Val Lys Val Gly His Ile Leu Ile Cys Gln Leu Arg Val
                165                 170                 175

Leu Gly Arg Trp Thr Phe Phe Leu Ala Thr Val Thr Pro Ser Leu Lys
            180                 185                 190

Arg Ser Ser
        195
```

<210> SEQ ID NO 35
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 35
cacgtaccca tcagccttca c                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cctgtggaag gagcatacag t                                              21

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
cccagtgacg agcaccatcc gg                                             22

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
caacactggc acctgcagat                                                20

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccaccccatg ccatcaa                                                   17

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
aagtggcaga gcagccccca gc                                             22

<210> SEQ ID NO 41
<211> LENGTH: 19
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 41
cccgcctctc caagaccat                                          19

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggtacactca tgtccccacc at                                      22

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcgcaccggg aagttcag                                           18

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgcaagcgat aggagtggaa                                         20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggttgtccac gtacccatca g                                       21

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
cccaccaggc ccagtgacga gc                                      22

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gcgcaccggg aagttcag                                                 18

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgaagaacaa aacagaatga gaatgtg                                       27

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
ccagctggag tcatttattc accttccttc c                                  31

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccaccagtta ctttcagtat gaaagca                                       27

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tatcctttca gagaagcagc aaaaac                                        26

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
cagaaatgcc tgcggctttt cctg                                          24

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cgccccagac ccaagaatc                                                19

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
caggaagtgc ccatcagcct                                               20

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
cccgcctctc caagaccatc cct                                           23

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agcaccatcc ggaagtgaag                                               20

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gctgcaagat ctgtgcatag ga                                            22

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
ctgatggtga agagcctgga agaaaccca                                     29

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 59
caatttaggt cgctgctatg ga                                              22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tggtgactca aaggcctaat gg                                              22

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
cctggcctct taactcattt acccggg                                         27

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tggaggcagc ctcgcttta                                                  19

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttggaggaag agttctcatg ca                                              22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
cccgcagaac ctccacgctg tt                                              22

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
```

```
tctcccactg tatgctcctt cca                                          23
```

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66

```
ctctgccact tcatctgcag gt                                           22
```

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

```
cacgtaccca tcagccttca c                                            21
```

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

```
gaatctccca aatcccagaa ctca                                         24
```

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

```
acaccgggca tgacaccttc aagt                                         24
```

<210> SEQ ID NO 70
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
aagaacttta aaaatcacct aggtgtgggc cgggcacggt ggctaacgcc tgtaatccca    60
gcactttgag atgctgaggc aggtggatca cgaggtcagg agatcgagac catcctggat   120
aacacggaga aaccccg                                                 137
```

<210> SEQ ID NO 71
<211> LENGTH: 1203
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
tgcattcggc tgacagagca tgaggggag gaatcactga tgacaggcac tggcctgccc      60
agctgggggc ctttgtttat tcatttggtg ggcacttcct gggtgcctgc tctgggtcag    120
gcctgtgggg gggaccactg agggcaggaa acctggcctg tccctccagg aagcgaagtc    180
aacactggca cctgcagatg aagtggcaga gcagccccca gctttgatgg catgggtgg     240
ttgggggca cattctgcat gctcagaaga gagagcaact cgccctgtgg aaggagcata     300
cagtgggaga tggggacagg cccagtgacg agcaccatcc ggaagtgaag gctgatgggt    360
acgtggacaa cctcgcagag gcagtggacc tgctgctgca gcacgccgac aagtgatggc    420
ctcctgggag agccccgcct cctccacccc tgcctctcct ccaccccctgc ctcccctcca   480
cccctgcctc tcctccaccc gcccaggaga gcccacctc ctccaccct gcctctcctc     540
caccctgcc tccctccac ctgcccagt gcccagacca accaaggccc tgacagccct      600
gccttctgcc ctctgccctg catgggcagg catttgttcc ctacctggt ggcctgctcc     660
cctgcctggg ccctgacttc agctccctgt agtgaagtcc aggagggtgg acaggcctg    720
tcaggcctct gggaatctcc caaatcccag aactcaccac tcaccatggg cctttaaatg    780
cagtaaactc cacctaacca gattcagggg cactatgccc actgcctcct cttcagactc    840
tttgcatttc agtgaagagc ctggaagaaa cccaggggcc tcctatgcac agatcttgca    900
gcccagaacc aagtcagcct ccctgcgact gcccaggcac actgcccacc accccaccc    960
cgaaacaatg ccagcccgct gcttttcta tcctcccagt caccttttgca gacaaagacc    1020
aggggcagct cccgagggca ctgtgaaggc tcccatgcca cacagtgaga actgtagcct    1080
ctgcgtccaa ggcacacagg gtactttctg gacccactgc tggacagact tgaaggtgtc    1140
atgcccggtg tgtgcaggag gaaactaaca gttcagtaaa ctctgccttg accagcagcc    1200
ttt                                                                 1203
```

<210> SEQ ID NO 72
<211> LENGTH: 1143
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
gcatgagggg gaggaatcac tgatgacagg cactggcctg cccagctggg ggcctttgtt     60
tattcatttg gtgggcactt cctgggtgcc tgctctgggt caggcctgtg gggggggacca   120
ctgagggcag gaaacctggc ctgtccctcc aggaagcgaa gtcaacactg gcacctgcag    180
atgaagtggc agagcagccc ccagctttga tggcatgggg tggttggggg gcacattctg    240
catgctcaga gagagagca actcgccctg tggaaggagc atacagtggg agatggggac     300
aggcccagtg acgagcacca tccggaagtg aaggctgatg ggtacgtgga caacctcgca    360
gaggcagtgg acctgctgct gcagcacgcc gacaagtgat ggcctcctgg gagagccccg    420
cctcctccac ccctgcctct cctccacccc tgcctcccct ccaccctgc ctctcctcca    480
cccgcccagg agagcccac ctcctccacc cctgcctctc ctccaccct gcctcctc      540
cacctgcccc agtgcccaga ccaaccaagg ccctgacagc cctgccttct gccctctgcc    600
ctgcatgggc aggcatttgt tccctacctg ggtggcctgc tccctgcct gggccctgac    660
```

| | |
|---|---|
| ttcagctccc tgtagtgaag tccaggaggg tgggacaggc ctgtcaggcc tctgggaatc | 720 |
| tcccaaatcc cagaactcac cactcaccat gggcctttaa atgcagtaaa ctccacctaa | 780 |
| ccagattcag gggcactatg cccactgcct cctcttcaga ctctttgcat ttcagtgaag | 840 |
| agcctggaag aaacccaggg gcctcctatg cacagatctt gcagcccaga accaagtcag | 900 |
| cctccctgcg actgcccagg cacactgccc accaccccac ccccgaaaca atgccagccc | 960 |
| gctgcttttt ctatcctccc agtcacctttt gcagacaaag accaggggca gctcccgagg | 1020 |
| gcactgtgaa ggctcccatg ccacacagtg agaactgtag cctctgcgtc caaggcacac | 1080 |
| agggtacttt ctggacccac tgctggacag acttgaaggt gtcatgcccg gtgtgtgcag | 1140 |
| gag | 1143 |

<210> SEQ ID NO 73
<211> LENGTH: 1129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

| | |
|---|---|
| gcacttcctg ggtgcctgct ctgggtcagg cctgtggggg ggaccactga gggcaggaaa | 60 |
| cctggcctgt ccctccagga agcgaagtca acactggcac ctgcagatga agtggcagag | 120 |
| cggcccccag ctttgatggc atgggtggt tggggggcac attctgcatg ctcagaagag | 180 |
| agagcaactc gccctgtgga aggagcatac agtgggagat ggggacaggc ccagtgacga | 240 |
| gcaccatccg gaagtgaagg ctgatgggta cgtggacaac ctcgcagagg cagtggacct | 300 |
| gctgctgcag cacgccgaca agtgatggcc tcctgggaga gccccgcctc ctccacccct | 360 |
| gcctctcctc caccctgcc tccctccac ccctgcctct cctccacccg cccaggagag | 420 |
| ccccacctcc tccaccctg cctctcctc acccctgcct cccctccacc tgccccagtg | 480 |
| cccagaccaa ccaaggccct gacagccctg ccttctgccc tctgccctgc atgggcaggc | 540 |
| atttgttccc tacctgggtg gcctgctccc ctgcctgggc cctgacttca gctccctgta | 600 |
| gtgaagtcca ggagggtggg acaggcctgt caggcctctg ggaatctccc aaatcccaga | 660 |
| actcaccact caccatgggc ctttaaatgc agtaaactcc acctaaccag attcaggggc | 720 |
| actatgccca ctgcctcctc ttcagactct ttgcatttca gtgaagagcc tggaagaaac | 780 |
| ccaggggcct cctatgcaca gatcttgcag cccagaacca agtcagcctc cctgcgactg | 840 |
| cccaggcaca ctgcccacca ccccaccccc gaaacaatgc cagcccgctg ctttttctat | 900 |
| cctcccagtc acctttgcag acaaagacca ggggcagctc ccgagggcac tgtgaaggct | 960 |
| cccatgccac acagtgagaa ctgtagcctc tgcgtccaag gcacagggg tactttctgg | 1020 |
| acccactgct ggacagactt gaaggtgtca tgcccggtgt gtgcaggagg aaactaacag | 1080 |
| ttcagtaaac tctgccttga ccagcaaaaa aaaaaaaaa aaaaaaaa | 1129 |

<210> SEQ ID NO 74
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

| | |
|---|---|
| ctgagggcag gaaacctggc ctgtccctcc aggaagcgaa gtcaacactg gcacctgcag | 60 |

```
atgaagtggc agagcagccc ccagctttga tggcatgggg tggttggggg gcacattctg     120
catgctcaga agagagagca actcgccctg tggaaggagc atacagtggg agatggggac     180
aggcccagtg acgagcacca tccggaagtg aaggctgatg ggtacgtgga caacctcgca     240
gaggcagtgg acctgctgct gcagcacgcc gacaagtgat ggcctcctgg agagccccg      300 cctcctccac ccctgcctct cctccacccc tgcctcccct ccaccctgc ctctcctcca      360 cccgcccagg agagccccac ctcctccacc cctgcctctc ctcacccct gcctcccctc      420 cacctgcccc agtgcccaga ccaaccaagg ccctgacagc cctgccttct gccctctgcc     480
ctgcatgggc aggcatttgt tccctacctg ggtggcctgc tccctgcct gggccctgac      540 ttcagctccc tgtagtgaag tccaggaggg tgggacaggc ctgtcaggcc tctgggaatc     600
tcccaaatcc cagaactcac cactcaccat gggcctttaa atgcagtaaa ctccacctaa     660
ccagattcag gggcactatg cccactgcct cctcttcaga ctctttgcat tcagtgaag      720 agcctggaag aaacccaggg gcctcctatg cacagatctt gcagcccaga accaagtcag     780
cctccctgcg actgcccagg cacactgccc accacccac cccgaaaca atgccagccc       840 gctgcttttt ctatcctccc agtcacctt gcagacaaag accaggggca gctcccgagg      900
gcactgtgaa ggctcccatg ccacacagtg agaactgtag cctctgcgtc caaggcacac     960
agggtacttt ctggacccac tgctggacag acttgaaggt gtcatgcccg tgtgtgcag     1020 gaggaaacta acagttcagt aaactctgcc ttgaccagca aaaaaaaaa aaaaaaaaa      1080 aaa                                                                 1083
```

<210> SEQ ID NO 75
<211> LENGTH: 999
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
tacagtggga gatggggaca ggcccagtga cgagcaccat ccggaagtga aggctgatgg      60
gtacgtggac aacctcgcag aggcagtgga cctgctgctg cagcacgccg acaagtgatg    120
gcctcctggg agagcccgc ctcctccacc cctgcctctc ctcacccct gcctcccctc      180 caccctgcc tctcctccac ccgcccagga gagcccacc tcctcaccc ctgcctctcc       240 tcacccctg cctcccctcc acctgcccca gtgcccagac caaccaaggc cctgacagcc     300
ctgccttctg ccctctgccc tgcatgggca ggcatttgtt ccctacctgg gtggcctgct    360
cccctgcctg ggccctgact tcagctccct gtagtgaagt ccaggagggt gggacaggcc    420
tgtcaggcct ctgggaatct cccaaatccc agaactcacc actcaccatg ggcctttaaa    480
tgcagtaaac tccacctaac cagattcagg ggcactatgc ccactgcctc ctcttcagac    540
tctttgcatt tcagtgaaga gcctggaaga aacccagggg cctcctatgc acagatcttg    600
cagcccagaa ccaagtcagc ctccctgcga ctgcccaggc acactgccca ccacccacc     660 cccgaaacaa tgccagcccg ctgctttttc tatcctccca gtcacctttg cagacaaaga    720
ccaggggcag ctcccgaggg cactgtgaag gctcccatgc cacacagtga agaactgtagc   780 ctctgcgtcc aaggcacaca gggtactttc tggacccact gctggacaga cttgaaggtg    840
tcatgcccag tgtgtgcagg aggaaactaa cagttcagta aactctgcct tgaccagcaa    900
aaaaaaaaaa aaaaaaaaaa aactcgaggc atctatgtcg ggtgcggaga aagaggtaat    960
```

```
gaaatggcac atggtcatag ctgtttcctg acccagctt                                    999
```

<210> SEQ ID NO 76
<211> LENGTH: 20
<212> TYPE: PRT
<213> ORGANISM: Homo sapiens

<400> SEQUENCE: 76

Asp Gly Tyr Val Asp Asn Leu Ala Glu Ala Val Asp Leu Leu Leu Gln
1               5                   10                  15

His Ala Asp Lys
            20

<210> SEQ ID NO 77
<211> LENGTH: 58
<212> TYPE: PRT
<213> ORGANISM: Homo sapiens

<400> SEQUENCE: 77

Trp Pro Pro Gly Arg Ala Pro Pro Pro Pro Leu Pro Leu Leu His
1               5                   10                  15

Pro Cys Leu Pro Ser Thr Pro Ala Ser Pro Pro Ala Gln Glu Ser
            20                  25                  30

Pro Thr Ser Ser Thr Pro Ala Ser Pro Pro Leu Pro Pro Leu His
        35                  40                  45

Leu Pro Gln Cys Pro Asp Gln Pro Arg Pro
        50                  55

<210> SEQ ID NO 78
<211> LENGTH: 32
<212> TYPE: PRT
<213> ORGANISM: Homo sapiens

<400> SEQUENCE: 78

Gln Pro Cys Leu Leu Pro Ser Ala Leu His Gly Gln Ala Phe Val Pro
1               5                   10                  15

Tyr Leu Gly Gly Leu Leu Pro Cys Leu Gly Pro Asp Phe Ser Ser Leu
            20                  25                  30

<210> SEQ ID NO 79
<211> LENGTH: 26
<212> TYPE: PRT
<213> ORGANISM: Homo sapiens

<400> SEQUENCE: 79

Ser Pro Gly Gly Trp Asp Arg Pro Val Arg Pro Leu Gly Ile Ser Gln
1               5                   10                  15

Ile Pro Glu Leu Thr Thr His His Gly Pro
            20                  25

<210> SEQ ID NO 80
<211> LENGTH: 13
<212> TYPE: PRT
<213> ORGANISM: Homo sapiens

<400> SEQUENCE: 80

Tyr Ala His Cys Leu Leu Phe Arg Leu Phe Ala Phe Gln
1               5                   10

<210> SEQ ID NO 81
<211> LENGTH: 70

```
<212> TYPE: PRT
<213> ORGANISM: Homo sapiens

<400> SEQUENCE: 81

Arg Ala Trp Lys Lys Pro Arg Gly Leu Leu Cys Thr Asp Leu Ala Ala
1               5                   10                  15

Gln Asn Gln Val Ser Leu Pro Ala Thr Ala Gln Ala His Cys Pro Pro
                20                  25                  30

Pro His Pro Arg Asn Asn Ala Ser Pro Leu Leu Phe Leu Ser Ser Gln
            35                  40                  45

Ser Pro Leu Gln Thr Lys Thr Arg Gly Ser Ser Arg Gly His Cys Glu
        50                  55                  60

Gly Ser His Ala Thr Gln
65                  70

<210> SEQ ID NO 82
<211> LENGTH: 29
<212> TYPE: PRT
<213> ORGANISM: Homo sapiens

<400> SEQUENCE: 82

Pro Leu Arg Pro Arg His Thr Gly Tyr Phe Leu Asp Pro Leu Leu Asp
1               5                   10                  15

Arg Leu Glu Gly Val Met Pro Gly Val Cys Arg Arg Lys
                20                  25
```